(12) United States Patent
Wu et al.

(10) Patent No.: US 8,466,167 B2
(45) Date of Patent: Jun. 18, 2013

(54) COMPOUNDS AND COMPOSITIONS AS TLR ACTIVITY MODULATORS

(75) Inventors: Tom Yao Hsiang Wu, San Diego, CA (US); Yongkai Li, San Diego, CA (US); Alex Cortez, San Diego, CA (US); Yefen Zou, San Diego, CA (US); Pranab Mishra, San Diego, CA (US); Xiaoyue Zhang, San Diego, CA (US); David Skibinski, Siena (IT); Manmohan Singh, Lexington, MA (US); Nicholas Valiante, Cambridge, MA (US)

(73) Assignees: IRM LLC, Hamilton (BM); Novartis AG, Basel (CH)

( * ) Notice: Subject to any disclaimer, the term of this patent is extended or adjusted under 35 U.S.C. 154(b) by 313 days.

(21) Appl. No.: 12/921,129

(22) PCT Filed: Feb. 27, 2009

(86) PCT No.: PCT/US2009/035563
§ 371 (c)(1),
(2), (4) Date: Dec. 6, 2010

(87) PCT Pub. No.: WO2009/111337
PCT Pub. Date: Sep. 11, 2009

(65) Prior Publication Data
US 2011/0081365 A1    Apr. 7, 2011

Related U.S. Application Data

(60) Provisional application No. 61/033,139, filed on Mar. 3, 2008, provisional application No. 61/148,336, filed on Jan. 29, 2009.

(51) Int. Cl.
*A61K 31/44* (2006.01)
*C07D 471/00* (2006.01)

(52) U.S. Cl.
USPC ............................................ 514/292; 546/81

(58) Field of Classification Search
USPC ............................................ 514/292; 546/81
See application file for complete search history.

(56) References Cited

U.S. PATENT DOCUMENTS

| | | | |
|---|---|---|---|
| 4,689,338 A | 8/1987 | Gerster | |
| 4,698,348 A | 10/1987 | Gerster | |
| 5,346,905 A | 9/1994 | Gerster | |
| 5,741,909 A | 4/1998 | Gerster | |
| 6,953,804 B2 | 10/2005 | Dellaria | |
| 7,943,636 B2 | 5/2011 | Hays | |
| 2003/0078277 A1 | 4/2003 | Hibi | |
| 2003/0144283 A1 | 7/2003 | Coleman et al. | |
| 2007/0219228 A1 | 9/2007 | Niwas et al. | |
| 2007/0259881 A1 | 11/2007 | Dellaria, Jr. et al. | |
| 2008/0031852 A1 | 2/2008 | Ruebesam | |
| 2009/0023720 A1 | 1/2009 | Kshirsagar et al. | |
| 2009/0029988 A1 | 1/2009 | Kshirsagar et al. | |
| 2009/0069299 A1 | 3/2009 | Merrill et al. | |
| 2009/0069314 A1 | 3/2009 | Kshirsagar et al. | |
| 2009/0099161 A1 | 4/2009 | Rice et al. | |
| 2009/0124611 A1 | 5/2009 | Hays et al. | |
| 2009/0176821 A1 | 7/2009 | Kshirsagar et al. | |
| 2009/0253695 A1 | 10/2009 | Kshirsagar et al. | |
| 2010/0317684 A1 | 12/2010 | Kshirsagar et al. | |

FOREIGN PATENT DOCUMENTS

| | | |
|---|---|---|
| SU | 1766918 | 10/1992 |
| WO | WO2007109813 | 9/2007 |
| WO | WO2008004948 | 1/2008 |
| WO | WO2009108912 | 9/2009 |
| WO | WO2010030785 | 3/2010 |

OTHER PUBLICATIONS

Ferraris D, Ko YS, Pahutski T, et al. Design and synthesis of poly ADP-ribose polymerase-1 inhibitors. 2. Biological evaluation of aza-5[H]-phenanthridin-6-ones as potent, aqueous-soluble compounds for the treatment of ischemic injuries. J Med Chem. Jul. 3, 2003;46(14):3138-51.*

Chang, Yuchi C., et al., "Current and Potential Uses of Imiquimod", Southern Medical Journal. 2005, 913-919. vol. 98, No. 9.

Gordon, Keith B., et al., "Synthetic TLR Agonists Reveal Functional Differences between Human TLR7 and TLR8", The Journal of Immunology, 2005, 1259-1268, vol. 174.

Giuliani, Marzia M., et al., "A universal vaccine for serogroup B meningococcus", PNAS, 2006, 10834-10839, vol. 103, No. 29.

Tomai, Mark A., "Immune response modifiers: Imiquimod and future drugs for modulating the immune response", Drug Discovery Today: Therapeutic Strategies, 2006, 343-352, vol. 3, No. 3.

(Continued)

*Primary Examiner* — Paul Zarek
(74) *Attorney, Agent, or Firm* — Daniel E. Raymond; Genomics Institute of the Novartis Research Foundation

(57) ABSTRACT

The invention provides a novel class of compounds, pharmaceutical compositions comprising such compounds and methods of using such compounds to treat or prevent diseases or disorders associated with Toll-Like Receptors, including TLR7 and TLR8. In one aspect, the compounds are useful as adjuvants for enhancing the effectiveness of a vaccine (formula I) wherein: $X^3$ is N; $X^4$ is N Or $CR^3$; $X^5$ is —$CR^4$=$CR^5$.

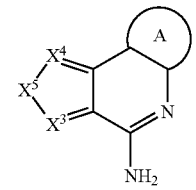

(I)

26 Claims, 5 Drawing Sheets

OTHER PUBLICATIONS

Kanzler, H., et al., "Therapeutic targeting of innate immunity with Toll-like receptor agonists and antagonists", Nature Medicine, 2007, 552-559, vol. 13, No. 5.

Gerster, John F., et al., "Synthesis and Structure-Activity-Relationships of 1 H-Imidazo[4,5-c]quinolines That Induce Interferon Production", J. Med. Chem., 2005, 3481-3491, vol. 48, No. 10.

Ferraris, Dana, et.al.,"Design and Synthesis of Poly ADP-ribose Polymerase-1 Inhibitors. 2. Biological Evaluation of Aza-5 HI-phenanthridin-6-ones as Potent, Aqueous-Soluble Compounds for the Treatment of Ischemic Injuries" J. Med. Chem., 2003, 3138-3151, vol. 46, No. 14.

* cited by examiner

COMPOUNDS AND COMPOSITIONS AS TLR ACTIVITY MODULATORS

CROSS-REFERENCE TO RELATED APPLICATIONS

This application is a 371 U.S. national phase application of international application number PCT/US2009/035563 filed 27 Feb. 2009, which application claims the benefit of priority under 35 U.S.C. §119(e) to U.S. Provisional Patent Application No. 61/033,139, filed Mar. 3, 2008 and U.S. Provisional Patent Application No. 61/148,336, filed Jan. 29, 2009. The disclosure of these applications is incorporated herein by reference in their entirety and for all purposes.

STATEMENT OF GOVERNMENT SUPPORT

This invention was made in part with Government support under DTRA Grant No. HDTRA1-07-9-0001 awarded by the Department of Defense. The Government has certain rights in the invention.

FIELD OF THE INVENTION

The invention relates to modulators of Toll-Like Receptors (TLRs), and methods of using such compounds.

BACKGROUND OF THE INVENTION

Early detection of specific classes of pathogens is accomplished by the innate immune system with the help of pattern recognition receptors (PRRs). The detected pathogens include viruses, bacteria, protozoa and fungi, and each constitutively expresses a set of class-specific, mutation-resistant molecules called pathogen-associated molecular patterns (PAMPs). These molecular markers may be composed of proteins, carbohydrates, lipids, nucleic acids or combinations thereof, and may be located internally or externally. Examples of PAMPs include bacterial carbohydrates (lipopolysaccharide or LPS, mannose), nucleic acids (bacterial or viral DNA or RNA), peptidoglycans and lipotechoic acids (from Gram positive bacteria), N-formylmethionine, lipoproteins and fungal glucans.

Pattern recognition receptors have evolved to take advantage of three PAMP qualities. First, constitutive expression allows the host to detect the pathogen regardless of its life cycle stage. Second, the PAMPs are class specific, which allows the host to distinguish between pathogens and thereby tailor its response. Third, mutation resistance allows the host to recognize the pathogen regardless of its particular strain.

Pattern recognition receptors are involved in more than just recognition of pathogens via their PAMPs. Once bound, pattern recognition receptors tend to cluster, recruit other extracellular and intracellular proteins to the complex, and initiate signaling cascades that ultimately impact transcription. Additionally, pattern recognition receptors are involved in activation of complement, coagulation, phagocytosis, inflammation, and apoptosis functions in response to pathogen detection.

Pattern recognition receptors (PRRs) may be divided into endocytic PRRs or signaling PRRs. The signaling PRRs include the large families of membrane-bound Toll-like receptors (TLRs) and cytoplasmic NOD-like receptors, while the endocytic PRRs promote the attachment, engulfment and destruction of microorganisms by phagocytes without relaying an intracellular signal, are found on all phagocytes and mediate removal of apoptotic cells. In addition, endocytic PRRs recognize carbohydrates and include mannose receptors of macrophages, glucan receptors present on all phagocytes and scavenger receptors that recognize charged ligands.

SUMMARY OF THE INVENTION

Provided herein are compounds and pharmaceutical compositions thereof, which are useful modulators of toll-like receptors.

In one aspect provided herein such compounds, and the pharmaceutically acceptable salts, pharmaceutically acceptable solvates (e.g. hydrates), the N-oxide derivatives, prodrug derivatives, protected derivatives, individual isomers and mixture of isomers thereof, having a structure according to Formula (I) as described herein. Certain embodiments of the invention include compounds of Formula (I-A), methods of using them, and pharmaceutical compositions comprising these compounds:

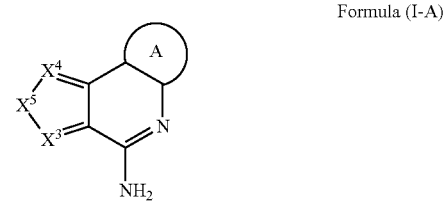

Formula (I-A)

wherein:
$X^3$ is N; $X^4$ is N or $CR^3$, and $X^5$ is $-CR^4=CR^5-$;
$R^1$ and $R^2$ are H; $R^3$ is H;
$R^4$ and $R^5$ are each independently selected from H, halogen, $-C(O)OR^7$, $-C(O)R^7$, $-C(O)N(R^{11}R^{12})$, $-N(R^{11}R^{12})$, $-N(R^9)_2$, $-NHN(R^9)_2$, $-SR^7$, $-(CH_2)_nOR^7$, $-(CH_2)_nR^7$, $-LR^8$, $-LR^{10}$, $-OLR^8$, $-OLR^{10}$, $-C_1-C_6$alkyl, $C_1-C_6$heteroalkyl, $C_1-C_6$haloalkyl, $C_2-C_8$alkene, $C_2-C_8$alkyne, $C_1-C_6$alkoxy, $C_1-C_6$haloalkoxy, aryl, heteroaryl, $C_3-C_8$cycloalkyl, and $C_3-C_8$heterocycloalkyl, wherein the $C_1-C_6$alkyl, $C_1-C_6$heteroalkyl, $C_1-C_6$haloalkyl, $C_2-C_8$alkene, $C_2-C_8$alkyne, $C_1-C_6$alkoxy, $C_1-C_6$haloalkoxy, aryl, heteroaryl, $C_3-C_8$cycloalkyl, and $C_3-C_8$heterocycloalkyl groups of $R^4$ and $R^5$ are each optionally substituted with 1 to 3 substituents independently selected from halogen, $-CN$, $-NO_2$, $-R^7$, $-OR^8$, $-C(O)R^8$, $-OC(O)R^8$, $-C(O)OR^8$, $-N(R^9)_2$, $-P(O)(OR^8)_2$, $-OP(O)(OR^8)_2$, $-P(O)(OR^{10})_2$, $-OP(O)(OR^{10})_2$, $-C(O)N(R^9)_2$, $-S(O)_2R^8$, $-S(O)_2N(R^9)_2$, and $-NR^9S(O)_2R^8$; or $R^3$ and $R^4$, or $R^4$ and $R^5$, when present on adjacent ring atoms, can optionally be linked together to form a 5-6 membered ring, wherein the 5-6 membered ring is optionally substituted with $R^7$;
each L is independently selected from a bond, $-(O(CH_2)_m)_t-$, $C_1-C_6$alkyl, $C_2-C_6$alkenylene and $C_2-C_6$alkynylene, wherein the $C_1-C_6$alkyl, $C_2-C_6$alkenylene and $C_2-C_6$alkynylene of L are each optionally substituted with 1 to 4 substituents independently selected from halogen, $-R^8$, $-OR^8$, $-N(R^9)_2$, $-P(O)(OR^8)_2$, $-OP(O)(OR^8)_2$, $-P(O)(OR^{10})_2$, and $-OP(O)(OR^{10})_2$;
$R^7$ is selected from H, $C_1-C_6$alkyl, aryl, heteroaryl, $C_3-C_8$cycloalkyl, $C_1-C_6$heteroalkyl, $C_1-C_6$haloalkyl, $C_2-C_8$alkene, $C_2-C_8$alkyne, $C_1-C_6$alkoxy, $C_1-C_6$haloalkoxy, and $C_3-C_8$heterocycloalkyl, wherein the $C_1$-$C_6$alkyl, aryl, heteroaryl, $C_3$-$C_8$cycloalkyl, $C_1$-$C_6$heteroalkyl, $C_1$-$C_6$haloalkyl, $C_2$-$C_8$alkene, $C_2$-$C_8$alkyne, $C_1$-$C_6$alkoxy, $C_1$-$C_6$haloalkoxy, and $C_3$-$C_8$heterocycloalkyl groups of $R^7$ are each optionally substituted with 1 to 3 $R^{13}$ groups, and each $R^{13}$ is independently selected from halogen, —CN, -$LR^9$, -$LOR^9$, —$OLR^9$, -$LR^{10}$, -$LOR^{10}$, —$OLR^{10}$, -$LR^8$, -$LOR^8$, —$OLR^8$, -$LSR^8$, -$LSR^{10}$, -$LC(O)R^8$, —$OLC(O)R^8$, -$LC(O)R^8$, -$LC(O)R^{10}$, -$LOC(O)OR^8$, -$LC(O)NR^9R^{11}$, -$LC(O)NR^9R^8$, -$LN(R^9)_2$, -$LNR^9R^8$, -$LNR^9R^{10}$, -$LC(O)N(R^9)_2$, -$LS(O)_2R^8$, -$LS(O)R^8$, -$LC(O)NR^8OH$, -$LNR^9C(O)R^8$, -$LNR^9C(O)OR^8$, -$LS(O)_2N(R^9)_2$, —$OLS(O)_2N(R^9)_2$, -$LNR^9S(O)_2R^8$, -$LC(O)NR^9LN(R^9)_2$, -$LP(O)(OR^8)_2$, -$LOP(O)(OR^8)_2$, -$LP(O)(OR^{10})_2$ and -$OLP(O)(OR^{10})$;

each $R^8$ is independently selected from H, —$CH(R^{10})_2$, $C_1$-$C_8$alkyl, $C_2$-$C_8$alkene, $C_2$-$C_8$alkyne, $C_1$-$C_6$haloalkyl, $C_1$-$C_6$alkoxy, $C_1$-$C_6$heteroalkyl, $C_3$-$C_8$cycloalkyl, $C_2$-$C_8$heterocycloalkyl, $C_1$-$C_6$hydroxyalkyl and $C_1$-$C_6$haloalkoxy, wherein the $C_1$-$C_8$alkyl, $C_2$-$C_8$alkene, $C_2$-$C_8$alkyne, $C_1$-$C_6$heteroalkyl, $C_1$-$C_6$haloalkyl, $C_1$-$C_6$alkoxy, $C_3$-$C_8$cycloalkyl, $C_2$-$C_8$heterocycloalkyl, $C_1$-$C_6$hydroxyalkyl and $C_1$-$C_6$haloalkoxy groups of $R^8$ are each optionally substituted with 1 to 3 substituents independently selected from —CN, $R^{11}$, —$OR^{11}$, —$SR^{11}$, —$C(O)R^{11}$, —$OC(O)R^{11}$, —$C(O)N(R^9)_2$, —$C(O)OR^{11}$, —$NR^9C(O)R^{11}$, —$NR^9R^{10}$, —$NR^{11}R^{12}$, —$N(R^9)_2$, —$OR^9$, —$OR^{10}$, —$C(O)NR^{11}R^{12}$, —$C(O)NR^{11}OH$, —$S(O)_2R^{11}$, —$S(O)R^{11}$, —$S(O)_2NR^{11}R^{12}$, —$NR^{11}S(O)_2R^{11}$, —$P(O)(OR^{11})_2$, and —$OP(O)(OR^{11})_2$;

each $R^9$ is independently selected from H, —$C(O)R^8$, —$C(O)OR^8$, —$C(O)R^{10}$, —$C(O)OR^{10}$, —$S(O)_2R^{10}$, —$C_1$-$C_6$ alkyl, $C_1$-$C_6$ heteroalkyl and $C_3$-$C_6$ cycloalkyl, or each $R^9$ is independently a $C_1$-$C_6$alkyl that together with N they are attached to form a $C_3$-$C_8$heterocycloalkyl, wherein the $C_3$-$C_8$heterocycloalkyl ring optionally contains an additional heteroatom selected from N, O and S, and wherein the $C_1$-$C_6$ alkyl, $C_1$-$C_6$ heteroalkyl, $C_3$-$C_6$ cycloalkyl, or $C_3$-$C_8$heterocycloalkyl groups of $R^9$ are each optionally substituted with 1 to 3 substituents independently selected from —CN, $R^{11}$, —$OR^{11}$, —$SR^{11}$, —$C(O)R^{11}$, —$OC(O)R^{11}$, —$C(O)OR^{11}$, —$NR^{11}R^{12}$, —$C(O)NR^{11}R^{12}$, —$C(O)NR^{11}OH$, —$S(O)_2R^{11}$, —$S(O)R^{11}$, —$S(O)_2NR^{11}R^{12}$, —$NR^{11}S(O)_2R^{11}$, —$P(O)(OR^{11})_2$, and —$OP(O)(OR^{11})_2$;

each $R^{10}$ is independently selected from aryl, $C_3$-$C_8$cycloalkyl, $C_3$-$C_8$heterocycloalkyl or a heteroaryl, wherein the aryl, $C_3$-$C_8$cycloalkyl, $C_3$-$C_8$heterocycloalkyl or heteroaryl groups are optionally substituted with 1 to 3 substituents selected from halogen, —$R^8$, —$OR^8$, —$N(R^9)_2$, —$NR^9C(O)R^8$, —$NR^9CO_2R^8$, —$CO_2R^8$, —$C(O)R^8$ and —$C(O)N(R^9)_2$;

$R^{11}$ and $R^{12}$ are independently selected from H, $C_1$-$C_6$alkyl, $C_1$-$C_6$heteroalkyl, $C_1$-$C_6$haloalkyl, aryl, heteroaryl, $C_3$-$C_8$cycloalkyl, and $C_3$-$C_8$heterocycloalkyl, wherein the $C_1$-$C_6$alkyl, $C_1$-$C_6$heteroalkyl, $C_1$-$C_6$haloalkyl, aryl, heteroaryl, $C_3$-$C_8$cycloalkyl, and $C_3$-$C_8$heterocycloalkyl groups of $R^{11}$ and $R^{12}$ are each optionally substituted with 1 to 3 substituents independently selected from halogen, —CN, $R^8$, —$OR^8$, —$C(O)R^8$, ⁻$OC(O)R^8$, —$C(O)OR^8$, —$N(R^9)_2$, —$NR^8C(O)R^8$, —$NR^8C(O)OR^8$, —$C(O)N(R^9)_2$, $C_3$-$C_8$heterocycloalkyl, —$S(O)_2R^8$, —$S(O)_2N(R^9)_2$, —$NR^9S(O)_2R^8$, $C_1$-$C_6$haloalkyl and $C_1$-$C_6$haloalkoxy, and wherein the aryl and heteroaryl groups of $R^{11}$ and $R^{12}$ are each optionally substituted with 1 to 3 substituents independently selected from halogen, —CN, $R^8$, —$OR^8$, —$C(O)R^8$, —$OC(O)R^8$, —$C(O)OR^8$, —$N(R^9)_2$, —$C(O)N(R^9)_2$, $C_3$-$C_8$heterocycloalkyl, —$S(O)_2R^8$, —$S(O)_2N(R^9)_2$, —$NR^9S(O)_2R^8$, $C_1$-$C_6$haloalkyl and $C_1$-$C_6$haloalkoxy; or $R^{11}$ and $R^{12}$ are each independently $C_1$-$C_6$alkyl and taken together with the N atom to which they are attached form an optionally substituted $C_3$-$C_8$heterocycloalkyl ring optionally containing an additional heteroatom selected from N, O and S;

Ring A is an aryl or a heteroaryl, wherein the aryl and heteroaryl groups of Ring A are optionally substituted with 1 to 3 $R^4$ groups, wherein each $R^4$ is independently selected from —$R^8$, —$R^7$, —$OR^7$, —$OR^8$, —$R^{10}$, —$OR^{10}$, —$SR^8$, —$NO_2$, —CN, —$N(R^9)_2$, —$NR^9C(O)R^8$, —$NR^9C(S)R^8$, —$NR^9C(O)N(R^9)_2$, —$NR^9C(S)N(R^9)_2$, —$NR^9CO_2R^8$, —$NR^9NR^9C(O)R^8$, —$NR^9NR^9C(O)N(R^9)_2$, —$NR^9NR^9CO_2R^8$, —$C(O)C(O)R^8$, —$C(O)CH_2C(O)R^8$, —$CO_2R^8$, —$(CH_2)_nCO_2R^8$, —$C(O)R^8$, —$C(S)R^8$, —$C(O)N(R^9)_2$, —$C(S)N(R^9)_2$, —$OC(O)N(R^9)_2$, —$OC(O)R^8$, —$C(O)N(OR^8)R^8$, —$C(NOR^8)R^8$, —$S(O)_2R^8$, —$S(O)_3R^8$, —$SO_2N(R^9)_2$, —$S(O)R^8$, —$NR^9SO_2N(R^9)_2$, —$NR^9SO_2R^8$, —$P(O)(OR^8)_2$, —$OP(O)(OR^8)_2$, —$P(O)(OR^{10})_2$, —$OP(O)(OR^{10})_2$, —$N(OR^8)R^8$, —$CH=CHCO_2R^8$, —$C(=NH)$—$N(R^9)_2$, and —$(CH_2)_nNHC(O)R^8$; or two adjacent $R^4$ substituents on Ring A form a 5-6 membered ring that contains up to two heteroatoms as ring members; n is, independently at each occurrence, 0, 1, 2, 3, 4, 5, 6, 7 or 8; each m is independently selected from 1, 2, 3, 4, 5 and 6, and t is 1, 2, 3, 4, 5, 6, 7 or 8.

In certain embodiments of such compounds of Formulas (I) or (I-A), one of $R^4$ and $R^5$ is H; and the other of $R^4$ and $R^5$ is selected from halogen, —$C(O)OR^7$, —$C(O)R^7$, —$C(O)N(R^{11}R^{12})$, —$N(R^{11}R^{12})$, —$N(R^9)_2$, —$NHN(R^9)_2$, -$LR^8$, -$LR^{10}$, —$OLR^8$, —$OLR^{10}$, —$SR^7$, —$(CH_2)_nOR^7$, —$(CH_2)_nR^7$, $C_1$-$C_6$alkyl, $C_1$-$C_6$heteroalkyl, $C_1$-$C_6$haloalkyl, $C_2$-$C_8$alkene, $C_2$-$C_8$alkyne, $C_1$-$C_6$alkoxy, $C_1$-$C_6$haloalkoxy, aryl, heteroaryl, $C_3$-$C_8$cycloalkyl, and $C_3$-$C_8$heterocycloalkyl, wherein the $C_1$-$C_6$alkyl, $C_1$-$C_6$heteroalkyl, $C_1$-$C_6$haloalkyl, $C_2$-$C_8$alkene, $C_2$-$C_8$alkyne, $C_1$-$C_6$alkoxy, $C_1$-$C_6$haloalkoxy, aryl, heteroaryl, $C_3$-$C_8$cycloalkyl, and $C_3$-$C_8$heterocycloalkyl groups of $R^4$ and $R^5$ are each optionally substituted with 1 to 3 substituents independently selected from halogen, —CN, —$R^7$, —$OR^8$, —$C(O)R^8$, —$OC(O)R^8$, —$C(O)OR^8$, —$N(R^9)_2$, —$P(O)(OR^8)_2$, —$OP(O)(OR^8)_2$, —$P(O)(OR^{10})_2$, —$OP(O)(OR^{10})_2$, —$C(O)N(R^9)_2$, —$S(O)_2R^8$, —$S(O)_2N(R^9)_2$, and —$NR^9S(O)_2R^8$.

In certain embodiments of such compounds of Formulas (I) or (I-A), Ring A is phenyl, naphthyl, fluorenyl, indenyl, azulenyl or anthracenyl, each of which is optionally substituted with 1 to 3 $R^4$ groups, wherein each $R^4$ is independently selected from —$R^8$, —$R^7$, —$OR^7$, —$OR^8$, —$R^{10}$, —$OR^{10}$, —$SR^8$, —$NO_2$, —CN, —$N(R^9)_2$, —$NR^9C(O)R^8$, —$NR^9C(S)R^8$, —$NR^9C(O)N(R^9)_2$, —$NR^9C(S)N(R^9)_2$, —$NR^9CO_2R^8$, —$NR^9NR^9C(O)R^8$, —$NR^9NR^9C(O)N(R^9)_2$, —$NR^9NR^9CO_2R^8$, —$C(O)C(O)R^8$, —$C(O)CH_2C(O)R^8$, —$CO_2R^8$, —$(CH_2)_nCO_2R^8$, —$C(O)R^8$, —$C(S)R^8$, —$C(O)N(R^9)_2$, —$C(S)N(R^9)_2$, —$OC(O)N(R^9)_2$, —$OC(O)R^8$, —$C(O)N(OR^8)R^8$, —$C(NOR^8)R^8$, —$S(O)_2R^8$, —$S(O)_3R^8$, —$SO_2N(R^9)_2$, —$S(O)R^8$, —$NR^9SO_2N(R^9)_2$, —$NR^9SO_2R^8$, —$P(O)(OR^8)_2$, —$OP(O)(OR^8)_2$, —$P(O)(OR^{10})_2$, —$OP(O)(OR^{10})_2$, —$N(OR^8)R^8$, —$CH=CHCO_2R^8$, —$C(=NH)$—$N(R^9)_2$, and —(CH$_2$)$_n$NHC(O)R$^8$. In certain embodiments of such compounds of Formulas (I) or (I-A), Ring A is phenyl or naphthyl.

In certain embodiments of the such compounds of Formulas (I) or (I-A), Ring A is benzofuranyl, benzofurazanyl, benzoxazolyl, benzopyranyl, benzthiazolyl, benzothienyl, benzazepinyl, benzimidazolyl, benzothiopyranyl, benzo[1,3]dioxole, benzo[b]furyl, benzo[b]thienyl, cinnolinyl, furazanyl, furyl, furopyridinyl, imidazolyl, indolyl, indolizinyl, indolin-2-one, indazolyl, isoindolyl, isoquinolinyl, isoxazolyl, isothiazolyl, 1,8-naphthyridinyl, oxazolyl, oxaindolyl, oxadiazolyl, pyrazolyl, pyrrolyl, phthalazinyl, pteridinyl, purinyl, pyridyl, pyridazinyl, pyrazinyl, pyrimidinyl, quinoxalinyl, quinolinyl, quinazolinyl, 4H-quinolizinyl, thiazolyl, thiadiazolyl, thienyl, triazinyl,triazolyl or tetrazolyl, each of which is optionally substituted with 1 to 3 R$^A$ groups, wherein each R$^A$ is independently selected from —R$^8$, —R$^7$, —OR$^7$, —OR$^8$, —R$^{10}$, —OR$^{10}$, —SR$^8$, —NO$_2$, —CN, —N(R$^9$)$_2$, —NR$^9$C(O)R$^8$, —NR$^9$C(S)R$^8$, —NR$^9$C(O)N(R$^9$)$_2$, —NR$^9$C(S)N(R$^9$)$_2$, —NR$^9$CO$_2$R$^8$, —NR$^9$NR$^9$C(O)R$^8$, —NR$^9$NR$^9$C(O)N(R$^9$)$_2$, —NR$^9$NR$^9$CO$_2$R$^8$, —C(O)C(O)R$^8$, —C(O)CH$_2$C(O)R$^8$, —CO$_2$R$^8$, —(CH$_2$)$_n$CO$_2$R$^8$, —C(O)R$^8$, —C(S)R$^8$, —C(O)N(R$^9$)$_2$, —C(S)N(R$^9$)$_2$, —OC(O)N(R$^9$)$_2$, —OC(O)R$^8$, —C(O)N(OR$^8$)R$^8$, —C(NOR$^8$)R$^8$, —S(O)$_2$R$^8$, —S(O)$_3$R$^8$, —SO$_2$N(R$^9$)$_2$, —S(O)R$^8$, —NR$^9$SO$_2$N(R$^9$)$_2$, —NR$^9$SO$_2$R$^8$, —P(O)(OR$^8$)$_2$, —OP(O)(OR$^8$)$_2$, —P(O)(OR$^{10}$)$_2$, —OP(O)(OR$^{10}$)$_2$, —N(OR$^8$)R$^8$, —CH=CHCO$_2$R$^8$, —C(=NH)—N(R$^9$)$_2$, and —(CH$_2$)$_n$NHC(O)R$^8$. In certain embodiments of such compounds of Formulas (I) or (I-A), Ring A is pyridyl, benzo[1,3]dioxole, thienyl, benzothienyl, benzofuranyl, or indolyl.

In certain embodiments of compounds of Formulas (I) and Formula (I-A), the compounds have a structure of Formula (X-A):

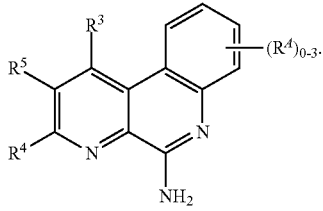

Formula (X-A)

In certain embodiments of compounds of Formulas (I) or Formula (I-A), the compounds have a structure of Formula (XI):

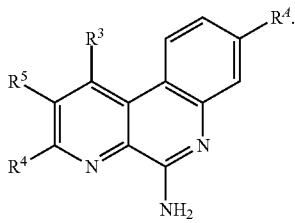

Formula (XI)

In certain embodiments of compounds of Formulas (I) or Formula (I-A), the compound have a structure of Formula (XII) or Formula (XIII):

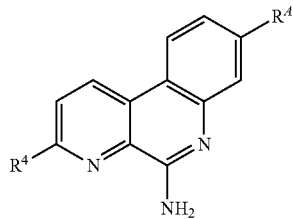

Formula (XII)

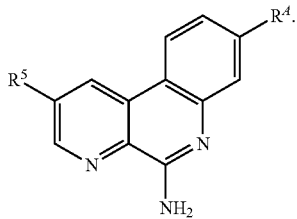

Formula (XIII)

In certain embodiments of such compounds of Formulas (I) or (I-A), Formulas (X-A) and (XI) to (XIII), R$^4$ and R$^5$ are independently selected from H, halogen, —C(O)OR$^7$, —C(O)R$^7$, —C(O)N(R$^{11}$R$^{12}$), —N(R$^{11}$R$^{12}$), —N(R$^9$)$_2$, —NHN(R$^9$)$_2$, -LR$^8$, -LR$^{10}$, —OLR$^8$, —OLR$^{10}$, —SR$^7$, —(CH$_2$)$_n$R$^7$, —(CH$_2$)$_n$OR$^7$, —C$_1$-C$_6$alkyl, C$_1$-C$_6$haloalkyl, C$_2$-C$_8$alkene, C$_2$-C$_8$alkyne and C$_1$-C$_6$alkoxy, wherein the C$_1$-C$_6$alkyl, C$_1$-C$_6$haloalkyl, C$_2$-C$_8$alkene, C$_2$-C$_8$alkyne and C$_1$-C$_6$alkoxy groups of R$^4$ and R$^5$ are each optionally substituted with 1 to 3 substituents independently selected from halogen, —CN, —R$^7$, —OR$^8$, —C(O)R$^8$, —OC(O)R$^8$, —C(O)OR$^8$, —N(R$^9$)$_2$, —P(O)(OR$^8$)$_2$, —OP(O)(OR$^8$)$_2$, —P(O)(OR$^{10}$)$_2$, —OP(O)(OR$^{10}$)$_2$, —C(O)N(R$^9$)$_2$, —S(O)$_2$R$^8$, —S(O)$_2$N(R$^9$)$_2$, and —NHS(O)$_2$R$^8$. In other embodiments of such compounds of Formulas (I) or (I-A), Formulas (X-A) and (XI) to (XIII), R$^4$ and R$^5$ are independently selected from H, halogen, —C(O)OR$^7$, —C(O)R$^7$, —C(O)N(R$^{11}$R$^{12}$), —N(R$^{11}$R$^{12}$), —N(R$^9$)$_2$, —NHN(R$^9$)$_2$, -LR$^8$, -LR$^{10}$, —OLR$^8$, —OLR$^{10}$, —SR$^7$, —(CH$_2$)$_n$OR$^7$, —(CH$_2$)$_n$R$^7$, —C$_1$-C$_6$alkyl, C$_1$-C$_6$haloalkyl, C$_2$-C$_8$alkene, C$_2$-C$_8$alkyne and C$_1$-C$_6$alkoxy, wherein the —C$_1$-C$_6$alkyl, C$_1$-C$_6$haloalkyl, C$_2$-C$_8$alkene, C$_2$-C$_8$alkyne and C$_1$-C$_6$alkoxy groups are each optionally substituted with R$^7$.

In certain embodiments of compounds of Formulas (I) and Formula (I-A), the compounds have a structure of Formula (XIV):

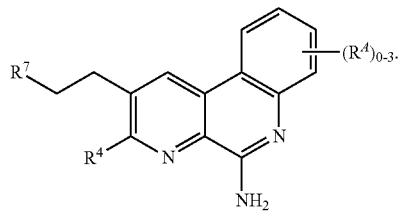

Formula (XIV)

In certain embodiments of such compounds of Formulas (XIV) R$^4$ is selected from H, halogen, —C(O)OR$^7$, —C(O)R$^7$, —C(O)N(R$^{11}$R$^{12}$), —N(R$^{11}$R$^{12}$), —SR$^7$, —(CH$_2$)$_n$R$^7$, —(CH$_2$)$_n$OR$^7$, —C$_1$-C$_6$alkyl, C$_1$-C$_6$haloalkyl, C$_2$-C$_8$alkene, C$_2$-C$_8$alkyne and C$_1$-C$_6$alkoxy, wherein the C$_1$-C$_6$alkyl, C$_1$-C$_6$haloalkyl, C$_2$-C$_8$alkene, C$_2$-C$_8$alkyne and C$_1$-C$_6$alkoxy groups of R$^4$ and R$^5$ are each optionally substituted with 1 to 3 substituents independently selected from halogen, —CN, —R⁷, —OR⁸, —C(O)R⁸, —OC(O)R⁸, —C(O)OR⁸, —N(R⁹)₂, —P(O)(OR⁸)₂, —OP(O)(OR⁸)₂, —P(O)(OR¹⁰)₂, —OP(O)(OR¹⁰)₂, —C(O)N(R⁹)₂, —S(O)₂R⁸, —S(O)₂N(R⁹)₂, and —NHS(O)₂R⁸. In other embodiments of such compounds of Formulas (XIV), R⁴ is selected from H, halogen, —C(O)OR⁷, —C(O)R⁷, —C(O)N(R¹¹R¹²), —N(R¹¹R¹²), —SR⁷, —(CH₂)ₙOR⁷, —(CH₂)ₙR⁷, —C₁-C₆alkyl, C₁-C₆haloalkyl, C₂-C₈alkene, C₂-C₈alkyne and C₁-C₆alkoxy, wherein the —C₁-C₆alkyl, C₁-C₆haloalkyl, C₂-C₈alkene, C₂-C₈alkyne and C₁-C₆alkoxy groups are each optionally substituted with R⁷.

In certain embodiments of such compounds of Formulas (I) or (I-A), Formulas (X-A) and (XI) to (XIV), R⁷ is selected from H, C₁-C₆alkyl, aryl, heteroaryl, C₃-C₈cycloalkyl, and C₃-C₈heterocycloalkyl, wherein the C₁-C₆alkyl, aryl, heteroaryl, C₃-C₈cycloalkyl and C₃-C₈heterocycloalkyl groups of R⁷ are each optionally substituted with 1 to 3 R¹³ groups and each R¹³ is independently selected from halogen, —CN, -LR⁹, -LOR⁹, —OLR⁹, -LR¹⁰, -LOR¹⁰, —OLR¹⁰, -LR⁸, -LOR⁸, —OLR⁸, -LSR⁸, -LSR¹⁰, -LC(O)R⁸, —OLC(O)R⁸, -LC(O)OR⁸, -LC(O)R¹⁰, -LOC(O)OR⁸, -LC (O)NR⁹R¹¹, -LC(O)NR⁹R⁸, -LN(R⁹)₂, -LNR⁹R⁸, -LNR⁹R¹⁰, -LC(O)N (R⁹)₂, -LS(O)₂R⁸, -LS (O)R⁸, -LC(O)NR⁸OH, -LNR⁹C(O)R⁸, -LNR⁹C(O)OR⁸, -LS(O)₂N(R⁹)₂, —OLS(O)₂N(R⁹)₂, -LNR⁹S(O)₂R⁸, -LC(O)NR⁹LN(R⁹)₂, -LP(O)(OR⁸)₂, -LOP(O)(OR⁸)₂, -LP(O)(OR¹⁰)₂ and —OLP(O)(OR¹⁰)₂.

In certain embodiments of such compounds of Formulas (I) or (I-A), Formulas (X-A) and (XI) to (XIV), R⁷ is selected from H, C₁-C₆alkyl, aryl, heteroaryl, C₃-C₈cycloalkyl, and C₃-C₈heterocycloalkyl, wherein the C₁-C₆alkyl, aryl, heteroaryl, C₃-C₈cycloalkyl, and C₃-C₈heterocycloalkyl groups are each optionally substituted with 1-3 R¹³ groups and each R¹³ is independently selected from halogen, C₁-C₆haloalkyl, LR⁸, LR⁹, -LOR⁸ and —OLR⁸.

In certain embodiments of compounds of Formulas (I) or (I-A), Formulas (X-A) and (XI) to (XIV), have a structure of Formula (XV) or Formula (XVI):

Formula (XV)

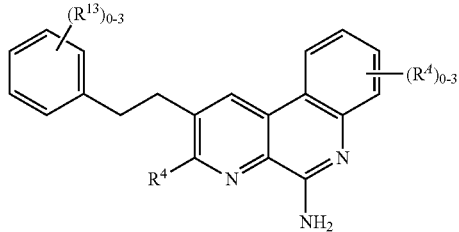

Formula (XVI)

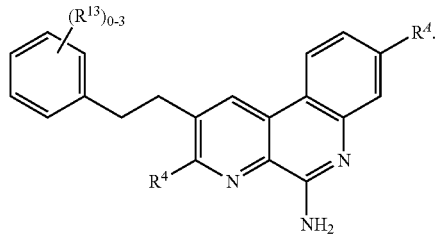

In certain embodiments of such compounds of Formulas (I) or (I-A), Formulas (X-A) and (XI) to (XVI), R¹³ is selected from -LR⁹, -LOR⁹, -OLR⁹, -LR¹⁰, -LOR¹⁰, —OLR¹⁰, -LR⁸, -LOR⁸, —OLR⁸, -LSR⁸, -LSR¹⁰, -LC(O)R⁸, —OLC(O)R⁸, -LC(O)OR⁸, -LC(O)R¹⁰, -LOC(O)OR⁸, -LC (O)NR⁹R¹¹, -LC(O)NR⁹R⁸, -LN(R⁹)₂, -LNR⁹R⁸, -LNR⁹R¹⁰, -LC(O)N(R⁹)₂, -LS(O)₂R⁸, -LS (O)R⁸, -LC(O)NR⁸OH, -LNR⁹C(O)R⁸, -LNR⁹C(O)OR⁸, -LS(O)₂N(R⁹)₂, —OLS(O)₂N(R⁹)₂, -LNR⁹S(O)₂R⁸, -LC(O)NR⁹LN(R⁹)₂, -LP(O)(OR⁸)₂, -LOP(O)(OR⁸)₂, -LP(O)(OR¹⁰)₂ and —OLP(O)(OR¹⁰)₂.

In certain embodiments of such compounds of Formulas (I) or (I-A), Formulas (X-A) and (XI) to (XVI), R¹⁰ is an aryl or a heteroaryl, wherein the aryl and heteroaryl groups are optionally substituted with 1 to 3 substituents selected from halogen, —R⁸, —OR⁸, and —N(R⁹)₂.

In certain embodiments of such compounds of Formulas (I) or (I-A) Formulas (X-A) and (XI) to (XVI), R¹⁰ is phenyl optionally substituted with 1 to 3 substituents selected from halogen, —R⁸, —OR⁸, and —N(R⁹)₂.

In certain embodiments of such compounds of Formulas (I) or (I-A), Formulas (X-A) and (XI) to (XVI), R⁸ is selected from H, C₁-C₆alkyl and C₁-C₆haloalkyl. In certain embodiments of the compounds of Formula XIII, XIV, XV or XVI, the compound is selected from: 2-(4-(2-(5-amino-8-methylbenzo[f][1,7]naphthyridin-2-yl)ethyl)-3-methylphenyl)propan-2-ol; 2-(4-methoxy-2-methylphenethyl)-8-methylbenzo[f][1,7]naphthyridin-5-amine; 2-(2,4-dimethylphenethyl)benzo[f][1,7]naphthyridin-5-amine; ethyl 4-(2-(5-amino-8-methylbenzo[f][1,7]naphthyridin-2-yl)ethyl)-3-methylbenzoate; 2-(4-(dimethylamino)phenethyl)-8-methylbenzo[f][1,7]naphthyridin-5-amine; and 2-(4-methoxyphenethyl)-8-methylbenzo[f][1,7]naphthyridin-5-amine. Each of these compounds individually comprises a preferred embodiment of the compounds, compositions, and methods described herein.

In certain embodiments of the compounds, compositions and methods described herein, the compound of Formulas (I) is selected from 2-methylbenzo[f][1,7]naphthyridin-5-amine; 2-propylbenzo[f][1,7]naphthyridin-5-amine; 2-ethylbenzo[f][1,7]naphthyridin-5-amine; 2-(3-(trifluoromethyl)phenethyl)benzo[f][1,7]naphthyridin-5-amine; 2-(2,4-difluorophenethyl)benzo[f][1,7]naphthyridin-5-amine; 2-(3-methoxyphenethyl)benzo[f][1,7]naphthyridin-5-amine; 8-methylbenzo[f][1,7]naphthyridin-5-amine; 8-methyl-2-phenethylbenzo[f][1,7]naphthyridin-5-amine; methyl 5-aminobenzo[f][1,7]naphthyridine-3-carboxylate; 5-amino-N-methylbenzo[f][1,7]naphthyridine-3-carboxamide; (5-aminobenzo[f][1,7]naphthyridin-3-yl)methanol; 8-phenylbenzo[f][1,7]naphthyridin-5-amine; 3-(ethoxymethyl)benzo[f][1,7]naphthyridin-5-amine; benzo[f][1,7]naphthyridine-3,5-diamine; benzo[f][1,7]naphthyridin-5-amine; methyl 5-aminobenzo[f][1,7]naphthyridine-8-carboxylate; 5-aminobenzo[f][1,7]naphthyridine-8-carboxylic acid; ethyl 5-aminobenzo[f][1,7]naphthyridine-8-carboxylate; (5-aminobenzo[f][1,7]naphthyridin-8-yl)methanol; 5-aminobenzo[f][1,7]naphthyridine-3-carboxylic acid; 5-aminobenzo[f][1,7]naphthyridine-3-carbaldehyde; 2-(2-methylphenethyl)benzo[f][1,7]naphthyridin-5-amine; 2-(3-methylphenethyl)benzo[f][1,7]naphthyridin-5-amine; 2-(4-methylphenethyl)benzo[f][1,7]naphthyridin-5-amine; 8-chlorobenzo[f][1,7]naphthyridin-5-amine; ethyl 5-aminobenzo[f][1,7]naphthyridine-9-carboxylate; 8-methoxybenzo[f][1,7]naphthyridin-5-amine; 8-(methylsulfonyl)benzo[f][1,7]naphthyridin-5-amine; 8-(trifluoromethyl)benzo[f][1,7]naphthyridin-5-amine; 8-fluorobenzo[f][1,7]naphthyridin-5-amine; 3-methoxybenzo[f][1,7]naphthyridin-5-amine; 3-butoxybenzo[f][1,7]naphthyridin-5-amine; 3-(benzyloxy)benzo[f][1,7]naphthyridin-5-amine; 3-methylbenzo[f][1,7]naphthyridin-5-amine; 3-chlorobenzo[f][1,7]naphthyridin-5-amine; N3,N3-dimethylbenzo[f][1,7]naphthyridine-3,5-diamine; N3-butylbenzo[f][1,7]naphthyridine-3,5-diamine; 3-vinylbenzo[f][1,7]naphthyridin-5-amine; 3-ethylbenzo[f]

[1,7]naphthyridin-5-amine; 3-fluorobenzo[f][1,7]naphthyridin-5-amine; 2-phenethylbenzo[f][1,7]naphthyridin-5-amine; 8-methyl-2-(2-(naphthalen-1-yl)ethyl)benzo[f][1,7]naphthyridin-5-amine; 8-methyl-2-(2-(naphthalen-2-yl)ethyl)benzo[f][1,7]naphthyridin-5-amine; 4-(2-(5-amino-8-methylbenzo[f][1,7]naphthyridin-2-yl)ethyl)benzoic acid; 3-(2-(5-amino-8-methylbenzo[f][1,7]naphthyridin-2-yl)ethyl)benzoic acid; 2-(3-chlorophenethyl)-8-methylbenzo[f][1,7]naphthyridin-5-amine; 2-(2-chlorophenethyl)-8-methylbenzo[f][1,7]naphthyridin-5-amine; (3-(2-(5-amino-8-methylbenzo[f][1,7]naphthyridin-2-yl)ethyl)phenyl)methanol; 2-(4-chlorophenethyl)-8-methylbenzo[f][1,7]naphthyridin-5-amine; 2-(4-butylphenethyl)benzo[f][1,7]naphthyridin-5-amine; 2-(4-butylphenethyl)-8-methylbenzo[f][1,7]naphthyridin-5-amine; 2-(4-propylphenethyl)benzo[f][1,7]naphthyridin-5-amine; 2-(4-(trifluoromethyl)phenethyl)benzo[f][1,7]naphthyridin-5-amine; 2-(2,5-dimethylphenethyl)-8-methylbenzo[f][1,7]naphthyridin-5-amine; 8-methyl-2-(4-propylphenethyl)benzo[f][1,7]naphthyridin-5-amine; 8-methyl-2-(2,4,5-trimethylphenethyl)benzo[f][1,7]naphthyridin-5-amine; 2-(2,5-dimethylphenethyl)benzo[f][1,7]naphthyridin-5-amine; 2-(4-isopropylphenethyl)-8-methylbenzo[f][1,7]naphthyridin-5-amine; 2-(4-heptylphenethyl)-8-methylbenzo[f][1,7]naphthyridin-5-amine; 2-(4-isobutoxyphenethyl)-8-methylbenzo[f][1,7]naphthyridin-5-amine; 2-(4-((2-methoxyethoxy)methoxy)phenethyl)-8-methylbenzo[f][1,7]naphthyridin-5-amine; 8-methyl-2-(4-(2-phenoxyethoxy)phenethyl)benzo[f][1,7]naphthyridin-5-amine; 2-(4-(2-(tert-butyldimethylsilyloxy)ethoxy)phenethyl)-8-methylbenzo[f][1,7]naphthyridin-5-amine; 8-methyl-2-(4-(4-phenylbutoxy)phenethyl)benzo[f][1,7]naphthyridin-5-amine; 2-(4-(allyloxy)phenethyl)-8-methylbenzo[f][1,7]naphthyridin-5-amine; 8-methyl-2-(4-(3-phenylpropoxy)phenethyl)benzo[f][1,7]naphthyridin-5-amine; 2-(4-(heptan-4-yloxy)phenethyl)-8-methylbenzo[f][1,7]naphthyridin-5-amine; 8-methyl-2-(4-(4-methylpent-3-enyloxy)phenethyl)benzo[f][1,7]naphthyridin-5-amine; 2-(4-(2-cyclohexylethoxy)phenethyl)-8-methylbenzo[f][1,7]naphthyridin-5-amine; 2-(4-isopropoxyphenethyl)-8-methylbenzo[f][1,7]naphthyridin-5-amine; 2-(4-(3,3-dimethylbutoxy)phenethyl)-8-methylbenzo[f][1,7]naphthyridin-5-amine; 2-(4-(2-(tert-butyldimethylsilyloxy)ethoxy)-2-methylphenethyl)-8-methylbenzo[f][1,7]naphthyridin-5-amine; 8-(2-cyclopropylethyl)-2-(4-(dimethylamino)phenethyl)benzo[f][1,7]naphthyridin-5-amine; 8-(2-cyclopropylethyl)-2-(2,4-dimethylphenethyl)benzo[f][1,7]naphthyridin-5-amine; N-(4-(2-(5-amino-8-methylbenzo[f][1,7]naphthyridin-2-yl)ethyl)phenyl)acetamide; N-(4-(2-(5-aminobenzo[f][1,7]naphthyridin-2-yl)ethyl)phenyl)acetamide; N-(4-(2-(5-amino-8-methylbenzo[f][1,7]naphthyridin-2-yl)ethyl)phenyl)-4-methylbenzenesulfonamide; 3-methyl-9-p-tolyl-9,10-dihydrobenzo[f]furo[2,3-b][1,7]naphthyridin-6-amine; 4-(2-(5-amino-8-methylbenzo[f][1,7]naphthyridin-2-yl)ethyl)-3-methylbenzonitrile; 4-(2-(5-amino-8-methylbenzo[f][1,7]naphthyridin-2-yl)ethyl)-N-(2-aminoethyl)-3-methylbenzamide; 8-methyl-2-(2-methyl-4-(1H-tetrazol-5-yl)phenethyl)benzo[f][1,7]naphthyridin-5-amine; methyl 2-(4-(2-(5-amino-8-methylbenzo[f][1,7]naphthyridin-2-yl)ethyl)-3-methylbenzamido)-4-methylpentanoate; methyl 2-(4-(2-(5-amino-8-methylbenzo[f][1,7]naphthyridin-2-yl)ethyl)-3-methylbenzamido)acetate; 2-(4-(2-(5-amino-8-methylbenzo[f][1,7]naphthyridin-2-yl)ethyl)-3-methylbenzamido)-4-methylpentanoic acid; 2-(4-(2-(5-amino-8-methylbenzo[f][1,7]naphthyridin-2-yl)ethyl)-3-methylbenzamido)acetic acid; 6-(5-amino-8-methylbenzo[f][1,7]naphthyridin-2-yl)hexan-1-ol; 7-(5-amino-8-methylbenzo[f][1,7]naphthyridin-2-yl)heptanoic acid; 11-(5-amino-8-methylbenzo[f][1,7]naphthyridin-2-yl)undecan-1-ol; ethyl 2-(4-(2-(5-amino-8-methylbenzo[f][1,7]naphthyridin-2-yl)ethyl)-3-methylphenoxy)acetate; 2-(4-(2-(5-amino-8-methylbenzo[f][1,7]naphthyridin-2-yl)ethyl)-3-methylphenoxy)acetic acid; 3-(4-(2-(5-amino-8-methylbenzo[f][1,7]naphthyridin-2-yl)ethyl)-3-methylphenoxy)propanoic acid; 6-(4-(2-(5-amino-8-methylbenzo[f][1,7]naphthyridin-2-yl)ethyl)-3-methylphenoxy)hexanoic acid; 8-methyl-2-(2-methyl-4-(methylthio)phenethyl)benzo[f][1,7]naphthyridin-5-amine; 8-methyl-2-(4-(methylsulfonyl)phenethyl)benzo[f][1,7]naphthyridin-5-amine; 2-(4-(hexyloxy)phenethyl)-8-methylbenzo[f][1,7]naphthyridin-5-amine; 8-methyl-2-(4-phenethoxyphenethyl)benzo[f][1,7]naphthyridin-5-amine; 8-methyl-2-(4-(pentyloxy)phenethyl)benzo[f][1,7]naphthyridin-5-amine; 8-methyl-2-(4-(4-methylpentyloxy)phenethyl)benzo[f][1,7]naphthyridin-5-amine; 2-(2-fluorophenethyl)benzo[f][1,7]naphthyridin-5-amine; 2-(3-fluorophenethyl)benzo[f][1,7]naphthyridin-5-amine; 2-(4-fluorophenethyl)benzo[f][1,7]naphthyridin-5-amine; 2-(2-(thiophen-3-yl)ethyl)benzo[f][1,7]naphthyridin-5-amine; (5-aminobenzo[f][1,7]naphthyridin-2-yl)methanol; 2-(3,4-dimethylphenethyl)benzo[f][1,7]naphthyridin-5-amine; 2-(3,4-dimethylphenethyl)-8-methylbenzo[f][1,7]naphthyridin-5-amine; 2-(3,5-dimethylphenethyl)-8-methylbenzo[f][1,7]naphthyridin-5-amine; 2-(2-(benzofuran-5-yl)ethyl)-8-methylbenzo[f][1,7]naphthyridin-5-amine; 8-methyl-2-(2-nitroethyl)benzo[f][1,7]naphthyridin-5-amine; 2-(aminomethyl)-8-methylbenzo[f][1,7]naphthyridin-5-amine; N2,8-dimethylbenzo[f][1,7]naphthyridine-2,5-diamine; 2-(5-amino-8-methylbenzo[f][1,7]naphthyridin-2-yl)-1-phenylethanol; 2-(5-amino-8-methylbenzo[f][1,7]naphthyridin-2-yl)-1-(4-methoxyphenyl)ethanol; 2-(biphenyl-2-yl)-8-methylbenzo[f][1,7]naphthyridin-5-amine; 2-(2-(2,6-dimethylpyridin-3-yl)ethyl)-8-methylbenzo[f][1,7]naphthyridin-5-amine; 2-(2-(5-methoxypyridin-2-yl)ethyl)-8-methylbenzo[f][1,7]naphthyridin-5-amine; 3-(4-(2-(5-amino-8-methylbenzo[f][1,7]naphthyridin-2-yl)ethyl)phenyl)propanoic acid; 5-(2-(5-amino-8-methylbenzo[f][1,7]naphthyridin-2-yl)ethyl)-4-methylpyridin-2(1H)-one; 6-(2-(5-amino-8-methylbenzo[f][1,7]naphthyridin-2-yl)ethyl)pyridin-3-ol; 8-methyl-2-(4-(trifluoromethoxy)phenethyl)benzo[f][1,7]naphthyridin-5-amine; 2-(2-(2,3-dihydro-1H-inden-5-yl)ethyl)-8-methylbenzo[f][1,7]naphthyridin-5-amine; 2-(2-(2,3-dihydro-1H-inden-5-yl)ethyl)benzo[f][1,7]naphthyridin-5-amine; (E)-3-(4-(2-(5-amino-8-methylbenzo[f][1,7]naphthyridin-2-yl)ethyl)-3-methylphenyl)acrylic acid; (E)-ethyl 3-(5-amino-2-(4-methoxy-2-methylphenethyl)benzo[f][1,7]naphthyridin-8-yl)acrylate; 8-(prop-1-en-2-yl)benzo[f][1,7]naphthyridin-5-amine; 5-aminobenzo[f][1,7]naphthyridine-8-carbonitrile; (E)-8-(3-methylbut-1-enyl)benzo[f][1,7]naphthyridin-5-amine; 8-(2-methylprop-1-enyl)benzo[f][1,7]naphthyridin-5-amine; (E)-8-(pent-1-enyl)benzo[f][1,7]naphthyridin-5-amine; (E)-8-styrylbenzo[f][1,7]naphthyridin-5-amine; (E)-8-(2-cyclopropylvinyl)-2-phenethylbenzo[f][1,7]naphthyridin-5-amine; 8-pentylbenzo[f][1,7]naphthyridin-5-amine; (E)-8-(2-cyclopropylvinyl)benzo[f][1,7]naphthyridin-5-amine; 8-(2-cyclopropylethyl)-2-phenethylbenzo[f][1,7]naphthyridin-5-amine; 9-phenethylpyrido[1,2-c][1,7]naphthyridin-6-amine; methyl 5-amino-2-(4-methoxyphenethyl)benzo[f][1,7]naphthyridine-8-carboxylate; 8-nitrobenzo[f][1,7]naphthyridin-5-amine; 3-chloro-8-methylbenzo[f][1,7]naphthyridin-5-amine; methyl 5-amino-3-chlorobenzo[f][1,7]

naphthyridine-8-carboxylate; methyl 5-amino-3-fluorobenzo[f][1,7]naphthyridine-8-carboxylate; 3-chloro-8-nitrobenzo[f][1,7]naphthyridin-5-amine; (5-amino-3-chlorobenzo[f][1,7]naphthyridin-8-yl)methanol; (5-amino-2-phenethylbenzo[f][1,7]naphthyridin-8-yl)methanol; 4-(2-(5-amino-8-fluorobenzo[f][1,7]naphthyridin-2-yl)ethyl)benzaldehyde; 2-(4-(2-(5-amino-8-fluorobenzo[f][1,7]naphthyridin-2-yl)ethyl)benzylamino)ethanol; 3-(4-(2-(5-amino-8-fluorobenzo[f][1,7]naphthyridin-2-yl)ethyl)benzylamino)propan-1-ol; 8-fluoro-2-(4-((2-methoxyethylamino)methyl)phenethyl)benzo[f][1,7]naphthyridin-5-amine; (5-amino-2-(4-methoxy-2-methylphenethyl)benzo[f][1,7]naphthyridin-8-yl)methanol; 3-(2-(5-aminobenzo[f][1,7]naphthyridin-2-yl)ethyl)phenol; 2-(2-methoxyphenethyl)benzo[f][1,7]naphthyridin-5-amine; 2-(4-ethylphenethyl)benzo[f][1,7]naphthyridin-5-amine; 2-(4-ethylphenethyl)-8-methylbenzo[f][1,7]naphthyridin-5-amine; 2-(4-(dimethylamino)phenethyl)benzo[f][1,7]naphthyridin-5-amine; 2-(4-(piperidin-1-yl)phenethyl)benzo[f][1,7]naphthyridin-5-amine; 2-(4-tert-butylphenethyl)-8-methylbenzo[f][1,7]naphthyridin-5-amine; 8-methyl-2-(4-(piperidin-1-yl)phenethyl)benzo[f][1,7]naphthyridin-5-amine; 2-(4-methoxyphenethyl)-8-methylbenzo[f][1,7]naphthyridin-5-amine; 2-(3,5-dimethoxyphenethyl)-8-methylbenzo[f][1,7]naphthyridin-5-amine; 8-methyl-2-(2-(trifluoromethyl)phenethyl)benzo[f][1,7]naphthyridin-5-amine; 4-(2-(5-amino-8-methylbenzo[f][1,7]naphthyridin-2-yl)ethyl)-N-hydroxybenzimidamide; 4-(2-(5-amino-8-methylbenzo[f][1,7]naphthyridin-2-yl)ethyl)benzonitrile; 8-methyl-2-(4-(1-morpholinoethyl)phenethyl)benzo[f][1,7]naphthyridin-5-amine; 2-(4-aminophenethyl)-8-methylbenzo[f][1,7]naphthyridin-5-amine; 1-(4-(2-(5-amino-8-methylbenzo[f][1,7]naphthyridin-2-yl)ethyl)phenyl)guanidine; 8-methyl-2-(4-(1-(phenethylamino)ethyl)phenethyl)benzo[f][1,7]naphthyridin-5-amine; 2-(4-(2-(5-amino-8-methylbenzo[f][1,7]naphthyridin-2-yl)ethyl)phenyl)acetonitrile; 2-(4-(piperidin-1-ylmethyl)phenethyl)benzo[f][1,7]naphthyridin-5-amine; 1-(4-(2-(5-aminobenzo[f][1,7]naphthyridin-2-yl)ethyl)benzyl)piperidin-4-ol; 2-(4-(aminomethyl)phenethyl)benzo[f][1,7]naphthyridin-5-amine; 2-(4-((ethylamino)methyl)phenethyl)benzo[f][1,7]naphthyridin-5-amine; 2-(4-(2-aminopropan-2-yl)phenethyl)benzo[f][1,7]naphthyridin-5-amine; 1-(1-(4-(2-(5-aminobenzo[f][1,7]naphthyridin-2-yl)ethyl)phenyl)ethyl)pyrrolidine-3-carboxylic acid; 8-methyl-2-(4-(1-(phenylamino)ethyl)phenethyl)benzo[f][1,7]naphthyridin-5-amine; 2-ethyl-8-methylbenzo[f][1,7]naphthyridin-5-amine; (5-amino-8-methylbenzo[f][1,7]naphthyridin-2-yl)methanol; 8-methyl-2-propylbenzo[f][1,7]naphthyridin-5-amine; 2-(2-(1H-indol-5-yl)ethyl)-8-methylbenzo[f][1,7]naphthyridin-5-amine; 2-(4-ethoxyphenethyl)-8-methylbenzo[f][1,7]naphthyridin-5-amine; 8-methyl-2-(4-phenoxyphenethyl)benzo[f][1,7]naphthyridin-5-amine; 2-(2,4-dimethylphenethyl)benzo[f][1,7]naphthyridin-5-amine; 2-(2,4-dimethylphenethyl)-8-methylbenzo[f][1,7]naphthyridin-5-amine; 2-(4-methoxy-2-methylphenethyl)-8-methylbenzo[f][1,7]naphthyridin-5-amine; 4-(2-(5-amino-8-methylbenzo[f][1,7]naphthyridin-2-yl)ethyl)-3-methylphenol; 2-(2-(2,3-dihydrobenzofuran-5-yl)ethyl)-8-methylbenzo[f][1,7]naphthyridin-5-amine; 2-(5-amino-8-methylbenzo[f][1,7]naphthyridin-2-yl)ethanol; 3-methyl-9-phenyl-9,10-dihydrobenzo[f]furo[2,3-b][1,7]naphthyridin-6-amine; 8-methylbenzo[f][1,7]naphthyridine-2,5-diamine; 1-(5-amino-8-methylbenzo[f][1,7]naphthyridin-2-yl)propan-2-ol; 2-(5-amino-8-methylbenzo[f][1,7]naphthyridin-2-yl)acetonitrile; N-(5-amino-8-methylbenzo[f][1,7]naphthyridin-2-yl)acetamide; 2-(5-amino-8-methylbenzo[f][1,7]naphthyridin-2-yl)-1-(2,4-dimethylphenyl)ethanol; 2-(2-(6-methoxy-4-methylpyridin-3-yl)ethyl)-8-methylbenzo[f][1,7]naphthyridin-5-amine; 4-(4-(2-(5-amino-8-methylbenzo[f][1,7]naphthyridin-2-yl)ethyl)phenyl)butan-1-ol; methyl 3-(4-(2-(5-amino-8-methylbenzo[f][1,7]naphthyridin-2-yl)ethyl)phenyl)propanoate; 3-(4-(2-(5-amino-8-methylbenzo[f][1,7]naphthyridin-2-yl)ethyl)phenyl)propan-1-ol; 4-(4-(2-(5-amino-8-methylbenzo[f][1,7]naphthyridin-2-yl)ethyl)phenyl)-2-methylbutan-2-ol; 2-(4-(aminomethyl)phenethyl)-8-methylbenzo[f][1,7]naphthyridin-5-amine; (E)-ethyl 3-(4-(2-(5-amino-8-methylbenzo[f][1,7]naphthyridin-2-yl)ethyl)-3-methylphenyl)acrylate; ethyl 3-(4-(2-(5-amino-8-methylbenzo[f][1,7]naphthyridin-2-yl)ethyl)-3-methylphenyl)propanoate; 2-(4-(2-(5-amino-8-methylbenzo[f][1,7]naphthyridin-2-yl)ethyl)-3-methylbenzyl)propane-1,3-diol; 3-(4-(2-(5-amino-8-methylbenzo[f][1,7]naphthyridin-2-yl)ethyl)-3-methylphenyl)propanoic acid; 5-amino-2-(4-methoxy-2-methylphenethyl)benzo[f][1,7]naphthyridine-8-carbaldehyde; ethyl 4-(2-(5-amino-8-methylbenzo[f][1,7]naphthyridin-2-yl)ethyl)benzoate; 8-methyl-2-(4-methylphenethyl)benzo[f][1,7]naphthyridin-5-amine; 2-(4-(2-(5-amino-8-methylbenzo[f][1,7]naphthyridin-2-yl)ethyl)phenyl)propan-2-ol; (4-(2-(5-amino-8-methylbenzo[f][1,7]naphthyridin-2-yl)ethyl)phenyl)methanol; ethyl 4-(2-(5-amino-8-methylbenzo[f][1,7]naphthyridin-2-yl)ethyl)-3-methylbenzoate; 4-(2-(5-amino-8-methylbenzo[f][1,7]naphthyridin-2-yl)ethyl)-3-methylbenzoic acid; (4-(2-(5-amino-8-methylbenzo[f][1,7]naphthyridin-2-yl)ethyl)-3-methylphenyl)methanol; 8-methyl-2-(2,4,6-trimethylphenethyl)benzo[f][1,7]naphthyridin-5-amine; 2-(4-(2-(5-amino-8-methylbenzo[f][1,7]naphthyridin-2-yl)ethyl)-3-methylphenyl)propan-2-ol; 8-methyl-2-(4-propoxyphenethyl)benzo[f][1,7]naphthyridin-5-amine; (E)-3-(5-amino-2-(4-methoxy-2-methylphenethyl)benzo[f][1,7]naphthyridin-8-yl)acrylic acid; ethyl 3-(5-amino-2-(4-methoxy-2-methylphenethyl)benzo[f][1,7]naphthyridin-8-yl)propanoate; 3-(5-amino-2-(4-methoxy-2-methylphenethyl)benzo[f][1,7]naphthyridin-8-yl)propanoic acid; 3-(5-amino-2-(4-methoxy-2-methylphenethyl)benzo[f][1,7]naphthyridin-8-yl)propan-1-ol; 5-aminobenzo[f][1,7]naphthyridin-8-ol; 5-aminobenzo[f][1,7]naphthyridine-8-carbaldehyde; 1-(5-aminobenzo[f][1,7]naphthyridin-8-yl)ethanone; 1-(5-aminobenzo[f][1,7]naphthyridin-8-yl)ethanone; 8-isopropylbenzo[f][1,7]naphthyridin-5-amine; 8-vinylbenzo[f][1,7]naphthyridin-5-amine; 8-ethylbenzo[f][1,7]naphthyridin-5-amine; 8-(methoxymethyl)benzo[f][1,7]naphthyridin-5-amine; (5-amino-2-(4-methoxyphenethyl)benzo[f][1,7]naphthyridin-8-yl)methanol; benzo[f][1,7]naphthyridine-5,8-diamine; 8-(aminomethyl)benzo[f][1,7]naphthyridin-5-amine; 3-fluoro-8-methylbenzo[f][1,7]naphthyridin-5-amine; (5-amino-3-fluorobenzo[f][1,7]naphthyridin-8-yl)methanol; 3-chlorobenzo[f][1,7]naphthyridine-5,8-diamine; 3-fluorobenzo[f][1,7]naphthyridine-5,8-diamine; 8-isobutylbenzo[f][1,7]naphthyridin-5-amine; (E)-8-(prop-1-enyl)benzo[f][1,7]naphthyridin-5-amine; 8-propylbenzo[f][1,7]naphthyridin-5-amine; 8-(2-cyclopropylethyl)benzo[f][1,7]naphthyridin-5-amine; 8-phenethylbenzo[f][1,7]naphthyridin-5-amine; (5-amino-2-(4-bromophenethyl)benzo[f][1,7]naphthyridin-8-yl)methanol; (5-amino-2-(4-methoxy-2-methylphenethyl)benzo[f][1,7]naphthyridin-8-yl)methanol; 2-(4-methoxy-2-methylphenethyl)-8-pentylbenzo[f][1,7]naphthyridin-5-amine; 8-(2-cyclopropylethyl)-2-(4-methoxy-2-methylphenethyl)benzo[f][1,7]naphthyridin-5-amine; (5-amino-2-(2,4,6-trimethylphenethyl)benzo[f][1,7]naphthyridin-8-yl)methanol; (5-amino-2-(4-propoxyphenethyl)

benzo[f][1,7]naphthyridin-8-yl)methanol; (2-(2-(1H-indol-5-yl)ethyl)-5-aminobenzo[f][1,7]naphthyridin-8-yl)methanol; methyl 4-(2-(5-amino-8-methylbenzo[f][1,7]naphthyridin-2-yl)ethyl)-3-methylbenzoate; 4-(2-(5-amino-8-methylbenzo[f][1,7]naphthyridin-2-yl)ethyl)-N,3-dimethylbenzamide; N-(2-acetamidoethyl)-4-(2-(5-amino-8-methylbenzo[f][1,7]naphthyridin-2-yl)ethyl)-3-methylbenzamide; 4-(2-(5-amino-8-methylbenzo[f][1,7]naphthyridin-2-yl)ethyl)-N-(2-(dimethylamino)ethyl)-N,3-dimethylbenzamide; 2-(4-methoxyphenethyl)benzo[f][1,7]naphthyridin-5-amine; 2-(4-methoxy-2-methylphenethyl)benzo[f][1,7]naphthyridin-5-amine; 4-(2-(5-amino-8-methylbenzo[f][1,7]naphthyridin-2-yl)ethyl)-3-methylbenzamide; 4-(2-(5-amino-8-methylbenzo[f][1,7]naphthyridin-2-yl)ethyl)-N,N,3-trimethylbenzamide; 4-(2-(5-amino-8-methylbenzo[f][1,7]naphthyridin-2-yl)ethyl)-N-(2-hydroxyethyl)-3-methylbenzamide; 4-(2-(5-amino-8-methylbenzo[f][1,7]naphthyridin-2-yl)ethyl)-N-(2-(dimethylamino)ethyl)-3-methylbenzamide; (4-(2-(5-amino-8-methylbenzo[f][1,7]naphthyridin-2-yl)ethyl)-3-methylphenyl)(pyrrolidin-1-yl)methanone; 4-(2-(5-amino-8-methylbenzo[f][1,7]naphthyridin-2-yl)ethyl)-N-(2-(diethylamino)ethyl)-3-methylbenzamide; (4-(2-(5-amino-8-methylbenzo[f][1,7]naphthyridin-2-yl)ethyl)-3-methylphenyl)(4-ethylpiperazin-1-yl)methanone; (4-(2-(5-amino-8-methylbenzo[f][1,7]naphthyridin-2-yl)ethyl)-3-methylphenyl)(piperazin-1-yl)methanone; 4-(2-(5-amino-8-methylbenzo[f][1,7]naphthyridin-2-yl)ethyl)-3-methyl-N-(2-(pyrrolidin-1-yl)ethyl)benzamide; 4-(2-(5-aminobenzo[f][1,7]naphthyridin-2-yl)ethyl)-N-(2-(dimethylamino)ethyl)-N3-dimethylbenzamide; 4-(2-(5-amino-8-methylbenzo[f][1,7]naphthyridin-2-yl)ethyl)-N-(2-(dimethylamino)ethyl)-N-methylbenzamide; 2-(4-(2-(5-aminobenzo[f][1,7]naphthyridin-2-yl)ethyl)-3-methylphenyl)propan-2-ol; 2-(4-butoxyphenethyl)-8-methylbenzo[f][1,7]naphthyridin-5-amine; 2-(2-(biphenyl-4-yl)ethyl)-8-methylbenzo[f][1,7]naphthyridin-5-amine; 2-((1,3-dihydroisobenzofuran-1-yl)methyl)-8-methylbenzo[f][1,7]naphthyridin-5-amine; 8-methyl-2-(4-(2-methylallyloxy)phenethyl)benzo[f][1,7]naphthyridin-5-amine; 2-(4-(isopentyloxy)phenethyl)-8-methylbenzo[f][1,7]naphthyridin-5-amine; 4-(2-(5-amino-8-methylbenzo[f][1,7]naphthyridin-2-yl)ethyl)phenyl propyl carbonate; ethyl 5-(4-(2-(5-amino-8-methylbenzo[f][1,7]naphthyridin-2-yl)ethyl)phenoxy)pentanoate; 2-(4-(cyclopentyloxy)phenethyl)-8-methylbenzo[f][1,7]naphthyridin-5-amine; 2-(4-(cyclobutylmethoxy)phenethyl)-8-methylbenzo[f][1,7]naphthyridin-5-amine; 8-methyl-2-(4-(2-morpholinoethoxy)phenethyl)benzo[f][1,7]naphthyridin-5-amine; 2-(4-(2-(5-amino-8-methylbenzo[f][1,7]naphthyridin-2-yl)ethyl)phenoxy)-1-phenylethanone; 5-(4-(2-(5-amino-8-methylbenzo[f][1,7]naphthyridin-2-yl)ethyl)phenoxy)pentanoic acid; 2-(4-(2-(5-amino-8-methylbenzo[f][1,7]naphthyridin-2-yl)ethyl)phenoxy)ethanol; 2-(4-(2-(5-amino-8-methylbenzo[f][1,7]naphthyridin-2-yl)ethyl)phenoxy)-N,N-dimethylacetamide; 8-methyl-2-(2-methyl-4-(2-morpholinoethoxy)phenethyl)benzo[f][1,7]naphthyridin-5-amine; 2-(2-(4-(2-(5-amino-8-methylbenzo[f][1,7]naphthyridin-2-yl)ethyl)-3-methylphenoxy)ethoxy)ethanol; diethyl 3-(4-(2-(5-amino-8-methylbenzo[f][1,7]naphthyridin-2-yl)ethyl)-3-methylphenoxy)propylphosphonate; 3-(4-(2-(5-amino-8-methylbenzo[f][1,7]naphthyridin-2-yl)ethyl)-3-methylphenoxy)propylphosphonic acid; 2-(4-butoxy-2-methylphenethyl)-8-methylbenzo[f][1,7]naphthyridin-5-amine; 2-(4-(2-(5-aminobenzo[f][1,7]naphthyridin-2-yl)ethyl)-3-methylphenoxy)ethanol; 2-(2-(4-(2-(5-aminobenzo[f][1,7]naphthyridin-2-yl)ethyl)-3-methylphenoxy)ethoxy)ethanol; ethyl 5-(4-(2-(5-amino-8-methylbenzo[f][1,7]naphthyridin-2-yl)ethyl)-3-methylphenoxy)pentanoate; 5-(4-(2-(5-amino-8-methylbenzo[f][1,7]naphthyridin-2-yl)ethyl)-3-methylphenoxy)pentanoic acid; 2-(4-(2-(5-amino-8-methylbenzo[f][1,7]naphthyridin-2-yl)ethyl)-3-methylphenoxy)ethanol; 4-(2-(5-amino-8-methylbenzo[f][1,7]naphthyridin-2-yl)ethyl)phenyl ethyl carbonate; methyl 4-(4-(2-(5-amino-8-methylbenzo[f][1,7]naphthyridin-2-yl)ethyl)phenoxy)butanoate; 4-(4-(2-(5-amino-8-methylbenzo[f][1,7]naphthyridin-2-yl)ethyl)phenoxy)butanoic acid; 4-(4-(2-(5-amino-8-methylbenzo[f][1,7]naphthyridin-2-yl)ethyl)-3-methylphenoxy)butanoic acid; 2-(4-(isopentyloxy)-2-methylphenethyl)-8-methylbenzo[f][1,7]naphthyridin-5-amine; 4-(2-(5-amino-8-methylbenzo[f][1,7]naphthyridin-2-yl)ethyl)phenyl hexyl carbonate; 2-(2,4,6-trimethylphenethyl)benzo[f][1,7]naphthyridin-5-amine; (5-amino-2-(2,4-dimethylphenethyl)benzo[f][1,7]naphthyridin-8-yl)methanol; diethyl 3-(2-(4-(2-(5-amino-8-methylbenzo[f][1,7]naphthyridin-2-yl)ethyl)-3-methylphenoxy)ethoxy)propylphosphonate; diethyl 3-(2-(2-(4-(2-(5-amino-8-methylbenzo[f][1,7]naphthyridin-2-yl)ethyl)-3-methylphenoxy)ethoxy)ethoxy)propylphosphonate; 4-(2-(5-amino-8-methylbenzo[f][1,7]naphthyridin-2-yl)ethyl)-3-methylphenyl dimethylsulfamate; (5-amino-2-(4-(dimethylamino)phenethyl)benzo[f][1,7]naphthyridin-8-yl)methanol; 2-(4-(dimethylamino)phenethyl)-8-methylbenzo[f][1,7]naphthyridin-5-amine; 4-(2-(5-amino-8-methylbenzo[f][1,7]naphthyridin-2-yl)ethyl)phenol; 1-(4-(2-(5-amino-8-methylbenzo[f][1,7]naphthyridin-2-yl)ethyl)phenyl)ethanone; 2-(4-((dimethylamino)methyl)phenethyl)-8-methylbenzo[f][1,7]naphthyridin-5-amine; 2-(4-(1-(dimethylamino)ethyl)phenethyl)-8-methylbenzo[f][1,7]naphthyridin-5-amine; 1-(4-(2-(5-amino-8-methylbenzo[f][1,7]naphthyridin-2-yl)ethyl)phenyl)ethanone oxime; 8-methyl-2-(4-((methylamino)methyl)phenethyl)benzo[f][1,7]naphthyridin-5-amine; (4-(2-(5-amino-8-methylbenzo[f][1,7]naphthyridin-2-yl)ethyl)benzylamino)ethanol; 8-methyl-2-(4-(pyrrolidin-1-ylmethyl)phenethyl)benzo[f][1,7]naphthyridin-5-amine; 2-(3,4-dimethoxyphenethyl)-8-methylbenzo[f][1,7]naphthyridin-5-amine; 2-(1-(4-(2-(5-amino-8-methylbenzo[f][1,7]naphthyridin-2-yl)ethyl)phenyl)ethylamino)ethanol; 1-(4-(2-(5-amino-8-methylbenzo[f][1,7]naphthyridin-2-yl)ethyl)phenyl)ethanol; 8-methyl-2-(4-(oxazol-5-yl)phenethyl)benzo[f][1,7]naphthyridin-5-amine; 3-(1-(4-(2-(5-amino-8-methylbenzo[f][1,7]naphthyridin-2-yl)ethyl)phenyl)ethylamino)propanenitrile; (2R)-2-(1-(4-(2-(5-amino-8-methylbenzo[f][1,7]naphthyridin-2-yl)ethyl)phenyl)ethylamino)propan-1-ol; 8-methyl-2-(4-(1-(piperazin-1-yl)ethyl)phenethyl)benzo[f][1,7]naphthyridin-5-amine; ((2S)-1-(1-(4-(2-(5-amino-8-methylbenzo[f][1,7]naphthyridin-2-yl)ethyl)phenyl)ethyl)pyrrolidin-2-yl)methanol; N1-(1-(4-(2-(5-amino-8-methylbenzo[f][1,7]naphthyridin-2-yl)ethyl)phenyl)ethyl)-N2,N2-dimethylethane-1,2-diamine; 3-(1-(4-(2-(5-amino-8-methylbenzo[f][1,7]naphthyridin-2-yl)ethyl)phenyl)ethylamino)propanoic acid; 8-methyl-2-(4-(1-(4-methylpiperazin-1-yl)ethyl)phenethyl)benzo[f][1,7]naphthyridin-5-amine; N2-(1-(4-(2-(5-amino-8-methylbenzo[f][1,7]naphthyridin-2-yl)ethyl)phenyl)ethyl)-N1,N1-dimethylpropane-1,2-diamine; 8-methyl-2-(4-(1-(2-(pyridin-4-yl)ethylamino)ethyl)phenethyl)benzo[f][1,7]naphthyridin-5-amine; N1-(1-(4-(2-(5-amino-8-methylbenzo[f][1,7]naphthyridin-2-yl)ethyl)phenyl)ethyl)-N2,N2-diethylethane-1,2-diamine; 2-(4-(dimethylamino)-2-methylphenethyl)-8-methylbenzo[f][1,7]naphthyridin-5-amine; 1-(1-(4-(2-(5-amino-8-methylbenzo[f][1,7]naphthyridin-2-yl)ethyl)phenyl)ethyl)pyrrolidine-3- carboxylic acid; 4-(1-(4-(2-(5-amino-8-methylbenzo[f][1,7] naphthyridin-2-yl)ethyl)phenyl)ethylamino)phenol; 1-(1-(4-(2-(5-amino-8-methylbenzo[f][1,7]naphthyridin-2yl)ethyl) phenyl)ethyl)pyrrolidin-3-ol, and 2-(4-(2-aminopropan-2-yl)phenethyl)-8-methylbenzo[f][1,7]naphthyridin-5-amine.

In certain embodiments of the compounds, compositions and methods described herein, the compound of Formulas (I-A) is selected from the following compounds and their pharmaceutically acceptable salts: 2-methylbenzo[f][1,7] naphthyridin-5-amine; 2-propylbenzo[f][1,7]naphthyridin-5-amine; 2-ethylbenzo[f][1,7]naphthyridin-5-amine; 2-(3-methoxyphenethyl)benzo[f][1,7]naphthyridin-5-amine; 8-methylbenzo[f][1,7]naphthyridin-5-amine; 8-methyl-2-phenethylbenzo[f][1,7]naphthyridin-5-amine; methyl 5-aminobenzo[f][1,7]naphthyridine-3-carboxylate; (5-aminobenzo[f][1,7]naphthyridin-3-yl)methanol; benzo[f][1,7] naphthyridin-5-amine; (5-aminobenzo[f][1,7]naphthyridin-8-yl)methanol; 2-(2-methylphenethyl)benzo[f][1,7] naphthyridin-5-amine; 2-(3-methylphenethyl)benzo[f][1,7] naphthyridin-5-amine; 2-(4-methylphenethyl)benzo[f][1,7] naphthyridin-5-amine; 8-chlorobenzo[f][1,7]naphthyridin-5-amine; ethyl 5-aminobenzo[f][1,7]naphthyridine-9-carboxylate; 8-methoxybenzo[f][1,7]naphthyridin-5-amine; 8-(trifluoromethyl)benzo[f][1,7]naphthyridin-5-amine; 8-fluorobenzo[f][1,7]naphthyridin-5-amine; 3-methylbenzo[f][1,7]naphthyridin-5-amine; 3-fluorobenzo[f][1,7]naphthyridin-5-amine; 2-phenethylbenzo[f][1,7]naphthyridin-5-amine; 8-methyl-2-(2-(naphthalen-1-yl)ethyl)benzo[f][1,7] naphthyridin-5-amine; 8-methyl-2-(2-(naphthalen-2-yl) ethyl)benzo[f][1,7]naphthyridin-5-amine; 4-(2-(5-amino-8-methylbenzo[f][1,7]naphthyridin-2-yl)ethyl)benzoic acid; 3-(2-(5-amino-8-methylbenzo[f][1,7]naphthyridin-2-yl) ethyl)benzoic acid; 2-(3-chlorophenethyl)-8-methylbenzo[f][1,7]naphthyridin-5-amine; 2-(2-chlorophenethyl)-8-methylbenzo[f][1,7]naphthyridin-5-amine; (3-(2-(5-amino-8-methylbenzo[f][1,7]naphthyridin-2-yl)ethyl)phenyl) methanol; 2-(4-chlorophenethyl)-8-methylbenzo[f][1,7] naphthyridin-5-amine; 2-(4-butylphenethyl)benzo[f][1,7] naphthyridin-5-amine; 2-(4-butylphenethyl)-8-methylbenzo [f][1,7]naphthyridin-5-amine; 2-(4-propylphenethyl)benzo [f][1,7]naphthyridin-5-amine; 2-(4-(trifluoromethyl) phenethyl)benzo[f][1,7]naphthyridin-5-amine; 2-(2,5-dimethylphenethyl)-8-methylbenzo[f][1,7]naphthyridin-5-amine; 8-methyl-2-(4-propylphenethyl)benzo[f][1,7] naphthyridin-5-amine; 8-methyl-2-(2,4,5-trimethylphenethyl)benzo[f][1,7]naphthyridin-5-amine; 2-(2,5-dimethylphenethyl)benzo[f][1,7]naphthyridin-5-amine; 2-(4-isopropylphenethyl)-8-methylbenzo[f][1,7] naphthyridin-5-amine; 2-(4-heptylphenethyl)-8-methylbenzo[f][1,7]naphthyridin-5-amine; 2-(4-isobutoxyphenethyl)-8-methylbenzo[f][1,7]naphthyridin-5-amine; 2-(4-((2-methoxyethoxy)methoxy)phenethyl)-8-methylbenzo[f][1,7]naphthyridin-5-amine; 8-methyl-2-(4-(2-phenoxyethoxy)phenethyl)benzo[f][1,7]naphthyridin-5-amine; 8-methyl-2-(4-(4-phenylbutoxy)phenethyl)benzo[f] [1,7]naphthyridin-5-amine; 2-(4-(allyloxy)phenethyl)-8-methylbenzo[f][1,7]naphthyridin-5-amine; 8-methyl-2-(4-(3-phenylpropoxy)phenethyl)benzo[f][1,7]naphthyridin-5-amine; 2-(4-(heptan-4-yloxy)phenethyl)-8-methylbenzo[f] [1,7]naphthyridin-5-amine; 8-methyl-2-(4-(4-methylpent-3-enyloxy)phenethyl)benzo[f][1,7]naphthyridin-5-amine; 2-(4-(2-cyclohexylethoxy)phenethyl)-8-methylbenzo[f][1, 7]naphthyridin-5-amine; 2-(4-isopropoxyphenethyl)-8-methylbenzo[f][1,7]naphthyridin-5-amine; 2-(4-(3,3-dimethylbutoxy)phenethyl)-8-methylbenzo[f][1,7]naphthyridin-5-amine; 8-(2-cyclopropylethyl)-2-(4-(dimethylamino) phenethyl)benzo[f][1,7]naphthyridin-5-amine; 8-(2-cyclopropylethyl)-2-(2,4-dimethylphenethyl)benzo[f][1,7] naphthyridin-5-amine; N-(4-(2-(5-amino-8-methylbenzo[f] [1,7]naphthyridin-2-yl)ethyl)phenyl)acetamide; N-(4-(2-(5-aminobenzo[f][1,7]naphthyridin-2-yl)ethyl)phenyl) acetamide; N-(4-(2-(5-amino-8-methylbenzo[f][1,7] naphthyridin-2-yl)ethyl)phenyl)-4-methylbenzenesulfonamide; 3-methyl-9-p-tolyl-9,10-dihydrobenzo[f]furo[2,3-b][1,7]naphthyridin-6-amine; 4-(2-(5-amino-8-methylbenzo[f][1,7]naphthyridin-2-yl)ethyl)-3-methylbenzonitrile; 4-(2-(5-amino-8-methylbenzo[f][1,7] naphthyridin-2-yl)ethyl)-N-(2-aminoethyl)-3-methylbenzamide; 8-methyl-2-(2-methyl-4-(1H-tetrazol-5-yl)phenethyl)benzo[f][1,7]naphthyridin-5-amine; methyl 2-(4-(2-(5-amino-8-methylbenzo[f][1,7]naphthyridin-2-yl) ethyl)-3-methylbenzamido)-4-methylpentanoate; methyl 2-(4-(2-(5-amino-8-methylbenzo[f][1,7]naphthyridin-2-yl) ethyl)-3-methylbenzamido)acetate; 2-(4-(2-(5-amino-8-methylbenzo[f][1,7]naphthyridin-2-yl)ethyl)-3-methylbenzamido)-4-methylpentanoic acid; 2-(4-(2-(5-amino-8-methylbenzo[f][1,7]naphthyridin-2-yl)ethyl)-3-methylbenzamido)acetic acid; 6-(5-amino-8-methylbenzo[f] [1,7]naphthyridin-2-yl)hexan-1-ol; 7-(5-amino-8-methylbenzo[f][1,7]naphthyridin-2-yl)heptanoic acid; 11-(5-amino-8-methylbenzo[f][1,7]naphthyridin-2-yl)undecan-1-ol; ethyl 2-(4-(2-(5-amino-8-methylbenzo[f][1,7] naphthyridin-2-yl)ethyl)-3-methylphenoxy)acetate; 2-(4-(2-(5-amino-8-methylbenzo[f][1,7]naphthyridin-2-yl)ethyl)-3-methylphenoxy)acetic acid; 3-(4-(2-(5-amino-8-methylbenzo[f][1,7]naphthyridin-2-yl)ethyl)-3-methylphenoxy)propanoic acid; 6-(4-(2-(5-amino-8-methylbenzo[f][1,7]naphthyridin-2-yl)ethyl)-3-methylphenoxy)hexanoic acid; 8-methyl-2-(2-methyl-4-(methylthio)phenethyl)benzo[f][1,7]naphthyridin-5-amine; 8-methyl-2-(4-(methylsulfonyl)phenethyl)benzo[f][1,7] naphthyridin-5-amine; 2-(4-(hexyloxy)phenethyl)-8-methylbenzo[f][1,7]naphthyridin-5-amine; 8-methyl-2-(4-phenethoxyphenethyl)benzo[f][1,7]naphthyridin-5-amine; 8-methyl-2-(4-(pentyloxy)phenethyl)benzo[f][1,7]naphthyridin-5-amine; 8-methyl-2-(4-(4-methylpentyloxy)phenethyl)benzo[f][1,7]naphthyridin-5-amine; 2-(2-fluorophenethyl)benzo[f][1,7]naphthyridin-5-amine; 2-(3-fluorophenethyl)benzo[f][1,7]naphthyridin-5-amine; 2-(4-fluorophenethyl)benzo[f][1,7]naphthyridin-5-amine; 2-(2-(thiophen-3-yl)ethyl)benzo[f][1,7]naphthyridin-5-amine; (5-aminobenzo[f][1,7]naphthyridin-2-yl)methanol; 2-(3,4-dimethylphenethyl)benzo[f][1,7]naphthyridin-5-amine; 2-(3,4-dimethylphenethyl)-8-methylbenzo[f][1,7]naphthyridin-5-amine; 2-(3,5-dimethylphenethyl)-8-methylbenzo[f] [1,7]naphthyridin-5-amine; 2-(2-(benzofuran-5-yl)ethyl)-8-methylbenzo[f][1,7]naphthyridin-5-amine; 8-methyl-2-(2-nitroethyl)benzo[f][1,7]naphthyridin-5-amine; 2-(aminomethyl)-8-methylbenzo[f][1,7]naphthyridin-5-amine; $N^2$,8-dimethylbenzo[f][1,7]naphthyridine-2,5-diamine; 2-(5-amino-8-methylbenzo[f][1,7]naphthyridin-2-yl)-1-phenylethanol; 2-(5-amino-8-methylbenzo[f][1,7] naphthyridin-2-yl)-1-(4-methoxyphenyl)ethanol; 2-(biphenyl-2-yl)-8-methylbenzo[f][1,7]naphthyridin-5-amine; 2-(2-(2,6-dimethylpyridin-3-yl)ethyl)-8-methylbenzo[f][1,7]naphthyridin-5-amine; 2-(2-(5-methoxypyridin-2-yl)ethyl)-8-methylbenzo[f][1,7]naphthyridin-5-amine; 3-(4-(2-(5-amino-8-methylbenzo[f][1,7] naphthyridin-2-yl)ethyl)phenyl)propanoic acid; 5-(2-(5-amino-8-methylbenzo[f][1,7]naphthyridin-2-yl)-4-methylpyridin-2(1H)-one; 6-(2-(5-amino-8-methylbenzo[f] [1,7]naphthyridin-2-yl)ethyl)pyridin-3-ol; 8-methyl-2-(4-(trifluoromethoxy)phenethyl)benzo[f][1,7]naphthyridin-5-amine; 2-(2-(2,3-dihydro-1H-inden-5-yl)ethyl)-8- methylbenzo[f][1,7]naphthyridin-5-amine; 2-(2-(2,3-dihydro-1H-inden-5-yl)ethyl)benzo[f][1,7]naphthyridin-5-amine; (E)-3-(4-(2-(5-amino-8-methylbenzo[f][1,7]naphthyridin-2-yl)ethyl)-3-methylphenyl)acrylic acid; (E)-ethyl 3-(5-amino-2-(4-methoxy-2-methylphenethyl)benzo[f][1,7]naphthyridin-8-yl)acrylate; (E)-8-(2-cyclopropylvinyl)-2-phenethylbenzo[f][1,7]naphthyridin-5-amine; 8-pentylbenzo[f][1,7]naphthyridin-5-amine; (E)-8-(2-cyclopropylvinyl)benzo[f][1,7]naphthyridin-5-amine; 8-(2-cyclopropylethyl)-2-phenethylbenzo[f][1,7]naphthyridin-5-amine; (5-amino-2-phenethylbenzo[f][1,7]naphthyridin-8-yl)methanol; (5-amino-2-(4-methoxy-2-methylphenethyl)benzo[f][1,7]naphthyridin-8-yl)methanol; 3-(2-(5-aminobenzo[f][1,7]naphthyridin-2-yl)ethyl)phenol; 2-(2-methoxyphenethyl)benzo[f][1,7]naphthyridin-5-amine; 2-(4-ethylphenethyl)benzo[f][1,7]naphthyridin-5-amine; 2-(4-ethylphenethyl)-8-methylbenzo[f][1,7]naphthyridin-5-amine; 2-(4-(dimethylamino)phenethyl)benzo[f][1,7]naphthyridin-5-amine; 2-(4-(piperidin-1-yl)phenethyl)benzo[f][1,7]naphthyridin-5-amine; 2-(4-tert-butylphenethyl)-8-methylbenzo[f][1,7]naphthyridin-5-amine; 8-methyl-2-(4-(piperidin-1-yl)phenethyl)benzo[f][1,7]naphthyridin-5-amine; 2-(4-methoxyphenethyl)-8-methylbenzo[f][1,7]naphthyridin-5-amine; 2-(3,5-dimethoxyphenethyl)-8-methylbenzo[f][1,7]naphthyridin-5-amine; 8-methyl-2-(2-(trifluoromethyl)phenethyl)benzo[f][1,7]naphthyridin-5-amine; 4-(2-(5-amino-8-methylbenzo[f][1,7]naphthyridin-2-yl)ethyl)-N-hydroxybenzimidamide; 4-(2-(5-amino-8-methylbenzo[f][1,7]naphthyridin-2-yl)ethyl)benzonitrile; 8-methyl-2-(4-(1-morpholinoethyl)phenethyl)benzo[f][1,7]naphthyridin-5-amine; 2-(4-aminophenethyl)-8-methylbenzo[f][1,7]naphthyridin-5-amine; 1-(4-(2-(5-amino-8-methylbenzo[f][1,7]naphthyridin-2-yl)ethyl)phenyl)guanidine; 8-methyl-2-(4-(1-(phenethylamino)ethyl)phenethyl)benzo[f][1,7]naphthyridin-5-amine; 2-(4-(2-(5-amino-8-methylbenzo[f][1,7]naphthyridin-2-yl)ethyl)phenyl)acetonitrile; 2-(4-(piperidin-1-ylmethyl)phenethyl)benzo[f][1,7]naphthyridin-5-amine; 1-(4-(2-(5-aminobenzo[f][1,7]naphthyridin-2-yl)ethyl)benzyl)piperidin-4-ol; 2-(4-(aminomethyl)phenethyl)benzo[f][1,7]naphthyridin-5-amine; 2-(4-((ethylamino)methyl)phenethyl)benzo[f][1,7]naphthyridin-5-amine; 2-(4-(2-aminopropan-2-yl)phenethyl)benzo[f][1,7]naphthyridin-5-amine; 1-(1-(4-(2-(5-aminobenzo[f][1,7]naphthyridin-2-yl)ethyl)phenyl)ethyl)pyrrolidine-3-carboxylic acid; 8-methyl-2-(4-(1-(phenylamino)ethyl)phenethyl)benzo[f][1,7]naphthyridin-5-amine; 2-ethyl-8-methylbenzo[f][1,7]naphthyridin-5-amine; (5-amino-8-methylbenzo[f][1,7]naphthyridin-2-yl)methanol; 8-methyl-2-propylbenzo[f][1,7]naphthyridin-5-amine; 2-(2-(1H-indol-5-yl)ethyl)-8-methylbenzo[f][1,7]naphthyridin-5-amine; 2-(4-ethoxyphenethyl)-8-methylbenzo[f][1,7]naphthyridin-5-amine; 8-methyl-2-(4-phenoxyphenethyl)benzo[f][1,7]naphthyridin-5-amine; 2-(2,4-dimethylphenethyl)benzo[f][1,7]naphthyridin-5-amine; 2-(2,4-dimethylphenethyl)-8-methylbenzo[f][1,7]naphthyridin-5-amine; 2-(4-methoxy-2-methylphenethyl)-8-methylbenzo[f][1,7]naphthyridin-5-amine; 4-(2-(5-amino-8-methylbenzo[f][1,7]naphthyridin-2-yl)ethyl)-3-methylphenol; 2-(2-(2,3-dihydrobenzofuran-5-yl)ethyl)-8-methylbenzo[f][1,7]naphthyridin-5-amine; 2-(5-amino-8-methylbenzo[f][1,7]naphthyridin-2-yl)ethanol; 3-methyl-9-phenyl-9,10-dihydrobenzo[f]furo[2,3-b][1,7]naphthyridin-6-amine; 8-methylbenzo[f][1,7]naphthyridine-2,5-diamine; 1-(5-amino-8-methylbenzo[f][1,7]naphthyridin-2-yl)propan-2-ol; 2-(5-amino-8-methylbenzo[f][1,7]naphthyridin-2-yl)acetonitrile; N-(5-amino-8-methylbenzo[f][1,7]naphthyridin-2-yl)acetamide; 2-(5-amino-8-methylbenzo[f][1,7]naphthyridin-2-yl)-1-(2,4-dimethylphenyl)ethanol; 2-(2-(6-methoxy-4-methylpyridin-3-yl)ethyl)-8-methylbenzo[f][1,7]naphthyridin-5-amine; 4-(4-(2-(5-amino-8-methylbenzo[f][1,7]naphthyridin-2-yl)ethyl)phenyl)butan-1-ol; methyl 3-(4-(2-(5-amino-8-methylbenzo[f][1,7]naphthyridin-2-yl)ethyl)phenyl)propanoate; 3-(4-(2-(5-amino-8-methylbenzo[f][1,7]naphthyridin-2-yl)ethyl)phenyl)propan-1-ol; 4-(4-(2-(5-amino-8-methylbenzo[f][1,7]naphthyridin-2-yl)ethyl)phenyl)-2-methylbutan-2-ol; 2-(4-(aminomethyl)phenethyl)-8-methylbenzo[f][1,7]naphthyridin-5-amine; (E)-ethyl 3-(4-(2-(5-amino-8-methylbenzo[f][1,7]naphthyridin-2-yl)ethyl)-3-methylphenyl)acrylate; ethyl 3-(4-(2-(5-amino-8-methylbenzo[f][1,7]naphthyridin-2-yl)ethyl)-3-methylphenyl)propanoate; 2-(4-(2-(5-amino-8-methylbenzo[f][1,7]naphthyridin-2-yl)ethyl)-3-methylbenzyl)propane-1,3-diol; 3-(4-(2-(5-amino-8-methylbenzo[f][1,7]naphthyridin-2-yl)ethyl)-3-methylphenyl)propanoic acid; 5-amino-2-(4-methoxy-2-methylphenethyl)benzo[f][1,7]naphthyridine-8-carbaldehyde; ethyl 4-(2-(5-amino-8-methylbenzo[f][1,7]naphthyridin-2-yl)ethyl)benzoate; 8-methyl-2-(4-methylphenethyl)benzo[f][1,7]naphthyridin-5-amine; 2-(4-(2-(5-amino-8-methylbenzo[f][1,7]naphthyridin-2-yl)ethyl)phenyl)propan-2-ol; (4-(2-(5-amino-8-methylbenzo[f][1,7]naphthyridin-2-yl)ethyl)phenyl)methanol; ethyl 4-(2-(5-amino-8-methylbenzo[f][1,7]naphthyridin-2-yl)ethyl)-3-methylbenzoate; 4-(2-(5-amino-8-methylbenzo[f][1,7]naphthyridin-2-yl)ethyl)-3-methylbenzoic acid; (4-(2-(5-amino-8-methylbenzo[f][1,7]naphthyridin-2-yl)ethyl)-3-methylphenyl)methanol; 8-methyl-2-(2,4,6-trimethylphenethyl)benzo[f][1,7]naphthyridin-5-amine; 2-(4-(2-(5-amino-8-methylbenzo[f][1,7]naphthyridin-2-yl)ethyl)-3-methylphenyl)propan-2-ol; 8-methyl-2-(4-propoxyphenethyl)benzo[f][1,7]naphthyridin-5-amine; (E)-3-(5-amino-2-(4-methoxy-2-methylphenethyl)benzo[f][1,7]naphthyridin-8-yl)acrylic acid; ethyl 3-(5-amino-2-(4-methoxy-2-methylphenethyl)benzo[f][1,7]naphthyridin-8-yl)propanoate; 3-(5-amino-2-(4-methoxy-2-methylphenethyl)benzo[f][1,7]naphthyridin-8-yl)propanoic acid; 3-(5-amino-2-(4-methoxy-2-methylphenethyl)benzo[f][1,7]naphthyridin-8-yl)propan-1-ol; 5-aminobenzo[f][1,7]naphthyridin-8-ol; 5-aminobenzo[f][1,7]naphthyridine-8-carbaldehyde; 1-(5-aminobenzo[f][1,7]naphthyridin-8-yl)ethanol; 1-(5-aminobenzo[f][1,7]naphthyridin-8-yl)ethanone; 8-isopropylbenzo[f][1,7]naphthyridin-5-amine; 8-vinylbenzo[f][1,7]naphthyridin-5-amine; 8-ethylbenzo[f][1,7]naphthyridin-5-amine; 8-(methoxymethyl)benzo[f][1,7]naphthyridin-5-amine; (5-amino-2-(4-methoxyphenethyl)benzo[f][1,7]naphthyridin-8-yl)methanol; benzo[f][1,7]naphthyridine-5,8-diamine; 8-(aminomethyl)benzo[f][1,7]naphthyridin-5-amine; 3-fluoro-8-methylbenzo[f][1,7]naphthyridin-5-amine; (5-amino-3-fluorobenzo[f][1,7]naphthyridin-8-yl)methanol; 3-chlorobenzo[f][1,7]naphthyridine-5,8-diamine; 3-fluorobenzo[f][1,7]naphthyridine-5,8-diamine; 8-isobutylbenzo[f][1,7]naphthyridin-5-amine; (E)-8-(prop-1-enyl)benzo[f][1,7]naphthyridin-5-amine; 8-propylbenzo[f][1,7]naphthyridin-5-amine; 8-(2-cyclopropylethyl)benzo[f][1,7]naphthyridin-5-amine; 8-phenethylbenzo[f][1,7]naphthyridin-5-amine; (5-amino-2-(4-bromophenethyl)benzo[f][1,7]naphthyridin-8-yl)methanol; 2-(4-methoxy-2-methylphenethyl)-8-pentylbenzo[f][1,7]naphthyridin-5-amine; 8-(2-cyclopropylethyl)-2-(4-methoxy-2-methylphenethyl)benzo[f][1,7]naphthyridin-5-amine; (5-amino-2-(2,4,6-trimethylphenethyl)benzo[f][1,7]naphthyridin-8-yl)methanol; (5-amino-2-(4-propoxyphenethyl)benzo[f][1,7]naphthyridin-8-yl)methanol; (2-(2-(1H-indol-5-yl)ethyl)-5-aminobenzo[f][1,7]naphthyridin-8-yl)methanol; methyl 4-(2-(5-amino-8-methylbenzo[f][1,7]naphthyridin-2-yl)ethyl)-3-methylbenzoate; 4-(2-(5-amino-8-methylbenzo[f][1,7]naphthyridin-2-yl)ethyl)-N,3-dimethylbenzamide; N-(2-acetamidoethyl)-4-(2-(5-amino-8-methylbenzo[f][1,7]naphthyridin-2-yl)ethyl)-3-methylbenzamide; 4-(2-(5-amino-8-methylbenzo[f][1,7]naphthyridin-2-yl)ethyl)-N-(2-(dimethylamino)ethyl)-N,3-dimethylbenzamide; 2-(4-methoxyphenethyl)benzo[f][1,7]naphthyridin-5-amine; 2-(4-methoxy-2-methylphenethyl)benzo[f][1,7]naphthyridin-5-amine; 4-(2-(5-amino-8-methylbenzo[f][1,7]naphthyridin-2-yl)ethyl)-3-methylbenzamide; 4-(2-(5-amino-8-methylbenzo[f][1,7]naphthyridin-2-yl)ethyl)-N,N,3-trimethylbenzamide; 4-(2-(5-amino-8-methylbenzo[f][1,7]naphthyridin-2-yl)ethyl)-N-(2-hydroxyethyl)-3-methylbenzamide; 4-(2-(5-amino-8-methylbenzo[f][1,7]naphthyridin-2-yl)ethyl)-N-(2-(dimethylamino)ethyl)-3-methylbenzamide; (4-(2-(5-amino-8-methylbenzo[f][1,7]naphthyridin-2-yl)ethyl)-3-methylphenyl)(pyrrolidin-1-yl)methanone; 4-(2-(5-amino-8-methylbenzo[f][1,7]naphthyridin-2-yl)ethyl)-N-(2-(diethylamino)ethyl)-3-methylbenzamide; (4-(2-(5-amino-8-methylbenzo[f][1,7]naphthyridin-2-yl)ethyl)-3-methylphenyl)(4-ethylpiperazin-1-yl)methanone; (4-(2-(5-amino-8-methylbenzo[f][1,7]naphthyridin-2-yl)ethyl)-3-methylphenyl)(piperazin-1-yl)methanone; 4-(2-(5-amino-8-methylbenzo[f][1,7]naphthyridin-2-yl)ethyl)-3-methyl-N-(2-(pyrrolidin-1-yl)ethyl)benzamide; 4-(2-(5-aminobenzo[f][1,7]naphthyridin-2-yl)ethyl)-N-(2-(dimethylamino)ethyl)-N,3-dimethylbenzamide; 4-(2-(5-amino-8-methylbenzo[f][1,7]naphthyridin-2-yl)ethyl)-N-(2-(dimethylamino)ethyl)-N-methylbenzamide; 2-(4-(2-(5-aminobenzo[f][1,7]naphthyridin-2-yl)ethyl)-3-methylphenyl)propan-2-ol; 2-(4-butoxyphenethyl)-8-methylbenzo[f][1,7]naphthyridin-5-amine; 2-(2-(biphenyl-4-yl)ethyl)-8-methylbenzo[f][1,7]naphthyridin-5-amine; 2-((1,3-dihydroisobenzofuran-1-yl)methyl)-8-methylbenzo[f][1,7]naphthyridin-5-amine; 8-methyl-2-(4-(2-methylallyloxy)phenethyl)benzo[f][1,7]naphthyridin-5-amine; 2-(4-(isopentyloxy)phenethyl)-8-methylbenzo[f][1,7]naphthyridin-5-amine; 4-(2-(5-amino-8-methylbenzo[f][1,7]naphthyridin-2-yl)ethyl)phenyl propyl carbonate; ethyl 5-(4-(2-(5-amino-8-methylbenzo[f][1,7]naphthyridin-2-yl)ethyl)phenoxy)pentanoate; 2-(4-(cyclopentyloxy)phenethyl)-8-methylbenzo[f][1,7]naphthyridin-5-amine; 2-(4-(cyclobutylmethoxy)phenethyl)-8-methylbenzo[f][1,7]naphthyridin-5-amine; 8-methyl-2-(4-(2-morpholinoethoxy)phenethyl)benzo[f][1,7]naphthyridin-5-amine; 2-(4-(2-(5-amino-8-methylbenzo[f][1,7]naphthyridin-2-yl)ethyl)phenoxy)-1-phenylethanone; 5-(4-(2-(5-amino-8-methylbenzo[f][1,7]naphthyridin-2-yl)ethyl)phenoxy)pentanoic acid; 2-(4-(2-(5-amino-8-methylbenzo[f][1,7]naphthyridin-2-yl)ethyl)phenoxy)ethanol; 2-(4-(2-(5-amino-8-methylbenzo[f][1,7]naphthyridin-2-yl)ethyl)phenoxy)-N,N-dimethylacetamide; 8-methyl-2-(2-methyl-4-(2-morpholinoethoxy)phenethyl)benzo[f][1,7]naphthyridin-5-amine; 2-(2-(4-(2-(5-amino-8-methylbenzo[f][1,7]naphthyridin-2-yl)ethyl)-3-methylphenoxy)ethoxy)ethanol; diethyl 3-(4-(2-(5-amino-8-methylbenzo[f][1,7]naphthyridin-2-yl)ethyl)-3-methylphenoxy)propylphosphonate; 3-(4-(2-(5-amino-8-methylbenzo[f][1,7]naphthyridin-2-yl)ethyl)-3-methylphenoxy)propylphosphonic acid; 2-(4-butoxy-2-methylphenethyl)-8-methylbenzo[f][1,7]naphthyridin-5-amine; 2-(4-(2-(5-aminobenzo[f][1,7]naphthyridin-2-yl)ethyl)-3-methylphenoxy)ethanol; 2-(2-(4-(2-(5-aminobenzo[f][1,7]naphthyridin-2-yl)ethyl)-3-methylphenoxy)ethoxy)ethanol; ethyl 5-(4-(2-(5-amino-8-methylbenzo[f][1,7]naphthyridin-2-yl)ethyl)-3-methylphenoxy)pentanoate; 5-(4-(2-(5-amino-8-methylbenzo[f][1,7]naphthyridin-2-yl)ethyl)-3-methylphenoxy)pentanoic acid; 2-(4-(2-(5-amino-8-methylbenzo[f][1,7]naphthyridin-2-yl)ethyl)-3-methylphenoxy)ethanol; 4-(2-(5-amino-8-methylbenzo[f][1,7]naphthyridin-2-yl)ethyl)phenyl ethyl carbonate; methyl 4-(4-(2-(5-amino-8-methylbenzo[f][1,7]naphthyridin-2-yl)ethyl)phenoxy)butanoate; 4-(4-(2-(5-amino-8-methylbenzo[f][1,7]naphthyridin-2-yl)ethyl)phenoxy)butanoic acid; 4-(4-(2-(5-amino-8-methylbenzo[f][1,7]naphthyridin-2-yl)ethyl)-3-methylphenoxy)butanoic acid; 2-(4-(isopentyloxy)-2-methylphenethyl)-8-methylbenzo[f][1,7]naphthyridin-5-amine; 4-(2-(5-amino-8-methylbenzo[f][1,7]naphthyridin-2-yl)ethyl)phenyl hexyl carbonate; 2-(2,4,6-trimethylphenethyl)benzo[f][1,7]naphthyridin-5-amine; (5-amino-2-(2,4-dimethylphenethyl)benzo[f][1,7]naphthyridin-8-yl)methanol; diethyl 3-(2-(4-(2-(5-amino-8-methylbenzo[f][1,7]naphthyridin-2-yl)ethyl)-3-methylphenoxy)ethoxy)propylphosphonate; diethyl 3-(2-(2-(4-(2-(5-amino-8-methylbenzo[f][1,7]naphthyridin-2-yl)ethyl)-3-methylphenoxy)ethoxy)ethoxy)propylphosphonate; 4-(2-(5-amino-8-methylbenzo[f][1,7]naphthyridin-2-yl)ethyl)-3-methylphenyl dimethylsulfamate; (5-amino-2-(4-(dimethylamino)phenethyl)benzo[f][1,7]naphthyridin-8-yl)methanol; 2-(4-(dimethylamino)phenethyl)-8-methylbenzo[f][1,7]naphthyridin-5-amine; 4-(2-(5-amino-8-methylbenzo[f][1,7]naphthyridin-2-yl)ethyl)phenol; 1-(4-(2-(5-amino-8-methylbenzo[f][1,7]naphthyridin-2-yl)ethyl)phenyl)ethanone; 2-(4-((dimethylamino)methyl)phenethyl)-8-methylbenzo[f][1,7]naphthyridin-5-amine; 2-(4-(1-(dimethylamino)ethyl)phenethyl)-8-methylbenzo[f][1,7]naphthyridin-5-amine; 1-(4-(2-(5-amino-8-methylbenzo[f][1,7]naphthyridin-2-yl)ethyl)phenyl)ethanone oxime; 8-methyl-2-(4-((methylamino)methyl)phenethyl)benzo[f][1,7]naphthyridin-5-amine; (4-(2-(5-amino-8-methylbenzo[f][1,7]naphthyridin-2-yl)ethyl)benzylamino)ethanol; 8-methyl-2-(4-(pyrrolidin-1-ylmethyl)phenethyl)benzo[f][1,7]naphthyridin-5-amine; 2-(3,4-dimethoxyphenethyl)-8-methylbenzo[f][1,7]naphthyridin-5-amine; 2-(1-(4-(2-(5-amino-8-methylbenzo[f][1,7]naphthyridin-2-yl)ethyl)phenyl)ethylamino)ethanol; 1-(4-(2-(5-amino-8-methylbenzo[f][1,7]naphthyridin-2-yl)ethyl)phenyl)ethanol; 8-methyl-2-(4-(oxazol-5-yl)phenethyl)benzo[f][1,7]naphthyridin-5-amine; 3-(1-(4-(2-(5-amino-8-methylbenzo[f][1,7]naphthyridin-2-yl)ethyl)phenyl)ethylamino)propanenitrile; (2R)-2-(1-(4-(2-(5-amino-8-methylbenzo[f][1,7]naphthyridin-2-yl)ethyl)phenyl)ethylamino)propan-1-ol; 8-methyl-2-(4-(1-(piperazin-1-yl)ethyl)phenethyl)benzo[f][1,7]naphthyridin-5-amine; ((2S)-1-(1-(4-(2-(5-amino-8-methylbenzo[f][1,7]naphthyridin-2-yl)ethyl)phenyl)ethyl)pyrrolidin-2-yl)methanol; $N^1$-(1-(4-(2-(5-amino-8-methylbenzo[f][1,7]naphthyridin-2-yl)phenyl)ethyl)-$N^2$,$N^2$-dimethylethane-1,2-diamine; 3-(1-(4-(2-(5-amino-8-methylbenzo[f][1,7]naphthyridin-2-yl)ethyl)phenyl)ethylamino)propanoic acid; 8-methyl-2-(4-(1-(4-methylpiperazin-1-yl)ethyl)phenethyl)benzo[f][1,7]naphthyridin-5-amine; $N^2$-(1-(4-(2-(5-amino-8-methylbenzo[f][1,7]naphthyridin-2-yl)ethyl)phenypethyl)-$N^1$,$N^1$-dimethylpropane-1,2-diamine; 8-methyl-2-(4-(1-(2-(pyridin-4-yl)ethylamino)ethyl)phenethyl)benzo[f][1,7]naphthyridin-5-amine; $N^1$-(1-(4-(2-(5-amino-8-methylbenzo[f][1,7]naphthyridin-2-yl)ethyl)phenyl)ethyl)-$N^2$,$N^2$-diethylethane-1,2-diamine; 2-(4-(dimethylamino)-2-methylphenethyl)-8-methylbenzo[f][1,7]naphthyridin-5-amine; 1-(1-(4-(2-(5-amino-8-methylbenzo[f][1,7]naphthyridin-2-yl)ethyl)phenyl)ethyl)pyrrolidine-3-carboxylic acid; 4-(1-(4-(2-(5-amino-8-methylbenzo[f][1,7]naphthyridin-2-yl)ethyl)phenyl)ethylamino)phenol; 1-(1-(4-

(2-(5-amino-8-methylbenzo[f][1,7]naphthyridin-2yl)ethyl) phenyl)ethyl)pyrrolidin-3-ol; and 2-(4-(2-aminopropan-2-yl)phenethyl)-8-methylbenzo[f][1,7]naphthyridin-5-amine.

In certain embodiments of compounds of Formula (XVI), or a pharmaceutically acceptable salt thereof, each $R^4$, $R^A$ and $R^{13}$ is independently selected from H, —$CH_3$, —$CH_2CH_3$, —$CF_3$, —$CH_2OH$, —$OCH_3$, —$COOCH_3$, F, Cl, Br, —$CH_2OCH_3$, —$COOCH_2CH_3$, $CH_2OCH_2CH_3$, —N$(CH_3)_2$, —$((O(CH_2)_2)_{2-4}$—OH, —$O(CH_2)_{2-4}$—OH, —$O(CH_2)_{2-4}$—$(PO_3H_2)$, —$O(CH_2)_{2-4}$—COOH, —$O(CH_2)_{2-4}$—CH$(CH_3)_2$, $C_2$-$C_6$ alkyl substituted with 1-3 substituents selected from —OH, —$CH_3$, cyclopropyl, —$O(CH_2)_{2-4}$—COOH, —$O(CH_2)_{2-4}(PO_3H_2)$, —COOH, COOCH$_3$, and —COOCH$_2$CH$_3$. In other embodiments of compounds of Formula (XVI), $R^4$ is H. In other embodiments such compounds of Formula (XVI), have one to three $R^{13}$ groups. In other embodiments of such compounds of Formula (XVI), $R^A$ is H or Me. In other embodiments such compounds of Formula (XVI), have two $R^{13}$ groups selected from the group consisting of —$CH_3$, —$CH_2CH_3$, —$CF_3$, —$CH_2OH$, —$OCH_3$, —$COOCH_3$, —$COOCH_2CH_3$, F, Cl, Br, —$CH_2OCH_3$, $CH_2OCH_2CH_3$, —N$(CH_3)_2$, —$((O(CH_2)_2)_{2-4}$ OH, —$O(CH_2)_{2-4}$—OH, —$O(CH_2)_{2-4}$—$(PO_3H_2)$, —$O(CH_2)_{2-4}$—COOH, —$O(CH_2)_{2-4}$—CH$(CH_3)_2$, $C_2$-$C_6$ alkyl substituted with 1-3 substituents selected from —OH, —$CH_3$, cyclopropyl, —$O(CH_2)_{2-4}$—COOH, —$O(CH_2)_{2-4}$ $(PO_3H_2)$, —COOH, COOCH$_3$, and —COOCH$_2$CH$_3$. In other embodiments such compounds of Formula (XVI) are selected from: 2-(4-(2-(5-amino-8-methylbenzo[f][1,7] naphthyridin-2-yl)ethyl)-3-methylphenyl)propan-2-ol; 2-(4-methoxy-2-methylphenethyl)-8-methylbenzo[f][1,7]naphthyridin-5-amine; dimethylphenethyl)benzo[f][1,7] naphthyridin-5-amine; ethyl 4-(2-(5-amino-8-methylbenzo [f][1,7]naphthyridin-2-yl)ethyl)-3-methylbenzoate; 2-(4-(dimethylamino)phenethyl)-8-methylbenzo[f][1,7] naphthyridin-5-amine, and 2-(4-methoxyphenethyl)-8-methylbenzo[f][1,7]naphthyridin-5-amine.

Another aspect provided herein are pharmaceutical compositions that include a therapeutically effective amount of a compound of Formula (I) described above and a pharmaceutically acceptable carrier.

In certain embodiments of this aspect, the pharmaceutical composition is formulated for intravenous administration, intravitrial administration, intramuscular administration, oral administration, rectal administration inhalation, nasal administration, topical administration, ophthalmic administration or otic administration. In other embodiments, the pharmaceutical compositions are in the form of a tablet, a pill, a capsule, a liquid, an inhalant, a nasal spray solution, a suppository, a solution, an emulsion, an ointment, eye drop or ear drop. In other embodiments, such pharmaceutical compositions further include one or more additional therapeutic agents.

Another aspect provided herein are medicaments for treating a disease or disorder in a patient where modulation of a TLR receptor is implicated and such medicaments include a therapeutically effective amount of a compound of Formula (I). In certain embodiments of such medicaments, the TLR receptor is TLR7. In other embodiments of such medicaments, the TLR receptor is TLR8. In certain embodiments of such medicaments, the compound is a TLR receptor agonist. In certain embodiments of such medicaments, the compound is a TLR7 receptor agonist. In certain embodiments of such medicaments, the compound is a TLR8 receptor agonist.

Another aspect provided herein is the use of a compound of Formula (I) in the manufacture of a medicament for treating a disease or disorder in a patient where modulation of a TLR receptor is implicated.

Another aspect provided herein includes methods for modulating a TLR receptor, wherein the method include administering to a system or a subject in need thereof, a therapeutically effective amount of a compound of Formula (I), or pharmaceutically acceptable salts or pharmaceutical compositions thereof, thereby modulating the TLR receptor. In certain embodiments of such methods, the TLR receptor is TLR7. In other embodiments of such methods, the TLR receptor is TLR8. In certain embodiments of such methods, the compound is a TLR receptor agonist. In certain embodiments of such methods, the compound is a TLR7 receptor agonist. In certain embodiments of such methods, the compound is a TLR8 receptor agonist. In certain embodiments of such methods, the methods include administering the compound to a cell or tissue system or to a human or animal subject.

In certain embodiments of the methods provided herein for the treatment of a subject for a specified condition or disorder where a TLR is implicated, such methods further comprise an optional step of identifying a subject in need of such treatment.

Another aspect provided herein includes methods for treating a disease or disorder where modulation of TLR receptor is implicated, wherein the method includes administering to a system or subject in need of such treatment an effective amount of a compound of Formula (I), or pharmaceutically acceptable salts or pharmaceutical compositions thereof, thereby treating the disease or disorder. In certain embodiments of such methods, the TLR receptor is TLR7. In other embodiments of such methods, the TLR receptor is TLR8. In certain embodiments of such methods, the compound is a TLR receptor agonist. In certain embodiments of such methods, the compound is a TLR7 receptor agonist. In certain embodiments of such methods, the compound is a TLR8 receptor agonist. In certain embodiments of such methods, the methods include administering the compound to a cell or tissue system or to a human or animal subject.

In certain embodiments of such methods, the disease or condition is an infectious disease, an inflammatory disease, a respiratory disease, a dermatological disease or an autoimmune disease. In certain embodiments of such methods, the disease or condition is asthma, chronic obstructive pulmonary disease (COPD), adult respiratory distress syndrome (ARDS), ulcerative colitis, Crohns disease, bronchitis, dermatitis, actinic keratosis, basal cell carcinoma, allergic rhinitis, psoriasis, scleroderma, urticaria, rheumatoid arthritis, multiple sclerosis, cancer, breast cancer, HIV or lupus.

Another aspect provided herein includes methods for treating a cell-proliferative disease, comprising administering to a system or subject in need of such treatment an effective amount of a compound of Formula (I), or pharmaceutically acceptable salts or pharmaceutical compositions thereof; wherein the cell-proliferative disease is lymphoma, osteosarcoma, melanoma, or a tumor of breast, renal, prostate, colorectal, thyroid, ovarian, pancreatic, neuronal, lung, uterine or gastrointestinal tumor.

Another aspect provided herein are pharmaceutical composition that include a compound of Formula (I) of (I-A), an antigen and a pharmaceutically acceptable carrier, wherein such pharmaceutical compositions are immunogenic compositions, and the compound is an immune potentiator and is present in an amount effective to enhance an immune response to the antigen, in a subject receiving the composition. In certain embodiments, such pharmaceutical compositions, further includes one or more immunoregulatory agents. In certain embodiments, the one or more immunoregulatory agents include one or more adjuvants. In certain embodiments, such adjuvants are selected from adjuvants that are a mineral-containing composition, an oil emulsion, a saponin formulation, a virosome, a virus-like particle, a bacterial derivative, a microbial derivative, a human immunomodulator, a bioadhesive, a mucoadhesive, a microparticle, a liposome, a polyoxyethylene ether formulation, a polyoxyethylene ester formulation, a polyphosphazene, a muramyl peptide, or an imidazoquinolone compound. In certain embodiments, the adjuvant is an oil emulsion. In certain embodiments the immunogenic compositions are useful as vaccines, and the compound is present in an amount sufficient to produce an immunostimulatory effect upon administration.

Another aspect provided herein includes methods for enhancing the effectiveness of an immunogenic composition, comprising adding an effective amount of a compound Formula (I) or (I-A) to the immunogenic composition.

Another aspect provided herein are immunogenic compositions comprising a compound of Formula (I-A), and an antigen, wherein the amount of the compound is an amount effective to enhance an immune response to the antigen in a subject to whom the composition is administered. In certain embodiments of such immunogenic compositions the antigen is a bacterial antigen. In certain embodiments of such immunogenic compositions the bacterial antigen is an antigen of a strain of *Neisseria meningitides*. In other embodiments of such immunogenic compositions the antigen is a viral antigen or a fungal antigen. In other embodiments such immunogenic compositions further comprising an additional adjuvant. In certain embodiments of such immunogenic compositions the antigen is a polypeptide. In certain embodiments of such immunogenic compositions the polypeptide has at least 85% identity to a sequence selected from the group consisting of SEQ ID NOs: 1-6 provided herein.

DETAILED DESCRIPTION OF THE INVENTION

Definitions

Figure 1:
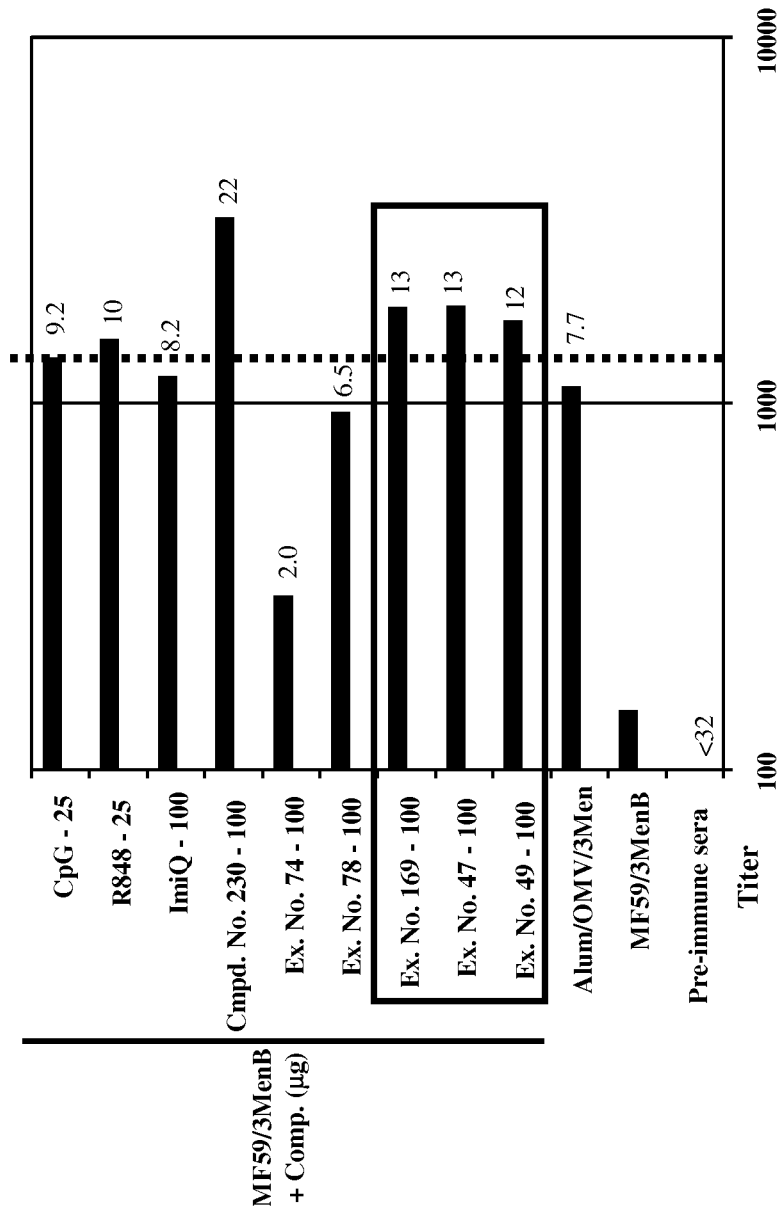
FIG. 1 shows the serum bactericidal antibody ("SBA") titer of certain compounds disclosed herein to enhance the immune response to a bacterial antigen. The dose of the compound in μg is indicated on the left, and the fold-change over the response elicited with MF59/3MenB is shown to the right of each bar. The results are compared to "CpG" (CpG oligonucleotide), R848, and Immiquimod (ImiQ).

The term "alkenyl," as used herein, refers to a partially unsaturated branched or straight chain hydrocarbon having at least one carbon-carbon double bond. Atoms oriented about the double bond are in either the cis (Z) or trans (E) conformation. An alkenyl group can be optionally substituted. As used herein, the terms "$C_2$-$C_3$alkenyl", "$C_2$-$C_4$alkenyl", "$C_2$-$C_5$alkenyl", "$C_2$-$C_6$alkenyl", "$C_2$-$C_7$alkenyl", and "$C_2$-$C_8$alkenyl" refer to an alkenyl group containing at least 2, and at most 3, 4, 5, 6, 7 or 8 carbon atoms, respectively. If not otherwise specified, an alkenyl group generally is a $C_2$-$C_6$ alkenyl. Non-limiting examples of alkenyl groups, as used herein, include ethenyl, propenyl, butenyl, pentenyl, hexenyl, heptenyl, octenyl, nonenyl, decenyl and the like.

The term "alkenylene," as used herein, refers to a partially unsaturated branched or straight chain divalent hydrocarbon radical derived from an alkenyl group. An alkenylene group can be optionally substituted. As used herein, the terms "$C_2$-$C_3$alkenylene", "$C_2$-$C_4$alkenylene", "$C_2$-$C_5$alkenylene", "$C_2$-$C_6$alkenylene", "$C_2$-$C_7$alkenylene", and "$C_2$-$C_8$alkenylene" refer to an alkenylene group containing at least 2, and at most 3, 4, 5, 6, 7 or 8 carbon atoms respectively. If not otherwise specified, an alkenylene group generally is a $C_1$-$C_6$ alkenylene. Non-limiting examples of alkenylene groups as used herein include, ethenylene, propenylene, butenylene, pentenylene, hexenylene, heptenylene, octenylene, nonenylene, decenylene and the like.

The term "alkyl," as used herein, refers to a saturated branched or straight chain hydrocarbon. An alkyl group can be optionally substituted. As used herein, the terms "$C_1$-$C_3$alkyl", "$C_1$-$C_4$alkyl", "$C_1$-$C_5$alkyl", "$C_1$-$C_6$alkyl", "$C_1$-$C_7$alkyl" and "$C_1$-$C_8$alkyl" refer to an alkyl group containing at least 1, and at most 3, 4, 5, 6, 7 or 8 carbon atoms, respectively. If not otherwise specified, an alkyl group generally is a $C_1$-$C_6$ alkyl. Non-limiting examples of alkyl groups as used herein include methyl, ethyl, n-propyl, isopropyl, n-butyl, isobutyl, sec-butyl, t-butyl, n-pentyl, isopentyl, hexyl, heptyl, octyl, nonyl, decyl and the like.

The term "alkylene," as used herein, refers to a saturated branched or straight chain divalent hydrocarbon radical derived from an alkyl group. An alkylene group can be optionally substituted. As used herein, the terms "$C_1$-$C_3$alkylene", "$C_1$-$C_4$alkylene", "$C_1$-$C_5$alkylene", "$C_1$-$C_6$alkylene", "$C_1$-$C_7$alkylene" and "$C_1$-$C_8$alkylene" refer to an alkylene group containing at least 1, and at most 3, 4, 5, 6, 7 or 8 carbon atoms respectively. If not otherwise specified, an alkylene group generally is a $C_1$-$C_6$ alkylene. Non-limiting examples of alkylene groups as used herein include, methylene, ethylene, n-propylene, isopropylene, n-butylene, isobutylene, sec-butylene, t-butylene, n-pentylene, isopentylene, hexylene and the like.

The term "alkynyl," as used herein, refers to a partially unsaturated branched or straight chain hydrocarbon having at least one carbon-carbon triple bond. An alkynyl group can be optionally substituted. As used herein, the terms "$C_2$-$C_3$alkynyl", "$C_2$-$C_4$alkynyl", "$C_2$-$C_5$alkynyl", "$C_2$-$C_6$alkynyl", "$C_2$-$C_7$alkynyl", and "$C_2$-$C_8$alkynyl" refer to an alkynyl group containing at least 2, and at most 3, 4, 5, 6, 7 or 8 carbon atoms, respectively. If not otherwise specified, an alkynyl group generally is a $C_2$-$C_6$ alkynyl. Non-limiting examples of alkynyl groups, as used herein, include ethynyl, propynyl, butynyl, pentynyl, hexynyl, heptynyl, octynyl, nonynyl, decynyl and the like.

The term "alkynylene," as used herein, refers to a partially unsaturated branched or straight chain divalent hydrocarbon radical derived from an alkynyl group. An alkynylene group can be optionally substituted. As used herein, the terms "$C_2$-$C_3$alkynylene", "$C_2$-$C_4$alkynylene", "$C_2$-$C_5$alkynylene", "$C_2$-$C_6$alkynylene", "$C_2$-$C_7$alkynylene", and "$C_2$-$C_8$alkynylene" refer to an alkynylene group containing at least 2, and at most 3, 4, 5, 6, 7 or 8 carbon atoms respectively. If not otherwise specified, an alkynylene group generally is a $C_2$-$C_6$ alkynylene. Non-limiting examples of alkynylene groups as used herein include, ethynylene, propynylene, butynylene, pentynylene, hexynylene, heptynylene, octynylene, nonynylene, decynylene and the like.

The term "alkoxy," as used herein, refers to the group —$OR_a$, where $R_a$ is an alkyl group as defined herein. An alkoxy group can be optionally substituted. As used herein, the terms "$C_1$-$C_3$alkoxy", "$C_1$-$C_4$alkoxy", "$C_1$-$C_5$alkoxy", "$C_1$-$C_6$alkoxy", "$C_1$-$C_7$alkoxy" and "$C_1$-$C_8$alkoxy" refer to an alkoxy group wherein the alkyl moiety contains at least 1, and at most 3, 4, 5, 6, 7 or 8, carbon atoms. Non-limiting examples of alkoxy groups, as used herein, include methoxy, ethoxy, n-propoxy, isopropoxy, n-butyloxy, t-butyloxy, pentyloxy, hexyloxy, heptyloxy, octyloxy, nonyloxy, decyloxy and the like.

The term "aryl," as used herein, refers to monocyclic, bicyclic, and tricyclic ring systems having a total of five to fourteen ring members, wherein at least one ring in the system is aromatic and wherein each ring in the system contains 3 to 7 ring members. An aryl group can be optionally substituted. Non-limiting examples of aryl groups, as used herein, include phenyl, naphthyl, fluorenyl, indenyl, azulenyl, anthracenyl and the like.

The term "arylene," as used means a divalent radical derived from an aryl group. An arylene group can be optionally substituted.

The term "cyano," as used herein, refers to a —CN group.

The term "cycloalkyl," as used herein, refers to a saturated or partially unsaturated, monocyclic, fused bicyclic, fused tricyclic or bridged polycyclic ring assembly. As used herein, the terms "$C_3$-$C_5$ cycloalkyl", "$C_3$-$C_6$ cycloalkyl", "$C_3$-$C_7$ cycloalkyl", "$C_3$-$C_8$ cycloalkyl, "$C_3$-$C_9$ cycloalkyl and "$C_3$-$C_{10}$ cycloalkyl refer to a cycloalkyl group wherein the saturated or partially unsaturated, monocyclic, fused bicyclic or bridged polycyclic ring assembly contain at least 3, and at most 5, 6, 7, 8, 9 or 10, carbon atoms. A cycloalkyl group can be optionally substituted. Non-limiting examples of cycloalkyl groups, as used herein, include cyclopropyl, cyclobutyl, cyclopentyl, cyclohexyl, cycloheptyl, cyclooctyl, cyclononyl, cyclodecyl, cyclopentenyl, cyclohexenyl, decahydronaphthalenyl, 2,3,4,5,6,7-hexahydro-1H-indenyl and the like.

The term "halogen," as used herein, refers to fluorine (F), chlorine (Cl), bromine (Br), or iodine (I).

The term "halo," as used herein, refers to the halogen radicals: fluoro (—F), chloro (—Cl), bromo (—Br), and iodo (—I).

The terms "haloalkyl" or "halo-substituted alkyl," as used herein, refers to an alkyl group as defined herein, substituted with one or more halogen groups, wherein the halogen groups are the same or different. A haloalkyl group can be optionally substituted. Non-limiting examples of such branched or straight chained haloalkyl groups, as used herein, include methyl, ethyl, propyl, isopropyl, isobutyl and n-butyl substituted with one or more halogen groups, wherein the halogen groups are the same or different, including, but not limited to, trifluoromethyl, pentafluoroethyl, and the like.

The terms "haloalkenyl" or "halo-substituted alkenyl," as used herein, refers to an alkenyl group as defined herein, substituted with one or more halogen groups, wherein the halogen groups are the same or different. A haloalkenyl group can be optionally substituted. Non-limiting examples of such branched or straight chained haloalkenyl groups, as used herein, include ethenyl, propenyl, butenyl, pentenyl, hexenyl, heptenyl, octenyl, nonenyl, decenyl and the like substituted with one or more halogen groups, wherein the halogen groups are the same or different.

The terms "haloalkynyl" or "halo-substituted alkynyl," as used herein, refers to an alkynyl group as defined above, substituted with one or more halogen groups, wherein the halogen groups are the same or different. A haloalkynyl group can be optionally substituted. Non-limiting examples of such branched or straight chained haloalkynyl groups, as used herein, include ethynyl, propynyl, butynyl, pentynyl, hexynyl, heptynyl, octynyl, nonynyl, decynyl, and the like substituted with one or more halogen groups, wherein the halogen groups are the same or different.

The term "haloalkoxy," as used herein, refers to an alkoxy group as defined herein, substituted with one or more halogen groups, wherein the halogen groups are the same or different. A haloalkoxy group can be optionally substituted. Non-limiting examples of such branched or straight chained haloalkynyl groups, as used herein, include methoxy, ethoxy, n-propoxy, isopropoxy, n-butyloxy, t-butyloxy, pentyloxy, hexyloxy, heptyloxy, octyloxy, nonyloxy, decyloxy and the like, substituted with one or more halogen groups, wherein the halogen groups are the same or different.

The term "heteroalkyl," as used herein, refers to an alkyl group as defined herein wherein one or more carbon atoms are independently replaced by one or more of oxygen, sulfur, nitrogen, or combinations thereof.

The term "heteroaryl," as used herein, refers to monocyclic, bicyclic, and tricyclic ring systems having a total of five to fourteen ring members, wherein at least one ring in the system is aromatic, at least one ring in the system contains one or more heteroatoms selected from nitrogen, oxygen and sulfur, and wherein each ring in the system contains 3 to 7 ring members. A heteroaryl group may contain one or more substituents. A heteroaryl group can be optionally substituted. Non-limiting examples of heteroaryl groups, as used herein, include benzofuranyl, benzofurazanyl, benzoxazolyl, benzopyranyl, benzthiazolyl, benzothienyl, benzazepinyl, benzimidazolyl, benzothiopyranyl, benzo[1,3]dioxole, benzo[b]furyl, benzo[b]thienyl, cinnolinyl, furazanyl, furyl, furopyridinyl, imidazolyl, indolyl, indolizinyl, indolin-2-one, indazolyl, isoindolyl, isoquinolinyl, isoxazolyl, isothiazolyl, 1,8-naphthyridinyl, oxazolyl, oxaindolyl, oxadiazolyl, pyrazolyl, pyrrolyl, phthalazinyl, pteridinyl, purinyl, pyridyl, pyridazinyl, pyrazinyl, pyrimidinyl, quinoxalinyl, quinolinyl, quinazolinyl, 4H-quinolizinyl, thiazolyl, thiadiazolyl, thienyl, triazinyl,triazolyl and tetrazolyl.

The term "heterocycloalkyl," as used herein, refers to a cycloalkyl, as defined herein, wherein one or more of the ring carbons are replaced by a moiety selected from —O—, —NR—, —C(O)—, —S—, —S(O)— or —S(O)2-, wherein R is hydrogen, $C_1$-$C_4$alkyl or a nitrogen protecting group, with the proviso that the ring of said group does not contain two adjacent O or S atoms. A heterocycloalkyl group can be optionally substituted. Non-limiting examples of heterocycloalkyl groups, as used herein, include morpholino, pyrrolidinyl, pyrrolidinyl-2-one, piperazinyl, piperidinyl, piperidinylone, 1,4-dioxa-8-aza-spiro[4.5]dec-8-yl, 2H-pyrrolyl, 2-pyrrolinyl, 3-pyrrolinyl, 1,3-dioxolanyl, 2-imidazolinyl, imidazolidinyl, 2-pyrazolinyl, pyrazolidinyl, 1,4-dioxanyl, 1,4-dithianyl, thiomorpholinyl, azepanyl, hexahydro-1,4-diazepinyl, tetrahydrofuranyl, dihydrofuranyl, tetrahydrothienyl, tetrahydropyranyl, dihydropyranyl, tetrahydrothiopyranyl, thioxanyl, azetidinyl, oxetanyl, thietanyl, oxepanyl, thiepanyl, 1,2,3,6-tetrahydropyridinyl, 2H-pyranyl, 4H-pyranyl, dioxanyl, 1,3-dioxolanyl, dithianyl, dithiolanyl, dihydropyranyl, dihydrothienyl, dihydrofuranyl, imidazolinyl, imidazolidinyl, 3-azabicyclo[3.1.0]hexanyl, and 3-azabicyclo[4.1.0]heptanyl.

The term "heteroatom," as used herein, refers to one or more of oxygen, sulfur, nitrogen, phosphorus, or silicon.

The term "hydroxyl," as used herein, refers to the group —OH.

The term "hydroxyalkyl," as used herein refers to an alkyl group as defined herein substituted with one or more hydroxyl group. Non-limiting examples of branched or straight chained "$C_1$-$C_6$ hydroxyalkyl groups as used herein include methyl, ethyl, propyl, isopropyl, isobutyl and n-butyl groups substituted with one or more hydroxyl groups.

The term "isocyanato," as used herein, refers to a —N═C═O group.

The term "isothiocyanato," as used herein, refers to a —N═C═S group.

The term "mercaptyl," as used herein, refers to an (alkyl)S— group.

The term "optionally substituted," as used herein, means that the referenced group may or may not be substituted with one or more additional group(s) individually and independently selected from alkyl, alkenyl, alkynyl, cycloalkyl, aryl, heteroaryl, heterocycloalkyl, hydroxyl, alkoxy, mercaptyl, cyano, halo, carbonyl, thiocarbonyl, isocyanato, thiocyanato, isothiocyanato, nitro, perhaloalkyl, perfluoroalkyl, and amino, including mono- and di-substituted amino groups, and the protected derivatives thereof. Non-limiting examples of optional substituents include, halo, —CN, ═O, ═N—OH, ═N—OR, ═N—R, —OR, —C(O)R, —C(O)OR, —OC(O)R, —OC(O)OR, —C(O)NHR, —C(O)NR$_2$, —OC(O)NHR, —OC(O)NR$_2$, —SR—, —S(O)R, —S(O)$_2$R, —NHR, —N(R)$_2$, —NHC(O)R, —NRC(O)R, —NHC(O)OR, —NRC(O)OR, S(O)$_2$NHR, —S(O)$_2$N(R)$_2$, —NHS(O)$_2$NR$_2$, —NRS(O)$_2$NR$_2$, —NHS(O)$_2$R, —NRS(O)$_2$R, $C_1$-$C_8$alkyl, $C_1$-$C_8$alkoxy, aryl, heteroaryl, cycloalkyl, heterocycloalkyl, halo-substituted $C_1$-$C_8$alkyl, and halo-substituted $C_1$-$C_8$alkoxy, where each R is independently selected from H, halo, $C_1$-$C_8$alkyl, $C_1$-$C_8$alkoxy, aryl, heteroaryl, cycloalkyl, heterocycloalkyl, halo-substituted $C_1$-$C_8$alkyl, and halo-substituted $C_1$-$C_8$alkoxy. The placement and number of such substituent groups is done in accordance with the well-understood valence limitations of each group, for example ═O is a suitable substituent for an alkyl group but not for an aryl group.

The term "solvate," as used herein, refers to a complex of variable stoichiometry formed by a solute (by way of example, a compound of Formula (I), or a salt thereof, as described herein) and a solvent. Non-limiting examples of a solvent are water, acetone, methanol, ethanol and acetic acid.

The term "acceptable" with respect to a formulation, composition or ingredient, as used herein, means having no persistent detrimental effect on the general health of the subject being treated.

The term "administration" or "administering" of the subject compound means providing a compound of Formula (I), a pharmaceutically acceptable salt, a pharmaceutically acceptable solvate, or prodrug thereof to a subject in need of treatment.

The term "cancer," as used herein refers to an abnormal growth of cells which tend to proliferate in an uncontrolled way and, in some cases, to metastasize (spread). The types of cancer include, but is not limited to, solid tumors (such as those of the bladder, bowel, brain, breast, endometrium, heart, kidney, lung, lymphatic tissue (lymphoma), ovary, pancreas or other endocrine organ (thyroid), prostate, skin (melanoma) or hematological tumors (such as the leukemias).

The term "carrier," as used herein, refers to chemical compounds or agents that facilitate the incorporation of a compound described herein into cells or tissues.

The terms "co-administration" or "combined administration" or the like as used herein are meant to encompass administration of the selected therapeutic agents to a single patient, and are intended to include treatment regimens in which the agents are not necessarily administered by the same route of administration or at the same time.

The term "dermatological disorder," as used herein refers to a skin disorder. Such dermatological disorders include, but are not limited to, proliferative or inflammatory disorders of the skin such as, atopic dermatitis, bullous disorders, collagenoses, contact dermatitis eczema, Kawasaki Disease, rosacea, Sjogren-Larsso Syndrome, actinic keratosis, basal cell carcinoma and urticaria.

The term "diluent," as used herein, refers to chemical compounds that are used to dilute a compound described herein prior to delivery. Diluents can also be used to stabilize compounds described herein.

The terms "effective amount" or "therapeutically effective amount," as used herein, refer to a sufficient amount of a compound described herein being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case may be determined using techniques, such as a dose escalation study.

The terms "enhance" or "enhancing," as used herein, means to increase or prolong either in potency or duration a desired effect. Thus, in regard to enhancing the effect of therapeutic agents, the term "enhancing" refers to the ability to increase or prolong, either in potency or duration, the effect of other therapeutic agents on a system. An "enhancing-effective amount," as used herein, refers to an amount adequate to enhance the effect of another therapeutic agent in a desired system.

The terms "fibrosis" or "fibrosing disorder," as used herein, refers to conditions that follow acute or chronic inflammation and are associated with the abnormal accumulation of cells and/or collagen and include but are not limited to fibrosis of individual organs or tissues such as the heart, kidney, joints, lung, or skin, and includes such disorders as idiopathic pulmonary fibrosis and cryptogenic fibrosing alveolitis.

The term "iatrogenic," as used herein, means a condition, disorder, or disease created or worsened by medical or surgical therapy.

The term "immunologically effective amount," as used herein, means that the administration of a sufficient amount to an individual, either in a single dose or as part of a series, that is effective for treatment or prevention of an immunological disease or disorder. This amount varies depending upon the health and physical condition of the individual to be treated, age, the taxonomic group of individual to be treated (e.g. non-human primate, primate, etc.), the capacity of the individual's immune system to synthesize antibodies, the degree of protection desired, the formulation of the vaccine, the treating doctor's assessment of the medical situation, and other relevant factors. It is expected that the amount will fall in a relatively broad range that can be determined through routine trials.

The term "inflammatory disorders," as used herein, refers to those diseases or conditions that are characterized by one or more of the signs of pain (dolor, from the generation of noxious substances and the stimulation of nerves), heat (calor, from vasodilatation), redness (rubor, from vasodilatation and increased blood flow), swelling (tumor, from excessive inflow or restricted outflow of fluid), and loss of function (functio laesa, which may be partial or complete, temporary or permanent). Inflammation takes many forms and includes, but is not limited to, inflammation that is one or more of the following: acute, adhesive, atrophic, catarrhal, chronic, cirrhotic, diffuse, disseminated, exudative, fibrinous, fibrosing, focal, granulomatous, hyperplastic, hypertrophic, interstitial, metastatic, necrotic, obliterative, parenchymatous, plastic, productive, proliferous, pseudomembranous, purulent, sclerosing, seroplastic, serous, simple, specific, subacute, suppurative, toxic, traumatic, and/or ulcerative. Inflammatory disorders further include, without being limited to those affecting the blood vessels (polyarteritis, temporal arthritis); joints (arthritis: crystalline, osteo-, psoriatic, reactive, rheumatoid, Reiter's); gastrointestinal tract (Disease); skin (dermatitis); or multiple organs and tissues (systemic lupus erythematosus).

The term "modulate," as used herein, means to interact with a target either directly or indirectly so as to alter the activity of the target, including, by way of example only, to enhance the activity of the target, to inhibit the activity of the target, to limit the activity of the target, or to extend the activity of the target.

The term "modulator," as used herein, refers to a molecule that interacts with a target either directly or indirectly. The interactions include, but are not limited to, the interactions of an agonist or an antagonist.

The terms "ocular disease" or "ophthalmic disease," as used herein, refer to diseases which affect the eye or eyes and potentially the surrounding tissues as well. Ocular or ophthalmic diseases include, but are not limited to, conjunctivitis, retinitis, scleritis, uveitis, allergic conjuctivitis, vernal conjunctivitis, papillary conjunctivitis and cytomegalovirus (CMV) retinitis.

The term "pharmaceutically acceptable," as used herein, refers a material, such as a carrier or diluent, which does not abrogate the biological activity or properties of the compounds described herein. Such materials are administered to an individual without causing undesirable biological effects or interacting in a deleterious manner with any of the components of the composition in which it is contained.

The term "pharmaceutically acceptable salt," as used herein, refers to a formulation of a compound that does not cause significant irritation to an organism to which it is administered and does not abrogate the biological activity and properties of the compounds described herein.

The terms "combination" or "pharmaceutical combination," as used herein mean a product that results from the mixing or combining of more than one active ingredient and includes both fixed and non-fixed combinations of the active ingredients. The tem "fixed combination" means that the active ingredients, by way of example, a compound of Formula (I) and an additional therapeutic agent, are both administered to a patient simultaneously in the form of a single entity or dosage. The term "non-fixed combination" means that the active ingredients, by way of example, a compound of Formula (I) and an additional therapeutic agent, are both administered to a patient as separate entities either simultaneously, concurrently or sequentially with no specific time limits, wherein such administration provides therapeutically effective levels of the 2 compounds in the body of the patient. The latter also applies to cocktail therapy, e.g. the administration of 3 or more active ingredients.

The terms "composition" or "pharmaceutical composition," as used herein, refers to a mixture of at least one compound, such as the compounds of Formula (I) described herein, with at least one and optionally more than one other pharmaceutically acceptable chemical components, such as carriers, stabilizers, diluents, dispersing agents, suspending agents, thickening agents, and/or excipients.

The term "prodrug," as used herein, refers to an agent that is converted into the parent drug in vivo. A non-limiting example of a prodrug of the compounds described herein is a compound described herein administered as an ester which is then metabolically hydrolyzed to a carboxylic acid, the active entity, once inside the cell. A further example of a prodrug is a short peptide bonded to an acid group where the peptide is metabolized to reveal the active moiety.

The term "respiratory disease," as used herein, refers to diseases affecting the organs that are involved in breathing, such as the nose, throat, larynx, trachea, bronchi, and lungs. Respiratory diseases include, but are not limited to, asthma, adult respiratory distress syndrome and allergic (extrinsic) asthma, non-allergic (intrinsic) asthma, acute severe asthma, chronic asthma, clinical asthma, nocturnal asthma, allergen-induced asthma, aspirin-sensitive asthma, exercise-induced asthma, isocapnic hyperventilation, child-onset asthma, adult-onset asthma, cough-variant asthma, occupational asthma, steroid-resistant asthma, seasonal asthma, seasonal allergic rhinitis, perennial allergic rhinitis, chronic obstructive pulmonary disease, including chronic bronchitis or emphysema, pulmonary hypertension, interstitial lung fibrosis and/or airway inflammation and cystic fibrosis, and hypoxia.

The term "subject" or "patient," as used herein, encompasses mammals and non-mammals. Examples of mammals include, but are not limited to, humans, chimpanzees, apes monkeys, cattle, horses, sheep, goats, swine; rabbits, dogs, cats, rats, mice, guinea pigs, and the like. Examples of non-mammals include, but are not limited to, birds, fish and the like. Frequently the subject is a human, and may be a human who has been diagnosed as in need of treatment for a disease or disorder disclosed herein.

The term "TLR modulator," as used herein, refers to a compound which modulates a TLR receptor.

The term "TLR disease" or a "disease or disorder associated with TLR activity," as used herein, refers to any disease state associated with a toll-like receptor. Such diseases or disorders include, but are not limited to, infectious diseases, inflammatory diseases, respiratory diseases and autoimmune diseases, such as, by way of example only, asthma, chronic obstructive pulmonary disease (COPD), adult respiratory distress syndrome (ARDs), Crohns disease, bronchitis, dermatitis, allergic rhinitis, psoriasis, scleroderma, urticaria, rheumatoid arthritis, multiple sclerosis, cancer, HIV and lupus.

The term "therapeutically effective amount," as used herein, refers to any amount of a compound which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

The terms "treat," "treating" or "treatment," as used herein, refers to methods of alleviating, abating or ameliorating a disease or condition symptoms, preventing additional symptoms, ameliorating or preventing the underlying metabolic causes of symptoms, inhibiting the disease or condition, arresting the development of the disease or condition, relieving the disease or condition, causing regression of the disease or condition, relieving a condition caused by the disease or condition, or stopping the symptoms of the disease or condition either prophylactically and/or therapeutically.

Other objects, features and advantages of the methods, compositions and combinations described herein will become apparent from the following detailed description. It should be understood, however, that the detailed description and the specific examples, while indicating specific embodiments, are given by way of illustration only.

Description of the Preferred Embodiments

Provided herein are compounds and pharmaceutical compositions thereof, which are modulators of toll-like receptors (TLRs). In certain embodiments, certain compounds described herein, and pharmaceutical compositions thereof, are agonists of toll-like receptors. In other embodiments, such compounds and pharmaceutical compositions thereof, are agonists of TLR7. In other embodiments, such compounds and pharmaceutical compositions thereof, are agonists of TLR8. In other embodiments, such compounds and pharmaceutical compositions thereof, are agonists of both TLR7 and TLR8, that is such compounds and pharmaceutical compositions thereof, are dual agonists of TLR7 and TLR8.

Provided herein are compounds, pharmaceutical compositions and methods for the treatment and/or prevention of diseases and/or disorders associated with TLR activity. In certain embodiments, such TLRs are TLR7 and TLR8.

The TLR modulators provided herein include compounds having the structure of Formula (I), and pharmaceutically acceptable salts, solvates, N-oxides, prodrugs and isomers thereof:

Provided herein are compounds, pharmaceutically acceptable salts, pharmaceutically acceptable solvates (e.g. hydrates), the N-oxide derivatives, prodrug derivatives, protected derivatives, individual isomers and mixture of isomers thereof, having the structure of Formula (I):

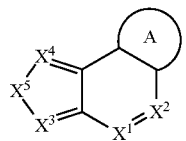

Formula (I)

wherein:
$X^1$ is N or $CN(R^1R^2)$; $X^2$ is N or $CN(R^1R^2)$, provided that when $X^1$ is $CN(R^1R^2)$ then $X^2$ is N;
$X^3$ is N or $CR^6$;
$X^4$ is N or $CR^3$; and $X^5$ is —$CR^4$=$CR^5$—, —$CR^4$=N— or —N=$CR^5$—;
$R^1$ and $R^2$ are each independently selected from H, —C(O)$R^8$, $C_1$-$C_6$alkyl, $C_1$-$C_6$heteroalkyl, $C_1$-$C_6$haloalkyl, aryl, heteroaryl, $C_3$-$C_8$cycloalkyl, and $C_3$-$C_8$heterocycloalkyl,
wherein the $C_1$-$C_6$alkyl, $C_1$-$C_6$heteroalkyl, $C_1$-$C_6$haloalkyl, $C_3$-$C_8$cycloalkyl, or $C_3$-$C_8$heterocycloalkyl groups of $R^1$ and $R^2$ are each optionally substituted with 1 to 3 substituents independently selected from halogen, —CN, =O, $C_1$-$C_6$alkyl, $C_1$-$C_6$haloalkyl, $C_1$-$C_6$alkoxy, $C_3$-$C_8$cycloalkyl, —$OR^8$, —$C(O)R^8$, —$OC(O)R^8$, —$C(O)OR^8$, —$N(R^9)_2$, —$C(O)N(R^9)_2$, $C_3$-$C_8$heterocycloalkyl, —$S(O)_2R^8$, —$S(O)_2N(R^9)_2$, —$NR^9S(O)_2R^8$, -LP(O)($OR^8$)$_2$, -LOP(O)($OR^8$)$_2$, -LP(O)($OR^{10}$)$_2$, —OLP(O)($OR^{10}$)$_2$, $C_1$-$C_6$haloalkyl and $C_1$-$C_6$haloalkoxy, and
wherein the aryl and heteroaryl groups of $R^1$ and $R^2$ are each optionally substituted with 1 to 3 substituents independently selected from halogen, —CN, $C_1$-$C_6$alkyl, $C_1$-$C_6$haloalkyl, $C_1$-$C_6$alkoxy, $C_3$-$C_8$cycloalkyl, —$OR^8$, —$C(O)R^8$, —$OC(O)R^8$, —$C(O)OR^8$, —$N(R^9)_2$, —$C(O)N(R^9)_2$, $C_3$-$C_8$heterocycloalkyl, —$S(O)_2R^8$, —$S(O)_2N(R^9)_2$, —$NR^9S(O)_2R^8$, -LP(O)($OR^8$)$_2$, -LOP(O)($OR^8$)$_2$, -LP(O)($OR^{10}$)$_2$, —OLP(O)($OR^{10}$)$_2$, $C_1$-$C_6$haloalkyl and $C_1$-$C_6$haloalkoxy,
or $R^1$ and $R^2$ are each independently $C_1$-$C_6$alkyl that can be substituted as described above and, taken together with the N atom to which they are attached, form an optionally substituted $C_3$-$C_8$heterocycloalkyl;
$R^3$ and $R^6$ are each independently selected from H, halogen, $C_1$-$C_6$alkyl, $C_2$-$C_8$alkene, $C_2$-$C_8$alkyne, $C_1$-$C_6$heteroalkyl, $C_1$-$C_6$haloalkyl, $C_1$-$C_6$alkoxy, $C_1$-$C_6$haloalkoxy, aryl, heteroaryl, $C_3$-$C_8$cycloalkyl, and $C_3$-$C_8$heterocycloalkyl,
wherein the $C_1$-$C_6$alkyl, $C_1$-$C_6$heteroalkyl, $C_1$-$C_6$haloalkyl, $C_1$-$C_6$alkoxy, $C_1$-$C_6$haloalkoxy, $C_3$-$C_8$cycloalkyl, or $C_3$-$C_8$heterocycloalkyl groups of $R^3$ and $R^6$ are each optionally substituted with 1 to 3 substituents independently selected from halogen, —CN, =O, $R^7$, —$OR^8$, —$C(O)R^8$, —$OC(O)R^8$, —$C(O)OR^8$, —$N(R^9)_2$, —$C(O)N(R^9)_2$, —$S(O)_2R^8$, —$S(O)_2N(R^9)_2$ and —$NR^9S(O)_2R^8$, and
wherein the aryl and heteroaryl groups of $R^3$ and $R^6$ are each optionally substituted with 1 to 3 substituents independently selected from halogen, —CN, $R^7$, —$OR^8$, —$C(O)R^8$, —$OC(O)R^8$, —$C(O)OR^8$, —$N(R^9)_2$, —$C(O)N(R^9)_2$, —$S(O)_2R^8$, —$S(O)_2N(R^9)_2$ and —$NR^9S(O)_2R^8$;
$R^4$ and $R^5$ are each independently selected from H, halogen, —$C(O)OR^7$, —$C(O)R^7$, —$C(O)N(R^{11}R^{12})$, —$N(R^{11}R^{12})$, —$N(R^9)_2$, —$NHN(R^9)_2$, —$SR^7$, —$(CH_2)_nOR^7$, —$(CH_2)_nR^7$, -$LR^8$, -$LR^{10}$, —$OLR^8$, —$OLR^{10}$, $C_1$-$C_6$alkyl, $C_1$-$C_6$heteroalkyl, $C_1$-$C_6$haloalkyl, $C_2$-$C_8$alkene, $C_2$-$C_8$alkyne, $C_1$-$C_6$alkoxy, $C_1$-$C_6$haloalkoxy, aryl, heteroaryl, $C_3$-$C_8$cycloalkyl, and $C_3$-$C_8$heterocycloalkyl,
wherein the $C_1$-$C_6$alkyl, $C_1$-$C_6$heteroalkyl, $C_1$-$C_6$haloalkyl, $C_2$-$C_8$alkene, $C_2$-$C_8$alkyne, $C_1$-$C_6$alkoxy, $C_1$-$C_6$haloalkoxy, $C_3$-$C_8$cycloalkyl, or $C_3$-$C_8$heterocycloalkyl groups of $R^4$ and $R^5$ are each optionally substituted with 1 to 3 substituents independently selected from halogen, —CN, =O, —$NO_2$, —$R^7$, —$OR^8$, —$C(O)R^8$, —$OC(O)R^8$, —$C(O)OR^8$, —$N(R^9)_2$, —$P(O)(OR^8)_2$, —$OP(O)(OR^8)_2$, —$P(O)(OR^{10})_2$, —$OP(O)(OR^{10})_2$, —$C(O)N(R^9)_2$, —$Si(R^8)_3$, —$S(O)_2R^8$, —$S(O)R^8$, —$S(O)_2N(R^9)_2$, and —$NR^9S(O)_2R^8$, and
wherein the aryl and heteroaryl groups of $R^4$ and $R^5$ are each optionally substituted with 1 to 3 substituents independently selected from halogen, —CN, —$R^7$, —$OR^8$, —$C(O)R^8$, —$OC(O)R^8$, —$C(O)OR^8$, —$N(R^9)_2$, —$P(O)(OR^8)_2$, —$OP(O)(OR^8)_2$, —$P(O)$ $(OR^{10})_2$, —$OP(O)(OR^{10})_2$, —$C(O)N(R^9)_2$, —$Si(R^8)_3$, —$S(O)_2R^8$, —$S(O)R^8$, —$S(O)_2N(R^9)_2$, and —$NR^9S(O)_2R^8$;

or $R^3$ and $R^4$, or $R^4$ and $R^5$, or $R^5$ and $R^6$, when present on adjacent ring atoms, can optionally be linked together to form a 5-6 membered ring, wherein the 5-6 membered ring is optionally substituted with $R^7$;

each L is independently selected from a bond, —$(O(CH_2)_m)_t$—, $C_1$-$C_6$alkyl, $C_2$-$C_6$alkenylene and $C_2$-$C_6$alkynylene, wherein the $C_1$-$C_6$alkyl, $C_2$-$C_6$alkenylene and $C_2$-$C_6$alkynylene of L are each optionally substituted with 1 to 4 substituents independently selected from halogen, —$R^8$, —$OR^8$, —$N(R^9)_2$, —$P(O)(OR^8)_2$, —$OP(O)(OR^8)_2$, —$P(O)(OR^{10})_2$, and —$OP(O)(OR^{10})_2$;

$R^7$ is selected from H, $C_1$-$C_6$alkyl, aryl, heteroaryl, $C_3$-$C_8$cycloalkyl, $C_1$-$C_6$heteroalkyl, $C_1$-$C_6$haloalkyl, $C_2$-$C_8$alkene, $C_2$-$C_8$alkyne, $C_1$-$C_6$alkoxy, $C_1$-$C_6$haloalkoxy, and $C_3$-$C_8$heterocycloalkyl, wherein the $C_1$-$C_6$alkyl, $C_3$-$C_8$cycloalkyl, $C_1$-$C_6$heteroalkyl, $C_1$-$C_6$haloalkyl, $C_2$-$C_8$alkene, $C_2$-$C_8$alkyne, $C_1$-$C_6$alkoxy, $C_1$-$C_6$haloalkoxy, or $C_3$-$C_8$heterocycloalkyl groups of $R^7$ are each optionally substituted with 1 to 3 $R^{13}$ groups, and each $R^{13}$ is independently selected from halogen, —CN, =O, -$LR^9$, -$LOR^9$, —$OLR^9$, -$LR^{10}$, -$LOR^{10}$, —$OLR^{10}$, -$LR^8$, -$LOR^8$, —$OLR^8$, -$LSR^8$, -$LSR^{10}$, -$LC(O)R^8$, —$OLC(O)R^8$, -$LC(O)OR^8$, -$LC(O)R^{10}$, -$LOC(O)OR^8$, -$LC(O)NR^9R^{11}$, -$LC(O)NR^9R^8$, -$LN(R^9)_2$, -$LNR^9R^8$, -$LNR^9R^{10}$, -$LC(O)N(R^9)_2$, -$LS(O)_2R^8$, -$LS(O)R^8$, -$LC(O)NR^8OH$, -$LNR^9C(O)R^8$, -$LNR^9C(O)R^8$, -$LC(=N—OR^8)R^8$, -$LC(=NH)$—$NHOR^8$, —$NHC(=NH)NH_2$, -$LS(O)_2N(R^9)_2$, —$OLS(O)_2N(R^9)_2$, -$LNR^9S(O)_2R^8$, -$LC(O)NR^9LN(R^9)_2$, -$LP(O)(OR^8)_2$, -$LOP(O)(OR^8)_2$, -$LP(O)(OR^{10})_2$ and) —$OLP(O)(OR^{10})_2$;

wherein the aryl and heteroaryl groups of $R^7$ are each optionally substituted with 1 to 3 $R^{13}$ groups, and each $R^{13}$ is independently selected from halogen, —CN, -$LR^9$, -$LOR^9$, —$OLR^9$, -$LR^{10}$, -$LOR^{10}$, —$OLR^{10}$, -$LR^8$, -$LOR^8$, —$OLR^8$, -$LSR^8$, -$LSR^{10}$, -$LC(O)R^8$, —$OLC(O)R^8$, -$LC(O)OR^8$, -$LC(O)R^{10}$, -$LOC(O)OR^8$, -$LC(O)NR^9R^{11}$, -$LC(O)NR^9R^8$, -$LN(R^9)_2$, -$LNR^9R^8$, -$LNR^9R^{10}$, -$LC(O)N(R^9)_2$, -$LS(O)_2R^8$, -$LS(O)R^8$, -$LC(O)NR^8OH$, -$LNR^9C(O)R^8$, -$LNR^9C(O)OR^8$, -$LC(=N—OR^8)R^8$, -$LC(=NH)$—$NHOR^8$, —$NHC(=NH)NH_2$, -$LS(O)_2N(R^9)_2$, —$OLS(O)_2N(R^9)_2$, -$LNR^9S(O)_2R^8$, -$LC(O)NR^9LN(R^9)_2$, -$LP(O)(OR^8)_2$, -$LOP(O)(OR^8)_2$, -$LP(O)(OR^{10})_2$ and -$OLP(O)(OR^{10})_2$;

each $R^8$ is independently selected from H, —$CH(R^{10})_2$, $C_1$-$C_8$alkyl, $C_2$-$C_8$alkene, $C_2$-$C_8$alkyne, $C_1$-$C_6$haloalkyl, $C_1$-$C_6$alkoxy, $C_1$-$C_6$heteroalkyl, $C_3$-$C_8$cycloalkyl, $C_2$-$C_8$heterocycloalkyl, $C_1$-$C_6$hydroxyalkyl and $C_1$-$C_6$haloalkoxy, wherein the $C_1$-$C_8$alkyl, $C_2$-$C_8$alkene, $C_2$-$C_8$alkyne, $C_1$-$C_6$heteroalkyl, $C_1$-$C_6$haloalkyl, $C_1$-$C_6$alkoxy, $C_3$-$C_8$cycloalkyl, $C_2$-$C_8$heterocycloalkyl, $C_1$-$C_6$hydroxyalkyl and $C_1$-$C_6$haloalkoxy groups of $R^8$ are each optionally substituted with 1 to 3 substituents independently selected from —CN, $R^{11}$, —$OR^{11}$, —$SR^{11}$, —$C(O)R^{11}$, —$OC(O)R^{11}$, —$C(O)N(R^9)_2$, —$C(O)OR^{11}$, —$NR^9C(O)R^{11}$, —$NR^9R^{10}$, —$NR^{11}R^{12}$, —$N(R^9)_2$, —$OR^9$, —$OR^{10}$, —$C(O)NR^{11}R^{12}$, —$C(O)NR^{11}OH$, —$S(O)_2R^{11}$, —$S(O)R^{11}$, —$S(O)_2NR^{11}R^{12}$, —$NR^{11}S(O)_2R^{11}$, —$P(O)(OR^{11})_2$, and —$OP(O)(OR^{11})_2$;

each $R^9$ is independently selected from H, —$C(O)R^8$, —$C(O)OR^8$, —$C(O)R^{10}$, —$C(O)OR^{10}$, —$Si(R^8)_3$, —$S(O)_2R^{10}$, —$C_1$-$C_6$ alkyl, $C_1$-$C_6$ heteroalkyl and $C_3$-$C_6$ cycloalkyl, or each $R^9$ is independently a $C_1$-$C_6$alkyl that together with N they are attached to form a $C_3$-$C_8$heterocycloalkyl, wherein the $C_3$-$C_8$heterocycloalkyl ring optionally contains an additional heteroatom selected from N, O and S, and wherein the $C_1$-$C_6$ alkyl, $C_1$-$C_6$ heteroalkyl, $C_3$-$C_6$ cycloalkyl, or $C_3$-$C_8$heterocycloalkyl groups of $R^9$ are each optionally substituted with 1 to 3 substituents independently selected from —CN, $R^{11}$, —$OR^{11}$, —$SR^{11}$, —$C(O)R^{11}$, —$OC(O)R^{11}$, —$C(O)OR^{11}$, —$NR^{11}R^{12}$, —$C(O)NR^{11}R^{12}$, —$C(O)NR^{11}OH$, —$S(O)_2R^{11}$, —$S(O)_2NR^{11}R^{12}$, —$NR^{11}S(O)_2R^{11}$, —$P(O)(OR^{11})_2$, and —$OP(O)(OR^{11})_2$;

each $R^{10}$ is independently selected from aryl, $C_3$-$C_8$cycloalkyl, $C_3$-$C_8$heterocycloalkyl and heteroaryl, wherein the aryl, $C_3$-$C_8$cycloalkyl, $C_3$-$C_8$heterocycloalkyl and heteroaryl groups are optionally substituted with 1 to 3 substituents selected from halogen, —$R^8$, —$OR^8$, -$LR^9$, -$LOR^9$, —$N(R^9)_2$, —$NR^9C(O)R^8$, —$NR^9CO_2R^8$, —$CO_2R^8$, —$C(O)R^8$ and —$C(O)N(R^9)_2$;

$R^{11}$ and $R^{12}$ are independently selected from H, $C_1$-$C_6$alkyl, $C_1$-$C_6$heteroalkyl, $C_1$-$C_6$haloalkyl, aryl, heteroaryl, $C_3$-$C_8$cycloalkyl, and $C_3$-$C_8$heterocycloalkyl, wherein the $C_1$-$C_6$alkyl, $C_1$-$C_6$heteroalkyl, $C_1$-$C_6$haloalkyl, $C_3$-$C_8$cycloalkyl, and $C_3$-$C_8$heterocycloalkyl groups of $R^{11}$ and $R^{12}$ are each optionally substituted with 1 to 3 substituents independently selected from halogen, —CN, =O, $R^8$, —$OR^8$, —$C(O)R^8$, ⁻$OC(O)R^8$, —$C(O)OR^8$, —$N(R^9)_2$, —$NR^8C(O)R^8$, —$NR^8C(O)OR^8$, —$C(O)N(R^9)_2$, $C_3$-$C_8$heterocycloalkyl, —$S(O)_2R^8$, —$S(O)_2N(R^9)_2$, —$NR^9S(O)_2R^8$, $C_1$-$C_6$haloalkyl and $C_1$-$C_6$haloalkoxy, and wherein the aryl and heteroaryl groups of $R^{11}$ and $R^{12}$ are each optionally substituted with 1 to 3 substituents independently selected from halogen, —CN, $R^8$, —$OR^8$, —$C(O)R^8$, —$OC(O)R^8$, —$C(O)OR^8$, —$N(R^9)_2$, —$NR^8C(O)R^8$, —$NR^8C(O)OR^8$, —$C(O)N(R^9)_2$, $C_3$-$C_8$heterocycloalkyl, —$S(O)_2R^8$, —$S(O)_2N(R^9)_2$, —$NR^9S(O)_2R^8$, $C_1$-$C_6$haloalkyl and $C_1$-$C_6$haloalkoxy, or $R^{11}$ and $R^{12}$ are each independently $C_1$-$C_6$alkyl and taken together with the N atom to which they are attached form an optionally substituted $C_3$-$C_8$heterocycloalkyl ring optionally containing an additional heteroatom selected from N, O and S;

Ring A is an aryl or a heteroaryl, wherein the aryl or heteroaryl groups of Ring A are optionally substituted with 1 to 3 $R^A$ groups, wherein each $R^A$ is independently selected from halogen, —$R^8$, —$R^7$, —$OR^7$, —$OR^8$, —$R^{10}$, —$OR^{10}$, —$SR^8$, —$NO_2$, —CN, —$N(R^9)_2$, —$NR^9C(O)R^8$, —$NR^9C(S)R^8$, —$NR^9C(O)N(R^9)_2$, —$NR^9C(S)N(R^9)_2$, —$NR^9CO_2R^8$, —$NR^9NR^9C(O)R^8$, —$NR^9NR^9C(O)N(R^9)_2$, —$NR^9NR^9CO_2R^8$, —$C(O)C(O)R^8$, —$C(O)CH_2C(O)R^8$, —$CO_2R^8$, —$(CH_2)_n$ $CO_2R^8$, $-C(O)R^8$, $-C(S)R^8$, $-C(O)N(R^9)_2$, $-C(S)N(R^9)_2$, $-OC(O)N(R^9)_2$, $-OC(O)R^8$, $-C(O)N(OR^8)R^8$, $-C(NOR^8)R^8$, $-S(O)_2R^8$, $-S(O)_3R^8$, $-SO_2N(R^9)_2$, $-S(O)R^8$, $-NR^9SO_2N(R^9)_2$, $-NR^9SO_2R^8$, $-P(O)(OR^8)_2$, $-OP(O)(OR^8)_2$, $-P(O)(OR^{10})_2$, $-OP(O)(OR^{10})_2$, $-N(OR^8)R^8$, $-CH=CHCO_2R^8$, $-C(=NH)-N(R^9)_2$, and $-(CH_2)_nNHC(O)R^8$, and two adjacent substituents on Ring A can be joined to form a 5-6 membered ring that can contain up to two heteroatoms as ring members;

n is, independently at each occurrence, 0, 1, 2, 3, 4, 5, 6, 7 or 8;

each m is independently selected from 1, 2, 3, 4, 5 and 6, and t is 1, 2, 3, 4, 5, 6, 7 or 8.

In certain embodiments compounds of Formula (I), pharmaceutically acceptable salts, pharmaceutically acceptable solvates (e.g. hydrates), the N-oxide derivatives, prodrug derivatives, protected derivatives, individual isomers and mixture of isomers thereof, have a structure of Formula (I-A),

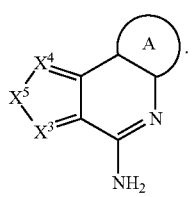

Formula (I-A)

In certain embodiments compounds of Formula (I), pharmaceutically acceptable salts, pharmaceutically acceptable solvates (e.g. hydrates), the N-oxide derivatives, prodrug derivatives, protected derivatives, individual isomers and mixture of isomers thereof, have a structure of Formula (I-B),

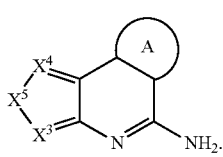

Formula (I-B)

In certain embodiments compounds of Formula (I), pharmaceutically acceptable salts, pharmaceutically acceptable solvates (e.g. hydrates), the N-oxide derivatives, prodrug derivatives, protected derivatives, individual isomers and mixture of isomers thereof, have a structure of Formula (II),

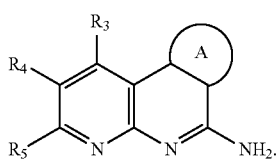

Formula (II)

In certain embodiments compounds of Formula (I), pharmaceutically acceptable salts, pharmaceutically acceptable solvates (e.g. hydrates), the N-oxide derivatives, prodrug derivatives, protected derivatives, individual isomers and mixture of isomers thereof, have a structure of Formula (III),

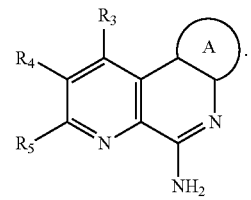

Formula (III)

In certain embodiments compounds of Formula (I), pharmaceutically acceptable salts, pharmaceutically acceptable solvates (e.g. hydrates), the N-oxide derivatives, prodrug derivatives, protected derivatives, individual isomers and mixture of isomers thereof, have a structure of Formula (IV),

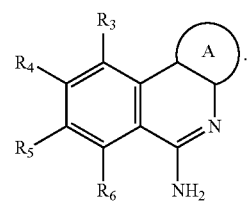

Formula (IV)

In certain embodiments compounds of Formula (I), pharmaceutically acceptable salts, pharmaceutically acceptable solvates (e.g. hydrates), the N-oxide derivatives, prodrug derivatives, protected derivatives, individual isomers and mixture of isomers thereof, have a structure of Formula (V),

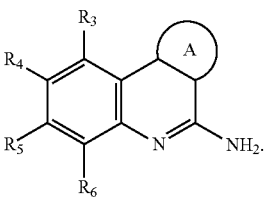

Formula (V)

In certain embodiments compounds of Formula (I), pharmaceutically acceptable salts, pharmaceutically acceptable solvates (e.g. hydrates), the N-oxide derivatives, prodrug derivatives, protected derivatives, individual isomers and mixture of isomers thereof, have a structure of Formula (VI),

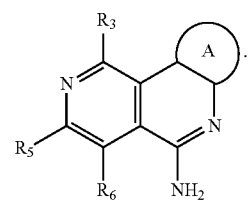

Formula (VI)

In certain embodiments compounds of Formula (I), pharmaceutically acceptable salts, pharmaceutically acceptable solvates (e.g. hydrates), the N-oxide derivatives, prodrug derivatives, protected derivatives, individual isomers and mixture of isomers thereof, have a structure of Formula (VII), Formula (VII)

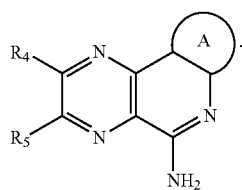

In certain embodiments compounds of Formula (I), pharmaceutically acceptable salts, pharmaceutically acceptable solvates (e.g. hydrates), the N-oxide derivatives, prodrug derivatives, protected derivatives, individual isomers and mixture of isomers thereof, have a structure of Formula (VIII), Formula (VIII)

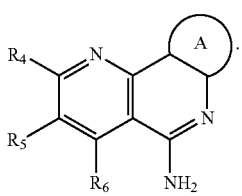

In certain embodiments compounds of Formula (I), pharmaceutically acceptable salts, pharmaceutically acceptable solvates (e.g. hydrates), the N-oxide derivatives, prodrug derivatives, protected derivatives, individual isomers and mixture of isomers thereof, have a structure of Formula (IX), Formula (IX)

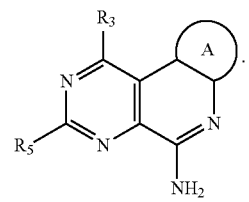

In certain embodiments of compounds of Formulas (I)-(IX), Formula (I-A) and Formula (I-B), ring A is selected from phenyl, naphthyl, fluorenyl, indenyl, azulenyl and anthracenyl, each of which is optionally substituted with 1 to 3 $R^A$ groups, wherein each $R^A$ is independently selected from —$R^8$, —$R^7$, —$OR^7$, —$OR^8$, —$R^{10}$, —$OR^{10}$, —$SR^8$, —$NO_2$, —CN, —N(R^9)_2, —NR^9C(O)R^8, —NR^9C(S)R^8, —NR^9C(O)N(R^9)_2, —NR^9C(S)N(R^9)_2, —NR^9CO_2R^8, —NR^9NR^9C(O)R^8, —NR^9NR^9C(O)N(R^9)_2, —NR^9NR^9CO_2R^8, —C(O)C(O)R^8, —C(O)CH_2C(O)R^8, —CO_2R^8, —(CH_2)_nCO_2R^8, —C(O)R^8, —C(S)R^8, —C(O)N(R^9)_2, —C(S)N(R^9)_2, —OC(O)N(R^9)_2, —OC(O)R^8, —C(O)N(OR^8)R^8, —C(NOR^8)R^8, —S(O)_2R^8, —S(O)_3R^8, —SO_2N(R^9)_2, —S(O)R^8, —NR^9SO_2N(R^9)_2, —NR^9SO_2R^8, —P(O)(OR^8)_2, —OP(O)(OR^8)_2, —P(O)(OR^{10})_2, —OP(O)(OR^{10})_2, —N(OR^8)R^8, —CH=CHCO_2R^8, —C(=NH)—N(R^9)_2, and —(CH_2)_nNHC(O)R^8. In other embodiments of compounds of Formulas (I)-(IX), Formula (I-A) and Formula (I-B), Ring A is phenyl or naphthyl, each of which is optionally substituted with 1 to 3 $R^A$ groups, wherein each $R^A$ is independently selected from —$R^8$, —$R^7$, —$OR^7$, —$OR^8$, —$R^{10}$, —$OR^{10}$, —$SR^8$, —$NO_2$, —CN, —N(R^9)_2, —NR^9C(O)R^8, —NR^9C(S)R^8, —NR^9C(O)N(R^9)_2, —NR^9C(S)N(R^9)_2, —NR^9CO_2R^8, —NR^9NR^9C(O)R^8, —NR^9NR^9C(O)N(R^9)_2, —NR^9NR^9CO_2R^8, —C(O)C(O)R^8, —C(O)CH_2C(O)R^8, —CO_2R^8, —(CH_2)_nCO_2R^8, —C(O)R^8, —C(S)R^8, —C(O)N(R^9)_2, —C(S)N(R^9)_2, —OC(O)N(R^9)_2, —OC(O)R^8, —C(O)N(OR^8)R^8, —C(NOR^8)R^8, —S(O)_2R^8, —S(O)_3R^8, —SO_2N(R^9)_2, —S(O)R^8, —NR^9SO_2N(R^9)_2, —NR^9SO_2R^8, —P(O)(OR^8)_2, —OP(O)(OR^8)_2, —P(O)(OR^{10})_2, —OP(O)(OR^{10})_2, —N(OR^8)R^8, —CH=CHCO_2R^8, —C(=NH)—N(R^9)_2, and —(CH_2)_nNHC(O)R^8.

In certain embodiments of compounds of Formulas (I)-(IX), Formula (I-A) and Formula (I-B), ring A is selected from benzofuranyl, benzofurazanyl, benzoxazolyl, benzopyranyl, benzthiazolyl, benzothienyl, benzazepinyl, benzimidazolyl, benzothiopyranyl, benzo[1,3]dioxole, benzo[b]furyl, benzo[b]thienyl, cinnolinyl, furazanyl, furyl, furopyridinyl, imidazolyl, indolyl, indolizinyl, indolin-2-one, indazolyl, isoindolyl, isoquinolinyl, isoxazolyl, isothiazolyl, 1,8-naphthyridinyl, oxazolyl, oxaindolyl, oxadiazolyl, pyrazolyl, pyrrolyl, phthalazinyl, pteridinyl, purinyl, pyridyl, pyridazinyl, pyrazinyl, pyrimidinyl, quinoxalinyl, quinolinyl, quinazolinyl, 4H-quinolizinyl, thiazolyl, thiadiazolyl, thienyl, triazinyl,triazolyl and tetrazolyl, each of which is optionally substituted with 1 to 3 $R^A$ groups, wherein each $R^A$ is independently selected from —$R^8$, —$R^7$, —$OR^7$, —$OR^8$, —$R^{10}$, —$OR^{10}$, —$SR^8$, —$NO_2$, —CN, —N(R^9)_2, —NR^9C(O)R^8, —NR^9C(S)R^8, —NR^9C(O)N(R^9)_2, —NR^9C(S)N(R^9)_2, —NR^9CO_2R^8, —NR^9NR^9C(O)R^8, —NR^9NR^9C(O)N(R^9)_2, —NR^9NR^9CO_2R^8, —C(O)C(O)R^8, —C(O)CH_2C(O)R^8, —CO_2R^8, —(CH_2)_nCO_2R^8, —C(O)R^8, —C(S)R^8, —C(O)N(R^9)_2, —C(S)N(R^9)_2, —OC(O)N(R^9)_2, —OC(O)R^8, —C(O)N(OR^8)R^8, —C(NOR^8)R^8, —S(O)_2R^8, —S(O)_3R^8, —SO_2N(R^9)_2, —S(O)R^8, —NR^9SO_2N(R^9)_2, —NR^9SO_2R^8, —P(O)(OR^8)_2, —OP(O)(OR^8)_2, —P(O)(OR^{10})_2, —OP(O)(OR^{10})_2, —N(OR^8)R^8, —CH=CHCO_2R^8, —C(=NH)—N(R^9)_2, and —(CH_2)_nNHC(O)R^8. In other embodiments of compounds of Formulas (I)-(IX), Formula (I-A) and Formula (I-B), Ring A is selected from pyridyl, benzo[1,3]dioxole, thienyl, benzothienyl, benzofuranyl, or indolyl, each of which is optionally substituted with 1 to 3 $R^A$ groups, wherein each $R^A$ is independently selected from —$R^8$, —$R^7$, —$OR^7$, —$OR^8$, —$R^{10}$, —$OR^{10}$, —$SR^8$, —$NO_2$, —CN, —N(R^9)_2, —NR^9C(O)R^8, —NR^9C(S)R^8, —NR^9C(O)N(R^9)_2, —NR^9C(S)N(R^9)_2, —NR^9CO_2R^8, —NR^9NR^9C(O)R^8, —NR^9NR^9C(O)N(R^9)_2, —NR^9NR^9CO_2R^8, —C(O)C(O)R^8, —C(O)CH_2C(O)R^8, —CO_2R^8, —(CH_2)_nCO_2R^8, —C(O)R^8, —C(S)R^8, —C(O)N(R^9)_2, —C(S)N(R^9)_2, —OC(O)N(R^9)_2, —OC(O)R^8, —C(O)N(OR^8)R^8, —C(NOR^8)R^8, —S(O)_2R^8, —S(O)_3R^8, —SO_2N(R^9)_2, —S(O)R^8, —NR^9SO_2N(R^9)_2, —NR^9SO_2R^8, —P(O)(OR^8)_2, —OP(O)(OR^8)_2, —P(O)(OR^{10})_2, —OP(O)(OR^{10})_2, —N(OR^8)R^8, —CH=CHCO_2R^8, —C(=NH)—N(R^9)_2, and —(CH_2)_nNHC(O)R^8.

In certain embodiments of compounds of Formulas (I)-(IX), Formula (I-A) and Formula (I-B), Ring A is selected from phenyl, thienyl, and pyridyl, and in other embodiments such phenyl, thienyl, and pyridyl groups are optionally substituted with 1 to 3 $R^A$ groups, wherein each $R^A$ is independently selected from —$R^8$, —$R^7$, —$OR^7$, —$OR^8$, —$R^{10}$, —$OR^{10}$, —$SR^8$, —$NO_2$, —CN, —N(R^9)_2, —NR^9C(O)R^8, —NR^9C(S)R^8, —NR^9C(O)N(R^9)_2, —NR^9C(S)N(R^9)_2, —NR^9CO_2R^8, —NR^9NR^9C(O)R^8, —NR^9NR^9C(O)N(R^9)_2, —NR⁹NR⁹CO₂R⁸, —C(O)C(O)R⁸, —C(O)CH₂C(O)R⁸, —CO₂R⁸, —(CH₂)ₙCO₂R⁸, —C(O)R⁸, —C(S)R⁸, —C(O)N(R⁹)₂, —C(S)N(R⁹)₂, —OC(O)N(R⁹)₂, —OC(O)R⁸, —C(O)N(OR⁸)R⁸, —C(NOR⁸)R⁸, —S(O)₂R⁸, —S(O)₃R⁸, —SO₂N(R⁹)₂, —S(O)R⁸, —NR⁹SO₂N(R⁹)₂, —NR⁹SO₂R⁸, —P(O)(OR⁸)₂, —OP(O)(OR⁸)₂, —P(O)(OR¹⁰)₂, —OP(O)(OR¹⁰)₂, —N(OR⁸)R⁸, —CH=CHCO₂R⁸, —C(=NH)—N(R⁹)₂, and —(CH₂)ₙNHC(O)R⁸.

In certain embodiments of compounds of Formulas (I)-(IX), Formula (I-A) and Formula (I-B), Ring A is a phenyl optionally substituted with 1 to 3 R^A groups, wherein each R^A is independently selected from —R⁸, —R⁷, —OR⁷, —OR⁸, —R¹⁰, —OR¹⁰, —SR⁸, —NO₂, —CN, —N(R⁹)₂, —NR⁹C(O)R⁸, —NR⁹C(S)R⁸, —NR⁹C(O)N(R⁹)₂, —NR⁹C(S)N(R⁹)₂, —NR⁹CO₂R⁸, —NR⁹NR⁹C(O)R⁸, —NR⁹NR⁹C(O)N(R⁹)₂, —NR⁹NR⁹CO₂R⁸, —C(O)C(O)R⁸, —C(O)CH₂C(O)R⁸, —CO₂R⁸, —(CH₂)ₙCO₂R⁸, —C(O)R⁸, —C(S)R⁸, —C(O)N(R⁹)₂, —C(S)N(R⁹)₂, —OC(O)N(R⁹)₂, —OC(O)R⁸, —C(O)N(OR⁸)R⁸, —C(NOR⁸)R⁸, —S(O)₂R⁸, —S(O)₃R⁸, —SO₂N(R⁹)₂, —S(O)R⁸, —NR⁹SO₂N(R⁹)₂, —NR⁹SO₂R⁸, —P(O)(OR⁸)₂, —OP(O)(OR⁸)₂, —P(O)(OR¹⁰)₂, —OP(O)(OR¹⁰)₂, —N(OR⁸)R⁸, —CH=CHCO₂R⁸, —C(=NH)—N(R⁹)₂, and —(CH₂)ₙNHC(O)R⁸. In certain embodiments of compounds of Formulas (I)-(IX), Formula (I-A) and Formula (I-B), Ring A is a pyridyl optionally substituted with 1 to 3 R^A groups, wherein each R^A is independently selected from —R⁸, —R⁷, —OR⁷, —OR⁸, —R¹⁰, —OR¹⁰, —SR⁸, —NO₂, —CN, —N(R⁹)₂, —NR⁹C(O)R⁸, —NR⁹C(S)R⁸, —NR⁹C(O)N(R⁹)₂, —NR⁹C(S)N(R⁹)₂, —NR⁹CO₂R⁸, —NR⁹NR⁹C(O)R⁸, —NR⁹NR⁹C(O)N(R⁹)₂, —NR⁹NR⁹CO₂R⁸, —C(O)C(O)R⁸, —C(O)CH₂C(O)R⁸, —CO₂R⁸, —(CH₂)ₙCO₂R⁸, —C(O)R⁸, —C(S)R⁸, —C(O)N(R⁹)₂, —C(S)N(R⁹)₂, —OC(O)N(R⁹)₂, —OC(O)R⁸, —C(O)N(OR⁸)R⁸, —C(NOR⁸)R⁸, —S(O)₂R⁸, —S(O)₃R⁸, —SO₂N(R⁹)₂, —S(O)R⁸, —NR⁹SO₂N(R⁹)₂, —NR⁹SO₂R⁸, —P(O)(OR⁸)₂, —OP(O)(OR⁸)₂, —P(O)(OR¹⁰)₂, —OP(O)(OR¹⁰)₂, —N(OR⁸)R⁸, —CH=CHCO₂R⁸, —C(=NH)—N(R⁹)₂, and —(CH₂)ₙNHC(O)R⁸.

In certain embodiments compounds of Formula (I), pharmaceutically acceptable salts, pharmaceutically acceptable solvates (e.g. hydrates), the N-oxide derivatives, prodrug derivatives, protected derivatives, individual isomers and mixture of isomers thereof, have a structure of Formula (X),

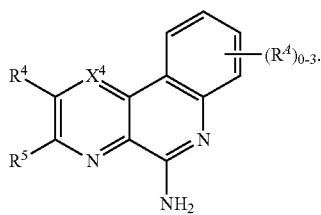

Formula (X)

In certain embodiments compounds of Formula (X), pharmaceutically acceptable salts, pharmaceutically acceptable solvates (e.g. hydrates), the N-oxide derivatives, prodrug derivatives, protected derivatives, individual isomers and mixture of isomers thereof, have a structure of Formula (X-A),

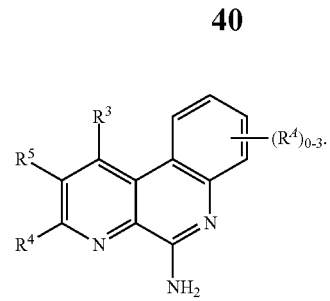

Formula (X-A)

In certain embodiments compounds of Formula (I), pharmaceutically acceptable salts, pharmaceutically acceptable solvates (e.g. hydrates), the N-oxide derivatives, prodrug derivatives, protected derivatives, individual isomers and mixture of isomers thereof, have a structure of Formula (XI),

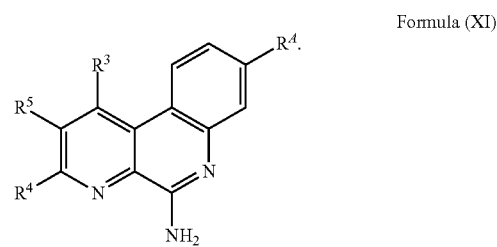

Formula (XI)

In certain embodiments compounds of Formula (I), pharmaceutically acceptable salts, pharmaceutically acceptable solvates (e.g. hydrates), the N-oxide derivatives, prodrug derivatives, protected derivatives, individual isomers and mixture of isomers thereof, have a structure of Formula (XII) or Formula (XIII),

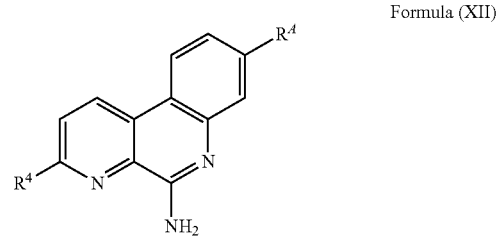

Formula (XII)

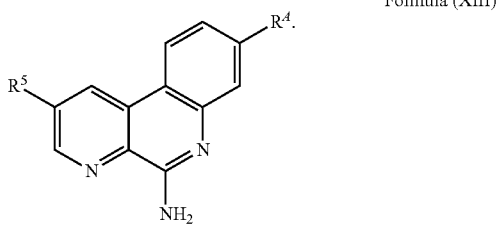

Formula (XIII)

In certain embodiments of compounds of Formulas (I), (I-A), (I-B) and (II)-(XIII), R⁴ and R⁵, when present, are independently selected from H, halogen, —C(O)OR⁷, —C(O)R⁷, —C(O)N(R¹¹R¹²), —N(R¹¹R¹²), —N(R⁹)₂, —NHN(R⁹)₂, —SR⁷, —(CH₂)ₙOR⁷, —(CH₂)ₙR⁷, -LR⁸, -LR¹⁰, —OLR⁸, —OLR¹⁰, C₁-C₆alkyl, C₁-C₆heteroalkyl, C₁-C₆haloalkyl, C₂-C₈alkene, C₂-C₈alkyne, C₁-C₆alkoxy, C₁-C₆haloalkoxy, aryl, heteroaryl, C₃-C₈cycloalkyl, and C₃-C₈heterocycloalkyl, wherein the C₁-C₆alkyl, C₁-C₆heteroalkyl, C₁-C₆haloalkyl, C₂-C₈alkene, $C_2$-$C_8$alkyne, $C_1$-$C_6$alkoxy, $C_1$-$C_6$haloalkoxy, $C_3$-$C_8$cycloalkyl, or $C_3$-$C_8$heterocycloalkyl groups of $R^4$ and $R^5$ are each optionally substituted with 1 to 3 substituents independently selected from halogen, —CN, =O, —NO$_2$, —$R^7$, —$OR^8$, —$C(O)R^8$, —$OC(O)R^8$, —$C(O)OR^8$, —$N(R^9)_2$, —$P(O)(OR^8)_2$, —$OP(O)(OR^8)_2$, —$P(O)(OR^{10})_2$, —$OP(O)(OR^{10})_2$, —$C(O)N(R^9)_2$, —$Si(R^8)_3$, —$S(O)_2R^8$, —$S(O)R^8$, —$S(O)_2N(R^9)_2$, and —$NR^9S(O)_2R^8$, and wherein the aryl and heteroaryl groups of $R^4$ and $R^5$ are each optionally substituted with 1 to 3 substituents independently selected from halogen, —CN, —$R^7$, —$OR^8$, —$C(O)R^8$, —$OC(O)R^8$, —$C(O)OR^8$, —$N(R^9)_2$, —$P(O)(OR^8)_2$, —$OP(O)(OR^8)_2$, —$P(O)(OR^{10})_2$, —$OP(O)(OR^{10})_2$, —$C(O)N(R^9)_2$, —$Si(R^8)_3$, —$S(O)_2R^8$, —$S(O)R^8$, —$S(O)_2N(R^9)_2$, and —$NR^9S(O)_2R^8$. In other embodiments, $R^3$ and $R^4$, or $R^4$ and $R^5$, or $R^5$ and $R^6$, when present on adjacent ring atoms, can optionally be linked together to form a 5-6 membered ring, wherein the 5-6 membered ring is optionally substituted with $R^7$.

In certain embodiments of compounds of Formulas (I), (I-A), (I-B) and (II)-(XIII), each L is independently selected from a bond, —$(O(CH_2)_m)_t$—, $C_1$-$C_6$alkyl, $C_2$-$C_6$alkenylene and $C_2$-$C_6$alkynylene, wherein the $C_1$-$C_6$alkyl, $C_2$-$C_6$alkenylene and $C_2$-$C_6$alkynylene of L are each optionally substituted with 1 to 4 substituents independently selected from halogen, —$R^8$, —$OR^8$, —$N(R^9)_2$, —$P(O)(OR^8)_2$, —$OP(O)(OR^8)_2$, —$P(O)(OR^{10})_2$, and —$OP(O)(OR^{10})_2$.

In certain embodiments of compounds of Formulas (I), (I-A), (I-B) and (II)-(XIII), $R^4$ and $R^5$, when present, are independently selected from H, halogen, —$C(O)OR^7$, —$C(O)R^7$, —$C(O)N(R^{11}R^{12})$, —$N(R^{11}R^{12})$, —$N(R^9)_2$, —$NHN(R^9)_2$, —$SR^7$, —$(CH_2)_nOR^7$, —$(CH_2)_nR^7$, -$LR^8$, -$LR^{10}$, —$OLR^8$, —$OLR^{10}$, $C_1$-$C_6$alkyl, $C_1$-$C_6$heteroalkyl, $C_1$-$C_6$haloalkyl, $C_2$-$C_8$alkene, $C_2$-$C_8$alkyne, $C_1$-$C_6$alkoxy, $C_1$-$C_6$haloalkoxy, aryl, heteroaryl, $C_3$-$C_8$cycloalkyl, and $C_3$-$C_8$heterocycloalkyl, wherein the $C_1$-$C_6$alkyl, $C_1$-$C_6$heteroalkyl, $C_1$-$C_6$haloalkyl, $C_2$-$C_8$alkene, $C_2$-$C_8$alkyne, $C_1$-$C_6$alkoxy, $C_1$-$C_6$haloalkoxy, $C_3$-$C_8$cycloalkyl, $C_3$-$C_8$heterocycloalkyl, aryl and heteroaryl groups of $R^4$ and $R^5$ are each optionally substituted with 1 to 3 $R^7$.

In certain embodiments compounds of Formula (I), pharmaceutically acceptable salts, pharmaceutically acceptable solvates (e.g. hydrates), the N-oxide derivatives, prodrug derivatives, protected derivatives, individual isomers and mixture of isomers thereof, have a structure of Formula (XIV),

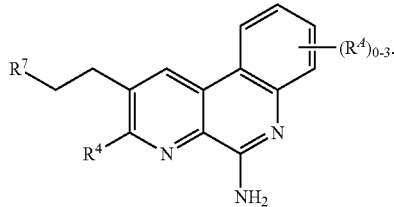

Formula (XIV)

In certain embodiments of compounds of Formulas (I), (I-A), (I-B) and (II)-(XIV), $R^7$ is selected from H, $C_1$-$C_6$alkyl, $C_3$-$C_8$cycloalkyl, $C_1$-$C_6$heteroalkyl, $C_1$-$C_6$haloalkyl, $C_2$-$C_8$alkene, $C_2$-$C_8$alkyne, $C_1$-$C_6$alkoxy, $C_1$-$C_6$haloalkoxy, and $C_3$-$C_8$heterocycloalkyl, wherein the $C_1$-$C_6$alkyl, $C_3$-$C_8$cycloalkyl, $C_1$-$C_6$heteroalkyl, $C_1$-$C_6$haloalkyl, $C_2$-$C_8$alkene, $C_2$-$C_8$alkyne, $C_1$-$C_6$alkoxy, $C_1$-$C_6$haloalkoxy, and $C_3$-$C_8$heterocycloalkyl groups of $R^7$ are each optionally substituted with 1 to 3 $R^{13}$ groups and each $R^{13}$ is independently selected from halogen —CN, =O, -$LR^9$, -$LOR^9$, —$OLR^9$, -$LR^{10}$, -$LOR^{10}$, —$OLR^{10}$, -$LR^8$, -$LOR^8$, —$OLR^8$, -$LSR^8$, -$LSR^{10}$, -$LC(O)R^8$, —$OLC(O)R^8$, -- $LC(O)OR^8$, -$LC(O)R^{10}$, -$LOC(O)R^8$, -$LC(O)NR^9R^{11}$, -$LC(O)NR^9R^8$, -$LN(R^9)_2$, -$LNR^9R^8$, -$LNR^9R^{10}$, -$LC(O)N(R^9)_2$, -$LS(O)_2R^8$, -$LS(O)R^8$, -$LC(O)NR^8OH$, -$LNR^9C(O)R^8$, -$LNR^9C(O)OR^8$, -$LC(=N-OR^8)R^8$, -$LC(=NH)-NHOR^8$, —$NHC(=NH)NH_2$, -$LS(O)_2N(R^9)_2$, —$OLS(O)_2N(R^9)_2$, -$LNR^9S(O)_2R^8$, -$LC(O)NR^9LN(R^9)_2$, -$LP(O)(OR^8)_2$, -$LOP(O)(OR^8)_2$, -$LP(O)(OR^{10})_2$ and —$OLP(O)(OR^{10})_2$.

In certain embodiments of compounds of Formulas (I), (I-A), (I-B) and (II)-(XIV), $R^7$ is an aryl or heteroaryl group optionally substituted with 1 to 3 $R^{13}$ groups and each $R^{13}$ is independently selected from halogen, —CN, -$LR^9$, -$LOR^9$, —$OLR^9$, -$LR^{10}$, -$LOR^{10}$, —$OLR^{10}$, -$LR^8$, -$LOR^8$, —$OLR^8$, -$LSR^8$, -$LSR^{10}$, -$LC(O)R^8$, —$OLC(O)R^8$, -$LC(O)OR^8$, -$LC(O)R^{10}$, -$LOC(O)R^8$, -$LC(O)NR^9R^{11}$, -$LC(O)NR^9R^8$, -$LN(R^9)_2$, -$LNR^9R^8$, -$LNR^9R^{10}$, -$LC(O)N(R^9)_2$, -$LS(O)_2R^8$, -$LS(O)R^8$, -$LC(O)NR^8OH$, -$LNR^9C(O)R^8$, -$LNR^9C(O)OR^8$, -$LC(=N-OR^8)R^8$, -$LC(=NH)-NHOR^8$, —$NHC(=NH)NH_2$, -$LS(O)_2N(R^9)_2$, —$OLS(O)_2N(R^9)_2$, -$LNR^9S(O)_2R^8$, -$LC(O)NR^9LN(R^9)_2$, -$LP(O)(OR^8)_2$, -$LOP(O)(OR^8)_2$, -$LP(O)(OR^{10})_2$ and —$OLP(O)(OR^{10})_2$.

In certain embodiments of compounds of Formulas (I), (I-A), (I-B) and (II)-(XIV), $R^7$ is selected from H, $C_1$-$C_6$alkyl, $C_3$-$C_8$cycloalkyl, and $C_3$-$C_8$heterocycloalkyl, and the $C_1$-$C_6$alkyl, $C_3$-$C_8$cycloalkyl, and $C_3$-$C_8$heterocycloalkyl groups are each optionally substituted with 1-3 $R^{13}$ groups and each $R^{13}$ is independently selected from halogen, =O, $C_1$-$C_6$haloalkyl, $LR^8$, $LR^9$, $OLR^8$ and -$LOR^8$.

In certain embodiments of compounds of Formulas (I), (I-A), (I-B) and (II)-(XIV), $R^7$ is an aryl or heteroaryl group optionally substituted with 1-3 $R^{13}$ groups and each $R^{13}$ is independently selected from halogen, $C_1$-$C_6$haloalkyl, $LR^8$, $LR^9$, $OLR^8$ and -$LOR^8$.

In certain embodiments of compounds of Formulas (I), (I-A), (I-B) and (II)-(XIV), each L is independently selected from a bond, —$(O(CH_2)_m)_t$—, $C_1$-$C_6$alkyl, $C_2$-$C_6$alkenylene and $C_2$-$C_6$alkynylene, wherein the $C_1$-$C_6$alkyl, $C_2$-$C_6$alkenylene and $C_2$-$C_6$alkynylene of L are each optionally substituted with 1 to 4 substituents independently selected from halogen, —$R^8$, —$OR^8$, —$N(R^9)_2$, —$P(O)(OR^8)_2$, —$OP(O)(OR^8)_2$, —$P(O)(OR^{10})_2$, and —$OP(O)(OR^{10})_2$.

In certain embodiments compounds of Formula (I), pharmaceutically acceptable salts, pharmaceutically acceptable solvates (e.g. hydrates), the N-oxide derivatives, prodrug derivatives, protected derivatives, individual isomers and mixture of isomers thereof, have a structure of Formula (XV),

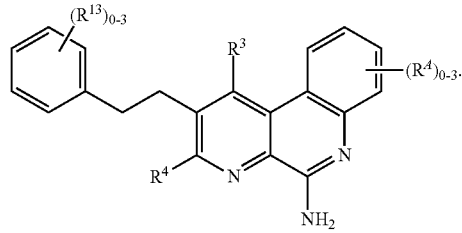

Formula (XV)

In certain embodiments compounds of Formula (I), pharmaceutically acceptable salts, pharmaceutically acceptable solvates (e.g. hydrates), the N-oxide derivatives, prodrug derivatives, protected derivatives, individual isomers and mixture of isomers thereof, have a structure of Formula (XVI),

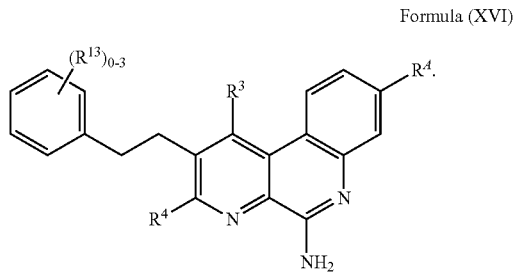

Formula (XVI)

In certain compounds of Formula (XV) or (XVI), $R^4$, $R^A$ and $R^{13}$ are independently selected from H, —$CH_3$, —$CH_2CH_3$, —$CF_3$, —$CH_2OH$, —$OCH_3$, —$COOCH_3$, —$COOCH_2CH_3$, F, Cl, Br, —$CH_2OCH_3$, $CH_2OCH_2CH_3$, —$N(CH_3)_2$, —$((O(CH_2)_2)_{2-4}OH$, —$O(CH_2)_{2-4}$—OH, —$O(CH_2)_{2-4}$—$(PO_3H_2)$, —$O(CH_2)_{2-4}$—COOH, —$O(CH_2)_{2-4}$—$CH(CH_3)_2$, $C_2$-$C_6$ alkyl substituted with 1-3 substituents selected from —OH, —$CH_3$, cyclopropyl, —$O(CH_2)_{2-4}$—COOH, —$O(CH_2)_{2-4}(PO_3H_2)$, —COOH, $COOCH_3$, and —$COOCH_2CH_3$. In some embodiments of such compounds, $R^4$ is H. In certain of these compounds, the phenyl ring of the phenethyl group has one to three $R^{13}$ groups. Optionally, $R^A$ is H or —$CH_3$. In certain embodiments, these compounds have two $R^{13}$ groups present, and those $R^{13}$ groups are selected from the group consisting of of —$CH_3$, —$CH_2CH_3$, —$CF_3$, —$CH_2OH$, —$OCH_3$, —$COOCH_3$, —$COOCH_2CH_3$, F, Cl, Br, —$CH_2OCH_3$, —$CH_2OCH_2CH_3$, —$N(CH_3)_2$, —$((O(CH_2)_2)_{2-4}OH$, —$O(CH_2)_{2-4}$—OH, —$O(CH_2)_{2-4}$—$(PO_3H_2)$, —$O(CH_2)_{2-4}$—COOH, —$O(CH_2)_{2-4}$—$CH(CH_3)_2$, $C_2$-$C_6$ alkyl substituted with 1-3 substituents selected from —OH, —$CH_3$, cyclopropyl, —$O(CH_2)_{2-4}$—COOH, —$O(CH_2)_{2-4}$ $(PO_3H_2)$, —COOH, $COOCH_3$, and —$COOCH_2CH_3$.

In certain embodiments of the compounds of Formula XIII, XIV, XV or XVI, the compound is selected from: 2-(4-(2-(5-amino-8-methylbenzo[f][1,7]naphthyridin-2-yl)ethyl)-3-methylphenyl)propan-2-ol; 2-(4-methoxy-2-methylphenethyl)-8-methylbenzo[f][1,7]naphthyridin-5-amine; 2-(2,4-dimethylphenethyl)benzo[f][1,7]naphthyridin-5-amine; ethyl 4-(2-(5-amino-8-methylbenzo[f][1,7]naphthyridin-2-yl)ethyl)-3-methylbenzoate; 2-(4-(dimethylamino)phenethyl)-8-methylbenzo[f][1,7]naphthyridin-5-amine; and 2-(4-methoxyphenethyl)-8-methylbenzo[f][1,7]naphthyridin-5-amine. Each of these compounds individually comprises a preferred embodiment of the compounds, compositions, and methods described herein.

In certain embodiments compounds of Formula (I) as described herein are combined with an antigen, and optionally a carrier, pharmaceutically acceptable excipient or adjuvant, to provide an immunogenic composition. In certain embodiments compounds of Formula (XVI) as described herein are combined with an antigen, and optionally a carrier, pharmaceutically acceptable excipient or adjuvant, to provide an immunogenic composition. In other embodiments, such immunogenic composition comprise a compound of Formula (I) and an antigen, wherein the antigen includes, but is not limited to, a bacterial antigen, a viral antigen, a fungal antigen, a tumor antigen, or an antigen associated with an STD, Alzheimer's, respiratory disorders, autoimmune disorders such as, by way of example only, rheumatoid arthritis or lupus, pediatric disorders and obesity, and wherein the amount of the compound is an amount effective to enhance an immune response to the antigen in a subject to whom the composition is administered. In other embodiments, such immunogenic composition comprise a compound of Formula (XVI) and an antigen, wherein the antigen includes, but is not limited to, a bacterial antigen, a viral antigen, a fungal antigen, a tumor antigen, or an antigen associated with an STD, Alzheimer's, respiratory disorders, autoimmune disorders such as, by way of example only, rheumatoid arthritis or lupus, pediatric disorders and obesity, and wherein the amount of the compound is an amount effective to enhance an immune response to the antigen in a subject to whom the composition is administered. Suitable antigens for use in such immunogenic compositions are described herein.

In certain embodiments, such immunogenic compositions include a bacterial antigen of a strain of *Neisseria meningitides*, such as serogroup A, C, W135, Y and/or B. Specific antigens for use in these compositions are described herein. In other embodiments, such immunogenic compositions, and others provided herein, are used as vaccines; their use in the treatment of disorders associated with the antigen included in the composition is described herein.

In certain embodiments of compounds of Formulas (I), (I-A), (I-B) and (II)-(XVI), each $R^{13}$ is independently selected from $LR^{10}$, $LOR^{10}$, $LR^8$, -$LOR^8$, -$LSR^8$, $LSR^{10}$, -$LC(O)R^8$, -$LN(R^9)_2$, -$LC(O)N(R^9)_2$, -$LS(O)_2R^8$, -$LS(O)R^8$, -$LP(O)(OR^8)_2$, —$OLP(O)(OR^8)_2$, -$LP(O)(OR^{10})_2$ and —$OLP(O)(OR^{10})_2$.

In certain embodiments of compounds of Formulas (I), (I-A), (I-B) and (II)-(XVI), each L is independently selected from a bond, —$(O(CH_2)_m)_t$—, $C_1$-$C_6$alkyl, $C_2$-$C_6$alkenylene and $C_2$-$C_6$alkynylene, wherein the $C_1$-$C_6$alkyl, $C_2$-$C_6$alkenylene and $C_2$-$C_6$alkynylene of L are each optionally substituted with 1 to 4 substituents independently selected from halogen, —$R^8$, —$OR^8$, —$N(R^9)_2$, —$P(O)(OR^8)_2$, —$OP(O)(OR^8)_2$, —$P(O)(OR^{10})_2$, and —$OP(O)(OR^{10})_2$.

In certain embodiments of compounds of Formulas (I), (I-A), (I-B) and (II)-(XVI), $R^1$ and $R^2$ are each H.

In certain embodiments of compounds of Formulas (I), (I-A), (I-B) and (II)-(XVI), $R^3$ and $R^6$, when present, are independently selected from H, halogen, $C_1$-$C_6$alkyl, $C_2$-$C_8$alkene, $C_2$-$C_8$alkyne and $C_1$-$C_6$alkoxy.

In certain embodiments of compounds of Formulas (I), (I-A), (I-B) and (II)-(XVI), $R^{10}$ is an aryl or a heteroaryl, wherein the aryl and heteroaryl groups are optionally substituted with 1 to 3 substituents selected from halogen, —$R^8$, —$OR^8$, $LR^9$ and —$N(R^9)_2$. In other embodiments of compounds of Formulas (I), (I-A), (I-B) and (II)-(XVI), $R^{10}$ is phenyl optionally substituted with 1 to 3 substituents selected from halogen, —$R^8$, —$OR^8$, and —$N(R^9)_2$.

In certain embodiments of compounds of Formulas (I), (I-A), (I-B) and (II)-(XIII), $R^8$ is selected from H, $C_1$-$C_6$alkyl and $C_1$-$C_6$haloalkyl.

In certain embodiments the compound of Formulas (I) is 3-chloro-2-methylbenzo[f][1,7]naphthyridin-5-amine; 2-methylbenzo[f][1,7]naphthyridin-5-amine; pyrimido[4,5-c]quinolin-5-amine; 2-(ethoxymethyl)benzo[f][1,7]naphthyridin-5-amine; pyrimido[4,5-c]quinoline-3,5-diamine; 3-(methylthio)pyrimido[4,5-c]quinolin-5-amine; (E)-2-(2-cyclopropylvinyl)benzo[f][1,7]naphthyridin-5-amine; (E)-2-(pent-1-enyl)benzo[f][1,7]naphthyridin-5-amine; 4-(5-aminobenzo[f][1,7]naphthyridin-2-yl)-2-methylbut-3-yn-2- ol; 2-pentylbenzo[f][1,7]naphthyridin-5-amine; (E)-2-(prop-1-enyl)benzo[f][1,7]naphthyridin-5-amine; (E)-2-(3-phenylprop-1-enyl)benzo[f][1,7]naphthyridin-5-amine; 2-(2-cyclopropylethyl)benzo[f][1,7]naphthyridin-5-amine; 4-(5-aminobenzo[f][1,7]naphthyridin-2-yl)-2-methylbutan-2-ol; 2-propylbenzo[f][1,7]naphthyridin-5-amine; 2-(3-phenylpropyl)benzo[f][1,7]naphthyridin-5-amine; 2-ethylbenzo[f][1,7]naphthyridin-5-amine; 2-(2-methylprop-1-enyl)benzo[f][1,7]naphthyridin-5-amine; 2-isobutylbenzo[f][1,7]naphthyridin-5-amine; (E)-2-(2,4-difluorostyryl)benzo[f][1,7]naphthyridin-5-amine; (E)-2-(hex-1-enyl)benzo[f][1,7]naphthyridin-5-amine; (E)-2-(2-cyclohexylvinyl)benzo[f][1,7]naphthyridin-5-amine; E)-2-(3-(trifluoromethyl)styryl)benzo[f][1,7]naphthyridin-5-amine; (E)-2-(3-methoxystyryl)benzo[f][1,7]naphthyridin-5-amine; 8-methyl-2-vinylbenzo[f][1,7]naphthyridin-5-amine; (E)-8-methyl-2-styrylbenzo[f][1,7]naphthyridin-5-amine; 2-(2-cyclohexylethyl)benzo[f][1,7]naphthyridin-5-amine; 2-fluorobenzo[f][1,7]naphthyridin-5-amine; 2-(3-(trifluoromethyl)phenethyl)benzo[f][1,7]naphthyridin-5-amine; 2-(2,4-difluorophenethyl)benzo[f][1,7]naphthyridin-5-amine; 2-(3-methoxyphenethyl)benzo[f][1,7]naphthyridin-5-amine; 2-hexylbenzo[f][1,7]naphthyridin-5-amine; 2-ethyl-8-methylbenzo[f][1,7]naphthyridin-5-amine; 8-methylbenzo[f][1,7]naphthyridin-5-amine; 8-methyl-2-phenethylbenzo[f][1,7]naphthyridin-5-amine; methyl 5-aminobenzo[f][1,7]naphthyridine-3-carboxylate; 5-amino-N-methylbenzo[f][1,7]naphthyridine-3-carboxamide; (5-aminobenzo[f][1,7]naphthyridin-3-yl)methanol; 8-phenylbenzo[f][1,7]naphthyridin-5-amine; 3-(ethoxymethyl)benzo[f][1,7]naphthyridin-5-amine; benzo[f][1,7]naphthyridine-3,5-diamine; benzo[f][1,7]naphthyridin-5-amine; methyl 5-aminobenzo[f][1,7]naphthyridine-8-carboxylate; 5-aminobenzo[f][1,7]naphthyridine-8-carboxylic acid; ethyl 5-aminobenzo[f][1,7]naphthyridine-8-carboxylate; (5-aminobenzo[f][1,7]naphthyridin-8-yl)methanol; 5-aminobenzo[f][1,7]naphthyridine-3-carboxylic acid; 5-aminobenzo[f][1,7]naphthyridine-3-carbaldehyde; 2-(o-tolylethynyl)benzo[f][1,7]naphthyridin-5-amine; 2-(m-tolylethynyl)benzo[f][1,7]naphthyridin-5-amine; 2-(p-tolylethynyl)benzo[f][1,7]naphthyridin-5-amine; 2-(2-methylphenethyl)benzo[f][1,7]naphthyridin-5-amine; 2-(3-methylphenethyl)benzo[f][1,7]naphthyridin-5-amine; 2-(4-methylphenethyl)benzo[f][1,7]naphthyridin-5-amine; 3-chloro-2-(ethoxymethyl)benzo[f][1,7]naphthyridin-5-amine; pyrazino[2,3-c]quinolin-5-amine; 9-chlorobenzo[f][1,7]naphthyridin-5-amine; 8-chlorobenzo[f][1,7]naphthyridin-5-amine; 9-methylbenzo[f][1,7]naphthyridin-5-amine; 10-methylbenzo[f][1,7]naphthyridin-5-amine; ethyl 5-aminobenzo[f][1,7]naphthyridine-9-carboxylate; 5-aminobenzo[f][1,7]naphthyridine-9-carboxylic acid; 8-methoxybenzo[f][1,7]naphthyridin-5-amine; 7-fluorobenzo[f][1,7]naphthyridin-5-amine; 8-(methylsulfonyl)benzo[f][1,7]naphthyridin-5-amine; 8-(trifluoromethyl)benzo[f][1,7]naphthyridin-5-amine; 8-fluorobenzo[f][1,7]naphthyridin-5-amine; 3-methoxybenzo[f][1,7]naphthyridin-5-amine; 3-butoxybenzo[f][1,7]naphthyridin-5-amine; 3-(benzyloxy)benzo[f][1,7]naphthyridin-5-amine; 3-methylbenzo[f][1,7]naphthyridin-5-amine; 3-chlorobenzo[f][1,7]naphthyridin-5-amine; $N^3,N^3$-dimethylbenzo[f][1,7]naphthyridine-3,5-diamine; $N^3$-butylbenzo[f][1,7]naphthyridine-3,5-diamine; 3-vinylbenzo[f][1,7]naphthyridin-5-amine; 3-ethylbenzo[f][1,7]naphthyridin-5-amine; 3-fluorobenzo[f][1,7]naphthyridin-5-amine; 2-(trifluoromethyl)benzo[f][1,7]naphthyridin-5-amine; 2-methoxybenzo[f][1,7]naphthyridin-5-amine; 2-(benzyloxy)benzo[f][1,7]naphthyridin-5-amine; 2-vinylbenzo[f][1,7]naphthyridin-5-amine; 2-phenylbenzo[f][1,7]naphthyridin-5-amine; (E)-2-styrylbenzo[f][1,7]naphthyridin-5-amine; 2-phenethylbenzo[f][1,7]naphthyridin-5-amine; (E)-2-(3-methoxyprop-1-enyl)benzo[f][1,7]naphthyridin-5-amine; 2-(3-methoxypropyl)benzo[f][1,7]naphthyridin-5-amine; 2-(prop-1-en-2-yl)benzo[f][1,7]naphthyridin-5-amine; 2-isopropylbenzo[f][1,7]naphthyridin-5-amine; 1-methylbenzo[f][1,7]naphthyridin-5-amine; benzo[c][1,8]naphthyridin-6-amine; pyrido[3,2-f][1,7]naphthyridin-6-amine; thieno[2,3-c]quinolin-4-amine; 8-methyl-2-(naphthalen-2-ylethynyl)benzo[f][1,7]naphthyridin-5-amine; 8-methyl-2-(2-(naphthalen-1-yl)ethyl)benzo[f][1,7]naphthyridin-5-amine; 8-methyl-2-(2-(naphthalen-2-yl)ethyl)benzo[f][1,7]naphthyridin-5-amine; 8-methyl-2-(naphthalen-1-ylethynyl)benzo[f][1,7]naphthyridin-5-amine; 4-(2-(5-amino-8-methylbenzo[f][1,7]naphthyridin-2-yl)ethyl)benzoic acid; 3-(2-(5-amino-8-methylbenzo[f][1,7]naphthyridin-2-yl)ethyl)benzoic acid; 2-(3-chlorophenethyl)-8-methylbenzo[f][1,7]naphthyridin-5-amine; 2-(2-chlorophenethyl)-8-methylbenzo[f][1,7]naphthyridin-5-amine; (3-(2-(5-amino-8-methylbenzo[f][1,7]naphthyridin-2-yl)ethyl)phenyl)methanol; 2-(4-chlorophenethyl)-8-methylbenzo[f][1,7]naphthyridin-5-amine; 8-(trifluoromethyl)phenanthridin-6-amine; benzo[c][2,7]naphthyridin-5-amine; 2-(trifluoromethyl)benzo[f][1,7]naphthyridin-5-amine; 2-tert-butoxybenzo[f][1,7]naphthyridin-5-amine; 5-aminobenzo[f][1,7]naphthyridin-2-ol; 2-((4-butylphenyl)ethynyl)benzo[f][1,7]naphthyridin-5-amine; 2-(4-butylphenethyl)benzo[f][1,7]naphthyridin-5-amine; 1-benzyl-5-chloro-7-(trifluoromethyl)-1,2-dihydropyrido[3,4-b]pyrazin-3(4H)-one; 2-(2-(6-methoxynaphthalen-2-yl)ethyl)benzo[f][1,7]naphthyridin-5-amine; 2-(4-butylphenethyl)-8-methylbenzo[f][1,7]naphthyridin-5-amine; 2-(4-propylphenethyl)benzo[f][1,7]naphthyridin-5-amine; 2-(4-(trifluoromethyl)phenethyl)benzo[f][1,7]naphthyridin-5-amine; dimethylphenethyl)-8-methylbenzo[f][1,7]naphthyridin-5-amine; 8-methyl-2-(4-propylphenethyl)benzo[f][1,7]naphthyridin-5-amine: 8-methyl-2-(2,4,5-trimethylphenethyl)benzo[f][1,7]naphthyridin-5-amine; dimethylphenethyl)benzo[f][1,7]naphthyridin-5-amine; 2-(4-isopropylphenethyl)-8-methylbenzo[f][1,7]naphthyridin-5-amine; 2-(4-heptylphenethyl)-8-methylbenzo[f][1,7]naphthyridin-5-amine; (Z)-2-(2-(biphenyl-4-yl)vinyl)-8-methylbenzo[f][1,7]naphthyridin-5-amine; 2-(4-isobutoxyphenethyl)-8-methylbenzo[f][1,7]naphthyridin-5-amine; 2-(4-((2-methoxyethoxy)methoxy)phenethyl)-8-methylbenzo[f][1,7]naphthyridin-5-amine; 8-methyl-2-(4-(2-phenoxyethoxy)phenethyl)benzo[f][1,7]naphthyridin-5-amine; 2-(4-(2-(tert-butyldimethylsilyloxy)ethoxy)phenethyl)-8-methylbenzo[f][1,7]naphthyridin-5-amine; 2-(4-butoxy-2-methylphenethyl)-N-butyl-8-methylbenzo[f][1,7]naphthyridin-5-amine; 8-methyl-2-(4-(4-phenylbutoxy)phenethyl)benzo[f][1,7]naphthyridin-5-amine; 2-(4-(allyloxy)phenethyl)-8-methylbenzo[f][1,7]naphthyridin-5-amine; 8-methyl-2-(4-(3-phenylpropoxy)phenethyl)benzo[f][1,7]naphthyridin-5-amine; 2-(4-(heptan-4-yloxy)phenethyl)-8-methylbenzo[f][1,7]naphthyridin-5-amine; 8-methyl-2-(4-(4-methylpent-3-enyloxy)phenethyl)benzo[f][1,7]naphthyridin-5-amine; 2-(4-(cyclohexylethoxy)phenethyl)-8-methylbenzo[f][1,7]naphthyridin-5-amine; 2-(4-isopropoxyphenethyl)-8-methylbenzo[f][1,7]naphthyridin-5-amine; 2-(4-(3,3-dimethylbutoxy)phenethyl)-8-methylbenzo[f][1,7]naphthyridin-5-amine; 2-(4-(2-(tert-butyldimethylsilyloxy)ethoxy)-2-methylphenethyl)-8-methylbenzo[f][1,7]naphthyridin-5-amine; 8-(2-cyclopropylethyl)-2-(4-(dimethylamino)phenethyl)benzo[f][1,7]naphthyridin-5-amine; 8-(2-cyclopropylethyl)-2-(2,4-dimethylphenethyl)benzo[f][1,7]

naphthyridin-5-amine; diethyl 3-(2-(4-(2-(2-hydroxyethoxy)ethoxy)-2-methylphenethyl)-8-methylbenzo[f][1,7]naphthyridin-5-ylamino)propylphosphonate; (E)-N-(4-(2-(5-aminobenzo[f][1,7]naphthyridin-2-yl)vinyl)phenyl)acetamide; N-(4-(2-(5-amino-8-methylbenzo[f][1,7]naphthyridin-2-yl)ethyl)phenyl)acetamide; N-(4-(2-(5-aminobenzo[f][1,7]naphthyridin-2-yl)ethyl)phenyl)acetamide; N-(4-(2-(5-amino-8-methylbenzo[f][1,7]naphthyridin-2-yl)ethyl)phenyl)-4-methylbenzenesulfonamide; 3-methyl-9-p-tolyl-9,10-dihydrobenzo[f]furo[2,3-b][1,7]naphthyridin-6-amine; 4-(2-(5-amino-8-methylbenzo[f][1,7]naphthyridin-2-yl)ethyl)-3-methylbenzonitrile; 4-(2-(5-amino-8-methylbenzo[f][1,7]naphthyridin-2-yl)ethyl)-N-(2-aminoethyl)-3-methylbenzamide; 2-(4-(2-(5-amino-3-chloro-8-methylbenzo[f][1,7]naphthyridin-2-yl)ethyl)-3-methylbenzamido)acetic acid; (S)-2-(4-(2-(5-amino-3-chloro-8-methylbenzo[f][1,7]naphthyridin-2-yl)ethyl)-3-methylbenzamido)-4-methylpentanoic acid; 4-(2-(5-amino-3-chloro-8-methylbenzo[f][1,7]naphthyridin-2-yl)ethyl)-N-(2-(dimethylamino)ethyl)-N,3-dimethylbenzamide; 8-methyl-2-(2-methyl-4-(1H-tetrazol-5-yl)phenethyl)benzo[f][1,7]naphthyridin-5-amine; methyl 2-(4-(2-(5-amino-8-methylbenzo[f][1,7]naphthyridin-2-yl)ethyl)-3-methylbenzamido)-4-methylpentanoate; methyl 2-(4-(2-(5-amino-8-methylbenzo[f][1,7]naphthyridin-2-yl)ethyl)-3-methylbenzamido)acetate; 2-(4-(2-(5-amino-8-methylbenzo[f][1,7]naphthyridin-2-yl)ethyl)-3-methylbenzamido)-4-methylpentanoic acid; 2-(4-(2-(5-amino-8-methylbenzo[f][1,7]naphthyridin-2-yl)ethyl)-3-methylbenzamido)acetic acid; 6-(5-amino-8-methylbenzo[f][1,7]naphthyridin-2-yl)hexan-1-ol; 7-(5-amino-8-methylbenzo[f][1,7]naphthyridin-2-yl)heptanoic acid; 11-(5-amino-8-methylbenzo[f][1,7]naphthyridin-2-yl)undecan-1-ol; 2-phenethylbenzo[f][1,7]naphthyridin-5-amine; ethyl 2-(4-(2-(5-amino-8-methylbenzo[f][1,7]naphthyridin-2-yl)ethyl)-3-methylphenoxy)acetate; 2-(4-(2-(5-amino-8-methylbenzo[f][1,7]naphthyridin-2-yl)ethyl)-3-methylphenoxy)acetic acid; 3-(4-(2-(5-amino-8-methylbenzo[f][1,7]naphthyridin-2-yl)ethyl)-3-methylphenoxy)propanoic acid; 6-(4-(2-(5-amino-8-methylbenzo[f][1,7]naphthyridin-2-yl)ethyl)-3-methylphenoxy)hexanoic acid; 8-methyl-2-(2-methyl-4-(methylthio)phenethyl)benzo[f][1,7]naphthyridin-5-amine; 8-methyl-2-(4-(methylsulfonyl)phenethyl)benzo[f][1,7]naphthyridin-5-amine; 2-(4-(hexyloxy)phenethyl)-8-methylbenzo[f][1,7]naphthyridin-5-amine; 8-methyl-2-(4-phenethoxyphenethyl)benzo[f][1,7]naphthyridin-5-amine; 2-(4-cyclobutoxyphenethyl)-8-methylbenzo[f][1,7]naphthyridin-5-amine; 8-methyl-2-(4-(pentyloxy)phenethyl)benzo[f][1,7]naphthyridin-5-amine; 8-methyl-2-(4-(4-methylpentyloxy)phenethyl)benzo[f][1,7]naphthyridin-5-amine; 8-bromo-3-methoxybenzo[f][1,7]naphthyridin-5-amine; 2-((tert-butyldimethylsilyl)ethynyl)benzo[f][1,7]naphthyridin-5-amine; 2-((2-fluorophenyl)ethynyl)benzo[f][1,7]naphthyridin-5-amine; 2-((3-fluorophenyl)ethynyl)benzo[f][1,7]naphthyridin-5-amine; 2-((4-fluorophenyl)ethynyl)benzo[f][1,7]naphthyridin-5-amine; 2-(thiophen-3-ylethynyl)benzo[f][1,7]naphthyridin-5-amine; 2-ethynylbenzo[f][1,7]naphthyridin-5-amine; 2-(2-fluorophenethyl)benzo[f][1,7]naphthyridin-5-amine; 2-(3-fluorophenethyl)benzo[f][1,7]naphthyridin-5-amine; 2-(4-fluorophenethyl)benzo[f][1,7]naphthyridin-5-amine; 2-(2-(thiophen-3-yl)ethyl)benzo[f][1,7]naphthyridin-5-amine; ethyl 5-aminobenzo[f][1,7]naphthyridine-2-carboxylate; ethyl 5-amino-8-methylbenzo[f][1,7]naphthyridine-2-carboxylate; (5-aminobenzo[f][1,7]naphthyridin-2-yl)methanol; 2-(3,4-dimethylphenethyl)benzo[f][1,7]naphthyridin-5-amine; 1-chloro-8-methylbenzo[f][1,7]naphthyridin-5-amine; 8-methyl-1-(3-phenylpropyl)benzo[f][1,7]naphthyridin-5-amine; (Z)-2-(2-(benzo[d][1,3]dioxol-5-yl)vinyl)-8-methylbenzo[f][1,7]naphthyridin-5-amine; (Z)-2-(4-methoxy-2-methylstyryl)-8-methylbenzo[f][1,7]naphthyridin-5-amine; dimethylphenethyl)-8-methylbenzo[f][1,7]naphthyridin-5-amine; 2-(3,5-dimethylphenethyl)-8-methylbenzo[f][1,7]naphthyridin-5-amine; 8-methyl-2-(1-phenylvinyl)benzo[f][1,7]naphthyridin-5-amine; 8-methyl-2-(4-phenylbutyl)benzo[f][1,7]naphthyridin-5-amine; 8-methyl-2-(1-phenylethyl)benzo[f][1,7]naphthyridin-5-amine; 2-(2-(benzofuran-5-yl)ethyl)-8-methylbenzo[f][1,7]naphthyridin-5-amine; (Z)-2-(2-ethoxyvinyl)-8-methylbenzo[f][1,7]naphthyridin-5-amine; 2-(2-ethoxyethyl)-8-methylbenzo[f][1,7]naphthyridin-5-amine; 2-(chloromethyl)-8-methylbenzo[f][1,7]naphthyridin-5-amine; 8-methyl-2-(2-nitroethyl)benzo[f][1,7]naphthyridin-5-amine; diethyl 2-((5-amino-8-methylbenzo[f][1,7]naphthyridin-2-yl)methyl)malonate; 2-(isopropylsulfonyl)-8-methylbenzo[f][1,7]naphthyridin-5-amine; 2-((methoxymethoxy)methyl)-8-methylbenzo[f][1,7]naphthyridin-5-amine; 8-methyl-2-((methylamino)methyl)benzo[f][1,7]naphthyridin-5-amine; tert-butyl 5-amino-8-methylbenzo[f][1,7]naphthyridin-2-ylcarbamate; 8-methyl-2-((phenylamino)methyl)benzo[f][1,7]naphthyridin-5-amine; 2-(aminomethyl)-8-methylbenzo[f][1,7]naphthyridin-5-amine; 8-methyl-2-(pyrrolidin-1-ylmethyl)benzo[f][1,7]naphthyridin-5-amine; $N^2$-(2,4-dimethoxybenzyl)-8-methylbenzo[f][1,7]naphthyridine-2,5-diamine; $N^2,N^2,8$-trimethylbenzo[f][1,7]naphthyridine-2,5-diamine; $N^2,8$-dimethylbenzo[f][1,7]naphthyridine-2,5-diamine; 8-methyl-2-(pyrrolidin-1-yl)benzo[f][1,7]naphthyridin-5-amine; 2-(5-amino-8-methylbenzo[f][1,7]naphthyridin-2-yl)-1-phenylethanol; 2-(2-aminoethyl)-8-methylbenzo[f][1,7]naphthyridin-5-amine; 2-hydrazinyl-8-methylbenzo[f][1,7]naphthyridin-5-amine; 1-(5-amino-8-methylbenzo[f][1,7]naphthyridin-2-yl)-2-methylpropan-2-ol; 2-(5-amino-8-methylbenzo[f][1,7]naphthyridin-2-yl)-1-(4-methoxyphenyl)ethanol; 2-(biphenyl-2-yl)-8-methylbenzo[f][1,7]naphthyridin-5-amine; 2-(2-(2,6-dimethylpyridin-3-yl)ethyl)-8-methylbenzo[f][1,7]naphthyridin-5-amine; 2-(2-(5-methoxypyridin-2-yl)ethyl)-8-methylbenzo[f][1,7]naphthyridin-5-amine; 3-(4-(2-(5-amino-8-methylbenzo[f][1,7]naphthyridin-2-yl)ethyl)phenyl)propanoic acid; 5-(2-(5-amino-8-methylbenzo[f][1,7]naphthyridin-2-yl)ethyl)-4-methylpyridin-2(1H)-one; 6-(2-(5-amino-8-methylbenzo[f][1,7]naphthyridin-2-yl)ethyl)pyridin-3-ol; 3-methyldibenzo[b,f][1,7]naphthyridin-6-amine; 8-methyl-2-(4-(trifluoromethoxy)phenethyl)benzo[f][1,7]naphthyridin-5-amine; 2-(2-(2,3-dihydro-1H-inden-5-yl)ethyl)-8-methylbenzo[f][1,7]naphthyridin-5-amine; 2-(2-(2,3-dihydro-1H-inden-5-yl)ethyl)benzo[f][1,7]naphthyridin-5-amine; (E)-3-(4-(2-(5-amino-8-methylbenzo[f][1,7]naphthyridin-2-yl)ethyl)-3-methylphenyl)acrylic acid; (E)-ethyl 3-(5-amino-2-(4-methoxy-2-methylphenethyl)benzo[f][1,7]naphthyridin-8-yl)acrylate; $N^3,N^5$-dibutylbenzo[f][1,7]naphthyridine-3,5-diamine; 8-(prop-1-en-2-yl)benzo[f][1,7]naphthyridin-5-amine; 5-aminobenzo[f][1,7]naphthyridine-8-carbonitrile; (E)-8-(3-methylbut-1-enyl)benzo[f][1,7]naphthyridin-5-amine; 8-(2-methylprop-1-enyl)benzo[f][1,7]naphthyridin-5-amine; (E)-8-(pent-1-enyl)benzo[f][1,7]naphthyridin-5-amine; (E)-8-styrylbenzo[f][1,7]naphthyridin-5-amine; (E)-8-(2-cyclopropylvinyl)-2-phenethylbenzo[f][1,7]naphthyridin-5-amine; 8-pentylbenzo[f][1,7]naphthyridin-5-amine; (E)-8-(2-cyclopropylvinyl)benzo[f][1,7]naphthyridin-5-amine; 8-(2-cyclopropylethyl)-2-phenethylbenzo[f][1,7]naphthyridin-5- amine; pyrido[1,2-c][1,7]naphthyridin-6-amine; 9-phenethylpyrido[1,2-c][1,7]naphthyridin-6-amine; methyl 5-amino-2-(4-methoxyphenethyl)benzo[f][1,7]naphthyridine-8-carboxylate; 8-nitrobenzo[f][1,7]naphthyridin-5-amine; 3-chloro-8-methylbenzo[f][1,7]naphthyridin-5-amine; methyl 5-amino-3-chlorobenzo[f][1,7]naphthyridine-8-carboxylate; methyl 5-amino-3-fluorobenzo[f][1,7]naphthyridine-8-carboxylate; 3-chloro-8-nitrobenzo[f][1,7]naphthyridin-5-amine; (5-amino-3-chlorobenzo[f][1,7]naphthyridin-8-yl)methanol; (5-amino-2-phenethylbenzo[f][1,7]naphthyridin-8-yl)methanol; 4-(2-(5-amino-8-fluorobenzo[f][1,7]naphthyridin-2-yl)ethyl)benzaldehyde; 2-(4-(2-(5-amino-8-fluorobenzo[f][1,7]naphthyridin-2-yl)ethyl)benzylamino)ethanol; 3-(4-(2-(5-amino-8-fluorobenzo[f][1,7]naphthyridin-2-yl)ethyl)benzylamino)propan-1-ol; 8-fluoro-2-(4-((2-methoxyethylamino)methyl)phenethyl)benzo[f][1,7]naphthyridin-5-amine; 8-((tert-butyldimethylsilyloxy)methyl)-2-(4-methoxy-2-methylphenethyl)benzo[f][1,7]naphthyridin-5-amine; (5-amino-2-(4-methoxy-2-methylphenethyl)benzo[f][1,7]naphthyridin-8-yl)methanol; 3-(2-(5-aminobenzo[f][1,7]naphthyridin-2-yl)ethyl)phenol; 2-(2-methoxyphenethyl)benzo[f][1,7]naphthyridin-5-amine; 2-(4-ethylphenethyl)benzo[f][1,7]naphthyridin-5-amine; 2-(4-ethylphenethyl)-8-methylbenzo[f][1,7]naphthyridin-5-amine; 2-(4-(dimethylamino)phenethyl)benzo[f][1,7]naphthyridin-5-amine; 2-(4-(piperidin-1-yl)phenethyl)benzo[f][1,7]naphthyridin-5-amine; 2-(4-tert-butylphenethyl)-8-methylbenzo[f][1,7]naphthyridin-5-amine; 8-methyl-2-(4-(piperidin-1-yl)phenethyl)benzo[f][1,7]naphthyridin-5-amine; 2-(4-methoxyphenethyl)-8-methylbenzo[f][1,7]naphthyridin-5-amine; 2-(3,5-dimethoxyphenethyl)-8-methylbenzo[f][1,7]naphthyridin-5-amine; 8-methyl-2-(2-(trifluoromethyl)phenethyl)benzo[f][1,7]naphthyridin-5-amine; 8-methyl-2-(2-(1-methyl-1H-imidazol-5-yl)ethyl)benzo[f][1,7]naphthyridin-5-amine; 4-(2-(5-amino-8-methylbenzo[f][1,7]naphthyridin-2-yl)ethyl)-N-hydroxybenzimidamide; 4-(2-(5-amino-8-methylbenzo[f][1,7]naphthyridin-2-yl)ethyl)benzonitrile; 8-methyl-2-(4-(1-morpholinoethyl)phenethyl)benzo[f][1,7]naphthyridin-5-amine; 2-(4-aminophenethyl)-8-methylbenzo[f][1,7]naphthyridin-5-amine; 1-(4-(2-(5-amino-8-methylbenzo[f][1,7]naphthyridin-2-yl)ethyl)phenyl)guanidine; 8-methyl-2-(4-(1-(phenethylamino)ethyl)phenethyl)benzo[f][1,7]naphthyridin-5-amine; 2-(4-(2-(5-amino-8-methylbenzo[f][1,7]naphthyridin-2-yl)ethyl)phenyl)acetonitrile; 2-(4-(piperidin-1-ylmethyl)phenethyl)benzo[f][1,7]naphthyridin-5-amine; 1-(4-(2-(5-aminobenzo[f][1,7]naphthyridin-2-yl)ethyl)benzyl)piperidin-4-ol; 2-(4-(aminomethyl)phenethyl)benzo[f][1,7]naphthyridin-5-amine; 2-(4-((ethylamino)methyl)phenethyl)benzo[f][1,7]naphthyridin-5-amine; 2-(4-(2-aminopropan-2-yl)phenethyl)benzo[f][1,7]naphthyridin-5-amine; 1-(1-(4-(2-(5-aminobenzo[f][1,7]naphthyridin-2-yl)ethyl)phenyl)ethyl)pyrrolidine-3-carboxylic acid; 8-methyl-2-(4-(1-(phenylamino)ethyl)phenethyl)benzo[f][1,7]naphthyridin-5-amine; 2-ethyl-8-methylbenzo[f][1,7]naphthyridin-5-amine; (5-amino-8-methylbenzo[f][1,7]naphthyridin-2-yl)methanol; 8-methyl-2-propylbenzo[f][1,7]naphthyridin-5-amine; 2-(2-(1H-indol-5-yl)ethyl)-8-methylbenzo[f][1,7]naphthyridin-5-amine; 2-(4-ethoxyphenethyl)-8-methylbenzo[f][1,7]naphthyridin-5-amine; 8-methyl-2-(4-phenoxyphenethyl)benzo[f][1,7]naphthyridin-5-amine; 2-(2,4-dimethylphenethyl)benzo[f][1,7]naphthyridin-5-amine; 2-(2,4-dimethylphenethyl)-8-methylbenzo[f][1,7]naphthyridin-5-amine; 2-(4-methoxy-2-methylphenethyl)-8-methylbenzo[f][1,7]naphthyridin-5-amine; 4-(2-(5-amino-8-methylbenzo[f][1,7]naphthyridin-2-yl)ethyl)-3-methylphenol; 2-(2-(2,3-dihydrobenzofuran-5-yl)ethyl)-8-methylbenzo[f][1,7]naphthyridin-5-amine; 2-(5-amino-8-methylbenzo[f][1,7]naphthyridin-2-yl)ethanol; 3-methyl-9-phenyl-9,10-dihydrobenzo[f]furo[2,3-b][1,7]naphthyridin-6-amine; 8-methylbenzo[f][1,7]naphthyridine-2,5-diamine; 1-(5-amino-8-methylbenzo[f][1,7]naphthyridin-2-yl)propan-2-ol; 2-(5-amino-8-methylbenzo[f][1,7]naphthyridin-2-yl)acetonitrile; N-(5-amino-8-methylbenzo[f][1,7]naphthyridin-2-yl)acetamide; 2-(5-amino-8-methylbenzo[f][1,7]naphthyridin-2-yl)-1-(2,4-dimethylphenyl)ethanol; 2-(2-(6-methoxy-4-methylpyridin-3-yl)ethyl)-8-methylbenzo[f][1,7]naphthyridin-5-amine; 4-(4-(2-(5-amino-8-methylbenzo[f][1,7]naphthyridin-2-yl)ethyl)phenyl)butan-1-ol; methyl 3-(4-(2-(5-amino-8-methylbenzo[f][1,7]naphthyridin-2-yl)ethyl)phenyl)propanoate; 3-(4-(2-(5-amino-8-methylbenzo[f][1,7]naphthyridin-2-yl)ethyl)phenyl)propan-1-ol; 4-(4-(2-(5-amino-8-methylbenzo[f][1,7]naphthyridin-2-yl)ethyl)phenyl)-2-methylbutan-2-ol; 2-(4-(aminomethyl)phenethyl)-8-methylbenzo[f][1,7]naphthyridin-5-amine; (E)-ethyl 3-(4-(2-(5-amino-8-methylbenzo[f][1,7]naphthyridin-2-yl)ethyl)-3-methylphenyl)acrylate; ethyl 3-(4-(2-(5-amino-8-methylbenzo[f][1,7]naphthyridin-2-yl)ethyl)-3-methylphenyl)propanoate; 2-(4-(2-(5-amino-8-methylbenzo[f][1,7]naphthyridin-2-yl)ethyl)-3-methylbenzyl)propane-1,3-diol; 3-(4-(2-(5-amino-8-methylbenzo[f][1,7]naphthyridin-2-yl)ethyl)-3-methylphenyl)propanoic acid; 5-amino-2-(4-methoxy-2-methylphenethyl)benzo[f][1,7]naphthyridine-8-carbaldehyde; ethyl 4-(2-(5-amino-8-methylbenzo[f][1,7]naphthyridin-2-yl)ethyl)benzoate; 8-methyl-2-(4-methylphenethyl)benzo[f][1,7]naphthyridin-5-amine; 2-(4-(2-(5-amino-8-methylbenzo[f][1,7]naphthyridin-2-yl)ethyl)phenyl)propan-2-ol; (4-(2-(5-amino-8-methylbenzo[f][1,7]naphthyridin-2-yl)ethyl)phenyl)methanol; ethyl 4-(2-(5-amino-8-methylbenzo[f][1,7]naphthyridin-2-yl)ethyl)-3-methylbenzoate; 4-(2-(5-amino-8-methylbenzo[f][1,7]naphthyridin-2-yl)ethyl)-3-methylbenzoic acid; (4-(2-(5-amino-8-methylbenzo[f][1,7]naphthyridin-2-yl)ethyl)-3-methylphenyl)methanol; 8-methyl-2-(2,4,6-trimethylphenethyl)benzo[f][1,7]naphthyridin-5-amine; 2-(4-(2-(5-amino-8-methylbenzo[f][1,7]naphthyridin-2-yl)ethyl)-3-methylphenyl)propan-2-ol; 8-methyl-2-(4-propoxyphenethyl)benzo[f][1,7]naphthyridin-5-amine; (E)-ethyl 3-(5-amino-2-(4-methoxy-2-methylphenethyl)benzo[f][1,7]naphthyridin-8-yl)acrylate; (E)-3-(5-amino-2-(4-methoxy-2-methylphenethyl)benzo[f][1,7]naphthyridin-8-yl)acrylic acid; ethyl 3-(5-amino-2-(4-methoxy-2-methylphenethyl)benzo[f][1,7]naphthyridin-8-yl)propanoate; 3-(5-amino-2-(4-methoxy-2-methylphenethyl)benzo[f][1,7]naphthyridin-8-yl)propanoic acid; 3-(5-amino-2-(4-methoxy-2-methylphenethyl)benzo[f][1,7]naphthyridin-8-yl)propan-1-ol; (5-aminobenzo[f][1,7]naphthyridin-8-yl)methanol; 5-aminobenzo[f][1,7]naphthyridin-8-ol; 5-aminobenzo[f][1,7]naphthyridine-8-carbaldehyde; 1-(5-aminobenzo[f][1,7]naphthyridin-8-yl)ethanol; 1-(5-aminobenzo[f][1,7]naphthyridin-8-yl)ethanone; 8-isopropylbenzo[f][1,7]naphthyridin-5-amine; 8-vinylbenzo[f][1,7]naphthyridin-5-amine; 8-ethylbenzo[f][1,7]naphthyridin-5-amine; 8-(methoxymethyl)benzo[f][1,7]naphthyridin-5-amine; (5-amino-2-phenethylbenzo[f][1,7]naphthyridin-8-yl)methanol; (5-amino-2-(4-methoxyphenethyl)benzo[f][1,7]naphthyridin-8-yl)methanol; benzo[f][1,7]naphthyridine-5,8-diamine; 8-(aminomethyl)benzo[f][1,7]naphthyridin-5-amine; 3-fluoro-8-methylbenzo[f][1,7]naphthyridin-5-amine; (5-amino-3-fluorobenzo[f][1,7]naphthyridin-8-yl)methanol; 3-chlorobenzo[f][1,7]naphthyridine-5,8-diamine; 3-fluorobenzo[f][1,7]naphthyridine-5,8-diamine; 8-isobutylbenzo [f][1,7]naphthyridin-5-amine; (E)-8-(prop-1-enyl)benzo[f][1,7]naphthyridin-5-amine; 8-propylbenzo[f][1,7]naphthyridin-5-amine; 8-(2-cyclopropylethyl)benzo[f][1,7]naphthyridin-5-amine; 8-phenethylbenzo[f][1,7]naphthyridin-5-amine; (5-amino-2-(4-bromophenethyl)benzo[f][1,7]naphthyridin-8-yl)methanol; 2-(4-methoxy-2-methylphenethyl)-8-pentylbenzo[f][1,7]naphthyridin-5-amine; 8-(2-cyclopropylethyl)-2-(4-methoxy-2-methylphenethyl)benzo[f][1,7]naphthyridin-5-amine; (5-amino-2-(2,4,6-trimethylphenethyl)benzo[f][1,7]naphthyridin-8-yl)methanol; (5-amino-2-(4-propoxyphenethyl)benzo[f][1,7]naphthyridin-8-yl)methanol; (2-(2-(1H-indol-5-yl)ethyl)-5-aminobenzo[f][1,7]naphthyridin-8-yl)methanol; N-(4-(2-(5-amino-8-methylbenzo[f][1,7]naphthyridin-2-yl)ethyl)phenyl)acetamide; methyl 4-(2-(5-amino-8-methylbenzo[f][1,7]naphthyridin-2-yl)ethyl)-3-methylbenzoate; 4-(2-(5-amino-8-methylbenzo[f][1,7]naphthyridin-2-yl)ethyl)-N,3-dimethylbenzamide; N-(2-acetamidoethyl)-4-(2-(5-amino-8-methylbenzo[f][1,7]naphthyridin-2-yl)ethyl)-3-methylbenzamide; 4-(2-(5-amino-8-methylbenzo[f][1,7]naphthyridin-2-yl)ethyl)-N-(2-(dimethylamino)ethyl)-N,3-dimethylbenzamide; 2-(4-methoxyphenethyl)benzo[f][1,7]naphthyridin-5-amine; 2-(4-methoxy-2-methylphenethyl)benzo[f][1,7]naphthyridin-5-amine; 4-(2-(5-amino-8-methylbenzo[f][1,7]naphthyridin-2-yl)ethyl)-3-methylbenzamide; 4-(2-(5-amino-8-methylbenzo[f][1,7]naphthyridin-2-yl)ethyl)-N,N,3-trimethylbenzamide; 4-(2-(5-amino-8-methylbenzo[f][1,7]naphthyridin-2-yl)ethyl)-N-(2-hydroxyethyl)-3-methylbenzamide; 4-(2-(5-amino-8-methylbenzo[f][1,7]naphthyridin-2-yl)ethyl)-N-(2-(dimethylamino)ethyl)-3-methylbenzamide; (4-(2-(5-amino-8-methylbenzo[f][1,7]naphthyridin-2-yl)ethyl)-3-methylphenyl)(pyrrolidin-1-yl)methanone; 4-(2-(5-amino-8-methylbenzo[f][1,7]naphthyridin-2-yl)ethyl)-N-(2-(diethylamino)ethyl)-3-methylbenzamide; (4-(2-(5-amino-8-methylbenzo[f][1,7]naphthyridin-2-yl)ethyl)-3-methylphenyl)(4-ethylpiperazin-1-yl)methanone; (4-(2-(5-amino-8-methylbenzo[f][1,7]naphthyridin-2-yl)ethyl)-3-methylphenyl)(piperazin-1-yl)methanone; 4-(2-(5-amino-8-methylbenzo[f][1,7]naphthyridin-2-yl)ethyl)-3-methyl-N-(2-(pyrrolidin-1-yl)ethyl)benzamide; 4-(2-(5-amino-8-methylbenzo[f][1,7]naphthyridin-2-yl)ethyl)-N-(2-aminoethyl)-3-methylbenzamide; 4-(2-(5-aminobenzo[f][1,7]naphthyridin-2-yl)ethyl)-N-(2-(dimethylamino)ethyl)-N,3-dimethylbenzamide; 4-(2-(5-amino-8-methylbenzo[f][1,7]naphthyridin-2-yl)ethyl)-N-(2-(dimethylamino)ethyl)-N-methylbenzamide; 2-(4-(2-(5-aminobenzo[f][1,7]naphthyridin-2-yl)ethyl)-3-methylphenyl)propan-2-ol; 2-(4-butoxyphenethyl)-8-methylbenzo[f][1,7]naphthyridin-5-amine; 2-(2-(biphenyl-4-yl)ethyl)-8-methylbenzo[f][1,7]naphthyridin-5-amine; 2-((1,3-dihydroisobenzofuran-1-yl)methyl)-8-methylbenzo[f][1,7]naphthyridin-5-amine; 8-methyl-2-(4-(2-methylallyloxy)phenethyl)benzo[f][1,7]naphthyridin-5-amine; 2-(4-(isopentyloxy)phenethyl)-8-methylbenzo[f][1,7]naphthyridin-5-amine; 4-(2-(5-amino-8-methylbenzo[f][1,7]naphthyridin-2-yl)ethyl)phenyl propyl carbonate; ethyl 5-(4-(2-(5-amino-8-methylbenzo[f][1,7]naphthyridin-2-yl)ethyl)phenoxy)pentanoate; 2-(4-(cyclopentyloxy)phenethyl)-8-methylbenzo[f][1,7]naphthyridin-5-amine; 2-(4-(cyclobutylmethoxy)phenethyl)-8-methylbenzo[f][1,7]naphthyridin-5-amine; 8-methyl-2-(4-(2-morpholinoethoxy)phenethyl)benzo[f][1,7]naphthyridin-5-amine; 2-(4-(5-amino-8-methylbenzo[f][1,7]naphthyridin-2-yl)ethyl)phenoxy)-1-phenylethanone; 5-(4-(2-(5-amino-8-methylbenzo[f][1,7]naphthyridin-2-yl)ethyl) phenoxy)pentanoic acid; 2-(4-(2-(5-amino-8-methylbenzo[f][1,7]naphthyridin-2-yl)ethyl)phenoxy)ethanol; 2-(4-(2-(5-amino-8-methylbenzo[f][1,7]naphthyridin-2-yl)ethyl)phenoxy)-N,N-dimethylacetamide; 8-methyl-2-(2-methyl-4-(2-morpholinoethoxy)phenethyl)benzo[f][1,7]naphthyridin-5-amine; 2-(2-(4-(2-(5-amino-8-methylbenzo[f][1,7]naphthyridin-2-yl)ethyl)-3-methylphenoxy)ethoxy)ethanol; diethyl 3-(4-(2-(5-amino-8-methylbenzo[f][1,7]naphthyridin-2-yl)ethyl)-3-methylphenoxy)propylphosphonate; 3-(4-(2-(5-amino-8-methylbenzo[f][1,7]naphthyridin-2-yl)ethyl)-3-methylphenoxy)propylphosphonic acid; 2-(4-butoxy-2-methylphenethyl)-8-methylbenzo[f][1,7]naphthyridin-5-amine; 2-(4-(2-(5-aminobenzo[f][1,7]naphthyridin-2-yl)ethyl)-3-methylphenoxy)ethanol; 2-(4-(2-(5-aminobenzo[f][1,7]naphthyridin-2-yl)ethyl)-3-methylphenoxy)ethanol; ethyl 5-(4-(2-(5-amino-8-methylbenzo[f][1,7]naphthyridin-2-yl)ethyl)-3-methylphenoxy)pentanoate; 5-(4-(2-(5-amino-8-methylbenzo[f][1,7]naphthyridin-2-yl)ethyl)-3-methylphenoxy)pentanoic acid; 2-(4-(2-(5-amino-8-methylbenzo[f][1,7]naphthyridin-2-yl)ethyl)-3-methylphenoxy)ethanol; 4-(2-(5-amino-8-methylbenzo[f][1,7]naphthyridin-2-yl)ethyl) phenyl ethyl carbonate; methyl 4-(4-(2-(5-amino-8-methylbenzo[f][1,7]naphthyridin-2-yl)ethyl)phenoxy)butanoate; 4-(4-(2-(5-amino-8-methylbenzo[f][1,7]naphthyridin-2-yl)ethyl)phenoxy)butanoic acid; 4-(4-(2-(5-amino-8-methylbenzo[f][1,7]naphthyridin-2-yl)ethyl)-3-methylphenoxy)butanoic acid; 2-(4-(isopentyloxy)-2-methylphenethyl)-8-methylbenzo[f][1,7]naphthyridin-5-amine; 4-(2-(5-amino-8-methylbenzo[f][1,7]naphthyridin-2-yl)ethyl)phenyl hexyl carbonate; 2-(2,4,6-trimethylphenethyl)benzo[f][1,7]naphthyridin-5-amine; (5-amino-2-(2,4-dimethylphenethyl)benzo[f][1,7]naphthyridin-8-yl)methanol; diethyl 3-(2-(4-(2-(5-amino-8-methylbenzo[f][1,7]naphthyridin-2-yl)ethyl)-3-methylphenoxy)ethoxy)propylphosphonate; diethyl 3-(2-(2-(4-(2-(5-amino-8-methylbenzo[f][1,7]naphthyridin-2-yl)ethyl)-3-methylphenoxy)ethoxy)ethoxy)propylphosphonate; 4-(2-(5-amino-8-methylbenzo[f][1,7]naphthyridin-2-yl)ethyl)-3-methylphenyl dimethylsulfamate; (5-amino-2-(4-(dimethylamino)phenethyl)benzo[f][1,7]naphthyridin-8-yl)methanol; 2-(4-(dimethylamino)phenethyl)-8-methylbenzo[f][1,7]naphthyridin-5-amine; 4-(2-(5-amino-8-methylbenzo[f][1,7]naphthyridin-2-yl)ethyl)phenol; 1-(4-(2-(5-amino-8-methylbenzo[f][1,7]naphthyridin-2-yl)ethyl)phenyl)ethanone; 2-(4-((dimethylamino)methyl)phenethyl)-8-methylbenzo[f][1,7]naphthyridin-5-amine; 2-(4-(1-(dimethylamino)ethyl)phenethyl)-8-methylbenzo[f][1,7]naphthyridin-5-amine; 1-(4-(2-(5-amino-8-methylbenzo[f][1,7]naphthyridin-2-yl)ethyl)phenyl)ethanone oxime; 8-methyl-2-(4-((methylamino)methyl)phenethyl)benzo[f][1,7]naphthyridin-5-amine; (4-(2-(5-amino-8-methylbenzo[f][1,7]naphthyridin-2-yl)ethyl)benzylamino)ethanol; 8-methyl-2-(4-(pyrrolidin-1-ylmethyl)phenethyl)benzo[f][1,7]naphthyridin-5-amine; 2-(3,4-dimethoxyphenethyl)-8-methylbenzo[f][1,7]naphthyridin-5-amine; 2-(1-(4-(2-(5-amino-8-methylbenzo[f][1,7]naphthyridin-2-yl)ethyl)phenyl)ethylamino)ethanol; 1-(4-(2-(5-amino-8-methylbenzo[f][1,7]naphthyridin-2-yl)ethyl)phenyl)ethanol; 8-methyl-2-(4-(oxazol-5-yl)phenethyl)benzo[f][1,7]naphthyridin-5-amine; 3-(1-(4-(2-(5-amino-8-methylbenzo[f][1,7]naphthyridin-2-yl)ethyl)phenyl)ethylamino)propanenitrile; (2R)-2-(1-(4-(2-(5-amino-8-methylbenzo[f][1,7]naphthyridin-2-yl)ethyl)phenyl)ethylamino)propan-1-ol; 8-methyl-2-(4-(1-(piperazin-1-yl)ethyl)phenethyl)benzo[f][1,7]naphthyridin-5-amine; ((2S)-1-(1-(4-(2-(5-amino-8-methylbenzo[f][1,7]naphthyridin-2- yl)ethyl)phenyl)ethyl)pyrrolidin-2-yl)methanol; $N^1$-(1-(4-(2-(5-amino-8-methylbenzo[f][1,7]naphthyridin-2-yl)ethyl)phenyl)ethyl)-$N^2,N^2$-dimethylethane-1,2-diamine; 3-(1-(4-(2-(5-amino-8-methylbenzo[f][1,7]naphthyridin-2-yl)ethyl)phenyl)ethylamino)propanoic acid; 8-methyl-2-(4-(1-(4-methylpiperazin-1-yl)ethyl)phenethyl)benzo[f][1,7]naphthyridin-5-amine; $N^2$-(1-(4-(2-(5-amino-8-methylbenzo[f][1,7]naphthyridin-2-yl)ethyl)phenyl)ethyl)-$N^1,N^1$-dimethylpropane-1,2-diamine; 8-methyl-2-(4-(1-(2-(pyridin-4-yl)ethylamino)ethyl)phenethyl)benzo[f][1,7]naphthyridin-5-amine; $N^1$-(1-(4-(2-(5-amino-8-methylbenzo[f][1,7]naphthyridin-2-yl)ethyl)phenyl)ethyl)-$N^2,N^2$-diethylethane-1,2-diamine; 2-(4-(dimethylamino)-2-methylphenethyl)-8-methylbenzo[f][1,7]naphthyridin-5-amine; 1-(1-(4-(2-(5-amino-8-methylbenzo[f][1,7]naphthyridin-2-yl)ethyl)phenyl)ethyl)pyrrolidine-3-carboxylic acid; 4-(1-(4-(2-(5-amino-8-methylbenzo[f][1,7]naphthyridin-2-yl)ethyl)phenyl)ethylamino)phenol; 1-(1-(4-(2-(5-amino-8-methylbenzo[f][1,7]naphthyridin-2 yl)ethyl)phenyl)ethyl)pyrrolidin-3-ol; and 2-(4-(2-aminopropan-2-yl)phenethyl)-8-methylbenzo[f][1,7]naphthyridin-5-amine.

The compounds of Formula (I), pharmaceutically acceptable salts, solvates, N-oxides, prodrugs and isomers thereof, and pharmaceutical compositions provided herein also includes all suitable isotopic variations of such compounds, and pharmaceutically acceptable salts, solvates, N-oxides, prodrugs and isomers thereof, and pharmaceutical compositions. An isotopic variation of a compound provided herein or a pharmaceutically acceptable salt thereof is defined as one in which at least one atom is replaced by an atom having the same atomic number but an atomic mass different from the atomic mass usually found in nature. Examples of isotopes that may be incorporated into the compounds provided herein and pharmaceutically acceptable salts thereof include but are not limited to isotopes of hydrogen, carbon, nitrogen and oxygen such as $^2H$, $^3H$, $^{11}C$, $^{13}C$, $^{14}C$, $^{15}N$, $^{17}O$, $^{18}O$, $^{35}S$, $^{18}F$, $^{36}Cl$ and $^{123}I$. Certain isotopic variations of the compounds provided herein and pharmaceutically acceptable salts thereof, for example, those in which a radioactive isotope such as $^3H$ or $^{14}C$ is incorporated, are useful in drug and/or substrate tissue distribution studies. In particular examples, $^3H$ and $^{14}C$ isotopes may be used for their ease of preparation and detectability. In other examples, substitution with isotopes such as $^2H$ may afford certain therapeutic advantages resulting from greater metabolic stability, such as increased in vivo half-life or reduced dosage requirements. Isotopic variations of the compounds, and pharmaceutically acceptable salts, solvates, N-oxides, prodrugs and isomers thereof, and pharmaceutical compositions provided herein are prepared by conventional procedures using appropriate isotopic variations of suitable reagents.

Processes for Making Compounds of Formula (I)

General procedures for preparing compounds of Formula (I) are described in the Examples, infra. In the reactions described, reactive functional groups, for example hydroxy, amino, imino, thio or carboxy groups, where these are desired in the final product, may be protected to avoid their unwanted participation in the reactions. Conventional protecting groups may be used in accordance with standard practice (see e.g., T. W. Greene and P. G. M. Wuts in "Protective Groups in Organic Chemistry," John Wiley and Sons, 1991).

In certain embodiments, the compounds of Formula (I) described herein are prepared as a pharmaceutically acceptable acid addition salt by reacting the free base form of the compound of Formula (I) with a pharmaceutically acceptable organic acid or inorganic acid. In other embodiments, a pharmaceutically acceptable base addition salt of compounds of Formula (I) described herein is prepared by reacting the free acid form of the compound of Formula (I) with a pharmaceutically acceptable organic base or inorganic base. Alternatively, the salt forms of the compounds of Formula (I) described herein are prepared using salts of the starting materials or intermediates. In certain embodiments, the compounds of Formula (I) described herein are in the form of other salts including, but not limited to, oxalates and trifluoroacetates. In certain embodiments, hemisalts of acids and bases are formed, for example, hemisulphate and hemicalcium salts.

Such pharmaceutically acceptable acid addition salts of compounds of Formula (I) include, but are not limited to, a hydrobromide, hydrochloride, sulfate, nitrate, succinate, maleate, formate, acetate, adipate, besylatye, bicarbonate/carbonate, propionate, fumarate, citrate, tartrate, lactate, benzoate, salicylate, glutamate, aspartate, p-toluenesulfonate, benzenesulfonate, methanesulfonate, ethanesulfonate, naphthalenesulfonate (e.g. 2-naphthalenesulfonate), hexanoate salt, bisulphate/sulphate, borate, camsylate, cyclamate, edisylate, esylate, gluceptate, gluconate, glucuronate, hexafluorophosphate, hibenzate, hydrochloride/chloride, hydrobromide/bromide, hydroiodide/iodide, isethionate, lactate, malate, malonate, mesylate, methylsulphate, naphthylate, 2-napsylate, nicotinate, orotate, oxalate, palmitate, pamoate, phosphate/hydrogen phosphate/dihydrogen phosphate, pyroglutamate, saccharate, stearate, tannate, tosylate, trifluoroacetate and xinofoate salts.

The organic acid or inorganic acids used to form certain pharmaceutically acceptable acid addition salts of compounds of Formula (I) include, but are not limited to, hydrobromic, hydrochloric, sulfuric, nitric, phosphoric, succinic, maleic, formic, acetic, propionic, fumaric, citric, tartaric, lactic, benzoic, salicylic, glutamic, aspartic, p-toluenesulfonic, benzenesulfonic, methanesulfonic, ethanesulfonic, naphthalenesulfonic such as 2-naphthalenesulfonic, or hexanoic acid.

Such pharmaceutically acceptable base addition salt of a compound of Formula (I) include, but are not limited to, aluminium, arginine, benzathine, calcium, choline, diethylamine, diolamine, glycine, lysine, magnesium, meglumine, olamine, potassium, sodium, tromethamine and zinc salts.

In certain embodiments, the free acid or free base forms of the compounds of Formula (I) described herein are prepared from the corresponding base addition salt or acid addition salt from, respectively. For example a compound Formula (I) in an acid addition salt form is converted to the corresponding free base by treating with a suitable base (by way of example only, an ammonium hydroxide solution, a sodium hydroxide, and the like). For example, a compound of Formula (I) in a base addition salt form is converted to the corresponding free acid by treating with a suitable acid (by way of example only, hydrochloric acid).

In certain embodiments, compounds of Formula (I) in unoxidized form are prepared from N-oxides of compounds Formula (I) by treating with a reducing agent (by way of example only, sulfur, sulfur dioxide, triphenyl phosphine, lithium borohydride, sodium borohydride, phosphorus trichloride, tribromide, or the like) in a suitable inert organic solvent (by way of example only, acetonitrile, ethanol, aqueous dioxane, or the like) at 0 to 80° C.

In certain embodiments, prodrug derivatives of compounds Formula (I) are prepared using methods known to those of ordinary skill in the art (e.g., for further details see Saulnier et al., (1994), Bioorganic and Medicinal Chemistry Letters, Vol. 4, p. 1985). For example, appropriate prodrugs are prepared by reacting a non-derivatized compound of Formula (I) with a suitable carbamylating agent (by way of example only, 1,1-acyloxyalkylcarbanochloridate, para-nitrophenyl carbonate, or the like).

In certain embodiments, compounds of Formula (I) are prepared as protected derivatives using methods known to those of ordinary skill in the art. A detailed description of the techniques applicable to the creation of protecting groups and their removal can be found in T. W. Greene, "Protecting Groups in Organic Chemistry," 3$^{rd}$ edition, John Wiley and Sons, Inc., 1999.

In certain embodiments, compounds of Formula (I) are prepared or formed, as solvates (e.g., hydrates). In certain embodiments, hydrates of compounds of Formula (I) are prepared by recrystallization from an aqueous/organic solvent mixture, using organic solvents such as dioxin, tetrahydrofuran or methanol.

In certain embodiments, compounds of Formula (I) are prepared as their individual stereoisomers. In other embodiments, the compounds of Formula (I) described herein are prepared as their individual stereoisomers by reacting a racemic mixture of the compound with an optically active resolving agent to form a pair of diastereoisomeric compounds, separating the diastereomers and recovering the optically pure enantiomers. In certain embodiments, resolution of enantiomers is carried out using covalent diastereomeric derivatives of the compounds of Formula (I), or by using dissociable complexes (e.g., crystalline diastereomeric salts). Diastereomers have distinct physical properties (e.g., melting points, boiling points, solubility, reactivity, etc.) and are readily separated by taking advantage of these dissimilarities. In certain embodiments, the diastereomers are separated by chromatography, or by separation/resolution techniques based upon differences in solubility. The optically pure enantiomer is then recovered, along with the resolving agent, by any practical means that would not result in racemization. A more detailed description of the techniques applicable to the resolution of stereoisomers of compounds from their racemic mixture can be found in Jean Jacques, Andre Collet, Samuel H. Wilen, "Enantiomers, Racemates and Resolutions," John Wiley And Sons, Inc., 1981.

Compounds of Formula (I) are made by processes described herein and as illustrated in the Examples. In certain embodiments, compounds of Formula (I) are made by:

(a) optionally converting a compound of Formula (I) into a pharmaceutically acceptable salt;
(c) optionally converting a salt form of a compound of Formula (I) to a non-salt form;
(d) optionally converting an unoxidized form of a compound of Formula (I) into a pharmaceutically acceptable N-oxide;
(e) optionally converting an N-oxide form of a compound of Formula (I) to its unoxidized form;
(f) optionally resolving an individual isomer of a compound of Formula (I) from a mixture of isomers;
(g) optionally converting a non-derivatized compound of Formula (I) into a pharmaceutically acceptable prodrug derivative; and
(h) optionally converting a prodrug derivative of a compound of Formula (I) to its non-derivatized form.

Non-limiting examples of synthetic schemes used to make compounds of Formula (I) described herein are illustrated in reaction schemes (I)-(XI).

Scheme (I) illustrates the synthesis of benzonaphthyridines (3) by coupling substituted or unsubsubstituted 2-(tert-butoxycarbonyl-amino)phenylboronic acids (1) with substituted or unsubsubstituted 3-halopicolinonitrile derivatives (2) in the presence of a palladium catalyst. By way of example only, the halo moiety of the 3-halopicolinonitrile derivatives is bromo or chloro. The functional groups ($R_1$, $R_2$, $R_3$, $R_4$) on benzonaphthyridines (3) are optionally further modified, as described herein.

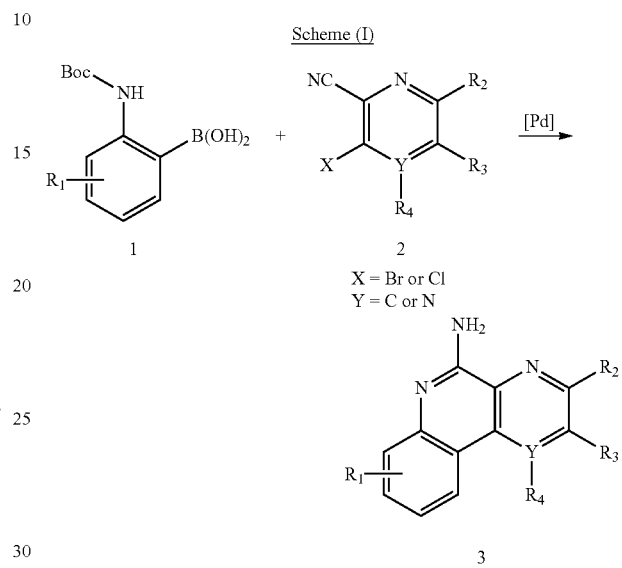

Scheme (I)

In certain embodiments, the phenyl boronic acids used in the synthesis of compounds of Formula (I) were synthesized according to scheme (II). In scheme (II) substituted or unsubsubstituted anilines (4) are Boc-protected under basic conditions to give (5), and then converted into the boronic acids (1) through ortho-lithiation and reaction with trimethyl borate followed by aqueous workup.

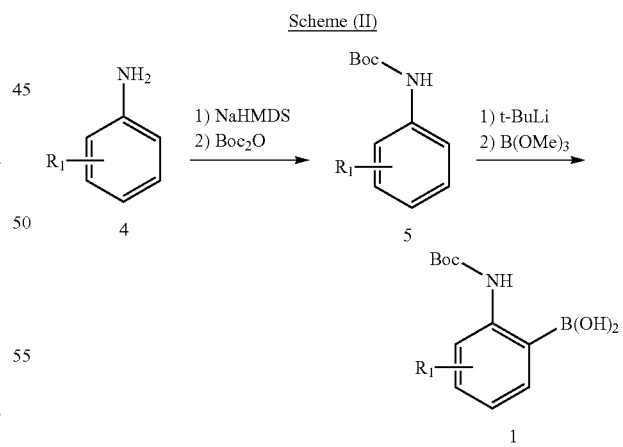

Scheme (II)

Boric acids (1) are used as in scheme (I) and reacted with substituted or unsubsubstituted cyanopyridines (2) to afford substituted or unsubsubstituted benzonaphthyridines (3).

In certain embodiments, boronic acid equivalents including, but not limited to, substituted or unsubstituted boronate esters were used in the synthesis of compounds of Formula (I). Scheme (III) illustrates the synthesis of such substituted or unsubsubstituted boronate esters (8), which were used as boronic acid equivalents in the synthesis of substituted or unsubsubstituted benzonaphthyridines (3). In scheme (III) substituted or unsubsubstituted 2-haloanilines (6) are Boc-protected under basic conditions to give (7), which are then converted into the substituted or unsubsubstituted boronate esters (8) using palladium-mediated catalysis. These boronate esters (8) are used as in scheme (I) and react with substituted or unsubsubstituted cyanopyridines (2) to afford substituted or unsubsubstituted benzonaphthyridines (3).

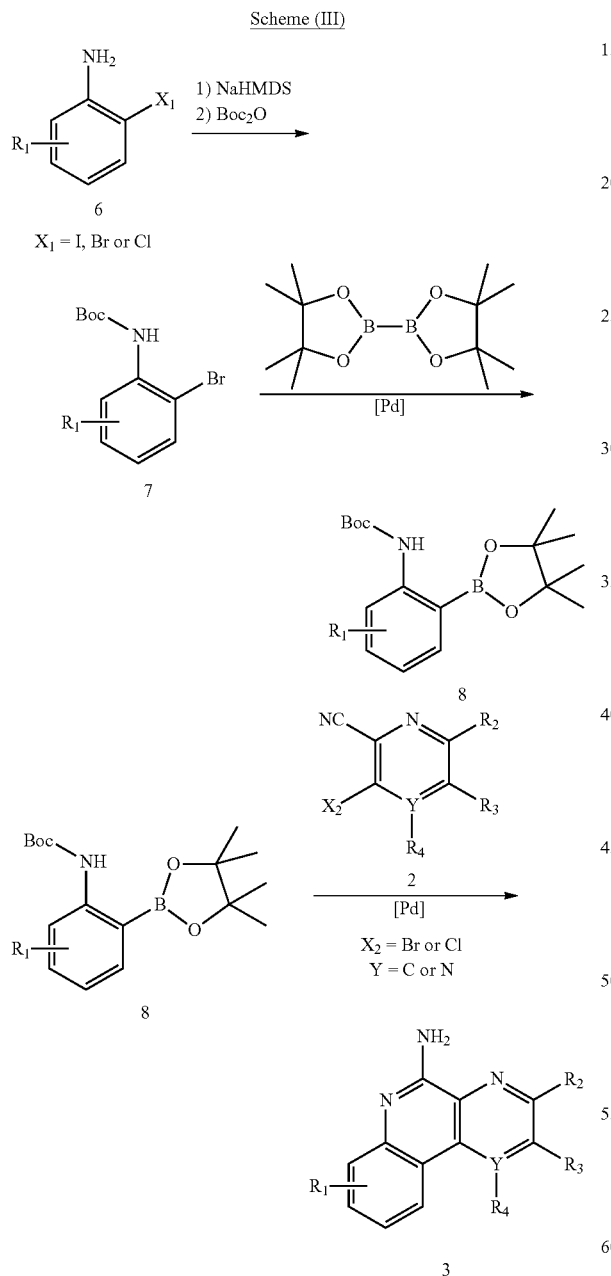

In certain embodiments, substituted or unsubsubstituted 2-bromoanilines used in scheme (III) were synthesized from their corresponding substituted or unsubsubstituted nitrobenzene compounds as illustrated below:

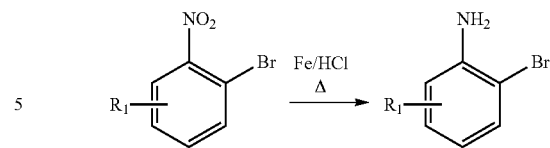

In certain embodiments, compounds of Formula (I) having oxygen-linked substituents were synthesized using the methodologies described in scheme (IV).

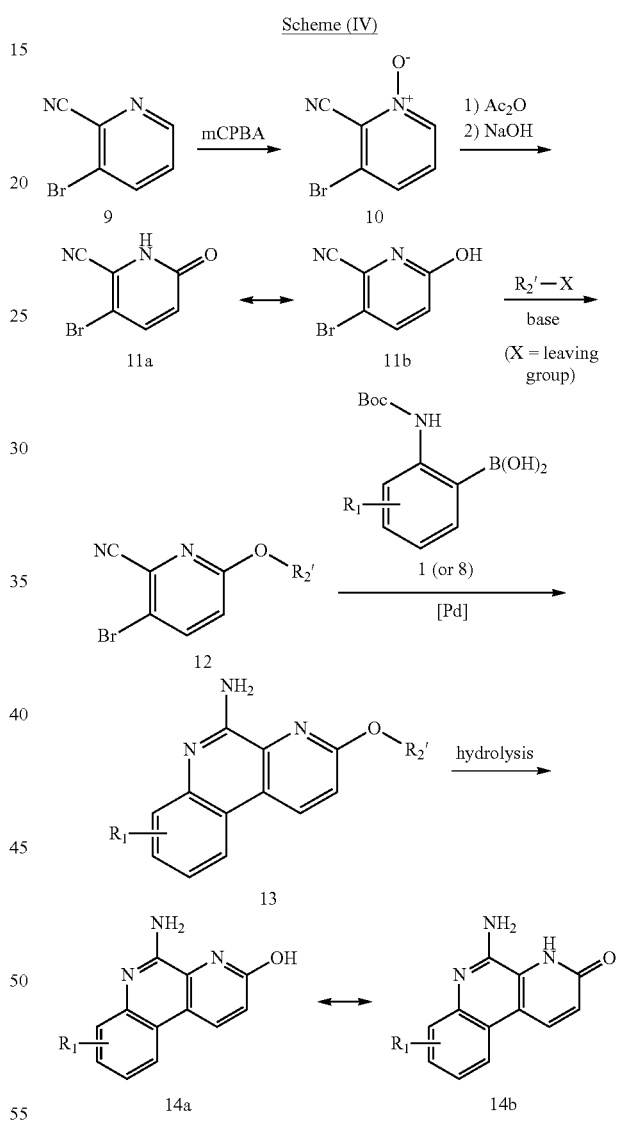

In scheme (IV) benzonitrile (9) is first oxidized to N-oxide (10) with meta-chloroperbenzoic acid (mCPBA), and then converted into pyridone (11). Under specific basic conditions, the pyridone (11) is selectively alkylated on the oxygen to give the alkoxypicolinonitrile (12). Using palladium-mediated conditions, as in scheme (I), derivatives of alkoxypicolinonitrile (12) are coupled with substituted or unsubstituted boronic acids (1) (or substituted or unsubstituted boronate esters (8) to give substituted or unsubstituted benzonaphthyridine (13) with oxygen-linked substituents. In certain embodiments, the benzonaphthyridine (13) with oxygen-linked substituents was hydrolyzed to obtain the corresponding benzonaphthyridone (14).

In other embodiments, compounds of Formula (I) having various substituents were synthesized using the methodologies described in scheme (V).

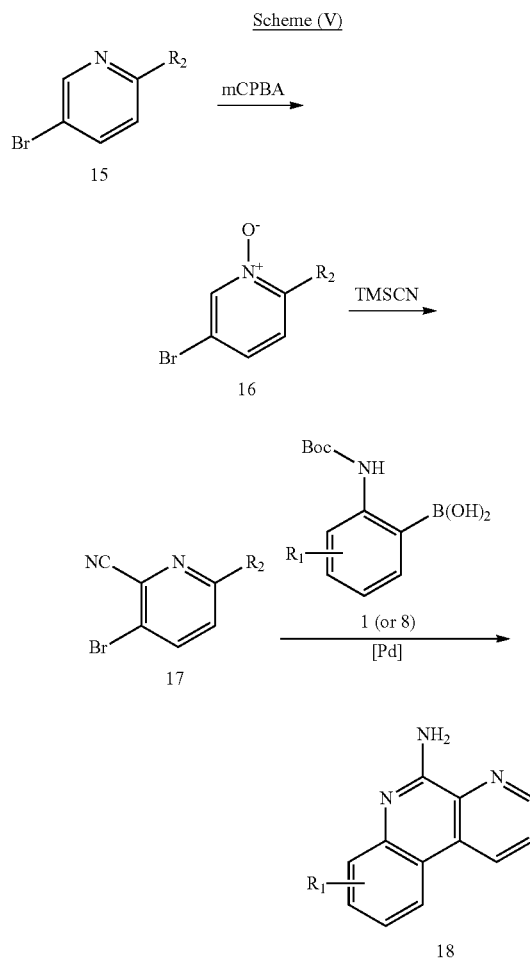

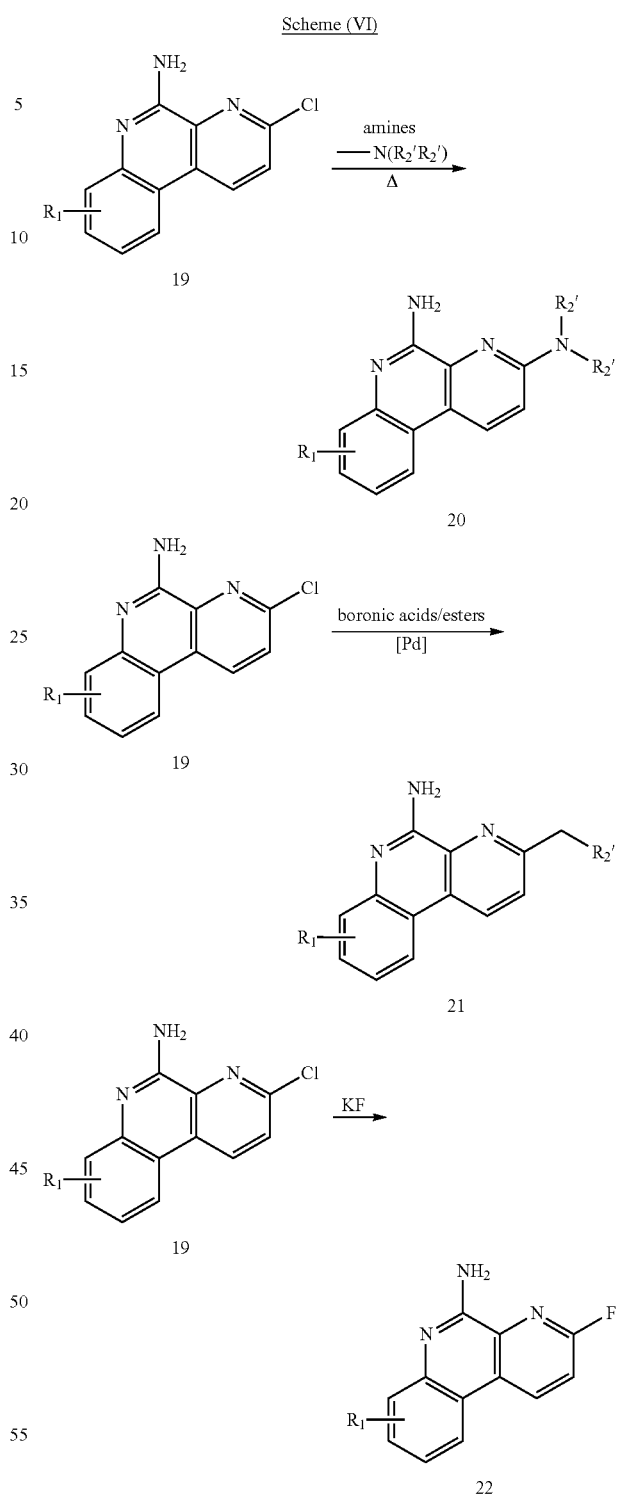

In scheme (V), 5-bromopyridines (15) substituted at the 2-position (shown as $R_2$ in scheme (V)) are first oxidized by meta-chloroperbenzoic acid (mCPBA) to give the N-oxide 16, which are then converted to the benzonitrile (17). Using palladium-mediated conditions, as in scheme (I), derivatives of benzonitrile (17) are coupled with substituted or unsubstituted boronic acids (1) (or substituted or unsubstituted boronate esters (8) to give substituted or unsubstituted benzonaphthyridine (18) with various substituents in the 3-position. In other embodiments, benzonaphthyridine having various substituents in the 2-position are obtained by starting with 5-bromopyridines substituted at the 3-position.

In certain embodiments, the substituent in the 3-position of the benzonaphthyridine (18) is a chlorine atom, and this 3-chloro-benzonaphthyridine (19) is further modified to obtain other substituents at the 3-position of the benzonaphthyridines. Non-limiting examples of such modifications are illustrated in scheme (VI).

In certain embodiments, as illustrated in scheme (VI), compounds of Formula (I) having N-linked substituents (derivatives of (20)) were obtained via $S_NAr$ reactions by heating such chloro-derivatives (19) with various amines. In certain embodiments, as illustrated in scheme (VI), compounds of Formula (I) having carbon-linked substituents (derivatives of (21)) were obtained via Suzuki couplings using palladium-mediated conditions with various boronic acids or boronate esters. In certain embodiments, as illustrated in scheme (VI), compounds of Formula (I) were fluorinated by treatment of such chloro-derivatives (19) with potassium fluoride to give (3-fluorobenzo[f][1,7]-naphthyridin-5-amine (22)).

In other embodiments, compounds of Formula (I) having various substituents were synthesized using the methodologies described in scheme (VII).

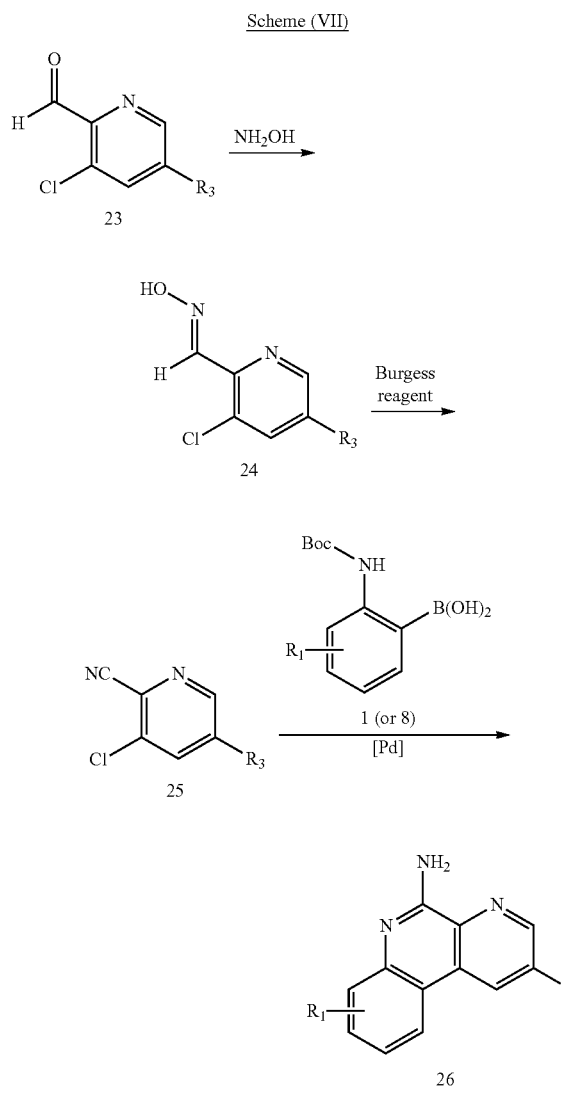

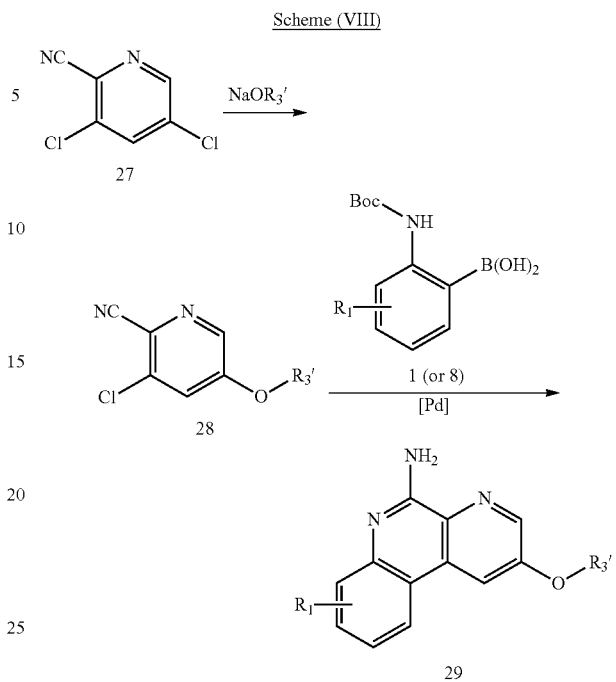

In scheme (VII), 3-chlorobenzaldehyde (23) (with a substituent $R_3$ at the 5-position) is first converted to the corresponding hydroxylamine (24), which is then used to make the corresponding nitrile (25). Using palladium-mediated conditions, as in scheme (I), derivatives of nitrile (25) are coupled with substituted or unsubstituted boronic acids (1) (or substituted or unsubstituted boronate esters (8) to give the benzonaphthyridine (26) with various substituents in the 2-position.

In other embodiments, certain compounds of Formula (I) having oxygen-linked substituents were synthesized using the methodologies described in scheme (VIII).

In scheme (VIII), benzonaphthyridines with various different oxygen-linked $R_3$ substituents at the 2-position are prepared using a 3,5-dihalopicolinonitrile, such as, by way of example only, 3,5-dichloropicolinonitrile (27), which is first mono-substituted with an alkoxy appendage to give the corresponding picolinonitrile (28). Then, using palladium-mediated conditions as in scheme (I), derivatives of nitrile (27) are coupled with substituted or unsubstituted boronic acids (1) (or substituted or unsubstituted boronate esters (8) to give the benzonaphthyridine (29) with various oxygen-linked substituents in the 2-position.

In certain embodiments, compounds of Formula (I) having hydroxy substituents, including benzonaphthyridines hydroxy substituents at the 2-position, were prepared using the synthetic route shown in scheme (IX).

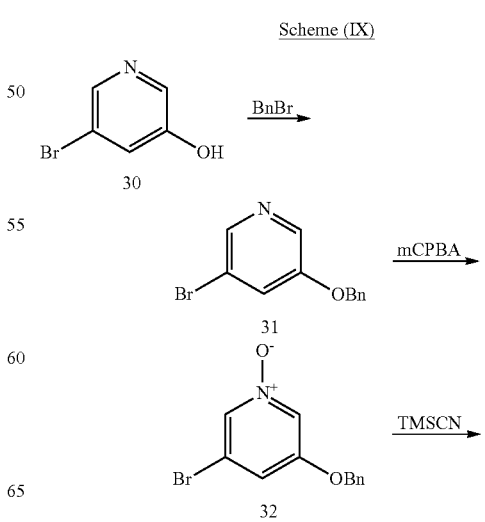

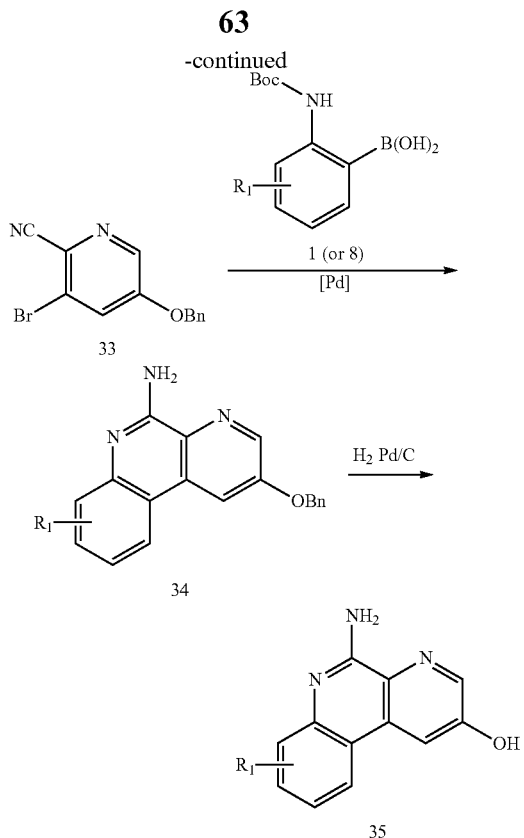

In scheme (IX), a 5-halopyridin-3-ol such as, by way of example only, 3,5-bromopyridin-3-ol (30), is benzyl-protected at the hydroxyl group to give (31), which is then converted to the corresponding N-oxide (32). The N-oxide (32) is further converted into the nitrile (33). Then, using palladium-mediated conditions as in scheme (I), derivatives of nitrile (33) are coupled with substituted or unsubstituted boronic acids (1) (or substituted or unsubstituted boronate esters (8) to give the benzonaphthyridine (34) which upon hydrogenation gives the benzonaphthyridine (35) with a hydroxyl substituent in the 2-position.

In other embodiments, certain compounds of Formula (I) having carbon-linked substituents, including benzonaphthyridines with various carbon-linked substituents at the 2-position, were prepared using the synthetic route shown in scheme (X).

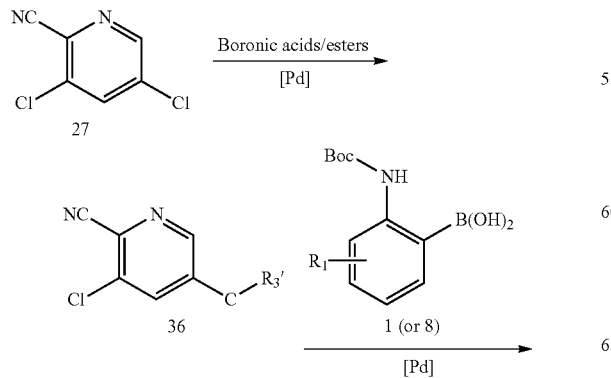

In scheme (X), a 3,5-dihalopicolinonitrile, such as, by way of example only, 3,5-dichloropicolinonitrile (27), is first mono-substituted using one equivalent of boronic acid/ester thereby giving the corresponding picolinonitrile (36). Using more vigorous palladium-mediated conditions as in scheme (I), derivatives of nitrile (36) are coupled with substituted or unsubstituted boronic acids (1) (or substituted or unsubstituted boronate esters (8) to give the benzonaphthyridine (37) having carbon-linked substituents at the 2-position. In certain embodiments the carbon-linked substituent is an alkene, while in other embodiments such alkenes are further modified by hydrogenation to give benzonaphthyridines with alkyl groups at the 2-position.

In other embodiments, certain compounds of Formula (I) having various substituents, including benzonaphthyridines with various substituents at the 1-position, were synthesized using the methodologies described in scheme (XI).

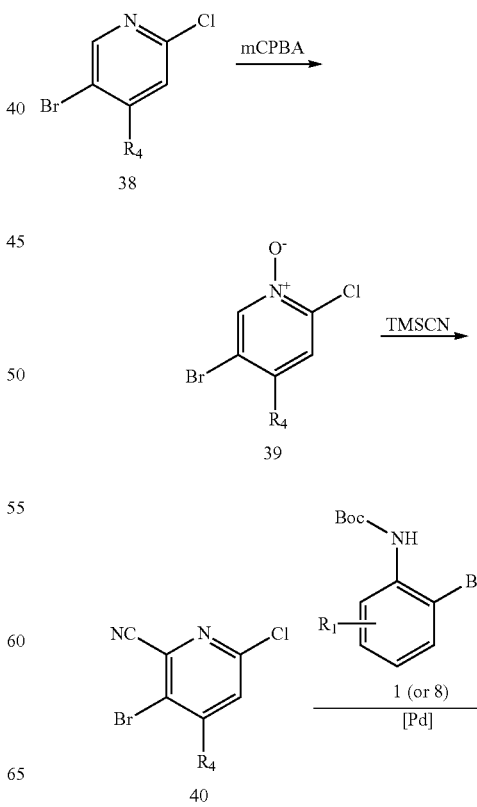

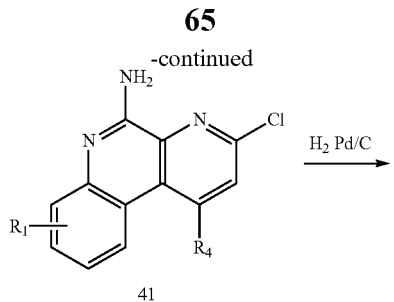

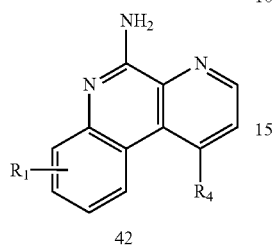

In scheme (XI), a 2,5-dihalopyridine substituted at the 4 position such as, by way of example only, 5-bromo-2-chloropyridine (38) is first converted to the corresponding N-oxide (39), which is then converted to the corresponding nitrile (40). Using palladium-mediated conditions as in scheme (I), derivatives of nitrile (40) are coupled with substituted or unsubstituted boronic acids (1) (or unsubstituted boronate esters (8) to give the benzonaphthyridine (41) having substituents at the 1-position. In certain embodiments, benzonaphthyridine (41) is further de-chlorinated to give benzonaphthyridine (42).

In other embodiments, certain compounds of Formula (I) having various substituents, including benzonaphthyridines with various substituents at the 2-position, were synthesized using the methodologies described in scheme (XII).

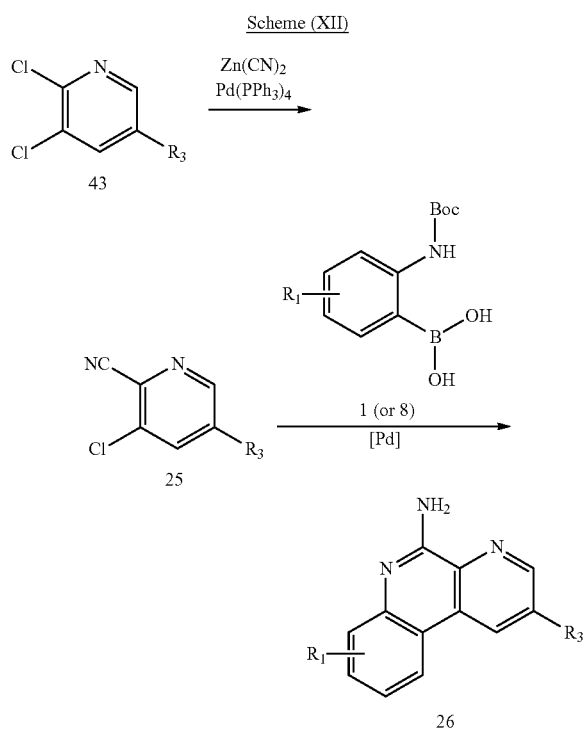

In scheme (XII), a 2,3-dihalopyridines substituted at the 5 position (43), such as, by way of example only, (5,6-dichloropyridin-3-yl)methanol, is first converted to the corresponding nitrile (25). Using palladium-mediated conditions as in scheme (I), derivatives of nitrile (25) are coupled with substituted or unsubstituted boronic acids (1) (or substituted or unsubstituted boronate esters (8) to give the benzonaphthyridine (26) having substituents at the 2-position.

Various 3-halo naphthyridines were prepared according to the general methods as exemplified in Scheme XIII.

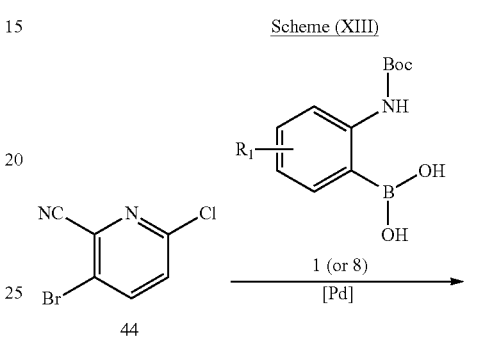

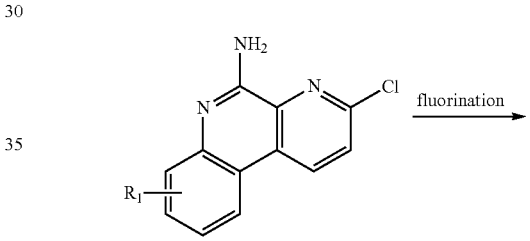

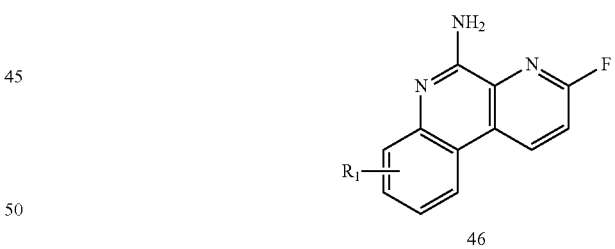

In scheme (XIII), using palladium-mediated conditions as in scheme (I), a 3,6-dihalo-2-cyanopyridines such as, by way of example only, 3-bromo-6-chloropicolinonitrile is coupled with substituted or unsubstituted boronic acids (1) (or substituted or unsubstituted boronate esters (8) to give the benzonaphthyridine (45) having halogen substitutions at the 3-position. Further halogen exchange of benzonaphthyridine (45) gave benzonaphthyridine (46) with different halaogen substituents at the 3-position.

In other embodiments, certain compounds of Formula (I) were synthesized using the methodologies described in scheme (XIV).

boronate esters (8) to give the benzonaphthyridine (52). Compound 52 is then subjected under hydrogenation conditions to give benzonaphthyridines 53 with different substitutents at the R₃' position.

In other embodiments, certain compounds of Formula (I) were synthesized using the methodologies described in scheme (XV).

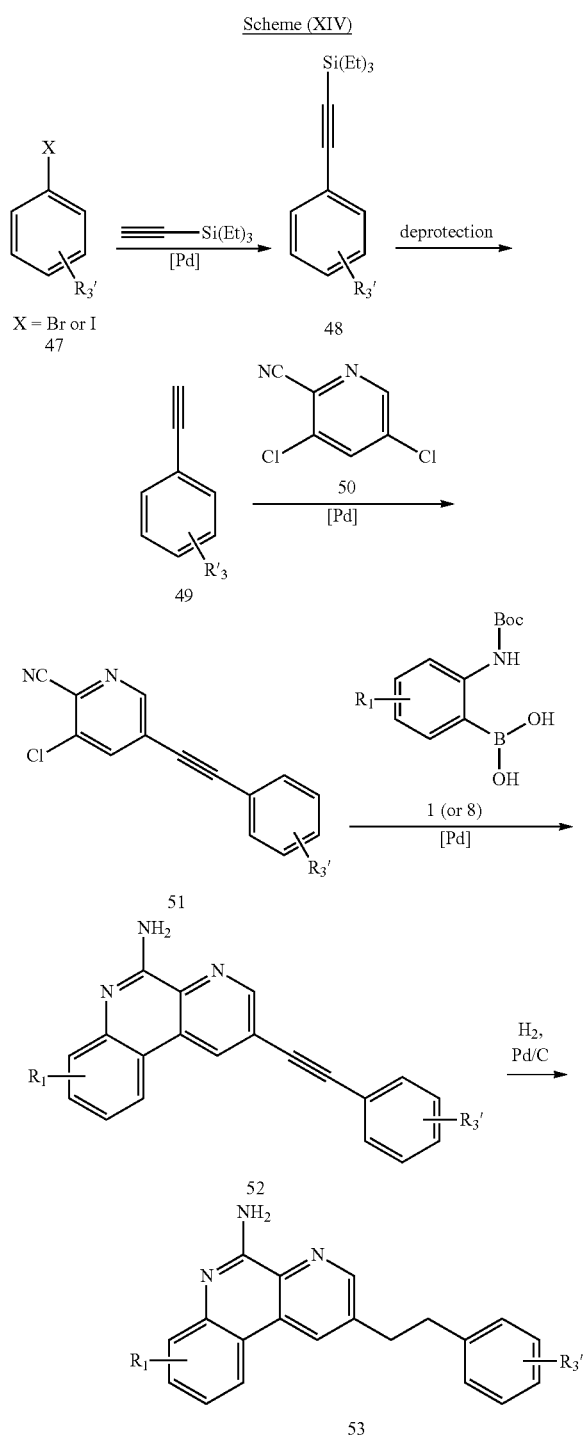

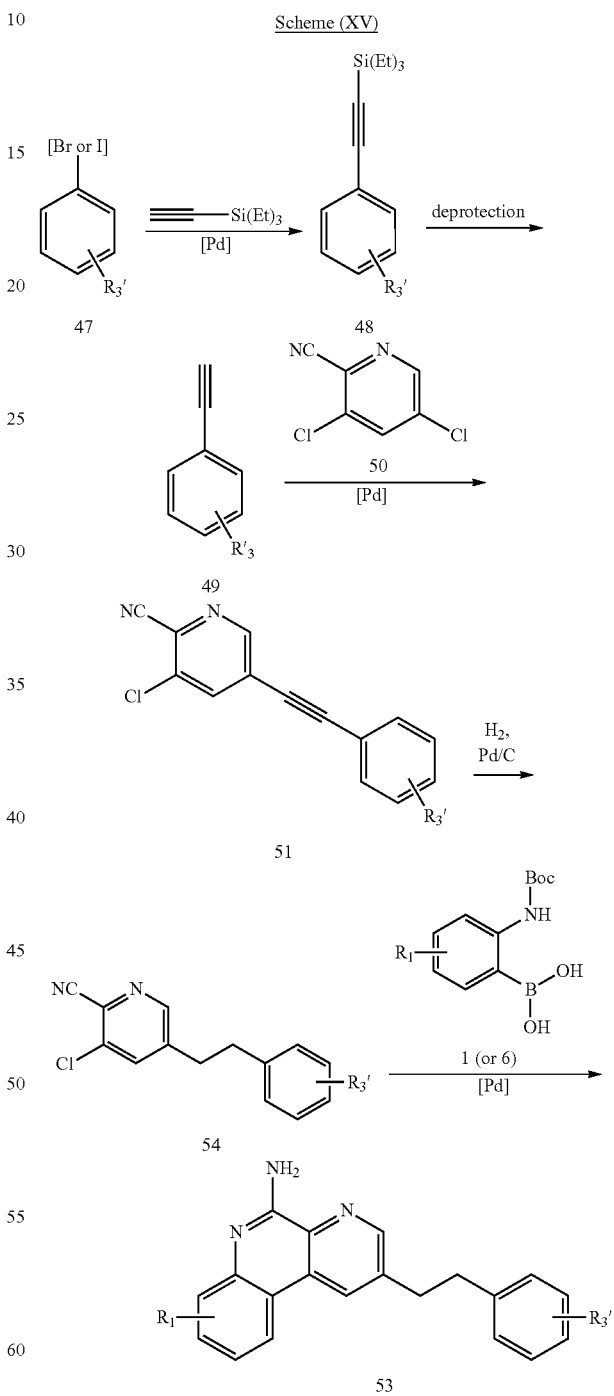

In scheme (XIV), aryl bromides or aryl iodides (47) substituted with various R₃' groups are coupled with triethyl (ethynyl)silane (or its equivalents) using palladium-mediated conditions to afford 48. After deprotection of the silyl protection group, acetylene derivatives (49) are coupled with 3,5-dichloropicolinonitrile (50) using palladium-mediated conditions to afford 3-chloro-2-cyanopyridines (51). Derivatives of 51 such as, by way of example only, 3-chloro-5-(phenylethynyl)picolinonitrile is coupled with substituted or unsubstituted boronic acids (1) (or substituted or unsubstituted In scheme (XV), aryl bromides or aryl iodides (47) substituted with various R₃' groups are coupled with triethyl(ethynyl)silane (or its equivalents) using palladium-mediated conditions to afford 48. After deprotection of the silyl protection group, acetylene derivatives (49) are coupled with 3,5-dichloropicolinonitrile (50) using palladium-mediated conditions to afford 3-chloro-2-cyanopyridines (51). Derivatives of 51 such as, by way of example only, 3-chloro-5-(phenylethynyl)picolinonitrile is reduced to the corresponding 3-chloro-5-phenethylpicolinonitrile (54) under hydrogenation conditions. Compound 54 is coupled with substituted or unsubstituted boronic acids (1) (or substituted or unsubstituted boronate esters (8) to give benzonaphthyridines 53 with different substitutents at the $R_3'$ position.

Benzonaphthyridines with various substitutions can be further converted into other functional groups using standard organic transformations. In certain embodiments, certain compounds of Formula (I) were synthesized using the methodologies described in scheme (XVI).

Scheme (XVI)

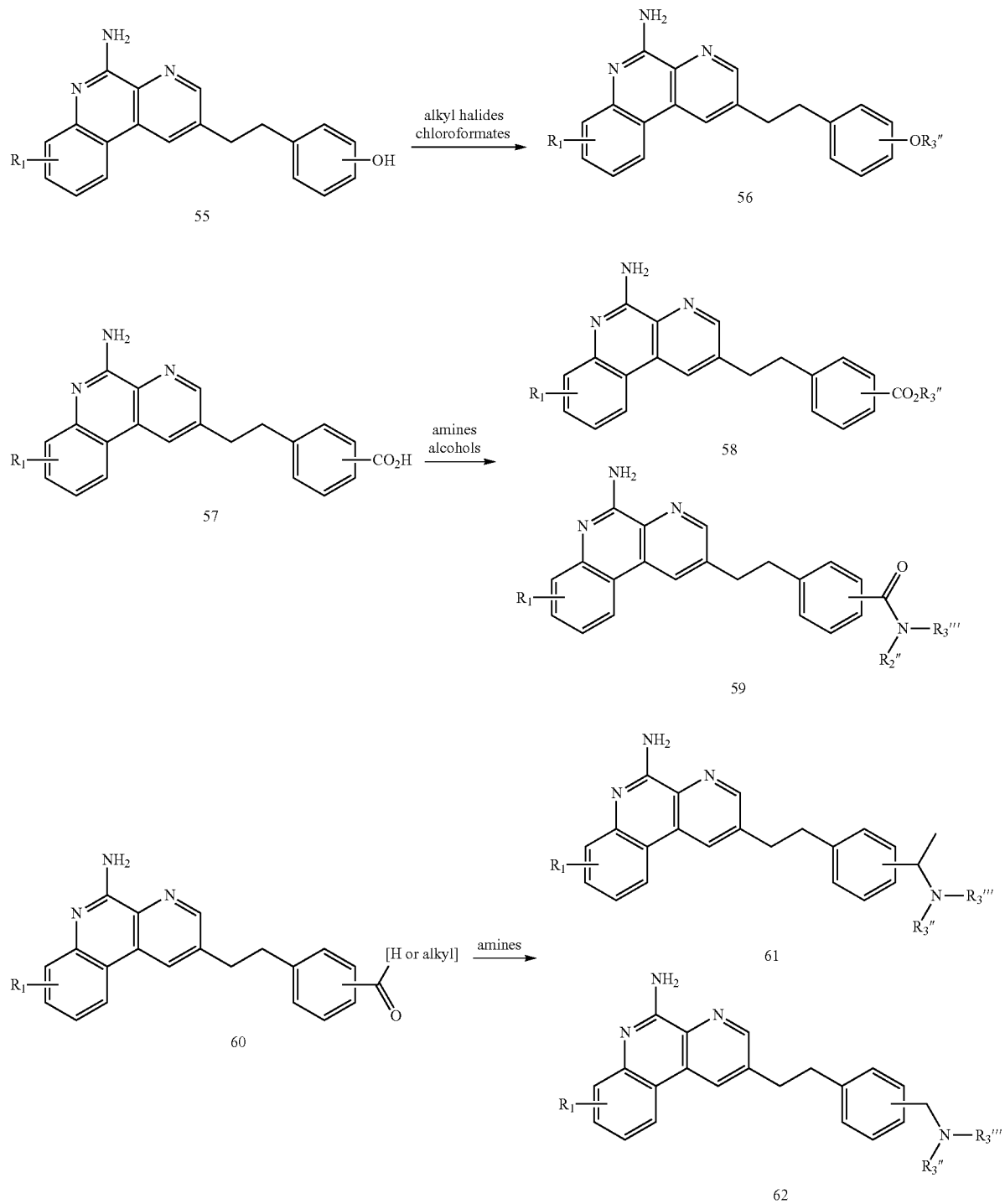

By way of example, in Scheme (XVI), benzonaphthyridines bearing a hydroxyl group (55) are converted to the corresponding ethers or carbonates (56). For example, benzonaphthyridines bearing a carboxylic acid group (57) are converted to the corresponding esters (58) or amides (59). For example, benzonaphthyridines bearing an aldehyde or ketone group (60) are converted to the corresponding amines (61 or 62). These benzonaphthyridines can be further modified using the standard organic transformations.

In certain embodiments, certain compounds of Formula (I) were synthesized using the methodologies described in scheme (XVII).

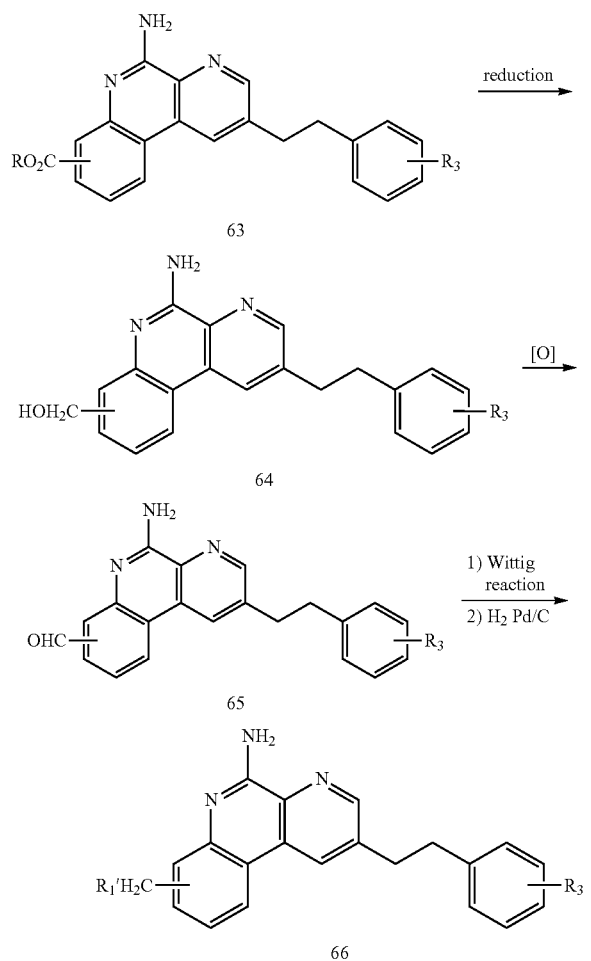

In scheme (XVII), benzonaphthyridines with various substitutions are further converted to different functional groups through standard organic transformations. For example, benzonaphthyridines bearing an ester group (63) are converted to the corresponding alcohol (64) by reduction using standard reducing agents. Compound 64 is oxidized to the corresponding aldehyde (65), which is further alkylated by a Wittig reaction followed by hydrogenation to give derivatives 66. These benzonaphthyridines can be further modified using the standard organic transformations.

In certain embodiments, certain compounds of Formula (I) were synthesized using the methodologies described in scheme (XVIII).

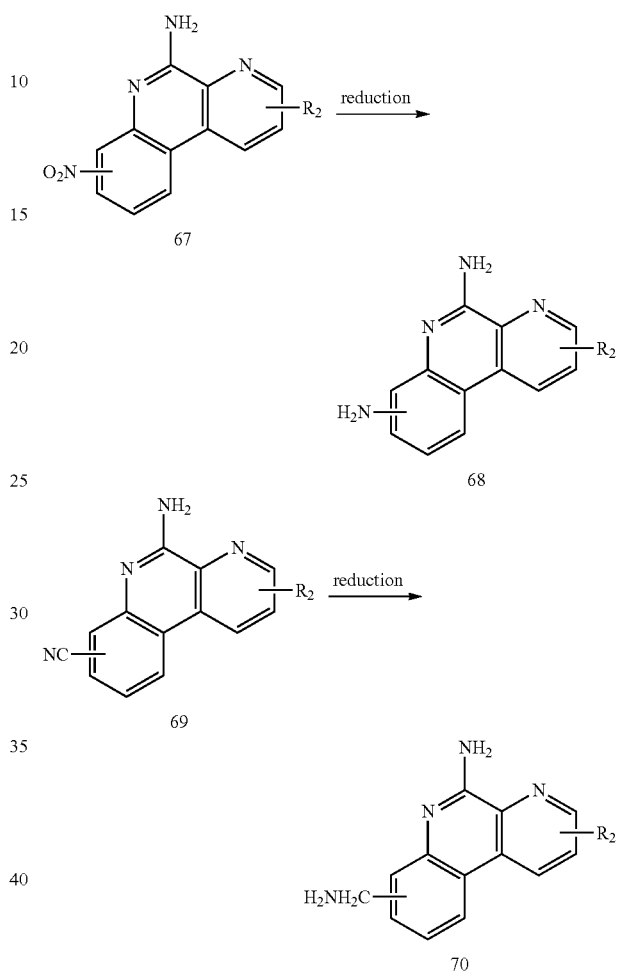

In scheme (XVIII), benzonaphthyridines with various substitutions are further converted to different functional groups through standard organic transformations. For example, benzonaphthyridines bearing a nitro group (67) or a cyano group (69) are converted to the corresponding amine (68) or methyl amine (70) by reduction using standard reducing agents. These benzonaphthyridines can be further modified using the standard organic transformations.

In certain embodiments, certain compounds of Formula (I) were synthesized using the methodologies described in scheme (XIX).

Scheme (XIX)

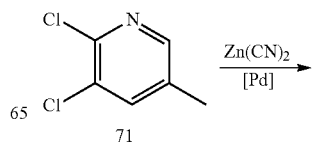

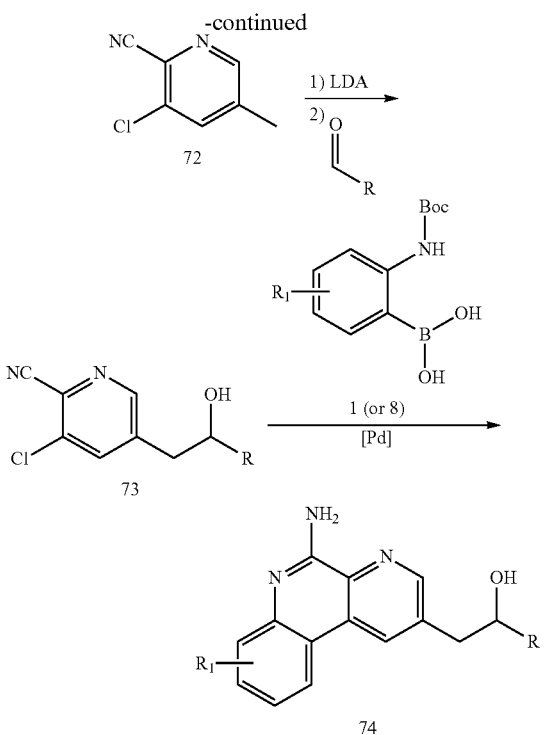

In scheme (XIX), 2,3-dichloro-5-methylpyridine (71) is converted to the corresponding nitrile (72). Alcohol 73 is formed under Aldol condensation conditions, wherein compound 72 reacts with an aldehyde or ketone. Derivatives of 73 are then coupled with boronic acids (1) or boronate esters (8) to give the benzonaphthyridine (74).

The following examples are offered to illustrate, but not to limit, the compounds of Formula (I) provided herein, and the preparation of such compounds.

Pharmacology and Utility

When a foreign antigen challenges the immune system it responds by launching a protective response that is characterized by the coordinated interaction of both the innate and acquired immune systems. These two interdependent systems fulfill two mutually exclusive requirements: speed (contributed by the innate system) and specificity (contributed by the adaptive system).

The innate immune system serves as the first line of defense against invading pathogens, holding the pathogen in check while the adaptive responses are matured. It is triggered within minutes of infection in an antigen-independent fashion, responding to broadly conserved patterns in the pathogens (though it is not non-specific, and can distinguish between self and pathogens). Crucially, it also generates the inflammatory and co-stimulatory milieu (sometimes referred to as the danger signal) that potentiates the adaptive immune system and steers (or polarizes it) towards the cellular or humoral responses most appropriate for combating the infectious agent. The development of TLR modulators for therapeutic targeting of innate immunity has been reviewed (see Nature Medicine, 2007, 13, 552-559; Drug Discovery Today: Therapeutic Stategies, 2006, 3, 343-352 and Journal of Immunology, 2005, 174, 1259-1268).

The adaptive response becomes effective over days or weeks, but ultimately provides the fine antigenic specificity required for complete elimination of the pathogen and the generation of immunologic memory. It is mediated principally by T and B cells that have undergone germline gene rearrangement and are characterized by specificity and long-lasting memory. However, it also involves the recruitment of elements of the innate immune system, including professional phagocytes (macrophages, neutrophils etc.) and granulocytes (basophils, eosinophils etc.) that engulf bacteria and even relatively large protozoal parasites. Once an adaptive immune response has matured, subsequent exposure to the pathogen results in its rapid elimination due to highly specific memory cells have been generated that are rapidly activated upon subsequent exposure to their cognate antigen.

Autoimmune diseases, are defined by (i) humoral or autoantibody response to a self antigen (by way of example only, Graves' primary hyperthyroidism with antibodies to the TSH receptor), or (ii) cellular response wherein immune cells destroy nonimmune cells from which the self-antigen is derived (by way of example only, the thyrocyte (Hashimoto's thyroiditis) or pancreatic β-islet cell (Type 1 diabetes). Many autoimmune diseases are a combination of both phenomena, for instance, Hashimoto's and Type 1 diabetes also have auto-antibodies, anti-thyroid peroxidase (TPO) or anti-glutamic acid decarboxylase (GAD)/Islet Cell. Autoimmune diseases often have an inflammatory component including, but not limited to, increases in adhesion molecules (by way of example only, vascular cell adhesion molecule-1 (VCAM-1), and altered leukocyte adhesion to the vasculature such as, by way of example only, colitis, systemic lupus, systemic sclerosis, and the vascular complications of diabetes.

Toll-like receptors (TLRs) are type-I transmembrane proteins characterized by an extracellular N-terminal leucine-rich repeat (LRR) domain, followed by a cysteine-rich region, a TM domain, and an intracellular (cytoplasmic) tail that contains a conserved region named the Toll/IL-1 receptor (TIR) domain. TLRs are pattern recognition receptors (PRR) that are expressed predominantly on immune cells including, but not limited to, dendritic cells, T lymphocytes, macrophages, monocytes and natural killer cells. The LLR domain is important for ligand binding and associated signaling and is a common feature of PRRs. The TIR domain is important in protein-protein interactions and is associated with innate immunity. The TIR domain also unites a larger IL-1 R/TLR superfamily that is composed of three subgroups. Members of the first group possess immunoglobin domains in their extracellular regions and include IL-1 and IL-18 receptors and accessory proteins as well as ST2. The second group encompasses the TLRs. The third group includes intracellular adaptor proteins important for signaling.

TLRs are a group of pattern recognition receptors which bind to pathogen-associated molecular patterns (PAMPS) from bacteria, fungi, protozoa and viruses, and act as a first line of defense against invading pathogens. TLRs are essential to induce expression of genes involved in inflammatory responses, and TLRs and the innate immune system are a critical step in the development of antigen-specific acquired immunity.

Adaptive (humoral or cell-mediated) immunity is associated with the TLR signal mechanism of innate immunity. Innate immunity is a protective immune cell response that functions rapidly to fight environmental insults including, but not limited to, bacterial or viral agents. Adaptive immunity is a slower response, which involves differentiation and activation of naive T lymphocytes into T helper 1 (Th1) or T helper 2 (Th2) cell types. Th1 cells mainly promote cellular immunity, whereas Th2 cells mainly promote humoral immunity. Though primarily a host protective system, pathologic expression of the innate immunity signals emanating from the TLR pathway are implicated in initiating autoimmune-inflammatory diseases.

All TLRs appear to function as either a homodimer or heterodimer in the recognition of a specific, or set of specific, molecular determinants present on pathogenic organisms including bacterial cell-surface lipopolysaccharides, lipoproteins, bacterial flagellin, DNA from both bacteria and viruses and viral RNA. The cellular response to TLR activation involves activation of one or more transcription factors, leading to the production and secretion of cytokines and co-stimulatory molecules such as interferons, TNF-, interleukins, MIP-1 and MCP-1 which contribute to the killing and clearance of the pathogenic invasion.

TLR spatial expression is coincident with the host's environmental interface. While only a few other Toll-like proteins have been cloned in *Drosophila*, the human TLR family is composed of at least 11 members, TLR1 through TLR11, that elicit overlapping yet distinct biological responses due to differences in cellular expression and signaling pathways they initiate. Each of the TLRs is expressed on a different subset of leukocytes and each of the TLRs is specific in its expression patterns and PAMP sensitivities and detects different subsets of pathogens allowing vigilant surveillance by the immune system.

Toll-Like Receptor 1 (TLR1)

TLR1 maps to chromosome 4p14 and its sequence encodes a putative 786 amino acid (aa) protein with 18 N-terminal LRRs and a calculated molecular weight of 84 kDa. TLR1 is most closely related to TLR6 and TLR10 with 68% and 48% overall (aa) sequence identity, respectively.

TLR1 mRNA is ubiquitously expressed and found at higher levels than the other TLRs. Of the major leukocyte populations, TLR1 is most highly expressed by monocytes, but is also expressed by macrophages, dendritic cells, polymorphonuclear leukocytes, B, T, and NK cells. In vivo, two different sized transcripts for TLR1 are observed suggesting that the mRNA is alternatively spliced to generate two different forms of the protein. In vitro, TLR1 mRNA and protein expression is upregulated in monocytic leukemic (THP-1) cells upon PMA-induced differentiation. TLR1 expression is upregulated by autocrine IL-6, and is also elevated by IFN-γβ, IL-10, and TNF-α. However, TLR1 level is unaffected by exposure to both Gram-positive and Gram-negative bacteria. Ex vivo, both monocyte and granulocyte TLR1 expression is downregulated after exposure to Gram-negative bacteria. TLR1 forms a heterodimer with TLR2. TLR1 also heterodimerizes with TLR4, which inhibits TLR4 activity.

Toll-Like Receptor 2 (TLR2)

TLR2 maps to chromosome 4q31-32 and encodes a putative 784 (aa) protein with 19 N-terminal LLRs and a calculated molecular weight of 84 kDa. TLR2 is most closely related to TLR6 with 31% overall (aa) sequence identity.

TLR2 mRNA expression is observed in brain, heart, lung, and spleen tissues and is highest in PBLs, specifically those of myelomonocytic origin. In vivo, two different sized transcripts for TLR2 are observed suggesting that the mRNA is alternatively spliced. In vitro, TLR2 mRNA and protein expression is upregulated in monocytic leukemic (THP-1) cells upon PMA-induced differentiation. TLR2 is upregulated by autocrine IL-6 and TNF-α, IL-1β, and IL-10. TLR2 mRNA expression is elevated after exposure to both Gram-positive and Gram-negative bacteria. TLR2 forms heterodimers with TLR1, TLR6, and possibly TLR10, where each complex is particularly sensitive to subsets of TLR2-associated PAMPs. TLR2 complexes recognize a wide range of PAMPs, mostly from bacteria. These include, but are not limited to, lipoarabinomannan (LAM), lipopolysaccharide (LPS), lipoteichoic acid (LTA), peptidoglycan (PGN), and other glycolipids, glycoproteins, and lipoproteins. TLR2 complexes are also capable of detecting viruses, including but not limited to, measles virus (MV), human cytomegalovirus (HCMV), and hepatitis C virus (HCV) and fungal PAMPs, including but not limited to, zymosan. TLR2 recognizes a variety of lipoproteins/lipopeptides from various pathogens such as, by way of example only, Gram-positive bacteria, mycobacteria, *Trypanosoma cruzi*, fungi and *Treponema*. In addition, TLR2 recognizes LPS preparations from non-enterobacteria such as, by way of example only, *Leptospira interrogans*, *Porphyromonas gingivalis* and *Helicobacter pylori*. TLR2 complexes are capable of both detection of non-self patterns and detecting altered self patterns, such as those displayed by necrotic cells. TLR2 is recruited to phagosomes and is involved in the internalization of microbial products by cells.

Toll-Like Receptor 3 (TLR3)

TLR3 maps to chromosome 4q35 and its sequence encodes a putative 904 (aa) protein with 24 N-terminal LRRs and a calculated molecular weight of 97 kDa. TLR3 is most closely related to TLR5, TLR7, and TLR8, each with 26% overall (aa) sequence identity.

TLR3 mRNA is expressed at highest levels in the placenta and pancreas. TLR3 is expressed by dendritic cells, T and NK cells. In vivo, two different sized transcripts for TLR3 are observed suggesting that the mRNA is alternatively spliced to generate two different forms of the protein. In vitro, PMA-differentiated THP-1 TLR3 is moderately upregulated by autocrine IFN-γ, IL-1β, IL-6, IL-10, and TNF-α. TLR3 mRNA is elevated after exposure to Gram-negative bacteria and to an even greater extent in response to Gram-positive bacteria. Ex vivo, TLR3 expression is elevated in both monocytes and granulocytes upon exposure to Gram-negative bacteria. TLR3 forms a homodimer and recognizes viral double stranded RNA (dsRNA). While it is generally assumed that TLRs are expressed on the cell surface, however those TLRs sensitive to internal PAMPs, such as dsRNA in the case of TLR3, are localized intracellularly in the lysosomal compartment.

Toll-Like Receptor 4 (TLR4)

TLR4 maps to chromosome 9q32-33, and shows a high degree of similarity to dToll over the entire (aa) sequence. The TLR4 sequence encodes an 839 (aa) protein with 22 N-terminal LRR regions and a calculated molecular weight of 90 kDa. TLR4 is most closely related to TLR1 and TLR6 each with 25% overall (aa) sequence identity.

In vivo, TLR4 mRNA is expressed as a single transcript, and found at highest levels in spleen and PBLs. Of the PBL populations, TLR4 is expressed by B cells, dendritic cells, monocytes, macrophages, granulocytes, and T cells. TLR4 is also expressed in myelomonocytic cells and is highest in mononuclear cells. In vitro, TLR4 mRNA and protein expression is upregulated in THP-1 cells upon PMA-induced differentiation. TLR4 is moderately upregulated by autocrine IFN-γ, IL1β. TLR4 mRNA expression in THP-1 cells is unaffected by exposure to both Gram-positive and Gram-negative bacteria. Ex vivo, granulocyte, and monocyte, TLR4 expression is upregulated upon exposure to Gram-negative bacteria.

TLR4 forms a homodimer and requires the extracellular association of an additional component, MD-2. Although TLR2 complexes are capable of recognizing lipopolysaccharide (LPS), TLR4 is generally considered the LPS receptor. MD-2-associated TLR4 homodimers do not bind LPS directly, however. LPS must first be bound by the soluble LPS binding protein (LBP). LBP is then bound by either soluble or GPI-linked CD14. Additional cell type-dependent components required for LPS detection by TLR4 include CXCR4, GDF-5, CD55, various heat shock proteins (HSPs), and complement receptors (CRs). The TLR4 complex also recognizes a few other bacterial PAMPs including LTA. Further, the TLR4 complex recognizes viruses including respiratory syncytial virus (RSV), hepatitis C virus (HCV), and mouse mammary tumor virus (MMTV). The TLR4 complex can also recognize endogenous ligands, for example, heat shock proteins (HSP60 and HSP70), fibrinogen, domain A of fibronectin, oligosaccharides of hyaluronic acid, heparan sulfate, surfactant protein A (SP-A), and β-defensins. TLR4 also forms heterodimers both with TLR5, which enhances its activity, and also with TLR1, which inhibits its activity.

Toll-Like Receptor 5 (TLR5)

TLR5 maps to chromosome 1q41-42, and the gene encodes a putative 858 (aa) protein with a calculated molecular weight of 91 kDa. It is most closely related to TLR3 with 26% overall (aa) sequence identity.

In vivo, TLR5 mRNA is expressed as a single transcript in ovary, prostate, and PBLs. TLR5 is expressed by several PBL populations with the highest expression found in monocytes. TLR5 is also expressed on the basolateral side of intestinal epithelial cells and intestinal endothelial cells of the subepithelial compartment. In vitro, TLR5 is upregulated in PMA-differentiated THP-1 cells by autocrine IL-6, IL-10, and TNF-α, but is also elevated by IFN-γβ. TLR5 mRNA expression is elevated after exposure to both Gram-positive and Gram-negative bacteria. Ex vivo, granulocyte and monocyte TLR5 expression is downregulated upon exposure to Gram-negative bacteria. TLR5 forms a homodimer as well as a heterodimer with TLR4. Both complexes function to recognize the Flagellin protein of flagellated bacteria. Expression of human TLR5 in CHO cells confers response to flagellin, a monomeric constituent of bacterial flagella. Flagellin activates lung epithelial cells to induce inflammatory cytokine production. A stop codon polymorphism in TLR5 has been associated with susceptibility to pneumonia caused by the flagellated bacterium *Legionella pneumophila*.

Toll-Like Receptor 6 (TLR6)

TLR6 maps to chromosome 4p14, and the TLR6 sequence encodes a 796 (aa) protein containing 20 N-terminal LRR motifs with a calculated molecular weight of 91 kDa. TLR6 is most closely related to TLR1, TLR10, and TLR2 with 68%, 46%, and 31% overall (aa) sequence identity, respectively.

In vivo, TLR6 transcript is observed in thymus, spleen, and lung. TLR6 mRNA expression is highest in B cells and monocytes. In vitro, TLR6 mRNA expression is upregulated in THP-1 cells upon PMA-induced differentiation. TLR6 is moderately upregulated by autocrine IFN-γ, IL-1β. However, TLR6 mRNA expression in THP-1 cells is unaffected by exposure to both Gram-positive and Gram-negative bacteria. Ex vivo, monocyte and granulocyte TLR6 expression is downregulated upon exposure to Gram-negative bacteria. TLR6 forms a heterodimer with TLR2. Like TLR1, TLR6 is thought to specify or enhance the PAMP sensitivity of TLR2 and contribute to its signaling capabilities through heterodimerization.

Toll-Like Receptor 7 (TLR7)

TLR7 maps to human chromosome Xp22, and the TLR7 sequence encodes a 1049 (aa) protein containing 27 N-terminal LRRs with a calculated molecular weight of 121 kDa. TLR7 is most closely related to TLR8 and TLR9 with 43% and 36% overall (aa) sequence identity, respectively.

In vivo, TLR7 mRNA is expressed in lung, placenta, spleen, lymph node, and tonsil. TLR7 mRNA expression is highest in monocytes, B cells, and plasmacytoid dendritic cells. In vitro, TLR7 mRNA expression is upregulated in THP-1 cells upon PMA-induced differentiation. TLR7 is highly upregulated by exposure to IL-6 and to a slightly lesser extent by autocrine IFN-γ, IL-1β. TLR7 mRNA expression in THP-1 cells is elevated after exposure to both Gram-positive and Gram-negative bacteria. Ex vivo, expression of TLR7 is elevated after exposure to both Gram-positive and Gram-negative bacteria in monocytes and to a greater degree in granulocytes. TLR7 is expressed in the endosome. The role of TLR7, is to detect the presence of "foreign" single-stranded RNA within a cell, as a means to respond to viral invasion. TLR7 is a structurally highly conserved protein which recognizes guanosine- or uridine-rich, single-stranded RNA (ssRNA) from viruses such as human immunodeficiency virus, vesicular stomatitis virus and influenza virus Toll-Like Receptor 8 (TLR8)

TLR8 maps to chromosome Xp22, and the TLR8 sequence encodes a 1041 (aa) protein containing 26 N-terminal LRRs with a calculated molecular weight of 120 kDa. TLR8 is most closely related to TLR7 and TLR9 with 43% and 35% overall (aa) sequence identity, respectively.

In vivo, TLR8 mRNA is expressed in lung, placenta, spleen, lymph node, bone marrow, and PBLs, with highest expression found in cells of myeloid origin, such as monocytes, granulocytes and myeloid dendritic cells. In vitro, TLR8 mRNA expression is upregulated in THP-1 cells upon PMA-induced differentiation. TLR8 is highly upregulated by autocrine IL-1β, IL-6, IL-10, and TNF-α, and is even more enhanced by exposure to IFN-γ. TLR8 mRNA expression in THP-1 cells is elevated after exposure to both Gram-positive and Gram-negative bacteria. Ex vivo, monocyte TLR8 expression increases while granulocyte expression decreases on exposure to Gram-negative bacteria. TLR8 is expressed in the endosome. The role of TLR8 is to detect the presence of "foreign" single-stranded RNA within a cell, as a means to respond to viral invasion. TLR8 is a structurally highly conserved protein which recognizes guanosine- or uridine-rich, single-stranded RNA (ssRNA) from viruses such as human immunodeficiency virus, vesicular stomatitis virus and influenza virus.

Toll-Like Receptor 9 (TLR9)

TLR9 maps to chromosome 3p21, and the TLR9 sequence encodes a 1032 (aa) protein containing 27 N-terminal LRRs with a calculated molecular weight of 116 kDa. TLR9 is most closely related to TLR7 and TLR8 with 36% and 35% overall (aa) sequence identity, respectively.

In vivo, TLR9 mRNA is expressed in spleen, lymph node, bone marrow, and PBLs. Specifically, TLR9 mRNA is expressed at the highest levels in B cells and dendritic cells. In vitro, TLR9 is moderately upregulated by autocrine IL-113, IL-6, IL-10, and TNF-α in PMA-differentiated THP-1 cells. TLR9 mRNA expression in THP-1 cells is unaffected by exposure to both Gram-positive and Gram-negative bacteria. Ex vivo, TLR9 expression in monocytes and particularly in granulocytes is downregulated in response to Gram-negative bacteria. TLR9 forms a homodimer and recognizes unmethylated bacterial DNA. TLR9 is involved in the inflammatory response to bacterial DNA and oligonucleotides that contain unmethylated CpG DNA sequences. TLR9 is localized internally, perhaps in lysosomic or endocytic compartments where it would more likely encounter PAMPs including unmethylated CpG DNA sequences.

TLR9 is a receptor for CpG DNA, and recognizes bacterial and viral CpG DNA. Bacterial and viral DNA contains unmethylated CpG motifs, which confer its immunostimulatory activity. In vertebrates, the frequency of CpG motifs is severely reduced and the cytosine residues of CpG motifs are highly methylated, leading to abrogation of the immunostimulatory activity. Structurally, there are at least two types of CpG DNA: B/K-type CpG DNA is a potent inducer of inflammatory cytokines such as IL-12 and TNF-α; A/D-type CpG DNA has a greater ability to induce IFN-α production from plasmacytoid dendritic cells (PDC). TLR9 is also involved in pathogenesis of autoimmune disorders, and may be important in Graves' autoimmune hyperthyroidism and production of rheumatoid factor by auto-reactive B cells. Similarly, internalization by the Fc receptor can cause TLR9 mediated PDC induction of IFN-α by immune complexes containing IgG and chromatin, which are implicated in the pathogenesis of systemic lupus erythematosus (SLE). TLR9 is involved in the pathogenesis of several autoimmune diseases through recognition of the chromatin structure.

Toll-Like Receptor 10 (TLR10)

The TLR10 sequence encodes a putative 811 (aa) protein with molecular weight of 95 kDa. TLR10 is most closely related to TLR1 and TLR6 with 48% and 46% overall (aa) identity, respectively.

In vivo, TLR10 mRNA expression is highest in immune system-related tissues including spleen, lymph node, thymus, and tonsil. TLR10 mRNA is most highly expressed on B cells and plasmacytoid dendritic cells (PDCs). In vitro, TLR10 is moderately upregulated by autocrine IL-γ, IL-1β, IL-6, IL-10, and TNF-α in PMA-differentiated THP-1 cells. TLR10 mRNA expression in THP-1 cells is elevated after exposure to both Gram-positive and Gram-negative bacteria. Ex vivo, monocyte TLR10 expression increases, while granulocyte expression decreases on exposure to Gram-negative bacteria.

Toll-Like Receptor 11 (TLR11)

TLR11 is expressed in bladder epithelial cells and mediate resistance to infection by uropathogenic bacteria in mouse.

As presented above, TLR2 and TLR4 recognize Gram-positive and Gram-negative bacterial cell wall products, respectively; TLR5 recognizes a structural epitope of bacterial flagellin; TLR3, TLR7, TLR8, and TLR9 recognize different forms of microbial-derived nucleic acid.

The TIR domains interact with several TIR domain-containing adaptor molecules (MyD88), TIR domain-containing adaptor protein (TIRAP), TIR domain-containing adaptor-inducing IFN-β (TRIF), and TRIF-related adaptor molecule (TRAM) which activate a cascade of events resulting in transcription factor induction.

TLR Signaling Pathways.

TLRs are distributed throughout the cell. TLR1, TLR2, TLR3 and TLR4 are expressed on the cell surface, whereas, TLR3, TLR7, TLR8 and TLR9 are expressed in intracellular compartments such as endosomes. TLR3-, TLR7- or TLR9-mediated recognition of their ligands require endosomal maturation and processing. When macrophages, monocytes, dendritic cells or nonimmune cells that become antigen presenting cells engulf bacteria by phagocytosis, the bacteria degrade and CpG DNA is release into phagosomes-lysosomes or in endosomes-lysosomes wherein they can interact with TLR9 that has been recruited from the endoplasmic reticulum upon non-specific uptake of CpG DNA. Furthermore, when viruses invade cells by receptor-mediated endocytosis, the viral contents are exposed to the cytoplasm by fusion of the viral membrane with the endosomal membrane. This results in exposure of TLR ligands such as dsRNA, ssRNA and CpG DNA to TLR9 in the phagosomal/lysosomal or endosomal/lysosomal compartments.

In the signaling pathways downstream of the TIR domain, a TIR domain-containing adaptor, MyD88, is essential for induction of inflammatory cytokines such as TNF-α and IL-12 through all TLRs. Although TIR domain-containing adaptor molecules (MyD88) are common to all TLRs, individual TLR signaling pathways are divergent and activation of specific TLRs leads to slightly different patterns of gene expression profiles. By way of example only, activation of TLR3 and TLR4 signaling pathways results in induction of type I interferons (IFNs), while activation of TLR2- and TLR5-mediated pathways do not. However, activation of TLR7, TLR8 and TLR9 signaling pathways also leads to induction of Type I IFNs, although this occurs through mechanisms distinct from TLR3/4-mediated induction.

Once engaged, TLRs initiate a signal transduction cascade leading to activation of NFκB via the adapter protein myeloid differentiation primary response gene 88 (MyD88) and recruitment of the IL-1 receptor associated kinase (IRAK). The MyD88-dependent pathway is analogous to signaling by the IL-1 receptors, and it is regarded that MyD88, harboring a C-terminal TIR domain and an N-terminal death domain, associates with the TIR domain of TLRs. Upon stimulation, MyD88 recruits IRAK-4 to TLRs through interaction of the death domains of both molecules, and facilitates IRAK-4-mediated phosphorylation of IRAK-1. Phosphorylation of IRAK-1 then leads to recruitment of TNF-receptor associated factor 6 (TRAF6), leading to the activation of two distinct signaling pathways. One pathway leads to activation of AP-1 transcription factors through activation of MAP kinases. Another pathway activates the TAK1/TAB complex, which enhances activity of the IκB kinase (IKK) complex. Once activated, the IKK complex induces phosphorylation and subsequent degradation of the NFκB inhibitor IκB, which leads to nuclear translocation of transcription factor NFκB and the initiation of transcription of genes whose promoters contain NFκB binding sites, such as cytokines. The MyD88-dependent pathway plays a crucial role and is essential for inflammatory cytokine production through all TLRs.

Stimulation of TLR8-expressing cells, such as PBMCs results in production of high levels of IL-12, IFN-γ, IL-1, TNF-α, IL-6 and other inflammatory cytokines. Similarly, stimulation of TLR7-expressing cells, such as plasmacytoid dendritic cells, results in production of high levels of interferon-α (IFNα) and low levels of inflammatory cytokines. Thus, through activation of dendritic cells and other antigen-presenting cells, TLR7, TLR8 or TLR9 engagement and cytokine production is expected to activate diverse innate and acquired immune response mechanisms leading to the destruction of pathogens, infected cells or tumor cells.

Compounds of Formula (I), pharmaceutically acceptable salts, solvates, N-oxides, prodrugs and isomers thereof, pharmaceutical compositions, and/or combinations provided herein are useful as modulators of toll-like receptor activity, and are used in the treatment of a wide variety of diseases and/or disorders associated with such receptors. In certain embodiments, the compounds of Formula (I), pharmaceutically acceptable salts, solvates, N-oxides, prodrugs and isomers thereof, and pharmaceutical compositions provided herein are modulators of TLR7 activity and are useful in the treatment of diseases and/or disorders associated with TLR7. In certain embodiments, the compounds of Formula (I), pharmaceutically acceptable salts, solvates, N-oxides, prodrugs and isomers thereof, and pharmaceutical compositions provided herein are agonists of TLR7 activity and are useful in the treatment of diseases and/or disorders associated with TLR7. In certain embodiments, the compounds of Formula (I), pharmaceutically acceptable salts, solvates, N-oxides, prodrugs and isomers thereof, and pharmaceutical compositions provided herein are modulators of TLR8 activity and are useful in the treatment of diseases and/or disorders associated with TLR8. In certain embodiments, the compounds of Formula (I), pharmaceutically acceptable salts, solvates, N-oxides, prodrugs and isomers thereof, and pharmaceutical compositions provided herein are agonists of TLR8 activity and are useful in the treatment of diseases and/or disorders associated with TLR8.

In certain embodiments, the compounds of Formula (I), pharmaceutically acceptable salts, solvates, N-oxides, prodrugs and isomers thereof, pharmaceutical compositions, and/or combinations provided herein are used in the treatment of respiratory diseases and/or disorders including, but not limited to, asthma, bronchial asthma, allergic asthma, intrinsic asthma, extrinsic asthma, exercise-induced asthma, drug-induced asthma (including aspirin and NSAID-induced) and dust-induced asthma, chronic obstructive pulmonary disease (COPD); bronchitis, including infectious and eosinophilic bronchitis; emphysema; bronchiectasis; cystic fibrosis; sarcoidosis; farmer's lung and related diseases; hypersensitivity pneumonitis; lung fibrosis, including cryptogenic fibrosing alveolitis, idiopathic interstitial pneumonias, fibrosis complicating anti-neoplastic therapy and chronic infection, including tuberculosis and aspergillosis and other fungal infections; complications of lung transplantation; vasculitic and thrombotic disorders of the lung vasculature, and pulmonary hypertension; antitussive activity including treatment of chronic cough associated with inflammatory and secretory conditions of the airways, and iatrogenic cough; acute and chronic rhinitis including rhinitis medicamentosa, and vasomotor rhinitis; perennial and seasonal allergic rhinitis including rhinitis nervosa (hay fever); nasal polyposis; acute viral infection including the common cold, and infection due to respiratory syncytial virus, influenza, coronavirus (including SARS) and adenovirus.

In certain embodiments, the compounds of Formula (I), pharmaceutically acceptable salts, solvates, N-oxides, prodrugs and isomers thereof, pharmaceutical compositions, and/or combinations provided herein are used in the treatment of dermatological disorders including, but not limited to, psoriasis, atopic dermatitis, contact dermatitis or other eczematous dermatoses, and delayed-type hypersensitivity reactions; phyto- and photodermatitis; seborrhoeic dermatitis, dermatitis herpetiformis, lichen planus, lichen sclerosus et atrophica, pyoderma gangrenosum, skin sarcoid, basal cell carcinoma, actinic keratosis, discoid lupus erythematosus, pemphigus, pemphigoid, epidermolysis bullosa, urticaria, angioedema, vasculitides, toxic erythemas, cutaneous eosinophilias, alopecia areata, male-pattern baldness, Sweet's syndrome, Weber-Christian syndrome, erythema multiforme; cellulitis, both infective and non-infective; panniculitis; cutaneous lymphomas, non-melanoma skin cancer and other dysplastic lesions; drug-induced disorders including fixed drug eruptions.

In certain embodiments, the compounds of Formula (I), pharmaceutically acceptable salts, solvates, N-oxides, prodrugs and isomers thereof, pharmaceutical compositions, and/or combinations provided herein are used in the treatment of ocular diseases and/or disorders including, but not limited to, blepharitis; conjunctivitis, including perennial and vernal allergic conjunctivitis; iritis; anterior and posterior uveitis; choroiditis; autoimmune, degenerative or inflammatory disorders affecting the retina; ophthalmitis including sympathetic ophthalmitis; sarcoidosis; infections including viral, fungal, and bacterial.

In certain embodiments, the compounds of Formula (I), pharmaceutically acceptable salts, solvates, N-oxides, prodrugs and isomers thereof, pharmaceutical compositions, and/or combinations provided herein are used in the treatment of genitourinary diseases and/or disorders including, but not limited to, nephritis including interstitial and glomerulonephritis; nephrotic syndrome; cystitis including acute and chronic (interstitial) cystitis and Hunner's ulcer; acute and chronic urethritis, prostatitis, epididymitis, oophoritis and salpingitis; vulvo-vaginitis; Peyronie's disease; erectile dysfunction (both male and female).

In certain embodiments, the compounds of Formula (I), pharmaceutically acceptable salts, solvates, N-oxides, prodrugs and isomers thereof, pharmaceutical compositions, and/or combinations provided herein are used in the treatment of allograft rejection including, but not limited to, acute and chronic following, for example, transplantation of kidney, heart, liver, lung, bone marrow, skin or cornea or following blood transfusion; or chronic graft versus host disease.

In certain embodiments, the compounds of Formula (I), pharmaceutically acceptable salts, solvates, N-oxides, prodrugs and isomers thereof, pharmaceutical compositions, and/or combinations provided herein are used in the treatment of other auto-immune and allergic disorders including, but not limited to, rheumatoid arthritis, irritable bowel syndrome. systemic lupus erythematosus, multiple sclerosis, Hashimoto's thyroiditis, Crohns disease, inflammatory bowel disease (IBD), Graves' disease, Addison's disease, diabetes mellitus, idiopathic thrombocytopaenic purpura, eosinophilic fasciitis, hyper-IgE syndrome, antiphospholipid syndrome and Sazary syndrome.

In certain embodiments, the compounds of Formula (I), pharmaceutically acceptable salts, solvates, N-oxides, prodrugs and isomers thereof, and pharmaceutical compositions provided herein are used in the treatment of cancer including, but not limited to, prostate, breast, lung, ovarian, pancreatic, bowel and colon, stomach, skin and brain tumors and malignancies affecting the bone marrow (including the leukaemias) and lymphoproliferative systems, such as Hodgkin's and non-Hodgkin's lymphoma; including the prevention and treatment of metastatic disease and tumor recurrences, and paraneoplastic syndromes. In certain embodiments, the compounds of Formula (I), pharmaceutically acceptable salts, solvates, N-oxides, prodrugs and isomers thereof, and pharmaceutical compositions provided herein are useful as modulators of toll-like receptor activity, and are used in the treatment of neoplasias including, but not limited to, basal cell carcinoma, squamous cell carcinoma, actinic keratosis, melanoma, carcinomas, sarcomas, leukemias, renal cell carcinoma, Kaposi's sarcoma, myelogeous leukemia, chronic lymphocytic leukemia and multiple myeloma.

In certain embodiments, the compounds of Formula (I), pharmaceutically acceptable salts, solvates, N-oxides, prodrugs and isomers thereof, pharmaceutical compositions, and/or combinations provided herein are used in the treatment of infectious diseases including, but not limited to, viral diseases such as genital warts, common warts, plantar warts, respiratory syncytial virus (RSV), hepatitis B, hepatitis C, Dengue virus, herpes simplex virus (by way of example only, HSV-I, HSV-II, CMV, or VZV), molluscum contagiosum, vaccinia, variola, lentivirus, human immunodeficiency virus (HIV), human papilloma virus (HPV), cytomegalovirus (CMV), varicella zoster virus (VZV), rhinovirus, enterovirus, adenovirus, coronavirus (e.g., SARS), influenza, para-influenza, mumps virus, measles virus, papovavirus, hepadnavirus, flavivirus, retrovirus, arenavirus (by way of example only, LCM, Junin virus, Machupo virus, Guanarito virus and Lassa Fever) and filovirus (by way of example only, ebola virus or marbug virus).

In certain embodiments, the compounds of Formula (I), pharmaceutically acceptable salts, solvates, N-oxides, prodrugs and isomers thereof, pharmaceutical compositions, and/or combinations provided herein are used in the treatment of bacterial, fungal, and protozoal infections including, but not limited to, tuberculosis and mycobacterium avium, leprosy; pneumocystis carnii, cryptosporidiosis, histoplasmosis, toxoplasmosis, trypanosome infection, leishmaniasis, infections caused by bacteria of the genus *Escherichia, Enterobacter, Salmonella, Staphylococcus, Klebsiella, Proteus, Pseudomonas, Streptococcus*, and *Chlamydia*, and fungal infections such as candidiasis, aspergillosis, histoplasmosis, cryptococcal meningitis.

In certain embodiments, the compounds of Formula (I) and (I-A), pharmaceutically acceptable salts, solvates, N-oxides, prodrugs and isomers thereof, are used as immune potentiators. In certain embodiments, the compounds provided herein are included in immunogenic compositions or are used in combination with immunogenic compositions. In certain embodiments, the immunogenic compositions are useful as vaccines, and the compound is present in an amount sufficient to enhance an immune response to the vaccine, or to an antigen admixed with the compound. The vaccine comprises at least one antigen, which may be an bacterial antigen or a cancer-associated antigen, or a viral antigen. In certain embodiments, the compounds of Formula (I) or (I-A), pharmaceutically acceptable salts, solvates, N-oxides, prodrugs and isomers thereof, and pharmaceutical compositions provided herein are included in therapeutic vaccines or are used in combination with therapeutic vaccines. In certain embodiments, the compounds of Formula (I), pharmaceutically acceptable salts, solvates, N-oxides, prodrugs and isomers thereof, and pharmaceutical compositions provided herein are included in prophylactic vaccines or used in combination with prophylactic vaccines. In certain embodiments, the compounds of Formula (I), pharmaceutically acceptable salts, solvates, N-oxides, prodrugs and isomers thereof, and pharmaceutical compositions provided herein are included in, or are used in combination with, therapeutic viral vaccines. In certain embodiments, the compounds of Formula (I), pharmaceutically acceptable salts, solvates, N-oxides, prodrugs and isomers thereof, and pharmaceutical compositions provided herein are included in, or are used in combination with, with cancer vaccines.

In other embodiments, the compounds of Formula (I), or a pharmaceutically acceptable salt or solvate thereof, described herein are useful for the treatment of damaged or ageing skin such as scarring and wrinkles.

Administration and Pharmaceutical Compositions

For the therapeutic uses of compounds of Formula (I), or pharmaceutically acceptable salts, solvates, N-oxides, prodrugs and isomers thereof, described herein, such compounds are administered in therapeutically effective amounts either alone or as part of a pharmaceutical composition. Accordingly, provided herein are pharmaceutical compositions, which comprise at least one compound of Formulas (I) described herein, pharmaceutically acceptable salts and/or solvates thereof, and one or more pharmaceutically acceptable carriers, diluents, or excipients. In addition, such compounds and compositions are administered singly or in combination with one or more additional therapeutic agents. The method of administration of such compounds and compositions include, but are not limited to, oral administration, rectal administration, parenteral, intravenous administration, intravitreal administration, intramuscular administration, inhalation, intranasal administration, topical administration, ophthalmic administration or otic administration.

The therapeutically effective amount will vary depending on, among others, the disease indicated, the severity of the disease, the age and relative health of the subject, the potency of the compound administered, the mode of administration and the treatment desired. In certain embodiments, the daily dosage of a compound of Formula (I), satisfactory results are indicated to be obtained systemically at daily dosages of from about 0.03 to 2.5 mg/kg per body weight. In certain embodiments, the daily dosage of a compound of Formula (I), administered by inhalation, is in the range from 0.05 micrograms per kilogram body weight (μg/kg) to 100 micrograms per kilogram body weight (m/kg). In other embodiments, the daily dosage of a compound of Formula (I), administered orally, is in the range from 0.01 micrograms per kilogram body weight (μg/kg) to 100 milligrams per kilogram body weight (mg/kg). An indicated daily dosage in the larger mammal, e.g. humans, is in the range from about 0.5 mg to about 100 mg of a compound of Formula (I), conveniently administered, e.g. in divided doses up to four times a day or in controlled release form. In certain embodiment, unit dosage forms for oral administration comprise from about 1 to 50 mg of a compound of Formula (I).

Other aspects provided herein are processes for the preparation of pharmaceutical composition which comprise at least one compound of Formulas (I) described herein, or pharmaceutically acceptable salts and/or solvates thereof. In certain embodiments, such processes include admixing a compound of the Formula (I) described herein, and pharmaceutically acceptable salts and solvates thereof, with one or more pharmaceutically acceptable carriers, diluents or excipients. In certain embodiments, the pharmaceutical compositions comprising a compound of Formula (I) in free form or in a pharmaceutically acceptable salt or solvate form, in association with at least one pharmaceutically acceptable carrier, diluent or excipient are manufactured by mixing, granulating and/or coating methods. In other embodiments, such compositions are optionally contain excipients, such as preserving, stabilizing, wetting or emulsifying agents, solution promoters, salts for regulating the osmotic pressure and/or buffers. In other embodiments, such compositions are sterilized.

Oral Dosage Forms

In certain embodiments, the pharmaceutical compositions containing at least one compound of Formula (I) are administered orally as discrete dosage forms, wherein such dosage forms include, but are not limited to, capsules, gelatin capsules, caplets, tablets, chewable tablets, powders, granules, syrups, flavored syrups, solutions or suspensions in aqueous or non-aqueous liquids, edible foams or whips, and oil-in-water liquid emulsions or water-in-oil liquid emulsions.

The capsules, gelatin capsules, caplets, tablets, chewable tablets, powders or granules, used for the oral administration of at least one compound of Formula (I) are prepared by admixing at least one compound of Formula (I) (active ingredient) together with at least one excipient using conventional pharmaceutical compounding techniques. Non-limiting examples of excipients used in oral dosage forms described herein include, but are not limited to, binders, fillers, disintegrants, lubricants, absorbents, colorants, flavors, preservatives and sweeteners.

Non-limiting examples of such binders include, but are not limited to, corn starch, potato starch, starch paste, pre-gelatinized starch, or other starches, sugars, gelatin, natural and synthetic gums such as acacia, sodium alginate, alginic acid, other alginates, tragacanth, guar gum, cellulose and its derivatives (by way of example only, ethyl cellulose, cellulose acetate, carboxymethyl cellulose calcium, sodium carboxymethylcellulose, methyl cellulose, hydroxypropyl methylcellulose and microcrystalline cellulose), magnesium aluminum silicate, polyvinyl pyrrolidone and combinations thereof.

Non-limiting examples of such fillers include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof. In certain embodiments, the binder or filler in pharmaceutical compositions provided herein are present in from about 50 to about 99 weight percent of the pharmaceutical composition or dosage form.

Non-limiting examples of such disintegrants include, but are not limited to, agar-agar, alginic acid, sodium alginate, calcium carbonate, sodium carbonate, microcrystalline cellulose, croscarmellose sodium, crospovidone, polacrilin potassium, sodium starch glycolate, potato or tapioca starch, pre-gelatinized starch, other starches, clays, other algins, other celluloses, gums, and combinations thereof. In certain embodiments, the amount of disintegrant used in the pharmaceutical compositions provided herein is from about 0.5 to about 15 weight percent of disintegrant, while in other embodiments the amount is from about 1 to about 5 weight percent of disintegrant.

Non-limiting examples of such lubricants include, but are not limited to, sodium stearate, calcium stearate, magnesium stearate, stearic acid, mineral oil, light mineral oil, glycerin, sorbitol, mannitol, polyethylene glycol, other glycols, sodium lauryl sulfate, talc, hydrogenated vegetable oil (by way of example only, peanut oil, cottonseed oil, sunflower oil, sesame oil, olive oil, corn oil, and soybean oil), zinc stearate, sodium oleate, ethyl oleate, ethyl laureate, agar, silica, a syloid silica gel (AEROSIL 200, manufactured by W.R. Grace Co. of Baltimore, Md.), a coagulated aerosol of synthetic silica (marketed by Degussa Co. of Plano, Tex.), CAB-O-SIL (a pyrogenic silicon dioxide product sold by Cabot Co. of Boston, Mass.) and combinations thereof. In certain embodiments, the amount of lubricants used in the pharmaceutical compositions provided herein is in an amount of less than about 1 weight percent of the pharmaceutical compositions or dosage forms.

Non-limiting examples of such diluents include, but are not limited to, lactose, dextrose, sucrose, mannitol, sorbitol, cellulose, glycine or combinations thereof.

In certain embodiments, tablets and capsules are prepared by uniformly admixing at least one compound of Formula (I) (active ingredients) with liquid carriers, finely divided solid carriers, or both, and then shaping the product into the desired presentation if necessary. In certain embodiments, tablets are prepared by compression. In other embodiments, tablets are prepared by molding.

In certain embodiments, at least one compound of Formula (I) is orally administered as a controlled release dosage form. Such dosage forms are used to provide slow or controlled-release of one or more compounds of Formula (I). Controlled release is obtained using, for example, hydroxypropylmethyl cellulose, other polymer matrices, gels, permeable membranes, osmotic systems, multilayer coatings, microparticles, liposomes, microspheres, or a combination thereof. In certain embodiments, controlled-release dosage forms are used to extend activity of the compound of Formula (I), reduce dosage frequency, and increase patient compliance.

Administration of compounds of Formula (I) as oral fluids such as solution, syrups and elixirs are prepared in unit dosage forms such that a given quantity of solution, syrups or elixirs contains a predetermined amount of a compound of Formula (I). Syrups are prepared by dissolving the compound in a suitably flavored aqueous solution, while elixirs are prepared through the use of a non-toxic alcoholic vehicle. Suspensions are formulated by dispersing the compound in a non-toxic vehicle. Non-limiting examples of excipients used in as oral fluids for oral administration include, but are not limited to, solubilizers, emulsifiers, flavoring agents, preservatives, and coloring agents. Non-limiting examples of solubilizers and emulsifiers include, but are not limited to, water, glycols, oils, alcohols, ethoxylated isostearyl alcohols and polyoxy ethylene sorbitol ethers. Non-limiting examples of preservatives include, but are not limited to, sodium benzoate. Non-limiting examples of flavoring agents include, but are not limited to, peppermint oil or natural sweeteners or saccharin or other artificial sweeteners.

Parenteral Dosage Forms

In certain embodiments pharmaceutical compositions containing at least one compound of Formula (I) are administered parenterally by various routes including, but not limited to, subcutaneous, intravenous (including bolus injection), intramuscular, and intraarterial.

Such parenteral dosage forms are administered in the form of sterile or sterilizable injectable solutions, suspensions, dry and/or lyophylized products ready to be dissolved or suspended in a pharmaceutically acceptable vehicle for injection (reconstitutable powders) and emulsions. Vehicles used in such dosage forms include, but are not limited to, Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

Transdermal Dosage Forms

In certain embodiments pharmaceutical compositions containing at least one compound of Formula (I) are administered transdermally. Such transdermal dosage forms include "reservoir type" or "matrix type" patches, which are applied to the skin and worn for a specific period of time to permit the penetration of a desired amount of a compound of Formula (I). By way of example only, such transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin. In other embodiments, matrix transdermal formulations are used.

Formulations for transdermal delivery of a compound of Formula (I) include an effective amount of a compound of Formula (I), a carrier and an optional diluent. A carrier includes, but is not limited to, absorbable pharmacologically acceptable solvents to assist passage through the skin of the host, such as water, acetone, ethanol, ethylene glycol, propylene glycol, butane-1,3-diol, isopropyl myristate, isopropyl palmitate, mineral oil, and combinations thereof.

In certain embodiments, such transdermal delivery systems include penetration enhancers to assist in delivering one or more compounds of Formula (I) to the tissue. Such penetration enhancers include, but are not limited to, acetone; various alcohols such as ethanol, oleyl, and tetrahydrofuryl; alkyl sulfoxides such as dimethyl sulfoxide; dimethyl acetamide; dimethyl formamide; polyethylene glycol; pyrrolidones such as polyvinylpyrrolidone; Kollidon grades (Povidone, Polyvidone); urea; and various water-soluble or insoluble sugar esters such as Tween 80 (polysorbate 80) and Span 60 (sorbitan monostearate).

In other embodiments, the pH of such a transdermal pharmaceutical composition or dosage form, or of the tissue to which the pharmaceutical composition or dosage form is applied, is adjusted to improve delivery of one or more compounds of Formula (I). In other embodiments, the polarity of a solvent carrier, its ionic strength, or tonicity are adjusted to improve delivery. In other embodiments, compounds such as stearates are added to advantageously alter the hydrophilicity or lipophilicity of one or more compounds of Formula (I) so as to improve delivery. In certain embodiments, such stearates serve as a lipid vehicle for the formulation, as an emulsifying agent or surfactant, and as a delivery-enhancing or penetration-enhancing agent. In other embodiments, different salts, hydrates or solvates of the compounds of Formula (I) are used to further adjust the properties of the resulting composition.

Topical Dosage Forms

In certain embodiments at least one compound of Formula (I) is administered by topical application of pharmaceutical composition containing at least one compound of Formula (I) in the form of lotions, gels, ointments solutions, emulsions, suspensions or creams. Suitable formulations for topical application to the skin are aqueous solutions, ointments, creams or gels, while formulations for ophthalmic administration are aqueous solutions. Such formulations optionally contain solubilizers, stabilizers, tonicity enhancing agents, buffers and preservatives.

Such topical formulations include at least one carrier, and optionally at least one diluent. Such carriers and diluents include, but are not limited to, water, acetone, ethanol, ethylene glycol, propylene glycol, butane-1,3-diol, isopropyl myristate, isopropyl palmitate, mineral oil, and combinations thereof.

In certain embodiments, such topical formulations include penetration enhancers to assist in delivering one or more compounds of Formula (I) to the tissue. Such penetration enhancers include, but are not limited to, acetone; various alcohols such as ethanol, oleyl, and tetrahydrofuryl; alkyl sulfoxides such as dimethyl sulfoxide; dimethyl acetamide; dimethyl formamide; polyethylene glycol; pyrrolidones such as polyvinylpyrrolidone; Kollidon grades (Povidone, Polyvidone); urea; and various water-soluble or insoluble sugar esters such as Tween 80 (polysorbate 80) and Span 60 (sorbitan monostearate).

In certain embodiments pharmaceutical compositions containing at least one compound of Formula (I) are administered by inhalation. Dosage forms for inhaled administration are formulated as aerosols or dry powders. Aerosol formulations for inhalation administration comprise a solution or fine suspension of at least one compound of Formula (I) in a pharmaceutically acceptable aqueous or non-aqueous solvent. In addition, such pharmaceutical compositions optionally comprise a powder base such as lactose, glucose, trehalose, mannitol or starch, and optionally a performance modifier such as L-leucine or another amino acid, and/or metals salts of stearic acid such as magnesium or calcium stearate.

In certain embodiments, compounds of Formula (I) are be administered directly to the lung by inhalation using a Metered Dose Inhaler ("MDI"), which utilizes canisters that contain a suitable low boiling propellant, e.g., dichlorodifluoromethane, trichlorofluoromethane, dichlorotetrafluoroethane, carbon dioxide or other suitable gas, or a Dry Powder Inhaler (DPI) device which uses a burst of gas to create a cloud of dry powder inside a container, which is then be inhaled by the patient. In certain embodiments, capsules and cartridges of gelatin for use in an inhaler or insufflator are formulated containing a powder mixture of a compound of Formula (I) and a powder base such as lactose or starch. In certain embodiments, compounds of Formula (I) are delivered to the lung using a liquid spray device, wherein such devices use extremely small nozzle holes to aerosolize liquid drug formulations that can then be directly inhaled into the lung. In other embodiments, compounds of Formula (I) are delivered to the lung using a nebulizer device, wherein a nebulizers creates an aerosols of liquid drug formulations by using ultrasonic energy to form fine particles that can be readily inhaled. In other embodiments, compounds of Formula (I) are delivered to the lung using an electrohydrodynamic ("EHD") aerosol device wherein such EHD aerosol devices use electrical energy to aerosolize liquid drug solutions or suspensions.

In certain embodiments, the pharmaceutical composition containing at least one compound of Formula (I), or pharmaceutically acceptable salts and solvates thereof, described herein, also contain one or more absorption enhancers. In certain embodiments, such absorption enhancers include, but are not limited to, sodium glycocholate, sodium caprate, N-lauryl-β-D-maltopyranoside, EDTA, and mixed micelles.

In certain embodiments pharmaceutical compositions containing at least one compound of Formula (I) are administered nasally. The dosage forms for nasal administration are formulated as aerosols, solutions, drops, gels or dry powders.

In certain embodiments pharmaceutical compositions containing at least one compound of Formula (I) are administered rectally in the form of suppositories, enemas, ointment, creams rectal foams or rectal gels. In certain embodiments such suppositories are prepared from fatty emulsions or suspensions, cocoa butter or other glycerides.

In certain embodiments pharmaceutical compositions containing at least one compound of Formula (I) are administered opthamically as eye drops. Such formulations are aqueous solutions that optionally contain solubilizers, stabilizers, tonicity enhancing agents, buffers and preservatives.

In certain embodiments pharmaceutical compositions containing at least one compound of Formula (I) are administered otically as ear drops. Such formulations are aqueous solutions that optionally contain solubilizers, stabilizers, tonicity enhancing agents, buffers and preservatives.

In certain embodiments pharmaceutical compositions containing at least one compound of Formula (I) are formulated as a depot preparation. Such long acting formulations are administered by implantation (for example subcutaneously or intramuscularly) or by intramuscular injection. In certain embodiments, such formulations include polymeric or hydrophobic materials (for example, as an emulsion in an acceptable oil) or ion exchange resins, or as sparingly soluble derivatives, for example, as a sparingly soluble salt.

Provided herein are compounds of Formula (I), pharmaceutically acceptable salts and solvates thereof, and pharmaceutical compositions containing at least one compound of Formula (I) and/or pharmaceutically acceptable salts and solvates thereof, for use in modulating TLR activity, and thereby are used to in the prevention or treatment of diseases and/or disorders associated with TLR activity. In certain embodiments, such compounds of Formula (I), pharmaceutically acceptable salts and solvates thereof, and pharmaceutical compositions are agonists of TLR7, and thereby are used to in the treatment of diseases and/or disorders associated with TLR7. In certain embodiments, such compounds of Formula (I), pharmaceutically acceptable salts and solvates thereof, and pharmaceutical compositions are agonists of TLR8, and thereby are used to in the treatment of diseases and/or disorders associated with TLR8.

Also provided herein are methods for the treatment of a subject suffering from a disease and/or disorder associated with TLR activity, wherein the methods include administering to the subject an effective amount of a compound of Formula (I) or a pharmaceutically acceptable salt, solvate, either alone or as part of a pharmaceutical composition as described herein.

Provided herein is the use of a compound of Formula (I), or a pharmaceutically acceptable salt or solvate thereof, in the preparation of a medicament for the treatment of a disease or disorder associated with TLR activity. In certain embodiments, a compound of Formula (I), or a pharmaceutically acceptable salt or solvate thereof, is used in the preparation of a medicament for the treatment of a disease or disorder associated with TLR7. In certain embodiments, a compound of Formula (I), or a pharmaceutically acceptable salt or solvate thereof, is used in the preparation of a medicament for the treatment of a disease or disorder associated with TLR8.

In a further embodiment, the pharmaceutical compositions comprising at least one compound of Formula (I) are adapted for oral administration for the treatment of viral diseases and/or disorders associated with TLR7 or TLR8 activity.

In a further embodiment, the pharmaceutical compositions comprising at least one compound of Formula (I) are adapted for oral administration for the treatment of infectious diseases and/or disorders associated with TLR7 or TLR8 activity.

In a further embodiment, the pharmaceutical compositions comprising at least one compound of Formula (I) are adapted for oral administration for the treatment of bacterial diseases and/or disorders associated with TLR7 or TLR8 activity.

In a further embodiment, the pharmaceutical compositions comprising at least one compound of Formula (I) are adapted for oral administration for the treatment of fungal diseases and/or disorders associated with TLR7 or TLR8 activity.

In a further embodiment, the pharmaceutical compositions comprising at least one compound of Formula (I) are adapted for oral administration for the treatment of cancer associated with TLR7 or TLR8 activity.

In a further embodiment, the pharmaceutical compositions comprising at least one compound of Formula (I) are adapted for intravenous administration for the treatment of cancer associated with TLR7 or TLR8 activity.

In a further embodiment, the pharmaceutical compositions comprising at least one compound of Formula (I) are adapted for oral administration for the treatment of allograft rejection diseases and/or disorders associated with TLR7 or TLR8 activity.

In a further embodiment, the pharmaceutical compositions comprising at least one compound of Formula (I) are adapted for oral administration for the treatment of genitourinary diseases and/or disorders associated with TLR7 or TLR8 activity.

In a further embodiment, the pharmaceutical compositions comprising at least one compound of Formula (I) are adapted for administration as eye drops for the treatment of ophthalmic diseases and/or disorders associated with TLR7 or TLR8 activity.

In a further embodiment, the pharmaceutical compositions comprising at least one compound of Formula (I) are adapted for topical administration for the treatment of dermatological diseases and/or disorders associated with TLR7 or TLR8 activity.

In a further embodiment, the pharmaceutical compositions comprising at least one compound of Formula (I) are adapted for topical administration for the treatment of actinic keratosis. In a further embodiment, the pharmaceutical compositions comprising at least one compound of Formula (I) are adapted for topical administration as a cream for the treatment of actinic keratosis.

In a further embodiment, the pharmaceutical compositions comprising at least one compound of Formula (I) are adapted for topical administration for the treatment of basal cell carcinoma. In a further embodiment, the pharmaceutical compositions comprising at least one compound of Formula (I) are adapted for topical administration as a cream for the treatment of basal cell carcinoma.

In a further embodiment, the pharmaceutical compositions comprising at least one compound of Formula (I) are adapted for administration by inhalation for the treatment of respiratory diseases and/or disorders associated with TLR7 or TLR8 activity. In certain embodiments, the respiratory disease is allergic asthma.

Combination Treatment

In certain embodiments, a compound of Formulas (I)-(XVI) described herein, or a pharmaceutically acceptable salt or solvate thereof, or a pharmaceutical composition containing at least one compound of Formula (I)-(XVI) described herein, is administered alone (without an additional therapeutic agent) for the treatment of one or more of the disease and/or disorders associated with TLR activity described herein.

In other embodiments, a compound of Formulas (I)-(XVI) described herein, or a pharmaceutically acceptable salt or solvate thereof, or a pharmaceutical composition containing at least one compound of Formula (I)-(XVI) described herein, is administered in combination with one or more additional therapeutic agents, for the treatment of one or more of the disease and/or disorders associated with TLR activity described herein.

In other embodiments, a compound of Formulas (I)-(XVI) described herein, or a pharmaceutically acceptable salt or solvate thereof, or a pharmaceutical composition containing at least one compound of Formula (I)-(XVI) described herein, is formulated in combination with one or more additional therapeutic agents and administered for the treatment of one or more of the disease and/or disorders associated with TLR activity described herein.

In a compound of Formulas (I)-(XVI) described herein, or a pharmaceutically acceptable salt or solvate thereof, or a pharmaceutical composition containing at least one compound of Formula (I)-(XVI) described herein, is administered sequentially with one or more additional therapeutic agents, for the treatment of one or more of the disease and/or disorders associated with TLR activity described herein.

In other embodiments, the combination treatments provided herein include administration of a compound of Formula (I)-(XVI) described herein, or a pharmaceutically acceptable salt or solvate thereof, or a pharmaceutical composition containing a compound of Formula (I)-(XVI), prior to administration of one or more additional therapeutic agents, for the treatment of one or more of the disease and/or disorders associated with TLR activity described herein.

In other embodiments, the combination treatments provided herein include administration of a compound of Formula (I)-(XVI) described herein, or a pharmaceutically acceptable salt or solvate thereof, or a pharmaceutical composition containing a compound of Formula (I)-(XVI), subsequent to administration of one or more additional therapeutic agents, for the treatment of one or more of the disease and/or disorders associated with TLR activity described herein.

In certain embodiments, the combination treatments provided herein include administration of a compound of Formula (I)-(XVI) described herein, or a pharmaceutically acceptable salt or solvate thereof, or a pharmaceutical composition containing a compound of Formula (I)-(XVI), concurrently with one or more additional therapeutic agents, for the treatment of one or more of the disease and/or disorders associated with TLR activity described herein.

In certain embodiments, the combination treatments provided herein include administration of a compound of Formula (I)-(XVI) described herein, or a pharmaceutically acceptable salt or solvate thereof, or a pharmaceutical composition containing a compound of Formula (I)-(XVI) formulated with one or more additional therapeutic agents, for the treatment of one or more of the disease and/or disorders associated with TLR activity described herein.

In certain embodiments of the combination treatments described herein the compounds of Formula (I), or a pharmaceutically acceptable salts or solvates thereof, are modulators of TLR activity. In certain embodiments of the combination treatments described herein the compounds of Formula (I), or a pharmaceutically acceptable salts or solvates thereof, are TLR7 agonists. In certain embodiments of the combination treatments described herein the compounds of Formula (I), or a pharmaceutically acceptable salts or solvates thereof, are TLR8 agonists.

In certain embodiments of the combination therapies described herein, the compounds of Formula (I) described herein, or a pharmaceutically acceptable salts or solvates thereof, and the additional therapeutics agent(s) act additively. In certain embodiments of the combination therapies described herein, the compounds of Formula (I) described herein, or a pharmaceutically acceptable salts or solvates thereof, and the additional therapeutics agent(s) act synergistically.

In other embodiments, a compound of Formula (I) described herein, or a pharmaceutically acceptable salts or solvates thereof, or a pharmaceutical composition containing a compound of Formula (I), is administered to a patient who has not previously undergone or is not currently undergoing treatment with another therapeutic agent.

The additional therapeutic agents used in combination with at least one compound of Formula (I) described herein, or a pharmaceutically acceptable salt or solvate thereof, include, but are not limited to antibiotics or antibacterial agents, antiemetic agents, antifungal agents, anti-inflammatory agents, antiviral agents, immunomodulatory agents, cytokines, antidepressants, hormones, alkylating agents, antimetabolites, antitumour antibiotics, antimitotic agents, topoisomerase inhibitors, cytostatic agents, anti-invasion agents, antiangiogenic agents, inhibitors of growth factor function inhibitors of viral replication, viral enzyme inhibitors, anticancer agents, α-interferons, β-interferons, ribavirin, hormones, cytokines, and other toll-like receptor modulators.

The antibiotics or antibacterial agents used in combination with at least one compound of Formula (I) described herein, or a pharmaceutically acceptable salt or solvate thereof, include, but are not limited to, valganciclovir hydrochloride, metronidazole, a beta-lactam, macrolides (such as, by way of example only, azithromycin, tobramycin (TOBI™)), cephalosporins (such as, by way of example only, cefaclor, cefadroxil, cephalexin, cephradine, cefamandole, cefatrizine, cefazedone, cefixime, cefozopran, cefpimizole, cefuroxime, cefpiramide, cefprozil, cefpirome, KEFLEX™, VELOSEF™, CEFTIN™, CEFZIL™, CECLOR™, SUPRAX™ and DURICEF™), a clarithromycin (such as, by way of example only, clarithromycin and BIAXIN™), an erythromycin (such as, by way of example only, erythromycin and EMYCIN™), ciprofloxacin, CIPRO™, a norfloxacin (such as, by way of example only, NOROXIN™), aminoglycoside antibiotics (such as, by way of example only, apramycin, arbekacin, bambermycins, butirosin, dibekacin, neomycin, neomycin, undecylenate, netilmicin, paromomycin, ribostamycin, sisomicin, and spectinomycin), amphenicol antibiotics (such as, by way of example only, azidamfenicol, chloramphenicol, florfenicol, and thiamphenicol), ansamycin antibiotics (such as, by way of example only, rifamide and rifampin), carbacephems (such as, by way of example only, loracarbef), carbapenems (such as, by way of example only, biapenem and imipenem), cephamycins (such as, by way of example only, cefbuperazone, cefmetazole, and cefminox), monobactams (such as, by way of example only, aztreonam, carumonam, and tigemonam), oxacephems (such as, by way of example only, flomoxef, and moxalactam), penicillins (such as, by way of example only, amdinocillin, amdinocillin pivoxil, amoxicillin, bacampicillin, benzylpenicillinic acid, benzylpenicillin sodium, epicillin, fenbenicillin, floxacillin, penamccillin, penethamate hydriodide, penicillin o-benethamine, penicillin 0, penicillin V, penicillin V benzathine, penicillin V hydrabamine, penimepicycline, phencihicillin potassium, V-CILLIN K™ and PEN VEE K™), lincosamides (such as, by way of example only, clindamycin, and lincomycin), amphomycin, bacitracin, capreomycin, colistin, enduracidin, enviomycin, tetracyclines (such as, by way of example only, apicycline, chlortetracycline, clomocycline, and demeclocycline), 2,4-diaminopyrimidines (such as, by way of example only, brodimoprim), nitrofurans (such as, by way of example only, furaltadone, and furazolium chloride), quinolones and analogs thereof (such as, by way of example only, a fluoroquinolone, ofloxacin, cinoxacin, clinafloxacin, flumequine, grepagloxacin and FLOXIN™), sulfonamides (such as, by way of example only, acetyl sulfamethoxypyrazine, benzylsulfamide, noprylsulfamide, phthalylsulfacetamide, sulfachrysoidine, and sulfacytine), sulfones (such as, by way of example only, diathymosulfone, glucosulfone sodium, and solasulfone), cycloserine, mupirocin, tuberin and combinations thereof.

The antiemetic agents used in combination with at least one compound of Formula (I) described herein, or a pharmaceutically acceptable salt or solvate thereof, include, but are not limited to, metoclopromide, domperidone, prochlorperazine, promethazine, chlorpromazine, trimethobenzamide, ondansetron, granisetron, hydroxyzine, acethylleucine monoethanolamine, alizapride, azasetron, benzquinamide, bietanautine, bromopride, buclizine, clebopride, cyclizine, dimenhydrinate, diphenidol, dolasetron, meclizine, methallatal, metopimazine, nabilone, oxyperndyl, pipamazine, scopolamine, sulpiride, tetrahydrocannabinols, thiethylperazine, thioproperazine, tropisetron, and combinations thereof.

The antifungal agents used in combination with at least one compound of Formula (I) described herein, or a pharmaceutically acceptable salt or solvate thereof, include, but are not limited to, amphotericin B, itraconazole, ketoconazole, fluconazole, fosfluconazole, intrathecal, flucytosine, miconazole, butoconazole, itraconazole, clotrimazole, nystatin, terconazole, tioconazole, voriconazole, ciclopirox, econazole, haloprogrin, naftifine, terbinafine, undecylenate, and griseofulvin.

The anti-inflammatory agents used in combination with at least one compound of Formula (I) described herein, or a pharmaceutically acceptable salt or solvate thereof, include, but are not limited to, non-steroidal anti-inflammatory drugs such as salicylic acid, acetylsalicylic acid, methyl salicylate, diflunisal, salsalate, olsalazine, sulfasalazine, acetaminophen, indomethacin, sulindac, etodolac, mefenamic acid, meclofenamate sodium, tolmetin, ketorolac, dichlofenac, ibuprofen, naproxen, naproxen sodium, fenoprofen, ketoprofen, flurbinprofen, oxaprozin, piroxicam, meloxicam, ampiroxicam, droxicam, pivoxicam, tenoxicam, nabumetome, phenylbutazone, oxyphenbutazone, antipyrine, aminopyrine, apazone and nimesulide, leukotriene antagonists including, but not limited to, zileuton, aurothioglucose, gold sodium thiomalate and auranofin, steroids including, but not limited to, alclometasone diproprionate, amcinonide, beclomethasone dipropionate, betametasone, betamethasone benzoate, betamethasone diproprionate, betamethasone sodium phosphate, betamethasone valerate, clobetasol proprionate, clocortolone pivalate, hydrocortisone, hydrocortisone derivatives, desonide, desoximatasone, dexamethasone, flunisolide, flucoxinolide, flurandrenolide, halcinocide, medrysone, methylprednisolone, methprednisolone acetate, methylprednisolone sodium succinate, mometasone furoate, paramethasone acetate, prednisolone, prednisolone acetate, prednisolone sodium phosphate, prednisolone tebuatate, prednisone, triamcinolone, triamcinolone acetonide, triamcinolone diacetate, and triamcinolone hexacetonide and other anti-inflammatory agents including, but not limited to, methotrexate, colchicine, allopurinol, probenecid, thalidomide or a derivative thereof, 5-aminosalicylic acid, retinoid, dithranol or calcipotriol, sulfinpyrazone and benzbromarone.

The antiviral agents used in combination with at least one compound of Formula (I) described herein, or a pharmaceutically acceptable salt or solvate thereof, include, but are not limited to, protease inhibitors, nucleoside/nucleotide reverse transcriptase inhibitors (NRTIs), non-nucleoside reverse transcriptase inhibitors (NNRTIs), CCR1 antagonist, CCR5 antagonists, and nucleoside analogs. The antiviral agents include but are not limited to fomivirsen, didanosine, lamivudine, stavudine, zalcitabine, zidovudine, acyclovir, famciclovir, valaciclovir, ganciclovir, gangcyclovir, cidofovir, zanamivir, oseltamavir, vidarabine, idoxuridine, trifluridine, levovirin, viramidine and ribavirin, as well as foscarnet, amantadine, rimantadine, saquinavir, indinavir, nelfinavir, amprenavir, lopinavir, ritonavir, the α-interferons; β-interferons; adefovir, clevadine, entecavir, pleconaril, HCV-086, EMZ702, emtricitabine, celgosivir, valopicitabine, inhibitors of HCV protease, such as BILN 2061, SCH-503034, ITMN-191 or VX-950, inhibitors of NS5B polymerase such as NM107 (and its prodrug NM283), R1626, R7078, BILN1941, GSK625433, GILD9128 or HCV-796, efavirenz, HBY-097, nevirapine, TMC-120 (dapivirine), TMC-125, BX-471, etravirine, delavirdine, DPC-083, DPC-961, capravirine, rilpivirine, 5-{[3,5-diethyl-1-(2-hydroxyethyl)-1H-pyrazol-4-yl]oxy}isophthalonitrile, GW-678248, GW-695634, MIV-150, calanolide, TAK-779, SC-351125, ancriviroc, vicriviroc, maraviroc, PRO-140, aplaviroc 40, Ono-4128, AK-602), AMD-887 CMPD-167, methyl 1-endo-{8-[(3S)-3-(acetylamino)-3-(3-fluorophenyl)propyl]-8-azabicyclo[3.-2.1]oct-3-yl}-2-methyl-4,5,6,7-tetrahydro-1H-imidazo[4,5-c]pyridine-5-carboxylate, methyl 3-endo-{8-[(3S)-3-(acetamido)-3-(3-fluorophenyl)propyl]-8-azabicyclo[3.2.-1]oct-3-yl}-2-methyl-4,5,6,7-tetrahydro-3H-imidazo [4,5-c]pyridine-5-carboxylate ethyl 1-endo-{8-[(3S)-3-(acetylamino)-3-(3-fluorophenyl)propyl]-8-azabicyclo[3.-2.1]oct-3-yl}-2-methyl-4,5,6,7-tetrahydro-1H-imidazo[4,5-c]pyridine-5-carboxylate, and N-{(1S)-3-[3-endo-(5-Isobutyryl-2-methyl-4,5,6,7-tetrahydro-1H-imidazo[4,-5-c]pyridin-1-yl)-8-azabicyclo[3.2.1]oct-8-yl]-1-(3-fluorophenyl)propyl}acetamide), BMS-806, BMS-488043, 5-{(1S)-2-[(2R)-4-benzoyl-2-methyl-piperazin-1-yl]-1-methyl-2-oxo-ethoxy}-4-methoxy-pyridine-2-carboxylic acid methylamide and 4-{(1S)-2-[(2R)-4-benzoyl-2-methyl-piperazin-1-yl]-1-methyl-2-oxo-ethoxy}-3-methoxy-N-methyl-benzamide, enfuvirtide (T-20). sifuvirtide SP-01A, T1249, PRO 542, AMD-3100, soluble CD4, HMG CoA reductase inhibitors, atorvastatin, 3-O-(3'3'-dimethylsuccinyl)betulic acid (otherwise known as PA-457) and aHGA.

The immunomodulatory agents used in combination with at least one compound of Formula (I) described herein, or a pharmaceutically acceptable salt or solvate thereof, include, but are not limited to, azathioprine, tacrolimus, cyclosporin methothrexate, leflunomide, corticosteroids, cyclophosphamide, cyclosporine A, cyclosporin G, mycophenolate mofetil, ascomycin, rapamycin (sirolimus), FK-506, mizoribine, deoxyspergualin, brequinar, mycophenolic acid, malononitriloamindes (such as, by way of example only, leflunamide). T cell receptor modulators, and cytokine receptor modulators, peptide mimetics, and antibodies (such as, by way of example only, human, humanized, chimeric, monoclonal, polyclonal, Fvs, ScFvs, Fab or F(ab)2 fragments or epitope binding fragments), nucleic acid molecules (such as, by way of example only, antisense nucleic acid molecules and triple helices), small molecules, organic compounds, and inorganic compounds. Examples of T cell receptor modulators include, but are not limited to, anti-T cell receptor antibodies (such as, by way of example only, anti-CD4 antibodies (such as, by way of example only, cM-T412 (Boehringer), IDEC-CE9.1™ (IDEC and SKB), mAB 4162W94, Orthoclone and OKTcdr4a (Janssen-Cilag)), anti-CD3 antibodies (such as, by way of example only, Nuvion (Product Design Labs), OKT3 (Johnson & Johnson), or Rituxan (IDEC)), anti-CD5 antibodies (such as, by way of example only, an anti-CD5 ricin-linked immunoconjugate), anti-CD7 antibodies (such as, by way of example only, CHH-380 (Novartis)), anti-CD8 antibodies, anti-CD40 ligand monoclonal antibodies (such as, by way of example only, IDEC-131 (IDEC)), anti-CD52 antibodies (such as, by way of example only, CAMPATH 1H (Ilex)), anti-CD2 antibodies, anti-CD11a antibodies (such as, by way of example only, Xanelim (Genentech)), anti-B7 antibodies (such as, by way of example only, IDEC-114 (IDEC)), CTLA4-immunoglobulin, and other toll receptor-like (TLR) modulators. Examples of cytokine receptor modulators include, but are not limited to, soluble cytokine receptors (such as, by way of example only, the extracellular domain of a TNF-α receptor or a fragment thereof, the extracellular domain of an IL-1β receptor or a fragment thereof, and the extracellular domain of an IL-6 receptor or a fragment thereof), cytokines or fragments thereof (such as, by way of example only, interleukin (IL)-2, IL-3, IL-4, IL-5, IL-6, IL-7, IL-8, IL-9, IL-10, IL-11, IL-12, IL-15, TNF-.alpha., interferon (IFN)-α, IFN-β, IFN-γ, and GM-CSF), anti-cytokine receptor antibodies (such as, by way of example only, anti-IFN receptor antibodies, anti-IL-2 receptor antibodies (such as, by way of example only, Zenapax (Protein Design Labs)), anti-IL-4 receptor antibodies, anti-IL-6 receptor antibodies, anti-IL-10 receptor antibodies, and anti-IL-12 receptor antibodies), anti-cytokine antibodies (such as, by way of example only, anti-IFN antibodies, anti-TNF-α antibodies, anti-IL-1β antibodies, anti-IL-6 antibodies, anti-IL-8 antibodies (such as, by way of example only, ABX-IL-8 (Abgenix)), and anti-IL-12 antibodies).

The cytokines or modulator of cytokine function used in combination with at least one compound of Formula (I) described herein, or a pharmaceutically acceptable salt or solvate thereof, include, but are not limited to, interleukin-2 (IL-2), interleukin-3 (IL-3), interleukin-4 (IL-4), interleukin-5 (IL-5), interleukin-6 (IL-6), interleukin-7 (IL-7), interleukin-9 (IL-9), interleukin-10 (IL-10), interleukin-12 (IL-12), interleukin 15 (IL-15), interleukin 18 (IL-18), platelet derived growth factor (PDGF), erythropoietin (Epo), epidermal growth factor (EGF), fibroblast growth factor (FGF), granulocyte macrophage stimulating factor (GM-CSF), granulocyte colony stimulating factor (G-CSF), macrophage colony stimulating factor (M-CSF), prolactin, alpha-, beta-, and gamma-interferon, interferon β-1a, interferon β-1b, interferon α-1, interferon α-2a (roferon), interferon α-2b, pegylated interferons (by way of example only, peginterferon α-2a and peginterferon α-2b), intron, Peg-Intron, Pegasys, consensus interferon (infergen), albumin-interferon α and albuferon.

The antidepressants used in combination with at least one compound of Formula (I) described herein, or a pharmaceutically acceptable salt or solvate thereof, include, but are not limited to, binedaline, caroxazone, citalopram, dimethazan, fencamine, indalpine, indeloxazine hydrocholoride, nefopam, nomifensine, oxitriptan, oxypertine, paroxetine, sertraline, thiazesim, trazodone, benmoxine, echinopsidine iodide, etryptamine, iproclozide, iproniazid, isocarboxazid, mebanazine, metfendrazine, nialamide, pargyline, octamoxin, phenelzine, pheniprazine, phenoxypropazine, pivhydrazine, safrazine, selegiline, 1-deprenyl, cotinine, rolicyprine, rolipram, maprotiline, metralindole, mianserin, mirtazepine, adinazolam, amitriptyline, amitriptylinoxide, amoxapine, butriptyline, clomipramine, demexiptiline, desipramine, dibenzepin, dimetacrine, dothiepin, doxepin, fluacizine, imipramine, imipramine N-oxide, iprindole, lofepramine, melitracen, metapramine, nortriptyline, noxiptilin, opipramol, pizotyline, propizepine, protriptyline, quinupramine, tianeptine, trimipramine, adrafinil, benactyzine, bupropion, butacetin, dioxadrol, duloxetine, etoperidone, febarbamate, femoxetine, fenpentadiol, fluoxetine, fluvoxamine, hematoporphyrin, hypericin, levophacetoperane, medifoxamine, milnacipran, minaprine, moclobemide, nefazodone, oxaflozane, piberaline, prolintane, pyrisuccideanol, ritanserin, roxindole, rubidium chloride, sulpiride, tandospirone, thozalinone, tofenacin, toloxatone, tranylcypromine, L-tryptophan, venlafaxine, viloxazine, and zimeldine.

In certain embodiments, the antidepressants used in combination with at least one compound of Formula (I) described herein, or a pharmaceutically acceptable salt or solvate thereof, are MAO-inhibitors including, but are not limited to, benmoxin, echinopsidine iodide, etryptamine, iproclozide, iproniazid, isocarboxazid, mebanazine, metfendrazine, moclobamide, nialamide, pargyline, phenelzine, pheniprazine, phenoxypropazine, pivhydrazine, safrazine, selegiline, 1-deprenyl, toloxatone and tranylcypromine The hormones used in combination with at least one compound of Formula (I) described herein, or a pharmaceutically acceptable salt or solvate thereof, include, but are not limited to, luteinizing hormone releasing hormone (LHRH), growth hormone (GH), growth hormone releasing hormone, ACTH, somatostatin, somatotropin, somatomedin, parathyroid hormone, hypothalamic releasing factors, insulin, glucagon, enkephalins, vasopressin, calcitonin, heparin, low molecular weight heparins, heparinoids, thymostimulin, synthetic and natural opioids, insulin thyroid stimulating hormones, and endorphins The alkylating agents used in combination with at least one compound of Formula (I) described herein, or a pharmaceutically acceptable salt or solvate thereof, include, but are not limited to, nitrogen mustards, ethylenimines, methylmelamines, alkyl sulfonates, nitrosoureas, carmustine, lomustine, triazenes, melphalan, mechlorethamine, cis-platin, oxaliplatin, carboplatin, cyclophosphamide, ifosfamide, melphalan, chlorambucil, hexamethylmelaine, thiotepa, busulfan, carmustine, streptozocin, dacarbazine and temozolomide.

The antimetabolites used in combination with at least one compound of Formula (I) described herein, or a pharmaceutically acceptable salt or solvate thereof, include, but are not limited to, cytarabile, gemcitabine and antifolates such as, by way of example only, fluoropyrimidines (by way of example only, 5-fluorouracil and tegafur), raltitrexed, methotrexate, cytosine arabinoside, and hydroxyurea.

The antitumour antibiotics in combination with at least one compound of Formula (I) described herein, or a pharmaceutically acceptable salt or solvate thereof, include, but are not limited to, anthracyclines, bleomycin, doxorubicin, daunomycin, epirubicin, idarubicin, mitomycin-C, dactinomycin and mithramycin.

The antimitotic agents used in combination with at least one compound of Formula (I) described herein, or a pharmaceutically acceptable salt or solvate thereof, include, but are not limited to, vinca alkaloids (by way of example only, vincristine, vinblastine, vindesine and vinorelbine), taxoids (by way of example only, taxol, paclitaxel and taxotere) and polokinase inhibitors.

The topoisomerase inhibitors used in combination with at least one compound of Formula (I) described herein, or a pharmaceutically acceptable salt or solvate thereof, include, but are not limited to, epipodophyllotoxins by way of example only, etoposide and teniposide, amsacrine, topotecan, irinotecan and camptothecin.

The cytostatic agents used in combination with at least one compound of Formula (I) described herein, or a pharmaceutically acceptable salt or solvate thereof, include, but are not limited to, antioestrogens (such as, by way of example only, tamoxifen, fulvestrant, toremifene, raloxifene, droloxifene and iodoxyfene), antiandrogens (such as, by way of example only, bicalutamide, flutamide, nilutamide and cyproterone acetate), LHRH antagonists or LHRH agonists (such as, by way of example only, goserelin, leuprorelin, leuprolide and buserelin), progestogens (such as, by way of example only, megestrol acetate), aromatase inhibitors (such as, by way of example only, as anastrozole, letrozole, vorazole and exemestane) and inhibitors of 5α-reductase (such as, by way of example only, finasteride).

The anti-invasion agents used in combination with at least one compound of Formula (I) described herein, or a pharmaceutically acceptable salt or solvate thereof, include, but are not limited to, c-Src kinase family inhibitors (such as, by way of example only, 4-(6-chloro-2,3-methylenedioxyanilino)-7-[2-(4-methylpiperazin-1-yl)ethoxy]-5-tetrahydropyran-4-yloxyquinazoline (AZD0530) and N-(2-chloro-6-methylphenyl)-2-{6-[4-(2-hydroxyethyl)piperazin-1-yl]-2-methylpyrimidin-4-ylamino}thiazole-5-carboxamide (dasatinib, BMS-354825)), and metalloproteinase inhibitors (such as, by way of example only, marimastat, inhibitors of urokinase plasminogen activator receptor function andantibodies to Heparanase).

The antiangiogenic agents used in combination with at least one compound of Formula (I) described herein, or a pharmaceutically acceptable salt or solvate thereof, include, but are not limited to, those which inhibit the effects of vascular endothelial growth factor such as, by way of example only, anti-vascular endothelial cell growth factor antibody bevacizumab (AVASTIN™) and VEGF receptor tyrosine kinase inhibitors such as 4-(4-bromo-2-fluoroanilino)-6-methoxy-7-(1-methylpiperidin-4-ylmethoxy)quinazoline (ZD6474), 4-(4-fluoro-2-methylindol-5-yloxy)-6-methoxy-7-(3-pyrrolidin-1-ylpropoxy)quinazoline (AZD2171), vatalanib (PTK787) and SU1 1248 (sunitinib), linomide, and inhibitors of integrin αvβ3 function and angiostatin.

The inhibitors of growth factor function used in combination with at least one compound of Formula (I) described herein, or a pharmaceutically acceptable salt or solvate thereof, include, but are not limited to, growth factor antibodies and growth factor receptor antibodies (such as, by way of example only, the anti-erbB2 antibody trastuzumab (HERCEPTIN™), the anti-EGFR antibody panitumumab, the anti-erbB1 antibody cetuximab (Erbitux, C225), tyrosine kinase inhibitors, such as, by way of example only, inhibitors of the epidermal growth factor family (for example EGFR family tyrosine kinase inhibitors such as, by way of example only, N-(3-chloro-4-fluorophenyl)-7-methoxy-6-(3-orpholinopropoxy)quinazolin-4-amine (gefitinib, ZD1839), N-(3-ethynylphenyl)-6,7-bis(2-methoxyethoxy)quinazolin-4-amine (erlotinib, OSI-774) and 6-acrylamido-N-(3-chloro-4-fluorophenyl)-7-(3-morpholinopropoxy)-quinazolin-4-amine (CI 1033), erbB2 tyrosine kinase inhibitors such as, by way of example only, lapatinib, inhibitors of the hepatocyte growth factor family, inhibitors of the platelet-derived growth factor family such as imatinib, GLEEVEC™, inhibitors of serine/threonine kinases (such as, by way of example only, Ras/Raf signaling inhibitors such as farnesyl transferase inhibitors, for example sorafenib (BAY 43-9006)), inhibitors of cell signalling through MEK and/or AKT kinases, inhibitors of the hepatocyte growth factor family, c-kit inhibitors, abl kinase inhibitors, IGF receptor (insulin-like growth factor) kinase inhibitors; aurora kinase inhibitors (for example AZD1 152, PH739358, VX-680, MLv8054, R763, MP235, MP529, VX-528 AND AX39459) and cyclin dependent kinase inhibitors such as CDK2 and/or CDK4 inhibitors.

In other embodiments, at least one compound of Formula (I) described herein, or a pharmaceutically acceptable salt or solvate thereof, is used in combination with vascular damaging agents such as, by way of example only, Combretastatin A4.

In other embodiments, at least one compound of Formula (I) described herein, or a pharmaceutically acceptable salt or solvate thereof, is used in combination with antisense therapies, such as, by way of example only, ISIS 2503, an anti-ras antisense.

In other embodiments, at least one compound of Formula (I) described herein, or a pharmaceutically acceptable salt or solvate thereof, is used in combination with gene therapy approaches, including for example approaches to replace aberrant genes such as aberrant p53 or aberrant BRCA1 or BRCA2, GDEPT (gene-directed enzyme pro-drug s therapy) approaches such as those using cytosine deaminase, thymidine kinase or a bacterial nitroreductase enzyme and approaches to increase patient tolerance to chemotherapy or radiotherapy such as multi-drug resistance gene therapy.

In other embodiments, at least one compound of Formula (I) described herein, or a pharmaceutically acceptable salt or solvate thereof, is used in combination with immunotherapy approaches, including for example ex-vivo and in-vivo approaches to increase the immunogenicity of patient tumor cells, such as transfection with cytokines such o as interleukin 2, interleukin 4 or granulocyte-macrophage colony stimulating factor, approaches to decrease T-cell allergy, approaches using transfected immune cells such as cytokine-transfected dendritic cells, approaches using cytokine-transfected tumor cell lines and approaches using anti-idiotypic antibodies.

In other embodiments, at least one compound of Formula (I) described herein, or a pharmaceutically acceptable salt or solvate thereof, is used in combination with other treatment methods including, but not limited to, surgery and radiotherapy (γ-radiation, neutron beam radiotherapy, electron beam radiotherapy, proton therapy, brachytherapy, and systemic radioactive isotopes).

In certain embodiments, the compounds of Formula (I) described herein, or pharmaceutically acceptable salts and solvates thereof, are administered or formulated in combination with an absorption enhancer, including, but not limited to, sodium glycocholate, sodium caprate, N-lauryl-β-D-maltopyranoside, EDTA, and mixed micelles. In certain embodiments, such absorption enhancers target the lymphatic system.

In certain embodiments, the additional therapeutic agent(s) used in the combination therapies described herein include, but are not limited to, agents such as tumor necrosis factor alpha (TNF-α) inhibitors (such as anti-TNF monoclonal antibodies (by way of example only, Remicade, CDP-870 and adalimumab) and TNF receptor immunoglobulin molecules (by way of example only, Enbrel)); non-selective cyclo-oxygenase COX-1/COX-2 inhibitors (by way of example only, piroxicam, diclofenac, propionic acids such as naproxen, flubiprofen, fenoprofen, ketoprofen and ibuprofen, fenamates such as mefenamic acid, indomethacin, sulindac, azapropazone, pyrazolones such as phenylbutazone, salicylates such as aspirin), COX-2 inhibitors (by way of example only, meloxicam, celecoxib, rofecoxib, valdecoxib, lumarocoxib, parecoxib and etoricoxib); glucocorticosteroids; methotrexate, lefunomide; hydroxychloroquine, d-penicillamine, auranofin or other parenteral or oral gold preparations.

In other embodiments, the combinations described herein include combination of a compound of Formula (I) described herein, or a pharmaceutically acceptable salt or solvate thereof, with a leukotriene biosynthesis inhibitor, 5-lipoxygenase (5-LO) inhibitor or 5-lipoxygenase activating protein (FLAP) antagonist such as; zileuton; ABT-761; fenleuton; tepoxalin; Abbott-79175; Abbott-85761; a N-(5-substituted)-thiophene-2-alkylsulfonamide; 2,6-di-tert-butylphenolhydrazones; a methoxytetrahydropyrans such as Zeneca ZD-2138; the compound SB-210661; a pyridinyl-substituted 2-cyanonaphthalene compound such as L-739,010; a 2-cyanoquinoline compound such as L-746,530; or an indole or quinoline compound such as MK-591, MK-886, and BAYx1005.

In other embodiments, the combinations described herein include combination of a compound of Formula (I) described herein, or a pharmaceutically acceptable salt or solvate thereof, with a receptor antagonist for leukotrienes (LT B4, LTC4, LTD4, and LTE4) selected from the group consisting of the phenothiazin-3-ls such as L-651,392; amidino compounds such as CGS-25019c; benzoxalamines such as ontazolast; benzenecarboximidamides such as BIIL 284/260; and compounds such as zafirlukast, ablukast, montelukast, SINGULAIR™, pranlukast, verlukast (MK-679), RG-12525, Ro-245913, iralukast (CGP 45715A), and BAYx7195.

In other embodiments, the combinations described herein include combination of a compound of Formula (I) described herein, or a pharmaceutically acceptable salt or solvate thereof, with a phosphodiesterase (PDE) inhibitor such as a methylxanthanine including theophylline and aminophylline; a selective PDE isoenzyme inhibitor including a PDE4 inhibitor, including, but not limited to, cilomilast or roflumilast, an inhibitor of the isoform PDE4D, or an inhibitor of PDE5.

In other embodiments, the combinations described herein include combination of a compound of Formula (I) described herein, or a pharmaceutically acceptable salt or solvate thereof, with a histamine type 1 receptor antagonist such as cetirizine, loratadine, desloratadine, fexofenadine, acrivastine, terfenadine, astemizole, azelastine, levocabastine, chlorpheniramine, promethazine, cyclizine, or mizolastine.

In other embodiments, the combinations described herein include combination of a compound of Formula (I) described herein, or a pharmaceutically acceptable salt or solvate thereof, with a gastroprotective histamine type 2 receptor antagonist. In other embodiments, the combinations described herein include combination of a compound of Formula (I), or a pharmaceutically acceptable salt or solvate thereof, described herein, with an antagonist of the histamine type 4 receptor.

In other embodiments, the combinations described herein include combination of a compound of Formula (I) described herein, or a pharmaceutically acceptable salt or solvate thereof, with an alpha-1/alpha-2 adrenoceptor agonist vasoconstrictor sympathomimetic agent, such as propylhexedrine, phenylephrine, phenylpropanolamine, ephedrine, pseudoephedrine, naphazoline hydrochloride, oxymetazoline hydrochloride, tetrahydrozoline hydrochloride, xylometazoline hydrochloride, tramazoline hydrochloride or ethylnorepinephrine hydrochloride.

In other embodiments, the combinations described herein include combination of a compound of Formula (I) described herein, or a pharmaceutically acceptable salt or solvate thereof, with an anticholinergic agent including muscarinic receptor (M1, M2, and M3) antagonists such as atropine, hyoscine, glycopyrrrolate, ipratropium bromide, tiotropium bromide, oxitropium bromide, pirenzepine or telenzepine.

In other embodiments, the combinations described herein include combination of a compound of Formula (I) described herein, or a pharmaceutically acceptable salt or solvate thereof, with a beta-adrenoceptor agonist (including beta receptor subtypes 1-4) such as isoprenaline, salbutamol, albuterol, formoterol, salmeterol, terbutaline, orciprenaline, bitolterol mesylate, and pirbuterol.

In other embodiments, the combinations described herein include combination of a compound of Formula (I) described herein, or a pharmaceutically acceptable salt or solvate thereof, with a chromone, such as sodium cromoglycate or nedocromil sodium.

In other embodiments, the combinations described herein include combination of a compound of Formula (I) described herein, or a pharmaceutically acceptable salt or solvate thereof, with an insulin-like growth factor type I (IGF-I) mimetic.

In other embodiments, the combinations described herein include combination of a compound of Formula (I) described herein, or a pharmaceutically acceptable salt or solvate thereof, with a glucocorticoid, such as flunisolide, triamcinolone acetonide, beclomethasone dipropionate, budesonide, fluticasone propionate, ciclesonide or mometasone furoate.

In other embodiments, the combinations described herein include combination of a compound of Formula (I) described herein, or a pharmaceutically acceptable salt or solvate thereof, with an inhibitor of matrix metalloproteases (MMPs), i.e., the stromelysins, the collagenases, and the gelatinases, as well as aggrecanase; especially collagenase-1 (MMP-I), collagenase-2 (MMP-8), collagenase-3 (MMP-13), stromelysin-1 (MMP-3), stromelysin-2 (MMP-IO), and stromelysin-3 (MMP-I1) andMMP-9 and MMP-12.

In other embodiments, the combinations described herein include combination of a compound of Formula (I) described herein, or a pharmaceutically acceptable salt or solvate thereof, with modulators of chemokine receptor function such as antagonists of CCR1, CCR2, CCR2A, CCR2B, CCR3, CCR4, CCR5, CCR6, CCR7, CCR8, CCR9, CCRIO and CCR11 (for the C—C family); CXCR1, CXCR2, CXCR3, CXCR4 and CXCR5 (for the C—X—C family) and CX3CR1 for the C—X3-C family.

In other embodiments, the combinations described herein include combination of a compound of Formula (I) described herein, or a pharmaceutically acceptable salt or solvate thereof, with an immunoglobulin (Ig), gamma globulin, Ig preparation or an antagonist or antibody modulating Ig function such as anti-IgE (omalizumab).

Compounds of Formula (I) as Immune Potentiators

In certain embodiments, pharmaceutical compositions containing at least one compound of Formula (I) described herein, or a pharmaceutically acceptable salt or solvate thereof, are immunogenic compositions. In certain embodiments, such immunogenic compositions are useful as vaccines. In certain embodiments, such vaccines are prophylactic (i.e. to prevent infection), while in other embodiments, such vaccines are therapeutic (i.e. to treat infection).

In other embodiments, the compound(s) of Formula (I) described herein, or a pharmaceutically acceptable salt or solvate thereof, are immune potentiators and impart an immunostimulatory effect upon administration when compared to immunogenic formulations that do not contain compound(s) of Formula (I). In certain embodiments, compounds of Formula (I) impart an immunostimulatory effect upon administration when included in an immunogenic composition having one or more immunoregulatory agents, while in other embodiments, compounds of Formula (I) impart an immunostimulatory effect upon administration when included in an immunogenic composition without the presence of other immunoregulatory agents.

The immunostimulatory effect referred to herein is often an enhancement of the immunogenic composition's effect. In certain embodiments the enhancement of the efficacy of the immunogenic composition is by at least 10% relative to the effect of the immunogenic composition in the absence of the immune potentiator. In certain embodiments the enhancement of the efficacy of the immunogenic composition is by at least 20% relative to the effect of the immunogenic composition in the absence of the immune potentiator. In certain embodiments the enhancement of the efficacy of the immunogenic composition is by at least 30% relative to the effect of the immunogenic composition in the absence of the immune potentiator. In certain embodiments the enhancement of the efficacy of the immunogenic composition is by at least 40% relative to the effect of the immunogenic composition in the absence of the immune potentiator. In certain embodiments the enhancement of the efficacy of the immunogenic composition is by at least 50% relative to the effect of the immunogenic composition in the absence of the immune potentiator. In certain embodiments the enhancement of the efficacy of the immunogenic composition is by at least 60% relative to the effect of the immunogenic composition in the absence of the immune potentiator. In certain embodiments the enhancement of the efficacy of the immunogenic composition is by at least 70% relative to the effect of the immunogenic composition in the absence of the immune potentiator. In certain embodiments the enhancement of the efficacy of the immunogenic composition is by at least 80% relative to the effect of the immunogenic composition in the absence of the immune potentiator. In certain embodiments the enhancement of the efficacy of the immunogenic composition is by at least 90% relative to the effect of the immunogenic composition in the absence of the immune potentiator. In certain embodiments the enhancement of the efficacy of the immunogenic composition is by at least 100% relative to the effect of the immunogenic composition in the absence of the immune potentiator.

In certain embodiments, the enhancement of the immunogenic composition's effect is measured by the increased effectiveness of the immunogenic composition for achieving its protective effects. In certain embodiments, this increased effectiveness is measured as a decreased probability that a subject receiving the immunogenic composition will experience a condition for which the immunogenic composition is considered protective, or a decrease in duration or severity of the effects of such condition. In other embodiments, this increased effectiveness is measured as an increase in a titer of an antibody elicited by the immunogenic composition in a treated subject.

Along with one or more compounds of Formula (I) described herein, or a pharmaceutically acceptable salt or solvate thereof, such immunogenic compositions include an effective amount of one or more antigens, and a pharmaceutically acceptable carrier. Such carriers are include, but are not limited to, proteins, polysaccharides, polylactic acids, polyglycolic acids, polymeric amino acids, amino acid copolymers, sucrose, trehalose, lactose, lipid aggregates (such as oil droplets or liposomes), and inactive virus particles. The immunogenic compositions typically also contain diluents, such as water, saline, and glycerol, and optionally contain other excipients, such as wetting or emulsifying agents, and pH buffering substances.

In certain embodiments, immunogenic compositions optionally include one or more immunoregulatory agents. In certain embodiments, one or more of the immunoregulatory agents include one or more adjuvants. Such adjuvants include, but are not limited to, a TH1 adjuvant and/or a TH2 adjuvant, further discussed below. In certain embodiments, the adjuvants used in immunogenic compositions provide herein include, but are not limited to:
  A. Mineral-Containing Compositions;
  B. Oil Emulsions;
  C. Saponin Formulations;
  D. Virosomes and Virus-Like Particles;
  E. Bacterial or Microbial Derivatives;
  F. Human Immunomodulators;
  G. Bioadhesives and Mucoadhesives;
  H. Microparticles;
  I. Liposomes;
  J. Polyoxyethylene Ether and Polyoxyethylene Ester Formulations;
  K. Polyphosphazene (PCPP);
  L. Muramyl Peptides, and
  M. Imidazoquinolone Compounds.

Mineral-containing compositions suitable for use as adjuvants include, but are not limited to, mineral salts, such as aluminium salts and calcium salts. By way of example only, such mineral salts include, hydroxides (e.g. oxyhydroxides, including aluminium hydroxides and aluminium oxyhydroxides), phosphates (e.g. hydroxyphosphates and orthophosphates, including aluminium phosphates, aluminium hydroxyphosphates, aluminium orthophosphates and calcium phosphate), sulfates (e.g. aluminium sulfate), or mixtures of different mineral compounds. Such mineral salts are in any suitable form, such as, by way of example only, gel, crystalline, and amorphous forms. In certain embodiments, such mineral containing compositions are formulated as a particle of the metal salt. In certain embodiments, components of the immunogenic compositions described herein are adsorbed to such mineral salts. In certain embodiments, an aluminium hydroxide and/or aluminium phosphate adjuvant is used in the immunogenic compositions described herein. In other embodiments, antigens used in an immunogenic composition described herein are adsorbed to such aluminium hydroxide and/or aluminium phosphate adjuvants. In certain embodiments, a calcium phosphate adjuvant is used in the immunogenic compositions described herein. In other embodiments, antigens used in an immunogenic composition described herein are adsorbed to such calcium phosphate adjuvants.

In certain embodiments, aluminum phosphates are used as an adjuvant in the immunogenic compositions described herein. In other embodiments, aluminum phosphates are used as an adjuvant in the immunogenic compositions described herein, wherein such compositions include a *H. influenzae* saccharide antigen. In certain embodiments, the adjuvant is amorphous aluminium hydroxyphosphate with a $PO_4/Al$ molar ratio between 0.84 and 0.92, included at 0.6 mg $Al^{3+}$/ml. In other embodiments, adsorption with a low dose of aluminium phosphate is used, by way of example only, between 50 and 100 μg $Al^{3+}$ per conjugate per dose. Where there is more than one conjugate in a composition, not all conjugates need to be adsorbed.

Oil emulsions suitable for use as adjuvants include, but are not limited to, squalene-water emulsions (such as MF59 (5% Squalene, 0.5% Tween 80, and 0.5% Span 85, formulated into submicron particles using a microfluidizer), Complete Freund's adjuvant (CFA) and incomplete Freund's adjuvant (IFA).

Saponins are a heterologous group of sterol glycosides and triterpenoid glycosides that are found in the bark, leaves, stems, roots and even flowers of a wide range of plant species. Saponin formulations suitable for use as adjuvants include, but are not limited to, saponins from the bark of the *Quillaia saponaria* Molina tree, from *Smilax ornata* (sarsaprilla), *Gypsophilla paniculata* (brides veil), and *Saponaria officianalis* (soap root). In certain embodiments, saponin formulations suitable for use as adjuvants include, but are not limited to, purified formulations including, but not limited to, QS7, QS17, QS18, QS21, QH-A, QH-B and QH-C. QS21 is marketed as STIMULOM™. In other embodiments, saponin formulations include sterols, cholesterols and lipid formulations, such as unique particles formed by the combinations of saponins and cholesterols called immunostimulating complexes (ISCOMs). In certain embodiments, the ISCOMs also include a phospholipid such as phosphatidylethanolamine or phosphatidylcholine. Any known saponin can be used in ISCOMs. In certain embodiments, the ISCOM includes one or more of QuilA, QHA & QHC. In other embodiments, the ISCOMS are optionally devoid of an additional detergent.

Virosomes and virus-like particles (VLPs) suitable for use as adjuvants include, but are not limited to, one or more proteins from a virus optionally combined or formulated with a phospholipid. Such virosomes and VLPs are generally non-pathogenic, non-replicating and generally do not contain any of the native viral genome. In certain embodiments, the viral proteins are recombinantly produced, while in other embodiments the viral proteins are isolated from whole viruses.

The viral proteins suitable for use in virosomes or VLPs include, but are not limited to, proteins derived from influenza virus (such as HA or NA), Hepatitis B virus (such as core or capsid proteins), Hepatitis E virus, measles virus, Sindbis virus, Rotavirus, Foot-and-Mouth Disease virus, Retrovirus, Norwalk virus, human Papilloma virus, HIV, RNA-phages, Qβ-phage (such as coat proteins), GA-phage, fr-phage, AP205 phage, and Ty (such as retrotransposon Ty protein p1).

Bacterial or microbial derivatives suitable for use as adjuvants include, but are not limited to, bacterial or microbial derivatives such as non-toxic derivatives of enterobacterial lipopolysaccharide (LPS), Lipid A derivatives, immunostimulatory oligonucleotides and ADP-ribosylating toxins and detoxified derivatives thereof. Such non-toxic derivatives of LPS include, but are not limited to, monophosphoryl lipid A (MPL) and 3-O-deacylated MPL (3dMPL). 3dMPL is a mixture of 3 de-O-acylated monophosphoryl lipid A with 4, 5 or 6 acylated chains. Other non-toxic LPS derivatives include monophosphoryl lipid A mimics, such as aminoalkyl glucosaminide phosphate derivatives (e.g. RC-529). Lipid A derivatives include, but are not limited to, derivatives of lipid A from Escherichia coli (e.g. OM-174).

Immunostimulatory oligonucleotides used as adjuvants include, but are not limited to, nucleotide sequences containing a CpG motif (a dinucleotide sequence containing an unmethylated cytosine linked by a phosphate bond to a guanosine). Such CpG sequences can be double-stranded or single-stranded. In certain embodiments, such nucleotide sequences are double-stranded RNAs or oligonucleotides containing palindromic or poly(dG) sequences. In other embodiments, the CpG's include nucleotide modifications/analogs such as phosphorothioate modifications.

In certain embodiments the CpG sequence are directed to TLR9, and in certain embodiments the motif is GTCGTT or TTCGTT. In certain embodiments the CpG sequence is specific for inducing a Th1 immune response, such as, by way of example only, a CpG-A ODN, or in other embodiments the CpG sequence is more specific for inducing a B cell response, such as, by way of example only, a CpG-B ODN. In certain embodiments the CpG is a CpG-A ODN.

In certain embodiments the CpG oligonucleotide is constructed so that the 5' end is accessible for receptor recognition. In other embodiments two CpG oligonucleotide sequences are optionally attached at their 3' ends to form "immunomers".

A particularly useful adjuvant based around immunostimulatory oligonucleotides is known as IC-31™. In certain embodiments, an adjuvant used with immunogenic compositions described herein, includes a mixture of (i) an oligonucleotide (such as, by way of example only, between 15-40 nucleotides) including at least one (and preferably multiple) CpI motifs (such as, by way of example only, a cytosine linked to an inosine to form a dinucleotide), and (ii) a polycationic polymer, such as, by way of example only, an oligopeptide (such as, by way of example only, between 5-20 amino acids) including at least one (and preferably multiple) Lys-Arg-Lys tripeptide sequence(s). In certain embodiments, the oligonucleotide is a deoxynucleotide comprising 26-mer sequence 5'-(IC)$_{13}$-3'. In other embodiments, the polycationic polymer is a peptide comprising 11-mer amino acid sequence KLKLLLLLKLK.

In certain embodiments, bacterial ADP-ribosylating toxins and detoxified derivatives thereof are used as adjuvants in the immunogenic compositions described herein. In certain embodiments, such proteins are derived from E. coli (E. coli heat labile enterotoxin "LT"), cholera ("CT"), or pertussis ("PT"). In other embodiments, the toxin or toxoid is in the form of a holotoxin, comprising both A and B subunits. In other embodiments, the A subunit contains a detoxifying mutation; whereas the B subunit is not mutated. In other embodiments, the adjuvant is a detoxified LT mutant such as LT-K63, LT-R72, and LT-G192.

The human immunomodulators suitable for use as adjuvants include, but are not limited to, cytokines, such as, by way of example only, interleukins (IL-1, IL-2, IL-4, IL-5, IL-6, IL-7, IL-12), interferons (such as, by way of example only, interferon-γ), macrophage colony stimulating factor, and tumor necrosis factor.

The bioadhesives and mucoadhesives used as adjuvants in the immunogenic compositions described herein include, but are not limited to, esterified hyaluronic acid microspheres, and cross-linked derivatives of poly(acrylic acid), polyvinyl alcohol, polyvinyl pyrollidone, polysaccharides and carboxymethylcellulose. In certain embodiments, chitosan and derivatives thereof are used as in the vaccine compositions described herein adjuvants.

The microparticles suitable for use as adjuvants include, but are not limited to, microparticles formed from materials that are biodegradable and non-toxic (e.g. a poly(.alpha.-hydroxy acid), a polyhydroxybutyric acid, a polyorthoester, a polyanhydride, a polycaprolactone, etc.), with poly(lactide-co-glycolide). In certain embodiments, such microparticles are treated to have a negatively-charged surface (e.g. with SDS) or a positively-charged surface (e.g. with a cationic detergent, such as CTAB). The microparticles suitable for use as adjuvants have a particle diameter of about 100 nm to about 150 µm in diameter. In certain embodiments, the particle diameter is about 200 nm to about 30 µm, and in other embodiments the particle diameter is about 500 nm to 10 µm.

The polyoxyethylene ether and polyoxyethylene ester formulations suitable for use as adjuvants include, but are not limited to, polyoxyethylene sorbitan ester surfactants in combination with an octoxynol, and polyoxyethylene alkyl ethers or ester surfactants in combination with at least one additional non-ionic surfactant such as an octoxynol. In certain embodiments, the polyoxyethylene ethers are selected from polyoxyethylene-9-lauryl ether (laureth 9), polyoxyethylene-9-steoryl ether, polyoxytheylene-8-steoryl ether, polyoxyethylene-4-lauryl ether, polyoxyethylene-35-lauql ether, and polyoxyethylene-23-lauryl ether.

The muramyl peptides suitable for use as adjuvants include, but are not limited to, N-acetyl-muramyl-L-threonyl-D-isoglutamine (thr-MDP), N-acetyl-normuramyl-L-alanyl-D-isoglutamine (nor-MDP), and N-acetylmuramyl-L-alanyl-D-isoglutaminyl-L-alanine-2-(1'-2'-dipalmitoyl-s-n-glycero-3-hydroxyphosphoryloxy)-ethylamine MTP-PE).

In certain embodiments, one or more compounds of Formula (I) used as an immune potentiator are included in compositions having combinations of one or more of the adjuvants identified above. Such combinations include, but are not limited to,
(1) a saponin and an oil-in-water emulsion;
(2) a saponin (e.g. QS21)+a non-toxic LPS derivative (e.g. 3dMPL);
(3) a saponin (e.g. QS21)+a non-toxic LPS derivative (e.g. 3dMPL)+a cholesterol;
(4) a saponin (e.g. QS21)+3dMPTL+IL-12 (optionally including a sterol);
(5) combinations of 3dMPL with, for example, QS21 and/or oil-in-water emulsions;
(6) SAF, containing 10% squalane, 0.4% Tween 80™, 5% pluronic-block polymer L121, and thr-MDP, either microfluidized into a submicron emulsion or vortexed to generate a larger particle size emulsion.
(7) RIBI™ adjuvant system (RAS), (Ribi Immunochem) containing 2% squalene, 0.2% Tween 80, and one or more bacterial cell wall components from the group consisting of monophosphorylipid A (MPL), trehalose dimycolate (TDM), and cell wall skeleton (CWS), preferably MPL+CWS (Detox™); and
(8) one or more mineral salts (such as an aluminum salt)+a non-toxic derivative of LPS (such as 3dMPL).

In other embodiments, the adjuvant combinations used in the immunogenic combinations provided herein include combinations of Th1 and Th2 adjuvants such as, by way of example only, CpG and alum or resiquimod and alum.

In certain embodiments, the immunogenic compositions provided herein elicit both a cell mediated immune response as well as a humoral immune response. In other embodiments, the immune response induces long lasting (e.g. neutralising) antibodies and a cell mediated immunity that quickly responds upon exposure to the infectious agent.

Two types of T cells, CD4 and CD8 cells, are generally thought necessary to initiate and/or enhance cell mediated immunity and humoral immunity. CD8 T cells can express a CD8 co-receptor and are commonly referred to as Cytotoxic T lymphocytes (CTLs). CD8 T cells are able to recognized or interact with antigens displayed on MHC Class I molecules.

CD4 T cells can express a CD4 co-receptor and are commonly referred to as T helper cells. CD4 T cells are able to recognize antigenic peptides bound to MHC class II molecules. Upon interaction with a MHC class II molecule, the CD4 cells can secrete factors such as cytokines. These secreted cytokines can activate B cells, cytotoxic T cells, macrophages, and other cells that participate in an immune response. Helper T cells or CD4+ cells can be further divided into two functionally distinct subsets: TH1 phenotype and TH2 phenotypes which differ in their cytokine and effector function.

Activated TH1 cells enhance cellular immunity (including an increase in antigen-specific CTL production) and are therefore of particular value in responding to intracellular infections. Activated TH1 cells may secrete one or more of IL-2, IFN-γ, and TNF-β. A TH1 immune response may result in local inflammatory reactions by activating macrophages, NK (natural killer) cells, and CD8 cytotoxic T cells (CTLs). A TH1 immune response may also act to expand the immune response by stimulating growth of B and T cells with IL-12. TH1 stimulated B cells may secrete IgG2a.

Activated TH2 cells enhance antibody production and are therefore of value in responding to extracellular infections. Activated TH2 cells may secrete one or more of IL-4, IL-5, IL-6, and IL-10. A TH2 immune response may result in the production of IgG1, IgE, IgA and memory B cells for future protection.

An enhanced immune response may include one or more of an enhanced TH1 immune response and a TH2 immune response.

A TH1 immune response may include one or more of an increase in CTLs, an increase in one or more of the cytokines associated with a TH1 immune response (such as IL-2, IFN-γ, and TNF-β), an increase in activated macrophages, an increase in NK activity, or an increase in the production of IgG2a. Preferably, the enhanced TH1 immune response will include an increase in IgG2a production.

TH1 adjuvants can be used to elicit a TH1 immune response. A TH1 adjuvant will generally elicit increased levels of IgG2a production relative to immunization of the antigen without adjuvant. TH1 adjuvants suitable for use in immunogenic compositions provided herein include, but are not limited to, saponin formulations, virosomes and virus like particles, non-toxic derivatives of enterobacterial lipopolysaccharide (LPS), immunostimulatory oligonucleotides. In certain embodiments, the immunostimulatory oligonucleotides used as TH1 adjuvants in the immunogenic compositions provided herein contain a CpG motif.

A TH2 immune response may include one or more of an increase in one or more of the cytokines associated with a TH2 immune response (such as IL-4, IL-5, IL-6 and IL-10), or an increase in the production of IgG1, IgE, IgA and memory B cells. Preferably, the enhanced TH2 immune response will include an increase in IgG1 production.

TH2 adjuvants can be used to elicit a TH2 immune response. A TH2 adjuvant will generally elicit increased levels of IgG1 production relative to immunization of the antigen without adjuvant. TH2 adjuvants suitable for use in immunogenic compositions provided herein include, but are not limited to, mineral containing compositions, oil-emulsions, and ADP-ribosylating toxins and detoxified derivatives thereof. In certain embodiments, the mineral containing compositions used as TH2 adjuvants in the immunogenic compositions provided herein are aluminium salts.

In certain embodiments, the immunogenic compositions provided herein include a TH1 adjuvant and a TH2 adjuvant. In other embodiments, such compositions elicit an enhanced TH1 and an enhanced TH2 response, such as, an increase in the production of both IgG1 and IgG2a production relative to immunization without an adjuvant. In still other embodiments, such compositions comprising a combination of a TH1 and a TH2 adjuvant elicit an increased TH1 and/or an increased TH2 immune response relative to immunization with a single adjuvant (i.e., relative to immunization with a TH1 adjuvant alone or immunization with a TH2 adjuvant alone).

In certain embodiments, the immune response is one or both of a TH1 immune response and a TH2 response. In other embodiments, the immune response provides for one or both of an enhanced TH1 response and an enhanced TH2 response.

In certain embodiments, the enhanced immune response is one or both of a systemic and a mucosal immune response. In other embodiments, the immune response provides for one or both of an enhanced systemic and an enhanced mucosal immune response. In certain embodiments, the mucosal immune response is a TH2 immune response. In certain embodiments, the mucosal immune response includes an increase in the production of IgA.

In certain embodiments the immunogenic compositions provided herein are used as vaccines, wherein such compositions include an immunologically effective amount of one or more antigen).

Antigens for use with the immunogenic compositions provided herein include, but are not limited to, one or more of the following antigens set forth below, or antigens derived from one or more of the pathogens set forth below.

Bacterial Antigens

Bacterial antigens suitable for use in immunogenic compositions provided herein include, but are not limited to, proteins, polysaccharides, lipopolysaccharides, and outer membrane vesicles which are isolated, purified or derived from a bacteria. In certain embodiments, the bacterial antigens include bacterial lysates and inactivated bacteria formulations. In certain embodiments, the bacterial antigens are produced by recombinant expression. In certain embodiments, the bacterial antigens include epitopes which are exposed on the surface of the bacteria during at least one stage of its life cycle. Bacterial antigens are preferably conserved across multiple serotypes. In certain embodiments, the bacterial antigens include antigens derived from one or more of the bacteria set forth below as well as the specific antigens examples identified below:

*Neisseria meningitidis*: Meningitidis antigens include, but are not limited to, proteins, saccharides (including a polysaccharide, oligosaccharide, lipooligosaccharide or lipopolysaccharide), or outer-membrane vesicles purified or derived from *N. meningitides* serogroup such as A, C, W135, Y, X and/or B. In certain embodiments meningitides protein antigens are be selected from adhesions, autotransporters, toxins, Fe acquisition proteins, and membrane associated proteins (preferably integral outer membrane protein).

*Streptococcus pneumoniae*: *Streptococcus pneumoniae* antigens include, but are not limited to, a saccharide (including a polysaccharide or an oligosaccharide) and/or protein from *Streptococcus pneumoniae*. The saccharide may be a polysaccharide having the size that arises during purification of the saccharide from bacteria, or it may be an oligosaccharide achieved by fragmentation of such a polysaccharide. In the 7-valent PREVNAR™ product, for instance, 6 of the saccharides are presented as intact polysaccharides while one (the 18C serotype) is presented as an oligosaccharide. In certain embodiments saccharide antigens are selected from one or more of the following pneumococcal serotypes 1, 2, 3, 4, 5, 6A, 6B, 7F, 8, 9N, 9V, 10A, 11A, 12F, 14, 15B, 17F, 18C, 19A, 19F, 20, 22F, 23F, and/or 33F. An immunogenic composition may include multiple serotypes e.g. 2, 3, 4, 5, 6, 7, 8, 9, 10, 11, 12, 13, 14, 15, 16, 17, 18, 19, 20, 21, 22, 23 or more serotypes. 7-valent, 9-valent, 10-valent, 11-valent and 13-valent conjugate combinations are already known in the art, as is a 23-valent unconjugated combination. For example, an 10-valent combination may include saccharide from serotypes 1, 4, 5, 6B, 7F, 9V, 14, 18C, 19F and 23F. An 11-valent combination may further include saccharide from serotype 3. A 12-valent combination may add to the 10-valent mixture: serotypes 6A and 19A; 6A and 22F; 19A and 22F; 6A and 15B; 19A and 15B; r 22F and 15B; A 13-valent combination may add to the 11-valent mixture: serotypes 19A and 22F; 8 and 12F; 8 and 15B; 8 and 19A; 8 and 22F; 12F and 15B; 12F and 19A; 12F and 22F; 15B and 19A; 15B and 22F. etc. In certain embodiments, protein antigens may be selected from a protein identified in WO98/18931, WO98/18930, U.S. Pat. No. 6,699,703, U.S. Pat. No. 6,800,744, WO97/43303, WO97/37026, WO 02/079241, WO 02/34773, WO 00/06737, WO 00/06738, WO 00/58475, WO 2003/082183, WO 00/37105, WO 02/22167, WO 02/22168, WO 2003/104272, WO 02/08426, WO 01/12219, WO 99/53940, WO 01/81380, WO 2004/092209, WO 00/76540, WO 2007/116322, LeMieux et al., Infect. Imm (2006) 74:2453-2456, Hoskins et al., J. Bacteriol. (2001) 183: 5709-5717, Adamou et al., Infect. Immun (2001) 69(2): 949-958, Briles et al., J. Infect. Dis. (2000) 182:1694-1701, Talkington et al., Microb. Pathog. (1996) 21(1): 17-22, Bethe et al., FEMS Microbiol. Lett. (2001) 205 (1):99-104, Brown et al., Infect. Immun (2001) 69:6702-6706, Whalen et al., FEMS Immunol. Med. Microbiol. (2005) 43:73-80, Jomaa et al., Vaccine (2006) 24(24): 5133-5139. In other embodiments, *Streptococcus pneumoniae* proteins may be selected from the Poly Histidine Triad family (PhtX), the Choline Binding Protein family (CbpX), CbpX truncates, LytX family, LytX truncates, CbpX truncate-LytX truncate chimeric proteins, pneumolysin (Ply), PspA, PsaA, Sp128, SpIO1, Sp130, Sp125, Sp133, pneumococcal pilus subunits.

*Streptococcus pyogenes* (Group A *Streptococcus*): Group A *Streptococcus* antigens include, but are not limited to, a protein identified in WO 02/34771 or WO 2005/032582 (including GAS 40), fusions of fragments of GAS M proteins (including those described in WO 02/094851, and Dale, Vaccine (1999) 17:193-200, and Dale, Vaccine 14(10): 944-948), fibronectin binding protein (Sfb1), Streptococcal heme-associated protein (Shp), and Streptolysin S (SagA).

*Moraxella catarrhalis*: *Moraxella* antigens include, but are not limited to, antigens identified in WO 02/18595 and WO 99/58562, outer membrane protein antigens (HMW-OMP), C-antigen, and/or LPS.

*Bordetella pertussis*: Pertussis antigens include, but are not limited to, pertussis holotoxin (PT) and filamentous haemagglutinin (FHA) from *B. pertussis*, optionally also combination with pertactin and/or agglutinogens 2 and 3.

*Burkholderia*: *Burkholderia* antigens include, but are not limited to *Burkholderia mallei*, *Burkholderia pseudomallei* and *Burkholderia cepacia*.

*Staphylococcus aureus*: Staph aureus antigens include, but are not limited to, a polysaccharide and/or protein from *S. aureus*. *S. aureus* polysaccharides include, but are not limited to, type 5 and type 8 capsular polysaccharides (CP5 and CP8) optionally conjugated to nontoxic recombinant *Pseudomonas aeruginosa* exotoxin A, such as StaphVAX™, type 336 polysaccharides (336PS), polysaccharide intercellular adhesions (PIA, also known as PNAG). *S. aureus* proteins include, but are not limited to, antigens derived from surface proteins, invasins (leukocidin, kinases, hyaluronidase), surface factors that inhibit phagocytic engulfment (capsule, Protein A), carotenoids, catalase production, Protein A, coagulase, clotting factor, and/or membrane-damaging toxins (optionally detoxified) that lyse eukaryotic cell membranes (hemolysins, leukotoxin, leukocidin). In certain embodiments, *S. aureus* antigens may be selected from a protein identified in WO 02/094868, WO 2008/019162, WO 02/059148, WO 02/102829, WO 03/011899, WO 2005/079315, WO 02/077183, WO 99/27109, WO 01/70955, WO 00/12689, WO 00/12131, WO 2006/032475, WO 2006/032472, WO 2006/032500, WO 2007/113222, WO 2007/113223, WO 2007/113224. In other embodiments, *S. aureus* antigens may be selected from IsdA, IsdB, IsdC, SdrC, SdrD, SdrE, ClfA, ClfB, SasF, SasD, SasH (AdsA), Spa, EsaC, EsxA, EsxB, Emp, HlaH35L, CP5, CP8, PNAG, 336PS.

*Staphylococcus epidermis*: *S. epidermidis* antigens include, but are not limited to, slime-associated antigen (SAA).

*Clostridium tetani* (Tetanus): Tetanus antigens include, but are not limited to, tetanus toxoid (TT). In certain embodiments such antigens are used as a carrier protein in conjunction/conjugated with the immunogenic compositions provided herein.

*Clostridium perfringens*: Antigens include, but are not limited to, Epsilon toxin from *Clostridium perfringen*.

*Clostridium botulinums* (Botulism): Botulism antigens include, but are not limited to, those derived from *C. botulinum*.

*Cornynebacterium diphtheriae* (Diphtheria): Diphtheria antigens include, but are not limited to, diphtheria toxin, preferably detoxified, such as $CRM_{197}$. Additionally antigens capable of modulating, inhibiting or associated with ADP ribosylation are contemplated for combination/co-administration/conjugation with the immunogenic compositions provided herein. In certain embodiments, the diphtheria toxoids are used as carrier proteins.

*Haemophilus influenzae* B (Hib): Hib antigens include, but are not limited to, a Hib saccharide antigen.

*Pseudomonas aeruginosa*: *Pseudomonas* antigens include, but are not limited to, endotoxin A, Wzz protein, *P. aeruginosa* LPS, LPS isolated from PAO1 (O5 serotype), and/or Outer Membrane Proteins, including Outer Membrane Proteins F (OprF).

*Legionella pneumophila*. Bacterial antigens derived from *Legionella pneumophila*.

*Coxiella burnetii*. Bacterial antigens derived from *Coxiella burnetii*.

*Brucella*. Bacterial antigens derived from *Brucella*, including but not limited to, *B. abortus, B. canis, B. melitensis, B. neotomae, B. ovis, B. suis* and *B. pinnipediae*.

*Francisella*. Bacterial antigens derived from *Francisella*, including but not limited to, *F. novicida, F. philomiragia* and *F. tularensis*.

*Streptococcus agalactiae* (Group B *Streptococcus*): Group B *Streptococcus* antigens include, but are not limited to, a protein or saccharide antigen identified in WO 02/34771, WO 03/093306, WO 04/041157, or WO 2005/002619 (including proteins GBS 80, GBS 104, GBS 276 and GBS 322, and including saccharide antigens derived from serotypes Ia, Ib, Ia/c, II, III, IV, V, VI, VII and VIII).

*Neiserria gonorrhoeae*: Gonorrhoeae antigens include but are not limited to, Por (or porin) protein, such as PorB (see Zhu et al., *Vaccine* (2004) 22:660-669), a transferring binding protein, such as TbpA and TbpB (See Price et al., Infection and Immunity (2004) 71(1):277-283), a opacity protein (such as Opa), a reduction-modifiable protein (Rmp), and outer membrane vesicle (OMV) preparations (see Plante et al, J Infectious Disease (2000) 182:848-855), also see, e.g., WO99/24578, WO99/36544, WO99/57280, WO02/079243).

*Chlamydia trachomatis*: *Chlamydia trachomatis* antigens include, but are not limited to, antigens derived from serotypes A, B, Ba and C (agents of trachoma, a cause of blindness), serotypes $L_1$, $L_2$ & $L_3$ (associated with *Lymphogranuloma venereum*), and serotypes, D-K. In certain embodiments, chlamydia trachomas antigens include, but are not limited to, an antigen identified in WO 00/37494, WO 03/049762, WO 03/068811, or WO 05/002619, including PepA (CT045), LcrE (CT089), ArtJ (CT381), DnaK (CT396), CT398, OmpH-like (CT242), L7/L12 (CT316), OmcA (CT444), AtosS (CT467), CT547, Eno (CT587), HrtA (CT823), and MurG (CT761).

*Treponema pallidum* (Syphilis): Syphilis antigens include, but are not limited to, TmpA antigen.

*Haemophilus ducreyi* (causing chancroid): *Ducreyi* antigens include, but are not limited to, outer membrane protein (DsrA).

*Enterococcus faecalis* or *Enterococcus faecium*: Antigens include, but are not limited to, a trisaccharide repeat or other *Enterococcus* derived antigens.

*Helicobacter pylori*: *H pylori* antigens include, but are not limited to, Cag, Vac, Nap, HopX, HopY and/or urease antigen.

*Staphylococcus saprophyticus*: Antigens include, but are not limited to, the 160 kDa hemagglutinin of *S. saprophyticus* antigen.

*Yersinia enterocolitica* Antigens include, but are not limited to, LPS.

*E. coli*: *E. coli* antigens may be derived from enterotoxigenic *E. coli* (ETEC), enteroaggregative *E. coli* (EAggEC), diffusely adhering *E. coli* (DAEC), enteropathogenic *E. coli* (EPEC), extraintestinal pathogenic *E. coli* (ExPEC) and/or enterohemorrhagic *E. coli* (EHEC). ExPEC antigens include, but are not limited to, accessory colonization factor (orf3526), orf353, bacterial Ig-like domain (group 1) protein (orf405). orf1364, NodT-family outer-membrane-factor-lipoprotein efflux transporter (orf1767), gspK (orf3515), gspJ (orf3516), tonB-dependent siderophore receptor (orf3597), fimbrial protein (orf3613), upec-948, upec-1232, A chain precursor of the type-1 fimbrial protein (upec-1875), yap H homolog (upec-2820), and hemolysin A (recp-3768).

*Bacillus anthracis* (anthrax): *B. anthracis* antigens include, but are not limited to, A-components (lethal factor (LF) and edema factor (EF)), both of which can share a common B-component known as protective antigen (PA). In certain embodiments, *B. anthracis* antigens are optionally detoxified.

*Yersinia pestis* (plague): Plague antigens include, but are not limited to, F1 capsular antigen, LPS, *Yersinia pestis* V antigen.

*Mycobacterium tuberculosis*: Tuberculosis antigens include, but are not limited to, lipoproteins, LPS, BCG antigens, a fusion protein of antigen 85B (Ag85B), ESAT-6 optionally formulated in cationic lipid vesicles, *Mycobacterium tuberculosis* (Mtb) isocitrate dehydrogenase associated antigens, and MPT51 antigens.

Rickettsia: Antigens include, but are not limited to, outer membrane proteins, including the outer membrane protein A and/or B (OmpB), LPS, and surface protein antigen (SPA).

*Listeria monocytogenes*: Bacterial antigens include, but are not limited to, those derived from *Listeria monocytogenes*.

*Chlamydia pneumoniae*: Antigens include, but are not limited to, those identified in WO 02/02606.

*Vibrio cholerae*: Antigens include, but are not limited to, proteinase antigens, LPS, particularly lipopolysaccharides of *Vibrio cholerae* II, O1 Inaba O-specific polysaccharides, *V. cholera* O139, antigens of IEM108 vaccine and Zonula occludens toxin (Zot).

*Salmonella typhi* (typhoid fever): Antigens include, but are not limited to, capsular polysaccharides preferably conjugates (Vi, i.e. vax-TyVi).

*Borrelia burgdorferi* (Lyme disease): Antigens include, but are not limited to, lipoproteins (such as OspA, OspB, Osp C and Osp D), other surface proteins such as OspE-related proteins (Erps), decorin-binding proteins (such as DbpA), and antigenically variable VI proteins, such as antigens associated with P39 and P13 (an integral membrane protein, VlsE Antigenic Variation Protein.

*Porphyromonas gingivalis*: Antigens include, but are not limited to, *P. gingivalis* outer membrane protein (OMP).

*Klebsiella*: Antigens include, but are not limited to, an OMP, including OMP A, or a polysaccharide optionally conjugated to tetanus toxoid.

Other bacterial antigens used in the immunogenic compositions provided herein include, but are not limited to, capsular antigens, polysaccharide antigens or protein antigens of any of the above. Other bacterial antigens used in the immunogenic compositions provided herein include, but are not limited to, an outer membrane vesicle (OMV) preparation. Additionally, Other bacterial antigens used in the immunogenic compositions provided herein include, but are not limited to, live, attenuated, and/or purified versions of any of the aforementioned bacteria. In certain embodiments, the bacterial antigens used in the immunogenic compositions provided herein are derived from gram-negative, while in other embodiments they are derived from gram-positive bacteria. In certain embodiments, the bacterial antigens used in the immunogenic compositions provided herein are derived from aerobic bacteria, while in other embodiments they are derived from anaerobic bacteria.

In certain embodiments, any of the above bacterial-derived saccharides (polysaccharides, LPS, LOS or oligosaccharides) are conjugated to another agent or antigen, such as a carrier protein (for example $CRM_{197}$). In certain embodiments, such conjugations are direct conjugations effected by reductive amination of carbonyl moieties on the saccharide to amino groups on the protein. In other embodiments, the saccharides are conjugated through a linker, such as, with succinamide or other linkages provided in *Bioconjugate Techniques*, 1996 and *CRC, Chemistry of Protein Conjugation and Cross-Linking*, 1993.

In certain embodiments useful for the treatment or prevention of *Neisseria* infection and related diseases and disorders, recombinant proteins from *N. meningitidis* for use in the immunogenic compositions provided herein may be found in WO99/24578, WO99/36544, WO99/57280, WO00/22430, WO96/29412, WO01/64920, WO03/020756, WO2004/048404, and WO2004/032958. Such antigens may be used alone or in combinations. Where multiple purified proteins are combined then it is helpful to use a mixture of 10 or fewer (e.g. 9, 8, 7, 6, 5, 4, 3, 2) purified antigens.

A particularly useful combination of antigens for use in the immunogenic compositions provided herein is disclosed in Giuliani et al. (2006) *Proc Natl Acad Sci USA* 103(29):10834-9 and WO2004/032958, and so an immunogenic composition may include 1, 2, 3, 4 or 5 of: (1) a 'NadA' protein (aka GNA1994 and NMB1994); (2) a 'fHBP' protein (aka '741', LP2086, GNA1870, and NMB1870); (3) a '936' protein (aka GNA2091 and NMB2091); (4) a '953' protein (aka GNA1030 and NMB1030); and (5) a '287' protein (aka GNA2132 and NMB2132). Other possible antigen combinations may comprise a transferrin binding protein (e.g. TbpA and/or TbpB) and an Hsf antigen. Other possible purified antigens for use in the immunogenic compositions provided herein include proteins comprising one of the following amino acid sequences: SEQ ID NO:650 from WO99/24578; SEQ ID NO:878 from WO99/24578; SEQ ID NO:884 from WO99/24578; SEQ ID NO:4 from WO99/36544; SEQ ID NO:598 from WO99/57280; SEQ ID NO:818 from WO99/57280; SEQ ID NO:864 from WO99/57280; SEQ ID NO:866 from WO99/57280; SEQ ID NO:1196 from WO99/57280; SEQ ID NO:1272 from WO99/57280; SEQ ID NO:1274 from WO99/57280; SEQ ID NO:1640 from WO99/57280; SEQ ID NO:1788 from WO99/57280; SEQ ID NO:2288 from WO99/57280; SEQ ID NO:2466 from WO99/57280; SEQ ID NO:2554 from WO99/57280; SEQ ID NO:2576 from WO99/57280; SEQ ID NO:2606 from WO99/57280; SEQ ID NO:2608 from WO99/57280; SEQ ID NO:2616 from WO99/57280; SEQ ID NO:2668 from WO99/57280; SEQ ID NO:2780 from WO99/57280; SEQ ID NO:2932 from WO99/57280; SEQ ID NO:2958 from WO99/57280; SEQ ID NO:2970 from WO99/57280; SEQ ID NO:2988 from WO99/57280 (each of the forgoing amino acid sequences is hereby incorporated by reference from the cited document), or a polypeptide comprising an amino acid sequence which: (a) has 50% or more identity (e.g., 60%, 70%, 80%, 90%, 95%, 99% or more) to said sequences; and/or (b) comprises a fragment of at least n consecutive amino acids from said sequences, wherein n is 7 or more (e.g., 8, 10, 12, 14, 16, 18, 20, 25, 30, 35, 40, 50, 60, 70, 80, 90, 100, 150, 200, 250 or more). Preferred fragments for (b) comprise an epitope from the relevant sequence. More than one (e.g., 2, 3, 4, 5, 6) of these polypeptides may be included in the immunogenic compositions.

The fHBP antigen falls into three distinct variants (WO2004/048404). An *N. meningitidis* serogroup vaccine based upon the immunogenic compositions disclosed herein utilizing one of the compounds disclosed herein may include a single fHBP variant, but is will usefully include an fHBP from each of two or all three variants. Thus the immunogenic composition may include a combination of two or three different purified fHBPs, selected from: (a) a first protein, comprising an amino acid sequence having at least a % sequence identity to SEQ ID NO: 1 and/or comprising an amino acid sequence consisting of a fragment of at least x contiguous amino acids from SEQ ID NO: (b) a second protein, comprising an amino acid sequence having at least b % sequence identity to SEQ ID NO: 2 and/or comprising an amino acid sequence consisting of a fragment of at least y contiguous amino acids from SEQ ID NO: 2; and/or (c) a third protein, comprising an amino acid sequence having at least c % sequence identity to SEQ ID NO: 3 and/or comprising an amino acid sequence consisting of a fragment of at least z contiguous amino acids from SEQ ID NO: 3

SEQ ID NO: 1
VAADIGAGLADALTAPLDHKDKGLQSLTLDQSVRKNEKLKLAAQGAEKTYGNGDSLNT

GKLKNDKVSRFDFIRQIEVDGQLITLESGEFQVYKQSHSALTAFQTEQIQDSEHSGKMVAK

RQFRIGDIAGEHTSFDKLPEGGRATYRGTAFGSDDAGGKLTYTIDFAAKQGNGKIEHLKSP

ELNVDLAAADIKPDGKRHAVISGSVLYNQAEKGSYSLGIFGGKAQEVAGSAEVKTVNGIR

HIGLAAKQ

SEQ ID NO: 2
VAADIGAGLADALTAPLDHKDKSLQSLTLDQSVRKNEKLKLAAQGAEKTYGNGDSLNTG

KLKNDKVSRFDFIRQIEVDGQLITLESGEFQIYKQDHSAVVALQIEKINNPDKIDSLINQRSF

LVSGLGGEHTAFNQLPDGKAEYHGKAFSSDDAGGKLTYTIDFAAKQGHGKIEHLKTPEQ

NVELAAAELKADEKSHAVILGDTRYGSEEKGTYHLALFGDRAQEIAGSATVKIGEKVHEI

GIAGKQ

SEQ ID NO: 3
VAADIGTGLADALTAPLDHKDKGLKSLTLEDSIPQNGTLTLSAQGAEKTFKAGDKDNSLN

TGKLKNDKISRFDFVQKIEVDGQTITLASGEFQIYKQNHSAVVALQIEKINNPDKTDSLINQ

-continued

```
RSFLVSGLGGEHTAFNQLPGGKAEYHGKAFSSDDPNGRLHYSIDFTKKQGYGRIEHLKTL

EQNVELAAAELKADEKSHAVILGDTRYGSEEKGTYHLALFGDRAQEIAGSATVKIGEKVH

EIGIAGKQ.
```

The value of a is at least 85, e.g., 86, 87, 88, 89, 90, 91, 92, 93, 94, 95, 96, 97, 98, 99, 99.5, or more. The value of b is at least 85, e.g., 86, 87, 88, 89, 90, 91, 92, 93, 94, 95, 96, 97, 98, 99, 99.5, or more. The value of c is at least 85, e.g., 86, 87, 88, 89, 90, 91, 92, 93, 94, 95, 96, 97, 98, 99, 99.5, or more. The values of a, b and c are not intrinsically related to each other.

The value of x is at least 7, e.g., 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90, 100, 120, 140, 160, 180, 200, 225, 250). The value of y is at least 7, e.g., 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90, 100, 120, 140, 160, 180, 200, 225, 250). The value of z is at least 7, e.g., 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90, 100, 120, 140, 160, 180, 200, 225, 250). The values of x, y and z are not intrinsically related to each other.

In some embodiments, the immunogenic compositions as disclosed herein will include fHBP protein(s) that are lipidated, e.g., at a N-terminal cysteine. In other embodiments they will not be lipidated A useful immunogenic composition as disclosed herein includes purified proteins comprises a mixture of: (i) a first polypeptide having amino acid sequence SEQ ID NO: 4; (ii) a second polypeptide having amino acid sequence SEQ ID NO: 5; and (iii) a third polypeptide having amino acid sequence SEQ ID NO: 6. See Giuliani et al. (2006) *Proc Natl Acad Sci USA* 103(29):10834-9 and WO2004/032958. A useful immunogenic composition as disclosed herein includes purified proteins comprises a mixture of: (i) a first polypeptide having at least a % sequence identity to amino acid sequence SEQ ID NO: 4; (ii) a second polypeptide having at least b % sequence identity to amino acid sequence SEQ ID NO: 5; and (iii) a third polypeptide having at least a % sequence identity to amino acid sequence SEQ ID NO: 6.

```
                                                   SEQ ID NO: 4
MASPDVKSADTLSKPAAPVVSEKETEAKEDAPQAGSQGQGAPSAQGGQDMAAVSEENT

GNGGAAATDKPKNEDEGAQNDMPQNAADTDSLTPNHTPASNMPAGNMENQAPDAGES

EQPANQPDMANTADGMQGDDPSAGGENAGNTAAQGTNQAENNQTAGSQNPASSTNPSA

TNSGGDFGRTNVGNSVVIDGPSQNITLTHCKGDSCSGNNFLDEEVQLKSEFEKLSDADKIS

NYKKDGKNDGKNDKFVGLVADSVQMKGINQYIIFYKPKPTSFARFRRSARSRRSLPAEMP

LIPVNQADTLIVDGEAVSLTGHSGNIFAPEGNYRYLTYGAEKLPGGSYALRVQGEPSKGE

MLAGTAVYNGEVLHFHTENGRPSPSRGRFAAKVDFGSKSVDGIIDSGDGLHMGTQKFKA

AIDGNGFKGTWTENGGGDVSGKFYGPAGEEVAGKYSYRPTDAEKGGFGVFAGKKEQDG

SGGGGATYKVDEYHANARFAIDHFNTSTNVGGFYGLTGSVEFDQAKRDGKIDITIPVANL

QSGSQHFTDHLKSADIFDAAQYPDIRFVSTKFNFNGKKLVSVDGNLTMHGKTAPVKLKAE

KFNCYQSPMAKTEVCGGDFSTTIDRTKWGVDYLVNVGMTKSVRIDIQIEAAKQ

SEQ ID NO: 5
MVSAVIGSAAVGAKSAVDRRTTGAQTDDNVMALRIETTARSYLRQNNQTKGYTPQISVV

GYNRHLLLLGQVATEGEKQFVGQIARSEQAAEGVYNYITVASLPRTAGDIAGDTWNTSK

VRATLLGISPATQARVKIVTYGNVTYVMGILTPEEQAQITQKVSTTVGVQKVITLYQNYV

QRGSGGGVAADIGAGLADALTAPLDHKDKGLQSLTLDQSVRKNEKLKLAAQGAEKTY

GNGDSLNTGKLKNDKVSRFDFIRQIEVDGQLITLESGEFQVYKQSHSALTAFQTEQIQDSE

HSGKMVAKRQFRIGDIAGEHTSFDKLPEGGRATYRGTAFGSDDAGGKLTYTIDFAAKQG

NGKIEHLKSPELNVDLAAADIKPDGKRHAVISGSVLYNQAEKGSYSLGIFGGKAQEVAGS

AEVKTVNGIRHIGLAAKQ

SEQ ID NO: 6
ATNDDDVKKAATVAIAAAYNNGQEINGFKAGETIYDIDEDGTITKKDATAADVEADDFK

GLGLKKVVTNLTKTVNENKQNVDAKVKAAESEIEKLTTKLADTDAALADTDAALDATT

NALNKLGENITTFAEETKTNIVKIDEKLEAVADTVDKHAEAFNDIADSLDETNTKADEAV

KTANEAKQTAEETKQNVDAKVKAAETAAGKAEAAAGTANTAADKAEAVAAKVTDIKA
```

-continued
DIATNKDNIAKKANSADVYTREESDSKFVRIDGLNATTEKLDTRLASAEKSIADHDTRLN

GLDKTVSDLRKETRQGLAEQAALSGLFQPYNVG.

Bacterial Vesicle Antigens

The immunogenic compositions as disclosed herein may include outer membrane vesicles. Such outer membrane vesicles may be obtained from a wide array of pathogenic bacteria and used as antigenic components of the immunogenic compositions as disclosed herein. Vesicles for use as antigenic components of such immunogenic compositions include any proteoliposomic vesicle obtained by disrupting a bacterial outer membrane to form vesicles therefrom that include protein components of the outer membrane. Thus the tem includes OMVs (sometimes referred to as 'blebs'), microvesicles (MVs, see, e.g., WO02/09643) and 'native OMVs' ('NOMVs' see, e.g., Katial et al. (2002) *Infect. Immun.* 70:702-707) Immnogenic compositions as disclosed herein that include vesicles from one or more pathogenic bacteria can be used in the treatment or prevention of infection by such pathogenic bacteria and related diseases and disorders.

MVs and NOMVs are naturally-occurring membrane vesicles that form spontaneously during bacterial growth and are released into culture medium. MVs can be obtained by culturing bacteria such as *Neisseria* in broth culture medium, separating whole cells from the smaller MVs in the broth culture medium (e.g., by filtration or by low-speed centrifugation to pellet only the cells and not the smaller vesicles), and then collecting the MVs from the cell-depleted medium (e.g., by filtration, by differential precipitation or aggregation of MVs, by high-speed centrifugation to pellet the MVs). Strains for use in production of MVs can generally be selected on the basis of the amount of MVs produced in culture (see, e.g., U.S. Pat. No. 6,180,111 and WO01/34642 describing *Neisseria* with high MV production).

OMVs are prepared artificially from bacteria, and may be prepared using detergent treatment (e.g., with deoxycholate), or by non detergent means (see, e.g., WO04/019977). Methods for obtaining suitable OMV preparations are well known in the art. Techniques for forming OMVs include treating bacteria with a bile acid salt detergent (e.g., salts of lithocholic acid, chenodeoxycholic acid, ursodeoxycholic acid, deoxycholic acid, cholic acid, ursocholic acid, etc., with sodium deoxycholate (EP0011243 and Fredriksen et al. (1991) *NIPH Ann.* 14(2):67-80) being preferred for treating *Neisseria*) at a pH sufficiently high not to precipitate the detergent (see, e.g., WO01/91788). Other techniques may be performed substantially in the absence of detergent (see, e.g., WO04/019977) using techniques such as sonication, homogenisation, microfluidisation, cavitation, osmotic shock, grinding, French press, blending, etc. Methods using no or low detergent can retain useful antigens such as NspA in Neisserial OMVs. Thus a method may use an OMV extraction buffer with about 0.5% deoxycholate or lower, e.g., about 0.2%, about 0.1%, <0.05% or zero.

A useful process for OMV preparation is described in WO05/004908 and involves ultrafiltration on crude OMVs, rather than instead of high speed centrifugation. The process may involve a step of ultracentrifugation after the ultrafiltration takes place.

Vesicles can be prepared from any pathogenic strain such as *Neisseria minigtidis* for use with the invention. Vessicles from *Neisserial meningitidis* serogroup B may be of any serotype (e.g., 1, 2a, 2b, 4, 14, 15, 16, etc.), any serosubtype, and any immunotype (e.g., L1; L2; L3; L3,3,7; L10; etc.). The meningococci may be from any suitable lineage, including hyperinvasive and hypervirulent lineages, e.g., any of the following seven hypervirulent lineages: subgroup I; subgroup III; subgroup IV 1; ET 5 complex; ET 37 complex; A4 cluster; lineage 3. These lineages have been defined by multilocus enzyme electrophoresis (MLEE), but multilocus sequence typing (MLST) has also been used to classify meningococci, e.g., the ET 37 complex is the ST 11 complex by MLST, the ET 5 complex is ST-32 (ET-5), lineage 3 is ST 41/44, etc. Vesicles can be prepared from strains having one of the following subtypes: P1.2; P1.2,5; P1.4; P1.5; P1.5,2; P1.5,c; P1.5c,10; P1.7,16; P1.7,16b; P1.7h,4; P1.9; P1.15; P1.9,15; P1.12,13; P1.13; P1.14; P1.21,16; P1.22,14.

Vesicles included in the immunogenic compositions disclosed herein may be prepared from wild type pathogenic strains such as *N. meningitidis* strains or from mutant strains. By way of example, WO98/56901 discloses preparations of vesicles obtained from *N. meningitidis* with a modified fur gene. WO02/09746 teaches that nspA expression should be up regulated with concomitant porA and cps knockout. Further knockout mutants of *N. meningitidis* for OMV production are disclosed in WO02/0974, WO02/062378, and WO04/014417. WO06/081259 discloses vesicles in which fHBP is upregulated. Claassen et al. (1996) 14(10):1001-8, disclose the construction of vesicles from strains modified to express six different PorA subtypes. Mutant *Neisseria* with low endotoxin levels, achieved by knockout of enzymes involved in LPS biosynthesis, may also be used (see, e.g., WO99/10497 and Steeghs et al. (2001) i20:6937-6945). These or others mutants can all be used with the invention.

Thus *N. meningitidis* serogroup B strains included in the immunogenic compositions disclosed herein may in some embodiments express more than one PorA subtype. Six valent and nine valent PorA strains have previously been constructed. The strain may express 2, 3, 4, 5, 6, 7, 8 or 9 of PorA subtypes: P1.7,16; P1.5-1,2-2; P1.19,15-1; P1.5-2,10; P1.12 1,13; P1.7-2.4; P1.22,14; P1.7-1,1 and/or P1.18-1,3,6. In other embodiments a strain may have been down regulated for PorA expression, e.g., in which the amount of PorA has been reduced by at least 20% (e.g., >30%. >40%, >50%, >60%, >70%, >80%, >90%, >95%, etc.), or even knocked out, relative to wild type levels (e.g., relative to strain H44/76, as disclosed in WO03/105890).

In some embodiments *N. meningitidis* serogroup B strains may over express (relative to the corresponding wild-type strain) certain proteins. For instance, strains may over express NspA, protein 287 (WO01/52885—also referred to as NMB2132 and GNA2132), one or more fHBP (WO06/081259 and U.S. Pat. Pub. 2008/0248065—also referred to as protein 741, NMB1870 and GNA1870), TbpA and/or TbpB (WO00/25811), Cu,Zn-superoxide dismutase (WO00/25811), etc.

In some embodiments *N. meningitidis* serogroup B strains may include one or more of the knockout and/or over expression mutations. Preferred genes for down regulation and/or knockout include: (a) Cps, CtrA, CtrB, CtrC, CtrD, FrpB, GalE, HtrB/MsbB, LbpA, LbpB, LpxK, Opa, Opc, PilC, PorB, SiaA, SiaB, SiaC, SiaD, TbpA, and/or TbpB (WO01/09350); (b) CtrA, CtrB, CtrC, CtrD, FrpB, GalE, HtrB/MsbB, LbpA, LbpB, LpxK, Opa, Opc, PhoP, PilC, PmrE, PmrF, SiaA, SiaB, SiaC, SiaD, TbpA, and/or TbpB (WO02/09746); (c) ExbB, ExbD, rmpM, CtrA, CtrB, CtrD, GalE, LbpA, LpbB, Opa, Opc, Pi1C, PorB, SiaA, SiaB, SiaC, SiaD, TbpA, and/or TbpB (WO02/062378); and (d) CtrA, CtrB, CtrD, FrpB, OpA, OpC, Pi1C, PorB, SiaD, SynA, SynB, and/or SynC (WO04/014417).

Where a mutant strain is used, in some embodiments it may have one or more, or all, of the following characteristics: (i) down regulated or knocked-out LgtB and/or GalE to truncate the meningococcal LOS; (ii) up regulated TbpA; (iii) up regulated Hsf; (iv) up regulated Omp85; (v) up regulated LbpA; (vi) up regulated NspA; (vii) knocked-out PorA; (viii) down regulated or knocked-out FrpB; (ix) down regulated or knocked-out Opa; (x) down regulated or knocked-out Opc; (xii) deleted cps gene complex. A truncated LOS can be one that does not include a sialyl-lacto-N-neotetraose epitope, e.g., it might be a galactose-deficient LOS. The LOS may have no a chain.

If LOS is present in a vesicle then it is possible to treat the vesicle so as to link its LOS and protein components ("intra-bleb" conjugation (WO04/014417)).

The immunogenic compositions as disclosed herein may include mixtures of vesicles from different strains. By way of example, WO03/105890 discloses vaccine comprising multivalent meningococcal vesicle compositions, comprising a first vesicle derived from a meningococcal strain with a serosubtype prevalent in a country of use, and a second vesicle derived from a strain that need not have a serosubtype prevent in a country of use. WO06/024946 discloses useful combinations of different vesicles. A combination of vesicles from strains in each of the L2 and L3 immunotypes may be used in some embodiments.

Vesicle-based antigens can be prepared from *N. meningitidis* serogroups other than serogroup B (e.g., WO01/91788 discloses a process for serogroup A). The immunogenic compositions disclosed herein accordingly can include vesicles prepared serogroups other than B (e.g. A, C, W135 and/or Y) and from bacterial pathogens other than *Neisseria*.

Viral Antigens

Viral antigens suitable for use in the immunogenic compositions provided herein include, but are not limited to, inactivated (or killed) virus, attenuated virus, split virus formulations, purified subunit formulations, viral proteins which may be isolated, purified or derived from a virus, and Virus Like Particles (VLPs). In certain embodiments, viral antigens are derived from viruses propagated on cell culture or other substrate. In other embodiments, viral antigens are expressed recombinantly. In certain embodiments, viral antigens preferably include epitopes which are exposed on the surface of the virus during at least one stage of its life cycle. Viral antigens are preferably conserved across multiple serotypes or isolates. Viral antigens suitable for use in the immunogenic compositions provided herein include, but are not limited to, antigens derived from one or more of the viruses set forth below as well as the specific antigens examples identified below.

Orthomyxovirus: Viral antigens include, but are not limited to, those derived from an Orthomyxovirus, such as Influenza A, B and C. In certain embodiments, orthomyxovirus antigens are selected from one or more of the viral proteins, including hemagglutinin (HA), neuraminidase (NA), nucleoprotein (NP), matrix protein (M1), membrane protein (M2), one or more of the transcriptase components (PB1, PB2 and PA). In certain embodiments the viral antigen include HA and NA. In certain embodiments, the influenza antigens are derived from interpandemic (annual) flu strains, while in other embodiments, the influenza antigens are derived from strains with the potential to cause pandemic a pandemic outbreak (i.e., influenza strains with new haemagglutinin compared to the haemagglutinin in currently circulating strains, or influenza strains which are pathogenic in avian subjects and have the potential to be transmitted horizontally in the human population, or influenza strains which are pathogenic to humans).

Paramyxoviridae viruses: Viral antigens include, but are not limited to, those derived from Paramyxoviridae viruses, such as Pneumoviruses (RSV), Paramyxoviruses (PIV), Metapneumovirus and Morbilliviruses (Measles).

Pneumovirus: Viral antigens include, but are not limited to, those derived from a Pneumovirus, such as Respiratory syncytial virus (RSV), Bovine respiratory syncytial virus, Pneumonia virus of mice, and Turkey rhinotracheitis virus. Preferably, the Pneumovirus is RSV. In certain embodiments, pneumovirus antigens are selected from one or more of the following proteins, including surface proteins Fusion (F), Glycoprotein (G) and Small Hydrophobic protein (SH), matrix proteins M and M2, nucleocapsid proteins N, P and L and nonstructural proteins NS 1 and NS2. In other embodiments, pneumovirus antigens include F, G and M. In certain embodiments, pneumovirus antigens are also formulated in or derived from chimeric viruses, such as, by way of example only, chimeric RSV/PIV viruses comprising components of both RSV and NV Paramyxovirus: Viral antigens include, but are not limited to, those derived from a Paramyxovirus, such as Parainfluenza virus types 1-4 (PIV), Mumps, Sendai viruses, Simian virus 5, Bovine parainfluenza virus, Nipahvirus, Henipavirus and Newcastle disease virus. In certain embodiments, the Paramyxovirus is PIV or Mumps. In certain embodiments, paramyxovirus antigens are selected from one or more of the following proteins: Hemagglutinin-Neuraminidase (HN), Fusion proteins F1 and F2, Nucleoprotein (NP), Phosphoprotein (P), Large protein (L), and Matrix protein (M). In other embodiments, paramyxovirus proteins include HN, F1 and F2. In certain embodiments, paramyxovirus antigens are also formulated in or derived from chimeric viruses, such as, by way of example only, chimeric RSV/PIV viruses comprising components of both RSV and PIV. Commercially available mumps vaccines include live attenuated mumps virus, in either a monovalent form or in combination with measles and rubella vaccines (MMR). In other embodiments, the Paramyxovirus is Nipahvirus or Henipavirus and the anitgens are selected from one or more of the following proteins: Fusion (F) protein, Glycoprotein (G) protein, Matrix (M) protein, Nucleocapsid (N) protein, Large (L) protein and Phosphoprotein (P).

Poxviridae: Viral antigens include, but are not limited to, those derived from Orthopoxvirus such as Variola vera, including but not limited to, Variola major and Variola minor.

Metapneumovirus: Viral antigens include, but are not limited to, Metapneumovirus, such as human metapneumovirus (hMPV) and avian metapneumoviruses (aMPV). In certain embodiments, metapneumovirus antigens are selected from one or more of the following proteins, including surface proteins Fusion (F), Glycoprotein (G) and Small Hydrophobic protein (SH), matrix proteins M and M2, nucleocapsid proteins N, P and L. In other embodiments, metapneumovirus antigens include F, G and M. In certain embodiments, metapneumovirus antigens are also formulated in or derived from chimeric viruses.

Morbillivirus: Viral antigens include, but are not limited to, those derived from a Morbillivirus, such as Measles. In certain embodiments, morbillivirus antigens are selected from one or more of the following proteins: hemagglutinin (H), Glycoprotein (G), Fusion factor (F), Large protein (L), Nucleoprotein (NP), Polymerase phosphoprotein (P), and Matrix (M). Commercially available measles vaccines include live attenuated measles virus, typically in combination with mumps and rubella (MMR).

Picornavirus: Viral antigens include, but are not limited to, those derived from Picornaviruses, such as Enteroviruses, Rhinoviruses, Heparnavirus, Cardioviruses and Aphthoviruses. In certain embodiments, the antigens are derived from Enteroviruses, while in other embodiments the enterovirus is Poliovirus. In still other embodiments, the antigens are derived from Rhinoviruses. In certain embodiments, the antigens are formulated into virus-like particles (VLPs).

Enterovirus: Viral antigens include, but are not limited to, those derived from an Enterovirus, such as Poliovirus types 1, 2 or 3, Coxsackie A virus types 1 to 22 and 24, Coxsackie B virus types 1 to 6, Echovirus (ECHO) virus) types 1 to 9, 11 to 27 and 29 to 34 and Enterovirus 68 to 71. In certain embodiments, the antigens are derived from Enteroviruses, while in other embodiments the enterovirus is Poliovirus. In certain embodiments, the enterovirus antigens are selected from one or more of the following Capsid proteins VP0, VP1, VP2, VP3 and VP4. Commercially available polio vaccines include Inactivated Polio Vaccine (IPV) and Oral poliovirus vaccine (OPV). In certain embodiments, the antigens are formulated into virus-like particles.

Bunyavirus: Viral antigens include, but are not limted to, those derived from an Orthobunyavirus, such as California encephalitis virus, a Phlebovirus, such as Rift Valley Fever virus, or a Nairovirus, such as Crimean-Congo hemorrhagic fever virus.

Rhinovirus: Viral antigens include, but are not limted to, those derived from rhinoviruses. In certain embodiments, the rhinovirus antigens are selected from one or more of the following Capsid proteins: VP0, VP1, VP2. VP2 and VP4. In certain embodiments, the antigens are formulated into virus-like particles (VLPs).

Heparnavirus: Viral antigens include, but are not limited to, those derived from a Heparnavirus, such as, by way of example only, Hepatitis A virus (HAV). Commercially available HAV vaccines include inactivated HAV vaccine.

Togavirus: Viral antigens include, but are not limited to. those derived from a Togavirus, such as a Rubivirus, an Alphavirus, or an Arterivirus. In certain embodiments, the antigens are derived from Rubivirus, such as by way of example only, Rubella virus. In certain embodiments, the togavirus antigens are selected from E1, E2, E3, C, NSP-1, NSPO-2, NSP-3 or NSP-4. In certain embodiments, the togavirus antigens are selected from E1, E2 or E3. Commercially available Rubella vaccines include a live cold-adapted virus, typically in combination with mumps and measles vaccines (MMR).

Flavivirus: Viral antigens include, but are not limited to, those derived from a Flavivirus, such as Tick-borne encephalitis (TBE) virus, Dengue (types 1, 2, 3 or 4) virus, Yellow Fever virus, Japanese encephalitis virus, Kyasanur Forest Virus, West Nile encephalitis virus, St. Louis encephalitis virus, Russian spring-summer encephalitis virus, Powassan encephalitis virus. In certain embodiments, the flavivirus antigens are selected from PrM, M, C, E, NS-1, NS-2a, NS2b, NS3, NS4a, NS4b, and NS5. In certain embodiments, the flavivirus antigens are selected from PrM, M and E. Commercially available TBE vaccine includes inactivated virus vaccines. In certain embodiments, the antigens are formulated into virus-like particles (VLPs).

Pestivirus: Viral antigens include, but are not limited to, those derived from a Pestivirus, such as Bovine viral diarrhea (BVDV), Classical swine fever (CSFV) or Border disease (BDV).

Hepadnavirus: Viral antigens include, but are not limited to, those derived from a Hepadnavirus, such as Hepatitis B virus. In certain embodiments, the hepadnavirus antigens are selected from surface antigens (L, M and S), core antigens (HBc, HBe). Commercially available HBV vaccines include subunit vaccines comprising the surface antigen S protein.

Hepatitis C virus: Viral antigens include, but are not limited to, those derived from a Hepatitis C virus (HCV). In certain embodiments, the HCV antigens are selected from one or more of E1, E2, E1/E2, NS345 polyprotein, NS 345-core polyprotein, core, and/or peptides from the nonstructural regions. In certain embodiments, the Hepatitis C virus antigens include one or more of the following: HCV E1 and or E2 proteins, E1/E2 heterodimer complexes, core proteins and non-structural proteins, or fragments of these antigens, wherein the non-structural proteins can optionally be modified to remove enzymatic activity but retain immunogenicity. In certain embodiments, the antigens are formulated into virus-like particles (VLPs).

Rhabdovirus: Viral antigens include, but are not limited to, those derived from a Rhabdovirus, such as a Lyssavirus (Rabies virus) and Vesiculovirus (VSV). Rhabdovirus antigens may be selected from glycoprotein (G), nucleoprotein (N), large protein (L), nonstructural proteins (NS). Commercially available Rabies virus vaccine comprise killed virus grown on human diploid cells or fetal rhesus lung cells.

Caliciviridae; Viral antigens include, but are not limited to, those derived from Calciviridae, such as Norwalk virus, and Norwalk-like Viruses, such as Hawaii Virus and Snow Mountain Virus. In certain embodiments, the antigens are formulated into virus-like particles (VLPs).

Coronavirus: Viral antigens include, but are not limited to, those derived from a Coronavirus, SARS, Human respiratory coronavirus, Avian infectious bronchitis (IBV), Mouse hepatitis virus (MHV), and Porcine transmissible gastroenteritis virus (TGEV). In certain embodiments, the coronavirus antigens are selected from spike (S), envelope (E), matrix (M), nucleocapsid (N), and Hemagglutinin-esterase glycoprotein (HE). In certain embodiments, the coronavirus antigen is derived from a SARS virus. In certain embodiments, the coronavirus is derived from a SARS viral antigen as described in WO 04/92360.

Retrovirus: Viral antigens include, but are not limited to, those derived from a Retrovirus, such as an Oncovirus, a Lentivirus or a Spumavirus. In certain embodiments, the oncovirus antigens are derived from HTLV-1, HTLV-2 or HTLV-5. In certain embodiments, the lentivirus antigens are derived from HIV-1 or HIV-2. In certain embodiments, the antigens are derived from HIV-1 subtypes (or clades), including, but not limited to, HIV-1 subtypes (or clades) A, B, C, D, F, G, H, J. K, O. In other embodiments, the antigens are derived from HIV-1 circulating recombinant forms (CRFs), including, but not limited to, A/B, A/E, A/G, A/G/I, etc. In certain embodiments, the retrovirus antigens are selected from gag, pol, env, tax, tat, rex, rev, nef, vif, vpu, and vpr. In certain embodiments, the HIV antigens are selected from gag (p24gag and p55gag), env (gp160 and gp41), pol, tat, nef, rev vpu, miniproteins, (preferably p55 gag and gp140v delete). In certain embodiments, the HIV antigens are derived from one or more of the following strains: $HIV_{IIIb}$, $HIV_{SF2}$, $HIV_{LAV}$, $HIV_{LAI}$, $HIV_{MN}$, $HIV-1_{CM235}$, $HIV-1_{US4}$, $HIV-1_{SF162}$, $HIV-1_{TV1}$, $HIV-1_{MJ4}$. In certain embodiments, the antigens are derived from endogenous human retroviruses, including, but not limited to, HERV-K ("old" HERV-K and "new" HERV-K).

Reovirus: Viral antigens include, but are not limited to, those derived from a Reovirus, such as an Orthoreovirus, a Rotavirus, an Orbivirus, or a Coltivirus. In certain embodiments, the reovirus antigens are selected from structural proteins λ1, λ2, λ3, μ1, μ2, σ1, σ2, or σ3, or nonstructural proteins σNS, μNS, or σ1s. In certain embodiments, the reovirus antigens are derived from a Rotavirus. In certain embodiments, the rotavirus antigens are selected from VP1, VP2, VP3, VP4 (or the cleaved product VP5 and VP8), NSP 1, VP6, NSP3, NSP2, VP7, NSP4, or NSP5. In certain embodiments, the rotavirus antigens include VP4 (or the cleaved product VP5 and VP8), and VP7.

Parvovirus: Viral antigens include, but are not limited to, those derived from a Parvovirus, such as Parvovirus B19. In certain embodiments, the Parvovirus antigens are selected from VP-1, VP-2, VP-3, NS-1 and NS-2. In certain embodiments, the Parvovirus antigen is capsid protein VP1 or VP-2. In certain embodiments, the antigens are formulated into virus-like particles (VLPs).

Delta hepatitis virus (HDV): Viral antigens include, but are not limited to, those derived from HDV, particularly δ-antigen from HDV.

Hepatitis E virus (HEV): Viral antigens include, but are not limited to, those derived from HEV.

Hepatitis G virus (HGV): Viral antigens include, but are not limited to, those derived from HGV.

Human Herpesvirus: Viral antigens include, but are not limited to, those derived from a Human Herpesvirus, such as, by way of example only, Herpes Simplex Viruses (HSV), Varicella-zoster virus (VZV), Epstein-Ban virus (EBV), Cytomegalovirus (CMV), Human Herpesvirus 6 (HHV6), Human Herpesvirus 7 (HHV7), and Human Herpesvirus 8 (HHV8). In certain embodiments, the Human Herpesvirus antigens are selected from immediate early proteins (α), early proteins (β), and late proteins (γ). In certain embodiments, the HSV antigens are derived from HSV-1 or HSV-2 strains. In certain embodiments, the HSV antigens are selected from glycoproteins gB, gC, gD and gH, fusion protein (gB), or immune escape proteins (gC, gE, or gI). In certain embodiments, the VZV antigens are selected from core, nucleocapsid, tegument, or envelope proteins. A live attenuated VZV vaccine is commercially available. In certain embodiments, the EBV antigens are selected from early antigen (EA) proteins, viral capsid antigen (VCA), and glycoproteins of the membrane antigen (MA). In certain embodiments, the CMV antigens are selected from capsid proteins, envelope glycoproteins (such as gB and gH), and tegument proteins. In other embodiments, CMV antigens may be selected from one or more of the following proteins: pp65, IE1, gB, gD, gH, gL, gM, gN, gO, UL128, UL129, gUL130, UL150, UL131, UL33, UL78, US27, US28, RL5A, RL6, RL10, RL11, RL12, RL13, UL1, UL2, UL4, UL5, UL6, UL7, UL8, UL9, UL10, UL11, UL14, UL15A, UL16, UL17, UL18, UL22A, UL38, UL40, UL41A, UL42, UL116, UL119, UL120, UL121, UL124, UL132, UL147A, UL148, UL142, UL144, UL141, UL140, UL135, UL136, UL138, UL139, UL133, UL135, UL148A, UL148B, UL148C, UL148D, US2, US3, US6, US7, US8, US9, US10, US11, US12, US13, US14, US15, US16, US17, US18, US19, US20, US21, US29, US30 and US34A. CMV antigens may also be fusions of one or more CMV proteins, such as, by way of example only, pp65/IE1 (Reap et al., Vaccine (2007) 25:7441-7449). In certain embodiments, the antigens are formulated into virus-like particles (VLPs).

Papovaviruses: Antigens include, but are not limited to, those derived from Papovaviruses, such as Papillomaviruses and Polyomaviruses. In certain embodiments, the Papillomaviruses include HPV serotypes 1, 2, 4, 5, 6, 8, 11, 13, 16, 18, 31, 33, 35, 39, 41, 42, 47, 51, 57, 58, 63 and 65. In certain embodiments, the HPV antigens are derived from serotypes 6, 11, 16 or 18. In certain embodiments, the HPV antigens are selected from capsid proteins (L1) and (L2), or E1-E7, or fusions thereof. In certain embodiments, the HPV antigens are formulated into virus-like particles (VLPs). In certain embodiments, the Polyomyavirus viruses include BK virus and JK virus. In certain embodiments, the Polyomavirus antigens are selected from VP1, VP2 or VP3.

Adenovirus: Antigens include those derived from Adenovirus. In certain embodiments, the Adenovirus antigens are derived from Adenovirus serotype 36 (Ad-36). In certain embodiments, the antigen is derived from a protein or peptide sequence encoding an Ad-36 coat protein or fragment thereof (WO 2007/120362).

Further provided are antigens, compositions, methods, and microbes included in *Vaccines, 4th* Edition (Plotkin and Orenstein ed. 2004); *Medical Microbiology 4th* Edition (Murray et al. ed. 2002); *Virology,* 3rd Edition (W. K. Joklik ed. 1988); *Fundamental Virology,* 2nd Edition (B. N. Fields and D. M. Knipe, eds. 1991), which are contemplated in conjunction with the immunogenic compositions provided herein.

Fungal Antigens

Fungal antigens for use in the immunogenic compositions provided herein include, but are not limited to, those derived from one or more of the fungi set forth below.

Fungal antigens are derived from Dermatophytres, including: *Epidermophyton floccusum, Microsporum audouini, Microsporum canis, Microsporum distortum, Microsporum equinum, Microsporum gypsum, Microsporum nanum, Trichophyton concentricum, Trichophyton equinum, Trichophyton gallinae, Trichophyton gypseum, Trichophyton megnini, Trichophyton mentagrophytes, Trichophyton quinckeanum, Trichophyton rubrum, Trichophyton schoenleini, Trichophyton tonsurans, Trichophyton verrucosum, T verrucosum* var. *album,* var. *discoides,* var. *ochraceum, Trichophyton violaceum,* and/or *Trichophyton faviforme*; and Fungal pathogens are derived from *Aspergillus fumigatus, Aspergillus flavus, Aspergillus niger, Aspergillus nidulans, Aspergillus terreus, Aspergillus sydowi, Aspergillus flavatus, Aspergillus glaucus, Blastoschizotnyces capitatus, Candida albicans, Candida enolase, Candida* tropicalis, Candida glabrata, Candida krusei, Candida parapsilosis, Candida stellatoidea, Candida kusei, Candida parakwsei, Candida lusitaniae, Candida pseudotropicalis, Candida guilliermondi, Cladosporium carrionii, Coccidioides immitis, Blastomyces dermatidis, Cryptococcus neoformans, Geotrichum clavatum, Histoplasma capsulatum, Klebsiella pneumoniae, Microsporidia, Encephalitozoon spp., Septata intestinalis and Enterocytozoon bieneusi; the less common are Brachiola spp, Microsporidium spp., Nosema spp., Pleistophora spp., Trachipleistophora spp., Vittaforma spp Paracoccidioides brasiliensis, Pneumocystis carinii, Pythiumn insidiosum, Pityrosporum ovale, Sacharomyces cerevisae, Saccharomyces boulardii, Saccharomyces pombe, Scedosporium apiosperum, Sporothrix schenckii, Trichosporon beigelii, Toxoplasma gondii, Penicillium marneffei, Malassezia spp., Fonsecaea spp., Wangiella spp., Sporothrix spp., Basidiobolus spp., Conidiobolus spp., Rhizopus spp, Mucor spp, Absidia spp, Mortierella spp, Cunninghamella spp, Saksenaea spp., Alternaria spp, Curvularia spp, Helminthosporium spp, Fusarium spp, Aspergillus spp, Penicillium spp, Monolinia spp, Rhizoctonia spp, Paecilomyces spp, Pithomyces spp, and Cladosporium spp.

In certain embodiments, the process for producing a fungal antigen includes a method wherein a solubilized fraction extracted and separated from an insoluble fraction obtainable from fungal cells of which cell wall has been substantially removed or at least partially removed, characterized in that the process comprises the steps of: obtaining living fungal cells; obtaining fungal cells of which cell wall has been substantially removed or at least partially removed; bursting the fungal cells of which cell wall has been substantially removed or at least partially removed; obtaining an insoluble fraction; and extracting and separating a solubilized fraction from the insoluble fraction.

Protazoan Antigens/Pathogens

Protazoan antigens/pathogens for use in the immunogenic compositions provided herein include, but are not limited to, those derived from one or more of the following protozoa: Entamoeba histolytica, Giardia lambli, Cryptosporidium parvum, Cyclospora cayatanensis and Toxoplasma.

Plant Antigens/Pathogens

Plan antigens/pathogens for use in the immunogenic compositions provided herein include, but are not limited to, those derived from Ricinus communis.

STD Antigens

In certain embodiments, the immunogenic compositions provided herein include one or more antigens derived from a sexually transmitted disease (STD). In certain embodiments, such antigens provide for prophylactis for STD's such as chlamydia, genital herpes, hepatitis (such as HCV), genital warts, gonorrhea, syphilis and/or chancroid. In other embodiments, such antigens provide for therapy for STD's such as chlamydia, genital herpes, hepatitis (such as HCV), genital warts, gonorrhea, syphilis and/or chancroid. Such antigens are derived from one or more viral or bacterial STD's. In certain embodiments, the viral STD antigens are derived from HIV, herpes simplex virus (HSV-1 and HSV-2), human papillomavirus (HPV), and hepatitis (HCV). In certain embodiments, the bacterial STD antigens are derived from Neiserria gonorrhoeae, Chlamydia trachomatis, Treponema pallidum, Haemophilus ducreyi, E. coli, and Streptococcus agalactiae. Examples of specific antigens derived from these pathogens are described above.

Respiratory Antigens

In certain embodiments, the immunogenic compositions provided herein include one or more antigens derived from a pathogen which causes respiratory disease. By way of example only, such respiratory antigens are derived from a respiratory virus such as Orthomyxoviruses (influenza), Pneumovirus (RSV), Paramyxovirus (PIV), Morbillivirus (measles), Togavirus (Rubella), VZV, and Coronavirus (SARS). In certain embodiments, the respiratory antigens are derived from a bacteria which causes respiratory disease, such as, by way of example only, Streptococcus pneumoniae, Pseudomonas aeruginosa, Bordetella pertussis, Mycobacterium tuberculosis, Mycoplasma pneumoniae, Chlamydia pneumoniae, Bacillus anthracis, and Moraxella catarrhalis. Examples of specific antigens derived from these pathogens are described above.

Pediatric Vaccine Antigens

In certain embodiments, the immunogenic compositions provided herein include one or more antigens suitable for use in pediatric subjects. Pediatric subjects are typically less than about 3 years old, or less than about 2 years old, or less than about 1 years old. Pediatric antigens are administered multiple times over the course of 6 months, 1, 2 or 3 years. Pediatric antigens are derived from a virus which may target pediatric populations and/or a virus from which pediatric populations are susceptible to infection. Pediatric viral antigens include, but are not limited to, antigens derived from one or more of Orthomyxovirus (influenza), Pneumovirus (RSV), Paramyxovirus (PIV and Mumps), Morbillivirus (measles), Togavirus (Rubella), Enterovirus (polio), HBV, Coronavirus (SARS), and Varicella-zoster virus (VZV), Epstein Barr virus (EBV). Pediatric bacterial antigens include antigens derived from one or more of Streptococcus pneumoniae, Neisseria meningitides, Streptococcus pyogenes (Group A Streptococcus), Moraxella catarrhalis, Bordetella pertussis, Staphylococcus aureus, Clostridium tetani (Tetanus), Cornynebacterium diphtheriae (Diphtheria), Haemophilus influenzae B (Hib), Pseudomonas aeruginosa, Streptococcus agalactiae (Group B Streptococcus), and E. coli. Examples of specific antigens derived from these pathogens are described above.

Antigens Suitable for Use in Elderly or Immunocompromised Individuals

In certain embodiments, the immunogenic compositions provided herein include one or more antigens suitable for use in elderly or immunocompromised individuals. Such individuals may need to be vaccinated more frequently, with higher doses or with adjuvanted formulations to improve their immune response to the targeted antigens. Antigens which are targeted for use in Elderly or Immunocompromised individuals include antigens derived from one or more of the following pathogens: Neisseria meningitides, Streptococcus pneumoniae, Streptococcus pyogenes (Group A Streptococcus), Moraxella catarrhalis, Bordetella pertussis, Staphylococcus aureus, Staphylococcus epidermis, Clostridium tetani (Tetanus), Cornynebacterium diphtheriae (Diphtheria), Haemophilus influenzae B (Hib), Pseudomonas aeruginosa, Legionella pneumophila, Streptococcus agalactiae (Group B Streptococcus), Enterococcus faecalis, Helicobacter pylori, Chlamydia pneumoniae, Orthomyxovirus (influenza), Pneumovirus (RSV), Paramyxovirus (PIV and Mumps), Morbillivirus (measles), Togavirus (Rubella), Enterovirus (polio), HBV, Coronavirus (SARS), Varicella-zoster virus (VZV), Epstein Barr virus (EBV), Cytomegalovirus (CMV). Examples of specific antigens derived from these pathogens are described above.

Antigens Suitable for Use in Adolescent Vaccines

In certain embodiments, the immunogenic compositions provided herein include one or more antigens suitable for use in adolescent subjects. Adolescents are in need of a boost of a previously administered pediatric antigen. Pediatric antigens which are suitable for use in adolescents are described above. In addition, adolescents are targeted to receive antigens derived from an STD pathogen in order to ensure protective or therapeutic immunity before the beginning of sexual activity. STD antigens which are suitable for use in adolescents are described above.

Tumor Antigens

In certain embodiments, a tumor antigen or cancer antigen is used in conjunction with the immunogenic compositions provided herein. In certain embodiments, the tumor antigens is a peptide-containing tumor antigens, such as a polypeptide tumor antigen or glycoprotein tumor antigens. In certain embodiments, the tumor antigen is a saccharide-containing tumor antigen, such as a glycolipid tumor antigen or a ganglioside tumor antigen. In certain embodiments, the tumor antigen is a polynucleotide-containing tumor antigen that expresses a polypeptide-containing tumor antigen, for instance, an RNA vector construct or a DNA vector construct, such as plasmid DNA.

Tumor antigens appropriate for the use in conjunction with the immunogenic compositions provided herein encompass a wide variety of molecules, such as (a) polypeptide-containing tumor antigens, including polypeptides (which can range, for example, from 8-20 amino acids in length, although lengths outside this range are also common), lipopolypeptides and glycoproteins, (b) saccharide-containing tumor antigens, including poly-saccharides, mucins, gangliosides, glycolipids and glycoproteins, and (c) polynucleotides that express antigenic polypeptides.

In certain embodiments, the tumor antigens are, for example, (a) full length molecules associated with cancer cells, (b) homologs and modified forms of the same, including molecules with deleted, added and/or substituted portions, and (c) fragments of the same. In certain embodiments, the tumor antigens are provided in recombinant form. In certain embodiments, the tumor antigens include, for example, class I-restricted antigens recognized by CD8+ lymphocytes or class II-restricted antigens recognized by CD4+ lymphocytes.

In certain embodiments, the tumor antigens include, but are not limited to, (a) cancer-testis antigens such as NY-ESO-1, SSX2, SCP1 as well as RAGE, BAGE, GAGE and MAGE family polypeptides, for example, GAGE-1, GAGE-2, MAGE-1, MAGE-2, MAGE-3, MAGE-4, MAGE-5, MAGE-6, and MAGE-12 (which can be used, for example, to address melanoma, lung, head and neck, NSCLC, breast, gastrointestinal, and bladder tumors), (b) mutated antigens, for example, p53 (associated with various solid tumors, e.g., colorectal, lung, head and neck cancer), p21/Ras (associated with, e.g., melanoma, pancreatic cancer and colorectal cancer), CDK4 (associated with, e.g., melanoma), MUM1 (associated with, e.g., melanoma), caspase-8 (associated with, e.g., head and neck cancer), CIA 0205 (associated with, e.g., bladder cancer), HLA-A2-R1701, beta catenin (associated with, e.g., melanoma), TCR (associated with, e.g., T-cell non-Hodgkins lymphoma), BCR-abl (associated with, e.g., chronic myelogenous leukemia), triosephosphate isomerase, MA 0205, CDC-27, and LDLR-FUT, (c) over-expressed antigens, for example, Galectin 4 (associated with, e.g., colorectal cancer), Galectin 9 (associated with, e.g., Hodgkin's disease), proteinase 3 (associated with, e.g., chronic myelogenous leukemia), WT 1 (associated with, e.g., various leukemias), carbonic anhydrase (associated with, e.g., renal cancer), aldolase A (associated with, e.g., lung cancer), PRAME (associated with, e.g., melanoma), HER-2/neu (associated with, e.g., breast, colon, lung and ovarian cancer), alpha-fetoprotein (associated with, e.g., hepatoma), KSA (associated with, e.g., colorectal cancer), gastrin (associated with, e.g., pancreatic and gastric cancer), telomerase catalytic protein, MUC-1 (associated with, e.g., breast and ovarian cancer), G-250 (associated with, e.g., renal cell carcinoma), p53 (associated with, e.g., breast, colon cancer), and carcinoembryonic antigen (associated with, e.g., breast cancer, lung cancer, and cancers of the gastrointestinal tract such as colorectal cancer), (d) shared antigens, for example, melanoma-melanocyte differentiation antigens such as MART-1/Melan A, gp100, MC1R, melanocyte-stimulating hormone receptor, tyrosinase, tyrosinase related protein-1/TRP1 and tyrosinase related protein-2/TRP2 (associated with, e.g., melanoma), (e) prostate associated antigens such as PAP, PSA, PSMA, PSH-P1, PSM-P1, PSM-P2, associated with e.g., prostate cancer, (f) immunoglobulin idiotypes (associated with myeloma and B cell lymphomas, for example), and (g) other tumor antigens, such as polypeptide- and saccharide-containing antigens including (i) glycoproteins such as sialyl Tn and sialyl Le$^x$ (associated with, e.g., breast and colorectal cancer) as well as various mucins; glycoproteins are coupled to a carrier protein (e.g., MUC-1 are coupled to KLH); (ii) lipopolypeptides (e.g., MUC-1 linked to a lipid moiety); (iii) polysaccharides (e.g., Globo H synthetic hexasaccharide), which are coupled to a carrier proteins (e.g., to KLH), (iv) gangliosides such as GM2, GM12, GD2, GD3 (associated with, e.g., brain, lung cancer, melanoma), which also are coupled to carrier proteins (e.g., KLH).

In certain embodiments, the tumor antigens include, but are not limited to, p15, Hom/Mel-40, H-Ras, E2A-PRL, H4-RET, IGH-IGK, MYL-RAR, Epstein Barr virus antigens, EBNA, human papillomavirus (HPV) antigens, including E6 and E7, hepatitis B and C virus antigens, human T-cell lymphotropic virus antigens, TSP-180, p185erbB2, p180erbB-3, c-met, mn-23H1, TAG-72-4, CA 19-9, CA 72-4, CAM 17.1, NuMa, K-ras, p16, TAGE, PSCA, CT7, 43-9F, 5T4, 791 Tgp72, beta-HCG, BCA225, BTAA, CA 125, CA 15-3 (CA 27.29\BCAA), CA 195, CA 242, CA-50, CAM43, CD68\KP1, CO-029, FGF-5, Ga733 (EpCAM), HTgp-175, M344, MA-50, MG7-Ag, MOV18, NB/70K, NY-CO-1, RCAS1, SDCCAG16, TA-90 (Mac-2 binding protein\cyclophilin C-associated protein), TAAL6, TAG72, TLP, TPS, and the like.

Polynucleotide-containing antigens used in conjunction with the immunogenic compositions provided herein include polynucleotides that encode polypeptide cancer antigens such as those listed above. In certain embodiments, the polynucleotide-containing antigens include, but are not limited to, DNA or RNA vector constructs, such as plasmid vectors (e.g., pCMV), which are capable of expressing polypeptide cancer antigens in vivo.

In certain embodiments, the tumor antigens are derived from mutated or altered cellular components. After alteration, the cellular components no longer perform their regulatory functions, and hence the cell may experience uncontrolled growth. Representative examples of altered cellular components include, but are not limited to ras, p53, Rb, altered protein encoded by the Wilms' tumor gene, ubiquitin, mucin, protein encoded by the DCC, APC, and MCC genes, as well as receptors or receptor-like structures such as neu, thyroid hormone receptor, platelet derived growth factor (PDGF) receptor, insulin receptor, epidermal growth factor (EGF) receptor, and the colony stimulating factor (CSF) receptor.

Additionally, bacterial and viral antigens, are used in conjunction with the immunogenic compositions provided herein for the treatment of cancer. In certain embodiments, the, carrier proteins, such as $CRM_{197}$, tetanus toxoid, or *Salmonella typhimurium* antigen are used in conjunction/conjugation with compounds provided herein for treatment of cancer. The cancer antigen combination therapies will show increased efficacy and bioavailability as compared with existing therapies.

In certain embodiments, the immunogenic compositions containing at least one compound of Formula (I) include capsular saccharides from at least two of serogroups A, C, W135 and Y of *Neisseria meningitides*. In other embodiments, such vaccines further comprise an antigen from one or more of the following: (a) serogroup B *N. meningitidis*; (b) *Haemophilus influenzae* type B; and/or (c) *Streptococcus pneumoniae*.

In certain embodiments the immunogenic compositions containing at least one compound of Formula (I) include serogroups C, W135 & Y of *N. meningitides*. In certain embodiments the immunogenic compositions containing at least one compound of Formula (I) include serogroups A, C, W135 & Y of *N. meningitides*. In certain embodiments the immunogenic compositions containing at least one compound of Formula (I) include serogroups B, C, W135 & Y of *N. meningitides*. In certain embodiments the immunogenic compositions containing at least one compound of Formula (I) include serogroups A, B, C, W135 & Y of *N. meningitides*. In certain embodiments the immunogenic compositions containing at least one compound of Formula (I) include *H. influenzae* type B and serogroups C, W135 & Y of *N. meningitides*. In certain embodiments the immunogenic compositions containing at least one compound of Formula (I) include *H. influenzae* type B and serogroups A, C, W135 & Y of *N. meningitides*. In certain embodiments the immunogenic compositions containing at least one compound of Formula (I) include *H. infulenzae* type B and serogroups B, C, W135 & Y of *N. meningitides*. In certain embodiments the immunogenic compositions containing at least one compound of Formula (I) include *H. infulenzae* type B and serogroups A, B, C, W135 & Y of *N. meningitides*. In certain embodiments the immunogenic compositions containing at least one compound of Formula (I) include *S. pneumoniae* and serogroups C, W135 & Y of *N. meningitides*. In certain embodiments the immunogenic compositions containing at least one compound of Formula (I) include *S. pneumoniae* and serogroups A, C, W135 & Y of *N. meningitides*. In certain embodiments the immunogenic compositions containing at least one compound of Formula (I) include *S. pneumoniae* and serogroups B, C, W135 & Y of *N. meningitides*. In certain embodiments the immunogenic compositions containing at least one compound of Formula (I) include *S. pneumoniae* and serogroups A, B, C, W135 & Y of *N. meningitides*. In certain embodiments the immunogenic compositions containing at least one compound of Formula (I) include *H. infulenzae* type B, *S. pneumoniae* and serogroups C, W135 & Y of *N. meningitides*. In certain embodiments the immunogenic compositions containing at least one compound of Formula (I) include *H. infulenzae* type B, *S. pneumoniae* and serogroups A, C, W135 & Y of *N. meningitides*. In certain embodiments the immunogenic compositions containing at least one compound of Formula (I) include *H. infulenzae* type B, *S. pneumoniae* and serogroups B, C, W135 & Y of *N. meningitides*. In certain embodiments the immunogenic compositions containing at least one compound of Formula (I) include *H. infulenzae* type B, *S. pneumoniae* and serogroups A, B, C, W135 & Y of *N. meningitidis*.

Kits

Also provided herein are pharmaceutical packs or kits that include one or more containers containing a compound of Formula (I)-(XVI) useful for the treatment or prevention of a disease or disorder associated with toll-like receptors. In other embodiments, the such pharmaceutical packs or kits include one or more containers containing a compound of Formula (I)-(XVI) useful for the treatment or prevention of a disease or disorder associated with toll-like receptors and one or more containers containing an additional therapeutic agent, including but not limited to those listed above. In certain embodiments, such pharmaceutical packs or kits optionally include instructions for its administration of a compound of Formula (I)-(XVI) as disclosed herein. In some embodiments of such kits, the compound of Formula (I)-(XVI) is provided in the form of a vaccine composition as described herein, and optionally includes a syringe for injecting a subject with the vaccine composition Methods of Treatment, Prevention and Administration of Vaccines The immunogenic compositions as disclosed herein may be used in conjuction with vaccines to improve the immunogenicity of the vaccine or where the immunogenic composition includes one or more antigens, the immunogenic composition may be used as a vaccine. Therefore in certain embodiment, the immunogenic compositions disclosed herein may be used in a method for raising or enhancing an immune response in a mammal comprising the step of administering an effective amount of an immunogenic composition as disclosed herein. The immune response is preferably protective and preferably involves antibodies and/or cell-mediated immunity. The method may raise a booster response.

In certain embodimentsembodiments, the immunogenic compositions disclosed herein may be used as a medicament, e.g., for use in raising or enhancing an immune response in a mammal.

In certain embodiments, the immunogenic compositions disclosed herein may be used in the manufacture of a medicament for raising an immune response in a mammal.

The invention also provides a delivery device pre-filled with an immunogenic composition disclosed herein.

By raising an immune response in the mammal by these uses and methods, the mammal can be infection by pathogens comprising the antigen included in the immunogenic composition or administered in conjunction with the immunogenic composition can be reduced or even prevented. The mammal is preferably a human, but may be, e.g., a cow, a pig, a chicken, a cat or a dog, as the pathogens covered herein may be problematic across a wide range of species. Where the vaccine is for prophylactic use, the human is preferably a child (e.g., a toddler or infant) or a teenager; where the vaccine is for therapeutic use, the human is preferably a teenager or an adult. A vaccine intended for children may also be administered to adults, e.g., to assess safety, dosage, immunogenicity, etc.

One way of checking efficacy of therapeutic treatment involves monitoring pathogen infection after administration of the immunogenic compositions disclosed herein. One way of checking efficacy of prophylactic treatment involves monitoring immune responses, systemically (such as monitoring the level of IgG1 and IgG2a production) and/or mucosally (such as monitoring the level of IgA production), against the antigens included in or administered in conjunction with the immunogenic compositions disclosed herein after administration of the immunogenic composition (and the antigen if administered separately). Typically, antigen-specific serum antibody responses are determined post-immunisation but pre-challenge whereas antigen-specific mucosal antibody responses are determined post-immunisation and post-challenge.

Another way of assessing the immunogenicity of the immunogenic compositions disclosed herein where the antigen is a protein is to express the proteins recombinantly for screening patient sera or mucosal secretions by immunoblot and/or microarrays. A positive reaction between the protein and the patient sample indicates that the patient has mounted an immune response to the protein in question. This method may also be used to identify immunodominant antigens and/or epitopes within protein antigens.

The efficacy of the immunogenic compositions can also be determined in vivo by challenging appropriate animal models of the pathogen of interest infection.

The immunogenic compositions disclosed herein will generally be administered directly to a subject. Direct delivery may be accomplished by parenteral injection (e.g., subcutaneously, intraperitoneally, intravenously, intramuscularly, or to the interstitial space of a tissue), or mucosally, such as by rectal, oral (e.g., tablet, spray), vaginal, topical, transdermal or transcutaneous, intranasal, ocular, aural, pulmonary or other mucosal administration.

The immunogenic compositions may be used to elicit systemic and/or mucosal immunity, preferably to elicit an enhanced systemic and/or mucosal immunity.

Preferably the enhanced systemic and/or mucosal immunity is reflected in an enhanced TH1 and/or TH2 immune response. Preferably, the enhanced immune response includes an increase in the production of IgG1 and/or IgG2a and/or IgA.

Dosage can be by a single dose schedule or a multiple dose schedule. Multiple doses may be used in a primary immunisation schedule and/or in a booster immunisation schedule. In a multiple dose schedule the various doses may be given by the same or different routes, e.g., a parenteral prime and mucosal boost, a mucosal prime and parenteral boost, etc. Multiple doses will typically be administered at least 1 week apart (e.g., about 2 weeks, about 3 weeks, about 4 weeks, about 6 weeks, about 8 weeks, about 10 weeks, about 12 weeks, about 16 weeks, etc.).

The immunogenic compositions disclosed herein that include one or more antigens or are used in conjunction with one or more antigens may be used to treat both children and adults. Thus a human subject may be less than 1 year old, 1-5 years old, 5-15 years old, 15-55 years old, or at least 55 years old. Preferred subjects for receiving such immunogenic compositions are the elderly (e.g., >50 years old, >60 years old, and preferably >65 years), the young (e.g., <5 years old), hospitalised patients, healthcare workers, armed service and military personnel, pregnant women, the chronically ill, or immunodeficient patients. The immunogenic compositions are not suitable solely for these groups, however, and may be used more generally in a population.

The immunogenic compositions disclosed herein that include one or more antigens or are used in conjunction with one or more antigens may be administered to patients at substantially the same time as (e.g., during the same medical consultation or visit to a healthcare professional or vaccination centre) other vaccines, e.g., at substantially the same time as a measles vaccine, a mumps vaccine, a rubella vaccine, a MMR vaccine, a varicella vaccine, a MMRV vaccine, a diphtheria vaccine, a tetanus vaccine, a pertussis vaccine, a DTP vaccine, a conjugated *H. influenzae* type b vaccine, an inactivated poliovirus vaccine, a hepatitis B virus vaccine, a meningococcal conjugate vaccine (such as a tetravalent A C W135 Y vaccine), a respiratory syncytial virus vaccine, etc.

EXAMPLES

The following examples were offered to illustrate, but not to limit, the compounds of Formula (I) provided herein, and the preparation of such compounds.

Preparation of Benzo[f][1,7]naphthyridin-5-amine analogs

Example 1

Benzo[f][1,7]naphthyridin-5-amine

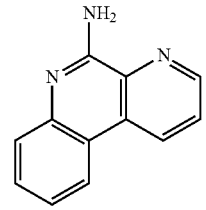 [SMILES: Nc1nc2ccccc2c2cccnc12]

A solution of 2-(tert-butoxycarbonylamino)phenylboronic acid (1.0 eq.) and 3-bromopicolino-nitrile (1.0 eq.) in toluene (0.44 M) was mixed with tetrakis(triphenyl-phosphine)palladium (5 mol %) and 2N aqueous potassium carbonate solution (2.0 eq.). The reaction was heated to 100° C. and stirred overnight. After cooling to ambient temperature, the reaction content was diluted with 2% methanol in dichloromethane and water. The two phases were separated, and the aqueous layer was extracted twice with 2% methanol in dichloromethane. The combined organic layers were washed with brine, dried over anhydrous MgSO$_4$, and concentrated en vacuo. The crude material was purified by flash chromatography on a COMBIFLASH® system (ISCO) using 0-80% ethyl acetate in hexane to give a white solid. $^1$H NMR (acetone d-6): δ 9.04 (d, 1H), 8.91 (d, 1H), 8.45 (d, 1H), 7.86 (dd, 1H), 7.53-7.62 (m, 2H), 7.35 (t, 1H), 6.65 (br, 2H). LRMS [M+H]=196.1

Example 2

Pyrazino[2,3-c]quinolin-5-amine

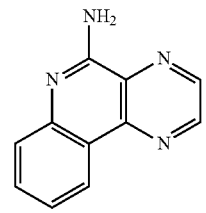 [SMILES: Nc1nc2ccccc2c2nccnc12]

A solution of 2-(tert-butoxycarbonylamino)phenylboronic acid (1.0 eq.) and 3-chloropyrazine-2-carbonitrile (1.0 eq.) in toluene (0.44 M) was mixed with tetrakis(triphenyl-phosphine)palladium (5 mol %) and 2N aqueous potassium carbonate solution (2.0 eq.). The reaction was heated to 100° C. and stirred overnight. After cooling to ambient temperature, the reaction content was diluted with 2% methanol in dichloromethane and water. The two phases were separated, and the aqueous layer was extracted twice with 2% methanol in dichloromethane. The combined organic layers were washed with brine, dried over anhydrous MgSO$_4$, and concentrated en vacuo. The crude product was purified by flash chromatography on a COMBIFLASH® system (ISCO) using 0-50% ethyl acetate in hexane to give a solid. $^1$H NMR (acetone d-6): δ9.14 (s, 1H), 8.95 (s, 1H), 8.77 (d, 1H), 7.63-7.66 (m, 2H), 7.38 (t, 1H), 6.77 (br, 2H). LRMS [M+H]=197.1

Example 3

9-chlorobenzo[f][1,7]naphthyridin-5-amine

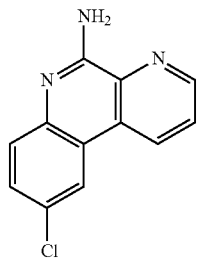 [SMILES: Nc1nc2ccc(Cl)cc2c2cccnc12]

Step 1: tert-butyl 2-bromo-4-chlorophenylcarbamate

To a solution of 2-bromo-4-chloroaniline (1.0 eq.) in tetrahydrofuran (0.2 M) at 0° C. under N$_2$ atmosphere was added dropwise 1M NaHMDS (2.5 eq.). The reaction was stirred for 15 minutes at 0° C., and a solution of di-tert-butyl dicarbonate in tetrahydrofuran was added. The reaction was warmed to room temperature overnight. The solvent was evaporated, and the resulting residue was quenched with 0.1N HCl aqueous solution. The aqueous suspension was extracted twice with ethyl acetate. The combined organic layers were washed with brine, dried over anhydrous MgSO$_4$, and concentrated en vacuo. The crude material was purified y by flash chromatography on a COMBIFLASH® system (ISCO) using 0-5% ethyl acetate in hexane to give the product as light yellow oil.

Step 2: tert-butyl 4-chloro-2-(4,4,5,5-tetramethyl-1,3,2-dioxaborolan-2-yl)phenyl-carbamate Tert-butyl 2-bromo-4-chlorophenylcarbamate (from step 1) (1.0 eq.), 4,4,4',4',5,5,5=,5'-octamethyl-2,2'-bi(1,3,2-dioxaborolane) (1.5 eq.), dichloro[1,1'-bis(diphenylphosphino) ferrocene]palladium (II) (5%), and sodium acetate (4.5 eq.) were mixed in dioxane (0.2 M) under N$_2$ atmosphere. The reaction was heated to 100° C. and stirred overnight. The resulting suspension was cooled to ambient temperature, diluted with ether, filtered through celite, and the filtrate was concentrated en vacuo. The crude mixture was purified by flash chromatography on a COMBIFLASH® system (ISCO) using 0-10% ethyl acetate in hexane to give Cert-butyl 4-chloro-2-(4,4,5,5-tetramethyl-1,3,2-dioxaborolan-2-yl) phenyl-carbamate.

Step 3: 9-chlorobenzo[f][1,7]naphthyridin-5-amine

A solution of tert-butyl 4-chloro-2-(4,4,5,5-tetramethyl-1,3,2-dioxaborolan-2-yl)phenyl-carbamate (from step 2) (1.0 eq.) and 3-bromopicolino-nitrile (1.0 eq.) in toluene (0.44 M) was mixed with tetrakis(triphenyl-phosphine)palladium (5 mol %) and 2N aqueous potassium carbonate solution (2.0 eq.). The reaction was heated to 100° C. and stirred overnight. After cooling to ambient temperature, the reaction content was diluted with 2% methanol in dichloromethane and water. The two phases were separated, and the aqueous layer was extracted twice with 2% methanol in dichloromethane. The combined organic layers were washed with brine, dried over anhydrous MgSO$_4$, and concentrated en vacuo. The crude product was purified by flash chromatography on a COMBIFLASH® system (ISCO) using 0-50% ethyl acetate in hexane and then re-purified using 0-5% methanol in dichloromethane to give a solid. $^1$H NMR (acetone d-6): δ 9.08 (d, 1H), 8.96 (d, 1H), 8.45 (s, 1H), 7.86-7.89 (dd, 1H), 7.60 (d, 1H), 7.54 (d, 1H), 6.78 (br, 2H). LRMS [M+H]=230.1

Example 4

8-chlorobenzo[f][1,7]naphthyridin-5-amine

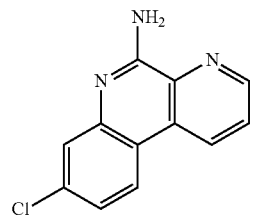 [SMILES: Nc1nc2cc(Cl)ccc2c2cccnc12]

Step 1: tert-butyl 2-bromo-5-chlorophenylcarbamate

To a solution of 2-bromo-5-chloroaniline (1.0 eq.) in tetrahydrofuran (0.2 M) at 0° C. under N$_2$ atmosphere was added dropwise 1M NaHMDS (2.5 eq.). The reaction was stirred for 15 minutes at 0° C., and a solution of di-tert-butyl dicarbonate in tetrahydrofuran was added. The reaction was warmed to room temperature overnight. The solvent was evaporated, and the resulting residue was quenched with 0.1N HCl aqueous solution. The aqueous suspension was extracted twice with ethyl acetate. The combined organic layers were washed with brine, dried over anhydrous MgSO$_4$, and concentrated en vacuo. The crude material was purified by flash chromatography on a COMBIFLASH® system (ISCO) using 0-5% ethyl acetate in hexane to give the product as light yellow oil.

Step 2: tert-butyl 5-chloro-2-(4,4,5,5-tetramethyl-1,3,2-dioxaborolan-2-yl)phenyl-carbamate Tert-butyl 2-bromo-5-chlorophenylcarbamate (from step 1) (1.0 eq.), 4,4,4',4',5,5,5',5'-octamethyl-2,2'-bi(1,3,2-dioxaborolane) (1.5 eq.), dichloro[1,1'-bis(diphenylphosphino) ferrocene]palladium (II) (5%), and sodium acetate (4.5 eq.) were mixed in dioxane (0.2 M) under N$_2$ atmosphere. The reaction was heated to 100° C. and stirred overnight. The resulting suspension was cooled to ambient temperature, diluted with ether, filtered through celite, and the filtrate was concentrated en vacuo. The crude mixture was purified by flash chromatography on a COMBIFLASH® system (ISCO) using 0-5% ethyl acetate in hexane to give tert-butyl 5-chloro-2-(4,4,5,5-tetramethyl-1,3,2-dioxaborolan-2-yl)phenyl-carbamate.

Step 3: 8-chlorobenzo[f][1,7]naphthyridin-5-amine

A solution of tert-butyl 5-chloro-2-(4,4,5,5-tetramethyl-1,3,2-dioxaborolan-2-yl)phenyl-carbamate (from step 2) (1.0 eq.) and 3-bromopicolino-nitrile (1.0 eq.) in toluene (0.44 M) was mixed with tetrakis(triphenyl-phosphine)palladium (5 mol %) and 2N aqueous potassium carbonate solution (2.0 eq.). The reaction was heated to 100° C. and stirred overnight. After cooling to ambient temperature, the reaction content was diluted with 2% methanol in dichloromethane and water. The two phases were separated, and the aqueous layer was extracted twice with 2% methanol in dichloromethane. The combined organic layers were washed with brine, dried over anhydrous MgSO₄, and concentrated en vacuo. The crude product was purified by flash chromatography on a COMBI-FLASH® system (ISCO) using 0-5% methanol in dichloromethane to give a semipure solid, which was then stirred in hot 10% ethyl acetate in hexane, filtered, and dried to give a pure solid. $^1$H NMR (acetone d-6): δ 9.03 (d, 1H), 8.93 (d, 1H), 8.46 (d, 1H), 7.85-7.88 (dd, 1H), 7.57 (s, 1H), 7.32 (d, 1H), 6.94 (br, 2H). LRMS [M+H]=230.1

Example 5

8-methylbenzo[f][1,7]naphthyridin-5-amine

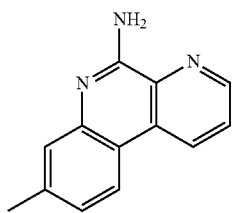 [SMILES: Cc1ccc2c(c1)nc(N)c1ncccc12]

Step 1: tert-butyl 2-bromo-5-methylphenylcarbamate

To a solution of 2-bromo-5-methylaniline (1.0 eq.) in tetrahydrofuran (0.2 M) at 0° C. under N₂ atmosphere was added dropwise 1M NaHMDS (2.5 eq.). The reaction was stirred for 15 minutes at 0° C., and a solution of di-tert-butyl dicarbonate in tetrahydrofuran was added. The reaction was warmed to room temperature overnight. The solvent was evaporated, and the resulting residue was quenched with 0.1N HCl aqueous solution. The aqueous suspension was extracted twice with ethyl acetate. The combined organic layers were washed with brine, dried over anhydrous MgSO₄, and concentrated en vacuo. The crude material was purified by flash chromatography on a COMBIFLASH® system (ISCO) using 0-5% ethyl acetate in hexane to give product as light yellow oil.

Step 2: tert-butyl 5-methyl-2-(4,4,5,5-tetramethyl-1,3,2-dioxaborolan-2-yl)phenylcarbamate Tert-butyl 2-bromo-5-methylphenylcarbamate (from step 1) (1.0 eq.), 4,4,4',4',5,5,5',5'-octamethyl-2,2'-bi(1,3,2-dioxaborolane) (1.5 eq.), dichloro[1,1'-bis(diphenylphosphino)ferrocene]palladium (II) (5%), and sodium acetate (4.5 eq.) were mixed in dioxane (0.2 M) under N₂ atmosphere. The reaction was heated to 100° C. and stirred overnight. The resulting suspension was cooled to ambient temperature, diluted with ether, filtered through celite, and the filtrate was concentrated en vacuo. The crude material was purified by flash chromatography on a COMBIFLASH® system (ISCO) using 0-8% ether in hexane to give tert-butyl 5-methyl-2-(4,4,5,5-tetramethyl-1,3,2-dioxaborolan-2-yl)phenylcarbamate.

Step 3: 8-methylbenzo[f][1,7]naphthyridin-5-amine

A solution of tert-butyl 5-methyl-2-(4,4,5,5-tetramethyl-1,3,2-dioxaborolan-2-yl)phenylcarbamate (from step 2) (1.0 eq.) and 3-bromopicolino-nitrile (1.0 eq.) in toluene (0.44 M) was mixed with tetrakis(triphenyl-phosphine)palladium (5 mol %) and 2N aqueous potassium carbonate solution (2.0 eq.). The reaction was heated to 100° C. and stirred overnight. After cooling to ambient temperature, the reaction content was diluted with 2% methanol in dichloromethane and water. The two phases were separated, and the aqueous layer was extracted twice with 2% methanol in dichloromethane. The combined organic layers were washed with brine, dried over anhydrous MgSO₄, and concentrated en vacuo. The crude product was purified by flash chromatography on a COMBI-FLASH® system (ISCO) using 0-40% ethyl acetate in toluene to give a pure solid. $^1$H NMR (acetone d-6): δ 8.98 (d, 1H), 8.87 (d, 1H), 8.32 (d, 1H), 7.79-7.82 (dd, 1H), 7.42 (s, 1H), 7.18 (d, 1H), 6.6 (br, 2H), 2.45 (s, 3H). LRMS [M+H]= 210.1

Example 6

9-methylbenzo[f][1,7]naphthyridin-5-amine

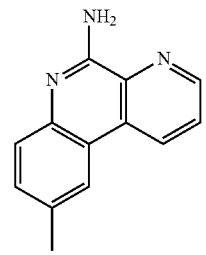 [SMILES: Cc1ccc2nc(N)c3ncccc3c2c1]

Step 1: tert-butyl 2-bromo-4-methylphenylcarbainate

To a solution of 2-bromo-4-methylaniline (1.0 eq.) in tetrahydrofuran (0.2 M) at 0° C. under N₂ atmosphere was added dropwise 1M NaHMDS (2.5 eq.). The reaction was stirred for 15 minutes at 0° C., and a solution of di-cert-butyl dicarbonate in tetrahydrofuran was added. The reaction was warmed to room temperature overnight. The solvent was evaporated, and the resulting residue was quenched with 0.1N HCl aqueous solution. The aqueous suspension was extracted twice with ethyl acetate. The combined organic layers were washed with brine, dried over anhydrous MgSO₄, and concentrated en vacuo. The crude material was purified by flash chromatography on a COMBIFLASH® system (ISCO) using 0-5% ethyl acetate in hexane to give product as light yellow oil.

Step 2: tert-butyl 4-methyl-2-(4,4,5,5-tetramethyl-1,3,2-dioxaborolan-2-yl)phenylcarbamate Tert-butyl 2-bromo-4-methylphenylcarbamate (from step 1) (1.0 eq.), 4,4,4',4',5,5,5',5'-octamethyl-2,2'-bi(1,3,2-dioxaborolane) (1.5 eq.), dichloro[1,1'-bis(diphenylphosphino)ferrocene]palladium (II) (5%), and sodium acetate (4.5 eq.) were mixed in dioxane (0.2 M) under N₂ atmosphere. The reaction was heated to 100° C. and stirred overnight. The resulting suspension was cooled to ambient temperature, diluted with ether, filtered through celite, and the filtrate was concentrated en vacuo. The crude material was purified by flash chromatography on a COMBIFLASH® system (ISCO) using 0-8% ether in hexane to give tert-butyl 4-methyl-2-(4,4,5,5-tetramethyl-1,3,2-dioxaborolan-2-yl)phenylcarbamate.

Step 3: 9-methylbenzo[f][1,7]naphthyridin-5-amine

A solution of tert-butyl 4-methyl-2-(4,4,5,5-tetramethyl-1,3,2-dioxaborolan-2-yl)phenylcarbamate (from step 2) (1.0 eq.) and 3-bromopicolino-nitrile (1.0 eq.) in toluene (0.44 M) was mixed with tetrakis(triphenyl-phosphine)palladium (5 mol %) and 2N aqueous potassium carbonate solution (2.0 eq.). The reaction was heated to 100° C. and stirred overnight. After cooling to ambient temperature, the reaction content was diluted with 2% methanol in dichloromethane and water. The two phases were separated, and the aqueous layer was extracted twice with 2% methanol in dichloromethane. The combined organic layers were washed with brine, dried over anhydrous MgSO$_4$, and concentrated en vacuo. The crude product was purified by flash chromatography on a COMBIFLASH® system (ISCO) using 0-5% methanol in dichloromethane to give a semipure solid, which was then swirled in hot ethyl acetate, filtered, and dried to give a pure solid. $^1$H NMR (acetone d-6): δ 9.02 (d, 1H), 8.89 (d, 1H), 8.25 (s, 1H), 8.70-7.84 (dd, 1H), 7.52 (d, 1H), 7.40 (d, 1H), 6.5 (br, 2H), 2.48 (s, 3H). LRMS [M+H]=210.2

Example 7

10-methylbenzo[f][1,7]naphthyridin-5-amine

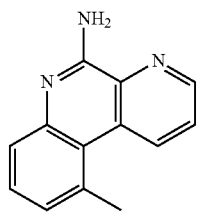 [SMILES: Cc1cccc2nc(N)c3ncccc3c12]

Step 1: tert-butyl 2-bromo-3-methylphenylcarbamate

To a solution of 2-bromo-3-methylaniline (1.0 eq.) in tetrahydrofuran (0.2 M) at 0° C. under N$_2$ atmosphere was added dropwise 1M NaHMDS (2.5 eq.). The reaction was stirred for 15 minutes at 0° C., and a solution of di-tert-butyl dicarbonate in tetrahydrofuran was added. The reaction was warmed to room temperature overnight. The solvent was evaporated, and the resulting residue was quenched with 0.1N HCl aqueous solution. The aqueous suspension was extracted twice with ethyl acetate. The combined organic layers were washed with brine, dried over anhydrous MgSO$_4$, and concentrated en vacuo. The crude material was purified by flash chromatography on a COMBIFLASH® system (ISCO) using 0-5% ethyl acetate in hexane to give product as light yellow oil.

Step 2: tert-butyl 3-methyl-2-(4,4,5,5-tetramethyl-1,3,2-dioxaborolan-2-yl)phenylcarbamate Tert-butyl 2-bromo-3-methylphenylcarbamate (from step 1) (1.0 eq.), 4,4,4',4',5,5,5',5'-octamethyl-2,2'-bi(1,3,2-dioxaborolane) (1.5 eq.), dichloro[1,1'-bis(diphenylphosphino)ferrocene]palladium (II) (5%), and sodium acetate (4.5 eq.) were mixed in dioxane (0.2 M) under N$_2$ atmosphere. The reaction was heated to 100° C. and stirred overnight. The resulting suspension was cooled to ambient temperature, diluted with ether, filtered through celite, and the filtrate was concentrated en vacuo. The crude material was purified by flash chromatography on a COMBIFLASH® system (ISCO) using 0-10% ether in hexane to tert-butyl 3-methyl-2-(4,4,5,5-tetramethyl-1,3,2-dioxaborolan-2-yl)phenylcarbamate.

Step 3: 10-methylbenzo[f][1,7]naphthyridin-5-amine

A solution of tert-butyl 3-methyl-2-(4,4,5,5-tetramethyl-1,3,2-dioxaborolan-2-yl)phenylcarbamate (from step 2) (1.0 eq.) and 3-bromopicolino-nitrile (1.0 eq.) in toluene (0.44 M) was mixed with tetrakis(triphenyl-phosphine)palladium (5 mol %) and 2N aqueous potassium carbonate solution (2.0 eq.). The reaction was heated to 100° C. and stirred overnight. After cooling to ambient temperature, the reaction content was diluted with 2% methanol in dichloromethane and water. The two phases were separated, and the aqueous layer was extracted twice with 2% methanol in dichloromethane. The combined organic layers were washed with brine, dried over anhydrous MgSO$_4$, and concentrated en vacuo. The crude product was purified by flash chromatography on a COMBIFLASH® system (ISCO) using 0-40% ethyl acetate in toluene to give a semipure solid, which was then swirled in hot 10% ethyl acetate in hexane, filtered, and dried to give a pure solid. $^1$H NMR (acetone d-6): δ 9.22 (d, 1H), 8.90 (d, 1H), 7.82-7.85 (dd, 1H), 7.54 (d, 1H), 7.45 (t, 1H), 7.19 (d, 1H), 6.6 (br, 2H), 2.98 (s, 3H). LRMS [M+H]=210.2.

Example 8

Ethyl 5-aminobenzo[f][1,7]naphthyridine-9-carboxylate

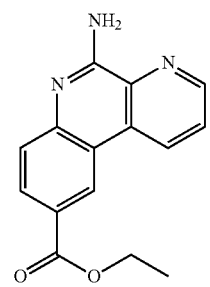 [SMILES: CCOC(=O)c1ccc2nc(N)c3ncccc3c2c1]

Step 1: ethyl 3-bromo-4-(tert-butoxycarbonylamino)benzoate

To a solution of 4-amino-3-bromobenzoate (1.0 eq.) in tetrahydrofuran (0.2 M) at 0° C. under N$_2$ atmosphere was added dropwise 1M NaHMDS (2.5 eq.). The reaction was stirred for 15 minutes at 0° C., and a solution of di-tert-butyl dicarbonate in tetrahydrofuran was added. The reaction was warmed to room temperature overnight. The solvent was evaporated, and the resulting residue was quenched with 0.1N HCl aqueous solution. The aqueous suspension was extracted twice with ethyl acetate. The combined organic layers were washed with brine, dried over anhydrous MgSO$_4$, and concentrated en vacuo. The crude material was purified by flash chromatography on a COMBIFLASH® system (ISCO) using 0-5% ethyl acetate in hexane to give product as light yellow oil.

Step 2: Ethyl 4-(tert-butoxycarbonylamino)-3-(4,4,5, 5-tetramethyl-1,3,2-dioxaborolan-2-yl)benzoate Ethyl 3-bromo-4-(tert-butoxycarbonylamino)benzoate (from step 1) (1.0 eq.), 4,4,4',4',5,5,5',5'-octamethyl-2,2'-bi (1,3,2-dioxaborolane) (1.5 eq.), dichloro[1,1'-bis(diphenylphosphino)ferrocene]palladium (II) (5%), and sodium acetate (4.5 eq.) were mixed in dioxane (0.2 M) under $N_2$ atmosphere. The reaction was heated to 100° C. and stirred overnight. The resulting suspension was cooled to ambient temperature, diluted with ether, filtered through celite, and the filtrate was concentrated en vacuo. The crude material was purified by flash chromatography on a COMBIFLASH® system (ISCO) using 0-10% ether in hexane to give ethyl 4-(tert-butoxycarbonylamino)-3-(4,4,5,5-tetramethyl-1,3,2-dioxaborolan-2-yl)benzoate.

Step 3: ethyl 5-aminobenzo[f][1,7]naphthyridine-9-carboxylate

A solution of ethyl 4-(tert-butoxycarbonylamino)-3-(4,4,5,5-tetramethyl-1,3,2-dioxaborolan-2-yl)benzoate (from step 2) (1.0 eq.) and 3-bromopicolino-nitrile (1.0 eq.) in toluene/ethanol (10:1, 0.23 M) was mixed with tetrakis(triphenylphosphine)palladium (5 mol %) and anhydrous potassium carbonate (2.0 eq.). The reaction was heated to 100° C. and stirred overnight. After cooling to ambient temperature, the reaction content was diluted with 2% methanol in dichloromethane and water. The two phases were separated, and the aqueous layer was extracted twice with 2% methanol in dichloromethane. The combined organic layers were washed with brine, dried over anhydrous $MgSO_4$, and concentrated en vacuo. The crude material was purified by flash chromatography on a COMBIFLASH® system (ISCO) using 0-40% ethyl acetate in toluene to give a semipure solid, which was then swirled in hot 10% ethyl acetate in hexane, filtered, and dried to give a pure solid. $^1$H NMR (acetone d-6): δ 9.11 (d, 1H), 9.05 (s, 1H), 8.95 (d, 1H), 8.14 (d, 1H), 7.89-7.92 (dd, 1H), 7.63 (d, 1H), 4.38 (q, 2H), 1.40 (t, 3H). LRMS [M+H]=268.2.

Example 9

5-aminobenzo[f][1,7]naphthyridine-9-carboxylic acid

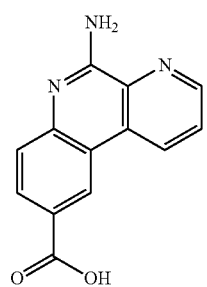 [SMILES: Nc1nc2ccc(C(=O)O)cc2c2cccnc12]

Ethyl 5-aminobenzo[f][1,7]naphthyridine-9-carboxylate (Example 8) (1.0 eq.) was mixed with 1N NaOH (2.0 eq.) in ethanol (0.12 M). The reaction was heated to 80° C. and stirred for 36 hours. The solvent was removed en vacuo. The residue was suspended in water, and the pH was adjusted to neutral using 5% citric acid aqueous solution. The suspension was centrifuged (2500 rpm, 5 min), and the supernatant was removed. The resulting solids was re-suspended in water by vortexing, centrifuged (2500 rpm, 5 min), and the supernatant was removed. The re-suspension, centrifugation, and removal of supernatant steps were repeated with hot methanol, hot ethyl acetate, and ether to give a pure solid. $^1$H NMR (DMSO): δ 12.86 (s, 1H), 9.15 (d, 1H), 9.00 (s, 1H), 8.97 (d, 1H), 8.07 (d, 1H), 7.88-7.91 (dd, 1H), 7.56-7.59 (m, 3H). LRMS [M+H]=240.1

Example 10

8-methoxybenzo[f][1,7]naphthyridin-5-amine

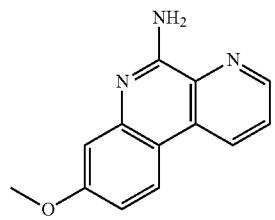 [SMILES: COc1ccc2c(c1)nc(N)c1ncccc12]

Step 1: 2-bromo-5-methoxyaniline

A solution of 1-bromo-4-methoxy-2-nitrobenzene (1.0 eq.), iron powder (3.0 eq.), and concentrated HCl (1.04 eq.) were mixed together in ethanol (0.64 M) and heated to reflux. The reaction was stirred for 24 hours, and the solvent was evaporated. The resulting residue was diluted with ethyl acetate and saturated aqueous ammonium chloride solution. The aqueous layer was extracted three times with ethyl acetate, and the combined organic layers were washed with water, brine, dried over anhydrous $MgSO_4$, and concentrated en vacuo. The crude material was purified by flash chromatography on a COMBIFLASH® system (ISCO) using 0-15% ethyl acetate in hexane to give the product as oil.

Step 2: tert-butyl 2-bromo-5-methoxyphenylcarbamate

To a solution of 2-bromo-5-methoxyaniline (1.0 eq.) (from step 1) in tetrahydrofuran (0.2 M) at 0° C. under $N_2$ atmosphere was added dropwise 1M NaHMDS (2.5 eq.). The reaction was stirred for 15 minutes at 0° C., and a solution of di-tert-butyl dicarbonate in tetrahydrofuran was added. The reaction was warmed to room temperature overnight. The solvent was evaporated, and the resulting residue was quenched with 0.1N HCl aqueous solution. The aqueous suspension was extracted twice with ethyl acetate. The combined organic layers were washed with brine, dried over anhydrous $MgSO_4$, and concentrated en vacuo. The crude material was purified by flash chromatography on a COMBIFLASH® system (ISCO) using 0-5% ethyl acetate in hexane to give product as light yellow oil.

Step 3: tert-butyl 5-methoxy-2-(4,4,5,5-tetramethyl-1,3,2-dioxaborolan-2-yl)phenylcarbamate Tert-butyl 2-bromo-5-methoxyphenylcarbamate (from step 2) (1.0 eq.), 4,4,4',4',5,5,5',5'-octamethyl-2,2'-bi(1,3,2-dioxaborolane) (1.5 eq.), dichloro[1,1'-bis(diphenylphosphino)ferrocene]palladium (II) (5%), and sodium acetate (4.5 eq.) were mixed in dioxane (0.2 M) under $N_2$ atmosphere. The reaction was heated to 100° C. and stirred overnight. The resulting suspension was cooled to ambient temperature, diluted with ether, filtered through celite, and the filtrate was concentrated en vacuo. The crude material was purified by flash chromatography on a COMBIFLASH® system (ISCO) using 0-15% ether in hexane to give tert-butyl 5-methoxy-2-(4,4,5,5-tetramethyl-1,3,2-dioxaborolan-2-yl)phenylcarbamate.

Step 4:
8-methoxybenzo[f][1,7]naphthyridin-5-amine

A solution of tert-butyl 5-methoxy-2-(4,4,5,5-tetramethyl-1,3,2-dioxaborolan-2-yl)phenylcarbamate (from step 3) (1.0 eq.) and 3-bromopicolino-nitrile (1.0 eq.) in toluene/ethanol (10:1, 0.23 M) was mixed with tetrakis(triphenyl-phosphine)palladium (5 mol %) and anhydrous potassium carbonate (2.0 eq.). The reaction was heated to 100° C. and stirred overnight. After cooling to ambient temperature, the reaction content was diluted with 2% methanol in dichloromethane and water. The two phases were separated, and the aqueous layer was extracted twice with 2% methanol in dichloromethane. The combined organic layers were washed with brine, dried over anhydrous MgSO$_4$, and concentrated en vacuo. The crude product was purified by flash chromatography on a COMBIFLASH® system (ISCO) using 0-5% methanol in dichloromethane to give a semipure solid, which was then recrystalized in ethyl acetate, filtered, and dried to give a pure solid. $^1$H NMR (acetone d-6): δ 8.91 (d, 1H), 8.82 (d, 1H), 8.33 (d, 1H), 7.76-7.79 (dd, 1H), 7.07 (s, 1H), 6.96 (d, 1H), 6.6 (br, 2H), 3.90 (s, 3H). LRMS [M+H]=226.1

Example 11

7-fluorobenzo[f][1,7]naphthyridin-5-amine

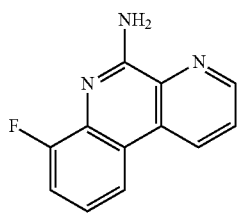 [SMILES: Nc1nc2c(F)cccc2c2cccnc12]

Step 1: tert-butyl 2-fluorophenylcarbamate

To a solution of 2-fluoroaniline (1.0 eq.) in tetrahydrofuran (0.2 M) at 0° C. under N$_2$ atmosphere was added dropwise 1M NaHMDS (2.5 eq.). The reaction was stirred for 15 minutes at 0° C., and a solution of di-tert-butyl dicarbonate in tetrahydrofuran was added. The reaction was warmed to room temperature overnight. The solvent was evaporated, and the resulting residue was quenched with 0.1N HCl aqueous solution. The aqueous suspension was extracted twice with ethyl acetate. The combined organic layers were washed with brine, dried over anhydrous MgSO$_4$, and concentrated en vacuo. The crude material was purified by flash chromatography on a COMBIFLASH® system (ISCO) using 0-5% ethyl acetate in hexane to give product as light yellow oil.

Step 2:
2-(tert-butoxycarbonylamino)-3-fluorophenylboronic acid

To a solution of Cert-butyl 2-fluorophenylcarbamate (from step 1) (1.0 eq.) in tetrahydrofuran (0.25 M) at −78° C. under N$_2$ atmosphere was added dropwise 1.7 M tert-butyllithium (2.4 eq.). The reaction was warmed to −40° C. slowly over 2 hours, and neat trimethyl borate (3.8 eq.) was added. The reaction was warmed to room temperature over 30 minutes. An aqueous solution of 1N NaOH was slowly added to the reaction and stirred for 15 minutes. The mixture was poured into ethyl acetate and acidified with 3N HCl to dissolve the solids. The aqueous layer was extracted twice with ethyl acetate, and the combined organic layers were washed with brine, dried over anhydrous MgSO$_4$, and concentrated en vacuo. The resulting solids were stirred in 1:1 ether/hexane, filtered, and dried. The solids were carried onto the next step without further purification.

Step 3: 7-fluorobenzo[f][1,7]naphthyridin-5-amine

A solution of 2-(tert-butoxycarbonylamino)-3-fluorophenylboronic acid (from step 2) (1.0 eq.) and 3-bromopicolino-nitrile (1.0 eq.) in toluene (0.44 M) was mixed with tetrakis(triphenyl-phosphine)palladium (5 mol %) and 2N aqueous potassium carbonate solution (2.0 eq.). The reaction was heated to 100° C. and stirred overnight. After cooling to ambient temperature, the reaction content was diluted with 2% methanol in dichloromethane and water. The two phases were separated, and the aqueous layer was extracted twice with 2% methanol in dichloromethane. The combined organic layers were washed with brine, dried over anhydrous MgSO$_4$, and concentrated en vacuo. After workup, the crude product was suspended in hot toluene, centrifuged (2500 rpm, 5 min), and the supernatant was removed. The suspension, centrifugation, and removal of supernatant steps were repeated with hot ethyl acetate, ether, and hexane to give a pure solid. $^1$H NMR (acetone d-6): δ 9.04 (d, 1H), 8.96 (d, 1H), 8.27 (d, 1H), 7.86-7.90 (dd, 1H), 7.28-7.34 (m, 2H), 6.9 (br, 2H). LRMS [M+H]=214.1

Example 12

8-(methylsulfonyl)benzo[f][1,7]naphthyridin-5-amine

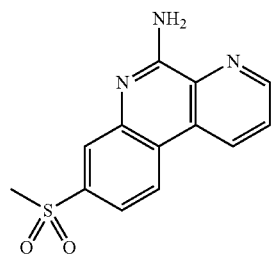 [SMILES: CS(=O)(=O)c1ccc2c(c1)nc(N)c1ncccc12]

Step 1: 2-bromo-5-(methylsulfonyl)aniline

A solution of 1-bromo-4-(methylsulfonyl)-2-nitrobenzene (1.0 eq.), iron powder (3.0 eq.), and concentrated HCl (1.04 eq.) were mixed together in ethanol (0.64 M) and heated to reflux. The reaction was stirred for 24 hours, and the solvent was evaporated. The resulting residue was diluted with ethyl acetate and saturated aqueous ammonium chloride solution. The aqueous layer was extracted three times with ethyl acetate, and the combined organic layers were washed with water, brine, dried over anhydrous MgSO$_4$, and concentrated en vacuo. The crude material was purified by triturating in 1:1 hexane/ether to give a light yellow solid.

Step 2: tert-butyl 2-bromo-5-(methylsulfonyl)phenylcarbainate

To a solution of 2-bromo-5-(methylsulfonyl)aniline (from step 1) (1.0 eq.) in tetrahydrofuran (0.2 M) at 0° C. under $N_2$ atmosphere was added dropwise 1M NaHMDS (2.5 eq.). The reaction was stirred for 15 minutes at 0° C., and a solution of di-tert-butyl dicarbonate in tetrahydrofuran was added. The reaction was warmed to room temperature overnight. The solvent was evaporated, and the resulting residue was quenched with 0.1N HCl aqueous solution. The aqueous suspension was extracted twice with ethyl acetate. The combined organic layers were washed with brine, dried over anhydrous $MgSO_4$, and concentrated en vacuo. The crude material was purified by flash chromatography on a COMBIFLASH® system (ISCO) using 0-5% ethyl acetate in hexane to give tert-butyl 2-bromo-5-(methylsulfonyl)phenylcarbamate.

Step 3: tert-butyl 5-(methylsulfonyl)-2-(4,4,5,5-tetramethyl-1,3,2-dioxaborolan-2-yl)phenylcarbamate Tert-butyl 2-bromo-5-(methylsulfonyl)phenylcarbamate (from step 2) (1.0 eq.), 4,4,4',4',5,5,5',5'-octamethyl-2,2'-bi (1,3,2-dioxaborolane) (1.5 eq.), dichloro[1,1'-bis(diphenylphosphino)ferrocene]palladium (II) (5%), and sodium acetate (4.5 eq.) were mixed in dioxane (0.2 M) under $N_2$ atmosphere. The reaction was heated to 100° C. and stirred overnight. The resulting suspension was cooled to ambient temperature, diluted with ether, filtered through celite, and the filtrate was concentrated en vacuo. The crude material was purified by flash chromatography on a COMBIFLASH® system (ISCO) using 0-50% ethyl acetate in hexane to give a solid which was then triturated in 10% ether/hexane to give tert-butyl 5-(methylsulfonyl)-2-(4,4,5,5-tetramethyl-1,3,2-dioxaborolan-2-yl)phenylcarbamate as a white solid.

Step 4: 8-(methylsulfonyl)benzo[f][1,7]naphthyridin-5-amine

A solution of tert-butyl 5-(methylsulfonyl)-2-(4,4,5,5-tetramethyl-1,3,2-dioxaborolan-2-yl)phenylcarbamate (from step 3) (1.0 eq.) and 3-bromopicolino-nitrile (1.0 eq.) in toluene (0.24 M) was mixed with tetrakis(triphenyl-phosphine) palladium (5 mol %) and 2N aqueous potassium carbonate solution (4.0 eq.). The reaction was heated to 100° C. and stirred overnight. After cooling to ambient temperature, the reaction content was diluted with 2% methanol in dichloromethane and water. The two phases were separated, and the aqueous layer was extracted twice with 2% methanol in dichloromethane. The combined organic layers were washed with brine, dried over anhydrous $MgSO_4$, and concentrated en vacuo. The crude material was purified by flash chromatography on a COMBIFLASH® system (ISCO) using 0-5% methanol in dichloromethane to give a solid which was then triturated in 1:1 hexane/ethyl acetate to give 8-(methylsulfonyl)benzo[f][1,7]naphthyridin-5-amine $^1$H NMR (acetone d-6): δ 9.16 (d, 1H), 9.03 (d, 1H), 8.71 (d, 1H), 8.11 (s, 1H), 7.93-7.96 (dd, 1H), 7.81 (d, 1H), 7.0 (br, 2H), 3.19 (s, 3H). LRMS [M+H]=274.1

Example 13

8-(trifluoromethyl)benzo[f][1,7]naphthyridin-5-amine

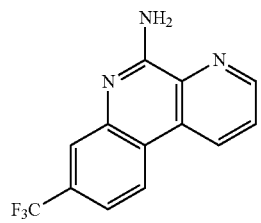 [SMILES: Nc1nc2cc(C(F)(F)F)ccc2c2cccnc12]

Step 1: tert-butyl 2-bromo-5-(trifluoromethyl)phenylcarbamate

To a solution of 2-bromo-5-(trifluoromethyl)aniline (1.0 eq.) in tetrahydrofuran (0.2 M) at 0° C. under $N_2$ atmosphere was added dropwise 1M NaHMDS (2.5 eq.). The reaction was stirred for 15 minutes at 0° C., and a solution of di-tert-butyl dicarbonate in tetrahydrofuran was added. The reaction was warmed to room temperature overnight. The solvent was evaporated, and the resulting residue was quenched with 0.1N HCl aqueous solution. The aqueous suspension was extracted twice with ethyl acetate. The combined organic layers were washed with brine, dried over anhydrous $MgSO_4$, and concentrated en vacuo. The crude material was purified by flash chromatography on a COMBIFLASH® system (ISCO) using 0-5% ethyl acetate in hexane to give product as light yellow oil.

Step 2: tert-butyl 2-(4,4,5,5-tetramethyl-1,3,2-dioxaborolan-2-yl)-5-(trifluoromethyl)phenylcarbamate Tert-butyl 2-bromo-5-(trifluoromethyl)phenylcarbamate (from step 1) (1.0 eq.), 4,4,4',4',5,5,5',5'-octamethyl-2,2'-bi (1,3,2-dioxaborolane) (1.5 eq.), dichloro[1,1'-bis(diphenylphosphino)feffocene]palladium (II) (5%), and sodium acetate (4.5 eq.) were mixed in dioxane (0.2 M) under $N_2$ atmosphere. The reaction was heated to 100° C. and stirred overnight. The resulting suspension was cooled to ambient temperature, diluted with ether, filtered through celite, and the filtrate was concentrated en vacuo. The crude material was purified by flash chromatography on a COMBIFLASH® system (ISCO) using 0-10% ether in hexane to give an impure product which was carried onto the next step without further purification.

Step 3: 8-(trifluoromethyl)benzo[f][1,7]naphthyridin-5-amine

A solution of tert-butyl 2-(4,4,5,5-tetramethyl-1,3,2-dioxaborolan-2-yl)-5-(trifluoromethyl)phenylcarbamate (from step 2) (1.0 eq.) and 3-bromopicolino-nitrile (1.0 eq.) in toluene (0.24 M) was mixed with tetrakis(triphenyl-phosphine) palladium (5 mol %) and 2N aqueous potassium carbonate solution (4.0 eq.). The reaction was heated to 100° C. and stirred overnight. After cooling to ambient temperature, the reaction content was diluted with 2% methanol in dichloromethane and water. The two phases were separated, and the aqueous layer was extracted twice with 2% methanol in dichloromethane. The combined organic layers were washed with brine, dried over anhydrous MgSO₄, and concentrated en vacuo. The crude product was purified by flash chromatography on a COMBIFLASH® system (ISCO) using 0-40% ethyl acetate in toluene to give a solid which was then triturated in 10% ethyl acetate in hexane to give 8-(trifluoromethyl)benzo[f][1,7]naphthyridin-5-amine. ¹H NMR (acetone d-6): δ 9.13 (d, 1H), 9.00 (d, 1H), 8.67 (d, 1H), 7.91-7.94 (dd, 1H), 7.86 (s, 1H), 7.58 (d, 1H), 6.9 (br, 2H). LRMS [M+H]= 264.1

Example 14

8-fluorobenzo[f][1,7]naphthyridin-5-amine

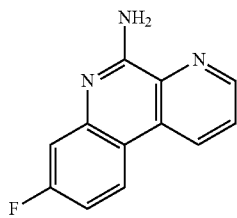 [SMILES: Nc1nc2cc(F)ccc2c2cccnc12]

Step 1: tert-butyl 2-bromo-5-fluorophenylcarbamate

To a solution of 2-bromo-5-fluoroaniline (1.0 eq.) in tetrahydrofuran (0.2 M) at 0° C. under N₂ atmosphere was added dropwise 1M NaHMDS (2.5 eq.). The reaction was stirred for 15 minutes at 0° C., and a solution of di-tert-butyl dicarbonate in tetrahydrofuran was added. The reaction was warmed to room temperature overnight. The solvent was evaporated, and the resulting residue was quenched with 0.1N HCl aqueous solution. The aqueous suspension was extracted twice with ethyl acetate. The combined organic layers were washed with brine, dried over anhydrous MgSO₄, and concentrated en vacuo. The crude material was purified by flash chromatography on a COMBIFLASH® system (ISCO) using 0-5% ethyl acetate in hexane to give the product as light yellow oil.

Step 2: tert-butyl 5-fluoro-2-(4,4,5,5-tetramethyl-1,3, 2-dioxaborolan-2-yl)phenylcarbamate Tert-butyl 2-bromo-5-fluorophenylcarbamate (from step 1) (1.0 eq.), 4,4,4',4',5,5,5',5'-octamethyl-2,2'-bi(1,3,2-dioxaborolane) (1.5 eq.), dichloro[1,1'-bis(diphenylphosphino)ferrocene]palladium (II) (5%), and sodium acetate (4.5 eq.) were mixed in dioxane (0.2 M) under N₂ atmosphere. The reaction was heated to 100° C. and stirred overnight. The resulting suspension was cooled to ambient temperature, diluted with ether, filtered through celite, and the filtrate was concentrated en vacuo. The crude material was purified by flash chromatography on a COMBIFLASH® system (ISCO) using 0-5% ether in hexane to give the product as a yellow solid.

Step 3: 8-fluorobenzo[f][1,7]naphthyridin-5-amine

A solution of tert-butyl 5-fluoro-2-(4,4,5,5-tetramethyl-1, 3,2-dioxaborolan-2-yl)phenylcarbamate (from step 2) (1.0 eq.) and 3-bromopicolino-nitrile (1.0 eq.) in toluene (0.24 M) was mixed with tetrakis(triphenyl-phosphine)palladium (5 mol %) and 2N aqueous potassium carbonate solution (4.0 eq.). The reaction was heated to 100° C. and stirred overnight. After cooling to ambient temperature, the reaction content was diluted with 2% methanol in dichloromethane and water. The two phases were separated, and the aqueous layer was extracted twice with 2% methanol in dichloromethane. The combined organic layers were washed with brine, dried over anhydrous MgSO₄, and concentrated en vacuo. The crude product was purified by flash chromatography on a COMBIFLASH® system (ISCO) using 0-40% ethyl acetate in toluene to give a solid which was then triturated in 10% ethyl acetate in hexane to give 8-fluorobenzo[f][1,7]naphthyridin-5-amine. ¹H NMR (acetone d-6): δ 9.00 (d, 1H), 8.90 (d, 1H), 8.46-8.50 (dd, 1H), 7.83-7.87 (dd, 1H), 7.26 (d, 1H), 7.15 (t, 1H), 6.9 (br, 2H). LRMS [M+H]=214.1

Example 15

5-aminobenzo[f][1,7]naphthyridin-3(4H)-one

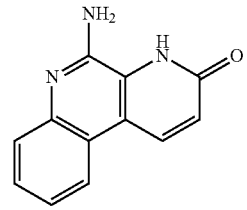 [SMILES: Nc1nc2ccccc2c2ccc(=O)[nH]c12]

Step 1: 3-bromo-2-cyanopyridine 1-oxide

To a solution of 3-bromopicolinonitrile (1.0 eq.) in chloroform (0.3 M) was added 77% meta-chloroperbenzoic acid (mCPBA) (1.8 eq.) and heated at 60° C. for 2 days. After cooling to room temperature, Ca(OH)₂ (2.5 eq.) was added, and the resulting precipitate was stirred for 30 minutes. The precipitate was filtered and washed with 5% methanol in dichloromethane. The filtrate was washed with saturated aqueous NaHCO₃ solution. The aqueous layer was extracted several times with 3% methanol in dichloromethane. The combined organic layers were dried over anhydrous MgSO₄ and concentrated en vacuo. The crude product was stirred in hot hexane/ethyl acetate (1:1), filtered, and dried to give the desired product as a white solid.

Step 2: 3-bromo-6-oxo-1,6-dihydropyridine-2-carbonitrile

A solution of 3-bromo-2-cyanopyridine 1-oxide (from step 1) in acetic anhydride (0.5 M) was heated at 150° C. for 24 hours. The reaction was cooled to room temperature, and the solvent was removed en vacuo. The residue was purified by a COMBIFLASH® system (ISCO) using 0-90% ethyl acetate in hexane to give the O-acetate which was hydrolyzed in 2N NaOH/methanol (1:1, 0.2 M) at room temperature for 2 hours. The resulting mixture was diluted with water and acidified with 5% citric acid. The pale yellow precipitate was filtered and washed with 9:1 hexane/ethyl acetate and ether to give 3-bromo-6-oxo-1,6-dihydropyridine-2-carbonitrile.

Step 3: 3-bromo-6-(tert-butyldimethylsilyloxy)picohnonitrile

A solution of 3-bromo-6-oxo-1,6-dihydropyridine-2-carbonitrile (from step 2) (1.0 eq.) tert-butyldimethylsilylchloride (TBSCl) (1.8 eq.), and imidazole (2.5 eq.) in DMF (0.2 M) was heated to 60° C. and stirred overnight. The reaction mixture was diluted with water and extracted with ether. The combined organic layers were dried over anhydrous MgSO₄ and concentrated en vacuo. The residue was purified by a COMBIFLASH® system (ISCO) using 0-20% ethyl acetate in hexane to give 3-bromo-6-(cert-butyldimethylsilyloxy)picolinonitrile.

Step 4: 3-(tert-butyldimethylsilyloxy)benzo[f][1,7]naphthyridin-5-amine

A solution of 2-(tert-butoxycarbonylamino)phenylboronic acid (1.0 eq.) and 3-bromo-6-(tert-butyldimethylsilyloxy)picolinonitrile (from step 3) (1.0 eq.) in toluene/ethanol (10:1, 0.2 M) was mixed with tetrakis(triphenyl-phosphine)palladium (5 mol %) and 2N aqueous potassium carbonate solution (2.0 eq.). The reaction was heated to 100° C. and stirred overnight. After cooling to ambient temperature, the reaction content was diluted with 2% methanol in dichloromethane and water. The two phases were separated, and the aqueous layer was extracted twice with 2% methanol in dichloromethane. The combined organic layers were washed with brine, dried over anhydrous MgSO₄, and concentrated en vacuo. The crude material was purified by flash chromatography on a COMBIFLASH® system (ISCO) using 0-50% ethyl acetate in hexane to give a solid.

Step 5: 5-aminobenzo[f][1,7]naphthyridin-3(4H)-one

To a solution of 3-(tert-butyldimethylsilyloxy)benzo[f][1,7]naphthyridin-5-amine (from step 4) (1.0 eq.) in tetrahydrofuran (0.05 M) was added tetra-n-butylammonium fluoride (TBAF) (1.0 eq.) and acetic acid (1.0 eq.). The reaction was stirred for 15 minutes, and then concentrated en vacuo. The crude residue was suspended in water and neutralized by addition of saturated aqueous NaHCO₃ solution to pH 7. The solids were filtered, washed with acetone, and dried to give 5-aminobenzo[f][1,7]naphthyridin-3(4H)-one. ¹H NMR (DMSO d-6): δ 8.59 (d, 1H), 8.20 (d, 1H), 7.49 (d, 1H), 7.37-7.41 (dd, 1H), 7.23-7.27 (dd, 1H), 6.88 (br, 2H), 6.79 (d, 1H). LRMS [M+H]=212.1

Example 16

3-methoxybenzo[f][1,7]naphthyridin-5-amine

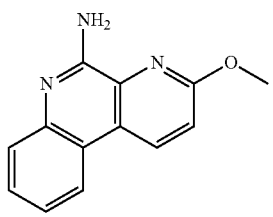 [SMILES: COc1ccc2c(n1)c(N)nc1ccccc12]

Step 1: 3-bromo-6-methoxypicolinonitrile

A solution of 3-bromo-6-oxo-1,6-dihydropyridine-2-carbonitrile (from Example 15/Step 2) (1.0 eq.), silver carbonate (1.3 eq.), and iodomethane (1.2 eq.) in toluene (0.2 M) was stirred in the dark at room temperature overnight. The solvent was concentrated en vacuo, and the resulting residue was purified by a COMBIFLASH® system (ISCO) using 0-80% ethyl acetate in hexane to give 3-bromo-6-methoxypicolinonitrile.

Step 2: 3-methoxybenzo[f][1,7]naphthyridin-5-amine

A solution of 2-(tert-butoxycarbonylamino)phenylboronic acid (1.0 eq.) and 3-bromo-6-methoxypicolinonitrile (from step 1) (1.0 eq.) in toluene (0.44 M) was mixed with tetrakis(triphenyl-phosphine)palladium (5 mol %) and 2N aqueous potassium carbonate solution (2.0 eq.). The reaction was heated to 100° C. and stirred overnight. After cooling to ambient temperature, the reaction content was diluted with 2% methanol in dichloromethane and water. The two phases were separated, and the aqueous layer was extracted twice with 2% methanol in dichloromethane. The combined organic layers were washed with brine, dried over anhydrous MgSO₄, and concentrated en vacuo. The crude product was purified by flash chromatography on a COMBIFLASH® system (ISCO) using 0-50% ethyl acetate in hexane to give 3-methoxybenzo[f][1,7]naphthyridin-5-amine as a yellow solid. ¹H NMR (acetone d-6): δ 8.91 (d, 1H), 8.34 (d, 1H), 7.63 (d, 1H), 7.51-7.53 (dd, 1H), 7.27-7.33 (m, 2H), 6.65 (br, 2H), 4.11 (s, 3H). LRMS [M+H]=226.1

Example 17

3-butoxybenzo[f][1,7]naphthyridin-5-amine

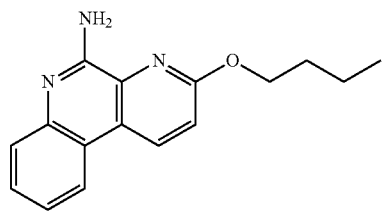 [SMILES: CCCCOc1ccc2c(n1)c(N)nc1ccccc12]

Step 1: 3-bromo-6-butoxypicolinonitrile

A solution of 3-bromo-6-oxo-1,6-dihydropyridine-2-carbonitrile (from Example 15/Step 2) (1.0 eq.), potassium carbonate (1.3 eq.), and 1-iodobutane (1.2 eq.) in acetone (0.3 M) was stirred at 70° C. overnight. The solvent was concentrated en vacuo, and the resulting residue was taken up in water and ethyl acetate. The aqueous layer was extracted with ethyl acetate three times. The combined organic layers were washed with brine, dried over anhydrous MgSO₄, and concentrated en vacuo. The crude product was purified by a COMBIFLASH® system (ISCO) using 0-30% ethyl acetate in hexane to give a colorless solid.

Step 2: 3-butoxybenzo[f][1,7]naphthyridin-5-amine

A solution of 2-(tert-butoxycarbonylamino)phenylboronic acid (1.0 eq.) and 3-bromo-6-butoxypicolinonitrile (from step 1) (1.0 eq.) in toluene (0.44 M) was mixed with tetrakis(triphenyl-phosphine)palladium (5 mol %) and 2N aqueous potassium carbonate solution (2.0 eq.). The reaction was heated to 100° C. and stirred overnight. After cooling to ambient temperature, the reaction content was diluted with 2% methanol in dichloromethane and water. The two phases were separated, and the aqueous layer was extracted twice with 2% methanol in dichloromethane. The combined organic layers were washed with brine, dried over anhydrous MgSO₄, and concentrated en vacuo. The crude product was purified by flash chromatography on a COMBIFLASH® system (ISCO) using 0-5% ethyl acetate in methanol to give 3-butoxybenzo[f][1,7]naphthyridin-5-amine as a white solid. $^1$H NMR (acetone d-6): δ 8.91 (d, 1H), 8.34 (d, 1H), 7.61 (d, 1H), 7.48-7.52 (dd, 1H), 7.27-7.33 (m, 2H), 6.51 (br, 2H), 6.55 (t, 2H), 1.81-1.88 (m, 2H), 1.50-1.59 (m, 2H), 1.00 (t, 3H). LRMS [M+H]=268.1

Example 18

3-(benzyloxy)benzo[f][1,7]naphthyridin-5-amine

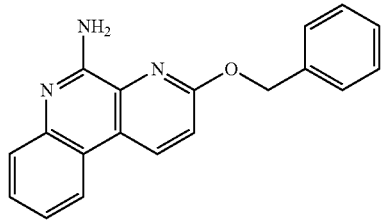 [SMILES: Nc1nc2ccccc2c2ccc(OCc3ccccc3)nc12]

Step 1: 6-(benzyloxy)-3-bromopicolinonitrile

A solution of 3-bromo-6-oxo-1,6-dihydropyridine-2-carbonitrile (from Example 15/Step 2) (1.0 eq.), silver carbonate (1.3 eq.), and benzyl bromide (1.2 eq.) in toluene (0.16 M) was stirred in the dark at 50° C. overnight. The solvent was concentrated en vacuo, and the resulting residue was purified by a COMBIFLASH® system (ISCO) using 0-20% ethyl acetate in hexane to give 6-(benzyloxy)-3-bromopicolinonitrile.

Step 2: 3-(benzyloxy)benzo[f][1,7]naphthyridin-5-amine

A solution of 2-(tert-butoxycarbonylamino)phenylboronic acid (1.0 eq.) and 6-(benzyloxy)-3-bromopicolinonitrile (from step 1) (1.0 eq.) in toluene (0.44 M) was mixed with tetrakis(triphenyl-phosphine)palladium (5 mol %) and 2N aqueous potassium carbonate solution (2.0 eq.). The reaction was heated to 100° C. and stirred overnight. After cooling to ambient temperature, the reaction content was diluted with 2% methanol in dichloromethane and water. The two phases were separated, and the aqueous layer was extracted twice with 2% methanol in dichloromethane. The combined organic layers were washed with brine, dried over anhydrous MgSO$_4$, and concentrated en vacuo. The crude product was purified by flash chromatography on a COMBIFLASH® system (ISCO) using 0-50% ethyl acetate in hexane to give 3-(benzyloxy)benzo[f][1,7]naphthyridin-5-amine as a yellow solid. $^1$H NMR (acetone d-6): δ 8.95 (d, 1H), 8.35 (d, 1H), 7.58-7.63 (m, 2H), 7.49-7.53 (dd, 1H), 7.30-7.44 (m, 5H), 6.61 (br, 2H), 5.64 (s, 2H). LRMS [M+H]=302.1

Example 19

3-methylbenzo[f][1,7]naphthyridin-5-amine

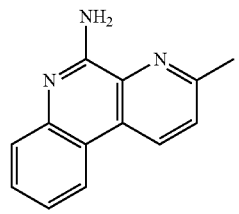 [SMILES: Cc1ccc2c(n1)c(N)nc1ccccc12]

Step 1: 5-bromo-2-methylpyridine 1-oxide

To a solution of 5-bromo-2-methylpyridine (1.0 eq.) in chloroform (0.38 M) was added 77% meta-chloroperbenzoic acid (mCPBA) (4.0 eq.) and heated at 60° C. for 20 hours. After cooling to room temperature, Ca(OH)$_2$ (5.3 eq.) was added, and the resulting precipitate was stirred for 30 minutes. The precipitate was filtered and washed with 3:1 CHCl$_3$/methanol. The filtrate was concentrated en vacuo to give a solid, which was stirred in 30% ethyl acetate in hexane and filtered to give the desired N-oxide. The filtrate was concentrated en vacuo, and the residue was purified by a COMBIFLASH® system (ISCO) using 0-100% ethyl acetate in hexane to give more of the desired N-oxide. The two batches were combined and carried onto the next step.

Step 2: 3-bromo-6-methylpicolinonitrile

To a solution of 5-bromo-2-methylpyridine 1-oxide (from step 1) (1.0 eq.) in acetonitrile (0.2 M) was added trimethylsilyl cyanide (TMSCN) (4.0 eq.) and triethylamine (3.0 eq.). The reaction was heated at 100° C. overnight. After cooling to room temperature, the solvent was concentrated en vacuo, and the residue was purified by a COMBIFLASH® system (ISCO) using 0-50% ethyl acetate in hexane to give 3-bromo-6-methylpicolinonitrile.

Step 3: 3-methylbenzo[f][1,7]naphthyridin-5-amine

A solution of 2-(tert-butoxycarbonylamino)phenylboronic acid (1.0 eq.) and 3-bromo-6-methylpicolinonitrile (from step 2) (1.0 eq.) in toluene (0.44 M) was mixed with tetrakis(triphenyl-phosphine)palladium (5 mol %) and 2N aqueous potassium carbonate solution (2.0 eq.). The reaction was heated to 100° C. and stirred overnight. After cooling to ambient temperature, the reaction content was diluted with 2% methanol in dichloromethane and water. The two phases were separated, and the aqueous layer was extracted twice with 2% methanol in dichloromethane. The combined organic layers were washed with brine, dried over anhydrous MgSO$_4$, and concentrated en vacuo. The crude product was purified by flash chromatography on a COMBIFLASH® system (ISCO) using 0-70% ethyl acetate in hexane to give 3-methylbenzo[f][1,7]naphthyridin-5-amine as a yellow solid. $^1$H NMR (methanol d-4): δ 8.85 (d, 1H), 8.38 (d, 1H), 7.72 (d, 1H), 7.53-7.61 (m, 2H), 7.34-7.38 (dd, 1H), 2.76 (s, 3H). LRMS [M+H]=210.1

Example 20

3-chlorobenzo[f][1,7]naphthyridin-5-amine

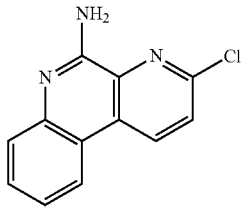 [SMILES: Nc1nc2ccccc2c2ccc(Cl)nc12]

Step 1: 5-bromo-2-chloropyridine 1-oxide

To a solution of 5-bromo-2-chloropyridine (1.0 eq.) in chloroform (0.38 M) was added 77% meta-chloroperbenzoic acid (mCPBA) (4.0 eq.) and heated at 60° C. for 20 hours. After cooling to room temperature, Ca(OH)$_2$ (5.3 eq.) was added, and the resulting precipitate was stirred for 30 minutes. The precipitate was filtered and washed with 3:1 CHCl$_3$/methanol. The filtrate was concentrated en vacuo to give a solid, which was stirred in 30% ethyl acetate in hexane and filtered to give the desired N-oxide. The filtrate was concentrated en vacuo, and the residue was purified by a COMBIFLASH® system (ISCO) using 0-100% ethyl acetate in hexane to give more of the desired N-oxide. The two batches were combined and carried onto the next step.

Step 2: 3-bromo-6-chloropicolinonitrile

To a solution of 5-bromo-2-chloropyridine 1-oxide (from step 1) (1.0 eq.) in acetonitrile (0.2 M) was added trimethylsilyl cyanide (TMSCN) (4.0 eq.) and triethylamine (3.0 eq.). The reaction was heated at 100° C. overnight. After cooling to room temperature, the solvent was concentrated en vacuo, and the residue was purified by a COMBIFLASH® system (ISCO) using 0-40% ethyl acetate in hexane to give 3-bromo-6-chloropicolinonitrile.

Step 3: 3-chlorobenzo[f][1,7]naphthyridin-5-amine

A solution of 2-(tert-butoxycarbonylamino)phenylboronic acid (1.0 eq.) and 3-bromo-6-chloropicolinonitrile (from step 2) (1.0 eq.) in toluene (0.44 M) was mixed with tetrakis(triphenyl-phosphine)palladium (5 mol %) and 2N aqueous potassium carbonate solution (2.0 eq.). The reaction was heated to 100° C. and stirred overnight. After cooling to ambient temperature, the reaction content was diluted with 2% methanol in dichloromethane and water. The two phases were separated, and the aqueous layer was extracted twice with 2% methanol in dichloromethane. The combined organic layers were washed with brine, dried over anhydrous MgSO$_4$, and concentrated en vacuo. The crude product was purified by flash chromatography on a COMBIFLASH® system (ISCO) using 0-50% ethyl acetate in hexane to give a solid, which was then triturated in 10% ethyl acetate in hexane to give 3-chlorobenzo[f][1,7]naphthyridin-5-amine. $^1$H NMR (acetone d-6): δ 9.10 (d, 1H), 8.45 (d, 1H), 7.89 (d, 1H), 7.58-7.65 (m, 2H), 7.35-7.39 (dd, 1H), 6.67 (br, 2H). LRMS [M+H]=230.1

Example 21

N$^3$,N$^3$-dimethylbenzo[f][1,7]naphthyridine-3,5-diamine

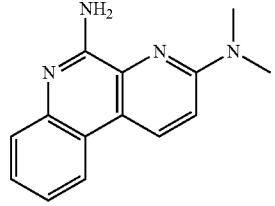 [SMILES: CN(C)c1ccc2c(n1)c(N)nc1ccccc12]

A solution of 3-chlorobenzo[f][1,7]naphthyridin-5-amine (Example 20) (1.0 eq.) was dissolved in 40% aqueous dimethylamine (0.26 M) and heated in a microwave reactor at 100° C. for 30 minutes. The reaction mixture was concentrated en vacuo, and the residue was purified by a COMBIFLASH® system (ISCO) using 0-90% ethyl acetate in hexane to give N$^3$,N$^3$-dimethylbenzo[f][1,7]naphthyridine-3,5-diamine. $^1$H NMR (methanol d-4): δ 8.63 (d, 1H), 8.20 (d, 1H), 7.55 (d, 1H), 7.41-7.45 (dd, 1H), 7.29-7.33 (dd, 1H), 7.27 (d, 1H), 3.26 (s, 6H). LRMS [M+H]=239.1

Example 22

N$^3$-butylbenzo[f][1,7]naphthyridine-3,5-diamine

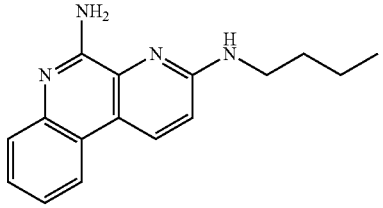 [SMILES: CCCCNc1ccc2c(n1)c(N)nc1ccccc12]

A solution of 3-chlorobenzo[f][1,7]naphthyridin-5-amine (Example 20) (1.0 eq.) was dissolved in n-butylamine (0.1 M) and heated at 110° C. overnight. The reaction mixture was concentrated en vacuo, and the residue was purified by a COMBIFLASH® system (ISCO) using 0-90% ethyl acetate in hexane to give N$^3$-butylbenzo[f][1,7]naphthyridine-3,5-diamine. $^1$H NMR (methanol d-4): δ 8.42 (d, 1H), 8.13 (d, 1H), 7.53 (d, 1H), 7.38-7.42 (dd, 1H), 7.25-7.29 (dd, 1H), 6.96 (d, 1H), 3.48 (t, 2H), 1.63-1.71 (m, 2H), 1.43-1.52 (m, 2H), 0.99 (t, 3H). LRMS [M+H]=267.2

Example 23

3-vinylbenzo[f][1,7]naphthyridin-5-amine

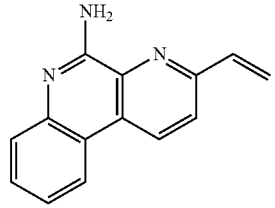 [SMILES: C=Cc1ccc2c(n1)c(N)nc1ccccc12]

A solution of 3-chlorobenzo[f][1,7]naphthyridin-5-amine (Example 20) (1.0 eq.), 4,4,5,5-tetramethyl-2-vinyl-1,3,2-dioxaborolane (1.2 eq.), tetrakis(triphenyl-phosphine)palladium (5 mol %), and 2N aqueous potassium carbonate solution (2.0 eq.) in toluene/ethanol (4:1, 0.1 M) was heated to 100° C. and stirred overnight. After cooling to ambient temperature, the reaction content was diluted with ethyl acetate and water. The two phases were separated, and the aqueous layer was extracted with ethyl acetate three times. The combined organic layers were washed with brine, dried over anhydrous MgSO$_4$, and concentrated en vacuo. The crude material was purified by flash chromatography on a COMBIFLASH® system (ISCO) using 0-50% ethyl acetate in hexane to give a solid, which was then triturated in 10% ethyl acetate in hexane to give 3-vinylbenzo[f][1,7]naphthyridin-5-amine. $^1$H NMR (acetone d-6): δ 8.99 (d, 1H), 8.42 (d, 1H), 8.01 (d, 1H), 7.53-7.62 (m, 2H), 7.30-7.35 (dd, 1H), 7.03-7.10 (dd, 1H), 6.77 (br, 2H), 6.56 (d, 1H), 5.66 (d, 1H). LRMS [M+H]=222.1

Example 24

3-ethylbenzo[f][1,7]naphthyridin-5-amine

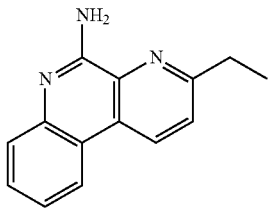 [SMILES: CCc1ccc2c(n1)c(N)nc1ccccc12]

To a solution of 3-vinylbenzo[f][1,7]naphthyridin-5-amine (Example 23) in ethyl acetate/ethanol (1:1, 0.07 M) was added 10% wt palladium on carbon (0.2 eq.). Hydrogen gas was introduced via a balloon, and the reaction was stirred overnight. The mixture was filtered through a pad of celite, washing with dichloromethane. The filtrate was concentrated en vacuo giving 3-ethylbenzo[f][1,7]naphthyridin-5-amine as a white solid. $^1$H NMR (acetone d-6): δ 8.93 (d, 1H), 8.41 (d, 1H), 7.76 (d, 1H), 7.61 (d, 1H), 7.51-7.55 (dd, 1H), 7.30-7.34 (dd, 1H), 6.55 (br, 2H), 6.03 (q, 2H), 1.41 (t, 3H). LRMS [M+H]=224.1

Example 25

3-fluorobenzo[f][1,7]naphthyridin-5-amine

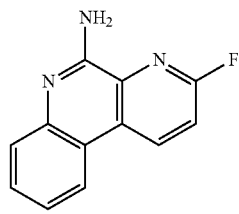 [SMILES: Nc1nc2ccccc2c2ccc(F)nc12]

A solution of 3-chlorobenzo[f][1,7]naphthyridin-5-amine (Example 20) (1.0 eq.), potassium fluoride (3.0 eq.), and 18-crown-6 (0.2 eq.) in N-methylpyrrolidone (NMP) (0.4 M) was heated in a microwave reactor at 210° C. for 80 minutes. After cooling to room temperature, the crude reaction mixture was purified by HPLC using 10-50% acetonitrile in water to give 3-fluorobenzo[f][1,7]naphthyridin-5-amine. $^1$H NMR (acetone d-6): δ 11.40 (br, 2H), 9.38-9.42 (dd, 1H), 8.60 (d, 1H), 7.89-7.92 (dd, 1H), 7.81-7.83 (m, 2H), 7.59-7.66 (m, 1H). LRMS [M+H]=214.1

Example 26

2-(trifluoromethyl)benzo[f][1,7]naphthyridin-5-amine

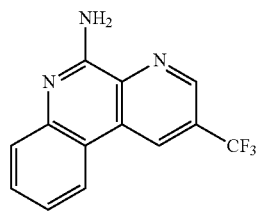 [SMILES: Nc1nc2ccccc2c2cc(C(F)(F)F)cnc12]

Step 1: 3-chloro-5-(trifluoromethyl)picolinaldehyde oxime

A solution of 3-chloro-5-(trifluoromethyl)picolinaldehyde (1.0 eq.), hydroxylamine hydrochloride (5.0 eq.), and pyridine (4.0 eq.) in ethanol was heated to 95° C. and stirred for 1 hour. The reaction was cooled to room temperature and diluted with ethyl acetate and water. The organic layer was washed with brine, water, dried over anhydrous MgSO$_4$, and concentrated en vacuo to give a solid that was carried onto the next step without further purification.

Step 2: 3-chloro-5-(trifluoromethyl)picolinonitrile

A solution of 3-chloro-5-(trifluoromethyl)picolinaldehyde oxime (1.0 eq.) and Burgess reagent (1.5 eq.) in tetrahydrofuran (0.5 M) was heated to 65° C. and stirred for 1 hour. The reaction was cooled to room temperature and diluted with ethyl acetate and water. The organic layer was washed with water, brine, dried over anhydrous MgSO$_4$, and concentrated en vacuo to give a solid that was carried onto the next step without further purification.

Step 3: 2-(trifluoromethyl)benzo[f][1,7]naphthyridin-5-amine

A solution of 2-(tert-butoxycarbonylamino)phenylboronic acid (1.0 eq.) and 3-chloro-5-(trifluoromethyl)picolinonitrile (from step 2) (1.0 eq.) in toluene (0.44 M) was mixed with tetrakis(triphenyl-phosphine)palladium (5 mol %) and 2N aqueous potassium carbonate solution (2.0 eq.). The reaction was heated to 100° C. and stirred overnight. After cooling to ambient temperature, the reaction content was diluted with 2% methanol in dichloromethane and water. The two phases were separated, and the aqueous layer was extracted twice with 2% methanol in dichloromethane. The combined organic layers were washed with brine, dried over anhydrous MgSO$_4$, and concentrated en vacuo. The crude product was purified by flash chromatography on a COMBIFLASH® system (ISCO) using 0-50% ethyl acetate in hexane to give 2-(trifluoromethyl)benzo[f][1,7]naphthyridin-5-amine. $^1$H NMR (acetone d-6): δ 9.44 (s, 1H), 9.20 (s, 1H), 8.65-8.63 (d, 1H), 7.70-7.61 (m, 2H), 7.44-7.36 (m, 1H), 6.84 (br, 2H). LRMS [M+H]=264.2

Example 27

2-methoxybenzo[f][1,7]naphthyridin-5-amine

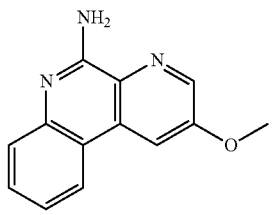 [SMILES: COc1cnc2c(N)nc3ccccc3c2c1]

Step 1: 3-chloro-5-methoxypicolinonitrile

To a solution of 3,5-dichloropicolinonitrile (1.0 eq.) in dimethyl formamide (DMF) (0.5 M) was added sodium methoxide (1.5 eq.) and heated to 75° C. After stirring for 14 hours, the reaction was diluted with ethyl acetate and water. The organic layer was washed with saturated aqueous NaHCO$_3$ three times, water twice, dried over anhydrous MgSO$_4$, and concentrated en vacuo. The crude residue was purified by a COMBIFLASH® system (ISCO) using 15% ethyl acetate in hexane to give a mixture of two methoxy regioisomers, one of which was the desired product. The mixture was carried onto the next step without further purification.

Step 2: 2-methoxybenzo[f][1,7]naphthyridin-5-amine

A solution of 2-(tert-butoxycarbonylamino)phenylboronic acid (1.0 eq.) and 3-chloro-5-methoxypicolinonitrile (from step 1) (1.0 eq.) in toluene (0.44 M) was mixed with tetrakis(triphenyl-phosphine)palladium (5 mol %) and 2N aqueous potassium carbonate solution (2.0 eq.). The reaction was heated to 100° C. and stirred overnight. After cooling to ambient temperature, the reaction content was diluted with 2% methanol in dichloromethane and water. The two phases were separated, and the aqueous layer was extracted twice with 2% methanol in dichloromethane. The combined organic layers were washed with brine, dried over anhydrous MgSO$_4$, and concentrated en vacuo. The crude product was purified by flash chromatography on a COMBIFLASH® system (ISCO) using 50-100% ethyl acetate in hexane to give 2-methoxybenzo[f][1,7]naphthyridin-5-amine.

Example 28

2-(benzyloxy)benzo[f][1,7]naphthyridin-5-amine

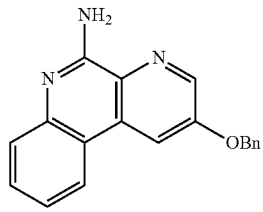 [SMILES: Nc1nc2ccccc2c2cc(OCc3ccccc3)cnc12]

Step 1: 3-(benzyloxy)-5-bromopyridine

A solution of 5-bromopyridin-3-ol (1.0 eq.), benzyl bromide (1.2 eq.), and silver carbonate (1.3 eq.) in toluene (0.1 M) was heated to 50° C. and stirred for 18 hours. After cooling to room temperature, the reaction mixture was filtered, eluting with ethyl acetate. The filtrate was concentrated en vacuo into a residue that was purified by a COMBIFLASH® system (ISCO) using 20% ethyl acetate in hexane to give 3-(benzyloxy)-5-bromopyridine.

Step 2: 3-(benzyloxy)-5-bromopyridine 1-oxide

A solution of 3-(benzyloxy)-5-bromopyridine (from step 1) (1.0 eq.) and meta-chloroperbenzoic acid (mCPBA) (4.0 eq.) in dichloromethane (0.1 M) was stirred at room temperature for 18 hours. The reaction was quenched with saturated aqueous NaHCO$_3$ solution and extracted with dichloromethane three times. The combined organic layers were dried over anhydrous MgSO$_4$ and concentrated en vacuo. The crude residue was purified by a COMBIFLASH® system (ISCO) using 0-100% ethyl acetate in hexane to give 3-(benzyloxy)-5-bromopyridine 1-oxide.

Step 3: 5-(benzyloxy)-3-bromopicolinonitrile

To a solution of 53-(benzyloxy)-5-bromopyridine 1-oxide (from step 2) (1.0 eq.) in acetonitrile (0.2 M) was added trimethylsilyl cyanide (TMSCN) (4.0 eq.) and triethylamine (3.0 eq.). The reaction was heated at 100° C. overnight. After cooling to room temperature, the solvent was concentrated en vacuo, and the residue was purified by a COMBIFLASH® system (ISCO) using 0-40% ethyl acetate in hexane to give a mixture of two benzoxy regioisomers, one of which was the desired product. The mixture was carried onto the next step without further purification.

Step 4: 2-(benzyloxy)benzo[f][1,7]naphthyridin-5-amine

A solution of 2-(tert-butoxycarbonylamino)phenylboronic acid (1.0 eq.) and 5-(benzyloxy)-3-bromopicolinonitrile (from step 3) (1.0 eq.) in toluene (0.44 M) was mixed with tetrakis(triphenyl-phosphine)palladium (5 mol %) and 2N aqueous potassium carbonate solution (2.0 eq.). The reaction was heated to 100° C. and stirred overnight. After cooling to ambient temperature, the reaction content was diluted with 2% methanol in dichloromethane and water. The two phases were separated, and the aqueous layer was extracted twice with 2% methanol in dichloromethane. The combined organic layers were washed with brine, dried over anhydrous MgSO$_4$, and concentrated en vacuo. The crude product was purified by flash chromatography on a COMBIFLASH® system (ISCO) using 50-100% ethyl acetate in hexane to give 2-(benzyloxy)benzo[f][1,7]naphthyridin-5-amine. $^1$H NMR (acetone d-6): δ 8.36 (s, 1H), 7.86 (s, 1H), 7.59-7.56 (d, 2H), 7.46-7.42 (dd, 2H), 7.40-7.37 (d, 1H), 7.20-7.15 (dd, 1H), 7.12-7.09 (d, 1H), 6.88-6.86 (d, 1H), 6.77-6.73 (dd, 1H), 5.51 (s, 2H), 4.74 (br, 2H). LRMS [M+H]=302.3.

Example 29

2-vinylbenzo[f][1,7]naphthyridin-5-amine

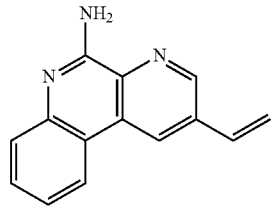 [SMILES: C=Cc1cnc2c(N)nc3ccccc3c2c1]

Step 1: 3-chloro-5-vinylpicolinonitrile

A solution of 3,5-dichloropicolinonitrile (1.0 eq.), 4,4,5,5-tetramethyl-2-vinyl-1,3,2-dioxaborolane (1.0 eq.), tetrakis(triphenyl-phosphine)palladium (5 mol %), and 2N aqueous sodium carbonate solution (3.4 eq.) in toluene/ethanol (2:1, 0.04 M) was stirred at 95° C. overnight. After cooling to ambient temperature, the reaction content was diluted with ethyl acetate and water. The two phases were separated, and the aqueous layer was extracted twice with ethyl acetate. The combined organic layers were washed with brine, dried over anhydrous MgSO$_4$, and concentrated en vacuo. The crude material was purified by flash chromatography on a COMBIFLASH® system (ISCO) using 0-80% ethyl acetate in hexane to give a white solid.

Step 2: 2-vinylbenzo[f][1,7]naphthyridin-5-amine

A solution of 2-(tert-butoxycarbonylamino)phenylboronic acid (1.0 eq.) and 3-chloro-5-vinylpicolinonitrile (from step 1) (1.0 eq.), tetrakis(triphenyl-phosphine)palladium (5 mol %), and 2N aqueous sodium carbonate solution (2.0 eq.) in toluene/ethanol (2:1, 0.03 M) was stirred at 100° C. overnight. After cooling to ambient temperature, the reaction content was diluted with methanol. The insoluble solids were filtered off, and the filtrate was concentrated en vacuo to obtain a crude residue. The crude material was purified by flash chromatography on a COMBIFLASH® system (ISCO) using 0-80% ethyl acetate in hexane to give 2-vinylbenzo[f][1,7]naphthyridin-5-amine as a yellow solid. $^1$H NMR (methanol-d4-CDCl$_3$): δ 8.87 (d, 1H), 8.69 (d, 1H), 8.28 (d, 1H), 7.49-7.58 (m, 2H), 7.32 (dt, 1H), 6.90 (dd, 1H), 6.09 (d, 1H), 5.54 (d, 1H). LRMS [M+H]=222.1.

Example 30

2-ethylbenzo[f][1,7]naphthyridin-5-amine

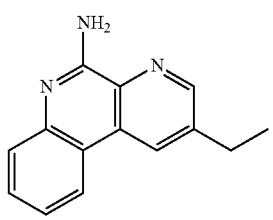 [SMILES: CCc1cnc2c(N)nc3ccccc3c2c1]

To a solution of 2-vinylbenzo[f][1,7]naphthyridin-5-amine (Example 29) in ethyl acetate/methanol (1:4, 0.05 M) was added 10% wt palladium on carbon (0.2 eq.). Hydrogen gas was introduced via a balloon, and the reaction was stirred for 3 hours. The mixture was filtered through a pad of celite, washing with dichloromethane. The filtrate was concentrated en vacuo and purified by a COMBIFLASH® system (ISCO) using 0-80% ethyl acetate in hexane to give 2-ethylbenzo[f][1,7]naphthyridin-5-amine as a solid. $^1$H NMR (methanol-d4): δ 8.78-8.81 (m, 2H), 8.45 (d, 1H), 7.55-7.63 (m, 2H), 7.35-7.40 (m, 1H), 2.97 (q, 2H), 1.43 (t, 2H). LRMS [M+H]=224.1.

Example 31

2-phenylbenzo[f][1,7]naphthyridin-5-amine

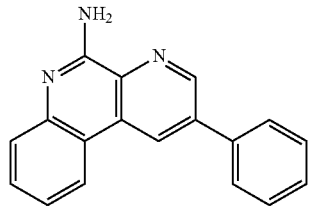 [SMILES: Nc1nc2ccccc2c2cc(-c3ccccc3)cnc12]

Step 1: 3-chloro-5-phenylpicolinonitrile

A solution of 3,5-dichloropicolinonitrile (1.0 eq.), 4,4,5,5-tetramethyl-2-phenyl-1,3,2-dioxaborolane (1.0 eq.), tetrakis(triphenyl-phosphine)palladium (5 mol %), and 2N aqueous sodium carbonate solution (3.4 eq.) in toluene/ethanol (2:1, 0.04 M) was stirred at 100° C. for 2 hours, then 80° C. for 4 hours. After cooling to ambient temperature, the reaction content was diluted with ethyl acetate and water. The two phases were separated, and the aqueous layer was extracted twice with ethyl acetate. The combined organic layers were washed with brine, dried over anhydrous MgSO$_4$, and concentrated en vacuo. The crude material was purified by flash chromatography on a COMBIFLASH® system (ISCO) using 0-80% ethyl acetate in hexane to give a white solid.

Step 2: 2-phenylbenzo[f][1,7]naphthyridin-5-amine

A solution of 2-(tert-butoxycarbonylamino)phenylboronic acid (1.0 eq.) and 3-chloro-5-phenylpicolinonitrile (from step 1) (1.0 eq.), tetrakis(triphenyl-phosphine)palladium (5 mol %), and 2N aqueous sodium carbonate solution (2.0 eq.) in toluene/ethanol (2:1, 0.03 M) was stirred at 100° C. overnight. After cooling to ambient temperature, the reaction content was diluted with methanol. The insoluble solids were filtered off, and the filtrate was concentrated en vacuo to obtain a crude residue. The crude product was purified by flash chromatography on a COMBIFLASH® system (ISCO) using 0-80% ethyl acetate in hexane to give 2-phenylbenzo[f][1,7]naphthyridin-5-amine as a white solid. $^1$H NMR (dmso-d6): δ 9.13 (d, 1H), 9.03 (d, 1H), 8.56 (d, 1H), 7.98 (d, 2H), 7.43-7.56 (m, 5H), 7.27 (m, 1H), 7.13 (bs, 2H). LRMS [M+H]=272.2.

Example 32

(E)-2-styrylbenzo[f][1,7]naphthyridin-5-amine

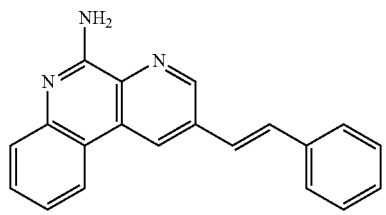 [SMILES: Nc1nc2ccccc2c2cc(/C=C/c3ccccc3)cnc12]

Step 1: (E)-3-chloro-5-styrylpicolinonitrile

A solution of 3,5-dichloropicolinonitrile (1.0 eq.), (E)-4,4,5,5-tetramethyl-2-styryl-1,3,2-dioxaborolane (1.0 eq.), tetrakis(triphenyl-phosphine)palladium (5 mol %), and 2N aqueous sodium carbonate solution (3.4 eq.) in toluene/ethanol (2:1, 0.04 M) was stirred at 100° C. for 2 hours, then 80° C. for 4 hours. After cooling to ambient temperature, the reaction content was diluted with ethyl acetate and water. The two phases were separated, and the aqueous layer was extracted twice with ethyl acetate. The combined organic layers were washed with brine, dried over anhydrous MgSO$_4$, and concentrated en vacuo. The crude product was purified by flash chromatography on a COMBIFLASH® system (ISCO) using 0-80% ethyl acetate in hexane to give a white solid.

Step 2: (E)-2-styrylbenzo[f][1,7]naphthyridin-5-amine

A solution of 2-(tert-butoxycarbonylamino)phenylboronic acid (1.0 eq.) and (E)-3-chloro-5-styrylpicolinonitrile (from step 1) (1.0 eq.), tetrakis(triphenyl-phosphine)palladium (5 mol %), and 2N aqueous sodium carbonate solution (2.0 eq.) in toluene/ethanol (2:1, 0.03 M) was stirred at 100° C. overnight. After cooling to ambient temperature, the reaction content was diluted with methanol. The insoluble solids were filtered off, and the filtrate was concentrated en vacuo to obtain a crude residue. The crude product was purified by flash chromatography on a COMBIFLASH® system (ISCO) using 0-80% ethyl acetate in hexane to give (E)-2-styrylbenzo[f][1,7]naphthyridin-5-amine as a brown solid. $^1$H NMR (dmso-d6): δ 9.22 (d, 1H), 9.06 (d, 1H), 8.51 (d, 1H), 7.78 (d, 1H), 7.66 (d, 2H), 7.46-7.56 (m, 3H), 7.70 (t, 2H), 7.26-7.32 (m, 2H), 7.08 (bs, 2H). LRMS [M+H]=298.2.

Example 33

2-phenethylbenzo[f][1,7]naphthyridin-5-amine

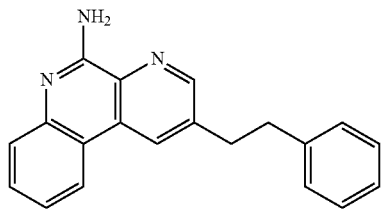 [SMILES: Nc1nc2ccccc2c2cc(CCc3ccccc3)cnc12]

To a solution of (E)-2-styrylbenzo[f][1,7]naphthyridin-5-amine (Example 32) in ethyl acetate/methanol (1:4, 0.05 M) was added 10% wt palladium on carbon (0.2 eq.). Hydrogen gas was introduced via a balloon, and the reaction was stirred for 3 hours. The mixture was filtered through a pad of celite, washing with dichloromethane. The filtrate was concentrated en vacuo and the crude product was purified by flash chromatography on a COMBIFLASH® system (ISCO) using 0-80% ethyl acetate in hexane to give 2-phenethylbenzo[f][1,7]naphthyridin-5-amine as a yellow solid. $^1$H NMR (CDCl$_3$): δ 8.54 (d, 1H), 8.32 (d, 1H), 8.10 (dd, 1H), 7.63 (dd, 1H), 7.51 (m, 1H), 7.03-7.32 (m, 6H), 6.16 (bs, 2H), 3.11 (t, 2H), 2.97 (t, 2H). LRMS [M+H]=300.1.

Example 34

(E)-2-(3-methoxyprop-1-enyl)benzo[f][1,7]naphthyridin-5-amine

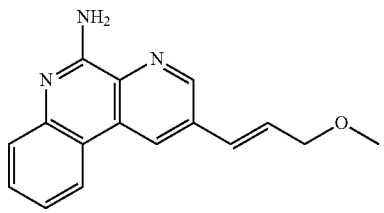 [SMILES: COC/C=C/c1cnc2c(N)nc3ccccc3c2c1]

Step 1: (E)-3-chloro-5-(3-methoxyprop-1-enyl)picolinonitrile

A solution of 3,5-dichloropicolinonitrile (1.0 eq.), (E)-2-(3-methoxyprop-1-enyl)-4,4,5,5-tetramethyl-1,3,2-dioxaborolane (1.0 eq.), tetrakis(triphenyl-phosphine)palladium (5 mol %), and 2N aqueous sodium carbonate solution (3.4 eq.) in toluene/ethanol (2:1, 0.04 M) was stirred at 100° C. for 2 hours, then 80° C. for 4 hours. After cooling to ambient temperature, the reaction content was diluted with ethyl acetate and water. The two phases were separated, and the aqueous layer was extracted twice with ethyl acetate. The combined organic layers were washed with brine, dried over anhydrous MgSO$_4$, and concentrated en vacuo. The crude product was purified by flash chromatography on a COMBIFLASH® system (ISCO) using 0-80% ethyl acetate in hexane to give (E)-3-chloro-5-(3-methoxyprop-1-enyl)picolinonitrile as a white solid.

Step 2: (E)-2-(3-methoxyprop-1-enyl)benzo[f][1,7]naphthyridin-5-amine

A solution of 2-(tert-butoxycarbonylamino)phenylboronic acid (1.0 eq.) and (E)-3-chloro-5-(3-methoxyprop-1-enyl)picolinonitrile (from step 1) (1.0 eq.), tetrakis(triphenyl-phosphine)palladium (5 mol %), and 2N aqueous sodium carbonate solution (2.0 eq.) in toluene/ethanol (2:1, 0.03 M) was stirred at 100° C. overnight. After cooling to ambient temperature, the reaction content was diluted with methanol. The insoluble solids were filtered off, and the filtrate was concentrated en vacuo to obtain a crude residue. The crude product was purified by flash chromatography on a COMBIFLASH® system (ISCO) using 0-80% ethyl acetate in hexane to give (E)-2-(3-methoxyprop-1-enyl)benzo[f][1,7]naphthyridin-5-amine as a yellow solid. $^1$H NMR (dmso-d6): δ 9.24 (d, 1H), 9.18 (d, 1H), 8.54 (d, 1H), 7.52-7.58 (m, 2H), 7.31 (m, 1H), 7.11 (bs, 2H), 6.86-7.00 (m, 2H), 4.18 (d, 2H), 3.36 (s, 3H). LRMS [M+H]=266.2.

Example 35

2-(3-methoxypropyl)benzo[f][1,7]naphthyridin-5-amine

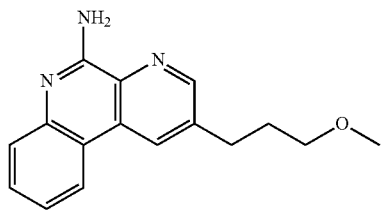 [SMILES: COCCCc1cnc2c(N)nc3ccccc3c2c1]

To a solution of (E)-2-(3-methoxyprop-1-enyl)benzo[f][1,7]naphthyridin-5-amine (Example 34) in ethyl acetate/methanol (1:4, 0.05 M) was added 10% wt palladium on carbon (0.2 eq.). Hydrogen gas was introduced via a balloon, and the reaction was stirred for 3 hours. The mixture was filtered through a pad of celite, washing with dichloromethane. The filtrate was concentrated en vacuo and the crude product was purified by flash chromatography on a COMBIFLASH® system (ISCO) using 0-80% ethyl acetate in hexane to give 2-(3-methoxypropyl)benzo[f][1,7]naphthyridin-5-amine as a white solid. $^1$H NMR (CDCl$_3$): δ 8.64 (d, 1H), 8.46 (d, 1H), 8.19 (d, 1H), 7.66 (d, 1H), 7.53 (m, 1H), 7.31 (m, 1H), 6.56 (bs, 2H), 3.37 (t, 2H), 3.31 (s, 3H), 2.91 (t, 2H), 1.93-2.00 (m, 2H). LRMS [M+H]=268.1.

Example 36

2-(prop-1-en-2-yl)benzo[f][1,7]naphthyridin-5-amine

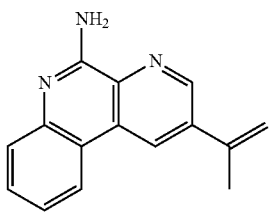 [SMILES: C=C(C)c1cnc2c(N)nc3ccccc3c2c1]

Step 1: 3-chloro-5-(prop-1-en-2-yl)picolinonitrile

A solution of 3,5-dichloropicolinonitrile (1.0 eq.), 4,4,5,5-tetramethyl-2-(prop-1-en-2-yl)-1,3,2-dioxaborolane (1.0 eq.), tetrakis(triphenyl-phosphine)palladium (5 mol %), and 2N aqueous sodium carbonate solution (3.4 eq.) in toluene/ethanol (2:1, 0.04 M) was stirred at 100° C. for 2 hours, then 80° C. for 4 hours. After cooling to ambient temperature, the reaction content was diluted with ethyl acetate and water. The two phases were separated, and the aqueous layer was extracted twice with ethyl acetate. The combined organic layers were washed with brine, dried over anhydrous MgSO$_4$, and concentrated en vacuo. The crude product was purified by flash chromatography on a COMBIFLASH® system (ISCO) using 0-80% ethyl acetate in hexane to give 3-chloro-5-(prop-1-en-2-yl)picolinonitrile as a white solid.

Step 2: 2-(prop-1-en-2-yl)benzo[f][1,7]naphthyridin-5-amine

A solution of 2-(tert-butoxycarbonylamino)phenylboronic acid (1.0 eq.) and 3-chloro-5-(prop-1-en-2-yl)picolinonitrile (from step 1) (1.0 eq.), tetrakis(triphenyl-phosphine)palladium (5 mol %), and 2N aqueous sodium carbonate solution (2.0 eq.) in toluene/ethanol (2:1, 0.03 M) was stirred at 100° C. overnight. After cooling to ambient temperature, the reaction content was diluted with methanol. The insoluble solids were filtered off, and the filtrate was concentrated en vacuo to obtain a crude residue. The crude product was purified by flash chromatography on a COMBIFLASH® system (ISCO) using 0-80% ethyl acetate in hexane to give 2-(prop-1-en-2-yl)benzo[f][1,7]naphthyridin-5-amine as a white solid. $^1$H NMR (dmso-d6): δ 9.03 (d, 1H), 8.96 (d, 1H), 8.55 (d, 1H), 7.47-7.53 (m, 2H), 7.25 (m, 1H), 7.07 (bs, 2H) 5.80 (s, 1H), 5.36 (s, 1H), 2.27 (s, 3H). LRMS [M+H]=236.2.

Example 37

2-isopropylbenzo[f][1,7]naphthyridin-5-amine

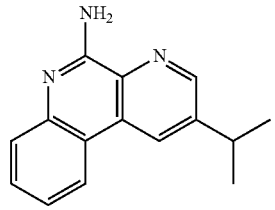 [SMILES: CC(C)c1cnc2c(N)nc3ccccc3c2c1]

To a solution of 2-(prop-1-en-2-yl)benzo[f][1,7]naphthyridin-5-amine (Example 36) in ethyl acetate/methanol (1:4, 0.05 M) was added 10% wt palladium on carbon (0.2 eq.). Hydrogen gas was introduced via a balloon, and the reaction was stirred for 3 hours. The mixture was filtered through a pad of celite, washing with dichloromethane. The filtrate was concentrated en vacuo and the crude product was purified by flash chromatography on a COMBIFLASH® system (ISCO) using 0-80% ethyl acetate in hexane to give 2-isopropylbenzo[f][1,7]naphthyridin-5-amine as a yellow solid. $^1$H NMR (CDCl$_3$): δ 8.69 (d, 1H), 8.49 (d, 1H), 8.25 (dd, 1H), 7.65 (dd, 1H), 7.53 (m, 1H), 7.31 (m, 1H), 6.02 (bs, 2H), 3.15 (septet, 1H), 1.37 (d, 6H). LRMS [M+H]=238.2.

Example 38

1-methylbenzo[f][1,7]naphthyridin-5-amine

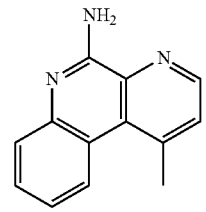 [SMILES: Cc1ccnc2c(N)nc3ccccc3c12]

Step 1: 5-bromo-2-chloro-4-methylpyridine 1-oxide

A solution of 5-bromo-2-chloro-4-methylpyridine (1.0 eq.) and meta-chloroperbenzoic acid (mCPBA) (2.5 eq.) in chloroform (0.1 M) was stirred at 50° C. overnight. After cooling to room temperature, Ca(OH)$_2$ (2.5 eq.) was added to the reaction mixture. The precipitate was filtered and washed with 5% methanol in dichloromethane and ethyl acetate. The filtrate was washed with saturated aqueous Na₂S₂O₃ solution and saturated aqueous NaHCO₃ solution. The combined organic layers were washed with brine, dried over anhydrous MgSO₄, and concentrated en vacuo into a pale solid that was carried onto the next step without further purification.

Step 2: 3-bromo-6-chloro-4-methylpicolinonitrile

To a solution of 5-bromo-2-chloro-4-methylpyridine 1-oxide (from step 1) (1.0 eq.) in acetonitrile (0.2 M) was added TMSCN (4.0 eq.) and triethylamine (3.0 eq.). The reaction was heated at 100° C. overnight. After cooling to room temperature, the solvent was concentrated en vacuo, and the residue was purified by a COMBIFLASH® system (ISCO) using 0-50% ethyl acetate in hexane to give 3-bromo-6-chloro-4-methylpicolinonitrile.

Step 3:
3-chloro-1-methylbenzo[f][1,7]naphthyridin-5-amine

A solution of 2-(tert-butoxycarbonylamino)phenylboronic acid (1.0 eq.) and 3-bromo-6-chloro-4-methylpicolinonitrile (from step 2) (1.0 eq.), tetrakis(triphenyl-phosphine)palladium (5 mol %), and 2N aqueous sodium carbonate solution (2.0 eq.) in toluene/ethanol (2:1, 0.03 M) was stirred at 100° C. overnight. After cooling to ambient temperature, the reaction content was diluted with methanol. The insoluble solids were filtered off, and the filtrate was concentrated en vacuo to obtain a crude residue. The crude product was purified by flash chromatography on a COMBIFLASH® system (ISCO) using 0-80% ethyl acetate in hexane to give 3-chloro-1-methylbenzo[f][1,7]naphthyridin-5-amine as a white solid. ¹H NMR (dmso-d6): δ 8.44 (d, 1H), 7.83 (s, 1H), 7.50-7.58 (m, 2H), 7.02 (bs, 2H), 2.98 (s, 3H). LRMS [M+H]=244.1.

Step 4: 1-methylbenzo[f][1,7]naphthyridin-5-amine

To a solution of 3-chloro-1-methylbenzo[f][1,7]naphthyridin-5-amine (from step 3) in ethyl acetate/methanol (1:2, 0.03 M) was added 10% wt palladium on carbon (0.2 eq.). The reaction vessel was shaken on a hydrogen Parr apparatus under 50 psi of hydrogen overnight. The mixture was filtered through a pad of celite, washing with dichloromethane. The filtrate was concentrated en vacuo and purified by a COMBIFLASH® system (ISCO) using 0-80% ethyl acetate in hexane to give 1-methylbenzo[f][1,7]naphthyridin-5-amine as a white solid. ¹H NMR (CDCl₃): δ 8.63 (d, 1H), 8.44 (d, 1H), 7.71 (dd, 1H), 7.54 (m, 1H), 7.45 (d, 1H), 7.30 (m, 1H), 6.20 (bs, 2H), 3.01 (s, 3H). LRMS [M+H]=210.1.

Example 39 benzo[c][1,8]naphthyridin-6-amine

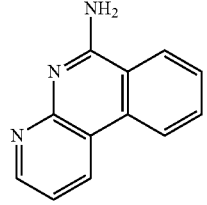 [SMILES: Nc1nc2ncccc2c2ccccc12]

A solution of tert-butyl 3-(4,4,5,5-tetramethyl-1,3,2-dioxaborolan-2-yl)pyridin-2-ylcarbamate (1.0 eq.) and 2-bromobenzonitrile (1.0 eq.), tetrakis(triphenyl-phosphine)palladium (5 mol %), and 2N aqueous sodium carbonate solution (2.0 eq.) in toluene/ethanol (2:1, 0.03 M) was stirred at 100° C. overnight. After cooling to ambient temperature, the reaction content was diluted with methanol. The insoluble solids were filtered off, and the filtrate was concentrated en vacuo to obtain a crude residue. The crude product was purified by flash chromatography on a COMBIFLASH® system (ISCO) using 0-80% ethyl acetate in hexane to give benzo[c][1,8]naphthyridin-6-amine as a white solid. ¹H NMR (methanol-d4): δ 8.88 (dd, 1H), 8.67-8.63 (m, 2H), 8.30 (d, 1H), 7.90 (dt, 1H), 7.74 (dt, 1H), 7.36 (dd, 1H). LRMS [M+H]=196.1

Example 40 pyrido[3,2-f][1,7]naphthyridin-6-amine

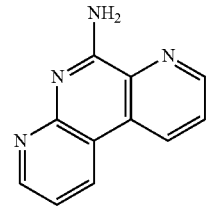 [SMILES: Nc1nc2ncccc2c2cccnc12]

A solution of tert-butyl 3-(4,4,5,5-tetramethyl-1,3,2-dioxaborolan-2-yl)pyridin-2-ylcarbamate (1.0 eq.) and 3-bromopicolinonitrile (1.0 eq.), tetrakis(triphenyl-phosphine)palladium (5 mol %), and 2N aqueous sodium carbonate solution (2.0 eq.) in toluene/ethanol (2:1, 0.03 M) was stirred at 100° C. overnight. After cooling to ambient temperature, the reaction content was diluted with methanol. The insoluble solids were filtered off, and the filtrate was concentrated en vacuo to obtain a crude residue. The crude product was purified by flash chromatography on a COMBIFLASH® system (ISCO) using 0-80% ethyl acetate in hexane to give pyrido[3,2-f][1,7]naphthyridin-6-amine as a white solid. ¹H NMR (dmso-d6): δ 9.14 (dd, 1H), 8.98 (dd, 1H), 8.90 (dd, 1H), 7.93 (dd, 1H), 7.60 (bs, 2H), 7.30 (dd, 1H). LRMS [M+H]=197.

Example 41

2-ethyl-8-methylbenzo[f][1,7]naphthyridin-5-amine

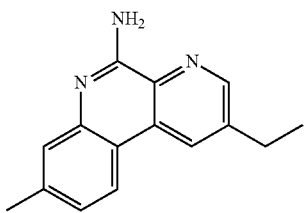 [SMILES: CCc1cnc2c(N)nc3cc(C)ccc3c2c1]

Step 1:
8-methyl-2-vinylbenzo[f][1,7]naphthyridin-5-amine

A solution of tert-butyl 5-methyl-2-(4,4,5,5-tetramethyl-1,3,2-dioxaborolan-2-yl)phenylcarbamate (from Example 5/step 2) (1.0 eq.) and 3-chloro-5-vinylpicolinonitrile (from Example 29/Step 1) (1.0 eq.), tetrakis(triphenyl-phosphine) palladium (5 mol %), and 2N aqueous sodium carbonate solution (2.0 eq.) in toluene/ethanol (2:1, 0.03 M) was stirred at 100° C. overnight. After cooling to ambient temperature, the reaction content was diluted with methanol. The insoluble solids were filtered off, and the filtrate was concentrated en vacuo to obtain a crude residue. The crude material was purified by flash chromatography on a COMBIFLASH® system (ISCO) using 0-80% ethyl acetate in hexane to give 8-methyl-2-vinylbenzo[f][1,7]naphthyridin-5-amine as a yellow solid.

Step 2: 2-ethyl-8-methylbenzo[f][1,7]naphthyridin-5-amine

To a solution of 8-methyl-2-vinylbenzo[f][1,7]naphthyridin-5-amine (from the previous step) in ethyl acetate/methanol (1:4, 0.05 M) was added 10% wt palladium on carbon (0.2 eq.). Hydrogen gas was introduced via a balloon, and the reaction was stirred for 3 hours. The mixture was filtered through a pad of celite and washed with dichloromethane. The filtrate was concentrated en vaccuo and purified by a COMBIFLASH® system (ISCO) using 0-80% ethyl acetate in hexane to give 2-ethyl-8-methylbenzo[f][1,7]naphthyridin-5-amine as an off white solid. $^1$H NMR (CDCl$_3$): δ 8.61 (d, 1H), 8.42 (d, 1H), 8.10 (d, 1H), 7.44 (s, 1H), 7.12 (dd, 1H), 6.00 (bs, 2H), 2.84 (q, 2H), 2.45 (s, 3H), 1.33 (t, 3H). LRMS [M+H]=238.1.

Example 42

(5-amino-8-methylbenzo[f][1,7]naphthyridin-2-yl)methanol

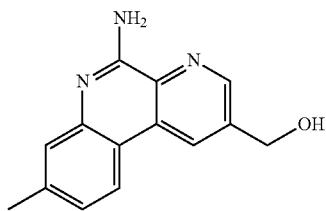 [SMILES: Cc1ccc2c(c1)nc(N)c1ncc(CO)cc12]

Step 1: ethyl 5-chloro-6-cyanonicotinate

A solution of ethyl 5,6-dichloronicotinate (1 eq), zinc cyanide (0.75 eq) and tetrakis(triphenyl-phosphine)palladium (0.10 eq.) in DMF (0.3 M) was degassed and then heated at 100° C. for 3 hours. Solvent was removed en vaccuo to obtain a crude residue. The crude material was purified by flash chromatography on a COMBIFLASH® system (ISCO) using 0-80% ethyl acetate in hexane to give ethyl 5-chloro-6-cyanonicotinate as a white solid.

Step 2: ethyl 5-amino-8-methylbenzo[f][1,7]naphthyridine-2-carboxylate

A solution of tert-butyl 5-methyl-2-(4,4,5,5-tetramethyl-1,3,2-dioxaborolan-2-yl)phenylcarbamate (from Example 5/step 2) (1.0 eq.) and ethyl 5-chloro-6-cyanonicotinate (from the previous step) (1.0 eq.), tetrakis(triphenyl-phosphine)palladium (5 mol %), and 2N aqueous sodium carbonate solution (2.0 eq.) in toluene/ethanol (2:1, 0.03 M) was stirred at 100° C. overnight. After cooling to ambient temperature, the reaction content was diluted with methanol. The insoluble solids were filtered off, and the filtrate was concentrated en vaccuo to obtain a crude residue. The crude material was purified by flash chromatography on a COMBIFLASH® system (ISCO) using 0-80% ethyl acetate in hexane to give ethyl 5-amino-8-methylbenzo[f][1,7]naphthyridine-2-carboxylate.

Step 3: 2-ethyl-8-methylbenzo[f][1,7]naphthyridin-5-amine

To a stirred solution of ethyl 5-amino-8-methylbenzo[f][1,7]naphthyridine-2-carboxylate (from the previous step) in THF (0.2 M) cooled in an ice-water bath was added 1 N solution of super hydride in THF (10 eq.). Upon completion of the reaction the reaction was quenched with 1 N HCl, and extracted with EtOAc. Combined organic extracts were concentrated en vaccuo to obtain a crude residue. The crude material was purified by flash chromatography on a COMBIFLASH® system (ISCO) using 0-80% ethyl acetate in hexane to give(5-amino-8-methylbenzo[f][1,7]naphthyridin-2-yl)methanol as a white solid. $^1$H NMR (CDCl$_3$): δ 8.68 (d, 1H), 8.52 (d, 1H), 8.04 (d, 1H), 7.44 (s, 1H), 7.12 (dd, 1H), 6.00 (bs, 2H), 4.90 (s, 2H), 2.45 (s, 3H). LRMS [M+H]=240.1

Example 43

8-methyl-2-propylbenzo[f][1,7]naphthyridin-5-amine

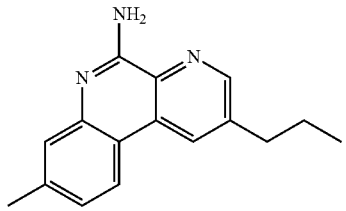 [SMILES: CCCc1cnc2c(N)nc3cc(C)ccc3c2c1]

Step 1: (E)-3-chloro-5-(prop-1-enyl)picolinonitrile

A solution of 3,5-dichloropicolinonitrile (1.0 eq.), (E)-4,4,5,5-tetramethyl-2-(prop-1-enyl)-1,3,2-dioxaborolane (1.0 eq.), tetrakis(triphenyl-phosphine)palladium (5 mol %), and 2N aqueous sodium carbonate solution (3.4 eq.) in toluene/ethanol (2:1, 0.04 M) was stirred at 95° C. overnight. After cooling to ambient temperature, the reaction content was diluted with ethyl acetate and water. The two phases were separated, and the aqueous layer was extracted twice with ethyl acetate. The combined organic layers were washed with brine, dried over anhydrous MgSO$_4$, and concentrated en vaccuo to obtain a crude residue. The crude material was purified by flash chromatography on a COMBIFLASH® system (ISCO) using 0-80% ethyl acetate in hexane to give a white solid (E)-3-chloro-5-(prop-1-enyl)picolinonitrile.

Step 2: (E)-8-methyl-2-(prop-1-enyl)benzo[f][1,7]naphthyridin-5-amine

A solution of tert-butyl 5-methyl-2-(4,4,5,5-tetramethyl-1,3,2-dioxaborolan-2-yl)phenylcarbamate (from Example 5/Step 2) (1.0 eq.) and (E)-3-chloro-5-(prop-1-enyl)picolinonitrile (from the previous step) (1.0 eq.), tetrakis(triphenyl-phosphine)palladium (5 mol %), and 2N aqueous sodium carbonate solution (2.0 eq.) in toluene/ethanol (2:1, 0.03 M) was stirred at 100° C. overnight. After cooling to ambient temperature, the reaction content was diluted with methanol. The insoluble solids were filtered off, and the filtrate was concentrated en vaccuo to obtain a crude residue. The crude material was purified by flash chromatography on a COMBI- FLASH® system (ISCO) using 0-80% ethyl acetate in hexane to give (E)-8-methyl-2-(prop-1-enyl)benzo[f][1,7]naphthyridin-5-amine as a yellow solid.

Step 3:
8-methyl-2-propylbenzo[f][1,7]naphthyridin-5-amine

To a solution of (E)-8-methyl-2-(prop-1-enyl)benzo[f][1,7]naphthyridin-5-amine (from the previous step) in ethyl acetate/methanol (1:4, 0.05 M) was added 10% wt palladium on carbon (0.2 eq.). Hydrogen gas was introduced via a balloon, and the reaction was stirred for 3 hours. The mixture was filtered through a pad of celite, washing with dichloromethane. The filtrate was concentrated en vaccuo and purified by a COMBIFLASH® system (ISCO) using 0-80% ethyl acetate in hexane to give 8-methyl-2-propylbenzo[f][1,7]naphthyridin-5-amine as off white solid. $^1$H NMR (CDCl$_3$): δ 8.59 (d, 1H), 8.41 (d, 1H), 8.10 (d, 1H), 7.43 (s, 1H), 7.13 (dd, 1H), 5.94 (bs, 2H), 2.78 (t, 2H), 2.44 (s, 3H), 1.75 (m, 2H), 0.95 (t, 3H). LRMS [M+H]=252.1

Example 44

2-(2-(1H-indol-5-yl)ethyl)-8-methylbenzo[f][1,7]naphthyridin-5-amine

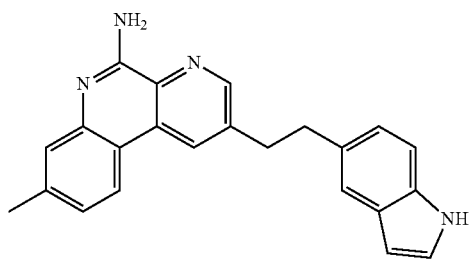 [SMILES: Cc1ccc2c(c1)nc(N)c1ncc(CCc3ccc4[nH]ccc4c3)cc12]

Step 1: 5-((triethylsilyl)ethynyl)-1H-indole

To a scintillation vial was added -iodo-1H-indole (1.1 eq.), triethyl(ethynyl)silane (1 eq.), triethylamine (5 eq.), and anhydrous DMF (0.2 M). Vacuumed and nitrogen flushed for three times. CuI (0.1 eq.) and bis(triphenylphosphine) dichloro-palladium(II) (0.1 eq) were added. The vial was sealed and heated at 60° C. overnight. Upon completion of the reaction as monitored by TLC, the content of the vial was loaded onto a silica gel column pretreated with hexanes. Column was washed with hexanes and diethylether until all eluents containing product were collected. Carefully distill off hexanes and ether using rotary evaporator with minimum heating afforded product 5-((triethylsilyl)ethynyl)-1H-indole as colorless oil, which was carried directly on to the next step.

Step 2: 5-ethynyl-1H-indole

To a stirred solution of 5-((triethylsilyl)ethynyl)-1H-indole (from the previous step) in THF (0.2 M) cooled at 0° C. was treated with a solution (0.5 eq.) of tetrabutylammonium fluoride in a dropwise fashion. The reaction mixture turned black and was continued to stir for 30 minutes before warming up to rt. TLC showed full conversion. The reaction was quenched with water and was extracted with diethylether. Combined organic layers were dried over anhydrous Na$_2$SO$_4$ and concentrated using rotary evaporator with minimum heating.

Chromatography (silica gel, diethylether) afforded the product 5-ethynyl-1H-indole as colorless oil.

Step 3:
5(1H-indol-5-yl)ethynyl)-3-chloropicolinonitrile

To a round bottom flask capped with septa was added 5-ethynyl-1H-indole (from the previous step) (1.1 eq), 3,5-dichloropicolinonitrile (1 eq.), triethylamine (5 eq.), and anhydrous DMF (0.2 M). Vacuumed and nitrogen flushed for three times. CuI (0.05 eq.) and bis(triphenylphosphine) dichloro-palladium(II) (0.05 eq) were added. The septum was replaced with a refluxing condenser and the flask was heated at 60° C. overnight under nitrogen atmosphere. Upon completion of the reaction as monitored by TLC, the content of the flask was loaded onto a large silica gel column pretreated with hexanes. Flash chromatography (silica gel, hexanes:EtOAc (1:4%)) afforded the product 5-((1H-indol-5-yl)ethynyl)-3-chloropicolinonitrile.

Step 4: 2-((1H-indol-5-yl)ethynyl)-8-methylbenzo[f][1,7]naphthyridin-5-amine

To a round bottom flask with refluxing condenser were added 5-((1H-indol-5-yl)ethynyl)-3-chloropicolinonitrile (from the previous step) (1 eq.), tert-butyl 2-(4,4,5,5-tetramethyl-1,3,2-dioxaborolan-2-yl)phenylcarbamate (from Example 5/Step 2) (1.25 eq.), K$_3$PO$_4$ (2 eq.), tris(dibenzylideneacetone)dipalladium(0) (0.05 eq.), and 2-Dicyclohexylphosphino-2',6'-dimethoxybiphenyl (0.1 eq.). n-Butanol and water (5:2, 0.2 M) were added, and the content were degassed (vacuum followed by nitrogen flush) for three times. The reaction mixture was stirred vigorously under nitrogen at 100° C. overnight in an oil bath. The content were cooled down and were taken up in 200 mL of water followed by extraction with methylene chloride. Combined organic layers were dried (Na$_2$SO$_4$) and concentrated. Flash chromatography (silica gel, 0-50% EtOAc in CH$_2$Cl$_2$) afforded the product 2-((1H-indol-5-yl)ethynyl)-8-methylbenzo[f][1,7]naphthyridin-5-amine as a yellow solid.

Step 5: 2-(2-(2,3-dihydrobenzofuran-5-yl)ethyl)-8-methylbenzo[f][1,7]naphthyridin-5-amine To a round bottom flask was added 2-((1H-indol-5-yl)ethynyl)-8-methylbenzo[f][1,7]naphthyridin-5-amine (from the previous step) (1 eq.) with a stirring bar. Ethanol and methylene chloride (1:2, 0.2 M) were added, followed by palladium in carbon (activated powder, wet, 10% on carbon, 0.1 eq.). The content were vacuumed followed by hydrogen flush for three times. The reaction mixture was stirred vigorously under hydrogen balloon at room temperature overnight. Afterwards the reaction mixture was filtered through a celite pad, and the celite pad was washed subsequently with methylene chloride and EtOAc until the filtrate had no UV absorption. Combined organic washes were concentrated. Flash chromatography (silica gel, 0-50% EtOAc in CH$_2$Cl$_2$) afforded the product 2-(2-(2,3-Dihydrobenzofuran-5-yl)ethyl)-8-methylbenzo[f][1,7]naphthyridin-5-amine as a yellow solid. $^1$H NMR (CDCl$_3$): δ 8.54 (d, 1H), 8.34 (d, 1H), 8.28 (s, 1H), 7.99 (d, 1H), 7.64-7.56 (m, 1H), 7.50-7.35 (m, 1H), 7.24 (d, 1H), 7.12 (t, 1H), 7.08 (dd, 1H), 6.92 (dd, 1H), 6.41 (s, 1H), 6.01 (bs, 2H), 3.16-3.12 (m, 2H), 3.10-3.05 (m, 2H), 2.43 (s, 3H). LRMS [M+H]=353.2

Example 45

2-(4-ethoxyphenethyl)-8-methylbenzo[f][1,7]naphthyridin-5-amine

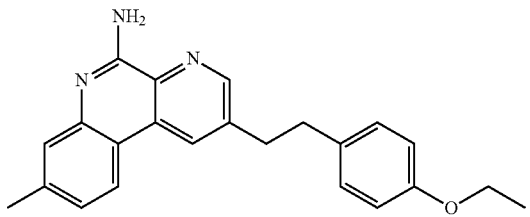 [SMILES: CCOc1ccc(CCc2cnc3c(N)nc4cc(C)ccc4c3c2)cc1]

Step 1: 3-chloro-5-((4-ethoxyphenyl)ethynyl)picolinonitrile

To a round bottom flask capped with septa was added 1-ethoxy-4-ethynylbenzene (1.1 eq), 3,5-dichloropicolinonitrile (1 eq.), triethylamine (5 eq.), and anhydrous DMF (0.2 M). Vacuumed and nitrogen flushed for three times. CuI (0.05 eq.) and bis(triphenylphosphine)dichloro-palladium(II) (0.05 eq) were added. The septum was replaced with a refluxing condenser and the flask was heated at 60° C. overnight under nitrogen atmosphere. Upon completion of the reaction as monitored by TLC, the content of the flask was loaded onto a large silica gel column pretreated with hexanes. Flash chromatography (silica gel, hexanes:EtOAc (1:4%)) afforded the product 3-chloro-5-((4-ethoxyphenyl)ethynyl)picolinonitrile.

Step 2: 2-((4-ethoxyphenyl)ethynyl)-8-methylbenzo[f][1,7]naphthyridin-5-amine

To a round bottom flask with refluxing condenser were added 3-chloro-5-((4-ethoxyphenyl)ethynyl)picolinonitrile (from the previous step) (1 eq.), tert-butyl 5-methyl-2-(4,4,5,5-tetramethyl-1,3,2-dioxaborolan-2-yl)phenylcarbamate (from Example 5/Step 2) (1.25 eq.), K₃PO₄ (2 eq.), tris(dibenzylideneacetone)dipalladium(0) (0.05 eq.), and 2-dicyclohexylphosphino-2',6'-dimethoxybiphenyl (0.1 eq.). n-Butanol and water (5:2, 0.2 M) were added, and the content were degassed (vacuum followed by nitrogen flush) for three times. The reaction mixture was stirred vigorously under nitrogen at 100° C. overnight in an oil bath. The content were cooled down and were taken up in 200 mL of water followed by extraction with methylene chloride. Combined organic layers were dried (Na₂SO₄) and concentrated. Flash chromatography (silica gel, 0-50% EtOAc in CH₂Cl₂) afforded the product 2-((4-ethoxyphenyl)ethynyl)-8-methylbenzo[f][1,7]naphthyridin-5-amine.

Step 3: 2-(4-ethoxyphenethyl)-8-methylbenzo[f][1,7]naphthyridin-5-amine

To a round bottom flask was added 2-((4-ethoxyphenyl)ethynyl)-8-methylbenzo[f][1,7]naphthyridin-5-amine (from the previous step) (1 eq.) with a stirring bar. Ethanol and methylene chloride (1:2, 0.2 M) were added, followed by palladium in carbon (activated powder, wet, 10% on carbon, 0.1 eq.). The contents were degassed under vacuum followed by hydrogen flush (three times). The reaction mixture was stirred vigorously under hydrogen balloon at room temperature overnight. Afterwards the reaction mixture was filtered through a celite pad, and the celite pad was washed subsequently with methylene chloride and EtOAc until the filtrate had no UV absorption. Combined organic washes were concentrated. Flash chromatography (silica gel, 0-50% EtOAc in CH₂Cl₂) afforded the product as a yellow solid. Further recrystallization using toluene afforded product 2-(4-ethoxyphenethyl)-8-methylbenzo[f][1,7]naphthyridin-5-amine as a white fine crystal. ¹H NMR (CDCl₃): δ 8.52 (d, 1H), 8.30 (d, 1H), 8.10 (d, 1H), 7.46 (s, 1H), 7.12 (dd, 1H), 7.06 (d, 2H), 6.75 (d, 2H), 5.95 (bs, 2H), 3.93 (q, 2H), 3.11-3.05 (dd, 2H), 2.95-2.90 (dd, 2H), 2.44 (s, 3H), 1.33 (t, 3H). LRMS [M+H]= 358.2

Example 46

8-methyl-2-(4-phenoxyphenethyl)benzo[f][1,7]naphthyridin-5-amine

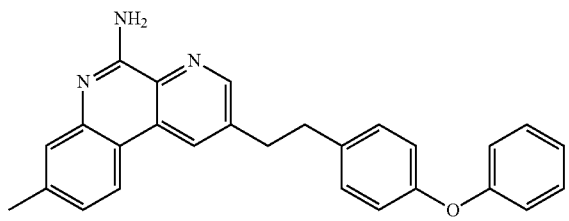 [SMILES: Cc1ccc2c(c1)nc(N)c1ncc(CCc3ccc(Oc4ccccc4)cc3)cc12]

Step 1: 3-chloro-5-((4-phenoxyphenyl)ethynyl)picolinonitrile

3-Chloro-5-((4-phenoxyphenyl)ethynyl)picolinonitrile was prepared from 1-ethynyl-4-phenoxybenzene (commercially available) following the procedures described for Example 45, step 1.

Step 2: 8-methyl-2-((4-phenoxyphenyl)ethynyl) benzo[f][1,7]naphthyridin-5-amine

8-Methyl-2-((4-phenoxyphenyl)ethynyl)benzo[f][1,7] naphthyridin-5-amine was prepared from 3-chloro-5-((4-phenoxyphenyl)ethynyl)picolinonitrile (from the previous step) following the procedures described for Example 45, step 2.

Step 3: 8-methyl-2-(4-phenoxyphenethyl)benzo[f][1,7]naphthyridin-5-amine

8-Methyl-2-(4-phenoxyphenethyl)benzo[f][1,7]naphthyridin-5-amine was prepared from 8-methyl-2-((4-phenoxyphenyl)ethynyl)benzo[f][1,7]naphthyridin-5-amine (from the previous step) following the procedures described for Example 45, step 3. ¹H NMR (CDCl₃): δ 8.54 (d, 1H), 8.30 (d, 1H), 8.01 (d, 1H), 7.45 (s, 1H), 7.25-7.20 (m, 2H), 7.12 (dd, 1H), 7.07-6.84 (m, 8H), 6.00 (bs, 2H), 3.13-3.08 (dd, 2H), 2.99-2.94 (dd, 2H), 2.44 (s, 3H). LRMS [M+H]=406.2

Example 47

2-(2,4-dimethylphenethyl)benzo[f][1,7]naphthyridin-5-amine

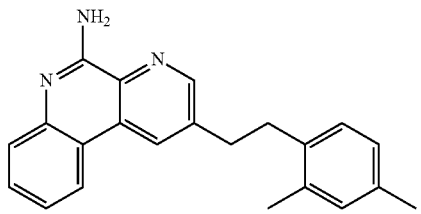 [SMILES: Cc1ccc(CCc2cnc3c(N)nc4ccccc4c3c2)c(C)c1]

Step 1: ((2,4-dimethylphenyl)ethynyl)triethylsilane ((2,4-Dimethylphenyl)ethynyl)triethylsilane was prepared from 1-iodo-2,4-dimethylbenzene (commercially available) following the procedures described for Example 44, step 1.

Step 2: 1-ethynyl-2,4-dimethylbenzene

1-Ethynyl-2,4-dimethylbenzene was prepared from ((2,4-dimethylphenyl)ethynyl)triethylsilane (from the previous step) following the procedures described for Example 44, step 2.

Step 3: 3-chloro-5-((2,4-dimethylphenyl)ethynyl) picolinonitrile

3-Chloro-5-((2,4-dimethylphenyl)ethynyl)picolinonitrile was prepared from 1-ethynyl-2,4-dimethylbenzene (from the previous step) following the procedures described for Example 44, step 3.

Step 4: 2-((2,4-dimethylphenyl)ethynyl)benzo[f][1,7]naphthyridin-5-amine 2-((2,4-Dimethylphenyl)ethynyl)benzo[f][1,7]naphthyridin-5-amine was prepared from 3-chloro-5-((2,4-dimethylphenyl)ethynyl)-picolinonitrile (from the previous step) following the procedures described for Example 44, step 4.

Step 5: 2-(2,4-dimethylphenethyl)benzo[f][1,7]naphthyridin-5-amine 2-(2,4-Dimethylphenethyl)benzo[f][1,7]naphthyridin-5-amine was prepared from 2-((2,4-dimethylphenyl)ethynyl)benzo[f][1,7]naphthyridin-5-amine (from the previous step) following the procedures described for Example 44, step 5. $^1$H NMR (CDCl$_3$): δ 8.60 (d, 1H), 8.33 (d, 1H), 8.14 (d, 1H), 7.67 (d, 1H), 7.54 (t, 1H), 7.31 (t, 1H), 6.96-6.86 (m, 3H), 6.29 (bs, 2H), 3.04-3.10 (dd, 2H), 2.97-2.91 (dd, 2H), 2.24 (s, 3H), 2.20 (s, 3H). LRMS [M+H]=328.2.

Example 48

2-(2,4-dimethylphenethyl)-8-methylbenzo[f][1,7]naphthyridin-5-amine

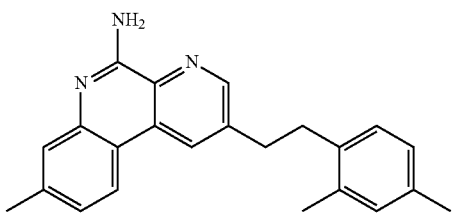

Step 1: 2-((2,4-dimethylphenyl)ethynyl)-8-methyl-benzo[f][1,7]naphthyridin-5-amine 2-((2,4-Dimethylphenyl)ethynyl)-8-methylbenzo[f][1,7]naphthyridin-5-amine was prepared from 3-chloro-5-((2,4-dimethylphenyl)ethynyl)picolinonitrile (from Example 47/Step 3) and tert-butyl 5-methyl-2-(4,4,5,5-tetramethyl-1,3,2-dioxaborolan-2-yl)phenylcarbamate (from Example 5/Step 2) following the procedures described for Example 44, step 4.

Step 2: 2-(2,4-dimethylphenethyl)-8-methylbenzo[f][1,7]naphthyridin-5-amine 2-(2,4-Dimethylphenethyl)-8-methylbenzo[f][1,7]naphthyridin-5-amine was prepared from 1-ethynyl-4-phenoxybenzene (from the previous step) following the procedures described for Example 44, step 5. $^1$H NMR (CDCl$_3$): δ 8.56 (d, 1H), 8.28 (d, 1H), 8.00 (d, 1H), 7.46 (s, 1H), 7.14 (dd, 1H), 6.95-6.85 (m, 3H), 6.26 (bs, 2H), 3.08-3.02 (dd, 2H), 2.96-2.90 (dd, 2H), 2.45 (s, 3H), 2.23 (s, 3H), 2.19 (s, 3H). LRMS [M+H]=342.2

Example 49

2-(4-methoxy-2-methylphenethyl)-8-methylbenzo[f][1,7]naphthyridin-5-amine

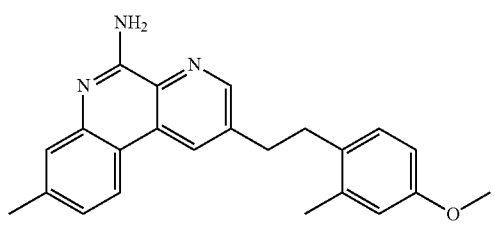

Step 1: 3-chloro-5-((4-methoxy-2-methylphenyl)ethynyl)picolinonitrile

3-Chloro-5-((4-methoxy-2-methylphenyl)ethynyl)picolinonitrile was prepared from 1-ethynyl-4-methoxy-2-methylbenzene (commercially available) following the procedure described for Example 44/Step 3.

Step 2: 2-((4-methoxy-2-methylphenyl)ethynyl)-8-methylbenzo[f][1,7]naphthyridin-5-amine 2-((4-Methoxy-2-methylphenyl)ethynyl)-8-methylbenzo[f][1,7]naphthyridin-5-amine was prepared from 3-chloro-5-(4-methoxy-2-methylphenethyl)picolinonitrile (from the previous step) following the procedures described for Example 44, step 4.

Step 3: 2-(4-methoxy-2-methylphenethyl)-8-methylbenzo[f][1,7]naphthyridin-5-amine 2-(4-Methoxy-2-methylphenethyl)-8-methylbenzo[f][1,7]naphthyridin-5-amine was prepared from 2-((4-methoxy-2-methylphenyl)ethynyl)-8-methylbenzo[f][1,7]naphthyridin-5-amine (from the previous step) following the procedures described for Example 44, step 5. $^1$H NMR (CDCl$_3$): δ 8.53 (d, 1H), 8.29 (d, 1H), 8.01 (d, 1H), 7.44 (s, 1H), 7.12 (dd, 1H), 6.93 (d, 1H), 6.67 (d, 1H), 6.60 (dd, 1H), 5.93 (bs, 2H), 3.70 (s, 3H), 3.05-3.00 (dd, 2H), 2.93-2.88 (dd, 2H), 2.44 (s, 3H), 2.19 (s, 3H). LRMS [M+H]=358.2

Example 50

4-(2-(5-amino-8-methylbenzo[f][1,7]naphthyridin-2-yl)ethyl)-3-methylphenol

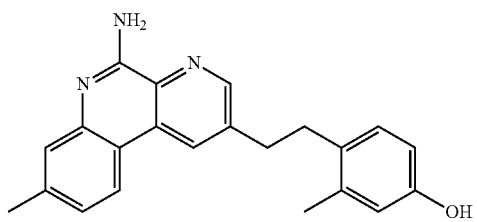 [SMILES: Cc1ccc2c(c1)nc(N)c1ncc(CCc3ccc(O)cc3C)cc12]

To a stirred solution of 2-(4-methoxy-2-methylphenethyl)-8-methylbenzo[f][1,7]naphthyridin-5-amine (Example 49) in methylene chloride (0.2 M) in an ice-water bath was added 1 N solution of BBr$_3$ (2 eq) in CH$_2$Cl$_2$ in a drop-wise fashion. In 30 minutes the reaction was quenched with methanol and was concentrated en vaccuo to obtain a crude residue. The crude material was purified by flash chromatography on a COMBIFLASH® system (ISCO) using 0-20% methanol in dichloromethane to give 4-(2-(5-amino-8-methylbenzo[f][1,7]naphthyridin-2-yl)ethyl)-3-methylphenol as a white solid. $^1$H NMR (DMSO-d$_6$): δ 8.99 (s, 1H), 8.75 (d, 1H), 8.60 (d, 1H), 8.27 (d, 1H), 7.28 (s, 1H), 7.09 (dd, 1H), 6.99 (bs, 2H), 6.88 (d, 1H), 6.49 (d, 1H), 6.42 (dd, 1H), 3.02-2.96 (dd, 2H), 2.86-2.81 (dd, 2H), 2.38 (s, 3H), 2.13 (s, 3H). LRMS [M+H]= 344.2

Example 51

2-(2-(2,3-dihydrobenzofuran-5-yl)ethyl)-8-methylbenzo[f][1,7]naphthyridin-5-amine

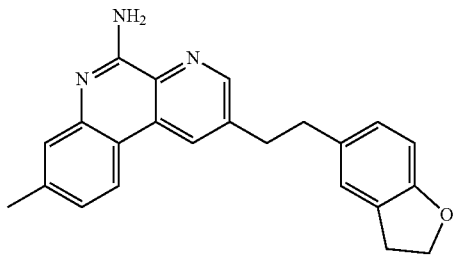 [SMILES: Cc1ccc2c(c1)nc(N)c1ncc(CCc3ccc4c(c3)CCO4)cc12]

Step 1: ((2,3-dihydrobenzofuran-5-yl)ethynyl)triethylsilane ((2,3-Dihydrobenzofuran-5-yl)ethynyl)triethylsilane was prepared from 5-iodo-2,3-dihydrobenzofuran (commercially available) following the procedures described for Example 44, step 1.

Step 2: 5-ethynyl-2,3-dihydrobenzofuran

5-Ethynyl-2,3-dihydrobenzofuran was prepared from ((2,3-dihydrobenzofuran-5-yl)ethynyl)triethylsilane (from the previous step) following the procedures described for Example 44/Step 2.

Step 3: 3-chloro-5-((2,3-dihydrobenzofuran-5-yl)ethynyl)picolinonitrile

3-Chloro-5-((2,3-dihydrobenzofuran-5-yl)ethynyl)picolinonitrile was prepared from 5-ethynyl-2,3-dihydrobenzofuran (from the previous step) following the procedures described for Example 44/Step 3.

Step 4: 2-((2,3-dihydrobenzofuran-5-yl)ethynyl)-8-methylbenzo[f][1,7]naphthyridin-5-amine 2-((2,3-Dihydrobenzofuran-5-yl)ethynyl)-8-methylbenzo[f][1,7]naphthyridin-5-amine was prepared from 3-chloro-5-(4-methoxy-2-methylphenethyl)picolinonitrile (from the previous step) following the procedures described for Example 44/Step 4.

Step 5: 2-(2-(2,3-dihydrobenzofuran-5-yl)ethyl)-8-methylbenzo[f][1,7]naphthyridin-5-amine 2-(2-(2,3-Dihydrobenzofuran-5-yl)ethyl)-8-methylbenzo[f][1,7]naphthyridin-5-amine was prepared from 2-((2,3-dihydrobenzofuran-5-yl)ethynyl)-8-methylbenzo[f][1,7]naphthyridin-5-amine (from the previous step) following the procedures described for Example 44/Step 5. $^1$H NMR (CDCl$_3$): δ 8.62 (d, 1H), 8.40 (d, 1H), 8.11 (d, 1H), 7.53 (s, 1H), 7.21 (dd, 1H), 6.99 (s, 1H), 6.95 (dd, 1H), 6.74 (d, 1H), 6.05 (bs, 2H), 4.57 (t, 2H), 3.19-3.13 (m, 4H), 3.03-2.98 (dd, 2H), 2.54 (s, 3H). LRMS [M+H]=356.2

Example 52

2-(5-amino-8-methylbenzo[f][1,7]naphthyridin-2-yl)ethanol

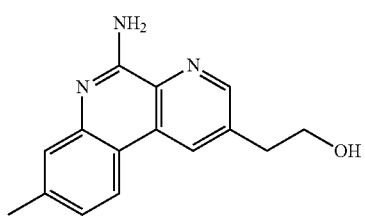 [SMILES: Cc1ccc2c(c1)nc(N)c1ncc(CCO)cc12]

Step 1: (Z)-3-chloro-5-(2-ethoxyvinyl)picolinonitrile (Z)-3-Chloro-5-(2-ethoxyvinyl)picolinonitrile was prepared from (Z)-2-(2-ethoxyvinyl)-4,4,5,5-tetramethyl-1,3,2- dioxaborolane (commercially available) following the procedures described for Example 43/Step 1.

Step 2: (Z)-2-(2-ethoxyvinyl)-8-methylbenzo[f][1,7]naphthyridin-5-amine (Z)-2-(2-Ethoxyvinyl)-8-methylbenzo[f][1,7]naphthyridin-5-amine was prepared from (Z)-3-chloro-5-(2-ethoxyvinyl)picolinonitrile (from the previous step) following the procedures described for Example 43/Step 2.

Step 3: 2-(5-amino-8-methylbenzo[f][1,7]naphthyridin-2-yl)ethanol

A solution of (Z)-2-(2-ethoxyvinyl)-8-methylbenzo[f][1,7]naphthyridin-5-amine (from the previous step) in a mixture of 2:5 conc. HCl and dioxane (0.1 M) was heated at 60° C. overnight. Upon cooling down to rt, the reaction mixture was treated with excess NaHCO₃ saturated solution, followed by extraction with EtOAc. Combined organic extracts were concentrated and was taken up in THF (0.2 M), and was treated with 1 N super hydride solution in THF (10 eq.) at 0° C. The reaction mixture was allowed to warm to room temperature and stirred overnight. The reaction was worked up following the procedures described for Example 42/Step 3, to afford 2-(5-amino-8-methylbenzo[f][1,7]naphthyridin-2-yl)ethanol as white solid. $^1$H NMR (CDCl₃): δ 8.61 (d, 1H), 8.47 (d, 1H), 8.01 (d, 1H), 7.41 (s, 1H), 7.10 (d, 1H), 6.40 (s, 1H), 6.01 (bs, 2H), 4.01 (t, 2H), 3.06 (t, 2H), 2.43 (s, 3H). LRMS [M+H]=254.1

Example 53

3-methyl-9-phenyl-9,10-dihydrobenzo[f]furo[2,3-b][1,7]naphthyridin-6-amine

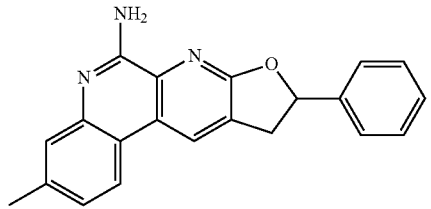 [SMILES: Cc1ccc2c(c1)nc(N)c1nc3c(cc12)CC(c1ccccc1)O3]

Step 1: 5-bromo-2-chloro-3-methylpyridine 1-oxide

5-Bromo-2-chloro-3-methylpyridine 1-oxide was prepared from 5-bromo-2-chloro-3-methylpyridine (commercially available) following the procedures described for Example 19/Step 1.

Step 2: 3-bromo-6-chloro-5-methylpicolinonitrile

3-Bromo-6-chloro-5-methylpicolinonitrile was prepared from (Z)-3-chloro-5-(2-ethoxyvinyl)picolinonitrile (from the previous step) following the procedures described for Example 19/Step 2.

Step 3: 3-bromo-6-chloro-5-(2-hydroxy-2-phenylethyl)picolinonitrile

A solution of 3-bromo-6-chloro-5-methylpicolinonitrile (from the previous step) in THF (0.2 M) was cooled to −78° C. LDA (2N solution, 2 eq) was added dropwise. The reaction was kept stirring at −78° C. for 1 hour, followed by addition of benzaldehyde (1 eq). The reaction was kept stirring at −78° C. for another 30 minutes before allowing it to slowly warm to room temperature. The reaction was quenched with sat. NH₄Cl and extracted with EtOAc. Combined organic washes were concentrated. Flash chromatography (silica gel, 20-50% EtOAc in hexanes) afforded the product 3-bromo-6-chloro-5-(2-hydroxy-2-phenylethyl)picolinonitrile as a yellow solid.

Step 4: 3-methyl-9-phenyl-9,10-dihydrobenzo[f]furo[2,3-b][1,7]naphthyridin-6-amine 3-Methyl-9-phenyl-9,10-dihydrobenzo[f]furo[2,3-b][1,7]naphthyridin-6-amine was prepared from 3-bromo-6-chloro-5-methylpicolinonitrile (from the previous step) following the procedures described for Example 44/Step 4. $^1$H NMR (CDCl₃): δ 8.45 (s, 1H), 7.98 (d, 1H), 7.45 (s, 1H), 7.40-7.28 (m, 5H), 7.12 (d, 1H), 5.93 (t, 1H), 5.93 (brs, 2H), 3.86 (dd, 1H), 3.40 (dd, 1H), 2.44 (s, 3H). LRMS [M+H]=328.1

Example 54

8-methylbenzo[f][1,7]naphthyridine-2,5-diamine

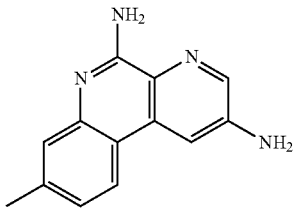 [SMILES: Cc1ccc2c(c1)nc(N)c1ncc(N)cc12]

Step 1: tert-butyl 5,6-dichloropyridin-3-ylcarbamate

To a solution of 5,6-dichloropyridin-3-amine (commercially available) in THF (0.2 M) stirred at 0° C. was added (BOC)₂O (1.2 eq). The reaction mixture was heated at 40° C. until full conversion as monitored by TLC. The reaction mixture was then concentrated. Flash chromatography (silica gel, 20-50% EtOAc in hexanes) of the crude afforded tert-butyl 5,6-dichloropyridin-3-ylcarbamate.

Step 2: tert-butyl 5-chloro-6-cyanopyridin-3-ylcarbamate

Tert-butyl 5-chloro-6-cyanopyridin-3-ylcarbamate was prepared from tert-butyl 5,6-dichloropyridin-3-ylcarbamate (from the previous step) following the procedures described for Example 42/Step 1.

Step 3: 8-methylbenzo[f][1,7]naphthyridine-2,5-diamine 8-methylbenzo[f][1,7]naphthyridine-2,5-diamine was prepared (as minor product) together with tert-butyl 5-amino-8-methylbenzo[f][1,7]naphthyridin-2-ylcarbamate (as major product) from tert-butyl 5-chloro-6-cyanopyridin-3-ylcarbamate (from the previous step) following the procedures described for Example 5/Step 2. $^1$H NMR (DMSO-d₆): δ

10.11 (s, 1H), 9.02 (s, 1H), 8.82 (d, 1H), 8.06 (d, 1H), 7.34 (s, 1H), 7.15 (dd, 1H), 6.99 (s, 2H), 2.44 (s, 3H). LRMS [M+H]= 225.1

Example 55

1-(5-amino-8-methylbenzo[f][1,7]naphthyridin-2-yl)propan-2-ol

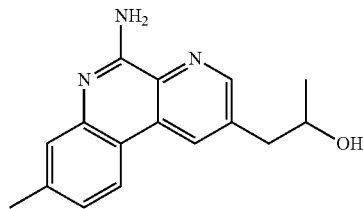 [SMILES: Cc1ccc2c(c1)nc(N)c1ncc(CC(C)O)cc12]

Step 1: 3-bromo-5-methylpicolinonitrile

3-Bromo-5-methylpicolinonitrile was prepared from 2,3-dibromo-5-methylpyridine (commercially available) following the procedures described for Example 42/Step 1.

Step 2: 3-bromo-5-(2-hydroxypropyl)picolinonitrile

3-Bromo-5-(2-hydroxypropyl)picolinonitrile was prepared from 3-bromo-5-methylpicolinonitrile (from the previous step) and acetaldehyde following the procedures described for Example 53/Step 3.

Step 3: 1-(5-amino-8-methylbenzo[f][1,7]naphthyridin-2-yl)propan-2-ol 1-(5-Amino-8-methylbenzo[f][1,7]naphthyridin-2-yl)propan-2-ol was prepared from 3-bromo-5-(2-hydroxypropyl)picolinonitrile (from the previous step) following the procedures described for Example 53, step 4. $^1$H NMR (methanol-d$_4$): δ 8.72 (d, 1H), 8.68 (d, 1H), 8.24 (d, 1H), 7.38 (s, 1H), 7.18 (dd, 1H), 4.16-4.07 (m, 1H), 3.05-2.99 (m, 2H), 2.97-2.90 (m, 2H), 2.47 (s, 3H), 1.28 (d, 3H). LRMS [M+H]= 268.1

Example 56

2-(5-amino-8-methylbenzo[f][1,7]naphthyridin-2-yl)acetonitrile

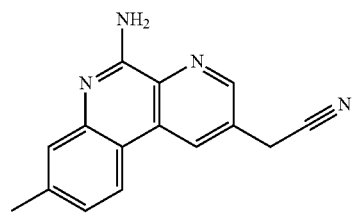 [SMILES: Cc1ccc2c(c1)nc(N)c1ncc(CC#N)cc12]

Step 1:
2,3-dichloro-5-((methoxymethoxy)methyl)pyridine

To a stirred solution of (5,6-dichloropyridin-3-yl)methanol (commercially available) in CH$_2$Cl$_2$ (0.2 M) at 0° C. was added triethylamine (3 eq.) and chloro(methoxy)methane (2 eq.). After stirring at 0° C. for 3 hours the reaction mixture was concentrated and the crude was purified by chromatography (silica gel, 20-50% EtOAc in hexanes) to afford 2,3-dichloro-5-((methoxymethoxy)methyl)pyridine as a colorless oil.

Step 2:
3-chloro-5-((methoxymethoxy)methyl)picolinonitrile

3-Chloro-5-((methoxymethoxy)methyl)picolinonitrile was prepared from 2,3-dichloro-5-((methoxymethoxy)methyl)pyridine (from the previous step) following the procedures described for Example 42/Step 1.

Step 3: 3-chloro-5-(hydroxymethyl)picolinonitrile

To a stirred solution of 2,3-dichloro-5-((methoxymethoxy)methyl)pyridine (from the previous step) in methanol (0.2 M) was added conc. HCl (10 eq). After stirring at room temperature overnight the reaction mixture was concentrated under vacuum and the resulting crude was purified by chromatography (silica gel, 20-50% EtOAc in hexanes) to afford 3-chloro-5-(hydroxymethyl)picolinonitrile.

Step 4: 3-chloro-5-(chloromethyl)picolinonitrile

To a stirred solution of 3-chloro-5-(hydroxymethyl)picolinonitrile (from the previous step) in CH$_2$Cl$_2$ (0.2 M) at 0° C. was added thionyl chloride (10 eq). After stirring at room temperature overnight the reaction mixture was concentrated under vacuum and the resulting crude was purified by chromatography (silica gel, 20-50% EtOAc in hexanes) to afford 3-chloro-5-(chloromethyl)picolinonitrile as a colorless oil.

Step 5: 3-chloro-5-(cyanomethyl)picolinonitrile

To a solution of 3-chloro-5-(chloromethyl)picolinonitrile (from the previous step) in DMSO (0.2 M) was added sodium cyanide (1.25 eq). The reaction mixture was heated at 130° C. under microwave irradiation. The reaction mixture taken up in water and EtOAc, and extracted with EtOAc. Organic phases were dried over anhydrous Na$_2$SO$_4$, and concentrated. Flash chromatography (silica gel, 20-50% EtOAc in hexanes) of the crude afforded 3-chloro-5-(cyanomethyl)picolinonitrile.

Step 6: 2-(5-amino-8-methylbenzo[f][1,7]naphthyridin-2-yl)acetonitrile 2-(5-amino-8-methylbenzo[f][1,7]naphthyridin-2-yl)acetonitrile was prepared from 3-chloro-5-(cyanomethyl)picolinonitrile (from the previous step) following the procedures described for Example 44/Step 4. $^1$H NMR (methanol-d$_4$): δ 8.79 (d, 1H), 8.78 (d, 1H), 8.20 (d, 1H), 7.66 (s, 2H), 7.36 (s, 1H), 7.18 (dd, 1H), 4.15 (d, 2H), 2.43 (s, 3H). LRMS [M+H]=249.1

Example 57

N-(5-amino-8-methylbenzo[f][1,7]naphthyridin-2-yl)acetamide

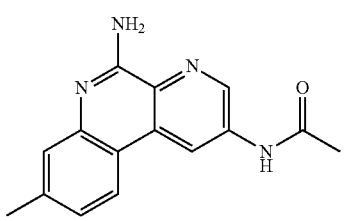 [SMILES: CC(=O)Nc1cnc2c(N)nc3cc(C)ccc3c2c1]

Step 1: N-(5,6-dichloropyridin-3-yl)acetamide

To a stirred solution of 5,6-dichloropyridin-3-amine (commercially available) and triethyl amine (3 eq) in $CH_2Cl_2$ (0.2 M) at 0° C. was added acetyl chloride (2 eq). After stirring at room temperature overnight the reaction mixture was concentrated under vacuum and the resulting crude residue was purified by chromatography (silica gel, 20-50% EtOAc in hexanes) to afford N-(5,6-dichloropyridin-3-yl)acetamide.

Step 2: N-(5-chloro-6-cyanopyridin-3-yl)acetamide

N-(5-chloro-6-cyanopyridin-3-yl)acetamide was prepared from N-(5,6-dichloropyridin-3-yl)acetamide (from the previous step) following the procedures described for Example 42/Step 1.

Step 3: N-(5-amino-8-methylbenzo[f][1,7]naphthyridin-2-yl)acetamide

N-(5-amino-8-methylbenzo[f][1,7]naphthyridin-2-yl)acetamide was prepared from N-(5-chloro-6-cyanopyridin-3-yl)acetamide (from the previous step) following the procedures described for Example 44/Step 4. $^1$H NMR (DMSO-$d_6$): δ 10.99 (s, 1H), 8.18 (d, 1H), 8.95 (d, 1H), 8.12 (d, 1H), 7.44 (s, 1H), 7.35 (dd, 1H), 2.43 (s, 3H), 2.16 (s, 3H). LRMS [M+H]=267.1

Example 58

2-(5-amino-8-methylbenzo[f][1,7]naphthyridin-2-yl)-1-(2,4-dimethylphenyl)ethanol

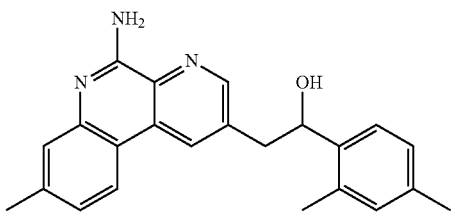

Step 1: 3-bromo-5-(2-(2,4-dimethylphenyl)-2-hydroxyethyl)picolinonitrile 3-bromo-5-(2-(2,4-dimethylphenyl)-2-hydroxyethyl)picolinonitrile was prepared from 3-bromo-5-methylpicolinonitrile (Example 55/Step 1) and 2,4-dimethylbenzaldehyde following the procedures described for Example 53/Step 3.

Step 2: 2-(5-amino-8-methylbenzo[f][1,7]naphthyridin-2-yl)-1-(2,4-dimethylphenyl)ethanol 2-(5-Amino-8-methylbenzo[f][1,7]naphthyridin-2-yl)-1-(2,4-dimethylphenyl)ethanol was prepared from 3-bromo-5-(2-(2,4-dimethylphenyl)-2-hydroxyethyl)picolinonitrile (from the previous step) following the procedures described for Example 53/Step 4. $^1$H NMR ($CDCl_3$): δ 8.67 (d, 1H), 8.45 (d, 1H), 8.06 (d, 1H), 7.57 (s, 1H), 7.42 (d, 1H), 7.23 (d, 1H), 7.11 (d, 1H), 7.01 (s, 1H), 5.31 (dd, 1H), 3.28-3.25 (m, 2H), 2.53 (s, 3H), 2.35 (s, 3H), 2.33 (s, 3H). LRMS [M+H]=358.2

Example 59

2-(2-(6-methoxy-4-methylpyridin-3-yl)ethyl)-8-methylbenzo[f][1,7]naphthyridin-5-amine

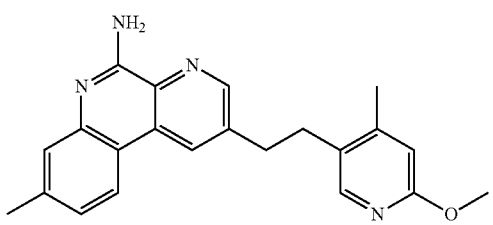

Step 1: 2-methoxy-4-methyl-5-((triethylsilyl)ethynyl)pyridine

2-Methoxy-4-methyl-5-((triethylsilyl)ethynyl)pyridine was prepared from 5-bromo-2-methoxy-4-methylpyridine (commercially available) following the procedures described for Example 44/Step 1.

Step 2: 5-ethynyl-2-methoxy-4-methylpyridine

5-Ethynyl-2-methoxy-4-methylpyridine was prepared from 2-methoxy-4-methyl-5-((triethylsilyl)ethynyl)pyridine (from the previous step) following the procedures described for Example 44/Step 2.

Step 3: 3-chloro-5-((6-methoxy-4-methylpyridin-3-yl)ethynyl)picolinonitrile 3-Chloro-5-((6-methoxy-4-methylpyridin-3-yl)ethynyl)picolinonitrile was prepared from 5-ethynyl-2-methoxy-4-methylpyridine (from the previous step) following the procedures described for Example 44/Step 3.

Step 4: 2-((6-methoxy-4-methylpyridin-3-yl)ethynyl)-8-methylbenzo[f][1,7]naphthyridin-5-amine 2-((6-Methoxy-4-methylpyridin-3-yl)ethynyl)-8-methylbenzo[f][1,7]naphthyridin-5-amine was prepared from 3-chloro-5-(((6-methoxy-4-methylpyridin-3-yl)ethynyl)picolinonitrile (from the previous step) following the procedures described for Example 44/Step 4.

Step 5: 2-(2-(6-methoxy-4-methylpyridin-3-yl)ethyl)-8-methylbenzo[f][1,7]naphthyridin-5-amine 2-(2-(6-Methoxy-4-methylpyridin-3-yl)ethyl)-8-methylbenzo[f][1,7]naphthyridin-5-amine was prepared from 2-((6-methoxy-4-methylpyridin-3-yl)ethynyl)-8-methylbenzo[f][1,7]naphthyridin-5-amine (from the previous step) following the procedures described for Example 44/Step 5. $^1$H NMR (CDCl$_3$): δ 8.65 (d, 1H), 8.43 (d, 1H), 8.13 (d, 1H), 7.87 (s, 1H), 7.57 (s, 1H), 7.24 (dd, 1H), 6.60 (s, 1H), 6.39 (bs, 2H), 3.91 (s, 3H), 3.17-3.11 (dd, 2H), 3.03-2.98 (dd, 2H), 2.54 (s, 3H), 2.28 (s, 3H). LRMS [M+H]=359.2

Example 60

4-(4-(2-(5-amino-8-methylbenzo[f][1,7]naphthyridin-2-yl)ethyl)phenyl)butan-1-ol

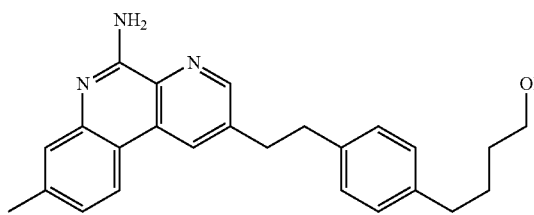

Step 1: 4-(4-((trimethylsilyl)ethynyl)phenyl)but-3-yn-1-ol 4-(4-((trimethylsilyl)ethynyl)phenyl)but-3-yn-1-ol was prepared from ((4-bromophenyl)ethynyl)trimethylsilane (commercially available) and but-3-yn-1-ol (commercially available) following the procedures described for Example 44/Step 1.

Step 2: 4-(4-ethynylphenyl)but-3-yn-1-ol 4-(4-ethynylphenyl)but-3-yn-1-ol was prepared from 4-(4-((trimethylsilyl)ethynyl)phenyl)but-3-yn-1-ol following the procedures described for Example 44/Step 2.

Step 3: 5-((4-(4-hydroxybut-1-ynyl)phenyl)ethynyl)-3-methylpicolinonitrile 5-((4-(4-hydroxybut-1-ynyl)phenyl)ethynyl)-3-methylpicolinonitrile was prepared from 4-(4-ethynylphenyl)but-3-yn-1-ol (from the previous step) following the procedures described for Example 44/Step 3.

Step 4: 4-(4-((5-amino-8-methylbenzo[f][1,7]naphthyridin-2-yl)ethynyl)phenyl)but-2-yn-1-ol 4-(4-((5-amino-8-methylbenzo[f][1,7]naphthyridin-2-yl)ethynyl)phenyl)but-2-yn-1-ol was prepared from 5-((4-(4-hydroxybut-1-ynyl)phenyl)ethynyl)-3-methylpicolinonitrile (from the previous step) following the procedures described for Example 44/Step 4.

Step 5: 4-(4-(2-(5-amino-8-methylbenzo[f][1,7]naphthyridin-2-yl)ethyl)phenyl)butan-1-ol 4-(4-(2-(5-amino-8-methylbenzo[f][1,7]naphthyridin-2-yl)ethyl)phenyl)butan-1-ol was prepared from 4-(4-((5-amino-8-methylbenzo[f][1,7]naphthyridin-2-yl)ethynyl)phenyl)but-2-yn-1-ol (from the previous step) following the procedures described for Example 44/Step 5. $^1$H NMR (CDCl$_3$): δ 8.58 (d, 1H), 8.36 (d, 1H), 8.07 (d, 1H), 7.53 (s, 1H), 7.20 (dd, 1H), 7.10 (dd, 4H), 6.20 (bs, 2H), 3.68 (t, 2H), 3.20-3.15 (dd, 2H), 3.06-3.01 (dd, 2H), 2.64 (t, 2H), 2.52 (s, 3H), 1.75-1.57 (m, 4H). LRMS [M+H]=386.2

Example 61 methyl 3-(4-(2-(5-amino-8-methylbenzo[f][1,7]naphthyridin-2-yl)ethyl)phenyl)propanoate

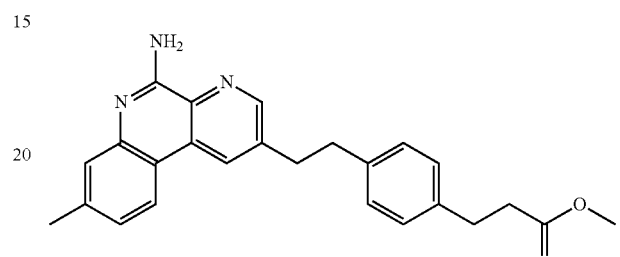

Step 1: methyl 3-(4-iodophenyl)propanoate

To a stirred solution of 3-(4-iodophenyl)propanoic acid (commercially available) in toluene and methanol (9:1, 0.2 M) 0° C. was added (diazomethyl)trimethylsilane (1 N solution in Et$_2$O, 2 eq). After stirring at room temperature overnight the reaction mixture was concentrated under vacuum and the resulting crude residue was purified by chromatography (silica gel, 20-50% EtOAc in hexanes) to afford methyl 3-(4-iodophenyl)propanoate.

Step 2: methyl 3-(4-ethynylphenyl)propanoate

Methyl 3-(4-ethynylphenyl)propanoate was prepared from methyl 3-(4-iodophenyl)propanoate (from the previous step) following the procedures described for Example 44/Steps 1 and 2.

Step 3: methyl 3-(4-((5-chloro-6-cyanopyridin-3-yl)ethynyl)phenyl)propanoate

Methyl 3-(4-((5-chloro-6-cyanopyridin-3-yl)ethynyl)phenyl)propanoate was prepared from methyl 3-(4-ethynylphenyl)propanoate (from the previous step) following the procedures described for Example 44/Step 3.

Step 4: methyl 3-(4-((5-amino-8-methylbenzo[f][1,7]naphthyridin-2-yl)ethynyl)phenyl)propanoate Methyl 3-(4-((5-amino-8-methylbenzo[f][1,7]naphthyridin-2-yl)ethynyl)phenyl)propanoate was prepared from methyl 3-(4-((5-chloro-6-cyanopyridin-3-yl)ethynyl)phenyl)propanoate (from the previous step) following the procedures described for Example 44/Step 4.

Step 5: methyl 3-(4-(2-(5-amino-8-methylbenzo[f][1,7]naphthyridin-2-yl)ethyl)phenyl)propanoate Methyl 3-(4-(2-(5-amino-8-methylbenzo[f][1,7]naphthyridin-2-yl)ethyl)phenyl)propanoate was prepared from methyl 3-(4-((5-amino-8-methylbenzo[f][1,7]naphthyridin- 2-yl)ethynyl)phenyl)propanoate (from the previous step) following the procedures described for Example 44/Step 5. $^1$H NMR (DMSO-d$_6$): δ 8.83 (d, 1H), 8.72 (d, 1H), 8.32 (d, 1H), 7.35 (s, 1H), 7.21-7.12 (m, 5H), 7.05 (br s, 2H), 7.05 (dd, 2H), 3.57 (s, 3H), 3.19-3.13 (dd, 2H), 3.06-3.00 (dd, 2H), 2.81 (t, 2H), 2.60 (t, 2H), 2.45 (s, 3H). LRMS [M+H]=400.2

Example 62

3-(4-(2-(5-amino-8-methylbenzo[f][1,7]naphthyridin-2-yl)ethyl)phenyl)propan-1-ol

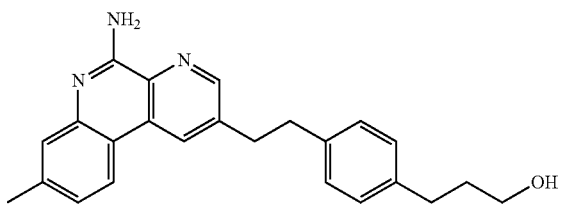 [SMILES: Cc1ccc2c(c1)nc(N)c1ncc(CCc3ccc(CCCO)cc3)cc12]

3-(4-(2-(5-amino-8-methylbenzo[f][1,7]naphthyridin-2-yl)ethyl)phenyl)propan-1-ol was prepared from methyl 3-(4-(2-(5-amino-8-methylbenzo[f][1,7]naphthyridin-2-yl)ethyl)phenyl)propanoate (from Example 61) following the procedures described for Example 42/Step 3. $^1$H NMR of the TFA salt: (DMSO-d$_6$): δ 9.56 (s, 1H), 9.24 (s, 1H), 8.92 (d, 1H), 8.81 (d, 1H), 8.43 (d, 1H), 7.44 (d, 1H), 7.35 (d, 1H), 7.13 (dd, 2H), 7.05 (dd, 2H), 3.32 (t, 2H), 3.18-3.12 (dd, 2H), 3.02-2.95 (dd, 2H), 2.50 (t, 2H), 2.44 (s, 3H), 1.65-1.57 (m, 2H). LRMS [M+H]=372.2

Example 63

4-(4-(2-(5-amino-8-methylbenzo[f][1,7]naphthyridin-2-yl)ethyl)phenyl)-2-methylbutan-2-ol

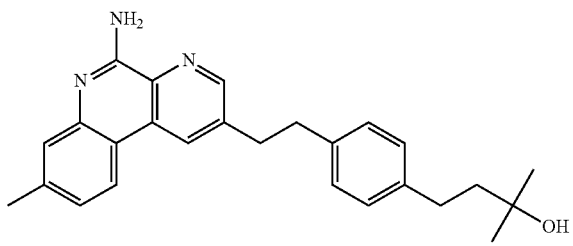 [SMILES: Cc1ccc2c(c1)nc(N)c1ncc(CCc3ccc(CCC(C)(C)O)cc3)cc12]

To a solution of methyl 3-(4-(2-(5-amino-8-methylbenzo[f][1,7]naphthyridin-2-yl)ethyl)phenyl)propanoate (from Example 61) in THF (0.2 M) at 0° C. was added in a dropwise fashion a solution of methylmagnesium bromide in THF (1.0 M, 2 eq). After stirring at room temperature overnight the reaction mixture was concentrated under vacuum and the resulting crude residue was purified by chromatography (silica gel, 50-100% EtOAc in hexanes) to afford 4-(4-(2-(5-amino-8-methylbenzo[f][1,7]naphthyridin-2-yl)ethyl)phenyl)-2-methylbutan-2-ol. $^1$H NMR (CDCl$_3$): δ 8.64 (d, 1H), 8.34 (d, 1H), 8.06 (t, 1H), 7.57 (d, 1H), 7.30-7.20 (m, 2H), 7.18-7.07 (m, 4H), 6.67 (bs, 2H), 3.24-3.16 (dd, 2H), 3.08-3.01 (dd, 2H), 2.73-2.66 (m, 2H), 2.53 (s, 3H), 1.82-1.75 (m, 2H), 1.31 (s, 3H), 1.29 (s, 3H). LRMS [M+H]=400.2

Example 64

2-(4-(aminomethyl)phenethyl)-8-methylbenzo[f][1,7]naphthyridin-5-amine

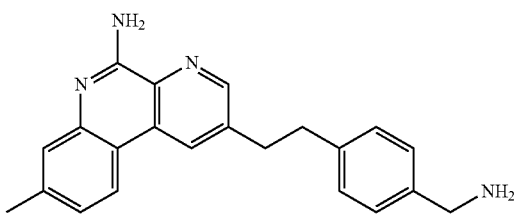 [SMILES: Cc1ccc2c(c1)nc(N)c1ncc(CCc3ccc(CN)cc3)cc12]

Step 1: 4-(2-(5-amino-8-methylbenzo[f][1,7]naphthyridin-2-yl)ethyl)benzonitrile 4-(2-(5-amino-8-methylbenzo[f][1,7]naphthyridin-2-yl)ethyl)benzonitrile was prepared from 4-ethynylbenzonitrile (commercially available) following the procedures described for Example 44/Steps 3 to 5.

Step 2: 2-(4-(aminomethyl)phenethyl)-8-methylbenzo[f][1,7]naphthyridin-5-amine

To a solution of 4-(2-(5-amino-8-methylbenzo[f][1,7]naphthyridin-2-yl)ethyl)benzonitrile (from the previous step) in ethanol and ammonium hydroxide (4:1, 0.2 M) stirred at room temperature was added raney nickel (10 eq). The reaction mixture was stirred under hydrogen atmosphere until the conversion was complete as shown by TLC. The reaction mixture was filtered through a short celite pad. The celite pad was washed with EtOAc. Combined organic extracts were concentrated under vacuum and the resulting crude residue was purified by chromatography (silica gel, 50-100% EtOAc in hexanes) to afford product 2-(4-(aminomethyl)phenethyl)-8-methylbenzo[f][1,7]naphthyridin-5-amine. $^1$H NMR of the TFA salt: (methanol-d$_4$): δ 8.81 (d, 1H), 8.79 (d, 1H), 8.38 (d, 1H), 7.51 (s, 1H), 7.44 (dd, 1H), 7.36 (dd, 4H), 4.07 (s, 2H), 3.29 (s, 2H), 3.20-3.14 (dd, 2H), 2.55 (s, 3H). LRMS [M+H]=343.2

Example 65

(E)-ethyl 3-(4-(2-(5-amino-8-methylbenzo[f][1,7]naphthyridin-2-yl)ethyl)-3-methylphenyl)acrylate

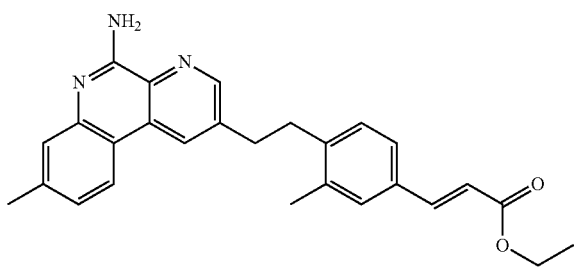 [SMILES: CCOC(=O)/C=C/c1ccc(CCc2cnc3c(N)nc4cc(C)ccc4c3c2)c(C)c1]

Step 1: (4-(2-(5-amino-8-methylbenzo[f][1,7]naphthyridin-2-yl)ethyl)-3-methylphenyl)methanol (4-(2-(5-amino-8-methylbenzo[f][1,7]naphthyridin-2-yl) ethyl)-3-methylphenyl)methanol was prepared from methyl 4-(2-(5-amino-8-methylbenzo[f][1,7]naphthyridin-2-yl) ethyl)-3-methylbenzoate (Example 115) following the procedures described for Example 42/Step 3.

Step 2: 4-(2-(5-amino-8-methylbenzo[f][1,7]naphthyridin-2-yl)ethyl)-3-methylbenzaldehyde To a solution of (4-(2-(5-amino-8-methylbenzo[f][1,7] naphthyridin-2-yl)ethyl)-3-methylphenyl)methanol (from the previous step) in DMSO was added 2-iodoxybenzoic acid (IBX, 2.5 eq). The reaction was stirred at room temperature for 3 hours before being diluted with water. Extraction with EtOAc followed by concentration gave a crude residue which was purified by chromatography (silica gel, 50-100% EtOAc in hexanes) to afford 4-(2-(5-amino-8-methylbenzo[f][1,7] naphthyridin-2-yl)ethyl)-3-methylbenzaldehyde.

Step 3: (E)-ethyl 3-(4-(2-(5-amino-8-methylbenzo[f] [1,7]naphthyridin-2-yl)ethyl)-3-methylphenyl)acrylate To a suspension of NaH (3 eq) in THF (0.2 M) stirred at 0° C. was added ethyl 2-(diethoxyphosphoryl)acetate (commercially available) (3 eq). After stirring for 30 minutes, a solution of 4-(2-(5-amino-8-methylbenzo[f][1,7]naphthyridin-2-yl)ethyl)-3-methylbenzaldehyde (from the previous step) in THF (0.2 M) was added dropwise. The reaction was allowed to warm to room temperature and stirred overnight. The reaction was quenched with sat. NH4Cl solution, and was extracted with EtOAc. Combined organic extracts were dried and concentrated to give a crude residue which was purified by chromatography (silica gel, 50-100% EtOAc in hexanes) to afford (E)-ethyl 3-(4-(2-(5-amino-8-methylbenzo[f][1,7] naphthyridin-2-yl)ethyl)-3-methylphenyl)acrylate as a white solid. $^1$H NMR: (CDCl$_3$): δ 8.54 (d, 1H), 8.29 (d, 1H), 7.99 (d, 1H), 7.57 (d, 1H), 7.44 (s, 1H), 7.23 (dd, 1H), 7.11 (dd, 1H), 7.05 (d, 1H), 6.33 (d, 1H), 5.93 (s, 2H), 4.19 (q, 2H), 3.10-2.95 (m, 4H), 2.44 (s, 3H), 2.23 (s, 3H), 1.26 (t, 3H). LRMS [M+H]=426.2

Example 66 ethyl 3-(4-(2-(5-amino-8-methylbenzo[f][1,7]naphthyridin-2-yl)ethyl)-3-methylphenyl)propanoate

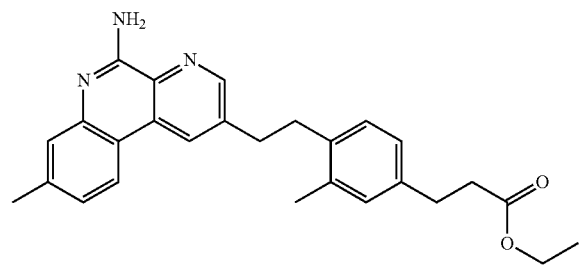 [SMILES: CCOC(=O)CCc1ccc(CCc2cnc3c(N)nc4cc(C)ccc4c3c2)c(C)c1]

Ethyl 3-(4-(2-(5-amino-8-methylbenzo[f][1,7]naphthyridin-2-yl)ethyl)-3-methylphenyl)propanoate was prepared from (E)-ethyl 3-(4-(2-(5-amino-8-methylbenzo[f][1,7] naphthyridin-2-yl)ethyl)-3-methylphenyl)acrylate (from Example 65) following the procedures described for Example 44/Step 5. $^1$H NMR: (CDCl$_3$): δ 8.55 (d, 1H), 8.26 (d, 1H), 7.99 (d, 1H), 7.45 (s, 1H), 7.12 (dd, 1H), 6.98-6.88 (m, 3H), 6.02 (s, 2H), 4.06 (q, 2H), 3.04 (dd, 2H), 2.93 (dd, 2H), 2.83 (t, 2H), 2.53 (t, 2H), 2.44 (s, 3H), 2.19 (s, 3H), 1.17 (t, 3H). LRMS [M+H]=428.2

Example 67

2-(4-(2-(5-amino-8-methylbenzo[f][1,7]naphthyridin-2-yl)ethyl)-3-methylbenzyl)propane-1,3-diol

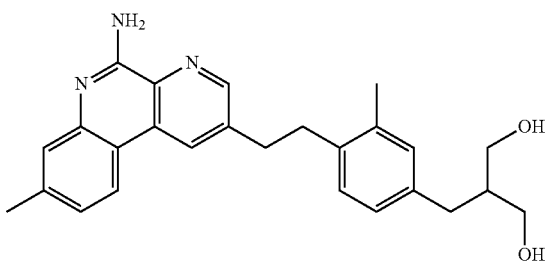 [SMILES: Cc1ccc2c(c1)nc(N)c1ncc(CCc3ccc(CC(CO)CO)cc3C)cc12]

Step 1: diethyl 2-(4-(2-(5-amino-8-methylbenzo[f][1, 7]naphthyridin-2-yl)ethyl)-3-methylbenzyl)malonate To a stirred solution of (4-(2-(5-amino-8-methylbenzo[f] [1,7]naphthyridin-2-yl)ethyl)-3-methylphenyl)methanol (from Example 65/Step 1) (0.2 M) and diethyl malonate (2 eq) in dry toluene was added tributylphosphine (2 eq) and N$^1$,N$^1$,N$^2$,N$^2$-tetramethyldiazene-1,2-dicarboxamide (2 eq). The reaction mixture was stirred at 120° C. overnight. Upon completion of the reaction, the reaction mixture was concentrated under vacuum and the resulting crude residue was purified by chromatography (silica gel, 50-100% EtOAc in hexanes) to afford diethyl 2-(4-(2-(5-amino-8-methylbenzo [f][1,7]naphthyridin-2-yl)ethyl)-3-methylbenzyl)malonate as a white solid.

Step 2: 2-(4-(2-(5-amino-8-methylbenzo[f][1,7] naphthyridin-2-yl)ethyl)-3-methylbenzyl)propane-1, 3-diol 2-(4-(2-(5-Amino-8-methylbenzo[f][1,7]naphthyridin-2-yl)ethyl)-3-methylbenzyl)propane-1,3-diol was prepared from diethyl 2-(4-(2-(5-amino-8-methylbenzo[f][1,7]naphthyridin-2-yl)ethyl)-3-methylbenzyl)malonate (from the previous step) following the procedures described for Example 42/Step 3. $^1$H NMR: (methanol-d$_4$): δ 8.51 (d, 1H), 8.39 (d, 1H), 8.05 (d, 1H), 7.45 (s, 1H), 7.10 (dd, 1H), 6.91-6.87 (m, 2H), 6.83 (dd, 1H), 3.42 (d, 4H), 3.08-3.02 (m, 2H), 2.96-2.91 (m, 2H), 2.47 (d, 2H), 2.38 (s, 3H), 2.13 (s, 3H). LRMS [M+H]=416.2

Example 68

3-(4-(2-(5-amino-8-methylbenzo[f][1,7]naphthyridin-2-yl)ethyl)-3-methylphenyl)propanoic acid

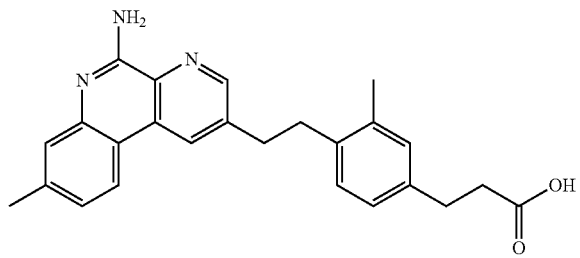 [SMILES: Cc1ccc2c(c1)nc(N)c1ncc(CCc3ccc(CCC(=O)O)cc3C)cc12]

A solution of ethyl 3-(4-(2-(5-amino-8-methylbenzo[f][1,7]naphthyridin-2-yl)ethyl)-3-methylphenyl)propanoate (from Example 66) in 1 N NaOH, THF and methanol (1:5:2, 0.1 N) was heated at 60° C. for 3 hours. After cooling to room temperature the reaction mixture was neutralized with 1 N HCl to pH 7, and was concentrated to give a crude residue which was purified by chromatography (silica gel, 0-20% methanol in dichloromethane) to afford (E)-ethyl 3-(4-(2-(5-amino-8-methylbenzo[f][1,7]naphthyridin-2-yl)ethyl)-3-methylphenyl)acrylate as a white solid. $^1$H NMR: (methanol-$d_4$): δ 8.73 (d, 1H), 8.54 (d, 1H), 8.20 (d, 1H), 7.45 (s, 1H), 7.37 (d, 1H), 7.00-6.97 (m, 2H), 6.92 (d, 1H), 3.19 (t, 2H), 3.04 (t, 2H), 2.81 (t, 2H), 2.53 (t, 2H), 2.50 (s, 3H), 2.25 (s, 3H). LRMS [M+H]=400.2

Example 69

5-amino-2-(4-methoxy-2-methylphenethyl)benzo[f][1,7]naphthyridine-8-carbaldehyde

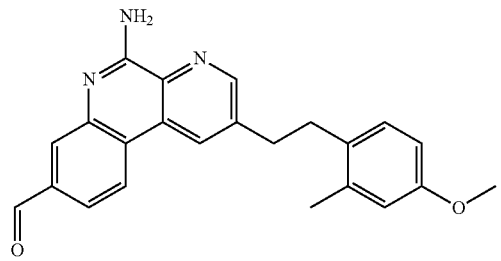 [SMILES: COc1ccc(CCc2cnc3c(N)nc4cc(C=O)ccc4c3c2)c(C)c1]

5-amino-2-(4-methoxy-2-methylphenethyl)benzo[f][1,7]naphthyridine-8-carbaldehyde was prepared from (5-amino-2-(4-methoxy-2-methylphenethyl)benzo[f][1,7]naphthyridin-8-yl)methanol (from Example 108) following the procedures described for Example 65/Step 2. $^1$H NMR: (CDCl$_3$): δ 10.19 (s, 1H), 8.74 (d, 1H), 8.43 (d, 1H), 8.32 (d, 1H), 8.18 (d, 1H), 7.88 (dd, 1H), 7.00 (d, 1H), 6.76 (d, 1H), 6.70 (dd, 1H), 6.30 (s, 2H), 3.80 (s, 3H), 3.16 (dd, 2H), 3.02 (dd, 2H), 2.29 (s, 3H). LRMS [M+H]=372.2

Example 70 ethyl 4-(2-(5-amino-8-methylbenzo[f][1,7]naphthyridin-2-yl)ethyl)benzoate

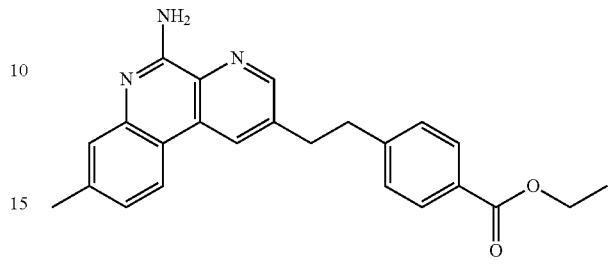

Step 1: ethyl 4-((5-chloro-6-cyanopyridin-3-yl)ethynyl)benzoate

A solution of 3,5-dichloropicolinonitrile (commercially available) (1.0 eq.), ethyl 4-ethynylbenzoate (commercially available) (1.0 eq.), trans-dichlororbis(triphenylphosphine)palladium (II) (10 mol %), copper (I) iodide (20 mol %), and triethylamine (5.0 eq.) in DMF (0.3 M) was stirred at 50° C. for 3 hours. After cooling to ambient temperature, the reaction mixture was diluted with ethyl acetate and 10% aqueous ammonium hydroxide. The two phases were separated, and the aqueous layer was extracted twice with ethyl acetate. The combined organic layers were washed with brine, dried over anhydrous MgSO$_4$, and concentrated en vaccuo. The crude material was purified by flash chromatography on a COMBIFLASH® system (ISCO) using 0-20% ethyl acetate in hexane to give ethyl 4-((5-chloro-6-cyanopyridin-3-yl)ethynyl)benzoate as a white solid.

Step 2: ethyl 4-((5-amino-8-methylbenzo[f][1,7]naphthyridin-2-yl)ethynyl)benzoate A solution of ethyl 4-((5-chloro-6-cyanopyridin-3-yl)ethynyl)benzoate (from the previous step) (1.0 eq.), tert-butyl 5-methyl-2-(4,4,5,5-tetramethyl-1,3,2-dioxaborolan-2-yl)phenylcarbamate (from Example 5/Step 2) (2.6 eq.), tetrakis(triphenylphosphine)palladium (10 mol %), and potassium carbonate (5.3 eq.) in toluene/ethanol (2:1, 0.2 M) was stirred at 100° C. overnight. After cooling to ambient temperature, the reaction mixture was diluted with 2% MeOH in DCM. The two phases were separated. The combined organic layers were washed with brine, dried over anhydrous MgSO$_4$, and concentrated en vaccuo. The crude material was purified by flash chromatography on a COMBIFLASH® system (ISCO) using 0-40% ethyl acetate in toluene to give ethyl 4-((5-amino-8-methylbenzo[f][1,7]naphthyridin-2-yl)ethynyl)benzoate.

Step 3: ethyl 4-(2-(5-amino-8-methylbenzo[f][1,7]naphthyridin-2-yl)ethyl)benzoate A solution of ethyl 4-((5-amino-8-methylbenzo[f][1,7]naphthyridin-2-yl)ethynyl)benzoate (from the previous step) (1.0 eq.) in THF/ethyl acetate (1:1, 0.05M) was flushed with nitrogen and palladium on carbon (10 wt %) was added. The reaction vessel was evacuated, flushed with hydrogen, and stirred overnight at room temperature. The reaction mixture was filtered through celite, washed with 2% MeOH in DCM, and concentrated en vaccuo. The crude material was purified by flash chromatography on a COMBIFLASH® system (ISCO) using 0-5% MeOH in DCM to give ethyl 4-(2-(5-amino-8-methylbenzo[f][1,7]naphthyridin-2-yl)ethyl)benzoate. $^1$H NMR (Acetone-$d_6$): δ 8.80 (s, 1H), 8.69 (s, 1H), 8.25 (d, 1H), 7.90 (d, 2H), 7.40-7.42 (m, 3H), 7.12 (d, 1H), 6.55 (br, 2H), 4.28 (q, 2H), 3.2-3.3 (m, 4H), 2.44 (s, 3H), 1.31 (t, 3H). LRMS [M+H]=386.2

Example 71

8-methyl-2-(4-methylphenethyl)benzo[f][1,7]naphthyridin-5-amine

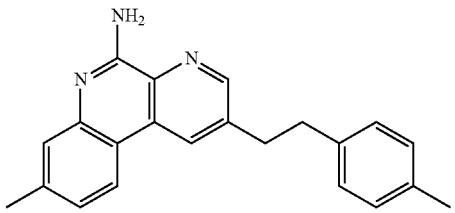

Step 1: 3-chloro-5-(p-tolylethynyl)picolinonitrile

A solution of 3,5-dichloropicolinonitrile (commercially available) (1.0 eq.), 1-ethynyl-4-methylbenzene (commercially available) (1.0 eq.), trans-dichlororbis(triphenylphosphine)palladium (II) (10 mol %), copper (I) iodide (20 mol %), and triethylamine (5.0 eq.) in DMF (0.3 M) was stirred at 50° C. for 3 hours. After cooling to ambient temperature, the reaction mixture was diluted with ethyl acetate and 10% aqueous ammonium hydroxide. The two phases were separated, and the aqueous layer was extracted twice with ethyl acetate. The combined organic layers were washed with brine, dried over anhydrous MgSO$_4$, and concentrated en vaccuo. The crude material was purified by stirring in hot ether/hexane mixtures and filtered to give 3-chloro-5-(p-tolylethynyl)picolinonitrile.

Step 2: 8-methyl-2-(p-tolylethynyl)benzo[f][1,7]naphthyridin-5-amine

A solution of 3-chloro-5-(p-tolylethynyl)picolinonitrile (from the previous step) (1.0 eq.), tert-butyl 5-methyl-2-(4,4,5,5-tetramethyl-1,3,2-dioxaborolan-2-yl)phenylcarbamate (from Example 5/Step 2) (1.2 eq.), tetrakis(triphenylphosphine)palladium (10 mol %), and 2N sodium carbonate aqueous solution (4.0 eq.) in toluene/ethanol (2:1, 0.2 M) was stirred at 100° C. overnight. After cooling to ambient temperature, the reaction mixture was diluted with 2% MeOH in DCM. The two phases were separated, and the aqueous layer was extracted with 2% MeOH in DCM twice. The combined organic layers were washed with brine, dried over anhydrous MgSO$_4$, and concentrated en vaccuo. The crude material was purified by flash chromatography on a COMBIFLASH® system (ISCO) using 0-40% ethyl acetate in toluene to give 8-methyl-2-(p-tolylethynyl)benzo[f][1,7]naphthyridin-5-amine.

Step 3: 8-methyl-2-(4-methylphenethyl)benzo[f][1,7]naphthyridin-5-amine

A solution of 8-methyl-2-(p-tolylethynyl)benzo[f][1,7]naphthyridin-5-amine (from the previous step) (1.0 eq.) in EtOH/ethyl acetate (1:1, 0.05M) was flushed with nitrogen and palladium on carbon (10 wt %) was added. The reaction vessel was evacuated, flushed with hydrogen, and stirred overnight at room temperature. The reaction mixture was filtered through celite, washed with 2% MeOH in DCM, and concentrated en vaccuo. The crude material was purified by flash chromatography on a COMBIFLASH® system (ISCO) using 0-5% MeOH in DCM to give 8-methyl-2-(4-methylphenethyl)benzo[f][1,7]naphthyridin-5-amine. $^1$H NMR (Acetone-$d_6$): δ 8.74 (s, 1H), 8.68 (s, 1H), 8.24 (d, 1H), 7.41 (s, 1H), 7.13-7.15 (m, 3H), 7.06 (d, 2H), 6.6 (br, 2H), 3.19 (t, 2H), 3.06 (t, 2H), 2.44 (s, 3H), 2.25 (s, 3H). LRMS [M+H]=328.1

Example 72

2-(4-(2-(5-amino-8-methylbenzo[f][1,7]naphthyridin-2-yl)ethyl)phenyl)propan-2-ol

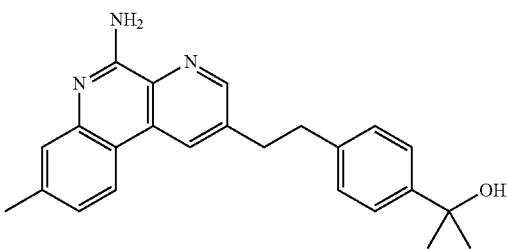 [SMILES: Cc1ccc2c(c1)nc(N)c1ncc(CCc3ccc(C(C)(C)O)cc3)cc12]

To a solution of ethyl 4-(2-(5-amino-8-methylbenzo[f][1,7]naphthyridin-2-yl)ethyl)benzoate (from Example 70) (1.0 eq.) in DCM at 0° C. was added 3.0 M methyl magnesium iodide (10 eq.) in ether and warmed to room temperature overnight. The reaction was cooled to 0° C. and quenched with 1N HCl aqueous solution and ether. After stirring for 15 minutes, the reaction mixture was neutralized with saturated aqueous sodium bicarbonate solution. The two phases were separated, and the aqueous layer was extracted with ether. The combined organic layers were washed with brine, dried over anhydrous MgSO$_4$, and concentrated en vaccuo. The crude material was purified by RP-HPLC using a 10-50% MeCN in water gradient followed by extraction in DCM to give 2-(4-(2-(5-amino-8 methylbenzo[f][1,7]naphthyridin-2-yl)ethyl)phenyl)propan-2-ol. $^1$H NMR (Acetone-$d_6$): δ 8.73 (m, 2H), 8.22 (d, 1H), 7.40-7.44 (m, 3H), 7.20 (d, 2H), 7.12 (d, 1H), 6.5 (br, 2H), 3.94 (s, 1H), 3.21 (t, 2H), 3.08 (t, 2H), 2.44 (s, 3H), 1.47 (s, 6H). LRMS [M+H]=372.2

Example 73

(4-(2-(5-amino-8-methylbenzo[f][1,7]naphthyridin-2-yl)ethyl)phenyl)methanol

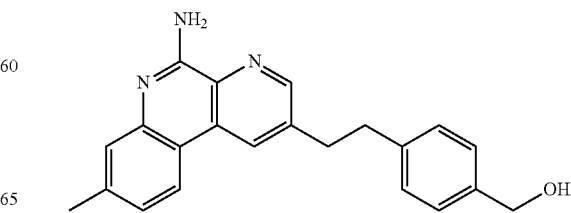

To a solution of ethyl 4-(2-(5-amino-8-methylbenzo[f][1,7]naphthyridin-2-yl)ethyl)benzoate (Example 70) (1.0 eq.) in THF (0.1 M) at 0° C. was added 1.0 M lithium triethylborohydride in THF (10 eq.) and warmed to room temperature over 2 hours. 1N HCl aqueous solution was added slowly to quench the reaction, and the mixture was heated to reflux for 30 minutes. The reaction mixture was neutralized with saturated aqueous sodium bicarbonate solution. The two phases were separated, and the aqueous layer was extracted with ethyl acetate (EA). The combined organic layers were washed with brine, dried over anhydrous $MgSO_4$, and concentrated en vaccuo. The crude material was purified by RP-HPLC using a 10-50% MeCN in water gradient followed by extraction in DCM to give (4-(2-(5-amino-8-methylbenzo[f][1,7]naphthyridin-2-yl)ethyl)phenyl)methanol. $^1H$ NMR (Acetone-$d_6$): δ 8.77 (s, 1H), 8.69 (s, 1H), 8.26 (d, 1H), 7.40 (s, 1H), 7.21-7.28 (m, 4H), 7.13 (d, 1H), 6.5 (br, 2H), 4.56 (s, 2H), 4.1 (br t, 1H), 3.10-3.23 (m, 4H), 2.44 (s, 3H). LRMS [M+H]=344.2

Example 74 ethyl 4-(2-(5-amino-8-methylbenzo[f][1,7]naphthyridin-2-yl)ethyl)-3-methylbenzoate

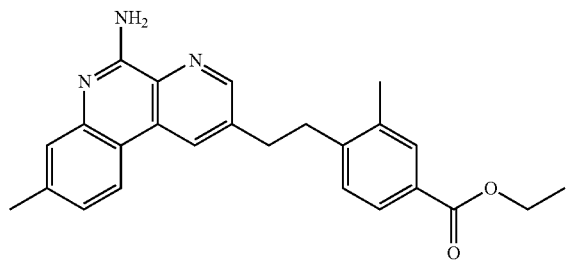 [SMILES: CCOC(=O)c1ccc(CCc2cnc3c(N)nc4cc(C)ccc4c3c2)c(C)c1]

Step 1: ethyl 4-bromo-3-methylbenzoate

To a solution of 4-bromo-3-methylbenzoic acid (commercially available) (1.0 eq.) in EtOH (0.3 M) was added thionyl chloride (1.5 eq.) and heated to reflux for 2 hours. The solvent was concentrated en vaccuo, and the residue was diluted in ether and neutralized with saturated aqueous sodium bicarbonate solution. The two phases were separated, and the aqueous layer was extracted with ether. The combined organic layers were washed with brine, dried over anhydrous $MgSO_4$, and concentrated en vaccuo to give ethyl 4-bromo-3-methylbenzoate.

Step 2: ethyl 3-methyl-4-((triethylsilyl)ethynyl)benzoate

A solution of ethyl 4-bromo-3-methylbenzoate (from the previous step) (1.0 eq.), triethyl(ethynyl)silane (1.1 eq.), trans-dichlororbis(triphenylphosphine)palladium (II) (10 mol %), copper (I) iodide (20 mol %), and triethylamine (5.0 eq.) in DMF (0.3 M) was stirred at 60° C. overnight. After cooling to ambient temperature, the reaction mixture was diluted with ethyl acetate and 10% aqueous ammonium hydroxide. The two phases were separated, and the aqueous layer was extracted twice with ethyl acetate. The combined organic layers were washed with brine, dried over anhydrous $MgSO_4$, and concentrated en vaccuo. The crude material was purified by flash chromatography on a COMBIFLASH® system (ISCO) using 0-5% ethyl acetate in hexane to give ethyl 3-methyl-4-((triethylsilyl)ethynyl)benzoate as a yellow oil.

Step 3: ethyl 4-ethynyl-3-methylbenzoate

To a solution of ethyl 3-methyl-4-((triethylsilyl)ethynyl) benzoate (from the previous step) (1.0 eq.) in THF (0.3 M) at 0° C. was added dropwise 1.0 M TBAF in THF (1.2 eq.). After stirring for 10 minutes at 0° C., the reaction was quenched with saturated aqueous sodium bicarbonate solution. The two phases were separated, and the aqueous layer was extracted with ether. The combined organic layers were washed with brine, dried over anhydrous $MgSO_4$, and concentrated en vaccuo. The crude material was purified by flash chromatography on a COMBIFLASH® system (ISCO) using 0-5% ethyl acetate in hexane to give ethyl 4-ethynyl-3-methylbenzoate as a white solid.

Step 4: ethyl 4-((5-chloro-6-cyanopyridin-3-yl)ethynyl)-3-methylbenzoate

A solution of 3,5-dichloropicolinonitrile (1.0 eq.), ethyl 4-ethynyl-3-methylbenzoate (from the previous step) (1.0 eq.), trans-dichlororbis(triphenylphosphine)palladium (II) (10 mol %), copper (I) iodide (20 mol %), and triethylamine (5.0 eq.) in DMF (0.3 M) was stirred at 50° C. for 3 hours. After cooling to ambient temperature, the reaction mixture was diluted with ethyl acetate and 10% aqueous ammonium hydroxide. The two phases were separated, and the aqueous layer was extracted twice with ethyl acetate. The combined organic layers were washed with brine, dried over anhydrous $MgSO_4$, and concentrated en vaccuo. The crude material was purified by flash chromatography on a COMBIFLASH® system (ISCO) using 0-10% ethyl acetate in hexane to give ethyl 4-((5-chloro-6-cyanopyridin-3-yl)ethynyl)-3-methylbenzoate as a white solid.

Step 5: ethyl 4-((5-amino-8-methylbenzo[f][1,7]naphthyridin-2-yl)ethynyl)-3-methylbenzoate A solution of ethyl 4-((5-chloro-6-cyanopyridin-3-yl)ethynyl)-3-methylbenzoate (from the previous step) (1.0 eq.), tert-butyl 5-methyl-2-(4,4,5,5-tetramethyl-1,3,2-dioxaborolan-2-yl)phenylcarbamate (from Example 5/Step 2) (1.1 eq.), tetrakis(triphenylphosphine)palladium (8 mol %), and potassium carbonate (3.0 eq.) in toluene/ethanol (9:1, 0.2 M) was stirred at 100° C. overnight. After cooling to ambient temperature, the reaction mixture was diluted with 2% MeOH in DCM. The two phases were separated. The combined organic layers were washed with brine, dried over anhydrous $MgSO_4$, and concentrated en vaccuo. The crude material was purified by flash chromatography on a COMBIFLASH® system (ISCO) using 0-40% ethyl acetate in toluene to give ethyl 4-((5-amino-8-methylbenzo[f][1,7]naphthyridin-2-yl)ethynyl)-3-methylbenzoate.

Step 6: ethyl 4-(2-(5-amino-8-methylbenzo[f][1,7]naphthyridin-2-yl)ethyl)-3-methylbenzoate A solution of ethyl 4-((5-amino-8-methylbenzo[f][1,7]naphthyridin-2-yl)ethynyl)-3-methylbenzoate (from the previous step) (1.0 eq.) in THF/ethyl acetate (1:1, 0.05M) was flushed with nitrogen and added 10% palladium on carbon (10 wt %). The reaction vessel was evacuated, flushed with hydrogen, and stirred overnight at room temperature. The reaction mixture was filtered through celite, washed with 2% MeOH in DCM, and concentrated en vaccuo. The crude material was purified by flash chromatography on a COMBI-FLASH® system (ISCO) using 30-100% EA in hexane to give ethyl 4-(2-(5-amino-8-methylbenzo[f][1,7]naphthyridin-2-yl)ethyl)-3-methylbenzoate. $^1$H NMR (Acetone-$d_6$): δ 8.79 (s, 1H), 8.71 (s, 1H), 8.24 (d, 1H), 7.80 (s, 1H), 7.73 (d, 1H), 7.40 (s, 1H), 7.31 (d, 1H), 7.12 (d, 1H), 6.5 (br, 2H), 4.29 (q, 2H), 3.19-3.22 (m, 4H), 2.44 (s, 3H), 2.39 (s, 3H), 1.31 (t, 3H). LRMS [M+H]=400.2

Example 75

4-(2-(5-amino-8-methylbenzo[f][1,7]naphthyridin-2-yl)ethyl)-3-methylbenzoic acid

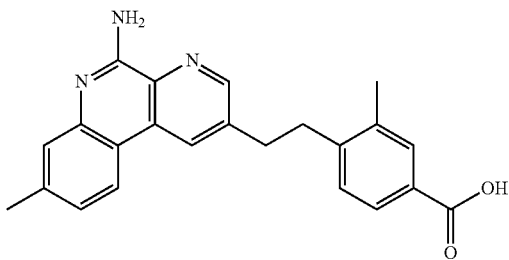 [SMILES: Cc1ccc2c(c1)nc(N)c1ncc(CCc3ccc(C(=O)O)cc3C)cc12]

To a solution of ethyl 4-(2-(5-amino-8-methylbenzo[f][1,7]naphthyridin-2-yl)ethyl)-3-methylbenzoate (from Example 74) (1.0 eq.) in EtOH was added 1N aqueous sodium hydroxide (1.5 eq.) and heated to 80° C. for 5 hours. The reaction mixture was neutralized by adding 1N aqueous HCl (1.5 eq.) and concentrated en vaccuo. The crude material was purified by RP-HPLC using a 10-50% MeCN in water gradient followed by concentration en vaccuo to give the TFA salt. $^1$H NMR (DMSO-$d_6$) of the TFA salt: δ 7.94-7.96 (m, 2H), 7.55 (d, 1H), 7.00 (s, 1H), 6.91 (d, 1H), 6.62-6.66 (m, 2H), 6.39 (d, 1H), 2.36-2.5 (m, 4H), 1.73 (s, 3H), 1.54 (s, 3H). LRMS [M+H]=372.2

Example 76

(4-(2-(5-amino-8-methylbenzo[f][1,7]naphthyridin-2-yl)ethyl)-3-methylphenyl)methanol

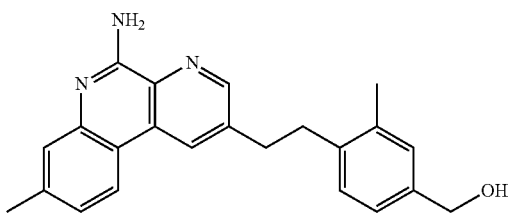 [SMILES: Cc1ccc2c(c1)nc(N)c1ncc(CCc3ccc(CO)cc3C)cc12]

To a solution of ethyl 4-(2-(5-amino-8-methylbenzo[f][1,7]naphthyridin-2-yl)ethyl)-3-methylbenzoate (from Example 74) (1.0 eq.) in THF (0.1M) at −78° C. was added 1.0 M DIBAL-H in toluene (10 eq.) and warmed to room temperature over 2 hours. 1.5 M Rochelle salt aqueous solution was added slowly to quench the reaction followed by addition of EA, and the mixture was stirred for 45 minutes. The two phases were separated, and the aqueous layer was extracted twice with EA. The combined organic layers were washed with brine, dried over anhydrous MgSO$_4$, and concentrated en vaccuo. The crude material was purified by RP-HPLC using a 10-50% MeCN in water gradient followed by extraction in DCM to give (4-(2-(5-amino-8-methylbenzo[f][1,7]naphthyridin-2-yl)ethyl)-3-methylphenyl)methanol. $^1$H NMR (Acetone-$d_6$): δ 8.77 (s, 1H), 8.71 (s, 1H), 8.25 (d, 1H), 7.41 (s, 1H), 7.10-7.15 (m, 4H), 6.5 (br, 2H), 4.54 (s, 2H), 4.05 (br, 1H), 3.08-3.18 (m, 4H), 2.44 (s, 3H), 2.31 (s, 3H). LRMS [M+H]=358.2

Example 77

8-methyl-2-(2,4,6-trimethylphenethyl)benzo[f][1,7]naphthyridin-5-amine

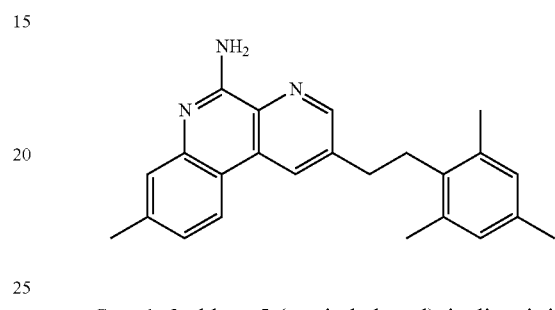

Step 1: 3-chloro-5-(mesitylethynyl)picolinonitrile

A solution of 3,5-dichloropicolinonitrile (1.0 eq.), 2-ethynyl-1,3,5-trimethylbenzene (commercially available) (1.0 eq.), trans-dichlororbis(triphenylphosphine)palladium (II) (10 mol %), copper (I) iodide (20 mol %), and triethylamine (5.0 eq.) in DMF (0.3 M) was stirred at 50° C. for 3 hours. After cooling to ambient temperature, the reaction mixture was diluted with ethyl acetate and 10% aqueous ammonium hydroxide. The two phases were separated, and the aqueous layer was extracted twice with ethyl acetate. The combined organic layers were washed with brine, dried over anhydrous MgSO$_4$, and concentrated en vaccuo. The crude material was purified by flash chromatography on a COMBIFLASH® system (ISCO) using 0-10% ethyl acetate in hexane to give 3-chloro-5-(mesitylethynyl)picolinonitrile a as white solid.

Step 2: 2-(mesitylethynyl)-8-methylbenzo[f][1,7]naphthyridin-5-amine

A solution of 3-chloro-5-(mesitylethynyl)picolinonitrile (from the previous step) (1.0 eq.), tert-butyl 5-methyl-2-(4,4,5,5-tetramethyl-1,3,2-dioxaborolan-2-yl)phenylcarbamate (from Example 5/Step 2) (1.1 eq.), tetrakis(triphenylphosphine)palladium (8 mol %), and 2N aqueous sodium carbonate solution (3.0 eq.) in toluene/ethanol (4:1, 0.2 M) was stirred at 100° C. overnight. After cooling to ambient temperature, the reaction mixture was diluted with 2% MeOH in DCM. The two phases were separated. The combined organic layers were washed with brine, dried over anhydrous MgSO$_4$, and concentrated en vaccuo. The crude material was purified by flash chromatography on a COMBIFLASH® system (ISCO) using 0-40% ethyl acetate in toluene to give 2-(mesitylethynyl)-8-methylbenzo[f][1,7]naphthyridin-5-amine.

Step 3: 8-methyl-2-(2,4,6-trimethylphenethyl)benzo[f][1,7]naphthyridin-5-amine

A solution of 2-(mesitylethynyl)-8-methylbenzo[f][1,7]naphthyridin-5-amine (from the previous step) (1.0 eq.) in EtOH (0.05M) was flushed with nitrogen and added palladium on carbon (10 wt %). The reaction vessel was evacuated, flushed with hydrogen, and stirred overnight at rt. The reaction mixture was filtered through celite, washed with 2% MeOH in DCM, and concentrated en vaccuo. The crude material was purified by flash chromatography on a COMBIFLASH® system (ISCO) using 0-50% ethyl acetate in hexane to give 8-methyl-2-(2,4,6-trimethylphenethyl)benzo[f][1,7]naphthyridin-5-amine. $^1$H NMR (Acetone-d$_6$): δ 8.73-8.74 (m, 2H), 8.25 (d, 1H), 7.42 (s, 1H), 7.14 (d, 1H), 6.83 (s, 2H), 6.55 (br, 2H), 3.07 (m, 4H), 2.47 (s, 3H), 2.29 (s, 6H), 2.22 (s, 3H). LRMS [M+H]=356.2

Example 78

2-(4-(2-(5-amino-8-methylbenzo[f][1,7]naphthyridin-2-yl)ethyl)-3-methylphenyl)propan-2-ol

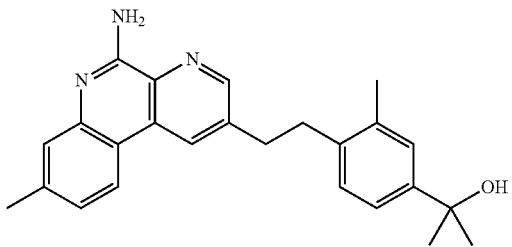 [SMILES: Cc1ccc2c(c1)nc(N)c1ncc(CCc3ccc(C(C)(C)O)cc3C)cc12]

To a solution of ethyl 4-(2-(5-amino-8-methylbenzo[f][1,7]naphthyridin-2-yl)ethyl)-3-methylbenzoate (from Example 74) (1.0 eq.) in DCM at 0° C. was added 3.0 M methyl magnesium iodide (10 eq.) in ether and warmed to room temperature overnight. The reaction was cooled to 0° C. and quenched with water. After stirring for 15 min, the reaction mixture was neutralized with saturated aqueous sodium bicarbonate solution and added EA. The two phases were separated, and the aqueous layer was extracted three times with EA. The combined organic layers were washed with brine, dried over anhydrous MgSO$_4$, and concentrated en vaccuo. The crude material was purified by flash chromatography on a COMBIFLASH® system (ISCO) using 0-5% MeOH in DCM to give a 2-(4-(2-(5-amino-8-methylbenzo[f][1,7]naphthyridin-2-yl)ethyl)-3-methylphenyl)propan-2-ol. $^1$H NMR (Acetone-d$_6$): δ 8.72-8.75 (m, 2H), 8.23 (d, 1H), 7.41 (s, 1H), 7.32 (s, 1H), 7.25 (d, 1H), 7.12-7.14 (m, 2H), 6.6 (br, 2H), 3.91 (s, 1H), 3.07-3.18 (m, 4H), 2.44 (s, 3H), 2.31 (s, 3H), 1.48 (s, 6H). LRMS [M+H]=386.2

Example 79

8-methyl-2-(4-propoxyphenethyl)benzo[f][1,7]naphthyridin-5-amine

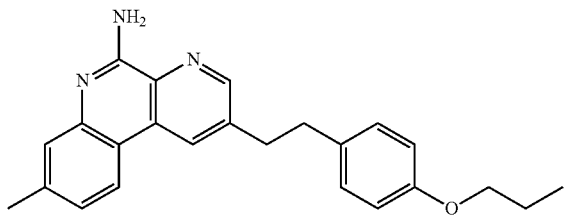 [SMILES: CCCOc1ccc(CCc2cnc3c(N)nc4cc(C)ccc4c3c2)cc1]

Step 1: 3-chloro-5-((4-propoxyphenyl)ethynyl)picolinonitrile

A solution of 3,5-dichloropicolinonitrile (1.0 eq.), 1-ethynyl-4-propoxybenzene (commercially available) (1.0 eq.), trans-dichlororbis(triphenylphosphine)palladium (II) (10 mol %), copper (I) iodide (20 mol %), and triethylamine (5.0 eq.) in DMF (0.3 M) was stirred at 50° C. for 3 hours. After cooling to ambient temperature, the reaction mixture was diluted with ethyl acetate and 10% aqueous ammonium hydroxide. The two phases were separated, and the aqueous layer was extracted twice with ethyl acetate. The combined organic layers were washed with brine, dried over anhydrous MgSO$_4$, and concentrated en vaccuo. The crude material was purified by flash chromatography on a COMBIFLASH® system (ISCO) using 0-10% ethyl acetate in hexane to give 3-chloro-5-((4-propoxyphenyl)ethynyl)picolinonitrile as a white solid.

Step 2:
3-chloro-5-(4-propoxyphenethyl)picolinonitrile

A solution of 3-chloro-5-((4-propoxyphenyl)ethynyl)picolinonitrile (from the previous step) (1.0 eq.) in EtOH (0.05M) was flushed with nitrogen and added platinum (VI) oxide (0.5 eq.). The reaction vessel was evacuated, flushed with hydrogen, and stirred for 5 hours at room temperature. The reaction mixture was filtered through celite, washed with 2% MeOH in DCM, and concentrated en vaccuo. The crude material was purified by flash chromatography on a COMBIFLASH® system (ISCO) using 0-15% ethyl acetate in hexane to give 3-chloro-5-(4-propoxyphenethyl)picolinonitrile.

Step 3: 8-methyl-2-(4-propoxyphenethyl)benzo[f][1,7]naphthyridin-5-amine

A solution of 3-chloro-5-(4-propoxyphenethyl)picolinonitrile (from the previous step) (1.0 eq.), tert-butyl 5-methyl-2-(4,4,5,5-tetramethyl-1,3,2-dioxaborolan-2-yl)phenylcarbamate (from Example 5/Step 2) (1.1 eq.), tetrakis(triphenylphosphine)palladium (8 mol %), and 2N aqueous sodium carbonate solution (3.0 eq.) in toluene (0.2 M) was stirred at 100° C. overnight. After cooling to ambient temperature, the reaction mixture was diluted with 2% MeOH in DCM. The two phases were separated. The combined organic layers were washed with brine, dried over anhydrous MgSO$_4$, and concentrated en vaccuo. The crude material was purified by flash chromatography on a COMBIFLASH® system (ISCO) using 0-40% ethyl acetate in toluene to give 8-methyl-2-(4-propoxyphenethyl)benzo[f][1,7]naphthyridin-5-amine. $^1$H NMR (Acetone-d$_6$): δ 8.74 (s, 1H), 8.67 (s, 1H), 8.24 (d, 1H), 7.41 (s, 1H), 7.15-7.17 (m, 3H), 6.81 (d, 2H), 6.5 (br, 2H), 3.87 (t, 2H), 3.18 (t, 2H), 3.04 (t, 2H), 2.44 (s, 3H), 1.73 (m, 2H), 0.99 (t, 3H). LRMS [M+H]=372.2

Example 80

(E)-ethyl 3-(5-amino-2-(4-methoxy-2-methylphenethyl)benzo[f][1,7]naphthyridin-8-yl)acrylate

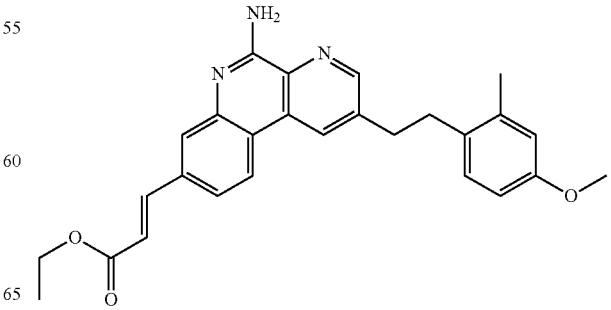

(E)-ethyl 3-(5-amino-2-(4-methoxy-2-methylphenethyl)benzo[f][1,7]naphthyridin-8-yl)acrylate was prepared from 5-amino-2-(4-methoxy-2-methylphenethyl)benzo[f][1,7]naphthyridine-8-carbaldehyde (from Example 69) and ethyl 2-(diethoxyphosphoryl)acetate (commercially available) following the procedures described for Example 65/Step 3. LRMS [M+H]=442.2

Example 81

(E)-3-(5-amino-2-(4-methoxy-2-methylphenethyl)benzo[f][1,7]naphthyridin-8-yl)acrylic acid

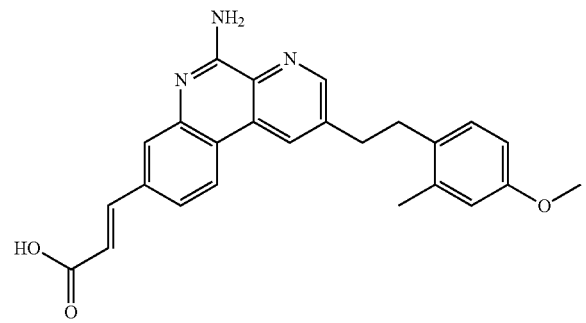 [SMILES: COc1ccc(CCc2cnc3c(N)nc4cc(/C=C/C(=O)O)ccc4c3c2)c(C)c1]

(E)-3-(5-amino-2-(4-methoxy-2-methylphenethyl)benzo[f][1,7]naphthyridin-8-yl)acrylic acid was prepared from (E)-ethyl 3-(5-amino-2-(4-methoxy-2-methylphenethyl)benzo[f][1,7]naphthyridin-8-yl)acrylate (from Example 80) following the procedures described for Example 68. $^1$H NMR of TFA salt (DMSO-$d_6$): δ 12.66 (s, 1H), 9.09 (s, 1H), 8.88 (s, 1H), 8.66 (d, 1H), 7.95 (d, 1H), 7.91 (s, 1H), 7.75 (d, 1H), 7.10 (d, 1H), 6.77-6.71 (m, 2H), 6.68 (dd, 1H), 3.70 (s, 3H), 3.16 (t, 2H), 3.00 (t, 2H), 2.30 (s, 3H). LRMS [M+H]=414.2

Example 82 ethyl 3-(5-amino-2-(4-methoxy-2-methylphenethyl)benzo[f][1,7]naphthyridin-8-yl)propanoate

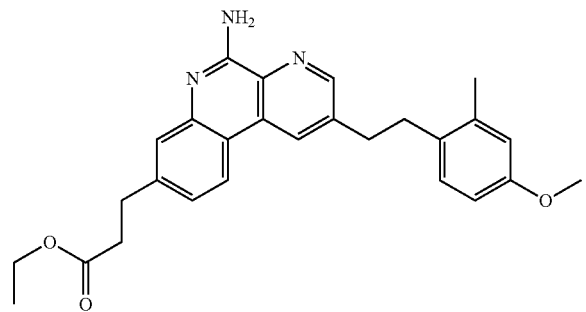 [SMILES: CCOC(=O)CCc1ccc2c(c1)nc(N)c1ncc(CCc3ccc(OC)cc3C)cc12]

Ethyl 3-(5-amino-2-(4-methoxy-2-methylphenethyl)benzo[f][1,7]naphthyridin-8-yl)propanoate was prepared from (E)-ethyl 3-(5-amino-2-(4-methoxy-2-methylphenethyl)benzo[f][1,7]naphthyridin-8-yl)acrylate (from Example 80) following the procedures described for Example 44/Step 5. $^1$H NMR (CDCl$_3$): δ 8.63 (d, 1H), 8.37 (d, 1H), 8.13 (d, 1H), 7.56 (d, 1H), 7.24 (d, 1H), 7.02 (d, 1H), 6.75 (d, 1H), 6.69 (dd, 1H), 6.15 (br s, 2H), 4.17 (q, 2H), 3.79 (s, 3H), 3.12 (dd, 4H), 2.99 (dd, 2H), 2.75 (t, 2H), 2.29 (s, 3H), 1.27 (t, 2H), 0.99 (t, 3H). LRMS [M+H]=444.2

Example 83

3-(5-amino-2-(4-methoxy-2-methylphenethyl)benzo[f][1,7]naphthyridin-8-yl)propanoic acid

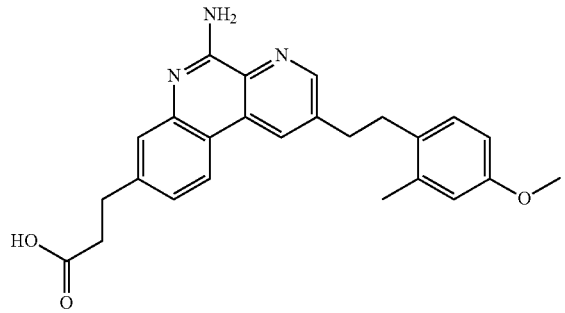 [SMILES: COc1ccc(CCc2cnc3c(N)nc4cc(CCC(=O)O)ccc4c3c2)c(C)c1]

3-(5-Amino-2-(4-methoxy-2-methylphenethyl)benzo[f][1,7]naphthyridin-8-yl)propanoic acid was prepared from ethyl 3-(5-amino-2-(4-methoxy-2-methylphenethyl)benzo[f][1,7]naphthyridin-8-yl)propanoate (from Example 82) following the procedures described for Example 68. $^1$H NMR (DMSO-$d_6$): δ 12.18 (s, 1H), 8.84 (d, 1H), 8.70 (d, 1H), 8.36 (d, 1H), 7.39 (d, 1H), 7.20 (dd, 1H), 7.09 (m, 2H), 6.74 (d, 1H), 6.68 (dd, 1H), 3.70 (s, 3H), 3.09 (dd, 2H), 2.96 (dd, 4H), 2.63 (t, 2H), 2.27 (s, 3H). LRMS [M+H]=416.2

Example 84

3-(5-amino-2-(4-methoxy-2-methylphenethyl)benzo[f][1,7]naphthyridin-8-yl)propan-1-ol

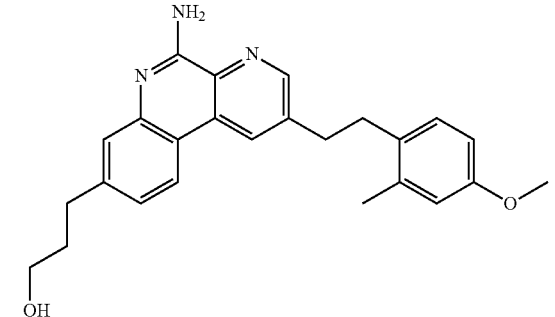 [SMILES: COc1ccc(CCc2cnc3c(N)nc4cc(CCCO)ccc4c3c2)c(C)c1]

3-(5-Amino-2-(4-methoxy-2-methylphenethyl)benzo[f][1,7]naphthyridin-8-yl)propan-1-ol was prepared from ethyl 3-(5-amino-2-(4-methoxy-2-methylphenethyl)benzo[f][1,7]naphthyridin-8-yl)propanoate (from Example 82) following the procedures described for Example 42/Step 3. $^1$H NMR (CDCl$_3$): δ 8.54 (d, 1H), 8.30 (d, 1H), 8.05 (d, 1H), 7.48 (d, 1H), 7.15 (dd, 1H), 6.93 (d, 1H), 6.66 (d, 1H), 6.61 (dd, 1H), 5.98 (br s, 2H), 3.71 (s, 3H), 3.66 (t, 2H), 3.03 (dd, 2H), 2.91 (dd, 2H), 2.81 (t, 2H), 2.20 (s, 3H), 1.98-1.90 (m, 2H). LRMS [M+H]=402.2

Example 85

(5-aminobenzo[f][1,7]naphthyridin-8-yl)methanol

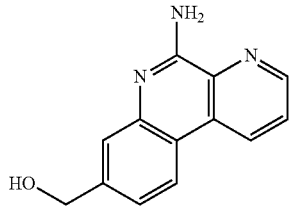 [SMILES: Nc1nc2cc(CO)ccc2c2cccnc12]

Step 1: 2-(tert-butoxycarbonylamino)-4-(methoxycarbonyl)phenylboronic acid

A solution of 2-amino-4-(methoxycarbonyl)phenylboronic acid hydrochloride (commercially available) (1.0 eq.), triethylamine (3.0 eq.), di-tert-butyl dicarbonate (1.1 eq.), and DMAP (0.1 eq.) in $CH_3CN$ (0.3 M) was stirred at 40° C. overnight. After cooling to ambient temperature, the reaction mixture was concentrated en vaccuo to obtain a crude residue. The crude material was purified by flash chromatography on a COMBIFLASH® system (ISCO) using 0-30% MeOH/DCM to give 2-(tert-butoxycarbonylamino)-4-(methoxycarbonyl)phenylboronic acid as a brown solid.

Step 2: methyl 5-aminobenzo[f][1,7]naphthyridine-8-carboxylate

A solution of 2-(tert-butoxycarbonylamino)-4-(methoxycarbonyl) phenylboronic acid (from the previous step) (1.0 eq.) and 3-bromopicolinonitrile (1.0 eq.), tetrakis(triphenylphosphine)palladium (5 mol %), and 2N aqueous sodium carbonate solution (2.0 eq.) in toluene/ethanol (2:1, 0.03 M) was stirred at 100° C. overnight. After cooling to ambient temperature, the reaction mixture was filtered to collect the precipitate. The precipitate was rinsed with EtOAc to give methyl 5-aminobenzo[f][1,7]naphthyridine-8-carboxylate as a pale brown solid.

Step 3: (5-aminobenzo[f][1,7]naphthyridin-8-yl)methanol

To a solution of methyl 5-aminobenzo[f][1,7]naphthyridine-8-carboxylate (from the previous step) (1.0 eq.) in EtOH (0.03M) was added $NaBH_4$ (10 eq.) at 25° C. The solution was heated to 80° C. for 5 hours. After cooling to ambient temperature, the reaction mixture was concentrated en vaccuo. The residue was portionized between saturated $NaHCO_3$ and EtOAc. The layers were separated and aqueous layer was extracted with EtOAc twice. The combined organic layer was washed with brine, dried over $MgSO_4$ and concentrated en vaccuo to obtain a crude residue. The crude material was purified by flash chromatography on a COMBIFLASH® system (ISCO) using 0-10% MeOH/DCM to give (5-aminobenzo[f][1,7]naphthyridin-8-yl)methanol as an off white solid: $^1H$ NMR (methanol-$d_4$): δ 8.82 (dd, 1H), 8.77 (dd, 1H), 7.26 (d, 1H), 7.70 (dd, 1H), 7.50 (d, 1H), 7.27 (dd, 1H), 4.66 (s, 2H). LRMS [M+H]=226.1.

Example 86

5-aminobenzo[f][1,7]naphthyridin-8-ol

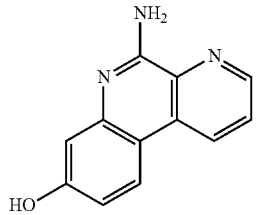 [SMILES: Nc1nc2cc(O)ccc2c2cccnc12]

To a solution of 8-methoxybenzo[f][1,7]naphthyridin-5-amine (from Example 10) (1.0 eq.) in DCM (0.04 M) was added $BBr_3$ (2.5 eq.) dropwise under $N_2$ at −20° C. The reaction was allowed to warm to ambient temperature over 30 minutes. The reaction was then stirred overnight. The reaction was quenched with saturated $NaHCO_3$ and extracted with EtOAc. The combined organic layer was washed with brine, dried over $MgSO_4$ and concentrated en vaccuo to obtain a crude residue. The crude material was purified by flash chromatography on a COMBIFLASH® system (ISCO) using 0-20% MeOH/DCM to give 5-aminobenzo[f][1,7] naphthyridin-8-ol as a yellow solid: $^1H$ NMR (acetone-$d_6$): δ 8.90 (dd, 1H), 8.83 (dd, 1H), 8.32 (d, 1H), 7.83 (dd, 1H), 7.11 (br s, 2H), 7.10 (d, 1H), 6.96 (dd, 1H), 5.86 (br s, 1H). LRMS [M+H]=212.1.

Example 87

5-aminobenzo[f][1,7]naphthyridine-8-carbaldehyde

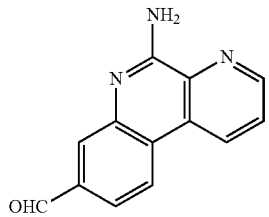 [SMILES: Nc1nc2cc(C=O)ccc2c2cccnc12]

A solution of (5-aminobenzo[f][1,7]naphthyridin-8-yl)methanol (from Example 85) (1.0 eq.) and activated $MnO_2$ (20 eq.) in DCM (0.1 M) was stirred at ambient temperature over night. The reaction mixture was diluted with DCM. The $MnO_2$ was filtered off, and the filtrate was concentrated en vaccuo to obtain a crude residue. The crude material was purified by flash chromatography on a COMBIFLASH® system (ISCO) using 0-10% MeOH/DCM to give 5-aminobenzo[f][1,7]naphthyridine-8-carbaldehyde as a yellow solid: $^1H$ NMR (acetone-$d_6$): δ 10.19 (s, 1H), 9.14 (dd, 1H), 9.01 (dd, 1H), 8.63 (d, 1H), 8.14 (d, 1H), 7.93 (dd, 1H), 7.81 (dd, 1H), 6.96 (br s, 2H). LRMS [M+H]=224.1

Example 88

1-(5-aminobenzo[f][1,7]naphthyridin-8-yl)ethanol

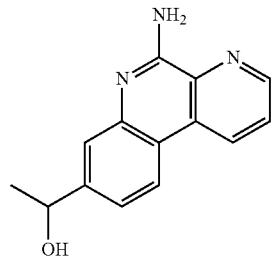 [SMILES: CC(O)c1ccc2c(c1)nc(N)c1ncccc12]

To a solution of 5-aminobenzo[f][1,7]naphthyridine-8-carbaldehyde (from Example 87) (1.0 eq.) in THF (0.02M) was added MeLi (2.5 eq.) at −78° C. The reaction was allowed to warm to ambient temperature overnight. The reaction was quenched by saturated $NH_4Cl$ and extracted with EtOAc. The combined organic layer was washed with brine, dried over $MgSO_4$ and concentrated en vaccuo to obtain a crude residue. The crude material was purified by flash chromatography on a COMBIFLASH® system (ISCO) using 0-5% MeOH/DCM to give 1-(5-aminobenzo[f][1,7]naphthyridin-8-yl)ethanol as a yellow solid: ¹H NMR (methanol-d₄): δ 8.94 (dd, 1H), 8.88 (dd, 1H), 8.38 (d, 1H), 7.81 (dd, 1H), 7.62 (d, 1H), 7.41 (dd, 1H), 4.97 (q, 1H), 1.53 (d, 3H). LRMS [M+H]=240.1.

Example 89

1-(5-aminobenzo[f][1,7]naphthyridin-8-yl)ethanone

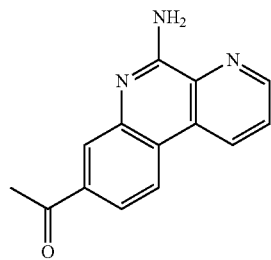 [SMILES: CC(=O)c1ccc2c(c1)nc(N)c1ncccc12]

A solution 1-(5-aminobenzo[f][1,7]naphthyridin-8-yl)ethanol (from Example 88) (1.0 eq.) and activated MnO₂ (20 eq.) in DCM (0.1 M) was stirred at ambient temperature over night. The reaction mixture was diluted with DCM. The MnO₂ was filtered off, and the filtrate was concentrated en vaccuo to obtain a crude residue. The crude material was purified by flash chromatography on a COMBIFLASH® system (ISCO) using 0-5% MeOH/DCM to give 1-(5-aminobenzo[f][1,7]naphthyridin-8-yl)ethanone as a yellow solid: ¹H NMR (acetone-d₆): δ 9.11 (dd, 1H), 8.99 (dd, 1H), 8.56 (d, 1H), 8.20 (d, 1H), 7.94-7.88 (m, 2H), 6.90 (br s, 2H), 2.70 (s, 3H). LRMS [M+H]=238.1.

Example 90

8-isopropylbenzo[f][1,7]naphthyridin-5-amine

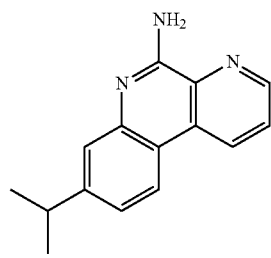 [SMILES: CC(C)c1ccc2c(c1)nc(N)c1ncccc12]

Step 1: 2-(5-aminobenzo[f][1,7]naphthyridin-8-yl)propan-2-ol

To a solution of methyl 5-aminobenzo[f][1,7]naphthyridine-8-carboxylate (from Example 85/Step 2) (1.0 eq.) in THF (0.02M) was added MeLi (10 eq.) at −78° C. The reaction was allowed to warm to ambient temperature overnight. The reaction was quenched by saturated NH₄Cl and extracted with EtOAc. The combined organic layer was washed with brine, dried over MgSO₄ and concentrated en vaccuo to obtain a crude residue. The crude material was purified by flash chromatography on a COMBIFLASH® system (ISCO) using 0-10% MeOH/DCM to give 2-(5-aminobenzo[f][1,7]naphthyridin-8-yl)propan-2-ol as a yellow oil.

Step 2: 8-(prop-1-en-2-yl)benzo[f][1,7]naphthyridin-5-amine

A solution of 2-(5-aminobenzo[f][1,7]naphthyridin-8-yl)propan-2-ol (from the previous step) (1.0 eq.) and p-TsOH (2 eq.) in toluene (0.01 M) was stirred at 90° C. for 6 hours. The reaction was quenched by saturated NaHCO₃ and extracted with EtOAc. The combined organic layer was washed with brine, dried over MgSO₄ and concentrated en vaccuo to obtain a crude residue. The crude material was purified by flash chromatography on a COMBIFLASH® system (ISCO) using 0-5% MeOH/DCM to give 8-(prop-1-en-2-yl)benzo[f][1,7]naphthyridin-5-amine as a yellow solid.

Step 3: 8-isopropylbenzo[f][1,7]naphthyridin-5-amine

A mixture of 8-(prop-1-en-2-yl)benzo[f][1,7]naphthyridin-5-amine (from the previous step) (1.0 eq) and Pd/C (wet, 10% wt) in EtOH was stirred under H₂ balloon overnight. The reaction mixture was diluted with DCM. The Pd/C was filtered off through celite, and the filtrate was concentrated en vaccuo to obtain a crude residue. The crude material was purified by flash chromatography on a COMBIFLASH® system (ISCO) using 0-60% EtOAc/Hexanes to give 8-isopropylbenzo[f][1,7]naphthyridin-5-amine as a yellow solid: ¹H NMR (acetone-d₆): δ 8.98 (dd, 1H), 8.88 (dd, 1H), 8.37 (d, 1H), 7.83 (dd, 1H), 7.49 (d, 1H), 7.27 (dd, 1H), 6.66 (br s, 2H), 3.10-3.00 (m, 1H), 1.33 (d, 6H). LRMS [M+H]=238.1.

Example 91

8-vinylbenzo[f][1,7]naphthyridin-5-amine

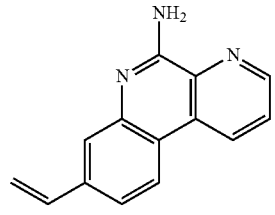 [SMILES: C=Cc1ccc2c(c1)nc(N)c1ncccc12]

To a solution of methyl triphenyl phosphonium iodide (6.0 eq.) was added nBuLi (7.0 eq.) at −78° C. The reaction mixture was allowed to warm to 0° C. and stirred for 30 minutes (deep orange color). The reaction was again cooled down to −78° C. and 5-aminobenzo[f][1,7]naphthyridine-8-carbaldehyde (from Example 87) (1.0 eq.) in THF was introduced dropwised to the reaction. The reaction was allowed to warm to ambient temperature overnight. The reaction was quenched by saturated NH₄Cl and extracted with EtOAc. The combined organic layer was washed with brine, dried over MgSO₄ and concentrated en vaccuo to obtain a crude residue. The crude material was purified by flash chromatography on a COMBIFLASH® system (ISCO) using 0-50% EtOAc/Hexanes to give 8-vinylbenzo[f][1,7]naphthyridin-5-amine as a white solid:¹H NMR (acetone-d₆): ¹H NMR (acetone-d₆): δ 9.00 (dd, 1H), 8.90 (dd, 1H), 8.41 (d, 1H), 7.84 (dd, 1H), 7.65 (d, 1H), 7.52 (dd, 1H), 6.91 (dd, 1H), 6.77 (br s, 2H), 5.97 (dd, 1H), 5.34 (dd, 1H). LRMS [M+H]=222.1.

Example 92

8-ethylbenzo[f][1,7]naphthyridin-5-amine

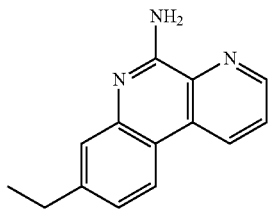 [SMILES: CCc1ccc2c(c1)nc(N)c1ncccc12]

A mixture of 8-vinylbenzo[f][1,7]naphthyridin-5-amine (1.0 eq) (from Example 91) and Pd/C (wet, 10% wt) in EtOH was stirred under H$_2$ balloon overnight. The reaction mixture was diluted with DCM. The Pd/C was filtered off through celite, and the filtrate was concentrated en vaccuo to obtain a crude residue. The crude material was purified by flash chromatography on a COMBIFLASH® system (ISCO) using 0-60% EtOAc/Hexanes to give 8-ethylbenzo[f][1,7]naphthyridin-5-amine as a white foam: $^1$H NMR (acetone-d$_6$): δ 8.98 (dd, 1H), 8.88 (dd, 1H), 8.35 (d, 1H), 7.82 (dd, 1H), 7.46 (d, 1H), 7.22 (dd, 1H), 6.63 (br s, 2H), 2.78 (q, 2H), 1.30 (t, 3H). LRMS [M+H]=224.1.

Example 93

8-(methoxymethyl)benzo[f][1,7]naphthyridin-5-amine

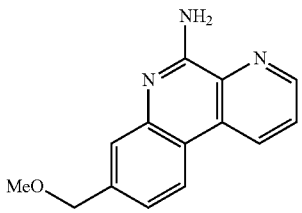

Step 1: tert-butyl 2-chloro-5-(methoxymethyl)phenylcarbamate

To a solution of 2-chloro-5-(methoxymethyl)aniline (commercially available) (1.0 eq.) in THF (0.2M) at 0° C. under N$_2$ atmosphere was added dropwise 1M NaHMDS (2.5 eq.). The reaction was stirred for 15 minutes at 0° C., and a solution of di-tert-butyl dicarbonate in THF was added. The reaction was warmed to ambient temperature overnight. The solvent was evaporated, and the resulting residue was quenched with 0.1N HCl aqueous solution. The aqueous suspension was extracted twice with EtOAc. The combined organic layers were washed with brine, dried over anhydrous MgSO$_4$, and concentrated en vaccuo. The crude material was purified by flash chromatography on a COMBIFLASH® system (ISCO) using 0-30% EtOAc/Hexanes to give tert-butyl 2-chloro-5-(methoxymethyl)phenylcarbamate as a colorless oil.

Step 2: tert-butyl 5-(methoxymethyl)-2-(4,4,5,5-tetramethyl-1,3,2-dioxaborolan-2-yl)phenylcarbamate Tert-butyl 2-chloro-5-(methoxymethyl)phenylcarbamate (from the previous step) (1.0 eq.), 4,4,4',4',5,5,5',5'-octamethyl-2,2'-bi(1,3,2-dioxaborolane) (3.0 eq.), Pd$_2$dba$_3$ (2.5%), XPhos (10%), and KOAc (3 eq.) were mixed in dioxane (0.2 M) under N$_2$ atmosphere. The reaction was heated to 110° C. and stirred overnight. The resulting suspension was cooled to ambient temperature, diluted with ether, filtered through celite, and the filtrate was concentrated en vaccuo. The combined organic layers were washed with brine, dried over anhydrous MgSO$_4$, and concentrated en vaccuo. The crude material was purified by flash chromatography on a COMBIFLASH® system (ISCO) using 0-20% EtOAc/Hexanes to give tert-butyl 5-(methoxymethyl)-2-(4,4,5,5-tetramethyl-1,3,2-dioxaborolan-2-yl)phenylcarbamate as a white foam.

Step 3: 8-(methoxymethyl)benzo[f][1,7]naphthyridin-5-amine

A solution of tert-butyl 5-(methoxymethyl)-2-(4,4,5,5-tetramethyl-1,3,2-dioxaborolan-2-yl)phenylcarbamate (from the previous step) (1.0 eq.) and 3-bromopicolino-nitrile (1.0 eq.) in toluene (0.44 M) was mixed with tetrakis(triphenylphosphine)palladium (5 mol %) and 2N aqueous potassium carbonate solution (2.0 eq.). The reaction was heated to 100° C. and stirred overnight. After cooling to ambient temperature, the reaction mixture was diluted with 2% MeOH in DCM and water. The two phases were separated, and the aqueous layer was extracted twice with 2% MeOH in DCM. The combined organic layers were washed with brine, dried over anhydrous MgSO$_4$, and concentrated en vaccuo. The crude material was purified by flash chromatography on a COMBIFLASH® system (ISCO) using 0-100% EtOAc/Hexanes to give 8-(methoxymethyl)benzo[f][1,7]naphthyridin-5-amine as a white solid: $^1$H NMR (methanol-d$_4$): δ 8.97 (dd, 1H), 8.91 (dd, 1H), 8.41 (dd, 1H), 7.83 (dd, 1H), 7.59 (d, 1H), 7.37 (dd, 1H), 4.62 (s, 2H), 3.45 (s, 3H). LRMS [M+H]=240.1.

Example 94

(5-amino-2-phenethylbenzo[f][1,7]naphthyridin-8-yl)methanol

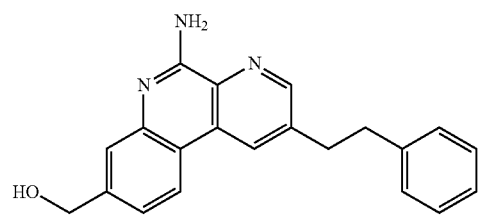 [SMILES: Nc1nc2cc(CO)ccc2c2cc(CCc3ccccc3)cnc12]

Step 1: methyl 5-amino-2-phenethylbenzo[f][1,7]naphthyridine-8-carboxylate

A solution of 2-(tert-butoxycarbonylamino)-4-(methoxycarbonyl) phenylboronic acid (from Example 85/Step1) (1.0 eq.) and 2-chloro-6-phenethylnicotinonitrile (prepared from (E)-3-chloro-5-styrylpicolinonitrile (from Example 32/Step 1) following the procedure described in Example 114/Step3)

(1.0 eq.), tetrakis(triphenyl-phosphine)palladium (5 mol %), and 2N aqueous sodium carbonate solution (2.0 eq.) in toluene/ethanol (2:1, 0.03 M) was stirred at 100° C. overnight. After cooling to ambient temperature, the reaction mixture was diluted with EtOAc and water. The two phases were separated, and the aqueous layer was extracted twice with EtOAc. The combined organic layers were washed with brine, dried over anhydrous MgSO$_4$, and concentrated en vaccuo. The crude material was purified by flash chromatography on a COMBIFLASH® system (ISCO) using 0-60% EtOAc/Hexanes to give methyl 5-amino-2-phenethylbenzo[f][1,7]naphthyridine-8-carboxylate as a white solid.

Step 2: (5-amino-2-phenethylbenzo[f][1,7]naphthyridin-8-yl)methanol

To a solution of methyl 5-amino-2-phenethylbenzo[f][1,7]naphthyridine-8-carboxylate (from the previous step) (1.0 eq.) in THF (0.03M) was added Super-H (10 eq.) at 0° C. The solution was allowed to warm to ambient temperature over 30 min The reaction was quenched by water until no bubbling. The layers were separated and aqueous layer was extracted with EtOAc. The combined organic layer was washed with brine, dried over MgSO$_4$ and concentrated en vaccuo to obtain a crude residue. The crude material was purified by flash chromatography on a COMBIFLASH® system (ISCO) using 0-10% MeOH/DCM to give (5-amino-2-phenethyl-benzo[f][1,7]naphthyridin-8-yl)methanol as an off white solid: $^1$H NMR (methanol-d$_4$): δ 8.63 (dd, 1H), 8.56 (dd, 1H), 8.24 (d, 1H), 7.57 (d, 1H), 7.35 (dd, 1H), 7.27-7.15 (m, 5H), 4.75 (s, 2H), 3.20 (t, 2H), 3.06 (t, 2H). LRMS [M+H]=330.1.

Example 95

(5-amino-2-(4-methoxyphenethyl)benzo[f][1,7]naphthyridin-8-yl)methanol

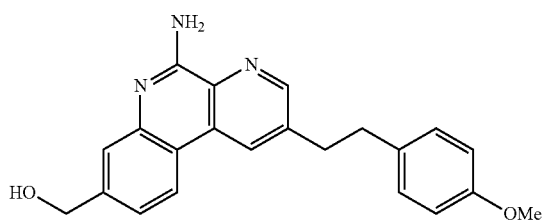 [SMILES: COc1ccc(CCc2cnc3c(N)nc4cc(CO)ccc4c3c2)cc1]

Step 1: methyl 5-amino-2-(4-methoxyphenethyl)benzo[f][1,7]naphthyridine-8-carboxylate A solution of 2-(tert-butoxycarbonylamino)-4-(methoxycarbonyl)phenylboronic acid (from Example 85/Step 1) (1.0 eq.) and 2-chloro-6-(4-methoxyphenethyl)nicotinonitrile (prepared from reaction of 3,5-dichloropicolinonitrile with 1-ethynyl-4-methoxybenzene following the procedure described in Example 44/Step 3 and reduction of the product following the procedure described in Example 114/Step3) (1.0 eq.), tetrakis(triphenyl-phosphine)palladium (5 mol %), and 2N aqueous sodium carbonate solution (2.0 eq.) in toluene/ethanol (2:1, 0.03 M) was stirred at 100° C. overnight. After cooling to ambient temperature, the reaction mixture was diluted with EtOAc and water. The two phases were separated, and the aqueous layer was extracted twice with EtOAc. The combined organic layers were washed with brine, dried over anhydrous MgSO$_4$, and concentrated en vaccuo. The crude material was purified by flash chromatography on a COMBIFLASH® system (ISCO) using 0-80% EtOAc/Hexanes to give methyl 5-amino-2-(4-methoxyphenethyl)benzo[f][1,7]naphthyridine-8-carboxylate as a white solid.

Step 2: (5-amino-2-(4-methaxyphenethyl)benzo[f][1,7]naphthyridin-8-yl)methanol

To a solution of methyl 5-amino-2-(4-methoxyphenethyl)benzo[f][1,7]naphthyridine-8-carboxylate (from the previous step) (1.0 eq.) in THF (0.03M) was added Super-H (10 eq.) at 0° C. The solution was allowed to warm to ambient temperature over 30 minutes. The reaction was quenched by water until no bubbling. The layers were separated and aqueous layer was extracted with EtOAc. The combined organic layer was washed with brine, dried over MgSO$_4$ and concentrated en vaccuo to obtain a crude residue. The crude material was purified by flash chromatography on a COMBIFLASH® system (ISCO) using 0-100% EtOAc/Hexanes to give (5-amino-2-(4-methoxyphenethyl)benzo[f][1,7]naphthyridin-8-yl)methanol as an off white solid (31%): $^1$H NMR (acetone-d$_6$): δ 8.79 (d, 1H), 8.70 (d, 1H), 8.35 (d, 1H), 7.61 (d, 1H), 7.33 (dd, 1H), 7.13 (d, 2H), 6.83 (d, 2H), 6.62 (br s, 2H), 4.47 (s, 2H), 4.40 (br s, 1H), 3.75 (s, 3H), 3.22 (t, 2H), 3.06 (t, 2H). LRMS [M+H]=360.2.

Example 96 benzo[f][1,7]naphthyridine-5,8-diamine

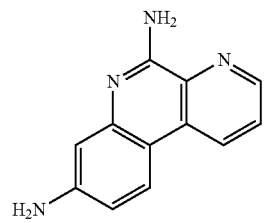 [SMILES: Nc1ccc2c(c1)nc(N)c1ncccc12]

Step 1: tert-butyl 2-bromo-5-nitrophenylcarbamate

To a solution of 2-bromo-5-nitroaniline (commercially available) (1.0 eq.) in THF (0.2M) at 0° C. under N$_2$ atmosphere was added dropwise 1M NaHMDS (2.5 eq.). The reaction was stirred for 15 minutes at 0° C., and a solution of di-tert-butyl dicarbonate in THF was added. The reaction was warmed to ambient temperature overnight. The solvent was evaporated, and the resulting residue was quenched with 0.1N HCl aqueous solution. The aqueous suspension was extracted twice with EtOAc. The combined organic layers were washed with brine, dried over anhydrous MgSO$_4$, and concentrated en vaccuo. The crude material was purified by flash chromatography on a COMBIFLASH® system (ISCO) using 0-30% EtOAc/Hexanes to give tert-butyl 2-bromo-5-nitrophenylcarbamate as a colorless oil.

Step 2: tert-butyl 5-nitro-2-(4,4,5,5-tetramethyl-1,3,2-dioxaborolan-2-yl)phenyl carbamate Tert-butyl 2-bromo-5-nitrophenylcarbamate (from the previous step) (1.0 eq.), 4,4,4',4',5,5,5',5'-octamethyl-2,2'-bi(1, 3,2-dioxaborolane) (1.8 eq.), dichloro[1,1'-bis(diphenyl phosphino)ferrocene]palladium (II) (5%), and sodium acetate (4.5 eq.) were mixed in dioxane (0.2 M) under N2 atmosphere. The reaction was heated to 100° C. and stirred overnight. The resulting suspension was cooled to ambient temperature, diluted with ether, filtered through celite, and the filtrate was concentrated en vaccuo. The residue was purified by flash chromatography on a COMBIFLASH® system (ISCO) using 0-30% EtOAc/Hexanes to give tert-butyl 5-nitro-2-(4,4,5,5-tetramethyl-1,3,2-dioxaborolan-2-yl)phenyl carbamate as a white foam.

Step 3: 8-nitrobenzo[f][1,7]naphthyridin-5-amine

A solution of tert-butyl 5-nitro-2-(4,4,5,5-tetramethyl-1,3,2-dioxaborolan-2-yl)phenylcarbamate (from the previous step) (1.0 eq.) and 3-bromopicolinonitrile (1.0 eq.) in toluene (0.44 M) was mixed with tetrakis(triphenyl-phosphine)palladium (5 mol %) and 2N aqueous potassium carbonate solution (2.0 eq.). The reaction was heated to 100° C. and stirred overnight. After cooling to ambient temperature, the reaction mixture was filtered to collect the precipitate. The precipitate was rinsed with EtOAc to give 8-nitrobenzo[f][1,7]naphthyridin-5-amine as a yellow solid.

Step 4: benzo[f][1,7]naphthyridine-5,8-diamine

A mixture of 8-nitrobenzo[f][1,7]naphthyridin-5-amine (from the previous step) (1.0 eq) and Pd/C (wet, 10% wt) in EtOH was stirred under H$_2$ balloon overnight. The reaction mixture was diluted with DCM. The insoluble solid was filtered off through celite, and the filtrate was concentrated en vaccuo to obtain a crude residue. The crude material was washed with acetone to give benzo[f][1,7]naphthyridine-5,8-diamine as an off white solid: $^1$H NMR (methanol-d$_4$): δ 8.73 (dd, 1H), 8.71 (dd, 1H), 8.11 (d, 1H), 7.69 (dd, 1H), 6.86 (d, 1H), 6.82 (dd, 1H). LRMS [M+H]=211.1.

Example 97

8-(aminomethyl)benzo[f][1,7]naphthyridin-5-amine

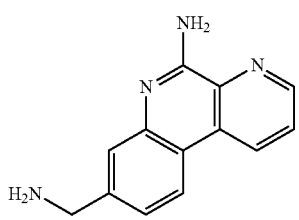 [SMILES: NCc1ccc2c(c1)nc(N)c1ncccc12]

Step 1:
2-(tert-butoxycarbonylamino)-4-cyanophenylboronic acid

The titled compound was prepared according to the procedure described in Example 85/Step 1, but using 2-amino-4-cyanophenylboronic acid hydrochloride (commercially available) as the starting material. The crude material was purified by flash chromatography on a COMBIFLASH® system (ISCO) using 0-30% MeOH/DCM to give 2-(tert-butoxycarbonylamino)-4-cyanophenylboronic acid as an off white solid.

Step 2:
5-aminobenzo[f][1,7]naphthyridine-8-carbonitrile

The titled compound was prepared according to the procedure described in Example 96/Step 3, but using 2-(tert-butoxycarbonylamino)-4-cyanophenylboronic acid (from the previous step) as the starting material. The crude material was rinsed with 1:1 EtOAc/Hexanes to give 5-aminobenzo[f][1,7]naphthyridine-8-carbonitrile as a pale yellow solid.

Step 4: benzo[f][1,7]naphthyridine-5,8-diamine

A mixture of 8-nitrobenzo[f][1,7]naphthyridin-5-amine (from the previous step) (1.0 eq) and Raney Nickel (wet, 10% wt) in EtOH/ammonia (2:1) was stirred under H$_2$ balloon overnight. The reaction mixture was diluted with DCM. The insoluble solid was filtered off through celite, and the filtrate was concentrated en vaccuo to obtain a crude residue. The crude material was washed with 10% MeOH/DCM and 70% EtOAc/Hexanes to give benzo[f][1,7]naphthyridine-5,8-diamine as an off white solid: $^1$H NMR (methanol-d$_4$): δ 8.97 (dd, 1H), 8.90 (dd, 1H), 8.41 (d, 1H), 7.83 (dd, 1H), 7.57 (d, 1H), 7.39 (dd, 1H), 3.96 (s, 2). LRMS [M+H]=229.1.

Example 98

3-fluoro-8-methylbenzo[f][1,7]naphthyridin-5-amine

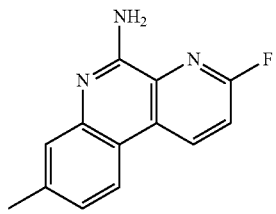 [SMILES: Cc1ccc2c(c1)nc(N)c1nc(F)ccc12]

Step 1:
3-chloro-8-methylbenzo[f][1,7]naphthyridin-5-amine

A solution of tert-butyl 5-methyl-2-(4,4,5,5-tetramethyl-1,3,2-dioxaborolan-2-yl)phenylcarbamate (from Example 5/Step 2) (1.0 eq.) and 3-bromo-6-chloropicolinonitrile (from Example 20/Step 2) (1.0 eq.), tetrakis(triphenyl-phosphine) palladium (5 mol %), and 2N aqueous sodium carbonate solution (2.0 eq.) in toluene/ethanol (2:1, 0.03 M) was stirred at 100° C. overnight. After cooling to ambient temperature, the reaction mixture was diluted with EtOAc and water. The two phases were separated, and the aqueous layer was extracted twice with EtOAc. The combined organic layers were washed with brine, dried over anhydrous MgSO$_4$, and concentrated en vaccuo. The crude material was purified by flash chromatography on a COMBIFLASH® system (ISCO) using 0-40% EtOAc/Hexanes to give 3-chloro-8-methylbenzo[f][1,7]naphthyridin-5-amine as a pale yellow solid.

Step 2:
3-fluoro-8-methylbenzo[f][1,7]naphthyridin-5-amine

A mixture of 3-chloro-8-methylbenzo[f][1,7]naphthyridin-5-amine (from the previous step) (1.0 eq.) potassium fluoride (4.0 eq.), and 18-crown-6 (0.4 eq.) in NMP (0.1M) was heated in microwave reactor at 210° C. for 2 hours. After cooling to ambient temperature, the reaction residue was purified by flash chromatography on a COMBIFLASH® system (ISCO) using 0-30% EtOAc/Hexanes to give 3-fluoro-8-methylbenzo[f][1,7]naphthyridin-5-amine as a white solid. $^1$H NMR (acetone-d$_6$): δ 9.20 (dd, 1H), 8.32 (d, 1H), 7.58 (dd, 1H), 7.46 (d, 1H), 7.21 (dd, 1H), 6.51 (br s, 2H), 2.47 (s, 3H). LRMS [M+H]=228.1.

Example 99

(5-amino-3-fluorobenzo[f][1,7]naphthyridin-8-yl)methanol

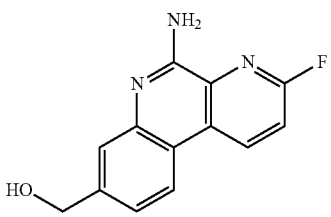 [SMILES: Nc1nc2cc(CO)ccc2c2ccc(F)nc12]

Step 1: tert-butyl 5-(((tert-butyldimethylsilyloxy)methyl)-2-(4,4,5,5-tetramethyl-1,3,2-dioxaborolan-2-yl)phenylcarbamate The titled compound was prepared according to the procedure described in Example 93/Step 1 and 2, but using 5-((tert-butyldimethylsilyloxy)methyl)-2-chloroaniline (commercially available) as the starting material. The crude material was purified by flash chromatography on a COMBIFLASH® system (ISCO) using 0-20% EtOAc/Hexanes to give tert-butyl 5-((tert-butyldimethylsilyloxy)methyl)-2-(4,4,5,5-tetramethyl-1,3,2-dioxaborolan-2-yl)phenylcarbamate as a white foam.

Step 2: 8-((tert-butyldimethylsilyloxy)methyl)-3-chlorobenzo[f][1,7]naphthyridin-5-amine The titled compound was prepared according to the procedure described in Example 98/Step 1, but using tert-butyl 5-((tert-butyldimethylsilyloxy)methyl)-2-(4,4,5,5-tetramethyl-1,3,2-dioxaborolan-2-yl)phenylcarbamate (from the previous step) as the starting material. The crude material was purified by flash chromatography on a COMBIFLASH® system (ISCO) using 0-15% EtOAc/Hexanes to give 8-((tert-butyldimethylsilyloxy)methyl)-3-chlorobenzo[f][1,7]naphthyridin-5-amine as a pale yellow solid.

Step 3: (5-amino-3-chlorobenzo[f][1,7]naphthyridin-8-yl)methanol

A solution of 8-((tert-butyldimethylsilyloxy)methyl)-3-chlorobenzo[f][1,7]naphthyridin-5-amine (from the previous step) (1.0 eq.) and TBAF (1.1 eq.) in THF was stirred at ambient temperature overnight. The reaction was quenched with saturated NaHCO$_3$. The two phases were separated, and the aqueous layer was extracted twice with Et$_2$O. The combined organic layers were washed with brine, dried over anhydrous MgSO$_4$, and concentrated en vaccuo. The crude material was purified by flash chromatography on a COMBI-FLASH® system (ISCO) using 0-5% MeOH/DCM to give (5-amino-3-chlorobenzo[f][1,7]naphthyridin-8-yl)methanol as a white solid.

Step 4: (5-amino-3-fluorobenzo[f][1,7]naphthyridin-8-yl)methanol

The titled compound was prepared according to the procedure described in Example 98/Step 2, but using (5-amino-3-chlorobenzo[f][1,7]naphthyridin-8-yl)methanol (from the previous step) as the starting material. The crude material was purified by flash chromatography on a COMBIFLASH® system (ISCO) using 0-40% EtOAc/Hexanes to give (5-amino-3-fluorobenzo[f][1,7]naphthyridin-8-yl)methanol as a white solid. $^1$H NMR (methanol-d$_4$): δ 9.15 (dd, 1H), 8.38 (d, 1H), 7.64 (d, 1H), 7.55 (dd, 1H), 7.41 (dd, 1H), 4.77 (s, 2H). LRMS [M+H]=244.1.

Example 100

3-chlorobenzo[f][1,7]naphthyridine-5,8-diamine

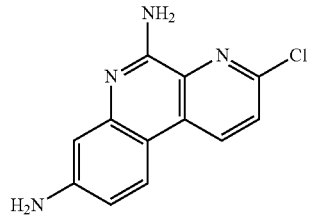 [SMILES: Nc1ccc2c(c1)nc(N)c1nc(Cl)ccc12]

Step 1: 3-chloro-8-nitrobenzo[f][1,7]naphthyridin-5-amine

The titled compound was prepared according to the procedure described in Example 98/Step 1, but using tent-butyl 5-nitro-2-(4,4,5,5-tetramethyl-1,3,2-dioxaborolan-2-yl)phenylcarbamate (commercially available) as the starting material. The crude material was purified by flash chromatography on a COMBIFLASH® system (ISCO) using 0-40% EtOAc/Hexanes to give 3-chloro-8-nitrobenzo[f][1,7]naphthyridin-5-amine as a pale yellow solid.

Step 2: 3-chlorobenzo[f][1,7]naphthyridine-5,8-diamine

A mixture of 8-nitrobenzo[f][1,7]naphthyridin-5-amine (from the previous step) (1.0 eq) and Raney Nickel (wet, 10% wt) in EtOH was stirred under H$_2$ balloon overnight. The reaction mixture was diluted with DCM. The insoluble solid was filtered off through celite, and the filtrate was concentrated en vaccuo to obtain a crude residue. The crude material was purified by flash chromatography on a COMBIFLASH® system (ISCO) using 0-100% EtOAc/Hexanes to give 3-chlorobenzo[f][1,7]naphthyridine-5,8-diamine as a white solid. $^1$H NMR (methanol-d$_4$): δ 8.75 (d, 1H), 8.08 (dd, 1H), 7.70 (d, 1H), 6.84-6.81 (m, 2H). LRMS [M+H]=245.1.

Example 101

3-fluorobenzo[f][1,7]naphthyridine-5,8-diamine

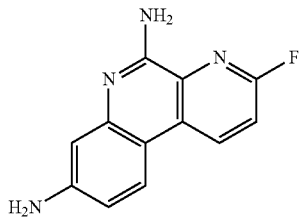 [SMILES: Nc1ccc2c(c1)nc(N)c1nc(F)ccc12]

The titled compound was prepared according to the procedure described in Example 98/Step 2, but using 3-chlorobenzo[f][1,7]naphthyridine-5,8-diamine (from Example 100) as the starting material. The crude material was purified by flash chromatography on a COMBIFLASH® system (ISCO) using 0-7% MeOH/DCM to give 3-fluorobenzo[f][1,7]naphthyridine-5,8-diamine as a white solid. $^1$H NMR (methanol-$d_4$): δ 8.93 (dd, 1H), 8.09 (d, 1H), 7.44 (dd, 1H), 6.86-6.83 (m, 2H). LRMS [M+H]=229.1.

Example 102

8-isobutylbenzo[f][1,7]naphthyridin-5-amine

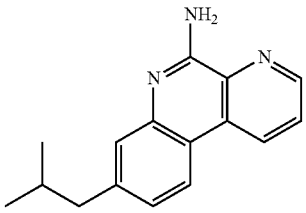 [SMILES: CC(C)Cc1ccc2c(c1)nc(N)c1ncccc12]

8-Isobutylbenzo[f][1,7]naphthyridin-5-amine was prepared from 5-aminobenzo[f][1,7]naphthyridine-8-carbaldehyde (from Example 87) with isopropyl(triphenyl)phosphonium bromide following the procedures described for Example 91 (wittig reaction) and Example 92 (reduction). $^1$H NMR (acetone-$d_6$): δ 8.98 (dd, 1H), 8.88 (dd, 1H), 8.35 (d, 1H), 7.82 (dd, 1H), 7.44 (d, 1H), 7.18 (dd, 1H), 6.73 (br s, 2H), 2.63 (d, 2H), 2.04-1.94 (m, 1H), 0.94 (d, 6H). LRMS [M+H]=252.1.

Example 103

(E)-8-(prop-1-enyl)benzo[f][1,7]naphthyridin-5-amine

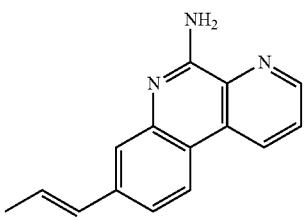 [SMILES: C/C=C/c1ccc2c(c1)nc(N)c1ncccc12]

(E)-8-(prop-1-enyl)benzo[f][1,7]naphthyridin-5-amine was prepared from 5-aminobenzo[f][1,7]naphthyridine-8-carbaldehyde (from Example 87) with ethyl(triphenyl)phosphonium bromide following the procedures described for Example 91. $^1$H NMR (acetone-$d_6$): δ 8.98 (dd, 1H), 8.88 (dd, 1H), 8.36 (d, 1H), 7.83 (dd, 1H), 7.54 (d, 1H), 7.43 (dd, 1H), 6.67 (br s, 2H), 6.60-6.42 (m, 2H), 1.92 (dd, 3H). LRMS [M+H]=236.1.

Example 104

8-propylbenzo[f][1,7]naphthyridin-5-amine

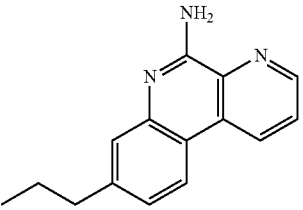 [SMILES: CCCc1ccc2c(c1)nc(N)c1ncccc12]

8-Propylbenzo[f][1,7]naphthyridin-5-amine was prepared from (E)-8-(prop-1-enyl)benzo[f][1,7]naphthyridin-5-amine (from Example 103) following the procedures described for Example 92. $^1$H NMR (acetone-$d_6$): δ 8.99 (dd, 1H), 8.88 (dd, 1H), 8.35 (d, 1H), 7.83 (dd, 1H), 7.45 (d, 1H), 7.21 (dd, 1H), 6.64 (br s, 2H), 2.74 (t, 2H), 1.74 (qt, 2H), 0.98 (t, 3H). LRMS [M+H]=238.1.

Example 105

8-(2-cyclopropylethyl)benzo[f][1,7]naphthyridin-5-amine

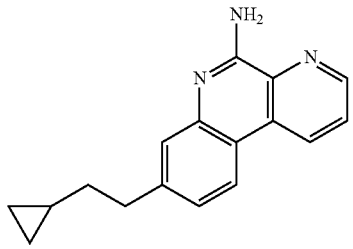 [SMILES: Nc1nc2cc(CCC3CC3)ccc2c2cccnc12]

8-(2-Cyclopropylethyl)benzo[f][1,7]naphthyridin-5-amine was prepared from 5-aminobenzo[f][1,7]naphthyridine-8-carbaldehyde (from Example 87) with (cyclopropylmethyl)triphenylphosphonium bromide following the procedures described for Example 91 (wittig reaction) and Example 92 (reduction). $^1$H NMR (acetone-$d_6$): δ 8.99 (dd, 1H), 8.88 (dd, 1H), 8.35 (d, 1H), 7.83 (dd, 1H), 7.47 (d, 1H), 7.23 (dd, 1H), 6.64 (br s, 2H), 1.60 (q, 2H), 1.34-1.25 (m, 1H), 0.91-0.72 (m, 2H), 0.45-0.41 (m, 2H), 0.11-0.07 (m, 2H). LRMS [M+H]=264.1.

Example 106

8-phenethylbenzo[f][1,7]naphthyridin-5-amine

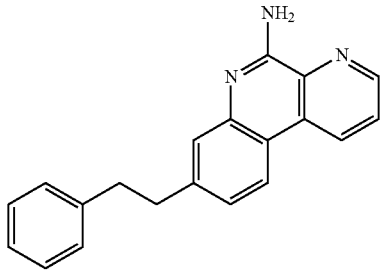 [SMILES: Nc1nc2cc(CCc3ccccc3)ccc2c2cccnc12]

8-Phenethylbenzo[f][1,7]naphthyridin-5-amine was prepared from 5-aminobenzo[f][1,7]naphthyridine-8-carbaldehyde (from Example 87) with benzyltriphenylphosphonium bromide following the procedures described for Example 91 (wittig reaction) and Example 92 (reduction). $^1$H NMR (acetone-d$_6$): δ 8.99 (dd, 1H), 8.88 (dd, 1H), 8.35 (d, 1H), 7.83 (dd, 1H), 7.49 (d, 1H), 7.29-7.15 (dd, 6H), 6.70 (br s, 2H), 3.10-3.00 (m, 4H). LRMS [M+H]=300.1.

Example 107

(5-amino-2-(4-bromophenethyl)benzo[f][1,7]naphthyridin-8-yl)methanol

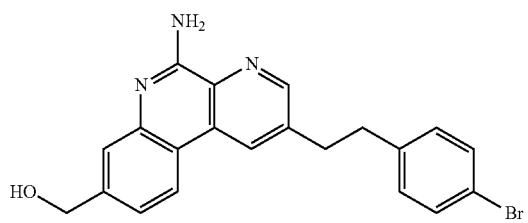 [SMILES: Nc1nc2cc(CO)ccc2c2cc(CCc3ccc(Br)cc3)cnc12]

(5-Amino-2-(4-bromophenethyl)benzo[f][1,7]naphthyridin-8-yl)methanol was prepared from (5-amino-2-(4-methoxyphenethyl)benzo[f][1,7]naphthyridin-8-yl)methanol (from Example 95) following the procedures described for Example 86. $^1$H NMR (acetone-d$_6$): δ 8.81 (d, 1H), 8.72 (d, 1H), 8.40 (d, 1H), 7.68 (d, 1H), 7.39 (dd, 1H), 7.08 (d, 2H), 6.74 (d, 2H), 6.66 (br s, 2H), 4.49 (s, 2H), 3.21 (t, 2H), 3.03 (t, 2H). LRMS [M+H]=408.1.

Example 108

(5-amino-2-(4-methoxy-2-methylphenethyl)benzo[f][1,7]naphthyridin-8-yl)methanol

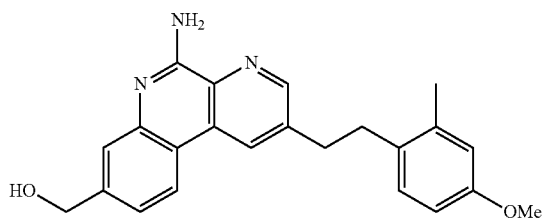 [SMILES: COc1ccc(CCc2cnc3c(N)nc4cc(CO)ccc4c3c2)c(C)c1]

(5-Amino-2-(4-methoxy-2-methylphenethyl)benzo[f][1,7]naphthyridin-8-yl)methanol was prepared from tert-butyl 5-(((tert-butyldimethylsilyloxy)methyl)-2-(4,4,5,5-tetramethyl-1,3,2-dioxaborolan-2-yl)phenylcarbamate (Example 99/Step 1) and 3-chloro-5-((4-methoxy-2-methylphenyl)ethynyl)picolinonitrile (from Example 49/Step 1) following the procedures described for Example 44/Step 4 and deprotection of TBS group following the procedure describes from Example 99/Step 3. $^1$H NMR (acetone-d$_6$): δ 8.79 (s, 1H), 8.73 (s, 1H), 8.35 (d, 1H), 7.61 (s, 1H), 7.33 (d, 1H), 7.09 (d, 1H), 6.75 (d, 1H), 6.68 (dd, 1H), 6.57 (br s, 2H), 4.47 (d, 2H), 4.32 (t, 1H), 3.58 (s, 3H), 3.17 (t, 2H), 3.04 (t, 2H), 2.30 (s, 3H). LRMS [M+H]=374.2.

Example 109

2-(4-methoxy-2-methylphenethyl)-8-pentylbenzo[f][1,7]naphthyridin-5-amine

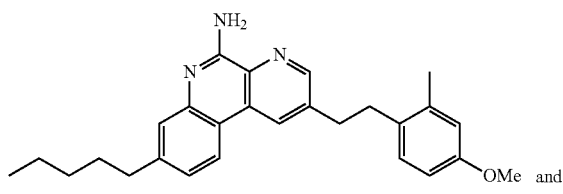 [SMILES: CCCCCc1ccc2c(c1)nc(N)c1ncc(CCc3ccc(OC)cc3C)cc12 ; "and"]

Example 110

8-(2-cyclopropylethyl)-2-(4-methoxy-2-methylphenethyl)benzo[f][1,7]naphthyridin-5-amine

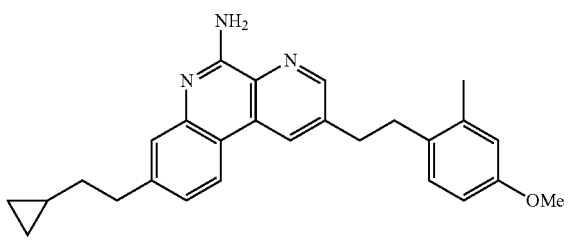 [SMILES: COc1ccc(CCc2cnc3c(N)nc4cc(CCC5CC5)ccc4c3c2)c(C)c1]

Step 1: tert-butyl 5-bromo-2-chlorophenylcarbamate

The titled compound was prepared according to the procedure described in Example 5/Step 1, but using 5-bromo-2-chloroaniline (commercially available) as the starting material. The crude material was purified by flash chromatography on a COMBIFLASH® system (ISCO) using 0-40% EtOAc/Hexanes to give tert-butyl 5-bromo-2-chlorophenylcarbamate as a pale yellow solid.

Step 2: (E)-tert-butyl 2-chloro-5-(2-cyclopropylvinyl)phenylcarbamate

A solution of tert-butyl 5-bromo-2-chlorophenylcarbamate (from the previous step) (1.0 eq.) and (E)-2-(2-cyclopropylvinyl)-4,4,5,5-tetramethyl-1,3,2-dioxaborolane (commercially available) (1.0 eq.) in toluene (0.2 M) was mixed with tetrakis(triphenyl-phosphine)palladium (5 mol %) and 2N aqueous potassium carbonate solution (2.0 eq.). The reaction was heated to 100° C. and stirred overnight. After cooling to ambient temperature, the reaction mixture was diluted with EtOAc and water. The two phases were separated, and the aqueous layer was extracted twice with EtOAc. The combined organic layers were washed with brine, dried over anhydrous MgSO$_4$, and concentrated en vaccuo. The crude product was purified by flash chromatography on a COMBIFLASH® system (ISCO) using 0-5% EtOAc/Hexanes to give (E)-tert-butyl 2-chloro-5-(2-cyclopropylvinyl)phenylcarbamate as a pale yellow solid.

Step 3: (E)-tert-butyl 5-(2-cyclopropylvinyl)-2-(4,4,5,5-tetramethyl-1,3,2-dioxaborolan-2-yl)phenylcarbamate The titled compound was prepared according to the procedure described in Example 93/Step 2, but using (E)-tert-butyl 2-chloro-5-(2-cyclopropylvinyl)phenylcarbamate (from previous step) as the starting material. The crude product was purified by flash chromatography on a COMBIFLASH® system (ISCO) using 0-10% EtOAc/Hexanes to give (E)-tert-butyl 5-(2-cyclopropylvinyl)-2-(4,4,5,5-tetramethyl-1,3,2-dioxaborolan-2-yl)phenylcarbamate as a pale yellow solid.

Step 4: 2-(4-methoxy-2-methylphenethyl)-8-pentyl-benzo[f][1,7]naphthyridin-5-amine and 8-(2-cyclopropylethyl)-2-(4-methoxy-2-methylphenethyl)benzo[f][1,7]naphthyridin-5-amine The titled compounds were prepared according to the procedure described in Example 44/Step 4 (Suzuki coupling) and 5 (reduction), but using (E)-tent-butyl 5-(2-cyclopropylvinyl)-2-(4,4,5,5-tetramethyl-1,3,2-dioxaborolan-2-yl)phenylcarbamate (from previous step) and 3-chloro-5-((4-methoxy-2-methylphenyl)ethynyl)picolinonitrile (from Example 49/Step1) as the starting material. The crude product was purified by flash chromatography on a COMBIFLASH® system (ISCO) using 0-40% EtOAc/Hexanes to give Example 109 as a white solid: $^1$H NMR (acetone-$d_6$): δ 8.76 (d, 1H), 8.70 (d, 1H), 8.29 (d, 1H), 7.44 (d, 1H), 7.18 (dd, 1H), 7.08 (d, 1H), 6.74 (d, 1H), 6.68 (dd, 1H), 6.59 (br s, 2H), 3.74 (s, 3H), 3.18 (t, 2H), 3.04 (t, 2H), 2.75 (t, 2H), 2.29 (s, 3H), 1.75-1.68 (m, 2H), 1.40-1.35 (m, 4H), 0.90 (s, 3H); LRMS [M+H]= 414.3; and Example 110 as an off white solid: $^1$H NMR (acetone-$d_6$): δ 8.76 (d, 1H), 8.70 (d, 1H), 8.28 (d, 1H), 7.45 (d, 1H), 7.19 (dd, 1H), 7.08 (d, 1H), 6.74 (d, 1H), 6.67 (dd, 1H), 6.55 (br s, 2H), 3.73 (s, 3H), 3.16 (t, 2H), 3.03 (t, 2H), 2.29 (s, 3H), 1.60 (q, 2H), 1.29-1.28 (m, 1H), 0.89-0.74 (m, 2H), 0.44-0.41 (m, 2H), 0.10-0.07 (m, 2H). LRMS [M+H]= 412.3.

Example 111

(5-amino-2-(2,4,6-trimethylphenethyl)benzo[f][1,7]naphthyridin-8-yl)methanol

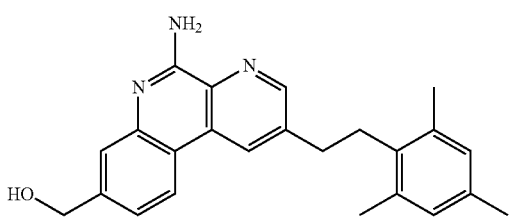 [SMILES: Cc1cc(C)c(CCc2cnc3c(N)nc4cc(CO)ccc4c3c2)c(C)c1]

(5-Amino-2-(2,4,6-trimethylphenethyl)benzo[f][1,7]naphthyridin-8-yl)methanol was prepared from tert-butyl5-((tert-butyldimethylsilyloxy)methyl)-2-(4,4,5,5-tetramethyl-1,3,2-dioxaborolan-2-yl)phenylcarbamate (from Example 99/step 1), 2-ethynyl-1,3,5-trimethylbenzene (commercially available) and 3-chloro-5-(mesitylethynyl)picolinonitrile (from Example 77/step 1) following the procedures described for Example 44/Step 4, Example 99/step 3 (deprotection of TBS) and Example 77/step 3 (reduction). $^1$H NMR (acetone-$d_6$): δ 8.77 (s, 2H), 8.34 (d, 1H), 7.61 (s, 1H), 7.33 (d, 1H), 6.84 (s, 2H), 6.60 (br s, 2H), 4.77 (d, 2H), 4.35 (t, 1H), 3.08 (s, 3H), 2.84 (s, 6H), 2.30-2.29 (m, 4H). LRMS [M+H]= 372.2.

Example 112

(5-amino-2-(4-propoxyphenethyl)benzo[f][1,7]naphthyridin-8-yl)methanol

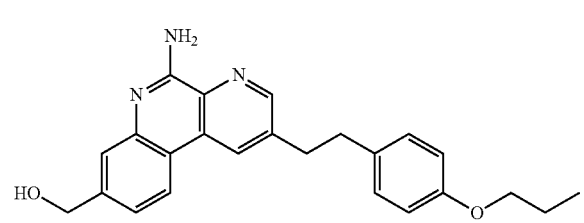 [SMILES: CCCOc1ccc(CCc2cnc3c(N)nc4cc(CO)ccc4c3c2)cc1]

(5-Amino-2-(4-propoxyphenethyl)benzo[f][1,7]naphthyridin-8-yl)methanol was prepared from 8-((tert-butyldimethylsilyloxy)methyl)-3-chlorobenzo[f][1,7]naphthyridin-5-amine (from Example 99/step 1) and 3-chloro-5-(4-propoxyphenethyl)picolinonitrile (from Example 79/step 2) following the procedures described for Example 44/Step 4 and Example 99/step 3 (deprotection of TBS). $^1$H NMR (acetone-$d_6$): δ 8.79 (d, 1H), 8.70 (d, 1H), 8.35 (d, 1H), 7.61 (d, 1H), 7.33 (dd, 1H), 7.17 (d, 2H), 6.83 (d, 2H), 6.57 (br s, 2H), 4.77 (d, 2H), 4.34 (t, 1H), 3.89 (t, 2H), 3.22 (t, 2H), 3.06 (t, 2H), 1.83-1.70 (m, 2H), 1.00 (t, 3H). LRMS [M+H]=388.2.

Example 113

(2-(2-(1H-indol-5-yl)ethyl)-5-aminobenzo[f][1,7]naphthyridin-8-yl)methanol

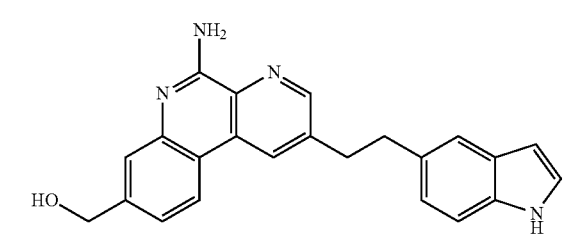 [SMILES: Nc1nc2cc(CO)ccc2c2cc(CCc3ccc4[nH]ccc4c3)cnc12]

(2-(2-(1H-indol-5-yl)ethyl)-5-aminobenzo[f][1,7]naphthyridin-8-yl)methanol was prepared from tert-butyl 5-((tert-butyldimethylsilyloxy)methyl)-2-(4,4,5,5-tetramethyl-1,3,2-dioxaborolan-2-yl)phenylcarbamate (from Example 99/step 1) and 5-((1H-indol-5-yl)ethynyl)-3-chloropicolinonitrile (from Example 44/step 3) following the procedures described for Example 44/Step 4 and Example 99/step 3 (deprotection of TBS). $^1$H NMR (acetone-$d_6$): δ 10.19 (t, 1H), 8.83 (d, 1H), 8.71 (d, 1H), 8.35 (d, 1H), 7.60 (d, 1H), 7.46 (d, 1H), 7.36-7.27 (m, 3H), 7.04 (dd, 1H), 6.57 (br s, 2H), 6.38 (dt, 1H), 4.77 (d, 2H), 4.36 (t, 1H), 3.29 (t, 2H), 3.19 (t, 2H). LRMS [M+H]=369.2.

Example 114

N-(4-(2-(5-amino-8-methylbenzo[f][1,7]naphthyridin-2-yl)ethyl)phenyl)acetamide

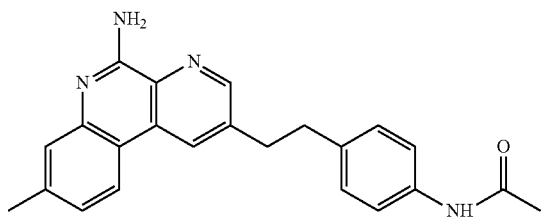 [SMILES: CC(=O)Nc1ccc(CCc2cnc3c(N)nc4cc(C)ccc4c3c2)cc1]

Step 1: N-(4-ethynylphenyl)acetamide

To a solution of 4-ethynylaniline (commercially available) (1.0 eq.), and triethylamine (1.0 eq.) in methylene chloride (0.04 M), acetyl chloride (1.5 eq.) was added slowly. Then the reaction mixture was stirred at 0° C. for 1 hour. After warmed to ambient temperature, the reaction mixture was diluted with ethyl acetate and water. The two phases were separated, and the aqueous layer was extracted twice with ethyl acetate. The combined organic layers were washed with brine, dried over anhydrous MgSO$_4$, and concentrated en vaccuo. The crude material was purified by flash chromatography on a COMBIFLASH® system (ISCO) using 0-80% ethyl acetate in hexane to give N-(4-ethynylphenyl)acetamide as a white solid.

Step 2: N-(4-((5-chloro-6-cyanopyridin-3-yl)ethynyl)phenyl)acetamide

A solution of 3,5-dichloropicolinonitrile (1.0 eq.), N-(4-ethynylphenyl)acetamide (from the previous step) (1.0 eq.), bis(triphenyl-phosphine)palladium chloride (10 mol %), copper iodide (10 mol %), and triethylamine (5.0 eq.) in DMF (0.04 M) was stirred at 60° C. for 4 hours. After cooling to ambient temperature, the reaction mixture was diluted with ethyl acetate and water. The two phases were separated. The organic layer was washed twice with water, dried over anhydrous MgSO$_4$, and concentrated en vaccuo. The crude material was purified by flash chromatography on a COMBIFLASH® system (ISCO) using 0-80% ethyl acetate in hexane to give N-(4-((5-chloro-6-cyanopyridin-3-yl)ethynyl)phenyl)acetamide as a white solid.

Step 3: N-(4-(2-(5-chloro-6-cyanopyridin-3-yl)ethyl)phenyl)acetamide

To a solution of N-(4-((5-chloro-6-cyanopyridin-3-yl)ethynyl)phenyl)acetamide (from the previous step) in ethyl acetate/methanol (1:4, 0.05 M) was added 10% wt palladium on carbon (0.2 eq.). Hydrogen gas was introduced via a balloon, and the reaction was stirred for 3 hours. The mixture was filtered through a pad of celite, washing with dichloromethane. The filtrate was concentrated en vaccuo and purified by a COMBIFLASH® system (ISCO) using 0-80% ethyl acetate in hexane to give N-(4-(2-(5-chloro-6-cyanopyridin-3-yl)ethyl)phenyl)acetamide.

Step 4: N-(4-(2-(5-amino-8-methylbenzo[f][1,7]naphthyridin-2-yl)ethyl)phenyl)acetamide A solution of N-(4-(2-(5-chloro-6-cyanopyridin-3-yl)ethyl)phenyl)acetamide (from the previous step) (1.0 eq.), tert-butyl 4-methyl-2-(4,4,5,5-tetramethyl-1,3,2-dioxaborolan-2-yl)phenylcarbamate (from Example 5/Step 2) (1.5 eq.), Tris(dibenzylideneacetone)dipalladium(0) (10 mol %), dicyclohexyl(2',6'-dimethoxybiphenyl-2-yl)phosphine (20 mol %), and potassium phosphate (2.0 eq.) in n-butanol/H$_2$O (2.5:1, 0.04 M) was stirred at 100° C. overnight. After cooling to ambient temperature, the reaction mixture was diluted with ethyl acetate and water. The two phases were separated, and the aqueous layer was extracted twice with ethyl acetate. The combined organic layers were washed with brine, dried over anhydrous MgSO$_4$, and concentrated en vaccuo. The crude material was purified by flash chromatography on a COMBIFLASH® system (ISCO) using 0-80% ethyl acetate in hexane to give N-(4-(2-(5-amino-8-methylbenzo[f][1,7]naphthyridin-2-yl)ethyl)phenyl)acetamide as a white solid. $^1$H NMR (CDCl$_3$): δ 8.51 (s, 1H), 8.32 (s, 1H), 8.01 (d, 1H), 7.44 (s, 1H), 7.33-7.36 (m, 2H), 7.03-7.19 (m, 3H), 5.98 (br, 2H), 3.07-3.11 (m, 2H), 2.94-2.98 (m, 2H), 2.44 (s, 3H), 2.10 (s, 3H). LRMS [M+H]=371.2.

Example 115 methyl 4-(2-(5-amino-8-methylbenzo[f][1,7]naphthyridin-2-yl)ethyl)-3-methylbenzoate

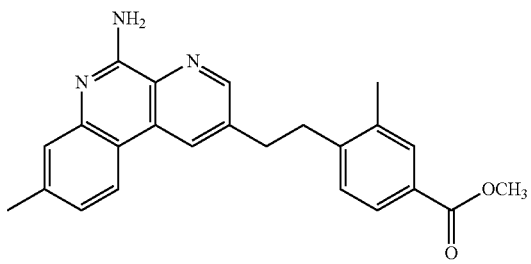 [SMILES: COC(=O)c1ccc(CCc2cnc3c(N)nc4cc(C)ccc4c3c2)c(C)c1]

Step 1: methyl 3-methyl-4-((triethylsilyl)ethynyl)benzoate

A solution of methyl 4-bromo-3-methylbenzoate (1.0 eq.), triethyl(ethynyl)silane (1.0 eq.), bis(triphenyl-phosphine)palladium chloride (10 mol %), copper iodide (10 mol %), and triethylamine (5.0 eq.) in DMF (0.04 M) was stirred at 60° C. for 4 hours. After cooling to ambient temperature, the reaction mixture was diluted with ethyl acetate and water. The two phases were separated. The organic layer was washed twice with water, dried over anhydrous MgSO$_4$, and concentrated en vaccuo. The crude material was purified by flash chromatography on a COMBIFLASH® system (ISCO) using 0-50% ethyl acetate in hexane to give methyl 3-methyl-4-((triethylsilyl)ethynyl)benzoate as a white solid.

Step 2: methyl 4-ethynyl-3-methylbenzoate

To a solution of methyl 3-methyl-4-((triethylsilyl)ethynyl)benzoate (from the previous step) (1.0 eq.) in THF (0.2 M), was added TBAF (0.2 eq.) slowly at 0° C. Then the reaction mixture was stirred at 0° C. for 1 hour. After warmed to ambient temperature, the reaction mixture was diluted with ethyl acetate and water. The two phases were separated, and the aqueous layer was extracted twice with ethyl acetate. The combined organic layers were washed with brine, dried over anhydrous MgSO$_4$, and concentrated en vaccuo. The crude material was purified by flash chromatography on a COMBI- FLASH® system (ISCO) using 0-80% ethyl acetate in hexane to give methyl 4-ethynyl-3-methylbenzoate as a white solid.

Step 3: methyl 4-((5-chloro-6-cyanopyridin-3-yl)ethynyl)-3-methylbenzoate

A solution of 3,5-dichloropicolinonitrile (1.0 eq.), methyl 4-ethynyl-3-methylbenzoate (from the previous step) (1.0 eq.), bis(triphenyl-phosphine)palladium chloride (10 mol %), copper iodide (10 mol %), and triethylamine (5.0 eq.) in DMF (0.04 M) was stirred at 60° C. for 4 hours. After cooling to ambient temperature, the reaction mixture was diluted with ethyl acetate and water. The two phases were separated. The organic layer was washed twice with water, dried over anhydrous MgSO$_4$, and concentrated en vaccuo. The crude material was purified by flash chromatography on a COMBIFLASH® system (ISCO) using 0-80% ethyl acetate in hexane to give methyl 4-((5-chloro-6-cyanopyridin-3-yl)ethynyl)-3-methylbenzoate as a white solid.

Step 4: methyl methyl 4-((5-amino-8-methylbenzo[f][1,7]naphthyridin-2-yl)ethynyl)-3-methylbenzoate A solution of methyl 4-((5-chloro-6-cyanopyridin-3-yl)ethynyl)-3-methylbenzoate (from the previous step) (1.0 eq.), tert-butyl 4-methyl-2-(4,4,5,5-tetramethyl-1,3,2-dioxaborolan-2-yl)phenylcarbamate (From Example 5/Step 2) (1.5 eq.), tris(dibenzylideneacetone)dipalladium(0) (10 mol %), dicyclohexyl(2',6'-dimethoxybiphenyl-2-yl)phosphine (20 mol %), and potassium phosphate (2.0 eq.) in n-butanol/H$_2$O (2.5:1, 0.04 M) was stirred at 100° C. overnight. After cooling to ambient temperature, the reaction mixture was diluted with ethyl acetate and water. The two phases were separated, and the aqueous layer was extracted twice with ethyl acetate. The combined organic layers were washed with brine, dried over anhydrous MgSO$_4$, and concentrated en vaccuo. The crude material was purified by flash chromatography on a COMBIFLASH® system (ISCO) using 0-80% ethyl acetate in hexane to give methyl methyl-4-((5-amino-8-methylbenzo[f][1,7]naphthyridin-2-yl)ethynyl)-3-methylbenzoate as a white solid.

Step 5: methyl 4-(2-(5-amino-8-methylbenzo[f][1,7]naphthyridin-2-yl)ethyl)-3-methylbenzoate To a solution of methyl methyl 4-((5-amino-8-methylbenzo[f][1,7]naphthyridin-2-yl)ethynyl)-3-methylbenzoate (from the previous step) in ethyl acetate/methanol (1:4, 0.05 M) was added 10% wt palladium on carbon (0.2 eq.). Hydrogen gas was introduced via a ballon, and the reaction was stirred for 3 hours. The mixture was filtered through a pad of celite, washing with dichloromethane. The filtrate was concentrated en vaccuo and purified by a COMBIFLASH® system (ISCO) using 0-80% ethyl acetate in hexane to give methyl 4-(2-(5-amino-8-methylbenzo[f][1,7]naphthyridin-2-yl)ethyl)-3-methylbenzoate. $^1$H NMR (CDCl$_3$): δ 8.61 (s, 1H), 8.40 (s, 1H), 8.09 (d, 1H), 7.83 (s, 1H), 7.81 (d, 1H), 7.54 (s, 1H), 7.18-7.20 (m, 2H), 6.17 (br, 2H), 3.92 (s, 3H), 3.10-3.16 (m, 4H), 2.53 (s, 3H), 2.36 (s, 3H). LRMS [M+H]= 386.2.

Example 116

4-(2-(5-amino-8-methylbenzo[f][1,7]naphthyridin-2-yl)ethyl)-N3-dimethylbenzamide

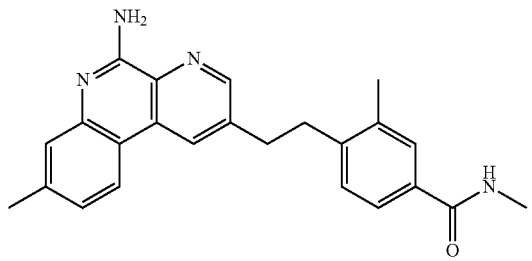

Step 1: 4-(2-(5-amino-8-methylbenzo[f][1,7]naphthyridin-2-yl)ethyl)-3-methylbenzoic acid A solution of methyl 4-(2-(5-amino-8-methylbenzo[f][1,7]naphthyridin-2-yl)ethyl)-3-methylbenzoate (from Example 115) (1.0 eq.), and 1N sodium hydroxide (1.5 eq.) in methanol (0.04 M) was stirred at 60° C. for 4 hours. After cooling to ambient temperature, the reaction mixture was diluted with ethyl acetate and water. The two phases were separated. The organic layer was washed twice with water, dried over anhydrous MgSO$_4$, and concentrated en vaccuo. The crude material was purified by flash chromatography on a COMBIFLASH® system (ISCO) using 0-50% ethyl acetate in hexane to give 4-(2-(5-amino-8-methylbenzo[f][1,7]naphthyridin-2-yl)ethyl)-3-methylbenzoic acid as a white solid.

Step 2: 4-(2-(5-amino-8-methylbenzo[f][1,7]naphthyridin-2-yl)ethyl)-3-methylbenzoyl chloride A solution of 4-(2-(5-amino-8-methylbenzo[f][1,7]naphthyridin-2-yl)ethyl)-3-methylbenzoic acid (from the previous step) in thionyl chloride was stirred at 60° C. for 3 hour. After cooling to ambient temperature, the reaction mixture was concentrated en vaccuo. The crude material was used for next step without purification.

Step 3: 4-(2-(5-amino-8-methylbenzo[f][1,7]naphthyridin-2-yl)ethyl)-N,3-dimethylbenzamide To a solution of 4-(2-(5-amino-8-methylbenzo[f][1,7]naphthyridin-2-yl)ethyl)-3-methylbenzoyl chloride (from the previous step) (Example 5) and triethylamine (2.5 eq.) in ether (0.05 M) was added methanamine (5.0 eq.). The reaction mixture was stirred for overnight. Then the reaction mixture was diluted with ethyl acetate and water. The two phases were separated, and the aqueous layer was extracted twice with ethyl acetate. The combined organic layers were washed with brine, dried over anhydrous MgSO$_4$, and concentrated en vaccuo. The crude material was purified by flash chromatography on a COMBIFLASH® system (ISCO) using 0-80% ethyl acetate in hexane to give 4-(2-(5-amino-8-methylbenzo[f][1,7]naphthyridin-2-yl)ethyl)-N,3-dimethylbenzamide as a white solid. $^1$H NMR (CDCl$_3$): δ 8.62 (s, 1H), 8.32 (s, 1H), 8.04 (d, 1H), 7.60 (s, 1H), 7.46-7.52 (m, 2H), 7.09-7.11 (m, 2H), 6.05 (br, 2H), 3.09-3.17 (m, 4H), 3.00 (d, 3H), 2.52 (s, 3H), 2.33 (s, 3H). LRMS [M+H]=385.2.

Example 117

4-(2-(5-amino-8-methylbenzo[f][1,7]naphthyridin-2-yl)ethyl)-N-(2-(dimethylamino)ethyl)-N,3-dimethylbenzamide

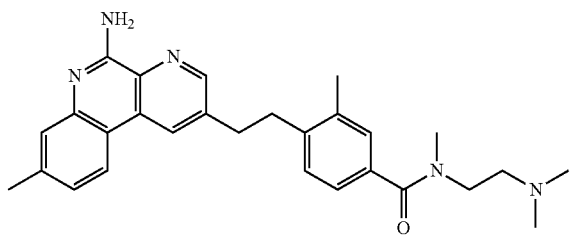

To a solution of 4-(2-(5-amino-8-methylbenzo[f][1,7]naphthyridin-2-yl)ethyl)-3-methylbenzoyl chloride (Example 116/Step 2) and triethylamine (2.5 eq.) in ether (0.05 M) was added $N^1,N^1,N^2$-trimethylethane-1,2-diamine (5.0 eq.). The reaction mixture was stirred for overnight. Then the reaction mixture was diluted with ethyl acetate and water. The two phases were separated, and the aqueous layer was extracted twice with ethyl acetate. The combined organic layers were washed with brine, dried over anhydrous MgSO$_4$, and concentrated en vaccuo. The crude material was purified by flash chromatography on a COMBIFLASH® system (ISCO) using 0-80% ethyl acetate in hexane to give 4-(2-(5-amino-8-methylbenzo[f][1,7]naphthyridin-2-yl)ethyl)-N-(2-(dimethylamino)ethyl)-N,3-dimethylbenzamide as a white solid. $^1$H NMR (CDCl$_3$): δ 8.66 (s, 1H), 8.37 (s, 1H), 8.07 (d, 1H), 7.63 (s, 1H), 7.09-7.30 (m, 4H), 3.90 (br, 2H), 3.01-3.19 (m, 4H), 3.08 (s, 6H), 2.72 (br, 5H), 2.52 (s, 3H), 2.33 (s, 3H). LRMS [M+H]=456.3.

Example 118

2-(4-methoxyphenethyl)benzo[f][1,7]naphthyridin-5-amine

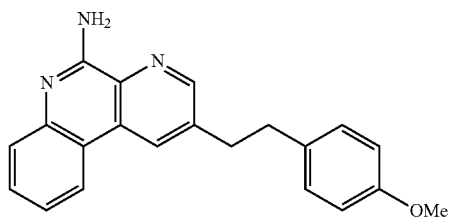 [SMILES: COc1ccc(CCc2cnc3c(N)nc4ccccc4c3c2)cc1]

2-(4-Methoxyphenethyl)benzo[f][1,7]naphthyridin-5-amine was prepared from 1-ethynyl-4-methoxybenzene (Example 116/Step 2) following the procedures described for Example 45/Steps 1 to 3. $^1$H NMR (CDCl$_3$): δ 8.69 (s, 1H), 8.47 (s, 1H), 8.27 (d, 1H), 7.80 (d, 2H), 7.58-7.66 (m, 1H), 7.33-7.42 (m, 1H), 7.15 (d, 2H), 6.90 (d, 2H), 6.25 (br, 2H), 3.86 (s, 3H), 3.13-3.23 (m, 2H), 2.97-3.10 (m, 2H). LRMS [M+H]=330.2.

Example 119

2-(4-methoxy-2-methylphenethyl)benzo[f][1,7]naphthyridin-5-amine

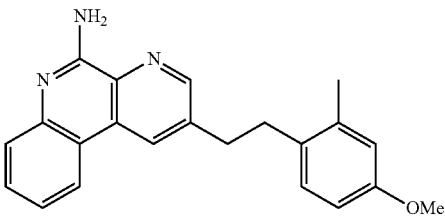 [SMILES: COc1ccc(CCc2cnc3c(N)nc4ccccc4c3c2)c(C)c1]

2-(4-Methoxy-2-methylphenethyl)benzo[f][1,7]naphthyridin-5-amine was prepared from 1-ethynyl-4-methoxy-2-methylbenzene (commercially available) following the procedures described for Example 45/Step 1 to 3. 1H NMR (CDCl$_3$): δ 8.60 (s, 1H), 8.37 (s, 1H), 8.18 (d, 1H), 7.69 (d, 1H), 7.49-7.57 (m, 1H), 7.24-7.34 (m, 1H), 6.98 (d, 1H), 6.56-6.70 (m, 2H), 6.00 (br, 2H), 3.70 (s, 3H), 3.00-3.09 (m, 2H), 2.83-2.96 (m, 2H), 2.20 (s, 3H). LRMS [M+H]=344.2.

Example 120

4-(2-(5-amino-8-methylbenzo[f][1,7]naphthyridin-2-yl)ethyl)-3-methylbenzamide

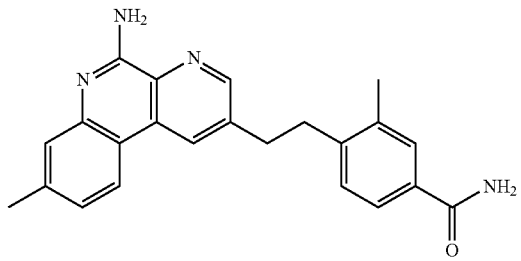 [SMILES: Cc1ccc2c(c1)nc(N)c1ncc(CCc3ccc(C(N)=O)cc3C)cc12]

4-(2-(5-Amino-8-methylbenzo[f][1,7]naphthyridin-2-yl)ethyl)-3-methylbenzamide was prepared from 4-(2-(5-amino-8-methylbenzo[f][1,7]naphthyridin-2-yl)ethyl)-3-methylbenzoyl chloride (Example 116/Step 2) and ammonia following the procedures described for Example 117. $^1$H NMR (CDCl$_3$): δ 8.60 (s, 1H), 8.35 (s, 1H), 8.05 (d, 1H), 7.65 (s, 1H), 7.51-7.53 (m, 2H), 7.13-7.21 (m, 2H), 3.09-3.16 (m, 4H), 2.51 (s, 3H), 2.34 (s, 3H). LRMS [M+H]=371.2

Example 121

4-(2-(5-amino-8-methylbenzo[f][1,7]naphthyridin-2-yl)ethyl)-N,N,3-trimethylbenzamide

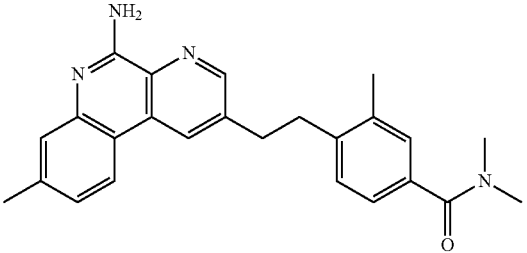

4-(2-(5-Amino-8-methylbenzo[f][1,7]naphthyridin-2-yl)ethyl)-N,N,3-trimethylbenzamide was prepared from 4-(2-(5-amino-8-methylbenzo[f][1,7]naphthyridin-2-yl)ethyl)-3-methylbenzoyl chloride (Example 116/Step 2) and dimethylamine following the procedures described for Example 117. ¹H NMR (CDCl₃): δ 8.68 (s, 1H), 8.32 (s, 1H), 8.04 (d, 1H), 7.66 (s, 1H), 7.31 (d, 1H), 7.06-7.18 (m, 3H), 3.08-3.19 (m, 4H), 2.96 (d, 3H), 2.54 (s, 3H), 2.33 (s, 3H), 2.05 (s, 3H). LRMS [M+H]=399.2

Example 122

4-(2-(5-amino-8-methylbenzo[f][1,7]naphthyridin-2-yl)ethyl)-N-(2-hydroxyethyl)-3-methylbenzamide

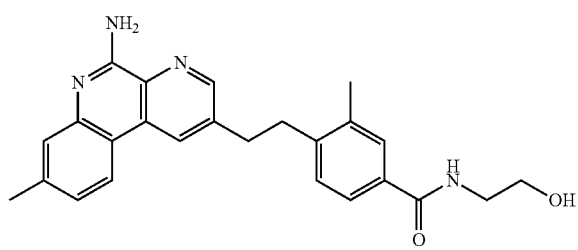 [SMILES: Cc1ccc2c(c1)nc(N)c1ncc(CCc3ccc(C(=O)NCCO)cc3C)cc12]

4-(2-(5-Amino-8-methylbenzo[f][1,7]naphthyridin-2-yl)ethyl)-N-(2-hydroxyethyl)-3-methylbenzamide was prepared from 4-(2-(5-amino-8-methylbenzo[f][1,7]naphthyridin-2-yl)ethyl)-3-methylbenzoyl chloride (Example 116/Step 2) and 2-aminoethanol following the procedures described for Example 117. ¹H NMR (CDCl₃): δ 8.59 (s, 1H), 8.34 (s, 1H), 8.04 (d, 1H), 7.50-7.62 (m, 3H), 7.08-7.25 (m, 2H), 3.80 (t, 2H), 3.63 (t, 2H), 3.07-3.16 (m, 4H), 2.51 (s, 3H), 2.32 (s, 3H). LRMS [M+H]=415.2

Example 123

4-(2-(5-amino-8-methylbenzo[f][1,7]naphthyridin-2-yl)ethyl)-N-(2-(dimethylamino)ethyl)-3-methylbenzamide

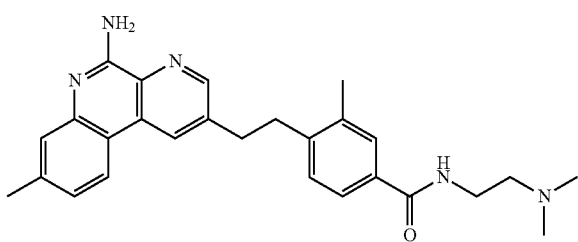

4-(2-(5-Amino-8-methylbenzo[f][1,7]naphthyridin-2-yl)ethyl)-N-(2-(dimethylamino)ethyl)-3-methylbenzamide was prepared from 4-(2-(5-amino-8-methylbenzo[f][1,7]naphthyridin-2-yl)ethyl)-3-methylbenzoyl chloride (Example 116/Step 2) and N¹,N¹-dimethylethane-1,2-diamine following the procedures described for Example 117. ¹H NMR (methanol-d₄): δ 8.60 (s, 1H), 8.39 (s, 1H), 8.08 (d, 1H), 7.68 (s, 1H), 7.57-7.59 (m, 2H), 7.19-7.22 (m, 2H), 3.57-3.61 (m, 2H), 3.07-3.16 (m, 4H), 2.64-2.67 (m, 2H), 2.52 (s, 3H), 2.38 (s, 6H), 2.35 (s, 3H). LRMS [M+H]=442.3

Example 124

(4-(2-(5-amino-8-methylbenzo[f][1,7]naphthyridin-2-yl)ethyl)-3-methylphenyl)(pyrrolidin-1-yl)methanone

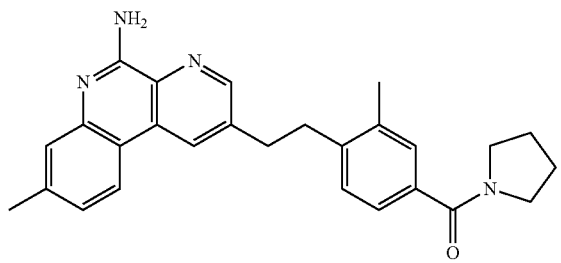 [SMILES: Cc1ccc2c(c1)nc(N)c1ncc(CCc3ccc(C(=O)N4CCCC4)cc3C)cc12]

(4-(2-(5-Amino-8-methylbenzo[f][1,7]naphthyridin-2-yl)ethyl)-3-methylphenyl)(pyrrolidin-1-yl)methanone was prepared from 4-(2-(5-amino-8-methylbenzo[f][1,7]naphthyridin-2-yl)ethyl)-3-methylbenzoyl chloride (Example 116/Step 2) and pyrrolidine following the procedures described for Example 117. ¹H NMR (methanol-d₄): δ 8.60 (s, 1H), 8.42 (s, 1H), 8.09 (d, 1H), 7.34 (s, 1H), 7.23 (s, 1H), 7.05-7.15 (m, 3H), 3.49 (t, 2H), 3.27 (t, 2H), 3.05-3.17 (m, 4H), 2.42 (s, 3H), 2.26 (s, 3H), 1.88-1.91 (m, 2H), 1.73-1.77 (m, 2H). LRMS [M+H]=425.2

Example 125

4-(2-(5-amino-8-methylbenzo[f][1,7]naphthyridin-2-yl)ethyl)-N-(2-(diethylamino)ethyl)-3-methylbenzamide

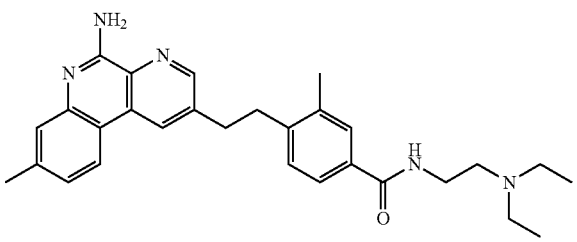 [SMILES: CCN(CC)CCNC(=O)c1ccc(CCc2cnc3c(N)nc4cc(C)ccc4c3c2)c(C)c1]

4-(2-(5-Amino-8-methylbenzo[f][1,7]naphthyridin-2-yl)ethyl)-N-(2-(diethylamino)ethyl)-3-methylbenzamide was prepared from 4-(2-(5-amino-8-methylbenzo[f][1,7]naphthyridin-2-yl)ethyl)-3-methylbenzoyl chloride (Example 116/Step 2) and N¹,N¹-diethylethane-1,2-diamine following the procedures described for Example 117. ¹H NMR (methanol-d₄): δ 8.55 (s, 1H), 8.48 (s, 1H), 8.10 (d, 1H), 7.56 (s, 1H), 7.47-7.50 (m, 1H), 7.33 (s, 1H), 7.10-7.14 (m, 2H), 3.44 (t, 2H), 3.25 (t, 2H), 3.08-3.14 (m, 4H), 2.62-2.72 (m, 4H), 2.42 (s, 3H), 2.27 (s, 3H), 1.05 (t, 6H). LRMS [M+H]=470.3

Example 126

(4-(2-(5-amino-8-methylbenzo[f][1,7]naphthyridin-2-yl)ethyl)-3-methylphenyl)(4-ethylpiperazin-1-yl)methanone

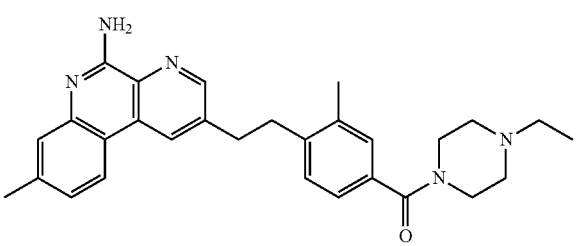 [SMILES: CCN1CCN(C(=O)c2ccc(CCc3cnc4c(N)nc5cc(C)ccc5c4c3)c(C)c2)CC1]

(4-(2-(5-Amino-8-methylbenzo[f][1,7]naphthyridin-2-yl)ethyl)-3-methylphenyl)(4-ethylpiperazin-1-yl)methanone was prepared from 4-(2-(5-amino-8-methylbenzo[f][1,7]naphthyridin-2-yl)ethyl)-3-methylbenzoyl chloride (Example 116/Step 2) and 1-ethylpiperazine following the procedures described for Example 117. $^1$H NMR (Methanol-d$_4$): δ 8.59 (s, 1H), 8.37 (s, 1H), 8.06 (d, 1H), 7.32 (s, 1H), 7.00-7.12 (m, 4H), 3.67 (br, 2H), 3.06-3.13 (m, 4H), 2.45 (br, 4H), 2.37 (q, 2H), 2.41 (s, 3H), 2.26 (s, 3H), 2.19 (br, 2H), 1.04 (t, 3H), LRMS [M+H]=468.3

Example 127

(4-(2-(5-amino-8-methylbenzo[f][1,7]naphthyridin-2-yl)ethyl)-3-methylphenyl)(piperazin-1-yl)methanone

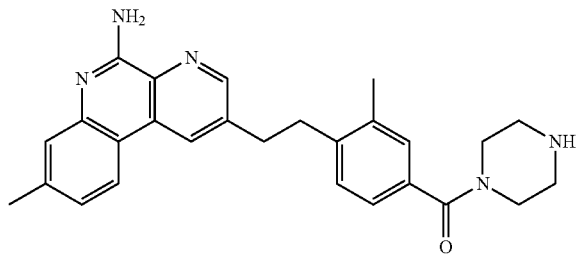 [SMILES: Cc1ccc2c(c1)nc(N)c1ncc(CCc3ccc(C(=O)N4CCNCC4)cc3C)cc12]

(4-(2-(5-Amino-8-methylbenzo[f][1,7]naphthyridin-2-yl)ethyl)-3-methylphenyl)(piperazin-1-yl)methanone was prepared from 4-(2-(5-amino-8-methylbenzo[f][1,7]naphthyridin-2-yl)ethyl)-3-methylbenzoyl chloride (Example 116/Step 2) and piperazine following the procedures described for Example 117. $^1$H NMR (methanol-d$_4$): δ 8.66 (s, 1H), 8.55 (s, 1H), 8.19 (d, 1H), 7.38 (s, 1H), 7.21-7.23 (m, 2H), 7.10-7.15 (m, 2H), 3.66 (br, 6H), 3.08-3.18 (m, 6H), 2.45 (s, 3H), 2.30 (s, 3H). LRMS [M+H]=440.2

Example 128

4-(2-(5-amino-8-methylbenzo[f][1,7]naphthyridin-2-yl)ethyl)-3-methyl-N-(2-(pyrrolidin-1-yl)ethyl)benzamide

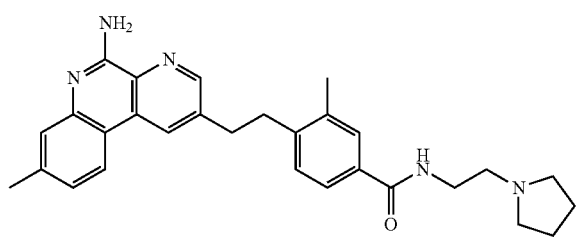 [SMILES: Cc1ccc2c(c1)nc(N)c1ncc(CCc3ccc(C(=O)NCCN4CCCC4)cc3C)cc12]

4-(2-(5-Amino-8-methylbenzo[f][1,7]naphthyridin-2-yl)ethyl)-3-methyl-N-(2-(pyrrolidin-1-yl)ethyl)benzamide was prepared from 4-(2-(5-amino-8-methylbenzo[f][1,7]naphthyridin-2-yl)ethyl)-3-methylbenzoyl chloride (Example 116/Step 2) and 2-(pyrrolidin-1-yl)ethanamine following the procedures described for Example 117. $^1$H NMR (CDCl$_3$): δ 8.58 (s, 1H), 8.38 (s, 1H), 8.07 (d, 1H), 7.64 (s, 1H), 7.51-7.55 (m, 2H), 7.12-7.20 (m, 2H), 6.26 (br, 2H), 3.61 (dd, 2H), 3.05-3.12 (m, 4H), 2.81 (t, 2H), 2.69 (br, 4H), 2.50 (s, 3H), 2.33 (s, 3H), 1.83-1.85 (m, 4H). LRMS [M+H]=468.3

Example 129

4-(2-(5-amino-8-methylbenzo[f][1,7]naphthyridin-2-yl)ethyl)-N-(2-aminoethyl)-3-methylbenzamide

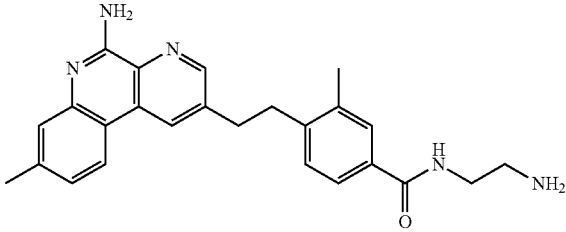 [SMILES: Cc1ccc2c(c1)nc(N)c1ncc(CCc3ccc(C(=O)NCCN)cc3C)cc12]

4-(2-(5-Amino-8-methylbenzo[f][1,7]naphthyridin-2-yl)ethyl)-N-(2-aminoethyl)-3-methylbenzamide was prepared from 4-(2-(5-amino-8-methylbenzo[f][1,7]naphthyridin-2-yl)ethyl)-3-methylbenzoyl chloride (Example 116/Step 2) and ethane-1,2-diamine following the procedures described for Example 117. $^1$H NMR (CDCl$_3$): δ 8.59 (s, 1H), 8.37 (s, 1H), 8.07 (d, 1H), 7.63 (s, 1H), 7.51 (br, 2H), 7.12-7.21 (m, 2H), 6.25 (br, 2H), 3.48-3.52 (m, 2H), 3.08-3.15 (m, 4H), 2.94 (t, 2H), 2.51 (s, 3H), 2.34 (s, 3H). LRMS [M+H]=414.2

Example 130

4-(2-(5-aminobenzo[f][1,7]naphthyridin-2-yl)ethyl)-N-(2-(dimethylamino)ethyl)-N,3-dimethylbenzamide

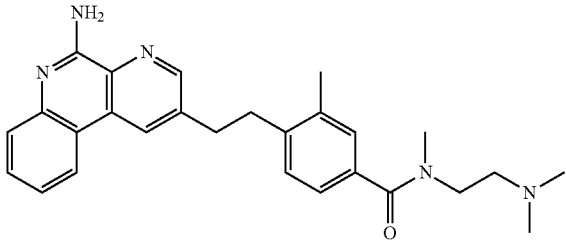 [SMILES: Cc1cc(C(=O)N(C)CCN(C)C)ccc1CCc1cnc2c(N)nc3ccccc3c2c1]

4-(2-(5-Aminobenzo[f][1,7]naphthyridin-2-yl)ethyl)-N-(2-(dimethylamino)ethyl)-N,3-dimethylbenzamide was prepared from 4-(2-(5-aminobenzo[f][1,7]naphthyridin-2-yl)ethyl)-3-methylbenzoyl chloride (Example 116/Step 2) and $N^1,N^1,N^2$-trimethylethane-1,2-diamine following the procedures described for Example 117. $^1$H NMR (methanol-d$_4$): δ 8.84 (s, 1H), 8.63 (s, 1H), 8.39 (d, 1H), 7.76-7.83 (m, 2H), 7.60-7.64 (m, 1H), 7.37 (s, 1H), 7.19-7.29 (m, 2H), 3.96 (t, 2H), 3.48 (t, 2H), 3.32 (t, 2H), 3.20 (t, 2H), 3.09 (s, 3H), 3.06 (s, 6H), 2.42 (s, 3H). LRMS [M+H]=442.3

Example 131

4-(2-(5-amino-8-methylbenzo[f][1,7]naphthyridin-2-yl)ethyl)-N-(2-(dimethylamino)ethyl)-N-methylbenzamide

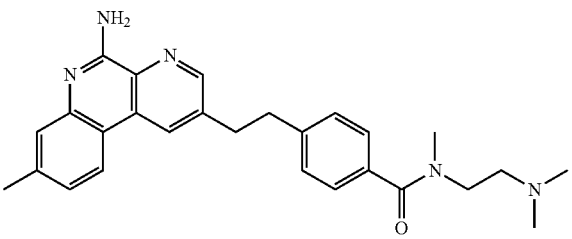

4-(2-(5-Amino-8-methylbenzo[f][1,7]naphthyridin-2-yl)ethyl)-N-(2-(dimethylamino)ethyl)-N-methylbenzamide was prepared from 4-(2-(5-amino-8-methylbenzo[f][1,7]naphthyridin-2-yl)ethyl)-3-methylbenzoyl chloride (Example 116/Step 2) and N$^1$,N$^1$,N$^2$-trimethylethane-1,2-diamine following the procedures described for Example 117. $^1$H NMR (CDCl$_3$): δ 8.64 (s, 1H), 8.36 (s, 1H), 8.05 (d, 1H), 7.60 (s, 1H), 7.41 (d, 2H), 7.31 (d, 1H), 7.21 (d, 2H), 3.91 (t, 2H), 3.44 (t, 2H), 3.25 (t, 2H), 3.12 (t, 2H), 3.03 (s, 3H), 3.01 (s, 6H), 2.53 (s, 3H). LRMS [M+H]=442.3

Example 132

2-(4-(2-(5-aminobenzo[f][1,7]naphthyridin-2-yl)ethyl)-3-methylphenyl)propan-2-ol

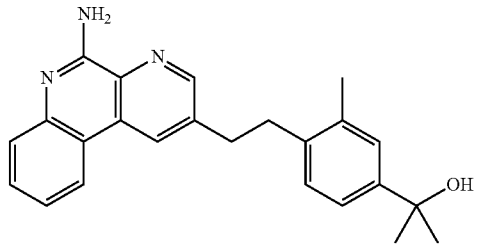 [SMILES: Cc1cc(C(C)(C)O)ccc1CCc1cnc2c(N)nc3ccccc3c2c1]

2-(4-(2-(5-Aminobenzo[f][1,7]naphthyridin-2-yl)ethyl)-3-methylphenyl)propan-2-ol was prepared following the procedures described for Example 78, but using methyl 4-(2-(5-aminobenzo[f][1,7]naphthyridin-2-yl)ethyl)-3-methylbenzoate which was prepared analogous to Example 115 but using tert-butyl 2-(4,4,5,5-tetramethyl-1,3,2-dioxaborolan-2-yl)phenylcarbamate in Step 4. LRMS [M+H]=372.2

Example 133

2-(4-butoxyphenethyl)-8-methylbenzo[f][1,7]naphthyridin-5-amine

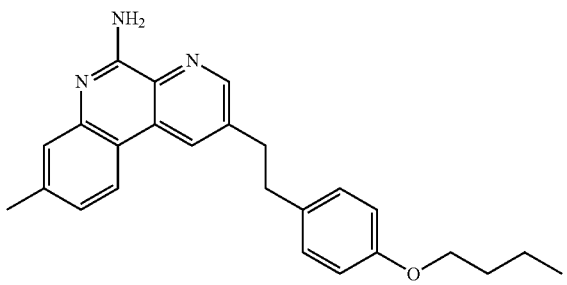 [SMILES: CCCCOc1ccc(CCc2cnc3c(N)nc4cc(C)ccc4c3c2)cc1]

2-(4-Butoxyphenethyl)-8-methylbenzo[f][1,7]naphthyridin-5-amine was prepared following the procedures described for Example 45/Steps 1 to 3, but using 1-butoxy-4-ethynylbenzene (commercially available) with 3,5-dichloropicolinonitrile (commercially available) in step 1. $^1$H NMR (Acetone-d$_6$): δ 8.75 (s, 1H), 8.68 (s, 1H), 8.28 (d, 1H), 7.42 (s, 1H), 7.10-7.18 (m, 3H), 6.84 (d, 2H), 6.58 (br, 2H), 3.94 (t, 2H), 3.21 (t, 2H), 3.05 (t, 2H), 2.46 (s, 3H), 1.65-1.75 (m, 2H), 1.41-1.58 (m, 2H), 0.94 (s, 3H). LRMS [M+H]=386.2.

Example 134

2-(2-(biphenyl-4-yl)ethyl)-8-methylbenzo[f][1,7]naphthyridin-5-amine

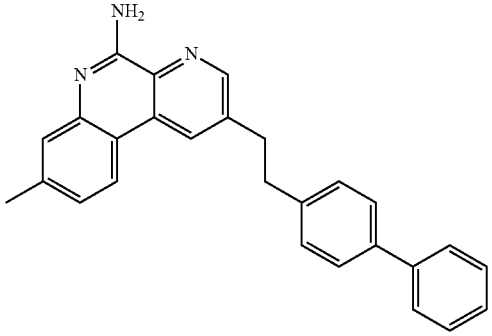 [SMILES: Cc1ccc2c(c1)nc(N)c1ncc(CCc3ccc(-c4ccccc4)cc3)cc12]

2-(2-(Biphenyl-4-yl)ethyl)-8-methylbenzo[f][1,7]naphthyridin-5-amine was prepared following the procedures described for Example 45/Steps 1 to 3, but using 4-ethynylbiphenyl (commercially available) with 3,5-dichloropicolinonitrile (commercially available) in Step 1. $^1$H NMR (Acetone-d$_6$): δ 8.80 (s, 1H), 8.75 (s, 1H), 8.26 (d, 2H), 7.55-7.69 (m, 4H), 7.30-7.46 (m, 4H), 7.13 (d, 2H), 6.58 (br, 2H), 3.30 (t, 2H), 3.18 (t, 2H), 2.45 (s, 3H). LRMS [M+H]=390.2

Example 135

2-((1,3-dihydroisobenzofuran-1-yl)methyl)-8-methylbenzo[f][1,7]naphthyridin-5-amine

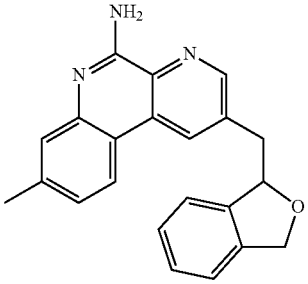 [SMILES: Cc1ccc2c(c1)nc(N)c1ncc(CC3OCc4ccccc43)cc12]

Step 1: 2-((5-amino-8-methylbenzo[f][1,7]naphthyridin-2-yl)ethynyl)phenyl)methanol 2-((5-Amino-8-methylbenzo[f][1,7]naphthyridin-2-yl)ethynyl)phenyl)methanol was prepared following the procedures described for Example 45/Steps 1 to 2, but using (2-ethynylphenyl)methanol (commercially available) with 3,5-dichloropicolinonitrile (commercially available) in Step 1.

Step 2: 2-((1,3-dihydroisobenzofuran-1-yl)methyl)-8-methylbenzo[f][1,7]naphthyridin-5-amine To a solution of 2-((5-amino-8-methylbenzo[f][1,7]naphthyridin-2-yl)ethynyl)phenyl)methanol (1.0 equiv.) (from the previous step) in ethanol (0.05 M) was added 10% wt palladium on carbon (0.2 equiv. by weight). Hydrogen gas was then introduced via a balloon, and the reaction was allowed to stir for 18 hours. At this point, the mixture was filtered through a pad of celite, washing with methanol. The volatiles were removed in vacuo and the resulting residue was purified by a COMBIFLASH® system (ISCO) using 0-60% ethyl acetate in hexanes to give 2-((1,3-dihydroisobenzofuran-1-yl)methyl)-8-methylbenzo[f][1,7]naphthyridin-5-amine as a solid. ¹H NMR (Acetone-d₆): δ 8.78 (s, 1H), 8.74 (s, 1H), 8.24 (d, 2H), 7.40-7.44 (m, 2H), 7.20-7.34 (m, 3H), 6.61 (br, 2H), 5.63-5.69 (m, 1H), 4.89-5.00 (dd, 2H), 3.51-3.56 (dd, 1H), 3.28-3.34 (dd, 1H), 2.46 (s, 3H). LRMS [M+H]=342.1

Example 136

8-methyl-2-(4-(2-methylallyloxy)phenethyl)benzo[f][1,7]naphthyridin-5-amine

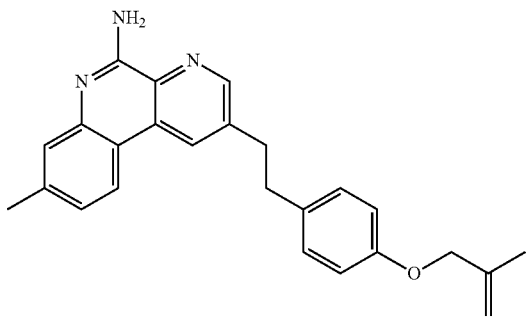 [SMILES: C=C(C)COc1ccc(CCc2cnc3c(N)nc4cc(C)ccc4c3c2)cc1]

To a solution of 4-(2-(5-amino-8-methylbenzo[f][1,7]naphthyridin-2-yl)ethyl)phenol (from Example 170) (1.0 equiv.) in dimethylformamide (0.10 M) was added anhydrous potassium carbonate (1.5 equiv.) followed by methallyl bromide (1.2 equiv.). The resulting mixture was allowed to stir for 18 hours at 100° C. After cooling to ambient temperature, the mixture was diluted with ethyl acetate and water. The biphasic layers were separated and the aqueous layer was washed twice with ethyl acetate. The combined organic layers were dried over anhydrous Na₂SO₄ and the volatiles were removed in vacuo. The resulting residue was purified by a COMBIFLASH® system (ISCO) using 0-60% ethyl acetate in hexanes to provide 8-methyl-2-(4-(2-methylallyloxy)phenethyl)benzo[f][1,7]naphthyridin-5-amine as a solid. ¹H NMR (Acetone-d₆): δ 8.75 (s, 1H), 8.68 (s, 1H), 8.27 (d, 1H), 7.41 (s, 1H), 7.12-7.19 (m, 3H), 6.87 (d, 2H), 6.60 (br, 2H), 5.06 (s, 1H), 4.93 (s, 1H), 4.43 (s, 2H), 3.20 (t, 2H), 3.05 (t, 2H), 2.45 (s, 3H), 1.79 (s, 3H). LRMS [M+H]=384.2

Example 137

2-(4-(isopentyloxy)phenethyl)-8-methylbenzo[f][1,7]naphthyridin-5-amine

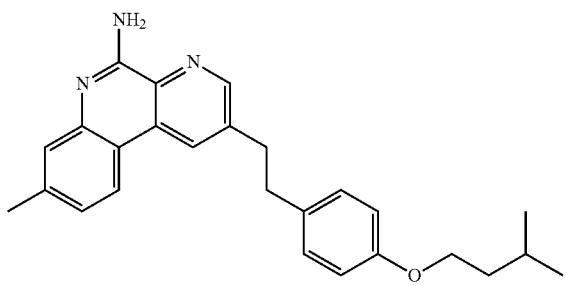 [SMILES: Cc1ccc2c(c1)nc(N)c1ncc(CCc3ccc(OCCC(C)C)cc3)cc12]

2-(4-(Isopentyloxy)phenethyl)-8-methylbenzo[f][1,7]naphthyridin-5-amine was prepared from 4-(2-(5-amino-8-methylbenzo[f][1,7]naphthyridin-2-yl)ethyl)phenol (from Example 170) following the procedure described for Example 136, but using 1-bromo-3-methylbutane. ¹H NMR (Acetone-d₆): δ 8.72 (s, 1H), 8.69 (s, 1H), 8.26 (d, 1H), 7.43 (s, 1H), 7.12-7.18 (m, 3H), 6.84 (d, 2H), 6.50 (br, 2H), 3.98 (t, 2H), 3.21 (t, 2H), 3.06 (t, 2H), 2.46 (s, 3H), 1.78-1.87 (m, 1H), 1.61-1.67 (dd, 2H), 0.96 (s, 3H), 0.95 (3H). LRMS [M+H]=400.2

Example 138

4-(2-(5-amino-8-methylbenzo[f][1,7]naphthyridin-2-yl)ethyl)phenyl propyl carbonate

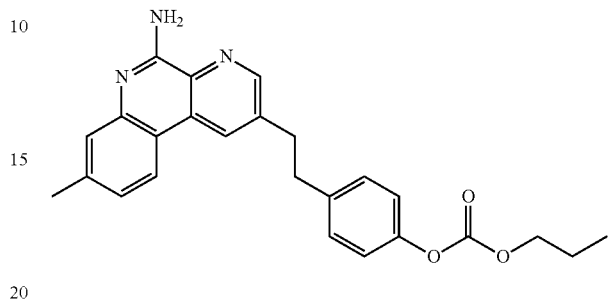

To a solution of 4-(2-(5-amino-8-methylbenzo[f][1,7]naphthyridin-2-yl)ethyl)phenol (from Example 170) (1.0 equiv.) and triethyl amine (2 equiv.) in dichloromethane (0.10 M) at 0° C. was added ethyl chloroformate (1.2 equiv.). The resulting mixture was allowed to stir for 30 minutes at 0° C., after which it was diluted with water and dichloromethane. The biphasic layers were separated and the aqueous layer was washed twice with dichloromethane. The combined organic layers were dried over anhydrous Na₂SO₄ and the volatiles were removed in vacuo. The resulting residue was purified by a COMBIFLASH® system (ISCO) using 0-50% ethyl acetate in hexanes to provide 4-(2-(5-amino-8-methylbenzo[f][1,7]naphthyridin-2-yl)ethyl)phenyl ethyl carbonate as a solid. ¹H NMR (Acetone-d₆): δ 8.78 (s, 1H), 8.73 (s, 1H), 8.28 (d, 1H), 7.43 (s, 1H), 7.33 (d, 2H), 7.10-7.17 (m, 3H), 6.64 (br, 2H), 4.18 (t, 2H), 3.25 (t, 2H), 3.14 (t, 2H), 2.45 (s, 3H), 1.68-1.77 (m, 2H), 0.97 (t, 3H). LRMS [M+H]=416.2

Example 139 ethyl 5-(4-(2-(5-amino-8-methylbenzo[f][1,7]naphthyridin-2-yl)ethyl)phenoxy)pentanoate

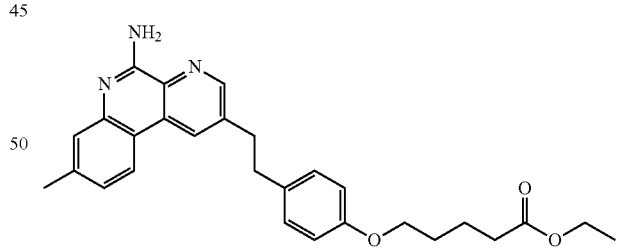

To a solution of 4-(2-(5-amino-8-methylbenzo[f][1,7]naphthyridin-2-yl)ethyl)phenol (from Example 170) (1.0 equiv.) in dimethylformamide (0.10 M) 22° C. was added 60% dispersion of sodium hydride in mineral oil (1.5 equiv.) and the resulting mixture was allowed to stir for 30 min At this point, ethyl 5-bromopentanoate (1.2 equiv.) was added to this mixture. The reaction mixture was then allowed to stir for 18 hours. after which it was diluted with ethyl acetate and water. The biphasic layers were separated and the organic layer was washed twice with water. The organic layer was dried over anhydrous Na₂SO₄ and the volatiles were removed in vacuo. The resulting residue was purified by RP-HPLC using a 10-50% MeCN in water gradient. The resulting trifluoroacetate salt was then converted to the free base form by utilizing a StratoSpheres™ PL-SO3H SPE ion exchange resin, delivering ethyl 5-(4-(2-(5-amino-8-methylbenzo[f][1,7]naphthyridin-2-yl)ethyl)phenoxy)pentanoate as a solid. $^1$H NMR (Acetone-d$_6$): δ 8.80 (s, 1H), 8.74 (s, 1H), 8.33 (d, 1H), 7.47 (s, 1H), 7.24 (d, 1H), 7.17 (d, 2H), 6.85 (d, 2H), 4.10 (q, 2H), 3.97 (t, 2H), 3.25 (t, 2H), 3.07 (t, 2), 2.50 (s, 3H), 2.37 (t, 3H), 1.74-1.84 (m, 4H), 1.21 (t, 3H). LRMS [M+H]=458.2

Example 140

2-(4-(cyclopentyloxy)phenethyl)-8-methylbenzo[f][1,7]naphthyridin-5-amine

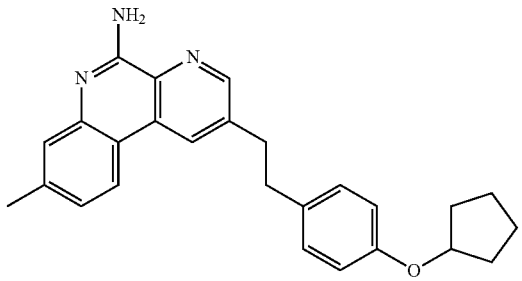 [SMILES: Cc1ccc2c(c1)nc(N)c1ncc(CCc3ccc(OC4CCCC4)cc3)cc12]

2-(4-(Cyclopentyloxy)phenethyl)-8-methylbenzo[f][1,7]naphthyridin-5-amine was prepared from 4-(2-(5-amino-8-methylbenzo[f][1,7]naphthyridin-2-yl)ethyl)phenol (from Example 170) following the procedure described for Example 136, but using bromocyclopentane. $^1$H NMR (Acetone-d$_6$): δ 8.75 (d, 2H), 8.30 (d, 1H), 7.45 (s, 1H), 7.20 (d, 1H), 7.14 (d, 2H), 6.79 (d, 2H), 4.73-4.81 (m, 1H), 3.22 (t, 2H), 3.05 (t, 2H), 2.47 (s, 3H), 1.85-1.96 (m, 2H), 1.70-1.79 (m, 4H), 1.56-1.64 (m, 2H). LRMS [M+H]=398.2

Example 141

2-(4-(cyclobutylmethoxy)phenethyl)-8-methylbenzo[f][1,7]naphthyridin-5-amine

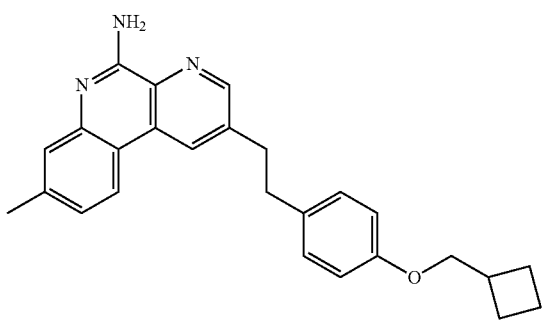 [SMILES: Cc1ccc2c(c1)nc(N)c1ncc(CCc3ccc(OCC4CCC4)cc3)cc12]

2-(4-(Cyclobutylmethoxy)phenethyl)-8-methylbenzo[f][1,7]naphthyridin-5-amine was prepared from 4-(2-(5-amino-8-methylbenzo[f][1,7]naphthyridin-2-yl)ethyl)phenol (from Example 170) following the procedure described for Example 136, but using (bromomethyl)cyclobutane. $^1$H NMR (Acetone-d$_6$): δ 8.79 (s, 1H), 8.73 (s, 1H), 8.33 (d, 1H), 7.47 (s, 1H), 7.26 (d, 1H), 7.16 (d, 2H), 6.82 (d, 2H), 3.90 (d, 2H), 3.23 (t, 2H), 3.06 (t, 2H), 2.68-2.79 (m, 1H), 2.49 (s, 3H), 2.05-2.14 (m, 2H), 1.80-1.98 (m, 4H). LRMS [M+H]=398.2

Example 142

8-methyl-2-(4-(2-morpholinoethoxy)phenethyl)benzo[f][1,7]naphthyridin-5-amine

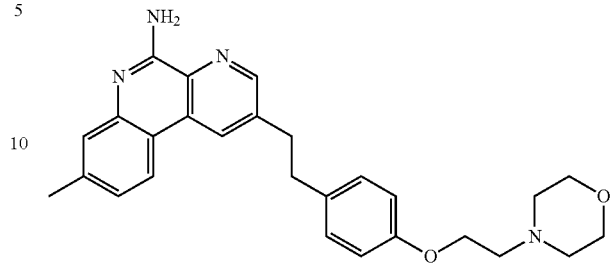

8-Methyl-2-(4-(2-morpholinoethoxy)phenethyl)benzo[f][1,7]naphthyridin-5-amine was prepared from 4-(2-(5-amino-8-methylbenzo[f][1,7]naphthyridin-2-yl)ethyl)phenol (from Example 170) following the procedure described for Example 139, but using 4-(2-bromoethyl)morpholine. $^1$H NMR (Acetone-d$_6$): δ 8.78 (s, 1H), 8.72 (s, 1H), 8.30 (d, 1H), 7.46 (s, 1H), 7.17-7.24 (m, 3H), 6.85 (d, 2H), 4.08 (t, 2H), 3.56-3.62 (m, 4H), 3.45-3.53 (m, 2H), 3.24 (t, 2H), 3.07 (t, 2H), 2.73 (t, 2H), 2.52-2.56 (m, 2H), 2.49 (s, 3H). LRMS [M+H]=443.2

Example 143

2-(4-(2-(5-amino-8-methylbenzo[f][1,7]naphthyridin-2-yl)ethyl)phenoxy)-1-phenylethanone

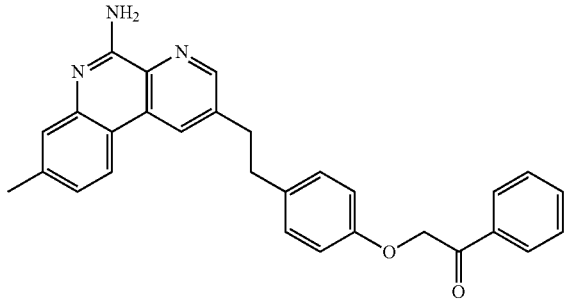 [SMILES: Cc1ccc2c(c1)nc(N)c1ncc(CCc3ccc(OCC(=O)c4ccccc4)cc3)cc12]

2-(4-(2-(5-Amino-8-methylbenzo[f][1,7]naphthyridin-2-yl)ethyl)phenoxy)-1-phenylethanone was prepared from 4-(2-(5-amino-8-methylbenzo[f][1,7]naphthyridin-2-yl)ethyl)phenol (from Example 170) following the procedure described for Example 139, but using 2-bromo-1-phenylethanone. $^1$H NMR (Acetone-d$_6$): δ 8.76 (s, 1H), 8.71 (s, 1H), 8.27 (d, 1H), 8.06 (d, 2H), 7.67 (t, 1H), 7.57 (t, 2H), 7.43 (s, 1H), 7.17 (d, 3H), 6.90 (d, 2H), 5.45 (s, 2H), 3.21 (t, 2H), 3.06 (t, 2H), 2.45 (s, 3H). LRMS [M+H]=448.2

Example 144

5-(4-(2-(5-amino-8-methylbenzo[f][1,7]naphthyridin-2-yl)ethyl)phenoxy)pentanoic acid

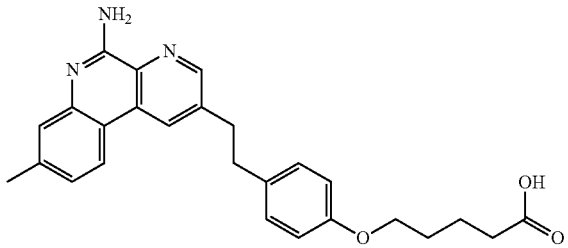 [SMILES: Cc1ccc2c(c1)nc(N)c1ncc(CCc3ccc(OCCCCC(=O)O)cc3)cc12]

To a solution of ethyl 5-(4-(2-(5-amino-8-methylbenzo[f][1,7]naphthyridin-2-yl)ethyl)phenoxy)pentanoate (1.0 equiv.) (from Example 139) in ethanol (0.10 M) was added anhydrous sodium hydroxide (2.0 equiv.) and the resulting mixture was allowed to stir at 80° C. for 2 hours. After cooling to ambient temperature, the mixture was diluted with ethyl acetate and water. The biphasic layers were separated and the aqueous layer was washed twice with ethyl acetate. The combined organic layers were dried over anhydrous $Na_2SO_4$ and the volatiles were removed in vacuo. The resulting residue was purified by a COMBIFLASH® system (ISCO) using 0-10% methanol in dichloromethane to furnish 5-(4-(2-(5-amino-8-methylbenzo[f][1,7]naphthyridin-2-yl)ethyl)phenoxy)pentanoic acid as a solid. $^1$H NMR (Methanol-$d_4$): δ 8.61 (s, 1H), 8.57 (s, 1H), 8.20 (d, 1H), 7.40 (s, 1H), 7.20 (d, 1H), 7.07 (d, 2H), 6.81 (d, 2H), 3.93 (t, 2H), 3.18 (t, 2H), 3.00 (t, 2H), 2.48 (s, 3H), 2.25 (t, 2H), 1.74-1.81 (m, 2H), 0.86-0.96 (m, 2H). LRMS [M+H]=430.2

Example 145

2-(4-(2-(5-amino-8-methylbenzo[f][1,7]naphthyridin-2-yl)ethyl)phenoxy)ethanol

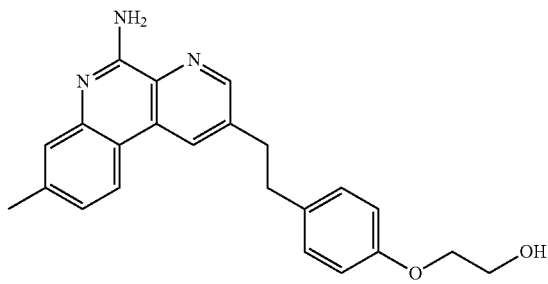 [SMILES: Cc1ccc2c(c1)nc(N)c1ncc(CCc3ccc(OCCO)cc3)cc12]

Step 1: 2-(4-(2-(tert-butyldimethylsilyloxy)ethoxy)phenethyl)-8-methylbenzo[f][1,7]naphthyridin-5-amine 2-(4-(2-(Tert-butyldimethylsilyloxy)ethoxy)phenethyl)-8-methylbenzo[f][1,7]naphthyridin-5-amine was prepared from 4-(2-(5-amino-8-methylbenzo[f][1,7]naphthyridin-2-yl)ethyl)phenol (from Example 170) following the procedure described for Example 139, but using (2-bromoethoxy)(tert-butyl)dimethylsilane.

Step 2: 2-(4-(2-(5-amino-8-methylbenzo[f][1,7]naphthyridin-2-yl)ethyl)phenoxy)ethanol To a solution of 2-(4-(2-(tert-butyldimethylsilyloxy)ethoxy)phenethyl)-8-methylbenzo[f][1,7]naphthyridin-5-amine (from the previous step) (1.0 equiv.) in tetrahydrofuran (0.10 M) was added a 1.0 M solution of tetrabutylammonium fluoride (5 equiv.) in THF and the resulting mixture was allowed to stir at 22° C. for 2 hours. At this point, the mixture was diluted with ethyl acetate and water. The biphasic layers were separated and the aqueous layer was washed twice with ethyl acetate. The combined organic layers were dried over anhydrous $Na_2SO_4$ and the volatiles were removed in vacuo. The resulting residue was purified by a COMBIFLASH® system (ISCO) using 0-10% methanol in dichloromethane to furnish 2-(4-(2-(5-amino-8-methylbenzo[f][1,7]naphthyridin-2-yl)ethyl)phenoxy)ethanol as a solid. $^1$H NMR (Acetone-$d_6$): δ 8.76 (s, 1H), 8.67 (s, 1H), 8.28 (d, 1H), 7.40 (s, 1H), 7.15 (t, 3H), 6.84 (d, 2H), 6.54 (br, 2H), 4.00 (t, 2H), 3.83 (t, 2H), 3.21 (t, 2H), 3.05 (t, 2H), 2.45 (s, 3H). LRMS [M+H]=374.2

Example 146

2-(4-(2-(5-amino-8-methylbenzo[f][1,7]naphthyridin-2-yl)ethyl)phenoxy)-N,N-dimethylacetamide

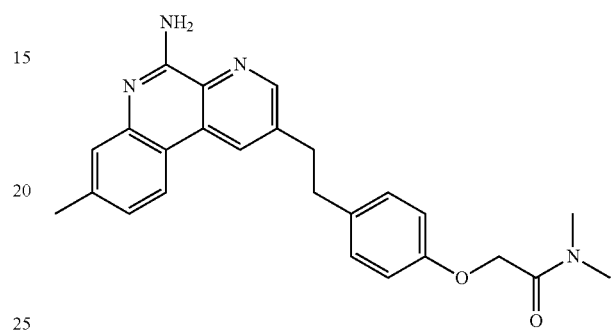

2-(4-(2-(5-Amino-8-methylbenzo[f][1,7]naphthyridin-2-yl)ethyl)phenoxy)-N,N-dimethylacetamide was prepared from 4-(2-(5-amino-8-methylbenzo[f][1,7]naphthyridin-2-yl)ethyl)phenol (from Example 170) and following the procedure described for Example 139, but using 2-bromo-N,N-dimethylacetamide. $^1$H NMR (Acetone-$d_6$): δ 8.75 (s, 1H), 8.70 (s, 1H), 8.28 (d, 1H), 7.40 (s, 1H), 7.18 (t, 3H), 6.87 (d, 2H), 6.56 (br, 2H), 4.72 (s, 2H), 3.20 (t, 2H), 3.07 (s, 3H), 3.05 (t, 2H), 2.87 (s, 3H), 2.45 (s, 3H). LRMS [M+H]=415.2

Example 147

8-methyl-2-(2-methyl-4-(2-morpholinoethoxy)phenethyl)benzo[f][1,7]naphthyridin-5-amine

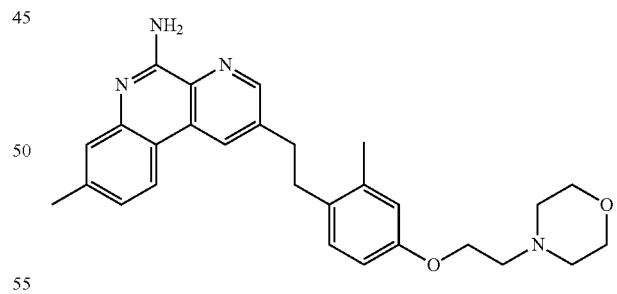

8-Methyl-2-(2-methyl-4-(2-morpholinoethoxy)phenethyl)benzo[f][1,7]naphthyridin-5-amine was prepared following an analogous procedure to the preparation described for Example 139, but using 4-(2-(5-amino-8-methylbenzo[f][1,7]naphthyridin-2-yl)ethyl)-3-methylphenol (from Example 50) and 4-(2-bromoethyl)morpholine. $^1$H NMR (Acetone-$d_6$): δ 8.73 (d, 2H), 8.26 (d, 1H), 7.44 (s, 1H), 7.17 (d, 1H), 7.05 (d, 1H), 6.76 (s, 1H), 6.67 (d, 1), 4.04-4.08 (m, 3H), 3.60-3.62 (m, 4H), 3.30 (s, 1H), 3.16 (t, 2H), 3.04 (t, 2H), 2.71 (t, 2H), 2.50-2.52 (m, 2H), 2.47 (s, 3H), 2.28 (s, 3H). LRMS [M+H]=457.3

Example 148

2-(2-(4-(2-(5-amino-8-methylbenzo[f][1,7]naphthyridin-2-yl)ethyl)-3-methylphenoxy)ethoxy)ethanol

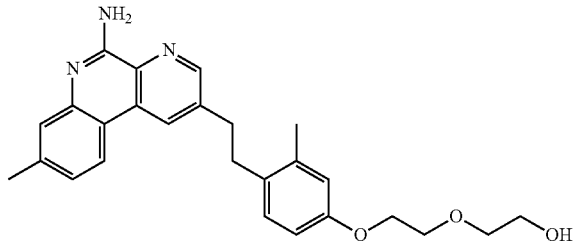 [SMILES: Cc1ccc2c(c1)nc(N)c1ncc(CCc3ccc(OCCOCCO)cc3C)cc12]

Step 1: 2-(4-(2-(2-(tert-butyldimethylsilyloxy)ethoxy)ethoxy)-2-methylphenethyl)-8-methylbenzo[f][1,7]naphthyridin-5-amine 2-(4-(2-(2-(Tert-butyldimethylsilyloxy)ethoxy)ethoxy)-2-methylphenethyl)-8-methylbenzo[f][1,7]naphthyridin-5-amine was prepared following an analogous procedure to the preparation described for Example 145/Step 1, but using 4-(2-(5-amino-8-methylbenzo[f][1,7]naphthyridin-2-yl)ethyl)-3-methylphenol (from Example 50) with tert-butyl(2-(2-chloroethoxy)ethoxy)dimethylsilane.

Step 2: 2-(2-(4-(2-(5-Amino-8-methylbenzo[f][1,7]naphthyridin-2-yl)ethyl)-3-methylphenoxy)ethoxy)ethanol 2-(2-(4-(2-(5-Amino-8-methylbenzo[f][1,7]naphthyridin-2-yl)ethyl)-3-methylphenoxy)ethoxy)ethanol was prepared from 2-(4-(2-(2-(tert-butyldimethylsilyloxy)ethoxy)ethoxy)-2-methylphenethyl)-8-methylbenzo[f][1,7]naphthyridin-5-amine (from the previous step) following the procedures described for Example 145/Step 2. $^1$H NMR (Acetone-$d_6$): δ 8.74 (s, 1H), 8.69 (s, 1H), 8.27 (d, 1H), 7.41 (s, 1H), 7.14 (d, 1H), 7.06 (d, 1H), 6.75 (s, 1H), 6.69 (d, 1), 6.54 (br, 2H), 4.07 (t, 2H), 3.79 (t, 2H), 3.64 (t, 2H), 3.59 (t, 2H), 3.16 (t, 2H), 3.03 (t, 2H), 2.45 (s, 3H), 2.29 (s, 3H). LRMS [M+H]=432.2

Example 149 diethyl 3-(4-(2-(5-amino-8-methylbenzo[f][1,7]naphthyridin-2-yl)ethyl)-3-methylphenoxy)propylphosphonate

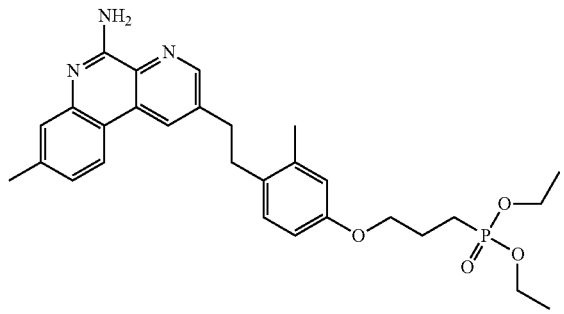 [SMILES: CCOP(=O)(CCCOc1ccc(CCc2cnc3c(N)nc4cc(C)ccc4c3c2)c(C)c1)OCC]

Diethyl 3-(4-(2-(5-amino-8-methylbenzo[f][1,7]naphthyridin-2-yl)ethyl)-3-methylphenoxy)propylphosphonate was prepared following an analogous procedure to the preparation described for Example 139, but using 4-(2-(5-amino-8-methylbenzo[f][1,7]naphthyridin-2-yl)ethyl)-3-methylphenol (from Example 50) with diethyl 3-bromopropylphosphonate. $^1$H NMR (Acetone-$d_6$): δ 9.52 (s, 1H), 9.47 (s, 1H), 9.03 (d, 1H), 8.21 (s, 1H), 7.93 (d, 1H), 7.84 (d, 1H), 7.60 (br, 2H), 7.53 (s, 1), 7.45 (d, 1H), 4.76-4.91 (m, 6H), 3.93 (t, 2H), 3.81 (t, 2H), 3.24 (s, 3H), 3.06 (s, 3H), 2.76-2.86 (m, 2H), 2.61-2.72 (m, 2H), 2.07 (t, 6H). LRMS [M+H]=522.2

Example 150

3-(4-(2-(5-amino-8-methylbenzo[f][1,7]naphthyridin-2-yl)ethyl)-3-methylphenoxy)propylphosphonic acid

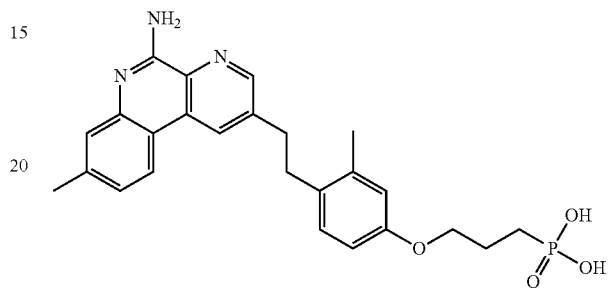

A 12 N solution of hydrochloric acid (0.10 M) was added to diethyl 3-(4-(2-(5-amino-8-methylbenzo[f][1,7]naphthyridin-2-yl)ethyl)-3-methylphenoxy)propylphosphonate (from Example 149) and the resulting mixture was allowed to stir at 100° C. for 18 hours. At this point, hydrochloric acid was removed under reduced pressure and the resulting residue was purified by RP-HPLC using a 10-50% MeCN in water gradient. The resulting trifluoroacetate salt was then converted to the free base form by the addition of a saturated aqueous solution of sodium bicarbonate, followed by washing three times with ethyl acetate. The combined organic layers were dried with anhydrous $Na_2SO_4$, and the volatiles were removed in vacuo to deliver 3-(4-(2-(5-amino-8-methylbenzo[f][1,7]naphthyridin-2-yl)ethyl)-3-methylphenoxy)propylphosphonic acid as a solid. $^1$H NMR (Dimethylsulfoxide-$d_6$): δ 9.72 (br, 1H), 9.01 (s, 1H), 8.96 (br, 1H), 8.85 (s, 1H), 8.54 (d, 1H), 7.54 (s, 1H), 7.42 (d, 1H), 7.08 (d, 1), 6.74 (s, 1H), 6.66 (d, 1H), 3.95 (t, 2H), 3.14 (t, 2H), 2.97 (t, 2H), 2.50 (s, 3H), 2.27 (s, 3H), 1.81-1.91 (m, 2H), 1.56-1.67 (m, 2H). LRMS [M+H]=466.2

Example 151

2-(4-butoxy-2-methylphenethyl)-8-methylbenzo[f][1,7]naphthyridin-5-amine

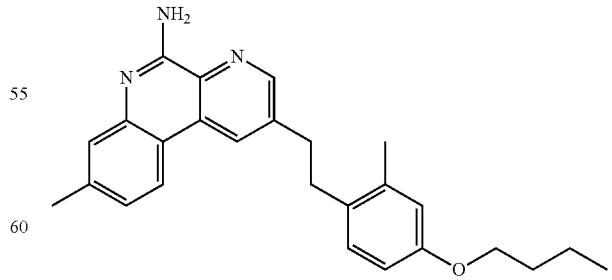

2-(4-Butoxy-2-methylphenethyl)-8-methylbenzo[f][1,7]naphthyridin-5-amine was prepared following an analogous procedure to the preparation described for Example 139, but using 4-(2-(5-amino-8-methylbenzo[f][1,7]naphthyridin-2- yl)ethyl)-3-methylphenol (from Example 50) with 1-bromobutane. $^1$H NMR (Acetone-d$_6$): δ 8.75 (s, 1H), 8.71 (s, 1H), 8.28 (d, 1H), 7.43 (s, 1H), 7.15 (d, 1H), 7.07 (d, 1H), 6.75 (s, 1H), 6.69 (d, 1H), 6.54 (br, 2H) 3.95 (t, 2H), 3.16 (t, 2H), 3.04 (t, 2H), 2.47 (s, 3H), 2.30 (s, 3H), 1.69-1.77 (m, 2H), 1.43-1.54 (m, 2H), 0.97 (t, 3H). LRMS [M+H]=400.2

Example 152

2-(4-(2-(5-aminobenzo[f][1,7]naphthyridin-2-yl)ethyl)-3-methylphenoxy)ethanol

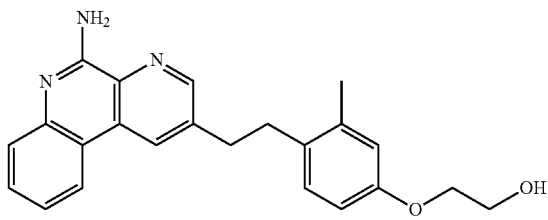 [SMILES: Cc1cc(OCCO)ccc1CCc1cnc2c(N)nc3ccccc3c2c1]

Step 1: 4-(2-(5-aminobenzo[f][1,7]naphthyridin-2-yl)ethyl)-3-methylphenol 4-(2-(5-Aminobenzo[f][1,7]naphthyridin-2-yl)ethyl)-3-methylphenol was prepared following an analogous procedure to the preparation described for Example 145, but using 2-(4-Methoxy-2-methylphenethyl)benzo[f][1,7]naphthyridin-5-amine (from Example 119).

Step 2: 2-(4-(2-(5-Aminobenzo[f][1,7]naphthyridin-2-yl)ethyl)-3-methylphenoxy)ethanol 2-(4-(2-(5-Aminobenzo[f][1,7]naphthyridin-2-yl)ethyl)-3-methylphenoxy)ethanol was prepared from 4-(2-(5-aminobenzo[f][1,7]naphthyridin-2-yl)ethyl)-3-methylphenol (from the previous step) following the procedures described for Example 145/Steps 1 to 2. LRMS [M+H]=374.2

Example 153

2-(4-(2-(5-aminobenzo[f][1,7]naphthyridin-2-yl)ethyl)-3-methylphenoxy)ethanol

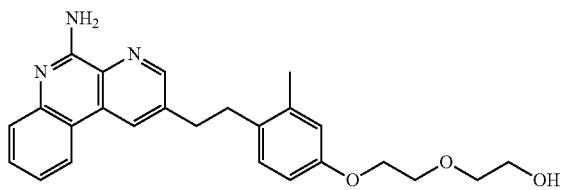 [SMILES: Cc1cc(OCCOCCO)ccc1CCc1cnc2c(N)nc3ccccc3c2c1]

Step 1: 4-(2-(5-aminobenzo[f][1,7]naphthyridin-2-yl)ethyl)-3-methylphenol 4-(2-(5-Aminobenzo[f][1,7]naphthyridin-2-yl)ethyl)-3-methylphenol was prepared following an analogous procedure to the preparation described for Example 50, but using 2-(4-Methoxy-2-methylphenethyl)benzo[f][1,7]naphthyridin-5-amine (from Example 119).

Step 2: 2-(4-(2-(5-aminobenzo[f][1,7]naphthyridin-2-yl)ethyl)-3-methylphenoxy)ethanol 2-(4-(2-(5-Aminobenzo[f][1,7]naphthyridin-2-yl)ethyl)-3-methylphenoxy)ethanol was prepared following the procedures described for Example 148/Steps 1 to 2. LRMS [M+H]=418.2

Example 154 ethyl 5-(4-(2-(5-amino-8-methylbenzo[f][1,7]naphthyridin-2-yl)ethyl)-3-methylphenoxy)pentanoate

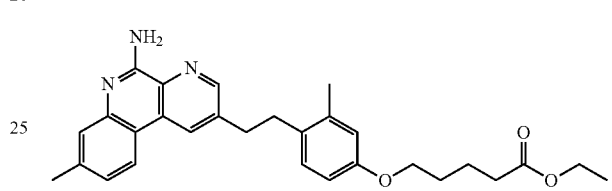

Ethyl 5-(4-(2-(5-amino-8-methylbenzo[f][1,7]naphthyridin-2-yl)ethyl)-3-methylphenoxy)pentanoate was prepared from 4-(2-(5-amino-8-methylbenzo[f][1,7]naphthyridin-2-yl)ethyl)-3-methylphenol (from Example 50) following the procedure described for Example 139, but using ethyl 5-bromopentanoate. $^1$H NMR (CDCl3): δ 8.64 (s, 1H), 8.27 (s, 1H), 8.02 (d, 1H), 7.66 (s, 1H), 7.32 (d, 1H), 6.91 (d, 1H), 6.66 (s, 1H), 6.63 (d, 1H), 4.13 (q, 2H), 3.93 (t, 2H), 3.14 (t, 2H), 2.99 (t, 2H), 2.54 (s, 3H), 2.38 (t, 2H), 2.25 (s, 3H), 1.79-1.83 (m, 4H), 1.26 (t, 3H). LRMS [M+H]=472.3

Example 155

5-(4-(2-(5-amino-8-methylbenzo[f][1,7]naphthyridin-2-yl)ethyl)-3-methylphenoxy)pentanoic acid

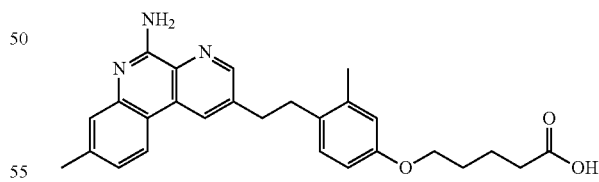

5-(4-(2-(5-Amino-8-methylbenzo[f][1,7]naphthyridin-2-yl)ethyl)-3-methylphenoxy)pentanoic acid was prepared from ethyl 5-(4-(2-(5-amino-8-methylbenzo[f][1,7]naphthyridin-2-yl)ethyl)-3-methylphenoxy)pentanoate (from the previous step) following the procedure described for Example 144. $^1$H NMR (CDCl3): δ 8.52 (s, 1H), 8.27 (s, 1H), 8.02 (d, 1H), 7.65 (s, 1H), 7.32 (d, 1H), 6.86 (d, 1H), 6.72 (s, 1H), 6.63 (d, 1H), 3.95 (t, 2H), 3.15 (t, 2H), 2.99 (t, 2H), 2.54 (s, 3H), 2.45 (t, 2H), 2.23 (s, 3H), 1.79-1.83 (m, 4H). LRMS [M+H]=444.2

Example 156

2-(4-(2-(5-amino-8-methylbenzo[f][1,7]naphthyridin-2-yl)ethyl)-3-methylphenoxy)ethanol

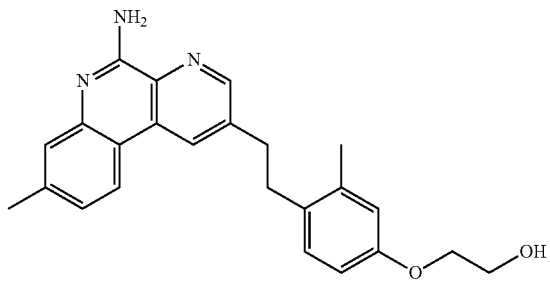 [SMILES: Cc1ccc2c(c1)nc(N)c1ncc(CCc3ccc(OCCO)cc3C)cc12]

2-(4-(2-(5-Amino-8-methylbenzo[f][1,7]naphthyridin-2-yl)ethyl)-3-methylphenoxy)ethanol was prepared following the procedures described for Example 145/Steps 1 to 2, but using 4-(2-(5-amino-8-methylbenzo[f][1,7]naphthyridin-2-yl)ethyl)-3-methylphenol (from Example 50). $^1$H NMR (Acetone-$d_6$): δ 8.76 (s, 1H), 8.69 (s, 1H), 8.28 (d, 1H), 7.40 (s, 1H), 7.15 (d, 1H), 7.09 (d, 1H), 6.75 (s, 1H), 6.68 (d, 1H), 6.57 (br, 2H), 4.00 (t, 2H), 3.79-3.88 (m, 2H), 3.17 (t, 2H), 3.04 (t, 2H), 2.46 (s, 2H), 2.29 (s, 2H). LRMS [M+H]=388.5.

Example 157

4-(2-(5-amino-8-methylbenzo[f][1,7]naphthyridin-2-yl)ethyl)phenyl ethyl carbonate

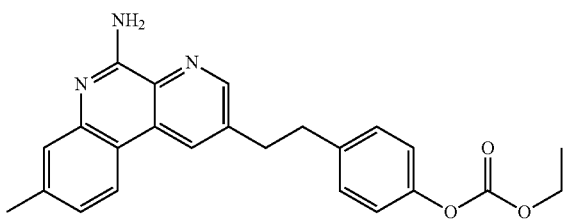 [SMILES: CCOC(=O)Oc1ccc(CCc2cnc3c(N)nc4cc(C)ccc4c3c2)cc1]

4-(2-(5-Amino-8-methylbenzo[f][1,7]naphthyridin-2-yl)ethyl)phenyl ethyl carbonate was prepared from 4-(2-(5-amino-8-methylbenzo[f][1,7]naphthyridin-2-yl)ethyl)phenol (from Example 170) following the procedure described for Example 138, but using ethyl carbonochloridate. LRMS [M+H]=402.2

Example 158 methyl 4-(4-(2-(5-amino-8-methylbenzo[f][1,7]naphthyridin-2-yl)ethyl)phenoxy)butanoate

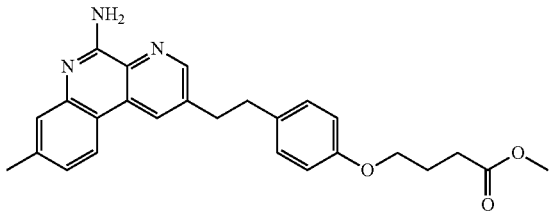

Methyl 4-(4-(2-(5-amino-8-methylbenzo[f][1,7]naphthyridin-2-yl)ethyl)phenoxy)butanoate was prepared from 4-(2-(5-amino-8-methylbenzo[f][1,7]naphthyridin-2-yl)ethyl)phenol (from Example 170) following the procedure described for the preparation of Example 139, but using methyl 4-bromobutanoate. $^1$H NMR (Acetone-$d_6$): δ 8.74 (s, 1H), 8.67 (s, 1H), 8.24 (d, 1H), 7.39 (s, 1H), 7.09-7.19 (m, 3H), 6.82 (d, 2H), 6.53 (br, 2H), 3.97 (t, 2H), 3.60 (s, 3H), 3.19 (t, 2H), 3.04 (t, 2H), 2.48 (t, 2H), 2.44 (s, 3H), 0.84-0.91 (m, 2H). LRMS [M+H]=430.2.

Example 159

4-(4-(2-(5-amino-8-methylbenzo[f][1,7]naphthyridin-2-yl)ethyl)phenoxy)butanoic acid

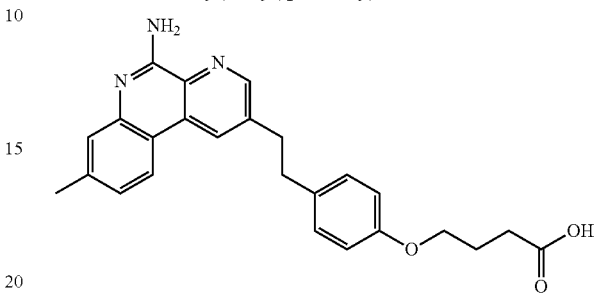

4-(4-(2-(5-Amino-8-methylbenzo[f][1,7]naphthyridin-2-yl)ethyl)phenoxy)butanoic acid was prepared from methyl 4-(4-(2-(5-amino-8-methylbenzo[f][1,7]naphthyridin-2-yl)ethyl)phenoxy)butanoate (from the previous step) following the procedure described for Example 144. $^1$H NMR (Acetone-$d_6$): δ 7.47 (s, 1H), 7.41 (s, 1H), 7.09 (d, 1H), 6.21 (s, 1H), 6.18 (d, 1H), 5.82 (d, 2H), 5.52 (d, 2H), 2.66 (t, 2H), 1.99 (t, 2H), 1.77 (t, 2H), 1.28 (s, 3H), 1.17 (t, 2H), 0.70-0.79 (m, 2H). LRMS [M+H]=416.2.

Example 160

4-(4-(2-(5-amino-8-methylbenzo[f][1,7]naphthyridin-2-yl)ethyl)-3-methylphenoxy)butanoic acid

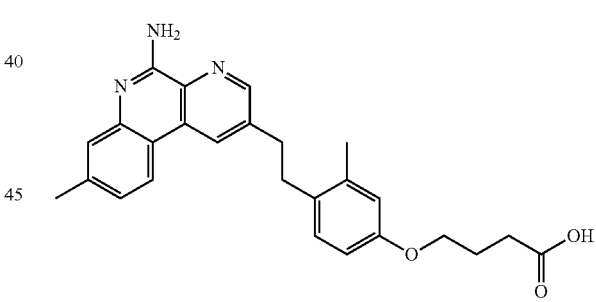

Step 1: methyl 4-(4-(2-(5-amino-8-methylbenzo[f][1,7]naphthyridin-2-yl)ethyl)-3-methylphenoxy)butanoate Methyl 4-(4-(2-(5-amino-8-methylbenzo[f][1,7]naphthyridin-2-yl)ethyl)-3-methylphenoxy)butanoate was prepared following the same procedure described for the preparation of Example 158, but using 4-(2-(5-amino-8-methylbenzo[f][1,7]naphthyridin-2-yl)ethyl)-3-methylphenol (from Example 50).

Step 2: 4-(4-(2-(5-Amino-8-methylbenzo[f][1,7]naphthyridin-2-yl)ethyl)-3-methylphenoxy)butanoic acid 4-(4-(2-(5-Amino-8-methylbenzo[f][1,7]naphthyridin-2-yl)ethyl)-3-methylphenoxy)butanoic acid was prepared from methyl 4-(4-(2-(5-amino-8-methylbenzo[f][1,7]naphthyridin-2-yl)ethyl)-3-methylphenoxy)butanoate (from the previous step) following the procedure described for Example 144. $^1$H NMR (Acetone-d$_6$): δ 8.38 (s, 1H), 8.24 (s, 1H), 7.90 (d, 1H), 6.90 (s, 1H), 6.68 (d, 1H), 6.54-6.63 (m, 2H), 6.27 (d, 1H), 6.20 (d, 1H), 3.40 (t, 2H), 2.62 (t, 2H), 2.47 (t, 2H), 1.99 (s, 3H), 1.80 (s, 2H), 1.45 (t, 2H), 1.27-1.39 (m, 2H). LRMS [M+H]=430.2.

Example 161

2-(4-(isopentyloxy)-2-methylphenethyl)-8-methyl-benzo[f][1,7]naphthyridin-5-amine

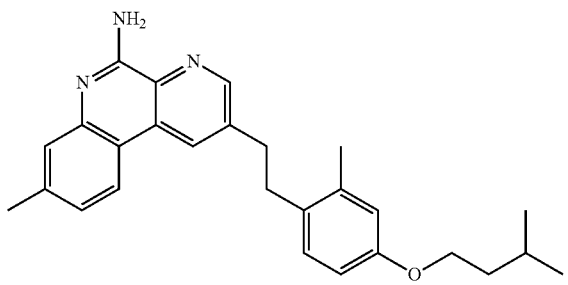 [SMILES: Cc1ccc2c(c1)nc(N)c1ncc(CCc3ccc(OCCC(C)C)cc3C)cc12]

2-(4-(Isopentyloxy)-2-methylphenethyl)-8-methylbenzo[f][1,7]naphthyridin-5-amine was prepared from 4-(2-(5-amino-8-methylbenzo[f][1,7]naphthyridin-2-yl)ethyl)-3-methylphenol (from Example 50) following the procedure described for Example 136, but using 1-bromo-3-methylbutane. $^1$H NMR (Acetone-d$_6$): δ 8.75 (s, 1H), 8.72 (s, 1H), 8.29 (d, 1H), 7.43 (s, 1H), 7.17 (D, 1H), 7.10 (d, 1H), 6.76 (d, 1H), 6.68 (d, 1H), 6.56 (br, 2H), 4.00 (t, 2H), 3.17 (t, 2H), 3.07 (t, 2H), 2.48 (s, 3H), 1.76-1.91 (m, 1H), 1.60-1.71 (m, 2H), 0.96 (s, 6H). LRMS [M+H]=414.2.

Example 162

4-(2-(5-amino-8-methylbenzo[f][1,7]naphthyridin-2-yl)ethyl)phenyl hexyl carbonate

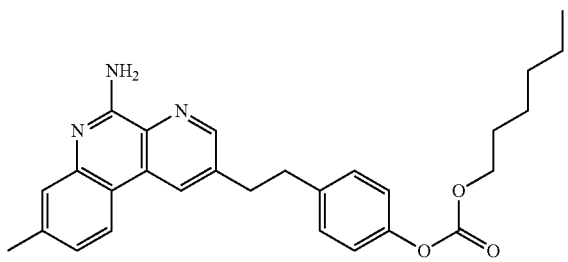 [SMILES: CCCCCCOC(=O)Oc1ccc(CCc2cnc3c(N)nc4cc(C)ccc4c3c2)cc1]

4-(2-(5-Amino-8-methylbenzo[f][1,7]naphthyridin-2-yl)ethyl)phenyl hexyl carbonate was prepared from 4-(2-(5-amino-8-methylbenzo[f][1,7]naphthyridin-2-yl)ethyl)phenol (from Example 170) following the procedures described for Example 138, but using hexyl carbonochloridate.

LRMS [M+H]=458.2.

Example 163

2-(2,4,6-trimethylphenethyl)benzo[f][1,7]naphthyridin-5-amine

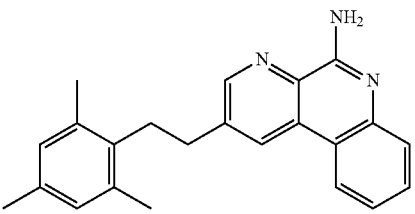 [SMILES: Cc1cc(C)c(CCc2cnc3c(N)nc4ccccc4c3c2)c(C)c1]

Step 1: 2-(mesitylethynyl)benzo[f][1,7]naphthyridin-5-amine 2-(Mesitylethynyl)benzo[f][1,7]naphthyridin-5-amine was prepared from 3-chloro-5-(mesitylethynyl)picolinonitrile (Example 77/Step 1) and tert-butyl 2-(4,4,5,5-tetramethyl-1,3,2-dioxaborolan-2-yl)phenylcarbamate (commercially available) following the procedures described for Example 45/Step 1.

Step 2: 2-(2,4,6-Trimethylphenethyl)benzo[f][1,7]naphthyridin-5-amine 2-(2,4,6-Trimethylphenethyl)benzo[f][1,7]naphthyridin-5-amine was prepared from 2-(mesitylethynyl)benzo[f][1,7]naphthyridin-5-amine (from the previous step) following the procedures described for Example 45/Step 2 to 3. $^1$H NMR (Acetone-d$_6$): δ 8.80 (s, 2H), 8.38 (d, 1H), 7.60 (d, 2H), 7.54 (d, 2H), 7.31 (t, 1H), 6.84 (s, 2H), 6.61 (br, 2H), 3.08 (s, 2H), 2.30 (s, 6H), 2.23 (s, 3H). LRMS [M+H]=342.2.

Example 164

(5-amino-2-(2,4-dimethylphenethyl)benzo[f][1,7]naphthyridin-8-yl)methanol

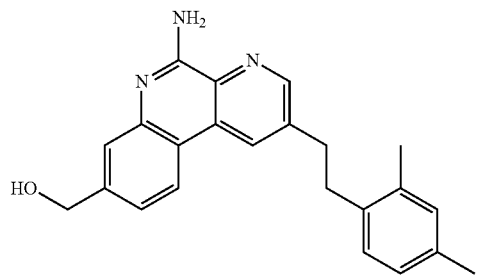 [SMILES: Cc1ccc(CCc2cnc3c(N)nc4cc(CO)ccc4c3c2)c(C)c1]

Step 1: methyl 5-amino-2-)(2,4-dimethylphenyl)ethynyl)benzo[f][1,7]naphthyridine-8-carboxylate Methyl 5-amino-2-((2,4-dimethylphenyl)ethynyl)benzo[f][1,7]naphthyridine-8-carboxylate was prepared from 3-chloro-5-((2,4-d methylphenyl)ethynyl)picolinonitrile (from Example 47/Step 3) and 2-(tert-butoxycarbonylamino)-4-(methoxycarbonyl)phenylboronic acid (from Example 85/Step1) following the procedures described in Example 95/step 1.

Step 2: methyl 5-amino-2-(2,4-dimethylphenethyl)benzo[f][1,7]naphthyridine-8-carbaxylate Methyl 5-amino-2-(2,4-dimethylphenethyl)benzo[f][1,7]naphthyridine-8-carboxylate was prepared from methyl 5-amino-2-((2,4-dimethylphenyl)ethynyl)benzo[f][1,7]naphthyridine-8-carboxylate (from the previous step) following the procedures described in Example 44/Step 5.

Step 3: (5-amino-2-(2,4-dimethylphenethyl)benzo[f][1,7]naphthyridin-8-yl)methanol (5-Amino-2-(2,4-dimethylphenethyl)benzo[f][1,7]naphthyridin-8-yl)methanol was prepared from methyl 5-amino-2-(2,4-dimethylphenethyl)benzo[f][1,7]naphthyridine-8-carboxylate (from the previous step) following the procedures described in Example 95/Step 2. $^1$H NMR (Acetone-$d_6$): δ 8.79 (s, 1H), 8.73 (s, 1H), 8.35 (d, 1H), 7.61 (s, 1H), 7.34 (d, 1H), 7.08 (d, 1H), 6.97 (s, 1H), 6.91 (d, 1H), 6.51 (br. 2H), 4.77 (s, 2H), 3.16-3.20 (m, 2H), 3.04-3.10 (m, 2H), 2.28 (s, 3H), 2.25 (s, 3H). LRMS [M+H]=358.2.

Example 165 diethyl 3-(2-(4-(2-(5-amino-8-methylbenzo[f][1,7]naphthyridin-2-yl)ethyl)-3-methylphenoxy)ethoxy)propylphosphonate

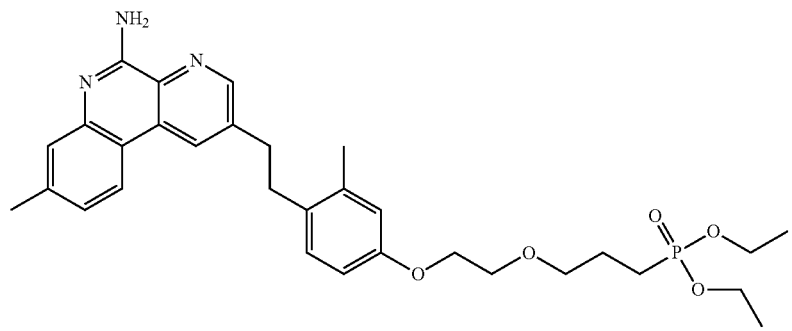 [SMILES: CCOP(=O)(CCCOCCOc1ccc(CCc2cnc3c(N)nc4cc(C)ccc4c3c2)c(C)c1)OCC]

Diethyl 3-(2-(4-(2-(5-amino-8-methylbenzo[f][1,7]naphthyridin-2-yl)ethyl)-3-methylphenoxy)ethoxy)propylphosphonate was prepared following the procedure described for Example 139, but using 4-(2-(5-amino-8-methylbenzo[f][1,7]naphthyridin-2-yl)ethyl)-3-methylphenol (from Example 156) and diethyl 3-(2-bromoethoxy)propylphosphonate. LRMS [M+H]=566.3.

Example 166 diethyl 3-(2-(2-(4-(2-(5-amino-8-methylbenzo[f][1,7]naphthyridin-2-yl)ethyl)-3-methylphenoxy)ethoxy)ethoxy)propylphosphonate

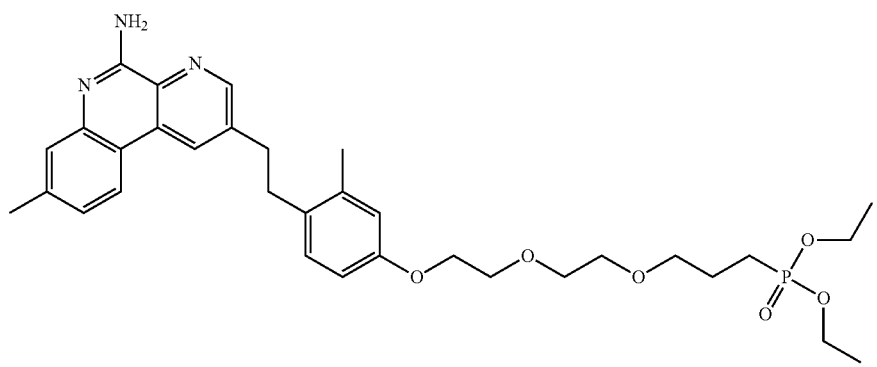 [SMILES: CCOP(=O)(CCCOCCOCCOc1ccc(CCc2cnc3c(N)nc4cc(C)ccc4c3c2)c(C)c1)OCC]

Diethyl 3-(2-(2-(4-(2-(5-amino-8-methylbenzo[f][1,7]naphthyridin-2-yl)ethyl)-3-methylphenoxy)ethoxy)ethoxy)propylphosphonate was prepared from following the procedure described for Example 139, but using 4-(2-(5-amino-8-methylbenzo[f][1,7]naphthyridin-2-yl)ethyl)-3-methylphenol (from Example148) and diethyl 3-(2-(2-bromoethoxy)ethoxy)propylphosphonate. $^1$H NMR (Acetone-d$_6$): δ 8.75 (s, 1H), 8.70 (s, 1H), 8.26 (d, 1H), 7.42 (s, 1H), 7.16 (d, 1H), 7.09 (d, 1H), 6.77 (s, 1H), 6.71 (d, 1H), 6.58 (br, 2H), 3.95-4.11 (m, 6H), 3.76-3.80 (m, 2H), 3.63-3.67 (m, 2H), 3.55-3.58 (m, 2H), 3.57-3.51 (m, 2H), 3.14-3.18 (m, 2H), 3.04-3.05 (m, 2H), 2.46 (s, 3H), 2.29 (s, 3H), 1.71-1.87 (m, 4H), 1.22-1.29 (m, 8H). LRMS [M+H]=610.3.

Example 167

4-(2-(5-amino-8-methylbenzo[f][1,7]naphthyridin-2-yl)ethyl)-3-methylphenyl dimethylsulfamate

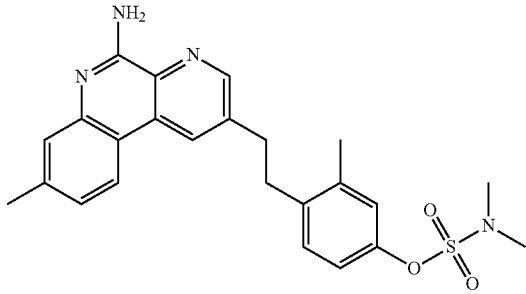

4-(2-(5-Amino-8-methylbenzo[f][1,7]naphthyridin-2-yl)ethyl)-3-methylphenyl dimethylsulfamate was prepared from 4-(2-(5-amino-8-methylbenzo[f][1,7]naphthyridin-2-yl)ethyl)-3-methylphenol (from Example 50) following the procedure described for Example 138, but using dimethylsulfamoyl chloride. $^1$H NMR (Acetone-d$_6$): δ 8.79 (s, 1H), 8.72 (s, 1H), 8.28 (d, 1H), 7.42 (s, 1H), 7.27 (d, 1H), 7.17 (s, 1H), 7.14 (t, 1H), 7.05-7.10 (d, 1H), 3.19-3.25 (m, 2H), 3.11-3.17 (m, 2H), 2.92 (s, 6H), 2.46 (s, 3H), 2.37 (s, 3H). LRMS [M+H]= 451.2.

Example 168

(5-amino-2-(4-(dimethylamino)phenethyl)benzo[f][1,7]naphthyridin-8-yl)methanol

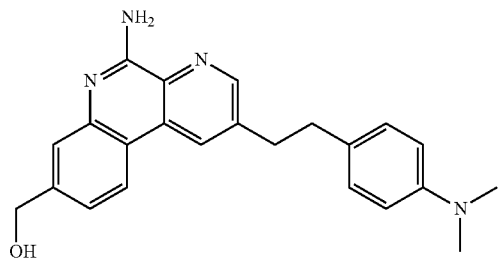 [SMILES: CN(C)c1ccc(CCc2cnc3c(N)nc4cc(CO)ccc4c3c2)cc1]

(5-Amino-2-(4-(dimethylamino)phenethyl)benzo[f][1,7]naphthyridin-8-yl)methanol was prepared from tert-butyl 5-(((tert-butyldimethylsilyloxy)methyl)-2-(4,4,5,5-tetramethyl-1,3,2-dioxaborolan-2-yl)phenylcarbamate (from Example 99/step 1) and 4-ethynyl-N,N-dimethylaniline (commercially available) following the procedures described in Example 45/Step 1 to 4 followed by deprotection of TBS group as in Example 99/Step 3. $^1$H NMR (Acetone-d$_6$): δ 8.78 (s, 1H), 8.73 (s, 1H), 8.35 (d, 1H), 7.61 (s, 1H), 7.31-7.35 (d, 1H), 7.08 (d, 1H), 6.68 (d, 2H), 6.50 (br, 2H), 4.78 (s, 2H), 4.34 (s, 1H), 3.16-3.20 (m, 2H), 3.03-3.10 (m, 2H), 2.83 (s, 3H), 2.80 (s, 3H), LRMS [M+H]=373.2.

Example 169

2-(4-(dimethylamino)phenethyl)-8-methylbenzo[f][1,7]naphthyridin-5-amine

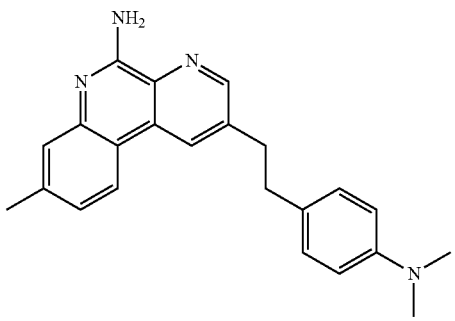

2-(4-(Dimethylamino)phenethyl)-8-methylbenzo[f][1,7]naphthyridin-5-amine was prepared following the procedures described for Example 45/Steps 1 to 3, but using 4-ethynyl-N,N-dimethylaniline in step 1. $^1$H NMR (Acetone-d$_6$) Free base: δ 8.60 (s, 1H), 8.55 (s, 1H), 8.15 (d, 1H), 7.28 (s, 1H), 7.03 (d, 1H), 6.96 (d, 2H), 6.56 (d, 2H), 6.55 (br s, 2H), 3.05 (t, 2H), 2.88 (t, 2H), 2.75 (s, 6H), 2.33 (s, 3H). LRMS [M+H]=357.2

Example 170

4-(2-(5-amino-8-methylbenzo[f][1,7]naphthyridin-2-yl)ethyl)phenol

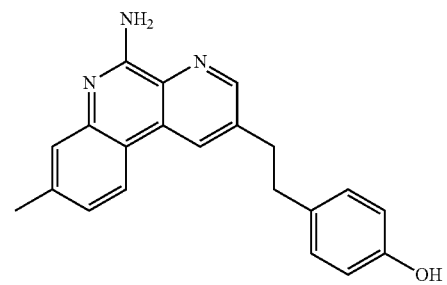 [SMILES: Cc1ccc2c(c1)nc(N)c1ncc(CCc3ccc(O)cc3)cc12]

Step 1: 2-(4-methoxyphenethyl)-8-methylbenzo[f][1,7]naphthyridin-5-amine 2-(4-methoxyphenethyl)-8-methylbenzo[f][1,7]naphthyridin-5-amine was prepared following the procedures described for Example 79/Steps 1 to 3, but using 1-ethynyl-4-methoxybenzene in Step 1.

Step 2: 4-(2-(5-Amino-8-methylbenzo[f][1,7]naph-thyridin-2-yl)ethyl)phenol 4-(2-(5-Amino-8-methylbenzo[f][1,7]naphthyridin-2-yl)ethyl)phenol was prepared from 2-(4-methoxyphenethyl)-8-methylbenzo[f][1,7]naphthyridin-5-amine (from the previous step) following the procedure described for Example 50. $^1$H NMR (Methanol-d$_4$): δ 8.59

Example 171

1-(4-(2-(5-amino-8-methylbenzo[f][1,7]naphthyridin-2-yl)ethyl)phenyl)ethanone

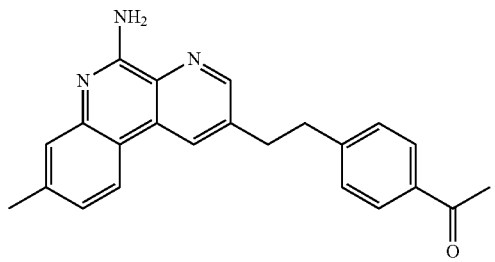 [SMILES: CC(=O)c1ccc(CCc2cnc3c(N)nc4cc(C)ccc4c3c2)cc1]

Step 1: 5-((4-acetylphenyl)ethynyl)-3-chloropicolinonitrile

To a solution of 1-(4-ethynylphenyl)ethanone (commercially available) (1 eq) 3,5-dichloropicolinonitrile (1 eq), dichlorobis(triphenylphosphine)-palladium (II) (20 mol %), copper iodide (10 mol %) and DMF: Triethylamine (10:1) (0.13 M) was stirred at ambient temperature overnight. The reaction mixture was then diluted with ethyl acetate and sodium bi-carbonate solution. The two phases were separated, and the aqueous phase was extracted twice with ethyl acetate. The combined organic layers were washed with brine, dried over sodium sulfate, and concentrated en vaccuo. The crude material was purified by flash chromatography on a COMBIFLASH® system (ISCO) using 0-100% ethyl acetate in hexane and 5-((4-acetylphenyl)ethynyl)-3-chloropicolinonitrile was isolated as a yellow solid

Step 2: 5-(4-acetylphenethyl)-3-chloropicolinonitrile

To a solution of 5-((4-acetylphenyl)ethynyl)-3-chloropicolinonitrile (from the previous step) (1 eq) in ethanol (0.1 M) was added Platinum Oxide (30 mol %). Hydrogen gas was introduced via a balloon, and the reaction was stirred for 0.5 hour. The mixture was filtered through a pad of celite, washing with dichloromethane. The filtrate was concentrated en vaccuo and purified by flash chromatography on a COMBIFLASH® system (ISCO) using 0-100% ethyl acetate in hexane to give 5-(4-acetylphenethyl)-3-chloropicolinonitrile as an off-white solid.

Step 3: 1-(4-(2-(5-amino-8-methylbenzo[f][1,7]naphthyridin-2-yl)ethyl)phenyl)ethanone To a solution of 5-(4-acetylphenethyl)-3-chloropicolinonitrile (from the previous step) (1 eq) and tert-butyl 5-methyl-2-(4,4,5,5-tetramethyl-1,3,2-dioxaborolan-2-yl)phenylcarbamate (1.0 eq.), tetrakis(triphenyl-phosphine)palladium (10 mol %), and 2N aqueous sodium carbonate solution (2.0 eq.) in toluene/ethanol (1:1, 0.09 M) was heated under microwave condition using a BIOTAGE INITIATOR 2.0 at 150° C. for 20 minutes. After cooling to ambient temperature, the reaction mixture was diluted with ethanol/water. The insoluble solids were filtered off, and the filtrate was concentrated en vaccuo to obtain a crude residue. The crude material was purified by flash chromatography on a COMBIFLASH® system (ISCO) using 0-80% ethyl acetate in hexane to give 1-(4-(2-(5-amino-8-methylbenzo[f][1,7]naphthyridin-2-yl)ethyl)phenyl)ethanone as a yellow solid. $^1$H NMR (Methanol-d$_4$) TFA Salt: δ 8.69 (d, 2H), 8.30 (d, 1H), 7.80 (d, 2H), 7.38 (s, 1H), 7.36 (d, 1H), 7.28 (d, 2H), 3.25 (t, 2H), 3.13 (t, 2H), 2.47 (s, 3H), 2.45 (s, 3H).

LRMS [M+H]=356.2

Example 172

2-(4-((dimethylamino)methyl)phenethyl)-8-methylbenzo[f][1,7]naphthyridin-5-amine

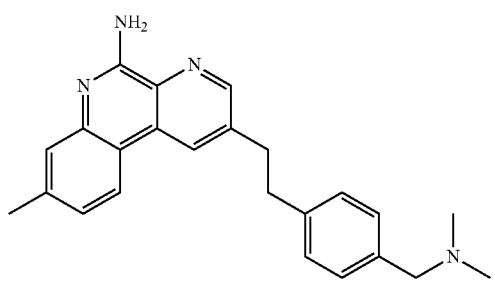

Step 1: 4-(2-(5-amino-8-methylbenzo[f][1,7]naphthyridin-2-yl)ethyl)benzaldehyde 4-(2-(5-Amino-8-methylbenzo[f][1,7]naphthyridin-2-yl)ethyl)benzaldehyde was prepared from 4-ethynylbenzaldehyde (commercially available) following the procedures described for Example 171/Steps 1 to 3.

Step 2: 2-(4-((dimethylamino)methyl)phenethyl)-8-methylbenzo[f][1,7]naphthyridin-5-amine A solution of 4-(2-(5-amino-8-methylbenzo[f][1,7]naphthyridin-2-yl)ethyl)benzaldehyde (from the previous step) (1 eq), sodium acetate (3.5 eq) and N,N'-dimethyl amine hydrochloride (3.5 eq) dissolved in 1-2, dichloroethane(0.04 M) was heated at 80° C. for 2 hours in a sealed vial. After cooling to ambient temperature, the reaction mixture was further cooled down to 0° C. and sodium tri-acetoxy borohydride (1.25 eq) was added. The reaction mixture was stirred at room temperature for one hour. The mixture was diluted with ethyl acetate and water. The two phases were separated, and the aqueous layer was extracted twice with ethyl acetate. The combined organic layers were washed with brine, dried over anhydrous MgSO$_4$, and concentrated en vaccuo. The crude material was purified by preparative HPLC using 10-90% acetonitrile/water as the gradient and 2-(4-((dimethylamino)methyl)phenethyl)-8-methylbenzo[f][1,7]naphthyridin-5-amine was isolated as a off-white powder as a TFA salt. $^1$H NMR (Methanol-d$_4$) TFA Salt: δ 8.83 (s, 1H), 8.81 (s, 1H), 8.41 (d, 1H), 7.52 (s, 1H), 7.45 (d, 1H), 7.43 (s, 1H), 7.40 (m, 3H), 4.29 (s, 2H), 3.30-3.24 (m, 4H), 2.79 (s, 6H), 2.60 (s, 3H). LRMS [M+H]=371.2

Example 173

2-(4-(1-(dimethylamino)ethyl)phenethyl)-8-methyl-benzo[f][1,7]naphthyridin-5-amine

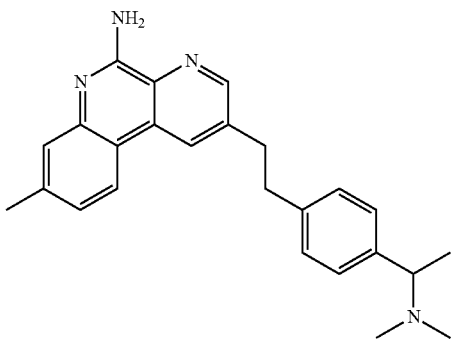

2-(4-(1-(Dimethylamino)ethyl)phenethyl)-8-methyl-benzo[f][1,7]naphthyridin-5-amine was prepared from 1-(4-(2-(5-amino-8-methylbenzo[f][1,7]naphthyridin-2-yl)ethyl)phenyl)ethanone (from Example 171) following the procedures described for Example 172/Step 2. $^1$H NMR (Methanol-$d_4$) TFA Salt: δ 8.84 (s, 1H), 8.79 (s, 1H), 8.40 (d, 1H), 7.52 (s, 1H), 7.44-7.46 (m, 2H), 7.38-7.42 (m, 3H), 4.45 (m, 1H), 3.31 (t, 2H), 3.19 (t, 2H), 2.83 (s, 3H), 2.66 (s, 3H), 2.56 (s, 3H), 1.70 (d, 3H). LRMS [M+H]=385.2

Example 174

1-(4-(2-(5-amino-8-methylbenzo[f][1,7]naphthyridin-2-yl)ethyl)phenyl)ethanone oxime

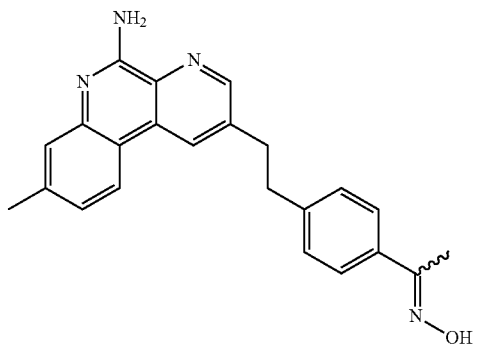

A solution of 1-(4-(2-(5-amino-8-methylbenzo[f][1,7]naphthyridin-2-yl)ethyl)phenyl)ethanone (from Example 171) (1eq), hydroxylamine hydrochloride (2eq) and 1 drop of HOAc, dissolved in absolute ethanol (0.028M) was stirred at room temperature for 1.5 hours. The mixture was diluted with ethyl acetate and water. The two phases were separated, and the aqueous layer was extracted twice with ethyl acetate. The combined organic layers were washed with brine, dried over anhydrous MgSO$_4$, and concentrated en vaccuo. The crude material was purified by flash chromatography on a COMBI-FLASH® system (ISCO) using 10-80% ethyl acetate in hexane to give 1-(4-(2-(5-amino-8-methylbenzo[f][1,7]naphthyridin-2-yl)ethyl)phenyl)ethanone oxime as a white solid. $^1$H NMR (Methanol-$d_4$): δ 8.56 (s, 1H), 8.52 (s, 1H), 8.12 (d, 1H), 7.45 (d, 2H), 7.31 (s, 1H), 7.12 (m, 3H), 4.51 (s, OH), 3.15 (t, 2H), 3.01 (t, 2H), 2.39 (s, 3H), 2.09 (s, 3H). LRMS [M+H]=371.2

Example 175

8-methyl-2-(4-((methylamino)methyl)phenethyl)benzo[f][1,7]naphthyridin-5-amine

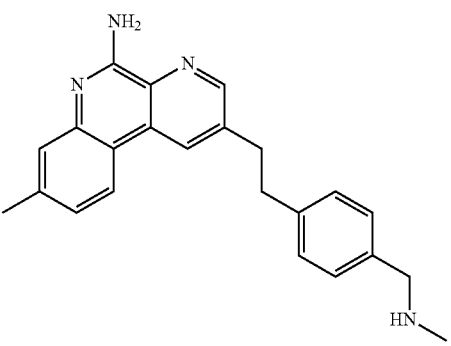

8-Methyl-2-(4-((methylamino)methyl)phenethyl)benzo[f][1,7]naphthyridin-5-amine was prepared from 4-(2-(5-Amino-8-methylbenzo[f][1,7]naphthyridin-2-yl)ethyl)benzaldehyde (from Example 172/Step 1) and methylamine following the procedures described for Example 172, step 2. $^1$H NMR (Acetone-$d_6$) TFA Salt: δ 8.95 (s, 1H), 8.88 (s. 1H), 8.43 (d, 1H), 7.58 (s, 1H), 7.54 (d, 2H), 7.42 (d, 1H), 7.37 (d, 2H), 4.30 (s, 2H), 3.32-3.37 (m, 4H), 2.75 (s, 3H), 2.55 (s, 3H). LRMS [M+H]=357.2

Example 176

(4-(2-(5-amino-8-methylbenzo[f][1,7]naphthyridin-2-yl)ethyl)benzylamino)ethanol

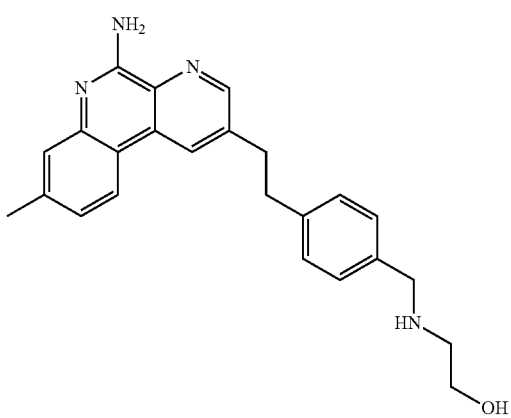 [SMILES: Cc1ccc2c(c1)nc(N)c1ncc(CCc3ccc(CNCCO)cc3)cc12]

A solution of 4-(2-(5-amino-8-methylbenzo[f][1,7]naphthyridin-2-yl)ethyl)benzaldehyde (from Example 172/Step 1) (1eq), ethanol amine (8eq) and 1 drop of HOAc, dissolved in absolute ethanol (0.018M) was stirred at 80° C. for 2 hours. The mixture was cooled down to 0° C. and NaBH$_4$ (3.5 eq)

was added and the reaction mixture was stirred for another one hour at room temperature. The mixture was diluted with ethyl acetate and water. The two phases were separated, and the aqueous layer was extracted twice with ethyl acetate. The combined organic layers were washed with brine, dried over anhydrous MgSO$_4$, and concentrated en vaccuo. The crude material was purified by Preparative HPLC on a 19×50 mm ATLANTIS® 10 micron C18 (Waters Corp.) system using 10-90% Acetonitrile (0.035% TFA) in Water (0.05% TFA) to give a light yellow solid as a TFA salt. $^1$H NMR (Acetone-d$_6$) TFA Salt: δ 8.82 (s, 1H), 8.75 (s, 1H), 8.30 (d, 1H), 7.44 (m, 3H), 7.28 (d, 1H), 7.21 (d, 2H), 4.22 (s, 2H), 3.72 (t, 2H), 3.22 (t, 2H), 3.09 (m, 2H), 3.07 (t, 2H), 3.01 (bs, OH), 2.41 (s, 3H), LRMS [M+H]=387.2

Example 177

8-methyl-2-(4-(pyrrolidin-1-ylmethyl)phenethyl) benzo[f][1,7]naphthyridin-5-amine

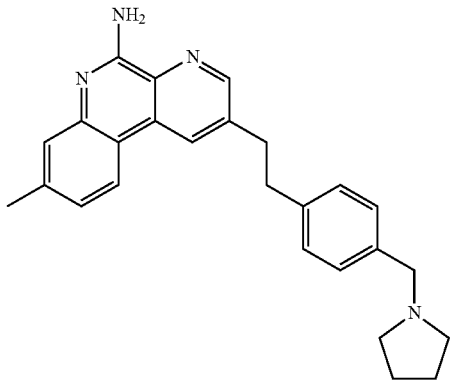 [SMILES: Cc1ccc2c(c1)nc(N)c1ncc(CCc3ccc(CN4CCCC4)cc3)cc12]

8-Methyl-2-(4-(pyrrolidin-1-ylmethyl)phenethyl)benzo [f][1,7]naphthyridin-5-amine was prepared from 4-(2-(5-Amino-8-methylbenzo[f][1,7]naphthyridin-2-yl)ethyl)benzaldehyde (from Example 172/Step 1) and pyrrolidine following the procedures described for Example 172, step 2. $^1$H NMR (Acetone-d$_6$) TFA Salt: δ 8.88 (s, 1H), 8.82 (s, 1H), 8.82 (s, 1H), 8.43 (d, 1H), 8.38 (d, 1H), 7.58 (s, 1H), 7.51 (m, 1H), 7.33 (d, 2H), 4.16 (s, 2H), 3.32-3.38 (m, 4H), 2.55 (s, 3H), 2.20-2.32 (m, 4H), 1.90-1.99 (m, 4H). LRMS [M+H]= 397.2

Example 178

2-(3,4-dimethoxyphenethyl)-8-methylbenzo[f][1,7] naphthyridin-5-amine

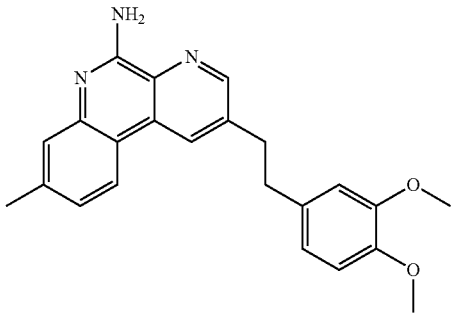

2-(3,4-Dimethoxyphenethyl)-8-methylbenzo[f][1,7] naphthyridin-5-amine was prepared from 4-ethynyl-1,2-dimethoxybenzene (commercially available) following the procedures described for Example 45/Steps 1 to 3. $^1$H NMR (Acetone-d$_6$): δ 8.64 (s, 1H), 8.56 (s, 1H), 8.14 (d, 1H), 7.29 (s, 1H), 7.03 (d, 1H), 6.77 (s, 1H), 6.71 (s, 1H), 6.62 (d, 1H), 6.45 (bs, 2H), 3.62 (s, 6H), 3.12 (t, 2H), 2.94 (t, 2H), 2.33 (s, 3H). LRMS [M+H]=374.2

Example 179

2-(1-(4-(2-(5-amino-8-methylbenzo[f][1,7]naphthyridin-2-yl)ethyl)phenyl)ethylamino)ethanol

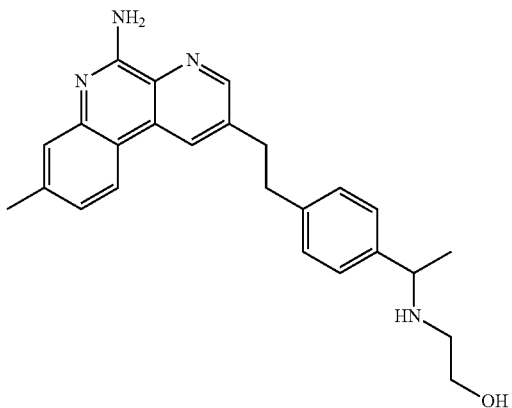 [SMILES: Cc1ccc2c(c1)nc(N)c1ncc(CCc3ccc(C(C)NCCO)cc3)cc12]

2-(1-(4-(2-(5-Amino-8-methylbenzo[f][1,7]naphthyridin-2-yl)ethyl)phenyl)ethylamino)ethanol (from Example 171) was prepared from 1-(4-(2-(5-amino-8-methylbenzo[f][1,7] naphthyridin-2-yl)ethyl)phenyl)ethanone and ethanol amine (commercially available) following the procedures described for Example 176. $^1$H NMR (Acetone-d$_6$) of TFA Salt: δ 8.78 (d, 1H), 8.29 (d, 1H), 7.83 (s, 1H), 7.45 (m, 3H), 7.28 (m, 3H), 4.22 (m, 1H), 3.52 (m, 2H), 3.23 (t, 2H), 3.09 (t, 2H), 2.85 (m, 1H), 2.65 (m, 1H), 2.41 (s, 3H), 1.61 (d, 3H). LRMS [M+H]= 401.2

Example 180

1-(4-(2-(5-amino-8-methylbenzo[f][1,7]naphthyridin-2-yl)ethyl)phenyl)ethanol

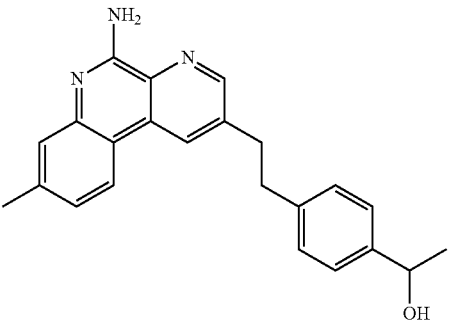 [SMILES: Cc1ccc2c(c1)nc(N)c1ncc(CCc3ccc(C(C)O)cc3)cc12]

1-(4-(2-(5-Amino-8-methylbenzo[f][1,7]naphthyridin-2-yl)ethyl)phenyl)ethanol (from Example 171) was isolated as a side product during the reductive amination as shown in Example 173. $^1$H NMR (Acetone-d$_6$) of TFA Salt: δ 8.90 (s, 1H), 8.88 (s, 1H), 8.42 (d, 1H), 7.57 (s, 1H), 7.43 (d, 1H), 7.33 (d, 2H), 7.26 (d, 2H), 4.82 (q, 1H), 3.32 (t, 2H), 3.17 (t, 2H), 3.01 2.55 (s, 3H), 1.41 (s, 3H). LRMS [M+H]=358.2

Example 181

8-methyl-2-(4-(oxazol-5-yl)phenethyl)benzo[f][1,7]naphthyridin-5-amine

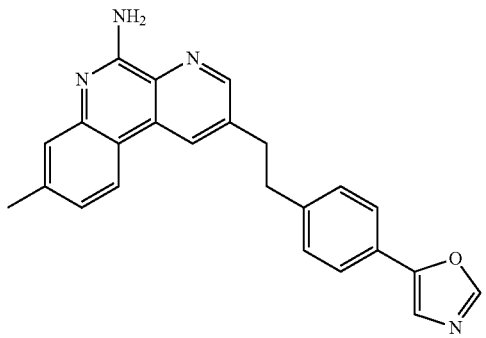 [SMILES: Cc1ccc2c(c1)nc(N)c1ncc(CCc3ccc(-c4cnco4)cc3)cc12]

8-Methyl-2-(4-(oxazol-5-yl)phenethyl)benzo[f][1,7]naphthyridin-5-amine was prepared from 5-(4-ethynylphenyl)oxazole (commercially available) following the procedures described for Example 45/Steps 1 to 3. $^1$H NMR (Acetone-$d_6$) of TFA Salt: 8.69 (s, 1H), 8.59 (s, 1H), 8.16 (d, 1H), 8.04 (s, 1H), 7.55 (m, 2H), 7.38 (s, 1H), 7.28 (m, 2H), 7.01 (m, 2H), 3.16 (t, 2H), 3.07 (t, 2H), 2.33 (s, 3H). LRMS [M+H]=381.2

Example 182

3-(1-(4-(2-(5-amino-8-methylbenzo[f][1,7]naphthyridin-2-yl)ethyl)phenyl)ethylamino)propanenitrile

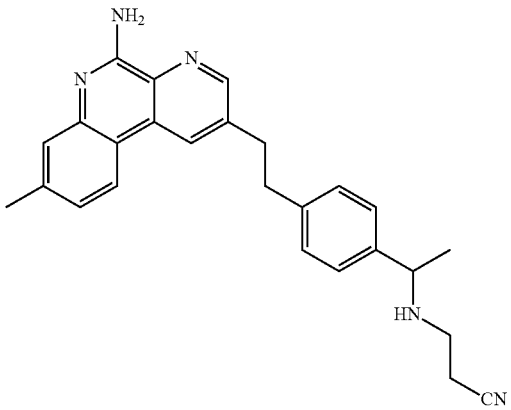 [SMILES: Cc1ccc2c(c1)nc(N)c1ncc(CCc3ccc(C(C)NCCC#N)cc3)cc12]

A solution of 1-(4-(2-(5-amino-8-methylbenzo[f][1,7]naphthyridin-2-yl)ethyl)phenyl)ethanone (from Example 171) (1 eq), 3-aminopropane nitrile (commercially available) (2.5 eq) dissolved in absolute ethanol (0.014M) was stirred at 80° C. for 2 hours. The mixture was cooled to 0° C. and NaCNBH$_3$ (2 eq) was added and the reaction mixture was stirred for another hour at room temperature. The mixture was diluted with ethyl acetate and ammonium chloride. The two phases were separated, and the aqueous layer was extracted twice with ethyl acetate. The combined organic layers were washed with brine, dried over anhydrous MgSO$_4$, and concentrated en vaccuo. The crude material was purified by Preparative HPLC on a 19×50 mm ATLANTIS® 10 micron C18 (Waters Corp.) system using 10-90% Acetonitrile (0.035% TFA) in Water (0.05% TFA) to give 3-(1-(4-(2-(5-amino-8-methylbenzo[f][1,7]naphthyridin-2-yl)ethyl)phenyl)ethylamino)propanenitrile as a light yellow solid as a TFA salt. $^1$H NMR (Acetone-$d_6$): δ 8.60 (s, 1H), 8.59 (s, 1H), 8.11 (d, 1H), 7.29 (s, 1H), 7.16 (d, 2H), 7.09 (d, 2H), 7.03 (d, 1H), 6.43 (bs, 2H), 3.65 (m, 1H), 3.12 (t, 2H), 2.99 (t, 2H), 2.56 (m, 2H), 2.35 (m, 2H), 2.32 (s, 3H), 1.16 (d, 3H). LRMS [M+H]=410.2

Example 183

(2R)-2-(1-(4-(2-(5-amino-8-methylbenzo[f][1,7]naphthyridin-2-yl)ethyl)phenyl)ethylamino)propan-1-ol

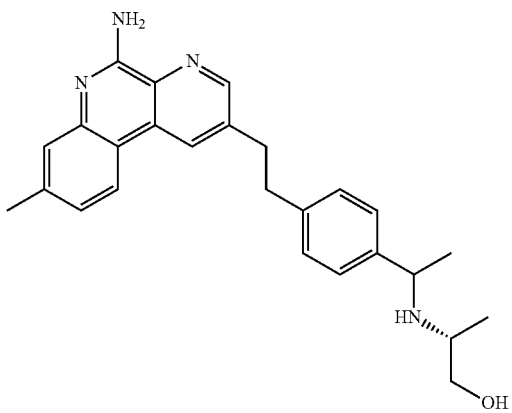 [SMILES: Cc1ccc2c(c1)nc(N)c1ncc(CCc3ccc(C(C)N[C@H](C)CO)cc3)cc12]

(2R)-2-(1-(4-(2-(5-amino-8-methylbenzo[f][1,7]naphthyridin-2-yl)ethyl)phenyl)ethylamino)propan-1-ol was prepared from 1-(4-(2-(5-amino-8-methylbenzo[f][1,7]naphthyridin-2-yl)ethyl)phenyl)ethanone (from Example 171) and (R)-2-aminopropan-1-ol (commercially available) following the procedures described for Example 182. $^1$H NMR (Acetone-$d_6$): δ: 8.94 (m, 2H), 8.45 (m, 1H), 7.64 (d, 2H), 7.59 (s, 1H), 7.55 (br s, 2H), 7.41 (m, 3H), 4.65 (m, 1H), 3.81 (m, 1H), 3.35 (t, 2H), 3.25 (t, 2H), 2.56 (s, 3H), 1.73 (m, 3H), 1.29 (d, 3H), 1.23 (d, 3H). LRMS [M+H]=415.2

Example 184

8-methyl-2-(4-(1-(piperazin-1-yl)ethyl)phenethyl)benzo[f][1,7]naphthyridin-5-amine

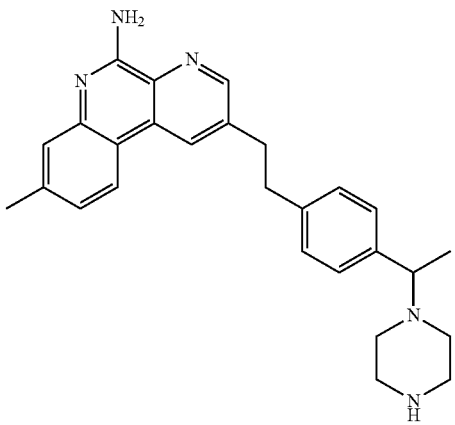 [SMILES: Cc1ccc2c(c1)nc(N)c1ncc(CCc3ccc(C(C)N4CCNCC4)cc3)cc12]

8-Methyl-2-(4-(1-(piperazin-1-yl)ethyl)phenethyl)benzo[f][1,7]naphthyridin-5-amine was prepared from 1-(4-(2-(5-amino-8-methylbenzo[f][1,7]naphthyridin-2-yl)ethyl)phenyl)ethanone (from Example 171) and piperazine (commercially available) following the procedures described for Example 182. $^1$H NMR (Methanol-$d_4$) TFA Salt: δ 8.83 (s, 1H), 8.75 (s, 1H), 8.39 (d, 1H), 7.51 (s, 1H), 7.46 (d, 1H), 7.26

(m, 4H), 3.62 (m, 1H), 3.25 (t, 2H), 3.12 (t, 2H), 2.80 (m, 4H), 2.69 (m, 4H), 2.56 (s, 3H), 1.42 (d, 3H). LRMS [M+H]=426.2

Example 185

((2S)-1-(1-(4-(2-(5-amino-8-methylbenzo[f][1,7]naphthyridin-2-yl)ethyl)phenyl)ethyl)pyrrolidin-2-yl)methanol

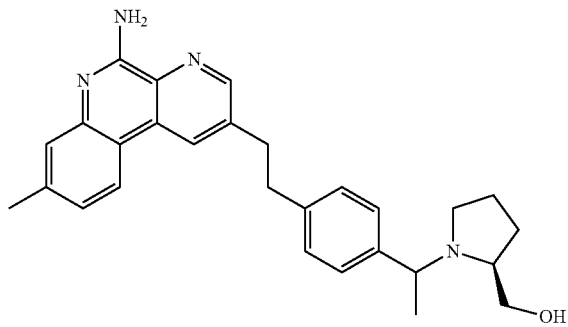 [SMILES: Cc1ccc2c(c1)nc(N)c1ncc(CCc3ccc(C(C)N4CCC[C@H]4CO)cc3)cc12]

((2S)-1-(1-(4-(2-(5-Amino-8-methylbenzo[f][1,7]naphthyridin-2-yl)ethyl)phenyl)ethyl)pyrrolidin-2-yl)methanol was prepared from 1-(4-(2-(5-amino-8-methylbenzo[f][1,7]naphthyridin-2-yl)ethyl)phenyl)ethanone (from Example 171) and (S)-pyrrolidin-2-ylmethanol (commercially available) following the procedures described for Example 182, $^1$H NMR (Acetone-$d_6$) TFA Salt: δ 8.83 (s, 1H), 8.80 (s, 1H), 8.43 (d, 1H), 7.36-7.53 (m, 6H), 4.68 (m, 1H), 3.69 (m, 2H), 3.19-3.21 (m, 4H), 2.55 (m, 4H), 1.75-1.78 (m, 6H), 1.74 (d, 3H).

LRMS [M+H]=441.2

Example 186

$N^1$-(1-(4-(2-(5-amino-8-methylbenzo[f][1,7]naphthyridin-2-yl)ethyl)phenyl)ethyl)-$N^2$,$N^2$-dimethylethane-1,2-diamine

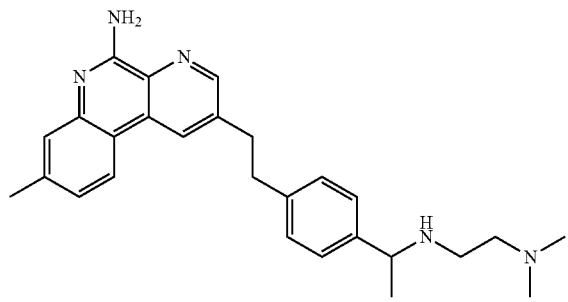

$N^1$-(1-(4-(2-(5-amino-8-methylbenzo[f][1,7]naphthyridin-2-yl)ethyl)phenyl)ethyl)-$N^2$,$N^2$-dimethylethane-1,2-diamine was prepared from 1-(4-(2-(5-amino-8-methylbenzo[f][1,7]naphthyridin-2-yl)ethyl)phenyl)ethanone (from Example 171) and $N^1$,$N^1$-dimethylethane-1,2-diamine (commercially available) following the procedures described for Example 182. $^1$H NMR (Acetone-$d_6$) TFA Salt: δ 8.85 (m, 2H), 8.43 (d, 1H), 7.52 (s, 1H), 7.48 (m, 2H), 7.40 (m, 2H), 6.69 (m, 1H), 4.39 (m, 1H), 3.42 (m, 2H), 3.18-3.25 (m, 6H), 2.87 (s, 6H), 2.56 (s, 3H), 1.69 (d, 3H). LRMS [M+H]=428.2

Example 187

3-(1-(4-(2-(5-amino-8-methylbenzo[f][1,7]naphthyridin-2-yl)ethyl)phenyl)ethylamino)propanoic acid

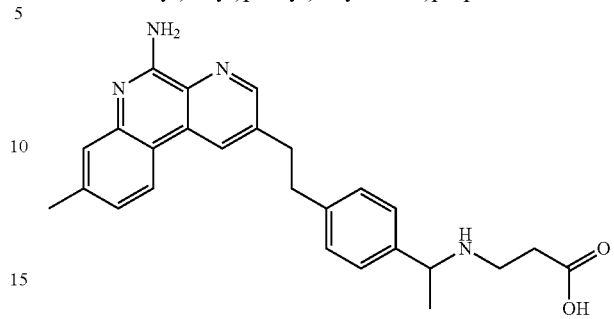

A solution of 1-(4-(2-(5-amino-8-methylbenzo[f][1,7]naphthyridin-2-yl)ethyl)phenyl)ethanone (from Example 171) (1 eq), 3-aminopropanoic acid (commercially available) (5 eq), triethylamine (3 eq) dissolved in absolute ethanol (0.042M) was stirred at 50° C. for 3 hours. The mixture was cooled to 0° C. and NaCNBH$_3$ (1 eq) was added and the reaction mixture was stirred for another six hours at room temperature. Then another equivalent of NaCNBH$_3$ was added and the reaction mixture was stirred at 50° C. for another hour. After cooling to ambient temperature the reaction mixture was diluted with ethyl acetate and saturated ammonium chloride. The two phases were separated, and the aqueous layer was extracted twice with ethyl acetate. The combined organic layers were washed with brine, dried over anhydrous MgSO$_4$, and concentrated en vaccuo. The crude material was purified by Preparative HPLC on a 19×50 mm ATLANTIS® 10 micron C18 (Waters Corp.) system using 10-90% Acetonitrile (0.035% TFA) in Water (0.05% TFA) to give 3-(1-(4-(2-(5-amino-8-methylbenzo[f][1,7]naphthyridin-2-yl)ethyl)phenyl)ethylamino)propanoic acid a white solid as a TFA salt. $^1$H NMR (Methanol-$d_4$) TFA Salt: δ 8.74 (s, 1H), 8.42 (d, 1H), 7.66 (m, 2H), 7.50 (m, 1H), 7.31 (d, 2H), 7.23 (m, 2H), 4.24 (m, 1H), 3.21 (t, 2H), 3.14 (t, 2H), 2.75-3.10 (m, 2H), 2.51 (t, 2H), 2.10 (s, 3H), 1.55 (d, 3H). LRMS [M+H]=429.2

Example 188

8-methyl-2-(4-(1-(4-methylpiperazin-1-yl)ethyl)phenethyl)benzo[f][1,7]naphthyridin-5-amine

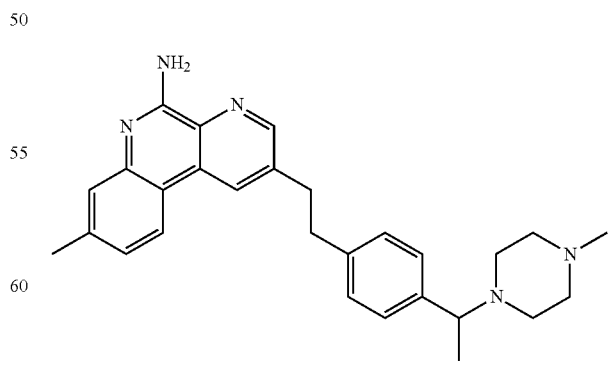

8-Methyl-2-(4-(1-(4-methylpiperazin-1-yl)ethyl)phenethyl)benzo[f][1,7]naphthyridin-5-amine was prepared from 1-(4-(2-(5-amino-8-methylbenzo[f][1,7]naphthyridin-2-yl)

ethyl)phenyl)ethanone (from Example 171) and 1-methylpiperazine (commercially available) following the procedures described for Example 182. $^1$H NMR (Acetone-$d_6$) TFA Salt: δ 8.84 (s, 1H), 8.80 (s, 1H), 8.41 (d, 1H), 7.52 (s, 1H), 7.42-7.46 (m, 3H), 7.36-7.38 (m, 2H), 3.53 (m, 1H), 3.18 (m, 2H), 3.12 (m, 2H), 2.92 (s, 2H), 2.66 (s, 2H), 2.56 (s, 2H), 2.16 (s, 3H), 1.99 (m, 2H), 1.69 (d, 3H), 1.30 (s, 3H). LRMS [M+H]=440.2

Example 189

$N^2$-(1-(4-(2-(5-amino-8-methylbenzo[f][1,7]naphthyridin-2-yl)ethyl)phenyl)ethyl)-$N^1$,$N^1$-dimethylpropane-1,2-diamine

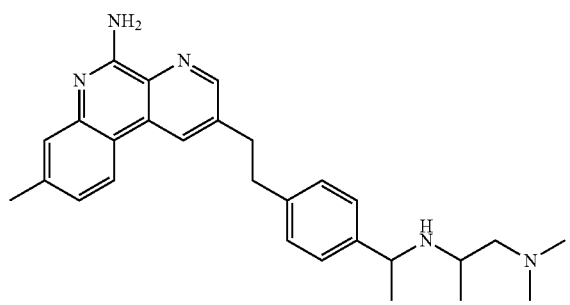

$N^2$-(1-(4-(2-(5-amino-8-methylbenzo[f][1,7]naphthyridin-2-yl)ethyl)phenyl)ethyl)-$N^1$,$N^1$-dimethylpropane-1,2-diamine was prepared from 1-(4-(2-(5-amino-8-methylbenzo[f][1,7]naphthyridin-2-yl)ethyl)phenyl)ethanone (from Example 171) and $N^1$,$N^1$-dimethylpropane-1,2-diamine (commercially available) following the procedures described for Example 182. $^1$H NMR (Acetone-$d_6$) TFA Salt: δ 8.83 (m, 2H), 8.40 (d, 1H), 7.46-7.51 (m, 3H), 7.43 (m, 1H), 7.37 (d, 2H), 4.54 (m, 1H), 3.74 (m, 1H), 3.19 (m, 4H), 2.90 (s, 3H), 2.77 (s, 3H), 2.55 (s, 3H), 2.41 (d, 2H), 1.66 (d, 3H), 1.39 (d, 3H). LRMS [M+H]=442.2

Example 190

8-methyl-2-(4-(1-(2-(pyridin-4-yl)ethylamino)ethyl)phenethyl)benzo[f][1,7]naphthyridin-5-amine

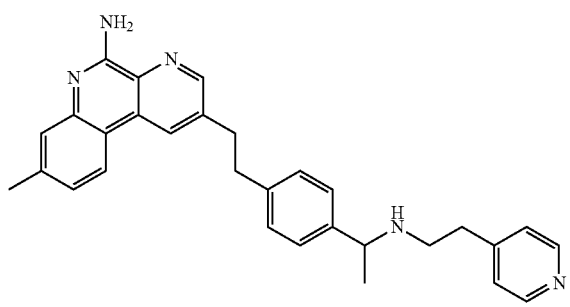 [SMILES: Cc1ccc2c(c1)nc(N)c1ncc(CCc3ccc(C(C)NCCc4ccncc4)cc3)cc12]

8-Methyl-2-(4-(1-(2-(pyridin-4-yl)ethylamino)ethyl)phenethyl)benzo[f][1,7]naphthyridin-5-amine was prepared from 1-(4-(2-(5-amino-8-methylbenzo[f][1,7]naphthyridin-2-yl)ethyl)phenyl)ethanone (from Example 171) and 2-(pyridin-4-yl)ethanamine (commercially available) following the procedures described for Example 182. $^1$H NMR (Acetone-$d_6$) TFA Salt: δ 8.94 (m, 2H), 8.92 (d, 2H), 8.73 (s, 1H), 8.43 (d, 1H), 7.60 (m, 2H), 7.40 (m, 2H), 7.16-7.26 (m, 3H), 4.55 (m, 1H), 3.55 (m, 4H), 2.56 (m, 4H), 2.12 (s, 3H), 1.73 (d, 3H) LRMS [M+H]=462.2

Example 191

$N^1$-(1-(4-(2-(5-amino-8-methylbenzo[f][1,7]naphthyridin-2-yl)ethyl)phenyl)ethyl)-$N^2$,$N^2$-diethylethane-1,2-diamine

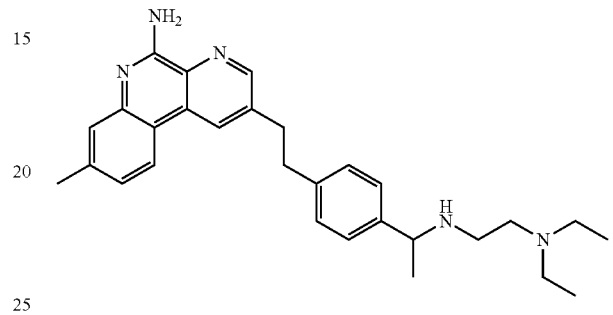

$N^1$-(1-(4-(2-(5-amino-8-methylbenzo[f][1,7]naphthyridin-2-yl)ethyl)phenyl)ethyl)-$N^2$,$N^2$-diethylethane-1,2-diamine was prepared from 1-(4-(2-(5-amino-8-methylbenzo[f][1,7]naphthyridin-2-yl)ethyl)phenyl)ethanone (from Example 171) and $N^1$,$N^1$-diethylethane-1,2-diamine (commercially available) following the procedures described for Example 182. $^1$H NMR (Acetone-$d_6$) TFA Salt: δ: 8.81 (s, 1H), 8.75 (s, 1H), 8.23 (d, 1H), 7.60 (d, 2H), 7.39 (d, 2H), 7.28 (m, 2H), 4.51 (m, 1H), 3.82 (m, 1H), 3.62 (m, 1H), 3.34 (m, 4H), 3.20 (t, 2H), 2.46 (s, 3H), 2.10 (m, 4H), 1.74 (d, 3H), 1.34 (t, 6H). LRMS [M+H]=456.2

Example 192

2-(4-(dimethylamino)-2-methylphenethyl)-8-methylbenzo[f][1,7]naphthyridin-5-amine

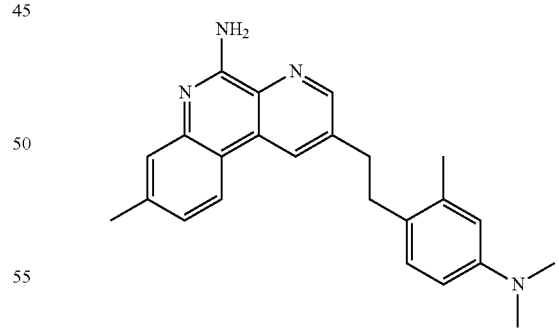

Step 1: 4-iodo-N,N,3-trimethylaniline

To a solution of 4-iodo-3-methylaniline (commercially available) (1 eq), NaHCO$_3$ (2.5 eq), and iodomethane (2.5 eq), in DMF ((0.2M) was stirred at ambient temperature overnight. The reaction mixture was then diluted with ethyl acetate and water. The two phases were separated, and the aqueous phase was extracted twice with ethyl acetate. The combined organic layers were washed with brine, dried over sodium sulfate, and concentrated en vaccuo. The crude material was purified by flash chromatography on a COMBIFLASH® system (ISCO) using 0-80% ethyl acetate in hexane and 4-iodo-N,N,3-trimethylaniline was isolated as a yellow solid.

Step 2: Syntheswas of:
N,N,3-trimethyl-4-((trimethylsilyl)ethynyl)aniline

To a solution of 4-iodo-N,N-3-trimethylaniline (from the previous step) (1 eq), ethynyltrimethylsilane (1.5 eq), dichlorobis(triphenylphosphine)-palladium (II) (20 mol %), copper iodide (20 mol %) and triethylamine (0.4 M) was stifled at ambient temperature overnight. The reaction mixture was then diluted with ethyl acetate and ammonium chloride solution. The two phases were separated, and the aqueous phase was extracted twice with ethyl acetate. The combined organic layers were washed with brine, dried over sodium sulfate, and concentrated en vaccuo. The crude material was purified by flash chromatography on a COMBIFLASH® system (ISCO) using 0-100% ethyl acetate in hexane and N,N,3-trimethyl-4-((trimethylsilyl)ethynyl)aniline was isolated as a yellow solid.

Step3: 4-ethynyl-N,N,3-trimethylaniline

To a solution of N,N-3-trimethyl-4-((trimethylsilyl)ethynyl)aniline (from the previous step) (1 eq), $K_2CO_3$ (2.5 eq), in MeOH ((0.15M) was stirred at ambient temperature for six hours. The solids were filtered out, and the liquid was concentrated en vaccuo. The crude material was purified by flash chromatography on a COMBIFLASH® system (ISCO) using 0-80% ethyl acetate in hexane and 4-ethynyl-N,N-3-trimethylaniline was isolated as a yellow solid.

Step 4: 3-chloro-5-((4-(dimethylamino)-2-methylphenyl)ethynyl)picolinonitrile

To a solution of 4-ethynyl-N,N-3-trimethylaniline (from the previous step) (1 eq) 3,5-dichloropicolinonitrile (1.2 eq), dichlorobis(triphenylphosphine)-palladium (II) (10 mol %), copper iodide (10 mol %) and DMF: triethylamine (0.28 M) was stirred at ambient temperature overnight. The reaction mixture was then diluted with ethyl acetate and ammonium chloride solution. The two phases were separated, and the aqueous phase was extracted twice with ethyl acetate. The combined organic layers were washed with brine, dried over sodium sulfate, and concentrated en vaccuo. The crude material was purified by flash chromatography on a COMBIFLASH® system (ISCO) using 0-100% ethyl acetate in hexane and 3-chloro-5-((4-(dimethylamino)-2-methylphenyl)ethynyl)picolinonitrile was isolated as a off-yellow solid.

Step 5: 2-((4-(dimethylamino)-2-methylphenyl)ethynyl)-8-methylbenzo[f][1,7]naphthyridin-5-amine A solution of tert-butyl 5-methyl-2-(4,4,5,5-tetramethyl-1,3,2-dioxaborolan-2-yl)phenylcarbamate (1.3 eq.) and 3-chloro-5-((4-(dimethylamino)-2-methylphenyl)ethynyl) picolinonitrile (from the previous step) (1.0 eq.), tetrakis (triphenyl-phosphine)palladium (10 mol %), and 2N aqueous sodium carbonate solution (2.0 eq.) in toluene/ethanol (2:1, 0.17 M) was stirred at 100° C. overnight. After cooling to ambient temperature, the reaction mixture was diluted with methanol. The insoluble solids were filtered off, and the filtrate was concentrated en vaccuo to obtain a crude residue. The crude material was purified by flash chromatography on a COMBIFLASH® system (ISCO) using 0-80% ethyl acetate in hexane to give 2-((4-(dimethylamino)-2-methylphenyl)ethynyl)-8-methylbenzo[f][1,7]naphthyridin-5-amine as a yellow solid.

Step 6: 2-(4-(dimethylamino)-2-methylphenethyl)-8-methylbenzo[f][1,7]naphthyridin-5-amine To a solution of 2-((4-(dimethylamino)-2-methylphenyl) ethynyl)-8-methylbenzo[f][1,7]naphthyridin-5-amine (1 eq), (from the previous step) in ethyl acetate/ethanol(1:5, 0.035 M) was added 10% wt palladium on carbon (0.2 eq.). Hydrogen gas was introduced via a balloon, and the reaction was stirred for 3.5 hours. The mixture was filtered through a pad of celite, washing with dichloromethane. The filtrate was concentrated en vaccuo and purified by preparative HPLC on a 19×50 mm ATLANTIS® 10 micron C18 (Waters Corp.) system using 10-90% Acetonitrile (0.035% TFA) in Water (0.05% TFA) to give 2-(4-(dimethylamino)-2-methylphenethyl)-8-methylbenzo[f][1,7]naphthyridin-5-amine as a white solid as a TFA salt. $^1$H NMR (Acetone-$d_6$) TFA Salt: δ 8.81 (s, 1H), 8.74 (s, 1H), 8.34 (d, 1H), 7.89 (s, 1H), 7.47 (m, 2H), 7.38 (m, 2H), 3.34 (s, 6H), 3.32 (t, 2H), 3.28 (t, 2H), 2.57 (s, 3H), 2.34 (s, 3H). LRMS [M+H]=371.2

Example 193

1-(1-(4-(2-(5-amino-8-methylbenzo[f][1,7]naphthyridin-2-yl)ethyl)phenyl)ethyl)pyrrolidine-3-carboxylic acid

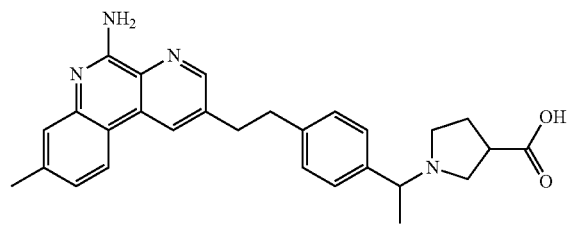 [SMILES: Cc1ccc2c(c1)nc(N)c1ncc(CCc3ccc(C(C)N4CCC(C(=O)O)C4)cc3)cc12]

1-(1-(4-(2-(5-Amino-8-methylbenzo[f][1,7]naphthyridin-2-yl)ethyl)phenyl)ethyl)pyrrolidine-3-carboxylic acid was prepared from 1-(4-(2-(5-amino-8-methylbenzo[f][1,7] naphthyridin-2-yl)ethyl)phenyl)ethanone (from Example 171) and pyrrolidine-3-carboxylic acid (commercially available) following the procedures described for Example 187, except that in this case, acetic acid was used instead of triethylamine (30%). $^1$H NMR (Acetone-$d_6$) TFA Salt: δ 8.81 (s, 1H), 8.75 (s, 1H), 8.70 (s, 1H), 8.28 (d, 1H), 7.59 (d, 2H), 7.37 (m, 3H), 4.46 (m, 1H), 4.21 (m 1H), 3.45 (m, 2H), 3.32 (m, 2H), 3.21 (m, 2H), 3.17 (m, 2H), 2.27 (m, 2H), 2.07 (s, 3H) 1.77 (d, 3H). LRMS [M+H]=455.2

Example 194

4-(1-(4-(2-(5-amino-8-methylbenzo[f][1,7]naphthyridin-2-yl)ethyl)phenyl)ethylamino)phenol

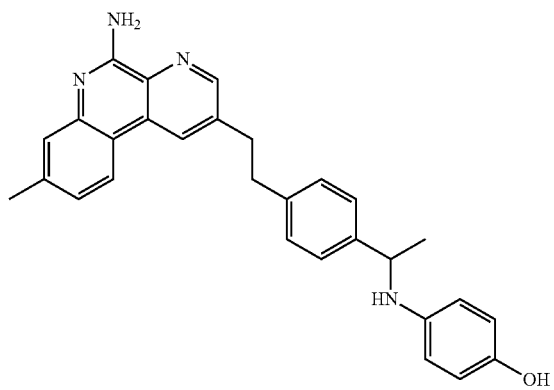 [SMILES: Cc1ccc2c(c1)nc(N)c1ncc(CCc3ccc(C(C)Nc4ccc(O)cc4)cc3)cc12]

4-(1-(4-(2-(5-Amino-8-methylbenzo[f][1,7]naphthyridin-2-yl)ethyl)phenyl)ethylamino)phenol was prepared from 1-(4-(2-(5-amino-8-methylbenzo[f][1,7]naphthyridin-2-yl)ethyl)phenyl)ethanone (from Example 171) and 4-aminophenol following the procedures described for Example 187, except that in this case, acetic acid was used instead of triethylamine (28%). $^1$H NMR (Acetone-$d_6$) TFA Salt: δ 8.83 (s, 1H), 8.73 (s, 1H), 8.33 (d, 1H), 7.44 (s, 1H), 7.40 (d, 2H), 7.36 (d, 1H), 7.24 (d, 2H), 7.10 (d, 2H), 6.76 (d, 2H), 4.72 (m, 1H) 3.27 (t, 2H), 3.12 (t, 2H), 2.50 (s, 3H), 2.06 (d, 3H). LRMS [M+H]=449.2

Example 195

1-(1-(4-(2-(5-amino-8-methylbenzo[f][1,7]naphthyridin-2yl)ethyl)phenyl)ethyl)pyrrolidin-3-ol

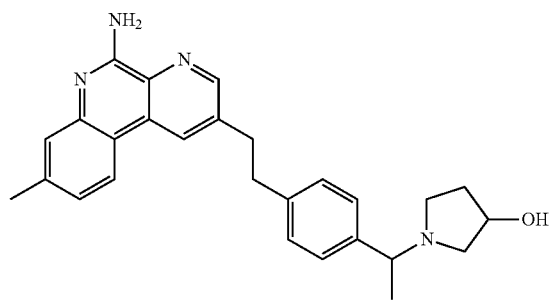 [SMILES: Cc1ccc2c(c1)nc(N)c1ncc(CCc3ccc(C(C)N4CCC(O)C4)cc3)cc12]

1-(1-(4-(2-(5-Amino-8-methylbenzo[f][1,7]naphthyridin-2yl)ethyl)phenyl)ethyl)pyrrolidin-3-ol was prepared from 1-(4-(2-(5-amino-8-methylbenzo[f][1,7]naphthyridin-2-yl)ethyl)phenyl)ethanone (from Example 171) and pyrrolidin-3-ol following the procedures described for Example 187, except that in this case, acetic acid was used instead of triethylamine (20%). $^1$H NMR (Acetone-$d_6$) TFA Salt: δ 8.83 (s, 1H), 8.76 (s, 1H), 8.72 (s, 1H), 8.29 (d, 1H), 7.57 (s, 1H), 7.42 (s, 1H), 7.33-7.38 (m, 3H), 4.41 (m, 2H), 3.77 (m, 2H), 3.33 (t, 2H), 3.21 (t, 2H), 3.19 (m, 2H), 3.10 (m, 2H), 2.10 (s, 3H), 1.75 (d, 3H). LRMS [M+H]=427.2

Example 196

2-(4-(2-aminopropan-2-yl)phenethyl)-8-methylbenzo[f][1,7]naphthyridin-5-amine

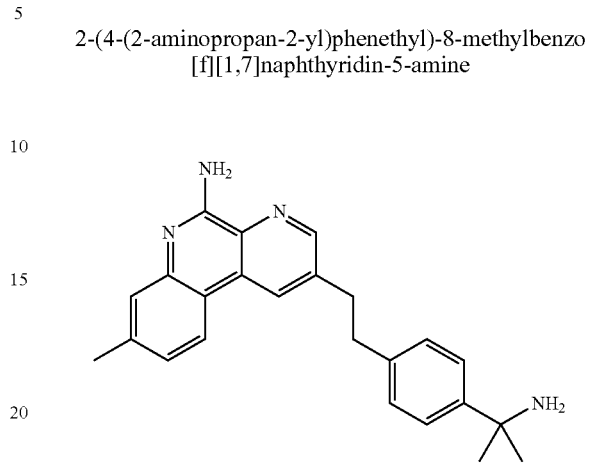

To a solution of 4-(2-(5-amino-8-methylbenzo[f][1,7]naphthyridin-2-yl)ethyl)benzonitrile (from Example 64, step 1) (1 eq), dissolved in dry THF (0.029M) was added very slowly methyl magnesium bromide (6 eq) and the reaction mixture was stirred at room temperature for half hour. Then was added to the reaction flask titanium tetra-isopropoxide (3 eq) over ten minutes. The reaction mixture was refluxed for 16 hours. After cooling to ambient temperature the reaction mixture was diluted with ethyl acetate and saturated ammonium chloride. The two phases were separated, and the aqueous layer was extracted twice with ethyl acetate. The combined organic layers were washed with brine, dried over anhydrous MgSO$_4$, and concentrated en vaccuo. The crude material was purified by Preparative HPLC on a 19×50 mm ATLANTIS® 10 micron C18 (Waters Corp.) system using 10-90% Acetonitrile (0.035% TFA) in Water (0.05% TFA) to give 2-(4-(2-aminopropan-2-yl)phenethyl)-8-methylbenzo[f][1,7]naphthyridin-5-amine as a white solid of TFA salt. $^1$H NMR (Methanol-$d_4$) TFA Salt δ: 9.01 (s, 2H), 8.92 (s, 1H), 8.42 (s, 1H), 7.65 (d, 2H), 7.56 (s, 1H), 7.39 (m, 2H), 3.19 (m, 4H), 2.54 (s, 3H), 1.82 (6H). LRMS [M+H]=371.2.

Example 197

N-(2-acetamidoethyl)-4-(2-(5-amino-8-methylbenzo[f][1,7]naphthyridin-2-yl)ethyl)-3-methylbenzamide

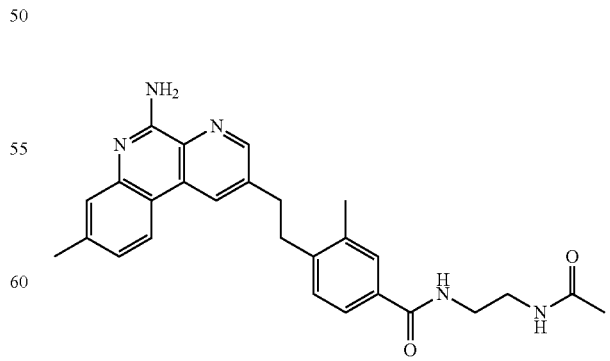

To a solution of 4-(2-(5-amino-8-methylbenzo[f][1,7]naphthyridin-2-yl)ethyl)-3-methylbenzoyl chloride (Example 116/Step 2) and triethylamine (2.5 eq.) in ether (0.05

M) was added N-(2-aminoethyl)acetamide (5.0 eq.). The reaction mixture was stirred for overnight. Then the reaction mixture was diluted with ethyl acetate and water. The two phases were separated, and the aqueous layer was extracted twice with ethyl acetate. The combined organic layers were washed with brine, dried over anhydrous MgSO$_4$, and concentrated en vaccuo. The crude material was purified by flash chromatography on a COMBIFLASH® system (ISCO) using 0-80% ethyl acetate in hexane to give N-(2-acetamidoethyl)-4-(2-(5-amino-8-methylbenzo[f][1,7]naphthyridin-2-yl)ethyl)-3-methylbenzamide as a white solid. $^1$H NMR (CDCl$_3$): δ 8.61 (s, 1H), 8.38 (s, 1H), 8.07 (d, 1H), 7.65 (s, 1H), 7.51-7.56 (m, 2H), 7.10-7.16 (m, 2H), 6.25 (br, 2H), 3.50-3.59 (m, 4H), 3.08-3.16 (m, 4H), 2.62 (s, 3H), 2.52 (s, 3H), 2.35 (s, 3H). LRMS [M+H]=455.2.

Additional representative compounds of Formula (I), prepared following the procedures described above, are set forth in Table 1.

TABLE 1

| Compound Number | Structure | Physical Data MS (m/z) [M + H] |
|---|---|---|
| 1 | 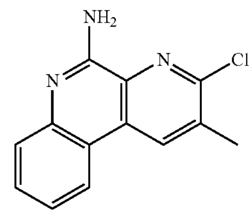 [SMILES: Cc1cc2c(nc1Cl)c(N)nc1ccccc12] | 244.0 |
| 2 | 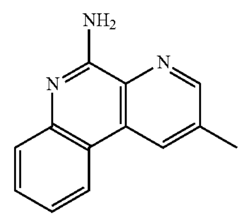 [SMILES: Cc1cnc2c(N)nc3ccccc3c2c1] | 210.2 |
| 3 | 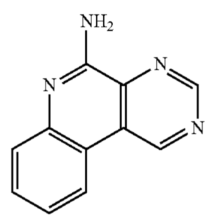 [SMILES: Nc1nc2ccccc2c2cncnc12] | 197.1 |
| 4 | 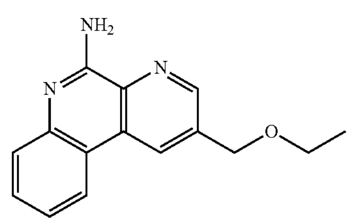 [SMILES: CCOCc1cnc2c(N)nc3ccccc3c2c1] | 254.1 |
| 5 | 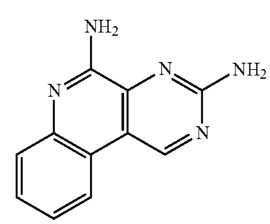 [SMILES: Nc1ncc2c(n1)c(N)nc1ccccc12] | 212.1 |
| 6 | 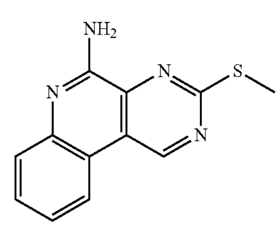 [SMILES: CSc1ncc2c(n1)c(N)nc1ccccc12] | 243.1 |

TABLE 1-continued

| Compound Number | Structure | Physical Data MS (m/z) [M + H] |
|---|---|---|
| 7 | 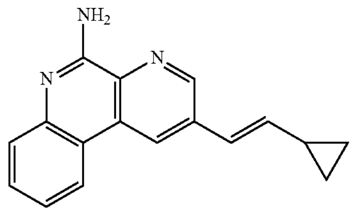 [SMILES: Nc1nc2ccccc2c2cc(/C=C/C3CC3)cnc12] | 262.1 |
| 8 | 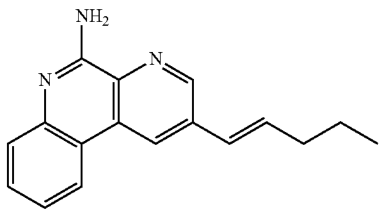 [SMILES: CCC/C=C/c1cnc2c(N)nc3ccccc3c2c1] | 264.1 |
| 9 | 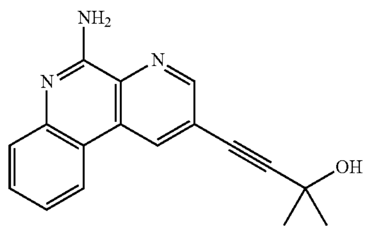 [SMILES: CC(C)(O)C#Cc1cnc2c(N)nc3ccccc3c2c1] | 278.1 |
| 10 | 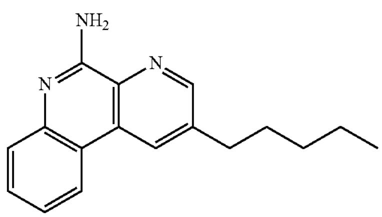 [SMILES: CCCCCc1cnc2c(N)nc3ccccc3c2c1] | 266.2 |
| 11 | 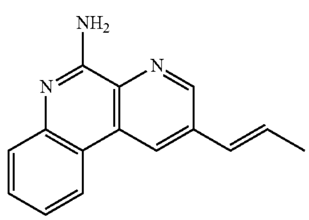 [SMILES: C/C=C/c1cnc2c(N)nc3ccccc3c2c1] | 236.2 |
| 12 | 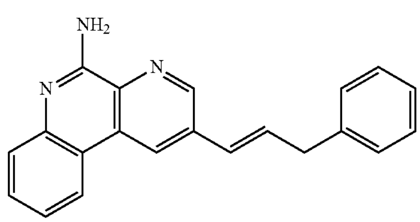 [SMILES: Nc1nc2ccccc2c2cc(/C=C/Cc3ccccc3)cnc12] | 312.1 |
| 13 | 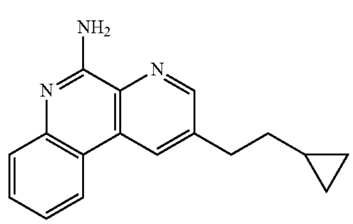 [SMILES: Nc1nc2ccccc2c2cc(CCC3CC3)cnc12] | 264.1 |

TABLE 1-continued

| Compound Number | Structure | Physical Data MS (m/z) [M + H] |
|---|---|---|
| 14 | 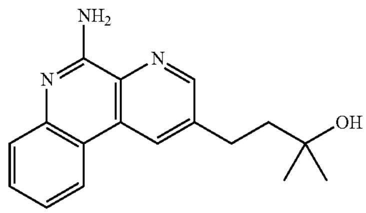 [SMILES: CC(C)(O)CCc1cnc2c(N)nc3ccccc3c2c1] | 282.1 |
| 15 | 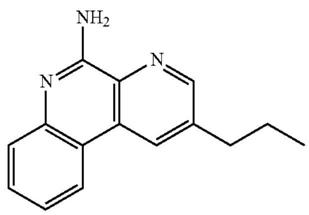 [SMILES: CCCc1cnc2c(N)nc3ccccc3c2c1] | 238.2 |
| 16 | 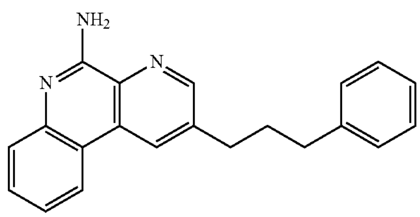 [SMILES: Nc1nc2ccccc2c2cc(CCCc3ccccc3)cnc12] | 314.2 |
| 17 | 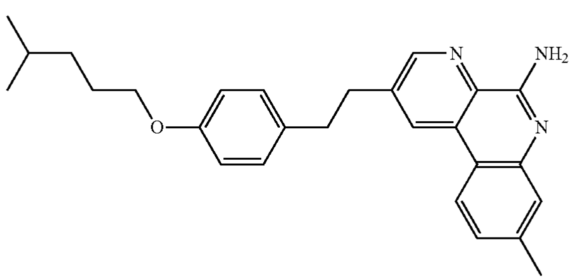 | 414.2 |
| 18 | 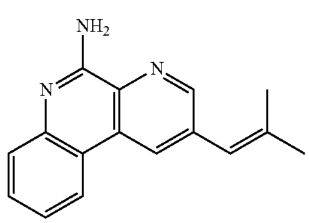 [SMILES: CC(C)=Cc1cnc2c(N)nc3ccccc3c2c1] | 250.1 |
| 19 | 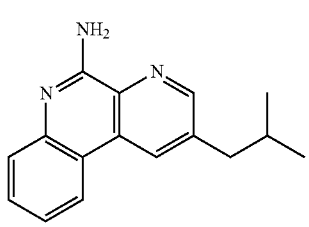 [SMILES: CC(C)Cc1cnc2c(N)nc3ccccc3c2c1] | 252.1 |

TABLE 1-continued

| Compound Number | Structure | Physical Data MS (m/z) [M + H] |
|---|---|---|
| 20 | 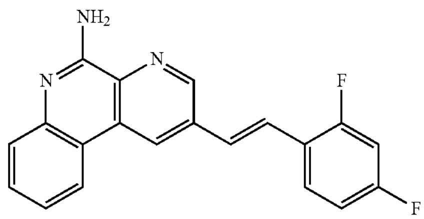 [SMILES: Nc1nc2ccccc2c2cc(/C=C/c3ccc(F)cc3F)cnc12] | 334.1 |
| 21 | 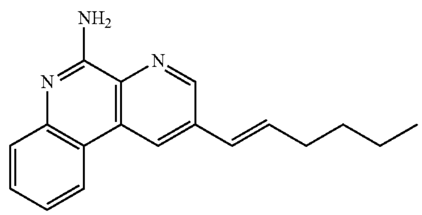 [SMILES: CCCC/C=C/c1cnc2c(N)nc3ccccc3c2c1] | 278.2 |
| 22 | 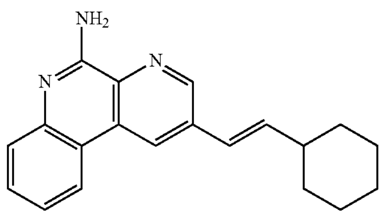 [SMILES: Nc1nc2ccccc2c2cc(/C=C/C3CCCCC3)cnc12] | 304.2 |
| 23 | 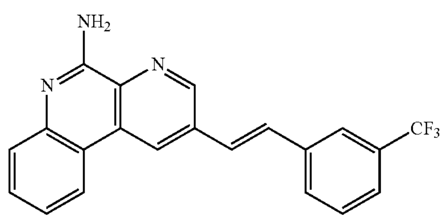 [SMILES: Nc1nc2ccccc2c2cc(/C=C/c3cccc(C(F)(F)F)c3)cnc12] | 366.2 |
| 24 | 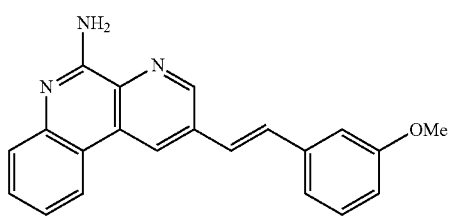 [SMILES: COc1cccc(/C=C/c2cnc3c(N)nc4ccccc4c3c2)c1] | 328.2 |
| 25 | 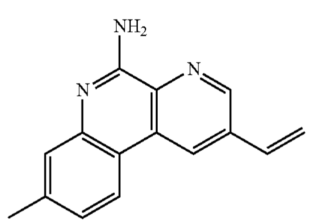 [SMILES: C=Cc1cnc2c(N)nc3cc(C)ccc3c2c1] | 236.1 |
| 26 | 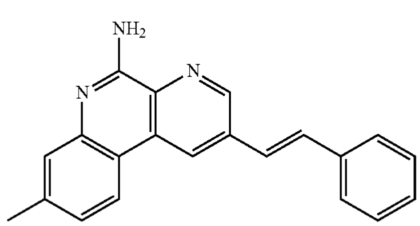 [SMILES: Cc1ccc2c(c1)nc(N)c1ncc(/C=C/c3ccccc3)cc12] | 312.2 |

TABLE 1-continued
| Compound Number | Structure | Physical Data MS (m/z) [M + H] |
|---|---|---|
| 27 | 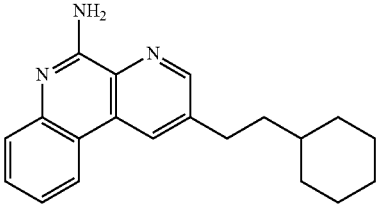 [SMILES: Nc1nc2ccccc2c2cc(CCC3CCCCC3)cnc12] | 306.1 |
| 28 | 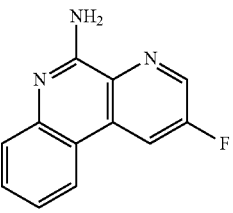 [SMILES: Nc1nc2ccccc2c2cc(F)cnc12] | 214.0 |
| 29 | 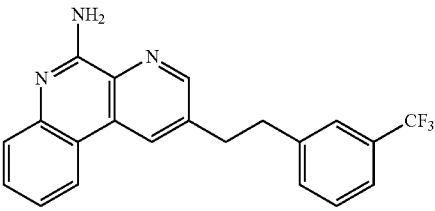 [SMILES: Nc1nc2ccccc2c2cc(CCc3cccc(C(F)(F)F)c3)cnc12] | 368.1 |
| 30 | 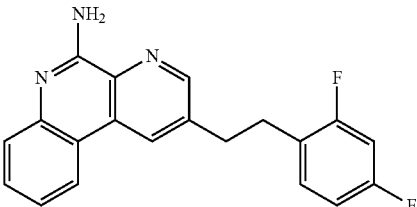 | 336.1 |
| 31 | 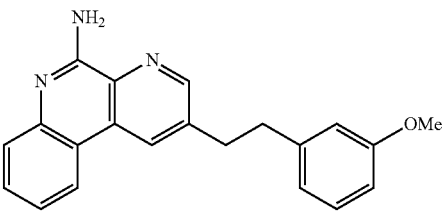 [SMILES: COc1cccc(CCc2cnc3c(N)nc4ccccc4c3c2)c1] | 330.2 |
| 32 | 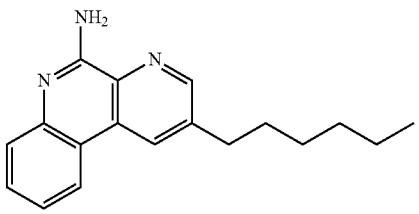 [SMILES: CCCCCCc1cnc2c(N)nc3ccccc3c2c1] | 280.2 |

TABLE 1-continued

| Compound Number | Structure | Physical Data MS (m/z) [M + H] |
|---|---|---|
| 33 | 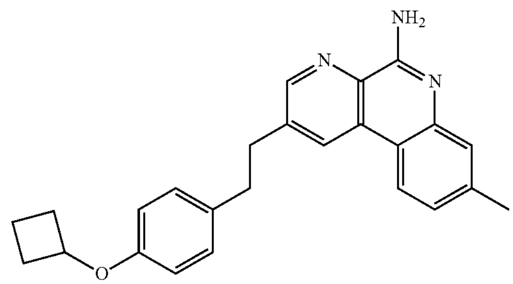 [SMILES: Cc1ccc2c(c1)nc(N)c1ncc(CCc3ccc(OC4CCC4)cc3)cc12] | 384.2 |
| 34 | 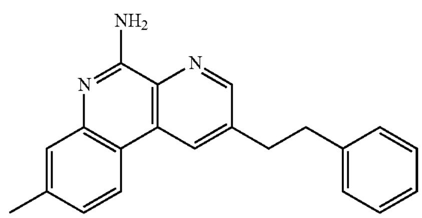 [SMILES: Cc1ccc2c(c1)nc(N)c1ncc(CCc3ccccc3)cc12] | 314.2 |
| 35 | 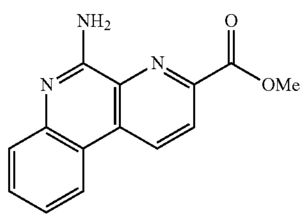 [SMILES: COC(=O)c1ccc2c(n1)c(N)nc1ccccc12] | 254.1 |
| 36 | 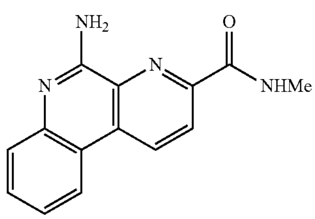 [SMILES: CNC(=O)c1ccc2c(n1)c(N)nc1ccccc12] | 253.1 |
| 37 | 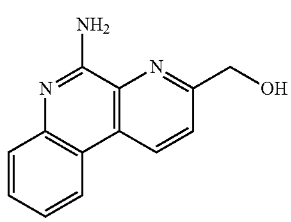 [SMILES: Nc1nc2ccccc2c2ccc(CO)nc12] | 226.1 |
| 38 | 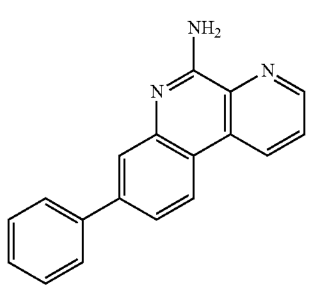 [SMILES: Nc1nc2cc(-c3ccccc3)ccc2c2cccnc12] | 272.1 |

TABLE 1-continued

| Compound Number | Structure | Physical Data MS (m/z) [M + H] |
|---|---|---|
| 39 | 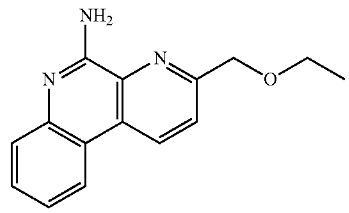 [SMILES: CCOCc1ccc2c(n1)c(N)nc1ccccc12] | 254.1 |
| 40 | 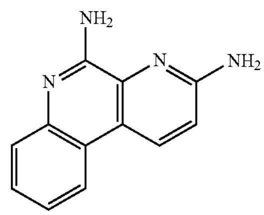 [SMILES: Nc1ccc2c(n1)c(N)nc1ccccc12] | 211.1 |
| 41 | 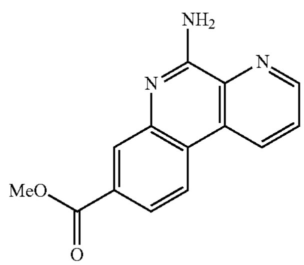 [SMILES: COC(=O)c1ccc2c(c1)nc(N)c1ncccc12] | 254.1 |
| 42 | 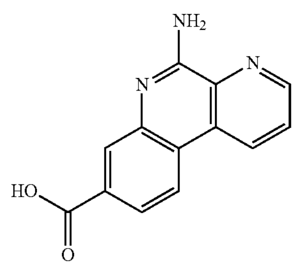 [SMILES: Nc1nc2cc(C(=O)O)ccc2c2cccnc12] | 240.1 |
| 43 | 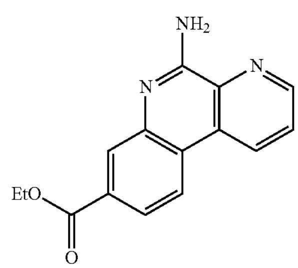 [SMILES: CCOC(=O)c1ccc2c(c1)nc(N)c1ncccc12] | 268.1 |
| 44 | 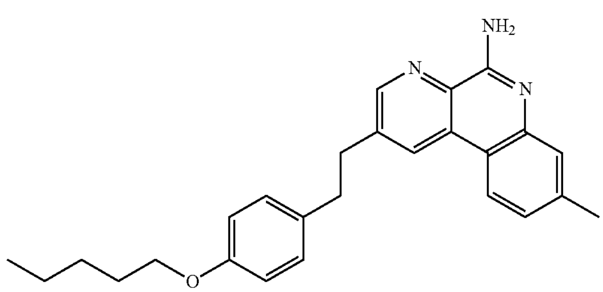 [SMILES: CCCCCOc1ccc(CCc2cnc3c(N)nc4cc(C)ccc4c3c2)cc1] | 400.2 |

TABLE 1-continued

| Compound Number | Structure | Physical Data MS (m/z) [M + H] |
|---|---|---|
| 45 | 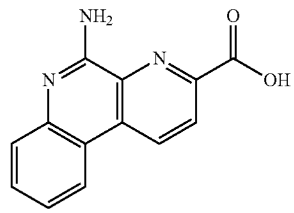 [SMILES: Nc1nc2ccccc2c2ccc(C(=O)O)nc12] | 240.1 |
| 46 | 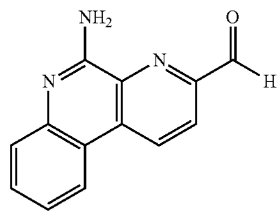 [SMILES: Nc1nc2ccccc2c2ccc(C=O)nc12] | 224.1 |
| 47 | 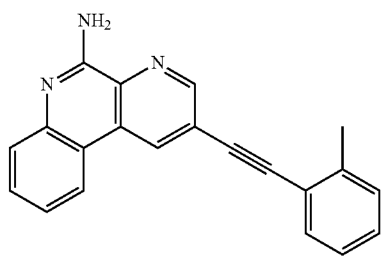 [SMILES: Cc1ccccc1C#Cc1cnc2c(N)nc3ccccc3c2c1] | 310.1 |
| 48 | 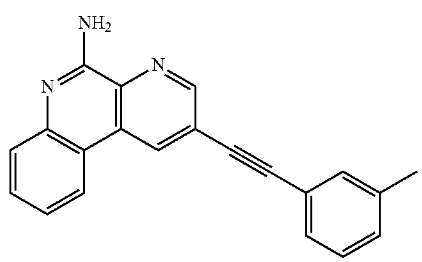 [SMILES: Cc1cccc(C#Cc2cnc3c(N)nc4ccccc4c3c2)c1] | 310.1 |
| 49 | 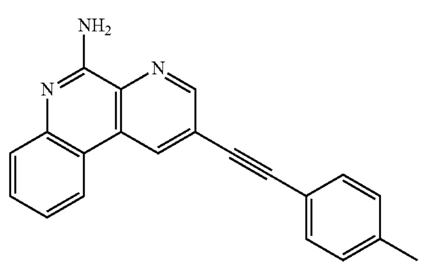 [SMILES: Cc1ccc(C#Cc2cnc3c(N)nc4ccccc4c3c2)cc1] | 310.1 |
| 50 | 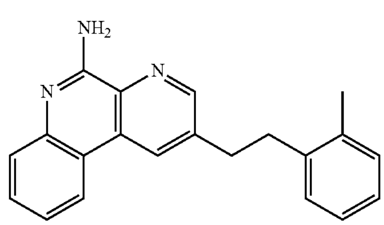 [SMILES: Cc1ccccc1CCc1cnc2c(N)nc3ccccc3c2c1] | 314.2 |

TABLE 1-continued

| Compound Number | Structure | Physical Data MS (m/z) [M + H] |
|---|---|---|
| 51 | 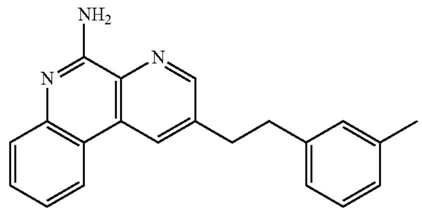 [SMILES: Cc1cccc(CCc2cnc3c(N)nc4ccccc4c3c2)c1] | 314.2 |
| 52 | 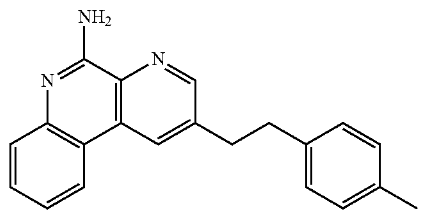 [SMILES: Cc1ccc(CCc2cnc3c(N)nc4ccccc4c3c2)cc1] | 314.2 |
| 53 | 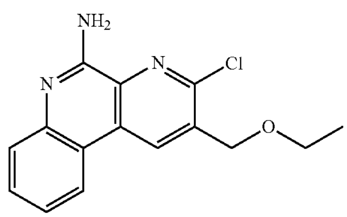 [SMILES: CCOCc1cc2c(nc1Cl)c(N)nc1ccccc12] | 288.1 |
| 54 | 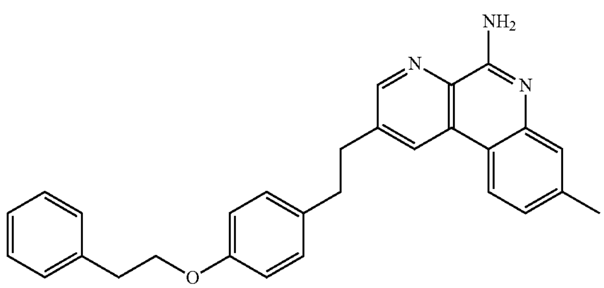 [SMILES: Cc1ccc2c(c1)nc(N)c1ncc(CCc3ccc(OCCc4ccccc4)cc3)cc12] | 434.2 |
| 55 | 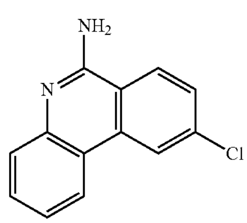 [SMILES: Nc1nc2ccccc2c2cc(Cl)ccc12] | 229.1 |
| 56 | 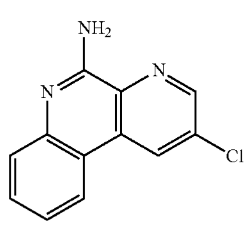 [SMILES: Nc1nc2ccccc2c2cc(Cl)cnc12] | 230.0 |

TABLE 1-continued

| Compound Number | Structure | Physical Data MS (m/z) [M + H] |
|---|---|---|
| 57 | 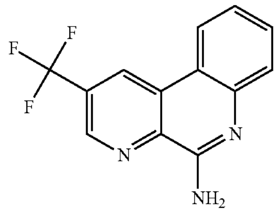 [SMILES: Nc1nc2ccccc2c2cc(C(F)(F)F)cnc12] | 264.1 |
| 58 | 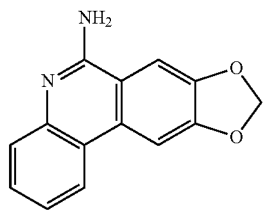 [SMILES: Nc1nc2ccccc2c2cc3c(cc12)OCO3] | 239.1 |
| 59 | 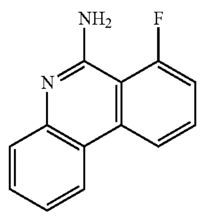 [SMILES: Nc1nc2ccccc2c2cccc(F)c12] | 213.1 |
| 60 | 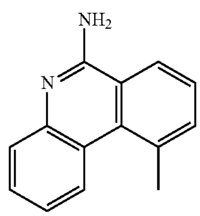 [SMILES: Cc1cccc2c(N)nc3ccccc3c12] | 209.1 |
| 61 | 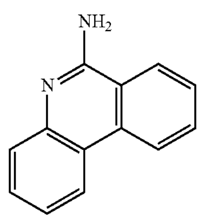 [SMILES: Nc1nc2ccccc2c2ccccc12] | 195.1 |
| 62 | 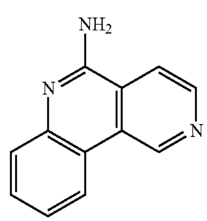 [SMILES: Nc1nc2ccccc2c2cnccc12] | 196.1 |
| 63 | 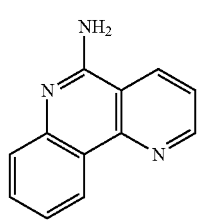 [SMILES: Nc1nc2ccccc2c2ncccc12] | 196.1 |

TABLE 1-continued

| Compound Number | Structure | Physical Data MS (m/z) [M + H] |
|---|---|---|
| 64 | 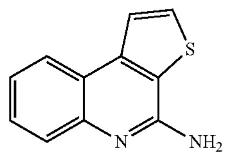 [SMILES: Nc1nc2ccccc2c2ccsc12] | 201.2 |
| 65 | 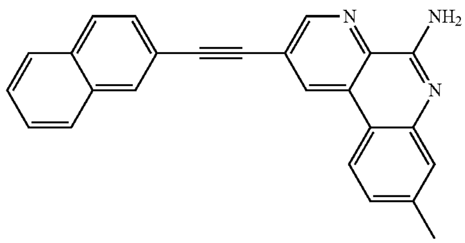 [SMILES: Cc1ccc2c(c1)nc(N)c1ncc(C#Cc3ccc4ccccc4c3)cc12] | 360.1 |
| 66 | 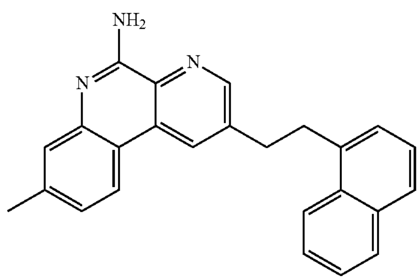 [SMILES: Cc1ccc2c(c1)nc(N)c1ncc(CCc3cccc4ccccc34)cc12] | 364.5 |
| 67 | 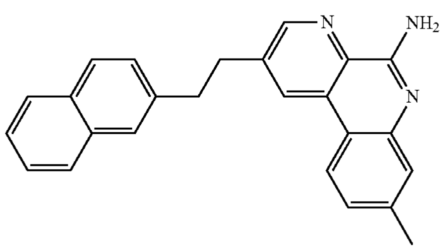 [SMILES: Cc1ccc2c(c1)nc(N)c1ncc(CCc3ccc4ccccc4c3)cc12] | 364.5 |
| 68 | 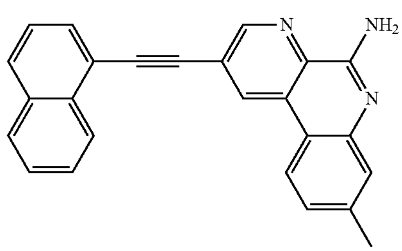 [SMILES: Cc1ccc2c(c1)nc(N)c1ncc(C#Cc3cccc4ccccc34)cc12] | 360.1 |
| 69 | 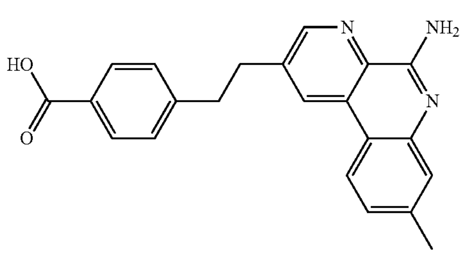 [SMILES: Cc1ccc2c(c1)nc(N)c1ncc(CCc3ccc(C(=O)O)cc3)cc12] | 358.4 |

TABLE 1-continued

| Compound Number | Structure | Physical Data MS (m/z) [M + H] |
|---|---|---|
| 70 | 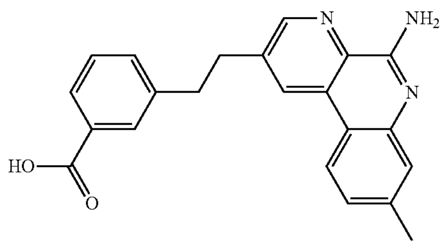 [SMILES: Cc1ccc2c(c1)nc(N)c1ncc(CCc3cccc(C(=O)O)c3)cc12] | 358.4 |
| 71 | 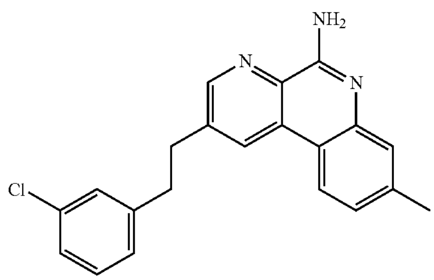 [SMILES: Cc1ccc2c(c1)nc(N)c1ncc(CCc3cccc(Cl)c3)cc12] | 348.8 |
| 72 | 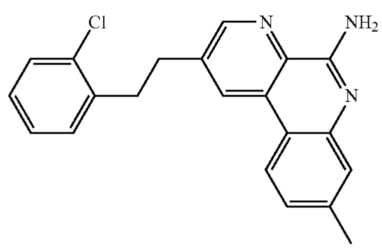 [SMILES: Cc1ccc2c(c1)nc(N)c1ncc(CCc3ccccc3Cl)cc12] | 348.8 |
| 73 | 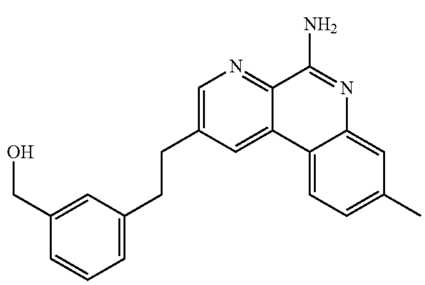 [SMILES: Cc1ccc2c(c1)nc(N)c1ncc(CCc3cccc(CO)c3)cc12] | 344.4 |
| 74 | 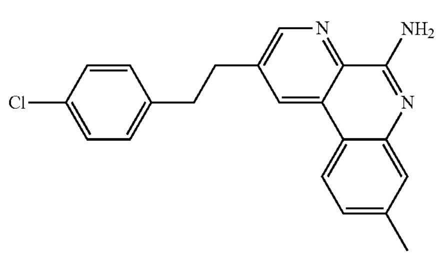 [SMILES: Cc1ccc2c(c1)nc(N)c1ncc(CCc3ccc(Cl)cc3)cc12] | 348.8 |
| 75 | 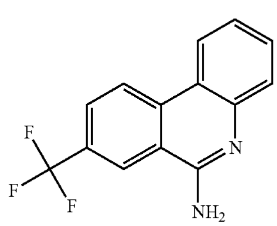 [SMILES: Nc1nc2ccccc2c2ccc(C(F)(F)F)cc12] | 263.0 |

TABLE 1-continued
| Compound Number | Structure | Physical Data MS (m/z) [M + H] |
|---|---|---|
| 76 | 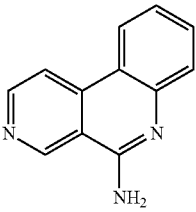 [SMILES: Nc1nc2ccccc2c2ccncc12] | 196.0 |
| 77 | 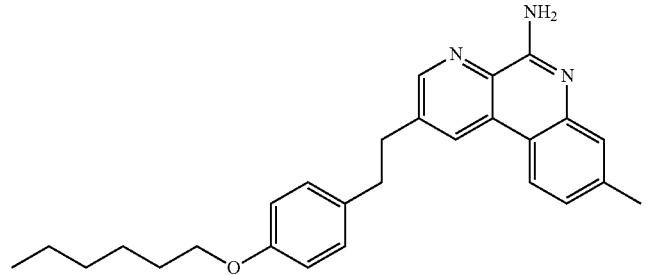 [SMILES: CCCCCCOc1ccc(CCc2cnc3c(N)nc4cc(C)ccc4c3c2)cc1] | 414.3 |
| 78 | 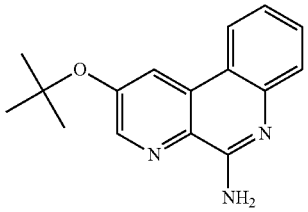 [SMILES: CC(C)(C)Oc1cnc2c(N)nc3ccccc3c2c1] | 268.1 |
| 79 | 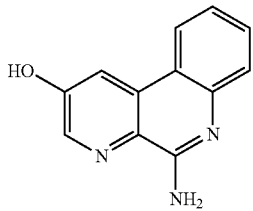 [SMILES: Nc1nc2ccccc2c2cc(O)cnc12] | 212.0 |
| 80 | 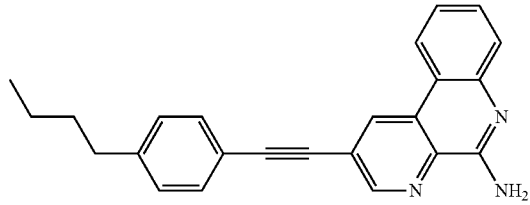 [SMILES: CCCCc1ccc(C#Cc2cnc3c(N)nc4ccccc4c3c2)cc1] | 352.1 |
| 81 | 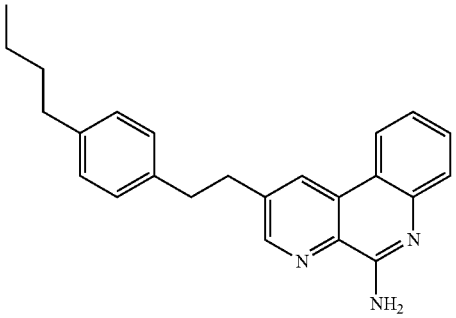 [SMILES: CCCCc1ccc(CCc2cnc3c(N)nc4ccccc4c3c2)cc1] | 356.2 |

TABLE 1-continued

| Compound Number | Structure | Physical Data MS (m/z) [M + H] |
|---|---|---|
| 82 | | |
| 83 | 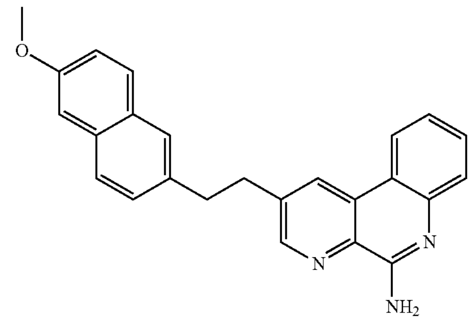 [SMILES: COc1ccc2cc(CCc3cnc4c(N)nc5ccccc5c4c3)ccc2c1] | 380.1 |
| 84 | 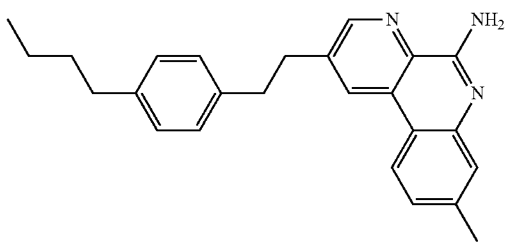 [SMILES: CCCCc1ccc(CCc2cnc3c(N)nc4cc(C)ccc4c3c2)cc1] | 370.2 |
| 85 | 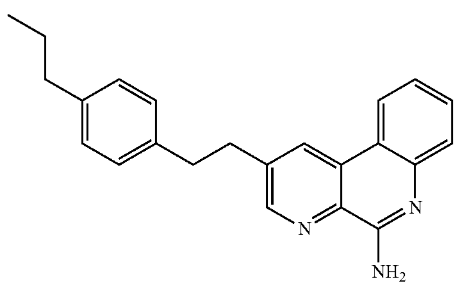 [SMILES: CCCc1ccc(CCc2cnc3c(N)nc4ccccc4c3c2)cc1] | 342.1 |
| 86 | 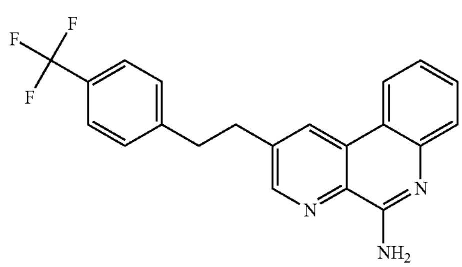 [SMILES: Nc1nc2ccccc2c2cc(CCc3ccc(C(F)(F)F)cc3)cnc12] | 368.1 |
| 87 | 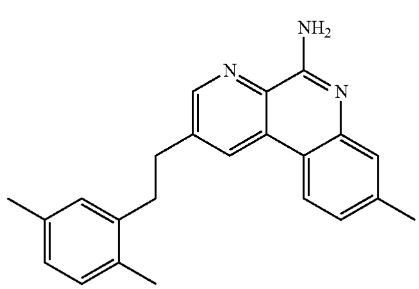 | 342.1 |

TABLE 1-continued

| Compound Number | Structure | Physical Data MS (m/z) [M + H] |
|---|---|---|
| 88 | 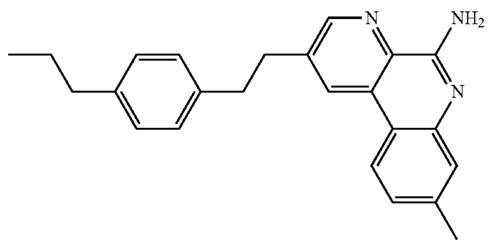 [SMILES: CCCc1ccc(CCc2cnc3c(N)nc4cc(C)ccc4c3c2)cc1] | 356.2 |
| 89 | 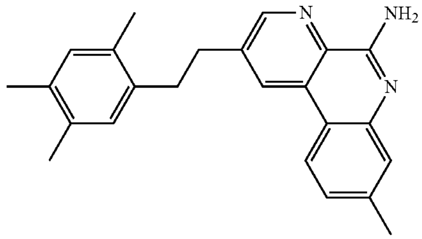 | 356.2 |
| 90 | 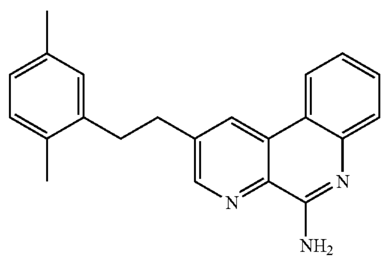 [SMILES: Cc1ccc(C)c(CCc2cnc3c(N)nc4ccccc4c3c2)c1] | 328.1 |
| 91 | 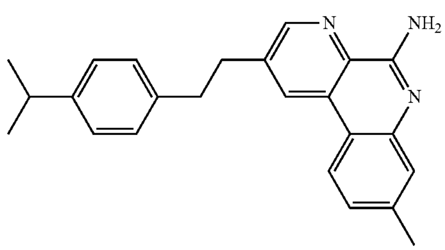 [SMILES: Cc1ccc2c(c1)nc(N)c1ncc(CCc3ccc(C(C)C)cc3)cc12] | 356.2 |
| 92 | 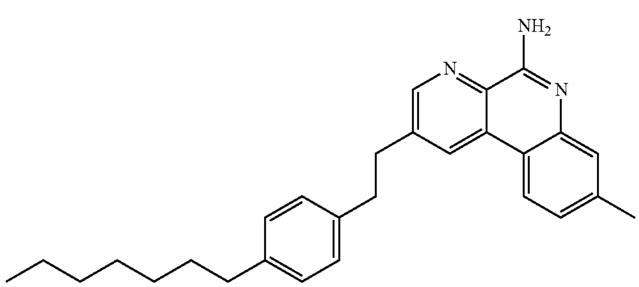 [SMILES: CCCCCCCc1ccc(CCc2cnc3c(N)nc4cc(C)ccc4c3c2)cc1] | 412.2 |
| 93 | 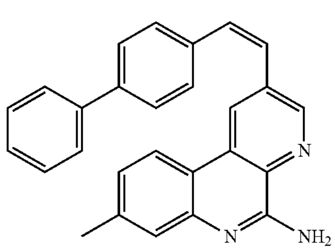 [SMILES: Cc1ccc2c(c1)nc(N)c1ncc(/C=C\c3ccc(-c4ccccc4)cc3)cc12] | 388.1 |

TABLE 1-continued

| Compound Number | Structure | Physical Data MS (m/z) [M + H] |
|---|---|---|
| 94 | 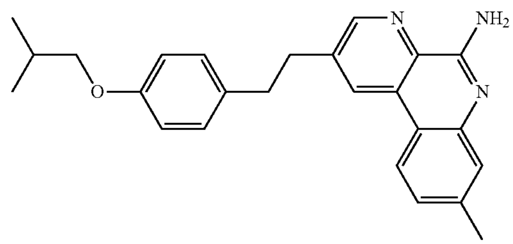 [SMILES: Cc1ccc2c(c1)nc(N)c1ncc(CCc3ccc(OCC(C)C)cc3)cc12] | 386.2 |
| 95 | 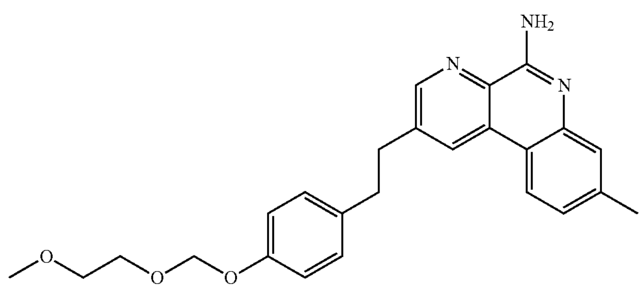 | 418.2 |
| 96 | 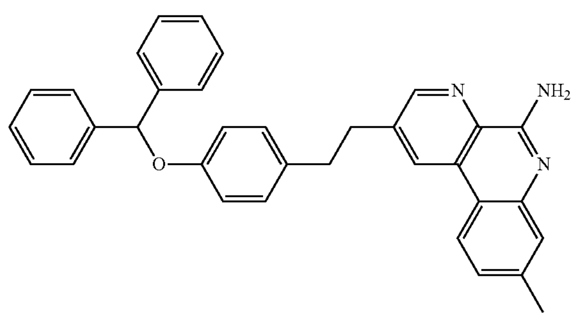 [SMILES: Cc1ccc2c(c1)nc(N)c1ncc(CCc3ccc(OC(c4ccccc4)c4ccccc4)cc3)cc12] | 496.2 |
| 97 | 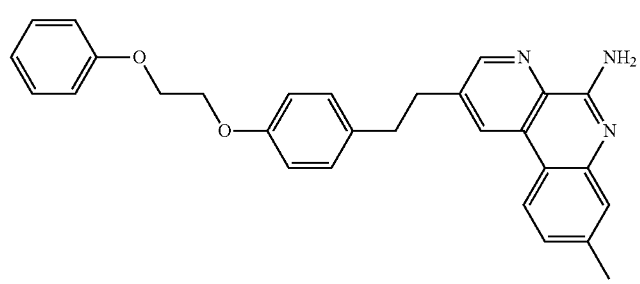 | 450.2 |
| 98 | 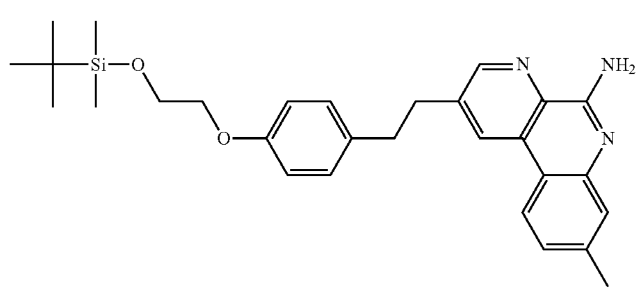 [SMILES: Cc1ccc2c(c1)nc(N)c1ncc(CCc3ccc(OCCO[Si](C)(C)C(C)(C)C)cc3)cc12] | 488.2 |

TABLE 1-continued

| Compound Number | Structure | Physical Data MS (m/z) [M + H] |
|---|---|---|
| 99 | 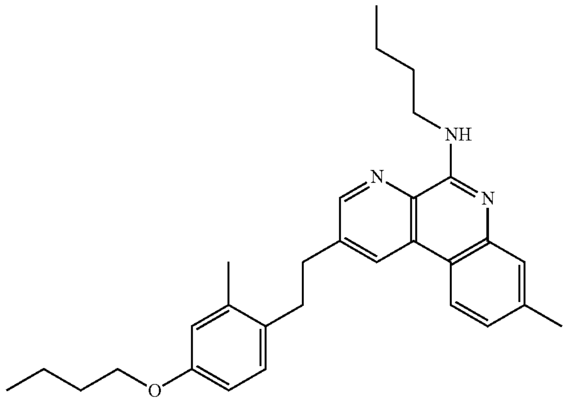 [SMILES: CCCCNc1nc2cc(C)ccc2c2cc(CCc3ccc(OCCCC)cc3C)cnc12] | 456.3 |
| 100 | 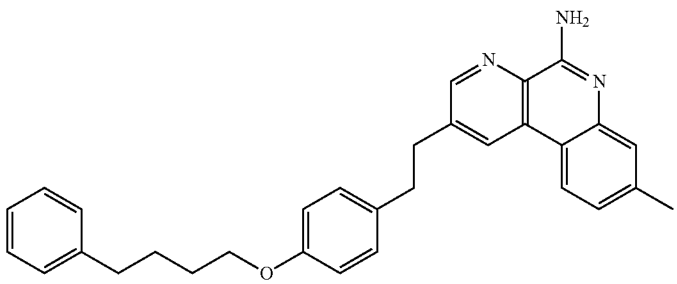 [SMILES: Cc1ccc2c(c1)nc(N)c1ncc(CCc3ccc(OCCCCc4ccccc4)cc3)cc12] | 462.3 |
| 101 | 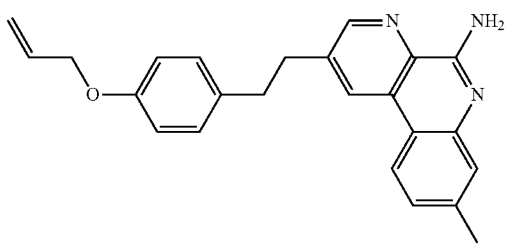 [SMILES: C=CCOc1ccc(CCc2cnc3c(N)nc4cc(C)ccc4c3c2)cc1] | 370.2 |
| 102 | 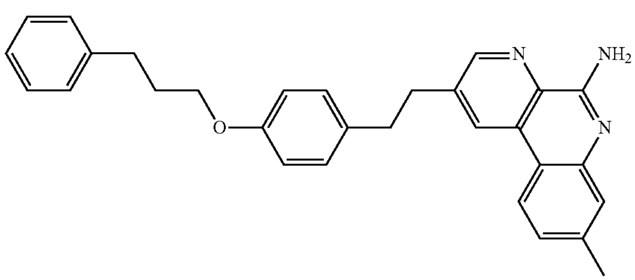 [SMILES: Cc1ccc2c(c1)nc(N)c1ncc(CCc3ccc(OCCCc4ccccc4)cc3)cc12] | 448.6 |
| 103 | 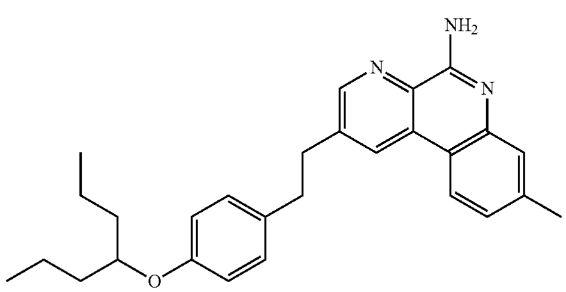 [SMILES: CCCC(CCC)Oc1ccc(CCc2cnc3c(N)nc4cc(C)ccc4c3c2)cc1] | 428.3 |

TABLE 1-continued

| Compound Number | Structure | Physical Data MS (m/z) [M + H] |
|---|---|---|
| 104 | 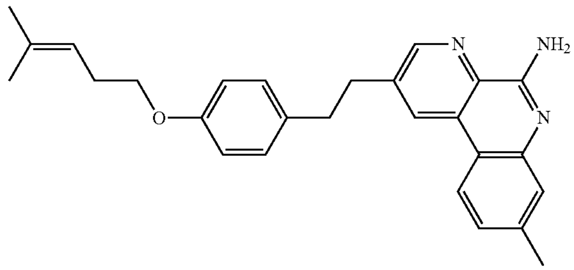 [SMILES: CC(C)=CCCOc1ccc(CCc2cnc3c(N)nc4cc(C)ccc4c3c2)cc1] | 412.2 |
| 105 | 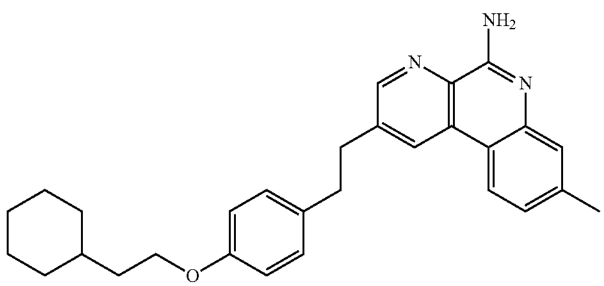 [SMILES: Cc1ccc2c(c1)nc(N)c1ncc(CCc3ccc(OCCC4CCCCC4)cc3)cc12] | 440.3 |
| 106 | 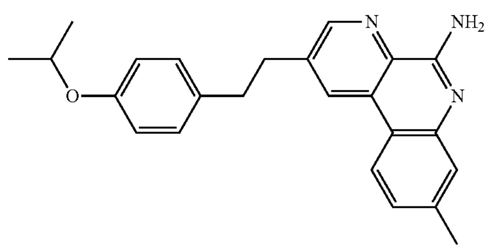 [SMILES: Cc1ccc2c(c1)nc(N)c1ncc(CCc3ccc(OC(C)C)cc3)cc12] | 372.2 |
| 107 | 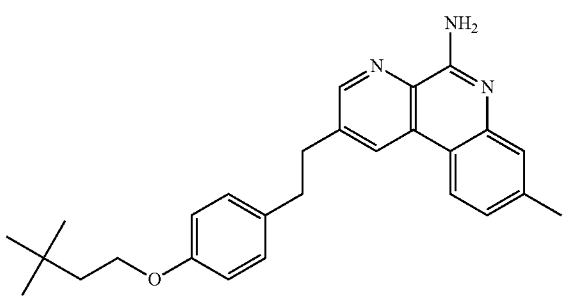 [SMILES: Cc1ccc2c(c1)nc(N)c1ncc(CCc3ccc(OCCC(C)(C)C)cc3)cc12] | 414.3 |
| 108 | 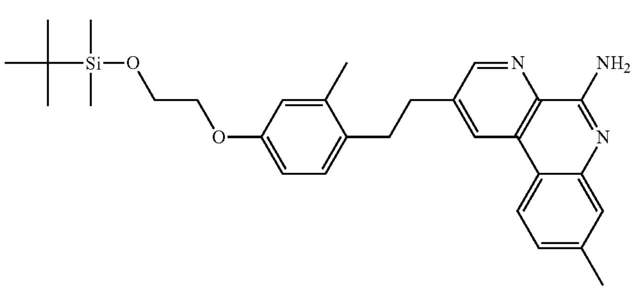 [SMILES: Cc1ccc2c(c1)nc(N)c1ncc(CCc3ccc(OCCO[Si](C)(C)C(C)(C)C)cc3C)cc12] | 502.3 |

TABLE 1-continued

| Compound Number | Structure | Physical Data MS (m/z) [M + H] |
|---|---|---|
| 109 | 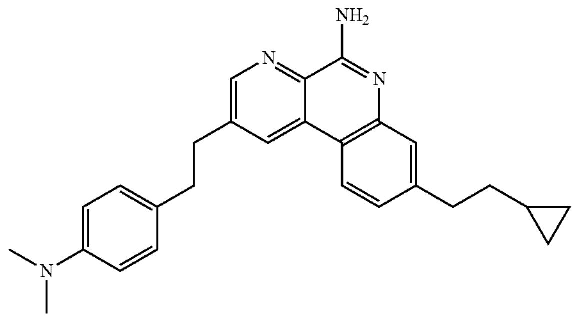 [SMILES: CN(C)c1ccc(CCc2cnc3c(N)nc4cc(CCC5CC5)ccc4c3c2)cc1] | 411.3 |
| 110 | 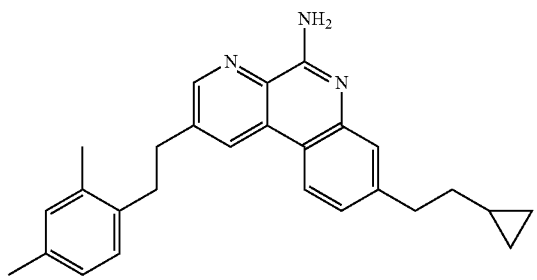 [SMILES: Cc1ccc(CCc2cnc3c(N)nc4cc(CCC5CC5)ccc4c3c2)c(C)c1] | 396.2 |
| 111 | 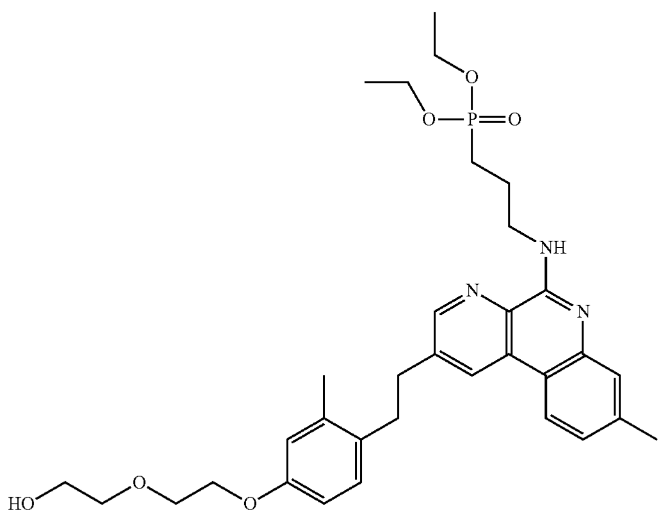 [SMILES: CCOP(=O)(CCCNc1nc2cc(C)ccc2c2cc(CCc3ccc(OCCOCCO)cc3C)cnc12)OCC] | 610.3 |
| 112 | 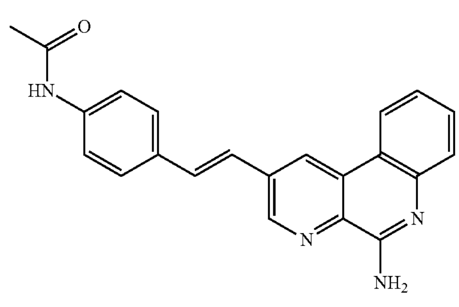 [SMILES: CC(=O)Nc1ccc(/C=C/c2cnc3c(N)nc4ccccc4c3c2)cc1] | 355.2 |

TABLE 1-continued
| Compound Number | Structure | Physical Data MS (m/z) [M + H] |
|---|---|---|
| 113 | 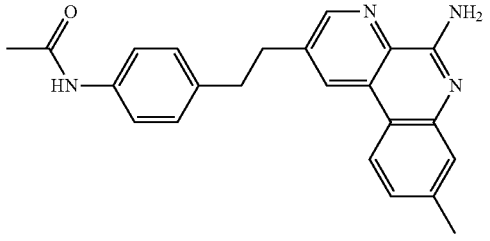 [SMILES: CC(=O)Nc1ccc(CCc2cnc3c(N)nc4cc(C)ccc4c3c2)cc1] | 371.2 |
| 114 | 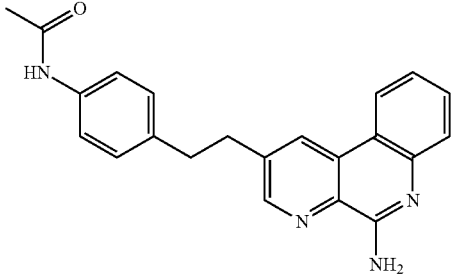 [SMILES: CC(=O)Nc1ccc(CCc2cnc3c(N)nc4ccccc4c3c2)cc1] | 357.2 |
| 115 | 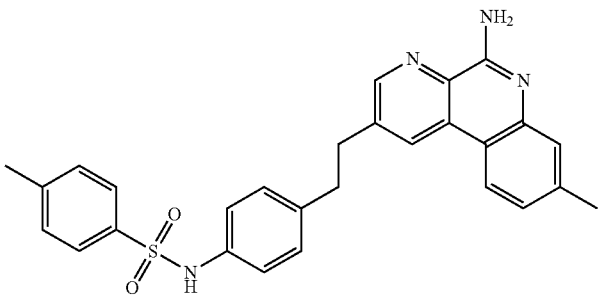 | 483.2 |
| 116 | 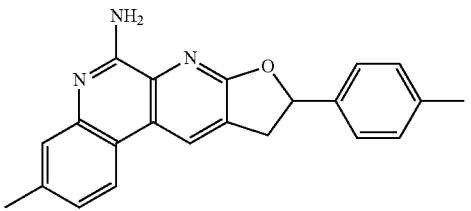 | 342.2 |
| 117 | 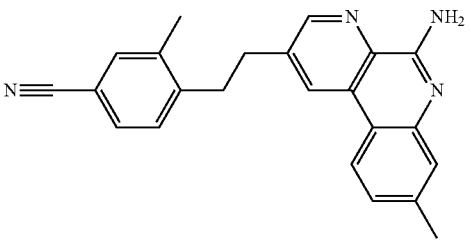 [SMILES: Cc1ccc2c(c1)nc(N)c1ncc(CCc3ccc(C#N)cc3C)cc12] | 353.2 |
| 118 | 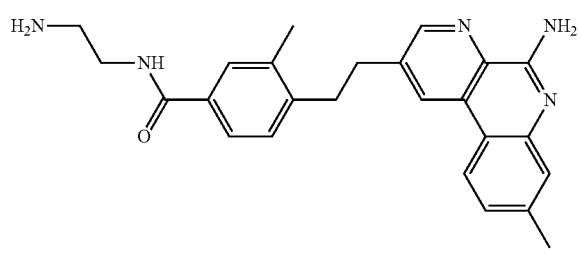 [SMILES: Cc1ccc2c(c1)nc(N)c1ncc(CCc3ccc(C(=O)NCCN)cc3C)cc12] | 414.2 |

TABLE 1-continued

| Compound Number | Structure | Physical Data MS (m/z) [M + H] |
|---|---|---|
| 119 | 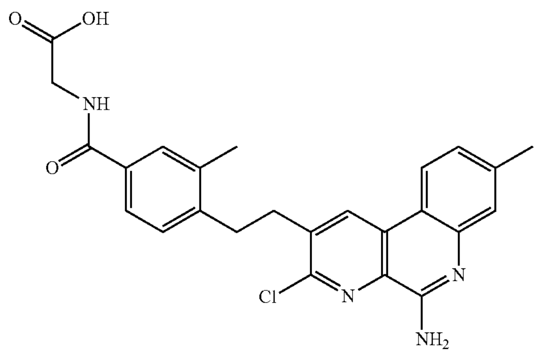 [SMILES: Cc1ccc2c(c1)nc(N)c1nc(Cl)c(CCc3ccc(C(=O)NCC(=O)O)cc3C)cc12] | 463.2 |
| 120 | 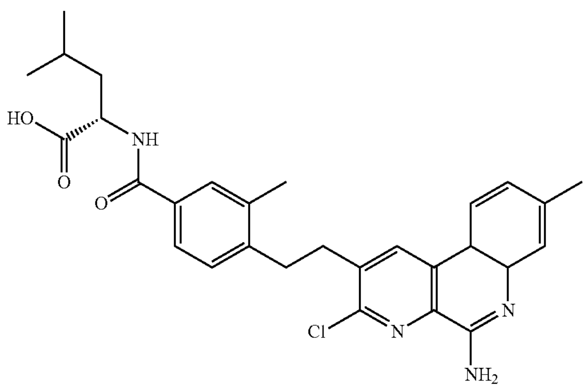 [SMILES: CC1=CC2N=C(N)c3nc(Cl)c(CCc4ccc(C(=O)N[C@@H](CC(C)C)C(=O)O)cc4C)cc3C2C=C1] | 519.2 |
| 121 | 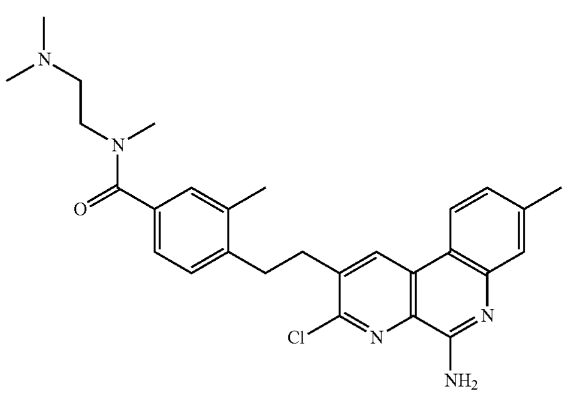 | 490.2 |
| 122 | 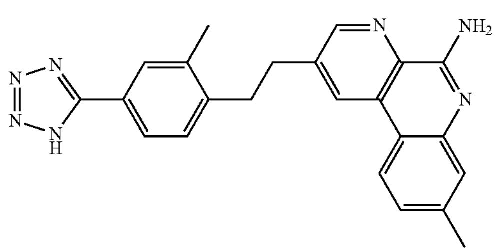 [SMILES: Cc1ccc2c(c1)nc(N)c1ncc(CCc3ccc(-c4nnn[nH]4)cc3C)cc12] | 396.2 |

TABLE 1-continued

| Compound Number | Structure | Physical Data MS (m/z) [M + H] |
|---|---|---|
| 123 | 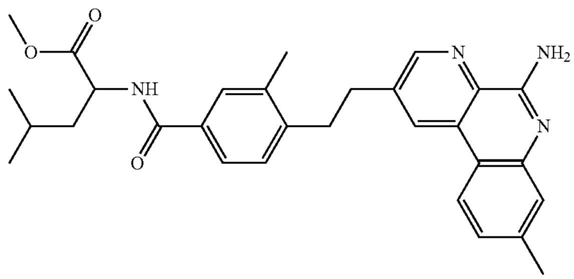 | 499.3 |
| 124 | 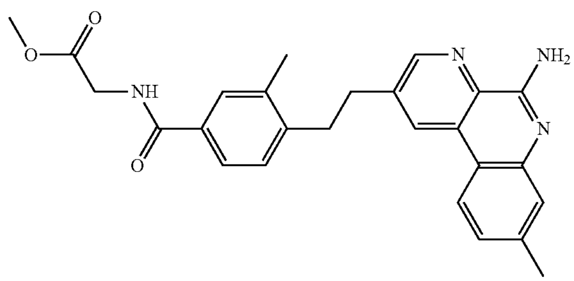 | 443.2 |
| 125 | 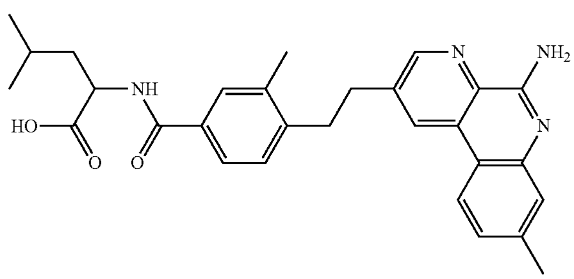 [SMILES: Cc1ccc2c(c1)nc(N)c1ncc(CCc3ccc(C(=O)NC(CC(C)C)C(=O)O)cc3C)cc12] | 485.3 |
| 126 | 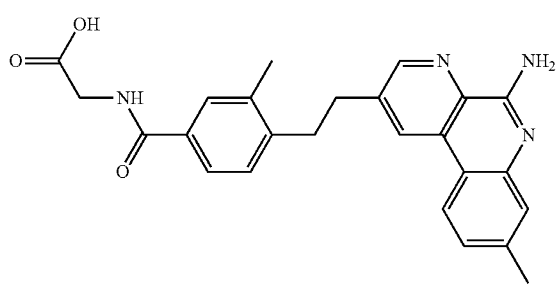 [SMILES: Cc1ccc2c(c1)nc(N)c1ncc(CCc3ccc(C(=O)NCC(=O)O)cc3C)cc12] | 429.2 |
| 127 | 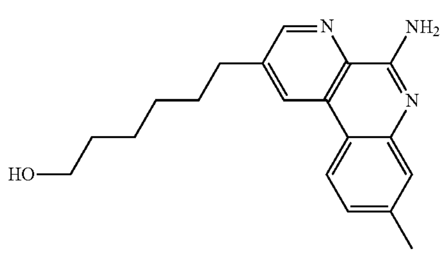 [SMILES: Cc1ccc2c(c1)nc(N)c1ncc(CCCCCCO)cc12] | 310.2 |

TABLE 1-continued

| Compound Number | Structure | Physical Data MS (m/z) [M + H] |
|---|---|---|
| 128 | 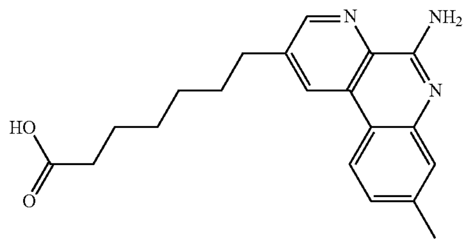 [SMILES: Cc1ccc2c(c1)nc(N)c1ncc(CCCCCCC(=O)O)cc12] | 338.2 |
| 129 | 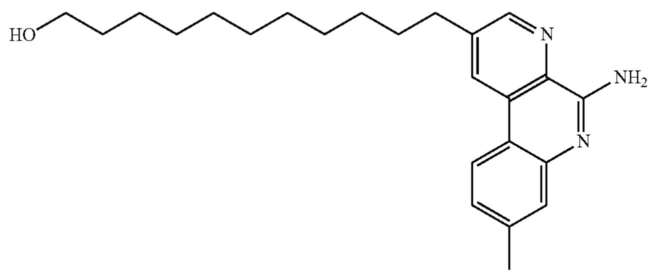 [SMILES: Cc1ccc2c(c1)nc(N)c1ncc(CCCCCCCCCCCO)cc12] | 380.3 |
| 130 | 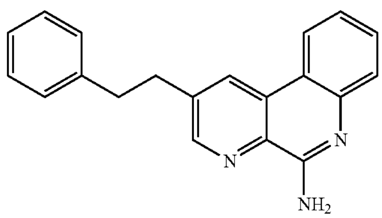 [SMILES: Nc1nc2ccccc2c2cc(CCc3ccccc3)cnc12] | 300.1 |
| 131 | 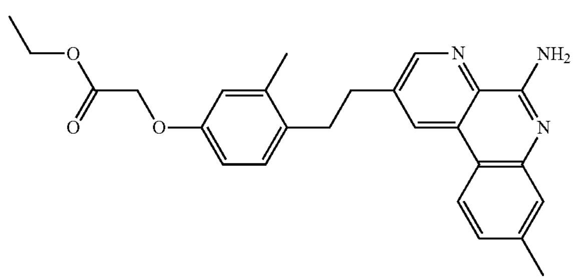 [SMILES: CCOC(=O)COc1ccc(CCc2cnc3c(N)nc4cc(C)ccc4c3c2)c(C)c1] | 430.2 |
| 132 | 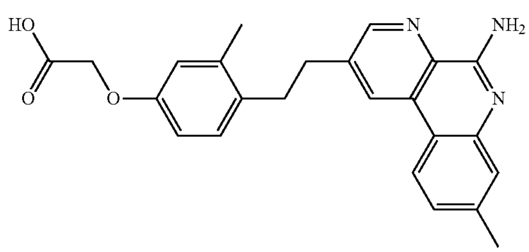 [SMILES: Cc1ccc2c(c1)nc(N)c1ncc(CCc3ccc(OCC(=O)O)cc3C)cc12] | 402.2 |
| 133 | 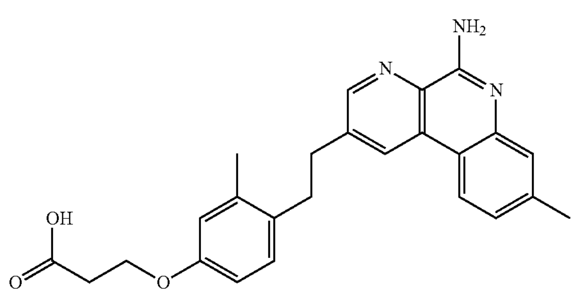 [SMILES: Cc1ccc2c(c1)nc(N)c1ncc(CCc3ccc(OCCC(=O)O)cc3C)cc12] | 416.2 |

US 8,466,167 B2
307                                                                 308
TABLE 1-continued
| Compound Number | Structure | Physical Data MS (m/z) [M + H] |
|---|---|---|
| 134 | 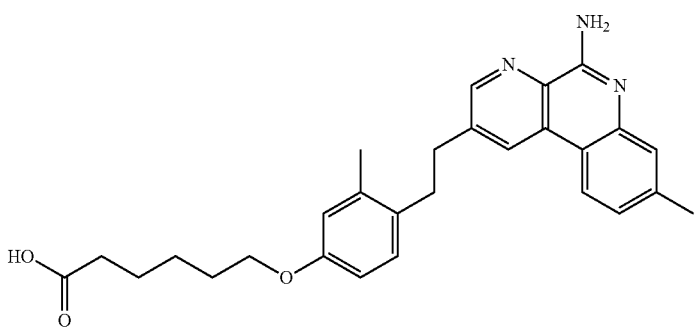 [SMILES: Cc1ccc2c(c1)nc(N)c1ncc(CCc3ccc(OCCCCCC(=O)O)cc3C)cc12] | 458.2 |
| 135 | 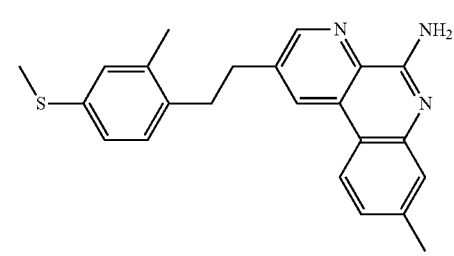 | 374.2 |
| 136 | 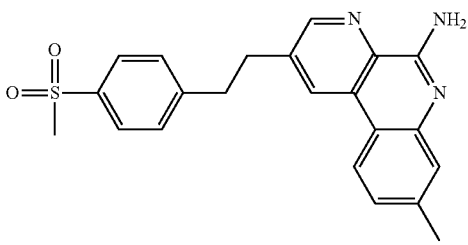 [SMILES: Cc1ccc2c(c1)nc(N)c1ncc(CCc3ccc(S(C)(=O)=O)cc3)cc12] | 392.1 |
| 137 | 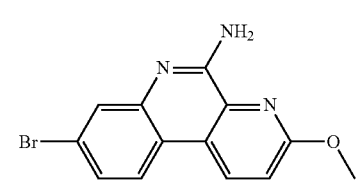 [SMILES: COc1ccc2c(n1)c(N)nc1cc(Br)ccc12] | 304.0 |
| 138 | 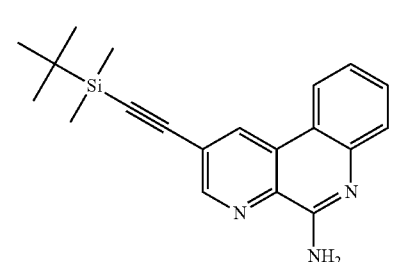 | 334.2 |
| 139 | 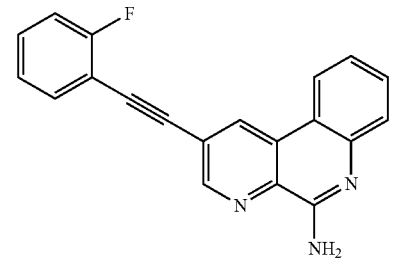 [SMILES: Nc1nc2ccccc2c2cc(C#Cc3ccccc3F)cnc12] | 314.1 |

TABLE 1-continued

| Compound Number | Structure | Physical Data MS (m/z) [M + H] |
|---|---|---|
| 140 | 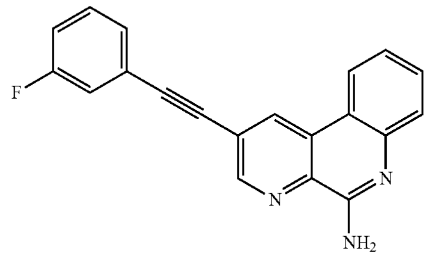 [SMILES: Nc1nc2ccccc2c2cc(C#Cc3cccc(F)c3)cnc12] | 314.1 |
| 141 | 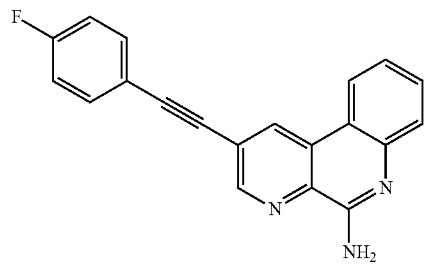 [SMILES: Nc1nc2ccccc2c2cc(C#Cc3ccc(F)cc3)cnc12] | 314.1 |
| 142 | 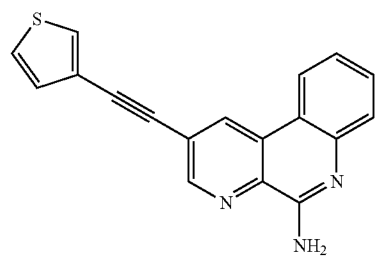 [SMILES: Nc1nc2ccccc2c2cc(C#Cc3ccsc3)cnc12] | 302.1 |
| 143 | 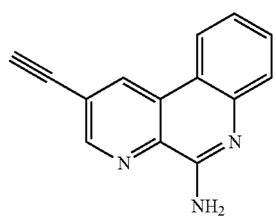 [SMILES: C#Cc1cnc2c(N)nc3ccccc3c2c1] | 220.1 |
| 144 | 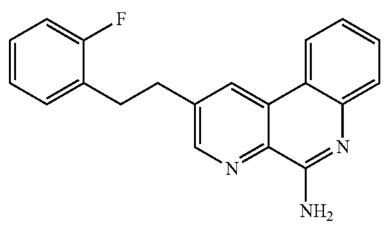 [SMILES: Nc1nc2ccccc2c2cc(CCc3ccccc3F)cnc12] | 318.1 |
| 145 | 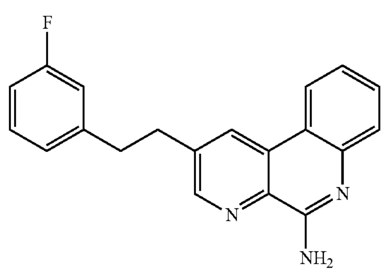 [SMILES: Nc1nc2ccccc2c2cc(CCc3cccc(F)c3)cnc12] | 318.1 |

TABLE 1-continued

| Compound Number | Structure | Physical Data MS (m/z) [M + H] |
|---|---|---|
| 146 | 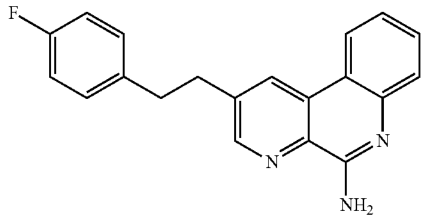 [SMILES: Nc1nc2ccccc2c2cc(CCc3ccc(F)cc3)cnc12] | 318.1 |
| 147 | 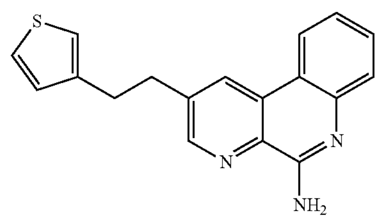 [SMILES: Nc1nc2ccccc2c2cc(CCc3ccsc3)cnc12] | 306.1 |
| 148 | 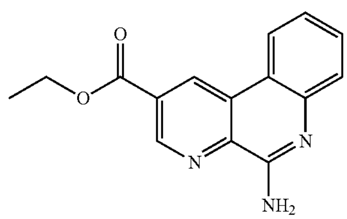 [SMILES: CCOC(=O)c1cnc2c(N)nc3ccccc3c2c1] | 268.1 |
| 149 | 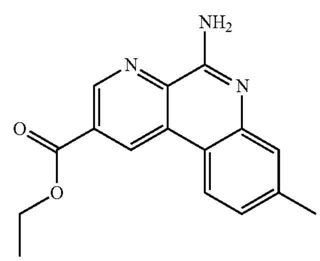 [SMILES: CCOC(=O)c1cnc2c(N)nc3cc(C)ccc3c2c1] | 282.1 |
| 150 | 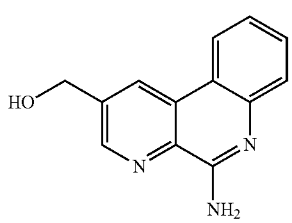 [SMILES: Nc1nc2ccccc2c2cc(CO)cnc12] | 226.1 |
| 151 | 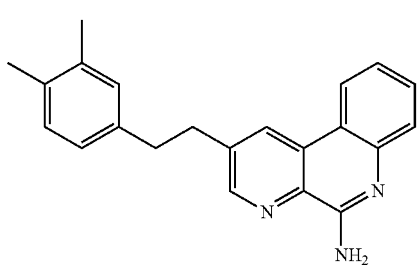 [SMILES: Cc1ccc(CCc2cnc3c(N)nc4ccccc4c3c2)cc1C] | 328.2 |

TABLE 1-continued
| Compound Number | Structure | Physical Data MS (m/z) [M + H] |
|---|---|---|
| 152 | 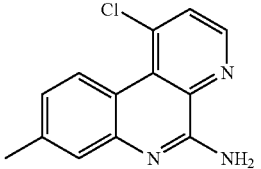 [SMILES: Cc1ccc2c(c1)nc(N)c1nccc(Cl)c12] | 244.1 |
| 153 | 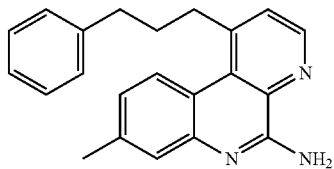 [SMILES: Cc1ccc2c(c1)nc(N)c1nccc(CCCc3ccccc3)c12] | 328.2 |
| 154 | 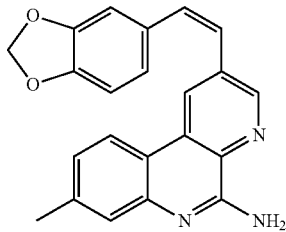 [SMILES: Cc1ccc2c(c1)nc(N)c1ncc(/C=C\c3ccc4c(c3)OCO4)cc12] | 356.1 |
| 155 | 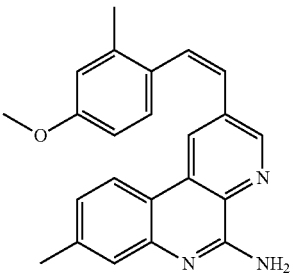 [SMILES: COc1ccc(/C=C\c2cnc3c(N)nc4cc(C)ccc4c3c2)c(C)c1] | 356.2 |
| 156 | 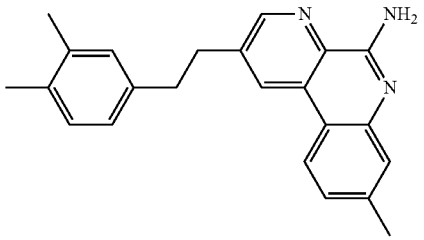 | 342.2 |
| 157 | 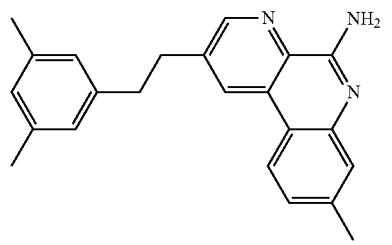 [SMILES: Cc1cc(C)cc(CCc2cnc3c(N)nc4cc(C)ccc4c3c2)c1] | 342.2 |

TABLE 1-continued

| Compound Number | Structure | Physical Data MS (m/z) [M + H] |
|---|---|---|
| 158 | 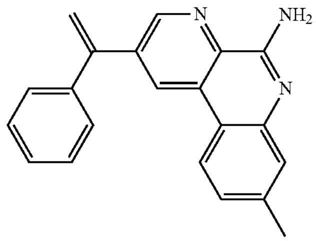 [SMILES: C=C(c1ccccc1)c1cnc2c(N)nc3cc(C)ccc3c2c1] | 312.1 |
| 159 | 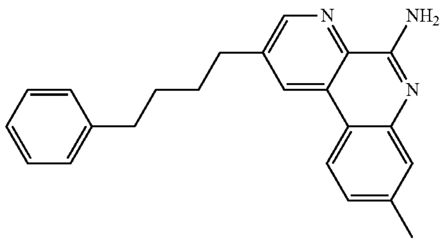 [SMILES: Cc1ccc2c(c1)nc(N)c1ncc(CCCCc3ccccc3)cc12] | 342.2 |
| 160 | 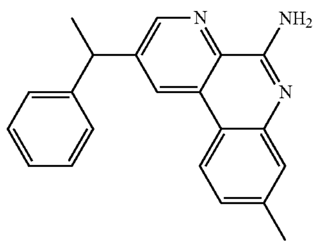 [SMILES: Cc1ccc2c(c1)nc(N)c1ncc(C(C)c3ccccc3)cc12] | 314.2 |
| 161 | 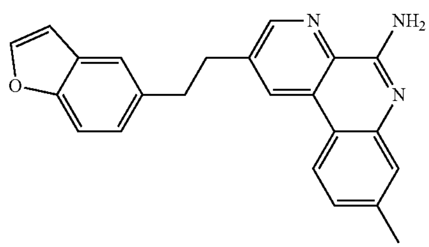 [SMILES: Cc1ccc2c(c1)nc(N)c1ncc(CCc3ccc4occc4c3)cc12] | 353.2 |
| 162 | 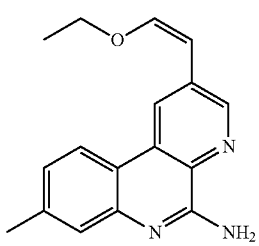 [SMILES: CCO/C=C\c1cnc2c(N)nc3cc(C)ccc3c2c1] | 280.1 |
| 163 | 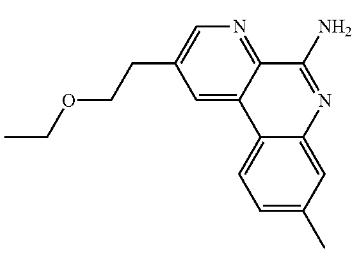 [SMILES: CCOCCc1cnc2c(N)nc3cc(C)ccc3c2c1] | 282.2 |

TABLE 1-continued

| Compound Number | Structure | Physical Data MS (m/z) [M + H] |
|---|---|---|
| 164 | 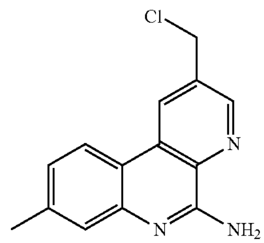 | 258.1 |
| 165 | 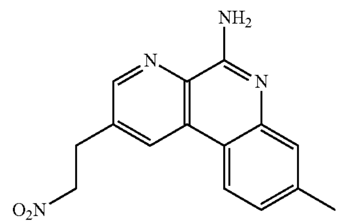 | 283.1 |
| 166 | 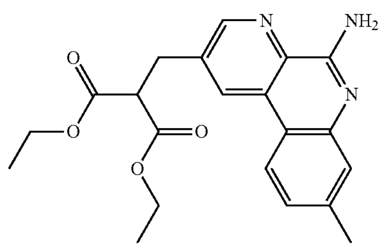 [SMILES: CCOC(=O)C(Cc1cnc2c(N)nc3cc(C)ccc3c2c1)C(=O)OCC] | 382.2 int |
| 167 | 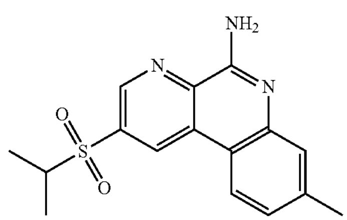 [SMILES: Cc1ccc2c(c1)nc(N)c1ncc(S(=O)(=O)C(C)C)cc12] | 316.1 |
| 168 | 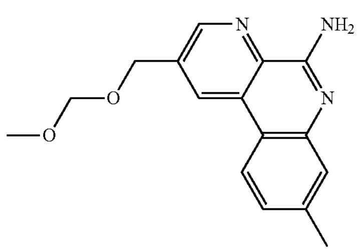 | 284.1 |
| 169 | 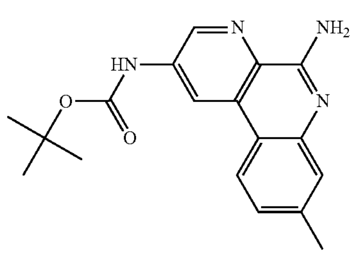 [SMILES: Cc1ccc2c(c1)nc(N)c1ncc(NC(=O)OC(C)(C)C)cc12] | 325.2 |

TABLE 1-continued
| Compound Number | Structure | Physical Data MS (m/z) [M + H] |
|---|---|---|
| 170 | 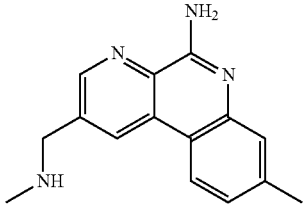 | 253.1 |
| 171 | 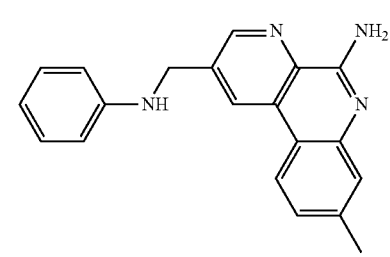 [SMILES: Cc1ccc2c(c1)nc(N)c1ncc(CNc3ccccc3)cc12] | 315.2 |
| 172 | 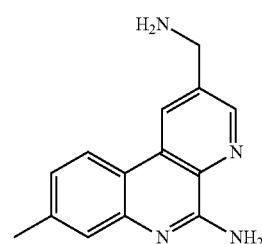 | 239.1 |
| 173 | 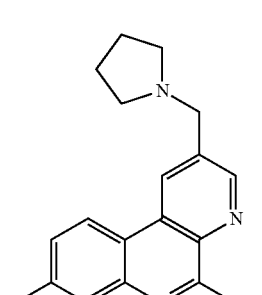 | 293.2 |
| 174 | 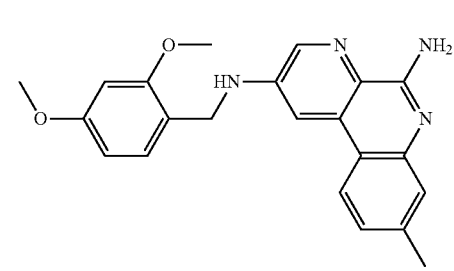 | 375.2 |
| 175 | 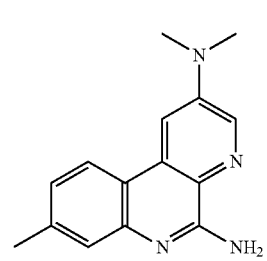 | 253.1 |

TABLE 1-continued
| Compound Number | Structure | Physical Data MS (m/z) [M + H] |
|---|---|---|
| 176 | 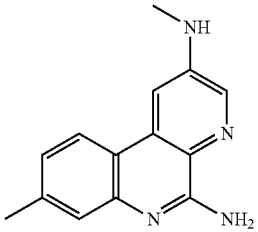 [SMILES: CNc1cnc2c(N)nc3cc(C)ccc3c2c1] | 239.1 |
| 177 | 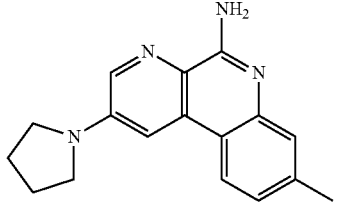 [SMILES: Cc1ccc2c(c1)nc(N)c1ncc(N3CCCC3)cc12] | 279.2 |
| 178 | 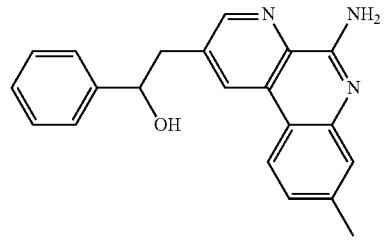 [SMILES: Cc1ccc2c(c1)nc(N)c1ncc(CC(O)c3ccccc3)cc12] | 330.2 |
| 179 | 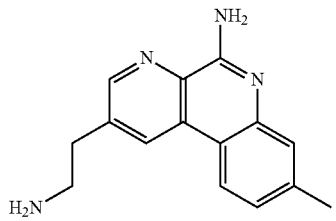 [SMILES: Cc1ccc2c(c1)nc(N)c1ncc(CCN)cc12] | 253.1 |
| 180 | 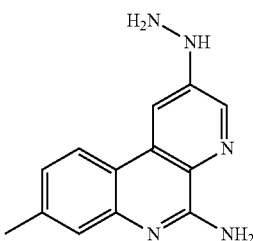 | 240.1 |
| 181 | 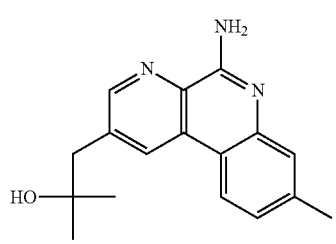 [SMILES: Cc1ccc2c(c1)nc(N)c1ncc(CC(C)(C)O)cc12] | 282.2 |

TABLE 1-continued

| Compound Number | Structure | Physical Data MS (m/z) [M + H] |
|---|---|---|
| 182 | 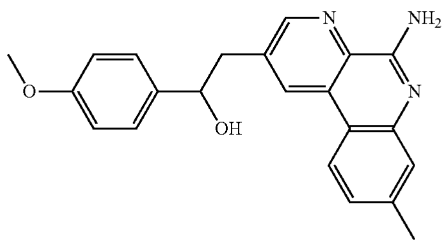 | 360.2 |
| 183 | 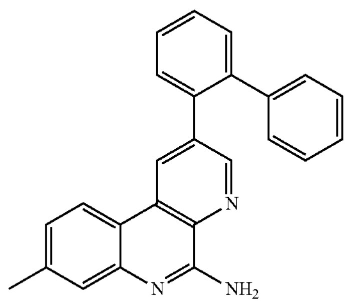 [SMILES: Cc1ccc2c(c1)nc(N)c1ncc(-c3ccccc3-c3ccccc3)cc12] | 362.2 |
| 184 | 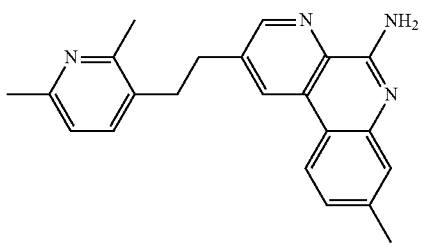 | 343.2 |
| 185 | 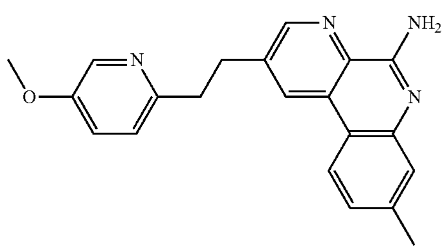 | 345.2 |
| 186 | 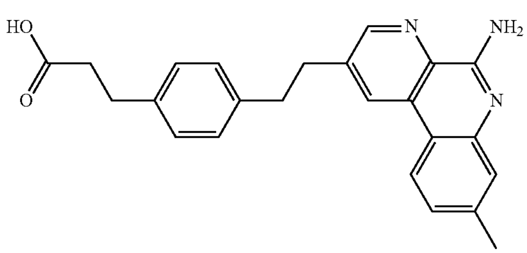 [SMILES: Cc1ccc2c(c1)nc(N)c1ncc(CCc3ccc(CCC(=O)O)cc3)cc12] | 386.2 |
| 187 | 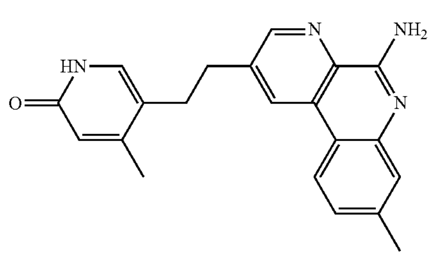 [SMILES: Cc1ccc2c(c1)nc(N)c1ncc(CCc3c[nH]c(=O)cc3C)cc12] | 345.2 |

TABLE 1-continued

| Compound Number | Structure | Physical Data MS (m/z) [M + H] |
|---|---|---|
| 188 | 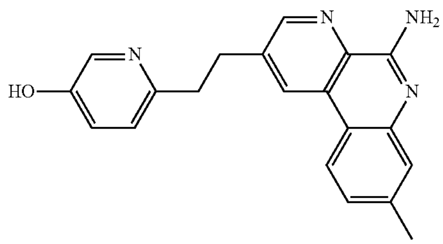 [SMILES: Cc1ccc2c(c1)nc(N)c1ncc(CCc3ccc(O)cn3)cc12] | 331.1 |
| 189 | 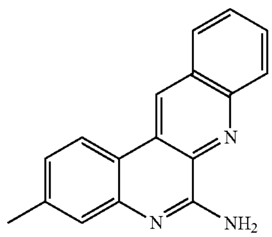 [SMILES: Cc1ccc2c(c1)nc(N)c1nc3ccccc3cc12] | 260.1 |
| 190 | 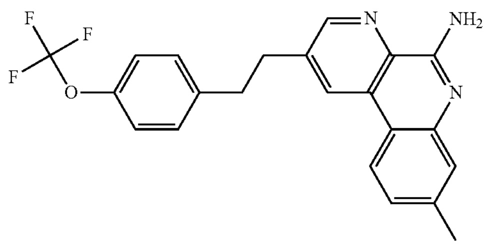 [SMILES: Cc1ccc2c(c1)nc(N)c1ncc(CCc3ccc(OC(F)(F)F)cc3)cc12] | 398.1 |
| 191 | 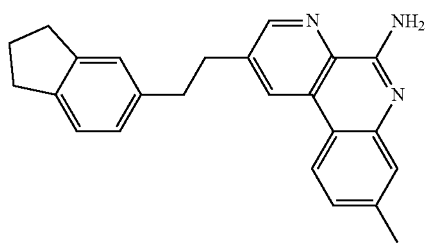 [SMILES: Cc1ccc2c(c1)nc(N)c1ncc(CCc3ccc4c(c3)CCC4)cc12] | 354.2 |
| 192 | 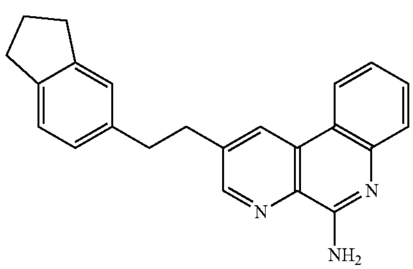 [SMILES: Nc1nc2ccccc2c2cc(CCc3ccc4c(c3)CCC4)cnc12] | 340.2 |
| 193 | 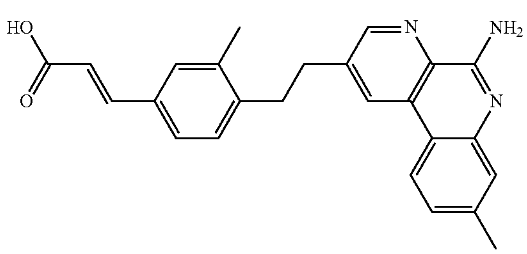 [SMILES: Cc1ccc2c(c1)nc(N)c1ncc(CCc3ccc(/C=C/C(=O)O)cc3C)cc12] | 398.2 |

TABLE 1-continued

| Compound Number | Structure | Physical Data MS (m/z) [M + H] |
|---|---|---|
| 194 | 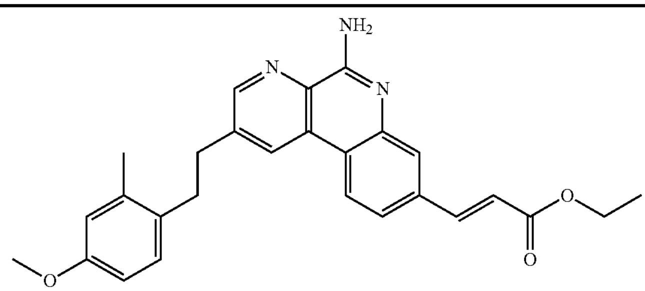 | 442.2 |
| 195 | 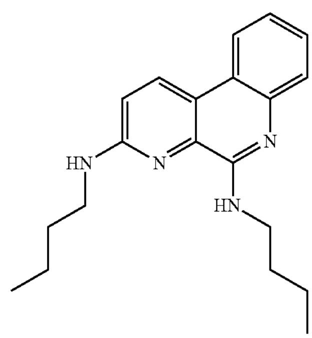 [SMILES: CCCCNc1ccc2c(n1)c(NCCCC)nc1ccccc12] | 323.2 |
| 196 | 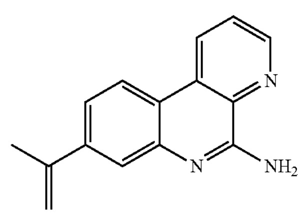 [SMILES: C=C(C)c1ccc2c(c1)nc(N)c1ncccc12] | 236.1 |
| 197 | 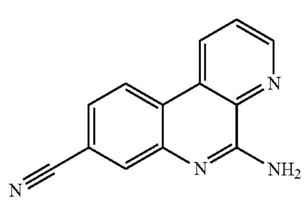 [SMILES: N#Cc1ccc2c(c1)nc(N)c1ncccc12] | 221.1 |
| 198 | 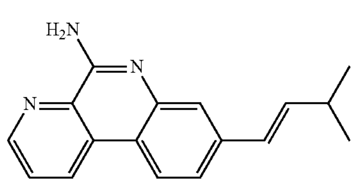 [SMILES: CC(C)/C=C/c1ccc2c(c1)nc(N)c1ncccc12] | 264.1 |
| 199 | 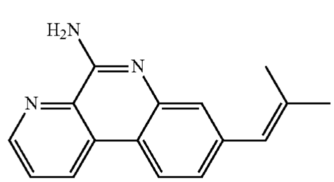 [SMILES: CC(C)=Cc1ccc2c(c1)nc(N)c1ncccc12] | 250.1 |
| 200 | 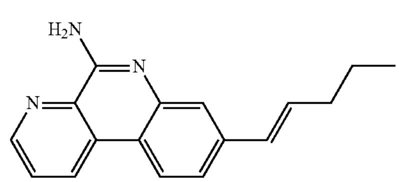 [SMILES: CCC/C=C/c1ccc2c(c1)nc(N)c1ncccc12] | 264.1 |

TABLE 1-continued

| Compound Number | Structure | Physical Data MS (m/z) [M + H] |
|---|---|---|
| 201 | 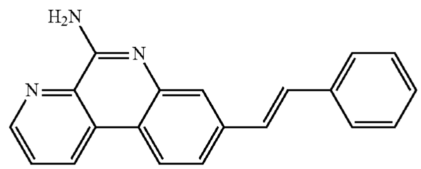 [SMILES: Nc1nc2cc(/C=C/c3ccccc3)ccc2c2cccnc12] | 298.1 |
| 202 | 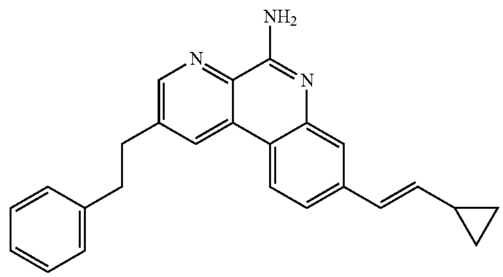 [SMILES: Nc1nc2cc(/C=C/C3CC3)ccc2c2cc(CCc3ccccc3)cnc12] | 366.2 |
| 203 | 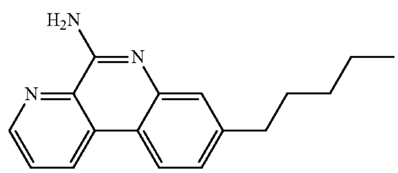 [SMILES: CCCCCc1ccc2c(c1)nc(N)c1ncccc12] | 266.2 |
| 204 | 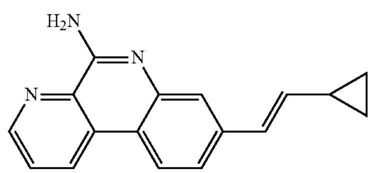 [SMILES: Nc1nc2cc(/C=C/C3CC3)ccc2c2cccnc12] | 262.1 |
| 205 | 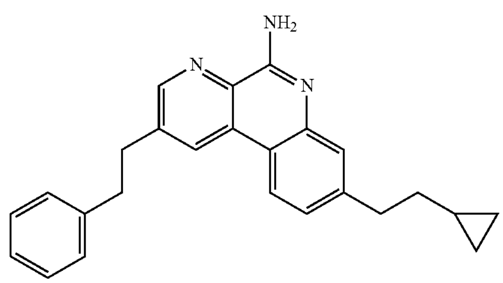 [SMILES: Nc1nc2cc(CCC3CC3)ccc2c2cc(CCc3ccccc3)cnc12] | 368.2 |
| 206 | 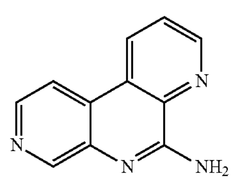 | 197.1 |
| 207 | 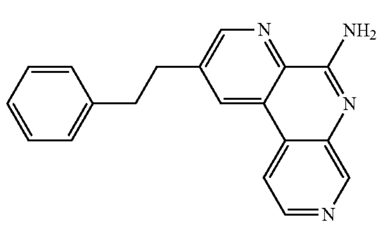 [SMILES: Nc1nc2cnccc2c2cc(CCc3ccccc3)cnc12] | 301.1 |

TABLE 1-continued

| Compound Number | Structure | Physical Data MS (m/z) [M + H] |
|---|---|---|
| 208 | 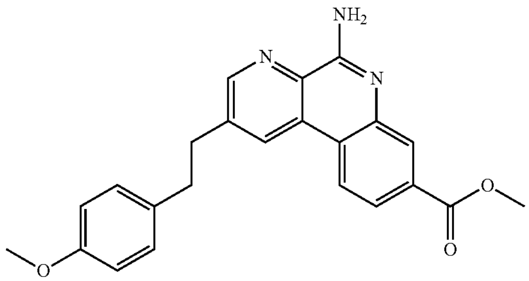 | 388.2 |
| 209 | 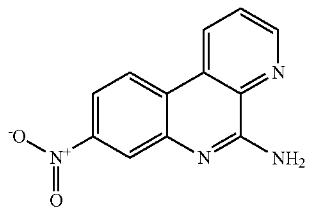 | 241.1 |
| 210 | 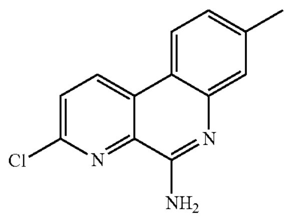 [SMILES: Cc1ccc2c(c1)nc(N)c1nc(Cl)ccc12] | 244.1 |
| 211 | 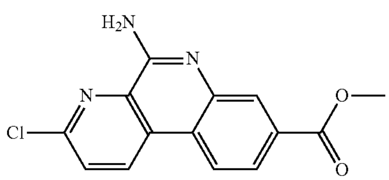 [SMILES: COC(=O)c1ccc2c(c1)nc(N)c1nc(Cl)ccc12] | 288.1 |
| 212 | 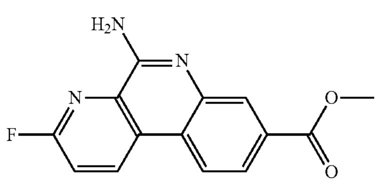 [SMILES: COC(=O)c1ccc2c(c1)nc(N)c1nc(F)ccc12] | 272.1 |
| 213 | 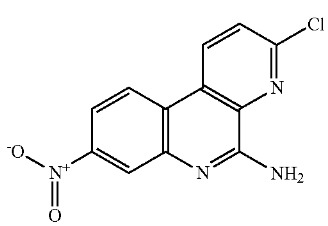 | 275.0 |
| 214 | 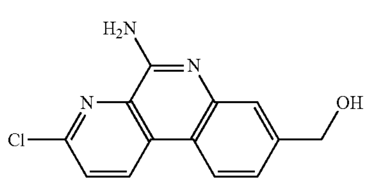 [SMILES: Nc1nc2cc(CO)ccc2c2ccc(Cl)nc12] | 260.1 |

TABLE 1-continued
| Compound Number | Structure | Physical Data MS (m/z) [M + H] |
|---|---|---|
| 215 | 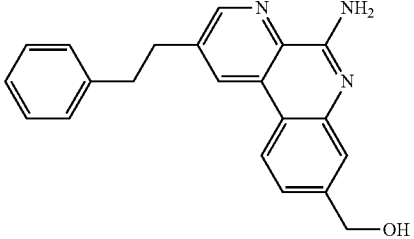 [SMILES: Nc1nc2cc(CO)ccc2c2cc(CCc3ccccc3)cnc12] | 330.2 |
| 216 | 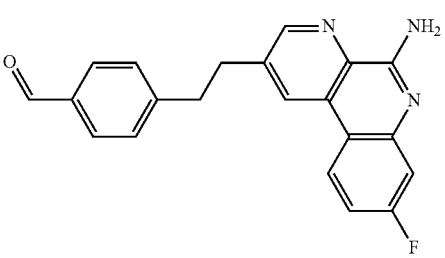 [SMILES: Nc1nc2cc(F)ccc2c2cc(CCc3ccc(C=O)cc3)cnc12] | 346.1 |
| 217 | 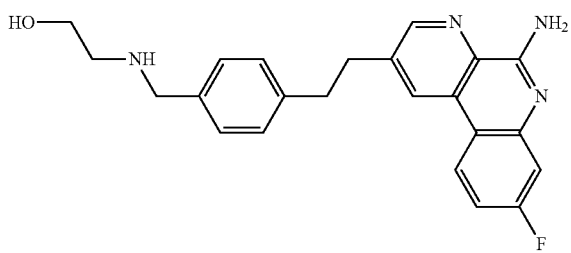 [SMILES: Nc1nc2cc(F)ccc2c2cc(CCc3ccc(CNCCO)cc3)cnc12] | 391.2 |
| 218 | 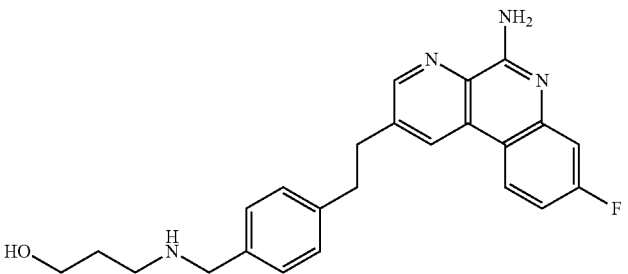 [SMILES: Nc1nc2cc(F)ccc2c2cc(CCc3ccc(CNCCCO)cc3)cnc12] | 405.2 |
| 219 | 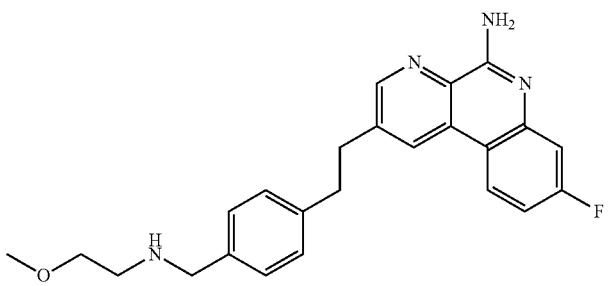 [SMILES: COCCNCc1ccc(CCc2cnc3c(N)nc4cc(F)ccc4c3c2)cc1] | 405.2 |

TABLE 1-continued

| Compound Number | Structure | Physical Data MS (m/z) [M + H] |
|---|---|---|
| 220 | 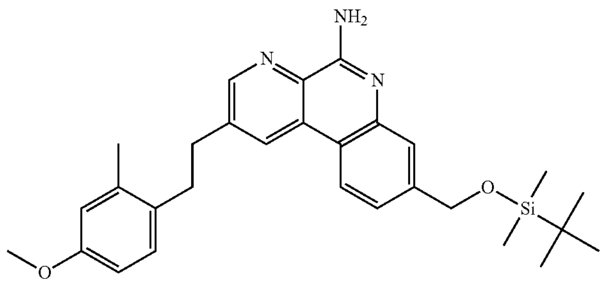 [SMILES: COc1ccc(CCc2cnc3c(N)nc4cc(CO[Si](C)(C)C(C)(C)C)ccc4c3c2)c(C)c1] | 488.3 |
| 221 | 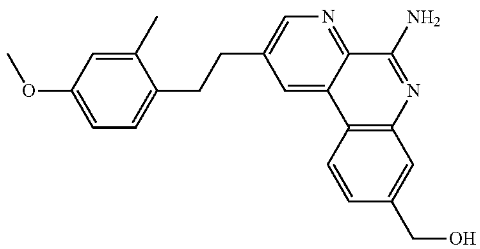 [SMILES: COc1ccc(CCc2cnc3c(N)nc4cc(CO)ccc4c3c2)c(C)c1] | 374.2 |
| 222 | 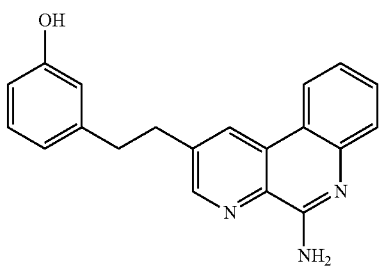 | 316.2 |
| 223 | 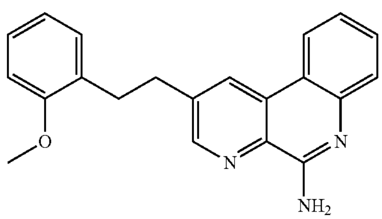 [SMILES: COc1ccccc1CCc1cnc2c(N)nc3ccccc3c2c1] | 330.2 |
| 224 | 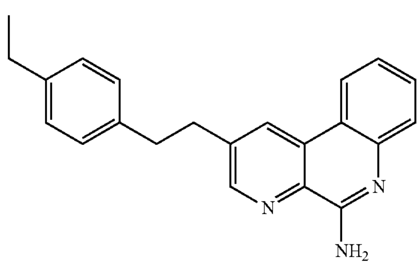 | 328.2 |
| 225 | 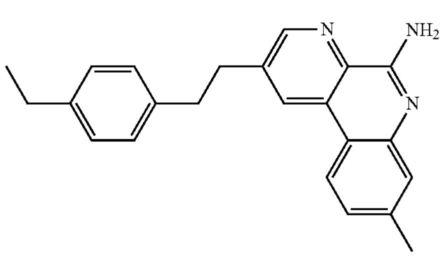 [SMILES: CCc1ccc(CCc2cnc3c(N)nc4cc(C)ccc4c3c2)cc1] | 342.2 |

TABLE 1-continued

| Compound Number | Structure | Physical Data MS (m/z) [M + H] |
|---|---|---|
| 226 | 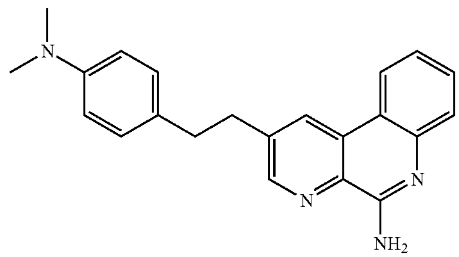 [SMILES: CN(C)c1ccc(CCc2cnc3c(N)nc4ccccc4c3c2)cc1] | 343.2 |
| 227 | 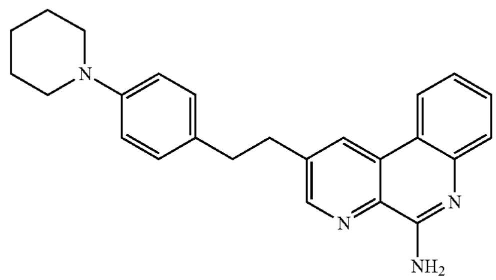 [SMILES: Nc1nc2ccccc2c2cc(CCc3ccc(N4CCCCC4)cc3)cnc12] | 383.2 |
| 228 | 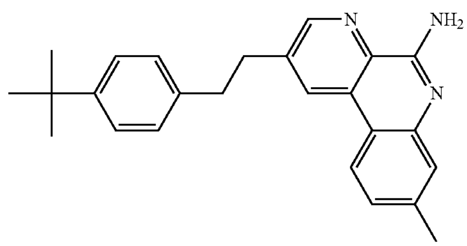 [SMILES: Cc1ccc2c(c1)nc(N)c1ncc(CCc3ccc(C(C)(C)C)cc3)cc12] | 370.2 |
| 229 | 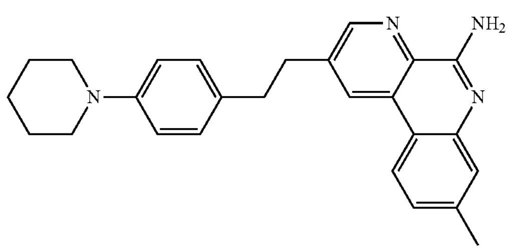 [SMILES: Cc1ccc2c(c1)nc(N)c1ncc(CCc3ccc(N4CCCCC4)cc3)cc12] | 397.2 |
| 230 | 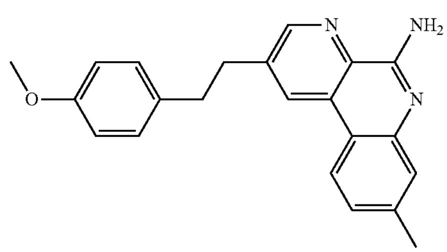 | 344.2 |
| 231 | 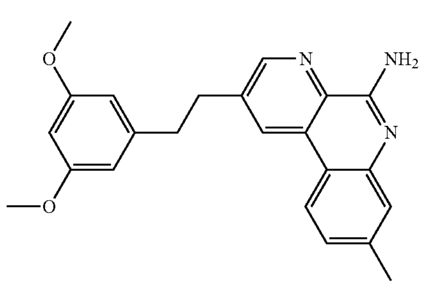 | 374.2 |

TABLE 1-continued

| Compound Number | Structure | Physical Data MS (m/z) [M + H] |
|---|---|---|
| 232 | 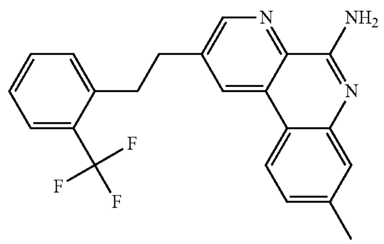 [SMILES: Cc1ccc2c(c1)nc(N)c1ncc(CCc3ccccc3C(F)(F)F)cc12] | 382.2 |
| 233 | 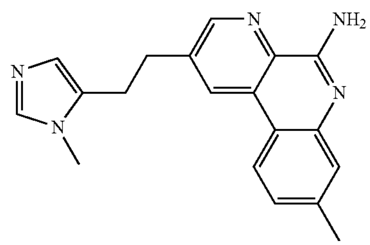 [SMILES: Cc1ccc2c(c1)nc(N)c1ncc(CCc3cncn3C)cc12] | 318.2 |
| 234 | 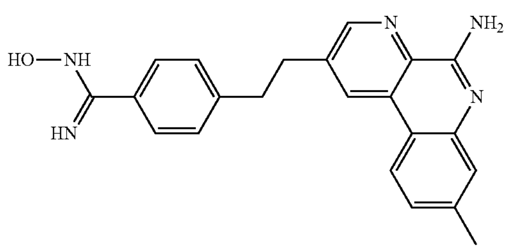 [SMILES: Cc1ccc2c(c1)nc(N)c1ncc(CCc3ccc(C(=N)NO)cc3)cc12] | 372.2 |
| 235 | 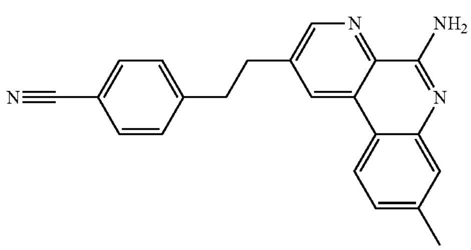 [SMILES: Cc1ccc2c(c1)nc(N)c1ncc(CCc3ccc(C#N)cc3)cc12] | 339.2 |
| 236 | 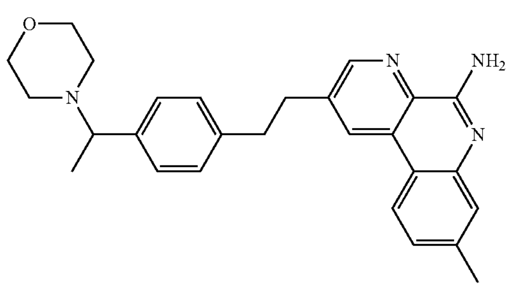 [SMILES: Cc1ccc2c(c1)nc(N)c1ncc(CCc3ccc(C(C)N4CCOCC4)cc3)cc12] | 427.2 |
| 237 | 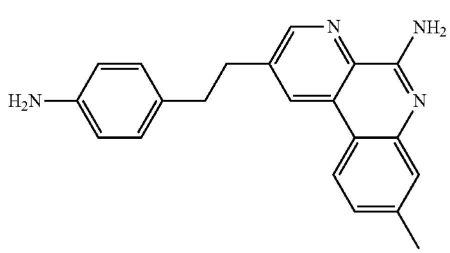 [SMILES: Cc1ccc2c(c1)nc(N)c1ncc(CCc3ccc(N)cc3)cc12] | 329.2 |

TABLE 1-continued

| Compound Number | Structure | Physical Data MS (m/z) [M + H] |
|---|---|---|
| 238 | 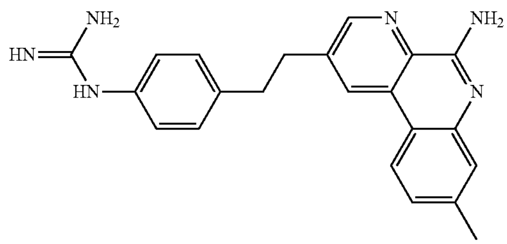 [SMILES: Cc1ccc2c(c1)nc(N)c1ncc(CCc3ccc(NC(=N)N)cc3)cc12] | 371.2 |
| 239 | 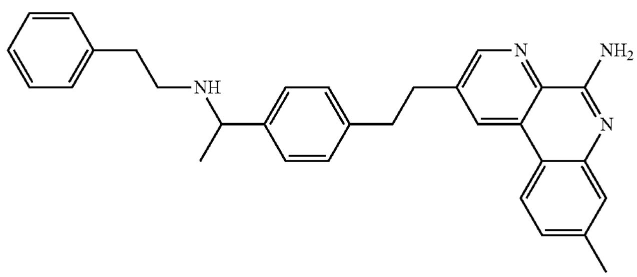 [SMILES: Cc1ccc2c(c1)nc(N)c1ncc(CCc3ccc(C(C)NCCc4ccccc4)cc3)cc12] | 461.3 |
| 240 | 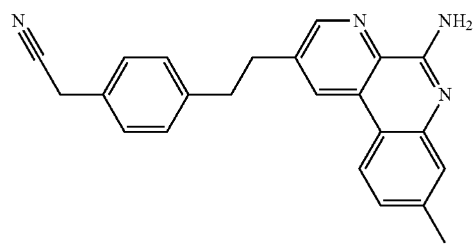 [SMILES: Cc1ccc2c(c1)nc(N)c1ncc(CCc3ccc(CC#N)cc3)cc12] | 353.2 |
| 241 | 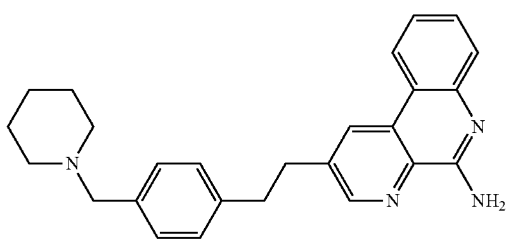 [SMILES: Nc1nc2ccccc2c2cc(CCc3ccc(CN4CCCCC4)cc3)cnc12] | 411.2 |
| 242 | 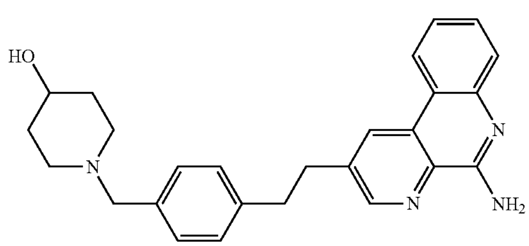 [SMILES: Nc1nc2ccccc2c2cc(CCc3ccc(CN4CCC(O)CC4)cc3)cnc12] | 427.2 |
| 243 | 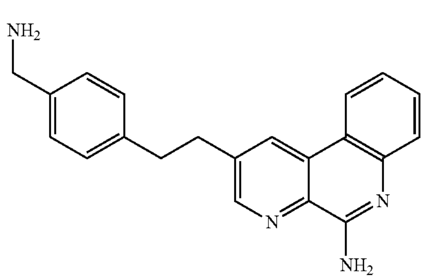 [SMILES: NCc1ccc(CCc2cnc3c(N)nc4ccccc4c3c2)cc1] | 443.2 |

TABLE 1-continued

| Compound Number | Structure | Physical Data MS (m/z) [M + H] |
|---|---|---|
| 244 | 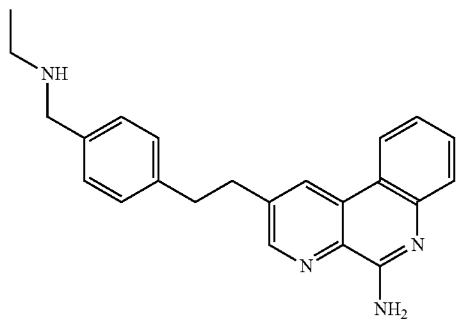 [SMILES: CCNCc1ccc(CCc2cnc3c(N)nc4ccccc4c3c2)cc1] | 371.2 |
| 245 | 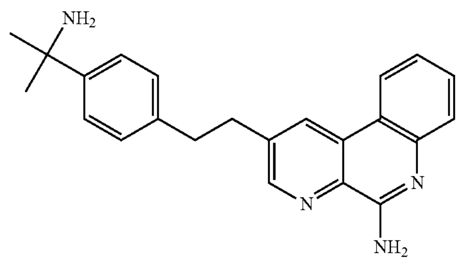 [SMILES: CC(C)(N)c1ccc(CCc2cnc3c(N)nc4ccccc4c3c2)cc1] | 357.2 |
| 246 | 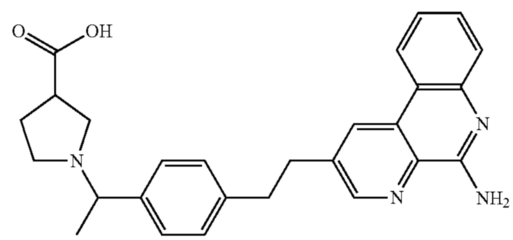 [SMILES: CC(c1ccc(CCc2cnc3c(N)nc4ccccc4c3c2)cc1)N1CCC(C(=O)O)C1] | 441.2 |
| 247 | 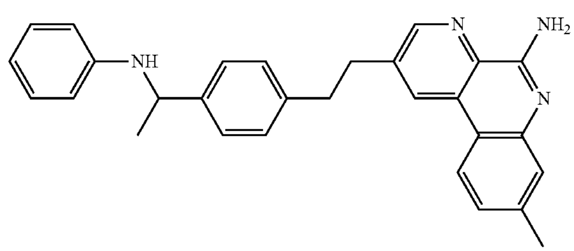 [SMILES: Cc1ccc2c(c1)nc(N)c1ncc(CCc3ccc(C(C)Nc4ccccc4)cc3)cc12] | 433.2 |

Example 198

In Vivo Efficacy of Compounds at Enhancing an Immune Response

To demonstrate the ability of the compounds disclosed herein to enhance the immune response to a bacterial antigen when administered to a subject with the antigen, three compounds were used in conjunction with a recombinant *N. meningitidis* serogroup B vaccine. The vaccine, which is more fully described in Giuliani et al. (2006) *Proc Natl Acad Sci USA* 103(29):10834-9 and WO2004/032958—referred to herein as "3MenB," was tested in vivo in mice either with MF59 or with MF59+ one of the compounds disclosed herein. Mice were immunized with two doses administered intramuscularly with 3MenB/MF59+ one of six of the compounds or, as a positive control, an amount of a CpG oligonucleotide ("CpG"), R848, or Immiquimod (ImiQ). An additional positive control of 3MenB/MF59+ OMV (outer membrane vesicles derived from the *N. meningitidis* serogroup B strain NZ98/254) was also compared. The serum bactericidal antibody ("SBA") titer was assayed two weeks after the second dose using the standeard CFU method or Alamar Blue method using a *N. meningitidis* serogroup strain NZ98. SBA titer is an FDA/EMEA accepted surrogate marker for efficacy of *N. meningitidis* vaccines in humans. The results are shown in FIG. 1 (with the dose of the compound in μg indicated on the left). The fold-change over the response elicited with MF59/3MenB is shown to the right of each bar in FIG. 1.

Figure 2:
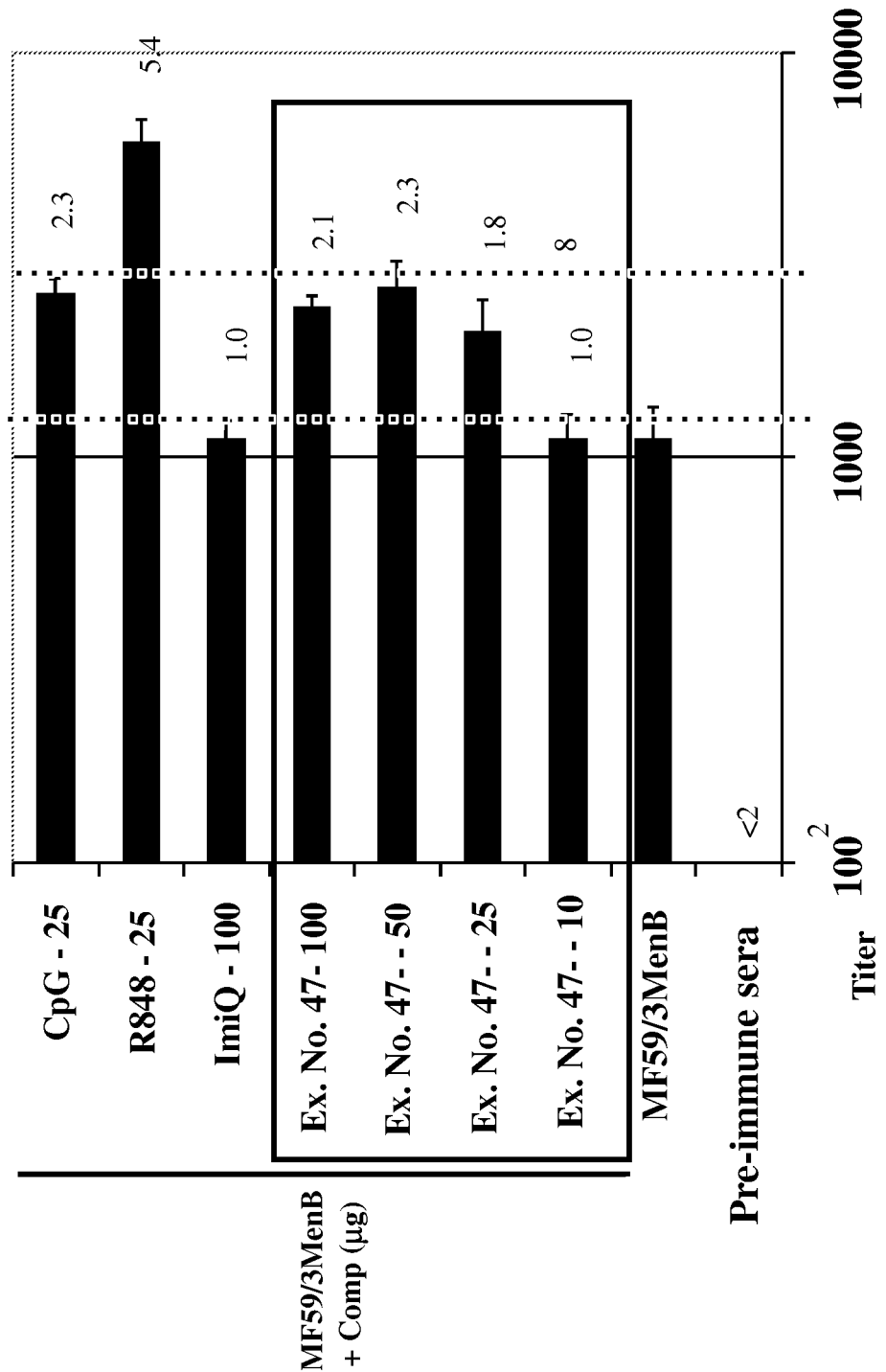
FIG. 2 shows the serum bactericidal antibody ("SBA") titer of compound 47 disclosed herein to enhance the immune response to a bacterial antigen. The dose of the compound in μg is indicated on the left, and the fold-change over the response elicited with MF59/3MenB is shown to the right of each bar. The results are compared to "CpG" (CpG oligonucleotide), R848, and Immiquimod (ImiQ).

In a second experiment, the dose response of one compound, Example No. 47, was tested using the same protocol. FIG. 2 shows the average result from three independent SBA studies with standard deviation shown as error bars. The SBA titers were measured in all cases using the standard CFU method. The dose of each compound in μg is indicated on the left of FIG. 2.

Figure 3:
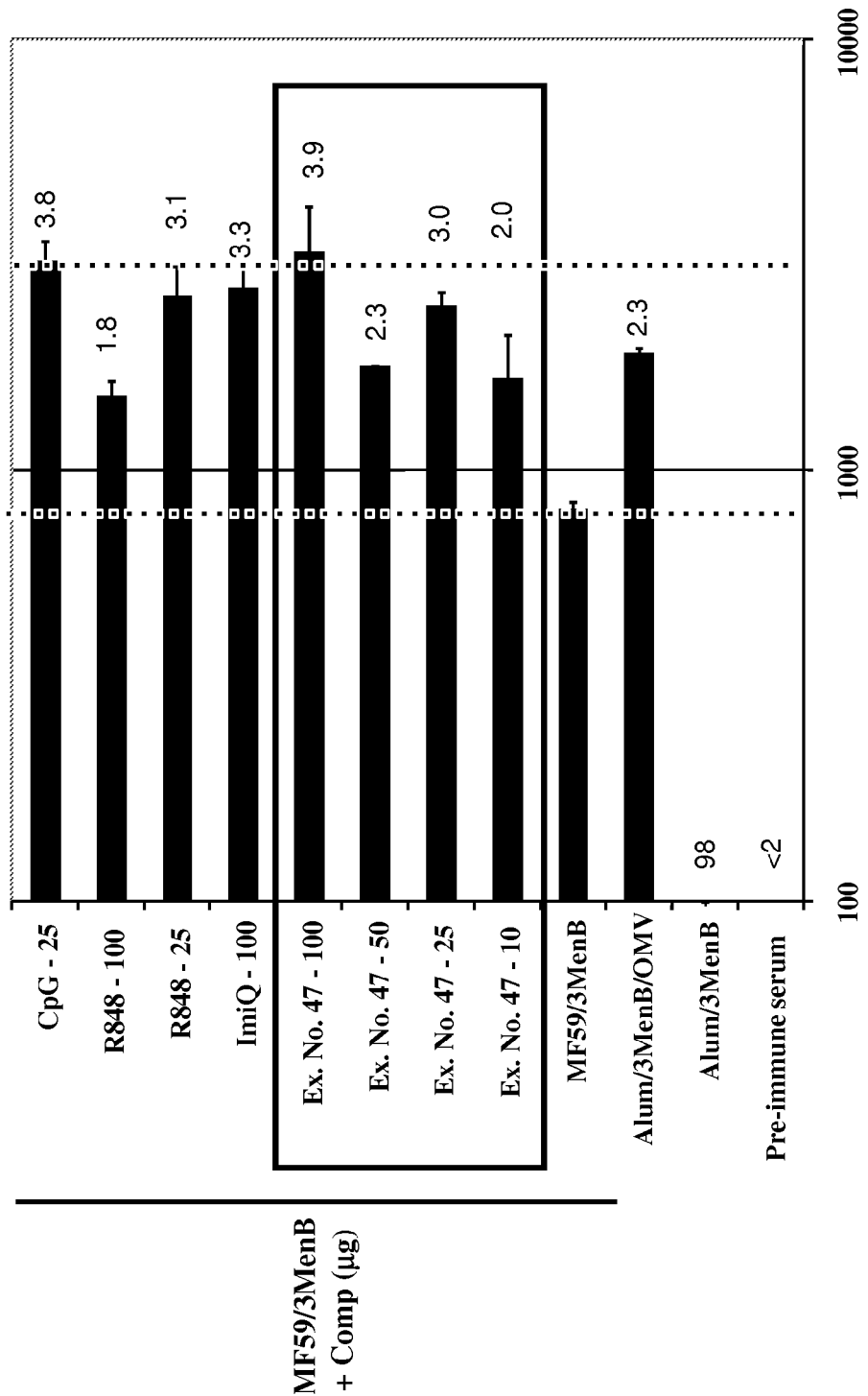
FIG. 3 shows the serum bactericidal antibody ("SBA") titer of compound 47 disclosed herein to enhance the immune response to a bacterial antigen. The dose of the compound in μg is indicated on the left, and the fold-change over the response elicited with MF59/3MenB is shown to the right of each bar. The results are compared to "CpG" (CpG oligonucleotide), R848, and Immiquimod (ImiQ).

FIG. 3 shows the SBA titers from two independent studies comparing the dose response to Example No. 47 with 3MenB adjuvanted with alum in place of the MF59 adjuvant.

Figure 4:
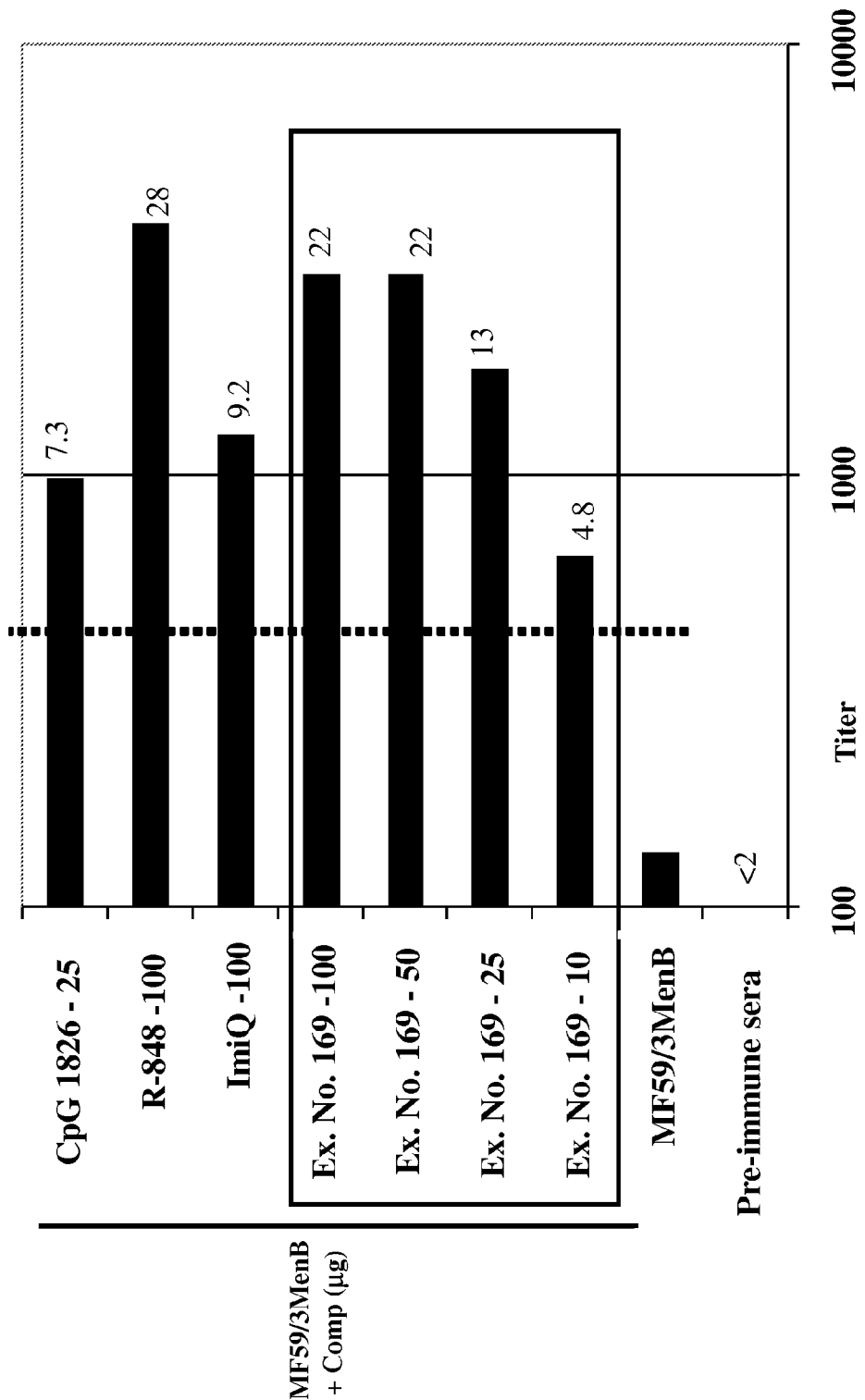
FIG. 4 shows the serum bactericidal antibody ("SBA") titer of compound 169 disclosed herein to enhance the immune response to a bacterial antigen. The dose of the compound in μg is indicated on the left, and the fold-change over the response elicited with MF59/3MenB is shown to the right of each bar. The results are compared to "CpG" (CpG oligonucleotide), R848, and Immiquimod (ImiQ).

FIG. 4 shows the SBA titers from another study comparing the dose response to another compound, Example No. 169.

Figure 5:
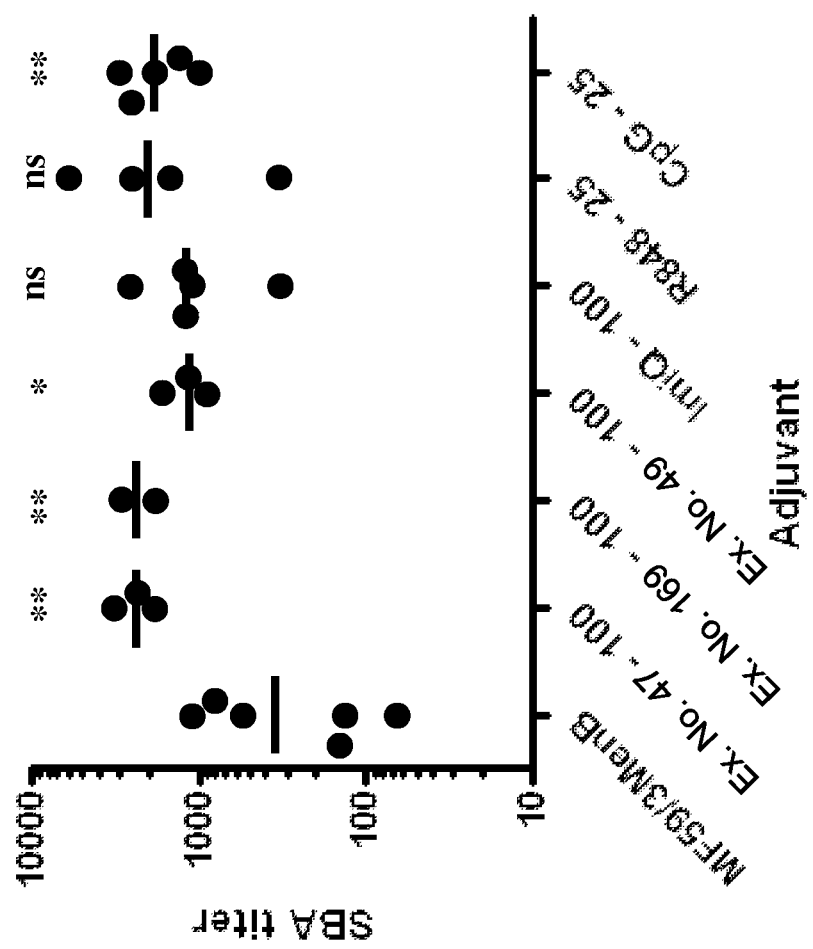
FIG. 5 is a compilation of the data shown in FIGS. 1-4.

FIG. 5 summarizes the data from the six total experiments. A titer of >1000 correlates with immunization providing protection against the pathogen tested in the SBA titer (i.e., the NZ/98 *N. meningitidis* serogroup B strain). Thus, at 100 μg, each of Example No. 47, Example No. 169, and Example No. 49 were able to provide a protective response in the mice thus demonstrating the ability of the compounds disclosed herein to enhance the immune response to an antigen. Only one of six experiments using 3MenB/MF59 produced a protective response against the NZ98 bacteria. By comparison, seven of eight experiments using the compounds disclosed herein produced a protective response against the NZ98 bacteria. ** and * above the compound in FIG. 5 indicates a statistically significant difference by p-value between immunization with the compound and immunization without the compound (i.e., compared to the 3MenB/MF59 control). ns—indicates the difference was not statistically significant by p-value Immunization with a CpG oligo versus Example No. 47 did not produce a statistically significant difference by p-value.

The body weight of the mice was measured at early (day 1 and day 2) and late (day 14 and day 28) time points after the immunization Immunization with 3MenB/MF59 versus 3MenB/MF59+ Example No. 169 did not produce a statatistically significant different in weight drop. Mice immunized with a CpG oliogo or with the 3MenB/OMV did produce a slight, but statistically significant weight drop on day one after immunization.

Assays

Compounds of Formula (I) provided herein are assayed to measure their capacity to modulate toll-like receptors.

Human Peripheral Blood Mononuclear Cell Assay

The bioactivity of the described compounds are tested in the human peripheral blood assay (human PBMC) using a panel of independent normal human donors according to approved guidelines by the institutional review committee. Human PBMC are isolated from freshly peripheral blood using a Ficoll density gradient (GE healthcare 17-1440-03). 30-35 mLs of peripheral human blood are layered onto 15 mLs of Ficoll in 50 ml conical tubes, followed by centrifugation at 1800 rpm (Eppendorf Centrifuge 5810R with biohazard caps over the tube buckets) at room temperature for 30 minutes with no acceleration and no brake. The buffy layers are then collected and transferred onto new 50 ml conical tubes and washed twice in complete media consisting of RAMI 1640 (11875085 from Invitrogen Corporation, Carlsbad, Calif.) supplemented with 10% heat inactivated fetal bovine serum (Gibco 10099-141), 1% Pen-Strep (Gibco#15140-122), 1 mM non essential amino acids (Gibco#11140-050), 1 mM sodium pyruvate (Gibco#11360-070), 2 mM L-Glutamine (Gibco#25030-081) and 1 mM HEPES (Gibco#15630-080). Viable cells are then counted using trypan blue staining, plated in 96 well flat bottom plates (Becton Dickinson #353070) at $2\times10^5$ cells per well in 200 μl total volume of complete media. Compounds are then added in a 10 point dose response format starting at 100 μM, 3 fold dilution. Negative controls wells received equal concentration of DMSO. Culture supernatants are collected after 18-24 hours incubation at 37° C., 5% $CO_2$, stored at −20° C. until further use.

IL-6 levels in the culture supernatants are measured using a Luminex kit (Biorad). Data analysis is performed using Prism software from GraphPad (San Diego, Calif.). Dose response curves are generated for each compound and EC50 values are determined as the concentration that gives 50% of the maximal signal.

Reporter Gene Assay

Human embryonic kidney 293 (HEK 293) cells are stably transfected with human TLR7 or TLR8 and an NF-kB-driven luciferase reporter vector (pNifty-Luciferase). As a control assay, normal Hek293 transfected with pNifty-Luc are used. Cells are cultured in DMEM supplemented with 2 mM L-glutamine, 10% heart inactivated FBS, 1% penicillin and streptomycin, 2 μg/ml puromycin (InvivoGen #ant-pr-5) and 5 μg/ml of blasticidin (Invitrogen #46-1120). Bright-Glo™ Luciferase assay buffer and substrate are supplied by Promega #E263B and #E264B (assay substrate and buffer respectively). 384 well clear-bottom plates are supplied by Greiner bio-one (#789163-G) and are GNF custom bar-coded plates.

Cells are plated at 25,000 cells/well in 384-well plates in a final volume of 50 μl of media. Cells are allowed to adhere to the plates after overnight (18 hours) culture at 37° C. 5% $CO_2$. Serially diluted experimental and positive control compounds are then dispensed to each well and incubated for 7 hours at 37° C. 5% $CO_2$. Cells stimulated with DMSO alone also serve as negative controls. After the incubation, 30 μl of the pre-mix assay buffer and substrate buffer are added to each well according to manufacturer's instructions. The luminescence signal is read on a CLIPR machine with an integration time of 20 seconds per plate.

Dose response curves are generated for each compound and EC50 values were determined as the concentration that gives 50% of the maximal signal.

Certain Assay Results

Various compounds of Formula (I)-(XVI) in free form or in pharmaceutically acceptable salt form, exhibit pharmacological properties, for example, as indicated by the in vitro tests described in this application. The $EC_{50}$ value in those experiments is given as that concentration of the test compound in question that provoke a response halfway between the baseline and maximum responses. In certain examples compounds of Formula (I)-(XVI) have $EC_{50}$ values from 1 nM to 200 μM. In some examples, compounds of Formula (I)-(XVI) have $EC_{50}$ values from 0.01 μM to 100 μM. In other examples, compounds of Formula (I)-(XVI) have $EC_{50}$ values from 0.01 μM to 50 μM. In other examples, compounds of Formula (I)-(XVI) have $EC_{50}$ values from 0.01 μM to 25 μM, In other examples, compounds of Formula (I)-(XVI) have $EC_{50}$ values from 0.01 μM to 20 μM. In other examples, compounds of Formula (I)-(XVI) have $EC_{50}$ values from 0.01 μM to 15 μM. In other examples, compounds of Formula (I)-(XVI) have $EC_{50}$ values from 0.01 μM to 10 μM. In other examples, compounds of Formula (I)-(XVI) have $EC_{50}$ values from 0.01 μM to 5 μM. In other examples, compounds of Formula (I)-(XVI) have $EC_{50}$ values from 0.01 μM to 2 μM. In other examples, compounds of Formula (I)-(XVI) have $EC_{50}$ values from 0.01 μM to 1 μM. In certain examples such $EC_{50}$ values are obtained relative to the activity of resiquimod set to 100%.

In other examples the following compounds of Formula (I)-(XVI) have $EC_{50}$ values from 1 nM to 200 μM: 2-methylbenzo[f][1,7]naphthyridin-5-amine; 2-propylbenzo[f][1,7]naphthyridin-5-amine; 2-ethylbenzo[f][1,7]naphthyridin-5-amine; 2-(3-methoxyphenethyl)benzo[f][1,7]naphthyridin-5-amine; 8-methylbenzo[f][1,7]naphthyridin-5-amine; 8-methyl-2-phenethylbenzo[f][1,7]naphthyridin-5-amine; methyl 5-aminobenzo[f][1,7]naphthyridine-3-carboxylate; (5-aminobenzo[f][1,7]naphthyridin-3-yl)methanol; benzo[f][1,7]naphthyridin-5-amine; (5-aminobenzo[f][1,7]naphthyridin-8-yl)methanol; 2-(2-methylphenethyl)benzo[f][1,7]naphthyridin-5-amine; 2-(3-methylphenethyl)benzo[f][1,7]naphthyridin-5-amine; 2-(4-methylphenethyl)benzo[f][1,7]naphthyridin-5-amine; 8-chlorobenzo[f][1,7]naphthyridin-5-amine; ethyl 5-aminobenzo[f][1,7]naphthyridine-9-carboxylate; 8-methoxybenzo[f][1,7]naphthyridin-5-amine; 8-(trifluoromethyl)benzo[f][1,7]naphthyridin-5-amine; 8-fluorobenzo[f][1,7]naphthyridin-5-amine; 3-methylbenzo[f][1,7]naphthyridin-5-amine; 3-fluorobenzo[f][1,7]naphthyridin-5-amine; 2-phenethylbenzo[f][1,7]naphthyridin-5-amine; 8-methyl-2-(2-(naphthalen-1-yl)ethyl)benzo[f][1,7]naphthyridin-5-amine; 8-methyl-2-(2-(naphthalen-2-yl)ethyl)benzo[f][1,7]naphthyridin-5-amine; 4-(2-(5-amino-8-methylbenzo[f][1,7]naphthyridin-2-yl)ethyl)benzoic acid; 3-(2-(5-amino-8-methylbenzo[f][1,7]naphthyridin-2-yl)ethyl)benzoic acid; 2-(3-chlorophenethyl)-8-methylbenzo[f][1,7]naphthyridin-5-amine; 2-(2-chlorophenethyl)-8-methylbenzo[f][1,7]naphthyridin-5-amine; (3-(2-(5-amino-8-methylbenzo[f][1,7]naphthyridin-2-yl)ethyl)phenyl)methanol; 2-(4-chlorophenethyl)-8-methylbenzo[f][1,7]naphthyridin-5-amine; 2-(4-butylphenethyl)benzo[f][1,7]naphthyridin-5-amine; 2-(4-butylphenethyl)-8-methylbenzo[f][1,7]naphthyridin-5-amine; 2-(4-propylphenethyl)benzo[f][1,7]naphthyridin-5-amine; 2-(4-(trifluoromethyl)phenethyl)benzo[f][1,7]naphthyridin-5-amine; 2-(2,5-dimethylphenethyl)-8-methylbenzo[f][1,7]naphthyridin-5-amine; 8-methyl-2-(4-propylphenethyl)benzo[f][1,7]naphthyridin-5-amine; 8-methyl-2-(2,4,5-trimethylphenethyl)benzo[f][1,7]naphthyridin-5-amine; 2-(2,5-dimethylphenethyl)benzo[f][1,7]naphthyridin-5-amine; 2-(4-isopropylphenethyl)-8-methylbenzo[f][1,7]naphthyridin-5-amine; 2-(4-heptylphenethyl)-8-methylbenzo[f][1,7]naphthyridin-5-amine; 2-(4-isobutoxyphenethyl)-8-methylbenzo[f][1,7]naphthyridin-5-amine; 2-(4-((2-methoxyethoxy)methoxy)phenethyl)-8-methylbenzo[f][1,7]naphthyridin-5-amine; 8-methyl-2-(4-(2-phenoxyethoxy)phenethyl)benzo[f][1,7]naphthyridin-5-amine; 8-methyl-2-(4-(4-phenylbutoxy)phenethyl)benzo[f][1,7]naphthyridin-5-amine; 2-(4-(allyloxy)phenethyl)-8-methylbenzo[f][1,7]naphthyridin-5-amine; 8-methyl-2-(4-(3-phenylpropoxy)phenethyl)benzo[f][1,7]naphthyridin-5-amine; 2-(4-(heptan-4-yloxy)phenethyl)-8-methylbenzo[f][1,7]naphthyridin-5-amine; 8-methyl-2-(4-(4-methylpent-3-enyloxy)phenethyl)benzo[f][1,7]naphthyridin-5-amine; 2-(4-(2-cyclohexylethoxy)phenethyl)-8-methylbenzo[f][1,7]naphthyridin-5-amine; 2-(4-isopropoxyphenethyl)-8-methylbenzo[f][1,7]naphthyridin-5-amine; 2-(4-(3,3-dimethylbutoxy)phenethyl)-8-methylbenzo[f][1,7]naphthyridin-5-amine; 8-(2-cyclopropylethyl)-2-(4-(dimethylamino)phenethyl)benzo[f][1,7]naphthyridin-5-amine; 8-(2-cyclopropylethyl)-2-(2,4-dimethylphenethyl)benzo[f][1,7]naphthyridin-5-amine; N-(4-(2-(5-amino-8-methylbenzo[f][1,7]naphthyridin-2-yl)ethyl)phenyl)acetamide; N-(4-(2-(5-aminobenzo[f][1,7]naphthyridin-2-yl)ethyl)phenyl)acetamide; N-(4-(2-(5-amino-8-methylbenzo[f][1,7]naphthyridin-2-yl)ethyl)phenyl)-4-methylbenzenesulfonamide; 3-methyl-9-p-tolyl-9,10-dihydrobenzo[f]furo[2,3-b][1,7]naphthyridin-6-amine; 4-(2-(5-amino-8-methylbenzo[f][1,7]naphthyridin-2-yl)ethyl)-3-methylbenzonitrile; 4-(2-(5-amino-8-methylbenzo[f][1,7]naphthyridin-2-yl)ethyl)-N-(2-aminoethyl)-3-methylbenzamide; 8-methyl-2-(2-methyl-4-(1H-tetrazol-5-yl)phenethyl)benzo[f][1,7]naphthyridin-5-amine; methyl 2-(4-(2-(5-amino-8-methylbenzo[f][1,7]naphthyridin-2-yl)ethyl)-3-methylbenzamido)-4-methylpentanoate; methyl 2-(4-(2-(5-amino-8-methylbenzo[f][1,7]naphthyridin-2-yl)ethyl)-3-methylbenzamido)acetate; 2-(4-(2-(5-amino-8-methylbenzo[f][1,7]naphthyridin-2-yl)ethyl)-3-methylbenzamido)-4-methylpentanoic acid; 2-(4-(2-(5-amino-8-methylbenzo[f][1,7]naphthyridin-2-yl)ethyl)-3-methylbenzamido)acetic acid; 6-(5-amino-8-methylbenzo[f][1,7]naphthyridin-2-yl)hexan-1-ol; 7-(5-amino-8-methylbenzo[f][1,7]naphthyridin-2-yl)heptanoic acid; 11-(5-amino-8-methylbenzo[f][1,7]naphthyridin-2-yl)undecan-1-ol; ethyl 2-(4-(2-(5-amino-8-methylbenzo[f][1,7]naphthyridin-2-yl)ethyl)-3-methylphenoxy)acetate; 2-(4-(2-(5-amino-8-methylbenzo[f][1,7]naphthyridin-2-yl)ethyl)-3-methylphenoxy)acetic acid; 3-(4-(2-(5-amino-8-methylbenzo[f][1,7]naphthyridin-2-yl)ethyl)-3-methylphenoxy)propanoic acid; 6-(4-(2-(5-amino-8-methylbenzo[f][1,7]naphthyridin-2-yl)ethyl)-3-methylphenoxy)hexanoic acid; 8-methyl-2-(2-methyl-4-(methylthio)phenethyl)benzo[f][1,7]naphthyridin-5-amine; 8-methyl-2-(4-(methylsulfonyl)phenethyl)benzo[f][1,7]naphthyridin-5-amine; 2-(4-(hexyloxy)phenethyl)-8-methylbenzo[f][1,7]naphthyridin-5-amine; 8-methyl-2-(4-phenethoxyl)phenethyl)benzo[f][1,7]naphthyridin-5-amine; 8-methyl-2-(4-(pentyloxy)phenethyl)benzo[f][1,7]naphthyridin-5-amine; 8-methyl-2-(4-(4-methylpentyloxy)phenethyl)benzo[f][1,7]naphthyridin-5-amine; 2-(2-fluorophenethyl)benzo[f][1,7]naphthyridin-5-amine; 2-(3-fluorophenethyl)benzo[f][1,7]naphthyridin-5-amine; 2-(4-fluorophenethyl)benzo[f][1,7]naphthyridin-5-amine; 2-(2-(thiophen-3-yl)ethyl)benzo[f][1,7]naphthyridin-5-amine; (5-aminobenzo[f][1,7]naphthyridin-2-yl)methanol; 2-(3,4-dimethylphenethyl)benzo[f][1,7]naphthyridin-5-amine; 2-(3,4-dimethylphenethyl)-8-methylbenzo[f][1,7]naphthyridin-5-amine; 2-(3,5-dimethylphenethyl)-8-methylbenzo[f][1,7]naphthyridin-5-amine; 2-(2-(benzofuran-5-yl)ethyl)-8-methylbenzo[f][1,7]naphthyridin-5-amine; 8-methyl-2-(2-nitroethyl)benzo[f][1,7]naphthyridin-5-amine; 2-(aminomethyl)-8-methylbenzo[f][1,7]naphthyridin-5-amine; $N^2$,8-dimethylbenzo[f][1,7]naphthyridine-2,5-diamine; 2-(5-amino-8-methylbenzo[f][1,7]naphthyridin-2-yl)-1-phenylethanol; 2-(5-amino-8-methylbenzo[f][1,7]naphthyridin-2-yl)-1-(4-methoxyphenyl)ethanol; 2-(biphenyl-2-yl)-8-methylbenzo[f][1,7]naphthyridin-5-amine; 2-(2-(2,6-dimethylpyridin-3-yl)ethyl)-8-methylbenzo[f][1,7]naphthyridin-5-amine; 2-(2-(5-methoxypyridin-2-yl)ethyl)-8-methylbenzo[f][1,7]naphthyridin-5-amine; 3-(4-(2-(5-amino-8-methylbenzo[f][1,7]naphthyridin-2-yl)ethyl)phenyl)propanoic acid; 5-(2-(5-amino-8-methylbenzo[f][1,7]naphthyridin-2-yl)ethyl)-4-methylpyridin-2(1H)-one; 6-(2-(5-amino-8-methylbenzo[f][1,7]naphthyridin-2-yl)ethyl)pyridin-3-ol; 8-methyl-2-(4-(trifluoromethoxy)phenethyl)benzo[f][1,7]naphthyridin-5-amine; 2-(2-(2,3-dihydro-1H-inden-5-yl)ethyl)-8-methylbenzo[f][1,7]naphthyridin-5-amine; 2-(2-(2,3-dihydro-1H-inden-5-yl)ethyl)benzo[f][1,7]naphthyridin-5-amine; (E)-3-(4-(2-(5-amino-8-methylbenzo[f][1,7]naphthyridin-2-yl)ethyl)-3-methylphenyl)acrylic acid; (E)-ethyl 3-(5-amino-2-(4-methoxy-2-methylphenethyl)benzo[f][1,7]naphthyridin-8-yl)acrylate; (E)-8-(2-cyclopropylvinyl)-2-phenethylbenzo[f][1,7]naphthyridin-5-amine; 8-pentylbenzo[f][1,7]naphthyridin-5-amine; (E)-8-(2-cyclopropylvinyl)benzo[f][1,7]naphthyridin-5-amine; 8-(2-cyclopropylethyl)-2-phenethylbenzo[f][1,7]naphthyridin-5-amine; (5-amino-2-phenethylbenzo[f][1,7]naphthyridin-8-yl)methanol; (5-amino-2-(4-methoxy-2-methylphenethyl)benzo[f][1,7]naphthyridin-8-yl)methanol; 3-(2-(5-aminobenzo[f][1,7]naphthyridin-2-yl)ethyl)phenol; 2-(2-methoxyphenethyl)benzo[f][1,7]naphthyridin-5-amine; 2-(4-ethylphenethyl)benzo[f][1,7]naphthyridin-5-amine; 2-(4-ethylphenethyl)-8-methylbenzo[f][1,7]naphthyridin-5- amine; 2-(4-(dimethylamino)phenethyl)benzo[f][1,7]naphthyridin-5-amine; 2-(4-(piperidin-1-yl)phenethyl)benzo[f][1,7]naphthyridin-5-amine; 2-(4-tert-butylphenethyl)-8-methylbenzo[f][1,7]naphthyridin-5-amine; 8-methyl-2-(4-(piperidin-1-yl)phenethyl)benzo[f][1,7]naphthyridin-5-amine; 2-(4-methoxyphenethyl)-8-methylbenzo[f][1,7]naphthyridin-5-amine; 2-(3,5-dimethoxyphenethyl)-8-methylbenzo[f][1,7]naphthyridin-5-amine; 8-methyl-2-(2-(trifluoromethyl)phenethyl)benzo[f][1,7]naphthyridin-5-amine; 4-(2-(5-amino-8-methylbenzo[f][1,7]naphthyridin-2-yl)ethyl)-N-hydroxybenzimidamide; 4-(2-(5-amino-8-methylbenzo[f][1,7]naphthyridin-2-yl)ethyl)benzonitrile; 8-methyl-2-(4-(1-morpholinoethyl)phenethyl)benzo[f][1,7]naphthyridin-5-amine; 2-(4-aminophenethyl)-8-methylbenzo[f][1,7]naphthyridin-5-amine; 1-(4-(2-(5-amino-8-methylbenzo[f][1,7]naphthyridin-2-yl)ethyl)phenyl)guanidine; 8-methyl-2-(4-(1-(phenethylamino)ethyl)phenethyl)benzo[f][1,7]naphthyridin-5-amine; 2-(4-(2-(5-amino-8-methylbenzo[f][1,7]naphthyridin-2-yl)ethyl)phenyl)acetonitrile; 2-(4-(piperidin-1-ylmethyl)phenethyl)benzo[f][1,7]naphthyridin-5-amine; 1-(4-(2-(5-aminobenzo[f][1,7]naphthyridin-2-yl)ethyl)benzyl)piperidin-4-ol; 2-(4-(aminomethyl)phenethyl)benzo[f][1,7]naphthyridin-5-amine; 2-(4-((ethylamino)methyl)phenethyl)benzo[f][1,7]naphthyridin-5-amine; 2-(4-(2-aminopropan-2-yl)phenethyl)benzo[f][1,7]naphthyridin-5-amine; 1-(1-(4-(2-(5-aminobenzo[f][1,7]naphthyridin-2-yl)ethyl)phenyl)ethyl)pyrrolidine-3-carboxylic acid; 8-methyl-2-(4-(1-(phenylamino)ethyl)phenethyl)benzo[f][1,7]naphthyridin-5-amine; 2-ethyl-8-methylbenzo[f][1,7]naphthyridin-5-amine; (5-amino-8-methylbenzo[f][1,7]naphthyridin-2-yl)methanol; 8-methyl-2-propylbenzo[f][1,7]naphthyridin-5-amine; 2-(2-(1H-indol-5-yl)ethyl)-8-methylbenzo[f][1,7]naphthyridin-5-amine; 2-(4-ethoxyphenethyl)-8-methylbenzo[f][1,7]naphthyridin-5-amine; 8-methyl-2-(4-phenoxyphenethyl)benzo[f][1,7]naphthyridin-5-amine; dimethylphenethyl)benzo[f][1,7]naphthyridin-5-amine; 2-(2,4-dimethylphenethyl)-8-methylbenzo[f][1,7]naphthyridin-5-amine; 2-(4-methoxy-2-methylphenethyl)-8-methylbenzo[f][1,7]naphthyridin-5-amine; 4-(2-(5-amino-8-methylbenzo[f][1,7]naphthyridin-2-yl)ethyl)-3-methylphenol; 2-(2-(2,3-dihydrobenzofuran-5-yl)ethyl)-8-methylbenzo[f][1,7]naphthyridin-5-amine; 2-(5-amino-8-methylbenzo[f][1,7]naphthyridin-2-yl)ethanol; 3-methyl-9-phenyl-9,10-dihydrobenzo[f]furo[2,3-b][1,7]naphthyridin-6-amine; 8-methylbenzo[f][1,7]naphthyridine-2,5-diamine; 1-(5-amino-8-methylbenzo[f][1,7]naphthyridin-2-yl)propan-2-ol; 2-(5-amino-8-methylbenzo[f][1,7]naphthyridin-2-yl)acetonitrile; N-(5-amino-8-methylbenzo[f][1,7]naphthyridin-2-yl)acetamide; 2-(5-amino-8-methylbenzo[f][1,7]naphthyridin-2-yl)-1-(2,4-dimethylphenyl)ethanol; 2-(2-(6-methoxy-4-methylpyridin-3-yl)ethyl)-8-methylbenzo[f][1,7]naphthyridin-5-amine; 4-(4-(2-(5-amino-8-methylbenzo[f][1,7]naphthyridin-2-yl)ethyl)phenyl)butan-1-ol; methyl 3-(4-(2-(5-amino-8-methylbenzo[f][1,7]naphthyridin-2-yl)ethyl)phenyl)propanoate; 3-(4-(2-(5-amino-8-methylbenzo[f][1,7]naphthyridin-2-yl)ethyl)phenyl)propan-1-ol; 4-(4-(2-(5-amino-8-methylbenzo[f][1,7]naphthyridin-2-yl)ethyl)phenyl)-2-methylbutan-2-ol; 2-(4-(aminomethyl)phenethyl)-8-methylbenzo[f][1,7]naphthyridin-5-amine; (E)-ethyl 3-(4-(2-(5-amino-8-methylbenzo[f][1,7]naphthyridin-2-yl)ethyl)-3-methylphenyl)acrylate; ethyl 3-(4-(2-(5-amino-8-methylbenzo[f][1,7]naphthyridin-2-yl)ethyl)-3-methylphenyl)propanoate; 2-(4-(2-(5-amino-8-methylbenzo[f][1,7]naphthyridin-2-yl)ethyl)-3-methylbenzyl)propane-1,3-diol; 3-(4-(2-(5-amino-8-methylbenzo[f][1,7]naphthyridin-2-yl)ethyl)-3-methylphenyl)propanoic acid; 5-amino-2-(4-methoxy-2-methylphenethyl)benzo[f][1,7]naphthyridine-8-carbaldehyde; ethyl 4-(2-(5-amino-8-methylbenzo[f][1,7]naphthyridin-2-yl)ethyl)benzoate; 8-methyl-2-(4-methylphenethyl)benzo[f][1,7]naphthyridin-5-amine; 2-(4-(2-(5-amino-8-methylbenzo[f][1,7]naphthyridin-2-yl)ethyl)phenyl)propan-2-ol; (4-(2-(5-amino-8-methylbenzo[f][1,7]naphthyridin-2-yl)ethyl)phenyl)methanol; ethyl 4-(2-(5-amino-8-methylbenzo[f][1,7]naphthyridin-2-yl)ethyl)-3-methylbenzoate; 4-(2-(5-amino-8-methylbenzo[f][1,7]naphthyridin-2-yl)ethyl)-3-methylbenzoic acid; (4-(2-(5-amino-8-methylbenzo[f][1,7]naphthyridin-2-yl)ethyl)-3-methylphenyl)methanol; 8-methyl-2-(2,4,6-trimethylphenethyl)benzo[f][1,7]naphthyridin-5-amine; 2-(4-(2-(5-amino-8-methylbenzo[f][1,7]naphthyridin-2-yl)ethyl)-3-methylphenyl)propan-2-ol; 8-methyl-2-(4-propoxyphenethyl)benzo[f][1,7]naphthyridin-5-amine; (E)-3-(5-amino-2-(4-methoxy-2-methylphenethyl)benzo[f][1,7]naphthyridin-8-yl)acrylic acid; ethyl 3-(5-amino-2-(4-methoxy-2-methylphenethyl)benzo[f][1,7]naphthyridin-8-yl)propanoate; 3-(5-amino-2-(4-methoxy-2-methylphenethyl)benzo[f][1,7]naphthyridin-8-yl)propanoic acid; 3-(5-amino-2-(4-methoxy-2-methylphenethyl)benzo[f][1,7]naphthyridin-8-yl)propan-1-ol; 5-aminobenzo[f][1,7]naphthyridin-8-ol; 5-aminobenzo[f][1,7]naphthyridine-8-carbaldehyde; 1-(5-aminobenzo[f][1,7]naphthyridin-8-yl)ethanol; 1-(5-aminobenzo[f][1,7]naphthyridin-8-yl)ethanone; 8-isopropylbenzo[f][1,7]naphthyridin-5-amine; 8-vinylbenzo[f][1,7]naphthyridin-5-amine; 8-ethylbenzo[f][1,7]naphthyridin-5-amine; 8-(methoxymethyl)benzo[f][1,7]naphthyridin-5-amine; (5-amino-2-(4-methoxyphenethyl)benzo[f][1,7]naphthyridin-8-yl)methanol; benzo[f][1,7]naphthyridine-5,8-diamine; 8-(aminomethyl)benzo[f][1,7]naphthyridin-5-amine; 3-fluoro-8-methylbenzo[f][1,7]naphthyridin-5-amine; (5-amino-3-fluorobenzo[f][1,7]naphthyridin-8-yl)methanol; 3-chlorobenzo[f][1,7]naphthyridine-5,8-diamine; 3-fluorobenzo[f][1,7]naphthyridine-5,8-diamine; 8-isobutylbenzo[f][1,7]naphthyridin-5-amine; (E)-8-(prop-1-enyl)benzo[f][1,7]naphthyridin-5-amine; 8-propylbenzo[f][1,7]naphthyridin-5-amine; 8-(2-cyclopropylethyl)benzo[f][1,7]naphthyridin-5-amine; 8-phenethylbenzo[f][1,7]naphthyridin-5-amine; (5-amino-2-(4-bromophenethyl)benzo[f][1,7]naphthyridin-8-yl)methanol; 2-(4-methoxy-2-methylphenethyl)-8-pentylbenzo[f][1,7]naphthyridin-5-amine; 8-(2-cyclopropylethyl)-2-(4-methoxy-2-methylphenethyl)benzo[f][1,7]naphthyridin-5-amine; (5-amino-2-(2,4,6-trimethylphenethyl)benzo[f][1,7]naphthyridin-8-yl)methanol; (5-amino-2-(4-propoxyphenethyl)benzo[f][1,7]naphthyridin-8-yl)methanol; (2-(2-(1H-indol-5-yl)ethyl)-5-aminobenzo[f][1,7]naphthyridin-8-yl)methanol; methyl 4-(2-(5-amino-8-methylbenzo[f][1,7]naphthyridin-2-yl)ethyl)-3-methylbenzoate; 4-(2-(5-amino-8-methylbenzo[f][1,7]naphthyridin-2-yl)ethyl)-N,3-dimethylbenzamide; N-(2-acetamidoethyl)-4-(2-(5-amino-8-methylbenzo[f][1,7]naphthyridin-2-yl)ethyl)-3-methylbenzamide; 4-(2-(5-amino-8-methylbenzo[f][1,7]naphthyridin-2-yl)ethyl)-N-(2-(dimethylamino)ethyl)-N,3-dimethylbenzamide; 2-(4-methoxyphenethyl)benzo[f][1,7]naphthyridin-5-amine; 2-(4-methoxy-2-methylphenethyl)benzo[f][1,7]naphthyridin-5-amine; 4-(2-(5-amino-8-methylbenzo[f][1,7]naphthyridin-2-yl)ethyl)-3-methylbenzamide; 4-(2-(5-amino-8-methylbenzo[f][1,7]naphthyridin-2-yl)ethyl)-N,N,3-trimethylbenzamide; 4-(2-(5-amino-8-methylbenzo[f][1,7]naphthyridin-2-yl)ethyl)-N-(2-hydroxyethyl)-3-methylbenzamide; 4-(2-(5-amino-8-methylbenzo[f][1,7]naphthyridin-2-yl)ethyl)-N-(2-(dimethylamino)ethyl)-3-methylbenzamide; (4-(2-(5-amino-8-methylbenzo[f][1,7]

naphthyridin-2-yl)ethyl)-3-methylphenyl)(pyrrolidin-1-yl)methanone; 4-(2-(5-amino-8-methylbenzo[f][1,7]naphthyridin-2-yl)ethyl)-N-(2-(diethylamino)ethyl)-3-methylbenzamide; (4-(2-(5-amino-8-methylbenzo[f][1,7]naphthyridin-2-yl)ethyl)-3-methylphenyl)(4-ethylpiperazin-1-yl)methanone; (4-(2-(5-amino-8-methylbenzo[f][1,7]naphthyridin-2-yl)ethyl)-3-methylphenyl)(piperazin-1-yl)methanone; 4-(2-(5-amino-8-methylbenzo[f][1,7]naphthyridin-2-yl)ethyl)-3-methyl-N-(2-(pyrrolidin-1-yl)ethyl)benzamide; 4-(2-(5-aminobenzo[f][1,7]naphthyridin-2-yl)ethyl)-N-(2-(dimethylamino)ethyl)-N,3-dimethylbenzamide; 4-(2-(5-amino-8-methylbenzo[f][1,7]naphthyridin-2-yl)ethyl)-N-(2-(dimethylamino)ethyl)-N-methylbenzamide; 2-(4-(2-(5-aminobenzo[f][1,7]naphthyridin-2-yl)ethyl)-3-methylphenyl)propan-2-ol; 2-(4-butoxyphenethyl)-8-methylbenzo[f][1,7]naphthyridin-5-amine; 2-(2-(biphenyl-4-yl)ethyl)-8-methylbenzo[f][1,7]naphthyridin-5-amine; 2-((1,3-dihydroisobenzofuran-1-yl)methyl)-8-methylbenzo[f][1,7]naphthyridin-5-amine; 8-methyl-2-(4-(2-methylallyloxy)phenethyl)benzo[f][1,7]naphthyridin-5-amine; 2-(4-(isopentyloxy)phenethyl)-8-methylbenzo[f][1,7]naphthyridin-5-amine; 4-(2-(5-amino-8-methylbenzo[f][1,7]naphthyridin-2-yl)ethyl)phenyl propyl carbonate; ethyl 5-(4-(2-(5-amino-8-methylbenzo[f][1,7]naphthyridin-2-yl)ethyl)phenoxy)pentanoate; 2-(4-(cyclopentyloxy)phenethyl)-8-methylbenzo[f][1,7]naphthyridin-5-amine; 2-(4-(cyclobutylmethoxy)phenethyl)-8-methylbenzo[f][1,7]naphthyridin-5-amine; 8-methyl-2-(4-(2-morpholinoethoxy)phenethyl)benzo[f][1,7]naphthyridin-5-amine; 2-(4-(2-(5-amino-8-methylbenzo[f][1,7]naphthyridin-2-yl)ethyl)phenoxy)-1-phenylethanone; 5-(4-(2-(5-amino-8-methylbenzo[f][1,7]naphthyridin-2-yl)ethyl)phenoxy)pentanoic acid; 2-(4-(2-(5-amino-8-methylbenzo[f][1,7]naphthyridin-2-yl)ethyl)phenoxy)ethanol; 2-(4-(2-(5-amino-8-methylbenzo[f][1,7]naphthyridin-2-yl)ethyl)phenoxy)-N,N-dimethylacetamide; 8-methyl-2-(2-methyl-4-(2-morpholinoethoxy)phenethyl)benzo[f][1,7]naphthyridin-5-amine; 2-(2-(4-(2-(5-amino-8-methylbenzo[f][1,7]naphthyridin-2-yl)ethyl)-3-methylphenoxy)ethoxy)ethanol; diethyl 3-(4-(2-(5-amino-8-methylbenzo[f][1,7]naphthyridin-2-yl)ethyl)-3-methylphenoxy)propylphosphonate; 3-(4-(2-(5-amino-8-methylbenzo[f][1,7]naphthyridin-2-yl)ethyl)-3-methylphenoxy)propylphosphonic acid; 2-(4-butoxy-2-methylphenethyl)-8-methylbenzo[f][1,7]naphthyridin-5-amine; 2-(4-(2-(5-aminobenzo[f][1,7]naphthyridin-2-yl)ethyl)-3-methylphenoxy)ethanol; 2-(2-(4-(2-(5-aminobenzo[f][1,7]naphthyridin-2-yl)ethyl)-3-methylphenoxy)ethoxy)ethanol; ethyl 5-(4-(2-(5-amino-8-methylbenzo[f][1,7]naphthyridin-2-yl)ethyl)-3-methylphenoxy)pentanoate; 5-(4-(2-(5-amino-8-methylbenzo[f][1,7]naphthyridin-2-yl)ethyl)-3-methylphenoxy)pentanoic acid; 2-(4-(2-(5-amino-8-methylbenzo[f][1,7]naphthyridin-2-yl)ethyl)-3-methylphenoxy)ethanol; 4-(2-(5-amino-8-methylbenzo[f][1,7]naphthyridin-2-yl)ethyl)phenyl ethyl carbonate; methyl 4-(4-(2-(5-amino-8-methylbenzo[f][1,7]naphthyridin-2-yl)ethyl)phenoxy)butanoate; 4-(4-(2-(5-amino-8-methylbenzo[f][1,7]naphthyridin-2-yl)ethyl)phenoxy)butanoic acid; 4-(4-(2-(5-amino-8-methylbenzo[f][1,7]naphthyridin-2-yl)ethyl)-3-methylphenoxy)butanoic acid; 2-(4-(isopentyloxy)-2-methylphenethyl)-8-methylbenzo[f][1,7]naphthyridin-5-amine; 4-(2-(5-amino-8-methylbenzo[f][1,7]naphthyridin-2-yl)ethyl)phenyl hexyl carbonate; 2-(2,4,6-trimethylphenethyl)benzo[f][1,7]naphthyridin-5-amine; (5-amino-2-(2,4-dimethylphenethyl)benzo[f][1,7]naphthyridin-8-yl)methanol; diethyl 3-(2-(4-(2-(5-amino-8-methylbenzo[f][1,7]naphthyridin-2-yl)ethyl)-3-methylphenoxy)ethoxy)propylphosphonate; diethyl 3-(2-(2-(4-(2-(5-amino-8-methylbenzo[f][1,7]naphthyridin-2-yl)ethyl)-3-methylphenoxy)ethoxy)ethoxy)propylphosphonate; 4-(2-(5-amino-8-methylbenzo[f][1,7]naphthyridin-2-yl)ethyl)-3-methylphenyl dimethylsulfamate; (5-amino-2-(4-(dimethylamino)phenethyl)benzo[f][1,7]naphthyridin-8-yl)methanol; 2-(4-(dimethylamino)phenethyl)-8-methylbenzo[f][1,7]naphthyridin-5-amine; 4-(2-(5-amino-8-methylbenzo[f][1,7]naphthyridin-2-yl)ethyl)phenol; 1-(4-(2-(5-amino-8-methylbenzo[f][1,7]naphthyridin-2-yl)ethyl)phenyl)ethanone; 2-(4-((dimethylamino)methyl)phenethyl)-8-methylbenzo[f][1,7]naphthyridin-5-amine; 2-(4-(1-(dimethylamino)ethyl)phenethyl)-8-methylbenzo[f][1,7]naphthyridin-5-amine; 1-(4-(2-(5-amino-8-methylbenzo[f][1,7]naphthyridin-2-yl)ethyl)phenyl)ethanone oxime; 8-methyl-2-(4-((methylamino)methyl)phenethyl)benzo[f][1,7]naphthyridin-5-amine; (4-(2-(5-amino-8-methylbenzo[f][1,7]naphthyridin-2-yl)ethyl)benzylamino)ethanol; 8-methyl-2-(4-(pyrrolidin-1-ylmethyl)phenethyl)benzo[f][1,7]naphthyridin-5-amine; 2-(3,4-dimethoxyphenethyl)-8-methylbenzo[f][1,7]naphthyridin-5-amine; 2-(1-(4-(2-(5-amino-8-methylbenzo[f][1,7]naphthyridin-2-yl)ethyl)phenyl)ethylamino)ethanol; 1-(4-(2-(5-amino-8-methylbenzo[f][1,7]naphthyridin-2-yl)ethyl)phenyl)ethanol; 8-methyl-2-(4-(oxazol-5-yl)phenethyl)benzo[f][1,7]naphthyridin-5-amine; 3-(1-(4-(2-(5-amino-8-methylbenzo[f][1,7]naphthyridin-2-yl)ethyl)phenyl)ethylamino)propanenitrile; (2R)-2-(1-(4-(2-(5-amino-8-methylbenzo[f][1,7]naphthyridin-2-yl)ethyl)phenyl)ethylamino)propan-1-ol; 8-methyl-2-(4-(1-(piperazin-1-yl)ethyl)phenethyl)benzo[f][1,7]naphthyridin-5-amine; ((2S)-1-(1-(4-(2-(5-amino-8-methylbenzo[f][1,7]naphthyridin-2-yl)ethyl)phenyl)ethyl)pyrrolidin-2-yl)methanol; $N^1$-(1-(4-(2-(5-amino-8-methylbenzo[f][1,7]naphthyridin-2-yl)ethyl)phenyl)ethyl)-$N^2$,$N^2$-dimethylethane-1,2-diamine; 3-(1-(4-(2-(5-amino-8-methylbenzo[f][1,7]naphthyridin-2-yl)ethyl)phenyl)ethylamino)propanoic acid; 8-methyl-2-(4-(1-(4-methylpiperazin-1-yl)ethyl)phenethyl)benzo[f][1,7]naphthyridin-5-amine; $N^2$-(1-(4-(2-(5-amino-8-methylbenzo[f][1,7]naphthyridin-2-yl)ethyl)phenyl)ethyl)-$N^1$,$N^1$-dimethylpropane-1,2-diamine; 8-methyl-2-(4-(1-(2-(pyridin-4-yl)ethylamino)ethyl)phenethyl)benzo[f][1,7]naphthyridin-5-amine; $N^1$-(1-(4-(2-(5-amino-8-methylbenzo[f][1,7]naphthyridin-2-yl)ethyl)phenyl)ethyl)-$N^2$,$N^2$-diethylethane-1,2-diamine; 2-(4-(dimethylamino)-2-methylphenethyl)-8-methylbenzo[f][1,7]naphthyridin-5-amine; 1-(1-(4-(2-(5-amino-8-methylbenzo[f][1,7]naphthyridin-2-yl)ethyl)phenyl)ethyl)pyrrolidine-3-carboxylic acid; 4-(1-(4-(2-(5-amino-8-methylbenzo[f][1,7]naphthyridin-2-yl)ethyl)phenyl)ethylamino)phenol; 1-(1-(4-(2-(5-amino-8-methylbenzo[f][1,7]naphthyridin-2 yl)ethyl)phenyl)ethyl)pyrrolidin-3-ol; and 2-(4-(2-aminopropan-2-yl)phenethyl)-8-methylbenzo[f][1,7]naphthyridin-5-amine By way of example only, the compound benzo[f][1,7]naphthyridin-5-amine (example 1) has an $EC_{50}$ of >100 μM, 14 μM and 0.84 μM in HEK293-TLR7, HEK293-TLR8 and IL-6 hPBMC assays, respectively.

By way of example only, the compound 8-methylbenzo[f][1,7]naphthyridin-5-amine (example 5) has an $EC_{50}$ of 15.8 μM, 9.01 μM and 0.396 μM in HEK293-TLR7, HEK293-TLR8 and IL-6 hPBMC assays, respectively.

By way of example only, the compound 8-fluorobenzo[f][1,7]naphthyridin-5-amine (example 14) has an $EC_{50}$ of 37 μM and 6.38 μM in HEK293-TLR8 and IL-6 hPBMC assays, respectively.

By way of example only, the compound 5-aminobenzo[f][1,7]naphthyridin-3(4H)-one (example 15) has an $EC_{50}$ of 24.1 μM in a HEK293-TLR7 assay.

By way of example only, the compound 2-ethylbenzo[f][1,7]naphthyridin-5-amine (example 30) has an $EC_{50}$ of 8.64 μM, 13 μM and 2.28 μM in HEK293-TLR7, HEK293-TLR8 and IL-6 hPBMC assays, respectively.

By way of example only, the compound 2-phenethylbenzo[f][1,7]naphthyridin-5-amine (example 33) has an $EC_{50}$ of 2.44 μM and 2.28 μM in HEK293-TLR7 and IL-6 hPBMC assays.

By way of example only, the $EC_{50}$ for TLR-7 stimulation by certain other compounds of Formula (I) are listed in Table 2 below. The identifying number for each compound is the number of the Example above that describes its synthesis

TABLE 2

| Example No. | Human TLR-7 $EC_{50}$ (nM) |
|---|---|
| 44 | 107 |
| 46 | 347 |
| 47 | 361 |
| 61 | 582 |
| 62 | 35 |
| 63 | 24 |
| 126 | 275 |
| 138 | 213 |
| 147 | 14 |
| 178 | 562 |

By way of example only, the $EC_{50}$ for TLR-8 stimulation by certain other compounds of Formula (I) are listed in Table 3 below. The identifying number for each compound is the number of the Example above that describes its synthesis

TABLE 3

| Example No. | Human TLR-8 $EC_{50}$ (μM) |
|---|---|
| 177 | 15 |
| 186 | 11 |
| 187 | 82 |
| 188 | >100 |
| 189 | 6.2 |
| 190 | 4.3 |
| 191 | 6 |
| 193 | 24 |
| 195 | 5.3 |
| 196 | 2.6 |

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

We claim:

1. A compound of Formula (I-A), or pharmaceutically acceptable salt thereof:

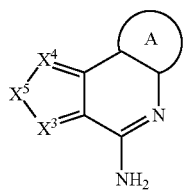

Formula (I-A)

wherein:
$X^3$ is N;
$X^4$ is $CR^3$;
$X^5$ is $-CR^4=CR^5-$;
$R^3$ is H;
$R^4$ is H;
$R^5$ is selected from halogen, $-C(O)OR^7$, $-C(O)R^7$, $-C(O)N(R^{11}R^{12})$, $-N(R^{11}R^{12})$, $-N(R^9)_2$, $-NHN(R^9)_2$, $-SR^7$, $-(CH_2)_nOR^7$, $-(CH_2)_nR^7$, $-LR^{10}$, $-OLR^8$, $-OLR^{10}$, $C_1$-$C_6$alkyl, $C_1$-$C_6$heteroalkyl, $C_1$-$C_6$haloalkyl, $C_2$-$C_8$alkenyl, $C_2$-$C_8$alkynyl, $C_1$-$C_6$alkoxy, $C_1$-$C_6$haloalkoxy, aryl, heteroaryl, $C_3$-$C_8$cycloalkyl, and $C_3$-$C_8$heterocycloalkyl, wherein the $C_1$-$C_6$alkyl, $C_1$-$C_6$heteroalkyl, $C_1$-$C_6$haloalkyl, $C_2$-$C_8$alkenyl, $C_2$-$C_8$alkynyl, $C_1$-$C_6$alkoxy, $C_1$-$C_6$haloalkoxy, aryl, heteroaryl, $C_3$-$C_8$cycloalkyl, and $C_3$-$C_8$heterocycloalkyl groups of $R^5$ are each optionally substituted with 1 to 3 substituents independently selected from halogen, $-CN$, $-NO_2$, $-R^7$, $-OR^8$, $-C(O)R^8$, $-OC(O)R^8$, $-C(O)OR^8$, $-N(R^9)_2$, $-P(O)(OR^8)_2$, $-OP(O)(OR^8)_2$, $-P(O)(OR^{10})_2$, $-OP(O)(OR^{10})_2$, $-C(O)N(R^9)_2$, $-S(O)_2R^8$, $-S(O)R^8$, $-S(O)_2N(R^9)_2$, and $-NR^9S(O)_2R^8$;

each L is independently selected from a bond, $-O(CH_2)_m)_t-$, $C_1$-$C_6$alkyl, $C_2$-$C_6$alkenylene and $C_2$-$C_6$alkynylene, wherein the $C_1$-$C_6$alkyl, $C_2$-$C_6$alkenylene and $C_2$-$C_6$alkynylene of L are each optionally substituted with 1 to 4 substituents independently selected from halogen, $-R^8$, $-OR^8$, $-N(R^9)_2$, $-P(O)(OR^8)_2$, $-OP(O)(OR^8)_2$, $-P(O)(OR^{10})_2$, and $-OP(O)(OR^{10})_2$;

$R^7$ is selected from $C_1$-$C_6$alkyl, aryl, heteroaryl, $C_3$-$C_8$cycloalkyl, $C_1$-$C_6$heteroalkyl, $C_1$-$C_6$haloalkyl, $C_2$-$C_8$alkenyl, $C_2$-$C_8$alkynyl, $C_1$-$C_6$alkoxy, $C_1$-$C_6$haloalkoxy, and $C_3$-$C_8$heterocycloalkyl, wherein the $C_1$-$C_6$alkyl, aryl, heteroaryl, $C_3$-$C_8$cycloalkyl, $C_1$-$C_6$heteroalkyl, $C_1$-$C_6$haloalkyl, $C_2$-$C_8$alkenyl, $C_2$-$C_8$alkynyl, $C_1$-$C_6$alkoxy, $C_1$-$C_6$haloalkoxy, and $C_3$-$C_8$heterocycloalkyl groups of $R^7$ are each optionally substituted with 1 to 3 $R^{13}$ groups, and each $R^{13}$ is independently selected from halogen, $-CN$, $-LR^9$, $-LOR^9$, $-OLR^9$, $-LR^{10}$, $-LOR^{10}$, $-OLR^{10}$, $-LR^8$, $-LOR^8$, $-OLR^8$, $-LSR^8$, $-LSR^{10}$, $-LC(O)R^8$, $-OLC(O)R^8$, $-LC(O)OR^8$, $-LC(O)R^{10}$, $-LOC(O)OR^8$, $-LC(O)NR^9R^{11}$, $-LC(O)NR^9R^8$, $-LN(R^9)_2$, $-LNR^9R^8$, $-LNR^9R^{10}$, $-LC(O)N(R^9)_2$, $-LS(O)_2R^8$, $-LS(O)R^8$, $-LC(O)NR^8OH$, $-LNR^9C(O)R^8$, $-LNR^9C(O)OR^8$, $-LS(O)_2N(R^9)_2$, $-OLS(O)_2N(R^9)_2$, $-LNR^9S(O)_2R^8$, $-LC(O)NR^9LN(R^9)_2$, $-LP(O)(OR^8)_2$, $-LOP(O)(OR^8)_2$, $-LP(O)(OR^{10})_2$ and $-OLP(O)(OR^{10})_2$;

each $R^8$ is independently selected from H, $-CH(R^{10})_2$, $C_1$-$C_8$alkyl, $C_2$-$C_8$alkene, $C_2$-$C_8$alkyne, $C_1$-$C_6$haloalkyl, $C_1$-$C_6$alkoxy, $C_1$-$C_6$heteroalkyl, $C_3$-$C_8$cycloalkyl, $C_2$-$C_8$heterocycloalkyl, $C_1$-$C_6$hydroxyalkyl and $C_1$-$C_6$haloalkoxy, wherein the $C_1$-$C_8$alkyl, $C_8$alkene, $C_2$-$C_8$alkyne, $C_1$-$C_6$heteroalkyl, $C_1$-$C_6$haloalkyl, $C_1$-$C_6$alkoxy, $C_3$-$C_8$cycloalkyl, $C_2$-$C_8$heterocycloalkyl, $C_1$-$C_6$hydroxyalkyl and $C_1$-$C_6$haloalkoxy groups of $R^8$ are each optionally substituted with 1 to 3 substituents independently selected from $-CN$, $R^{11}$, $-OR^{11}$, $-SR^{11}$, $-C(O)R^{11}$, $-OC(O)R^{11}$, $-C(O)N(R^9)_2$, $-C(O)OR^{11}$, $-NR^9C(O)R^{11}$, $-NR^9R^{10}$, $-NR^{11}R^{12}$, $-N(R^9)_2$, $-OR^9$, $-OR^{10}$, $-C(O)NR^{11}R^{12}$, $-C(O)NR^{11}OH$, $-S(O)_2R^{11}$, $-S(O)R^{11}$, $S(O)_2NR^{11}R^{12}$, $-NR^{11}S(O)_2R^{11}$, $-P(O)(OR^{11})_2$, and $-OP(O)(OR^{11})_2$;

each $R^9$ is independently selected from H, $-C(O)R^8$, $-C(O)OR^8$, $-C(O)R^{10}$, $-C(O)OR^{10}$, $-S(O)_2R^{10}$, $-C_1$-$C_6$ alkyl, $C_1$-$C_6$ heteroalkyl and $C_3$-$C_6$ cycloalkyl, or each $R^9$ is independently a $C_1$-$C_6$alkyl that together with N they are attached to form a $C_3$-$C_8$heterocycloalkyl, wherein the $C_3$-$C_8$heterocycloalkyl ring optionally contains an additional heteroatom selected from N, O and S, and wherein the $C_1$-$C_6$ alkyl, $C_1$-$C_6$ heteroalkyl, $C_3$-$C_6$ cycloalkyl, or $C_3$-$C_8$heterocycloalkyl groups of $R^9$ are each optionally substituted with 1 to 3 substituents independently selected from —CN, $R^{11}$, —$OR^{11}$, —$SR^{11}$, —$C(O)R^{11}$, —$OC(O)R^{11}$, —$C(O)OR^{11}$, —$NR^{11}R^{12}$, —$C(O)NR^{11}R^{12}$, —$C(O)NR^{11}OH$, —$S(O)_2R^{11}$, —$S(O)R^{11}$, —$S(O)_2NR^{11}R^{12}$, —$NR^{11}S(O)_2R^{11}$, —$P(O)(OR^{11})_2$, and —$OP(O)(OR^{11})_2$;

each $R^{10}$ is independently selected from aryl, $C_3$-$C_8$cycloalkyl, $C_3$-$C_8$heterocycloalkyl and heteroaryl, wherein the aryl, $C_3$-$C_8$cycloalkyl, $C_3$-$C_8$heterocycloalkyl and heteroaryl groups are optionally substituted with 1 to 3 substituents selected from halogen, —$R^8$, —$OR^8$, -$LR^9$, -$LOR^9$, —$N(R^9)_2$, —$NR^9C(O)R^8$, —$NR^9CO_2R^8$, —$CO_2R^8$, —$C(O)R^8$ and —$C(O)N(R^9)_2$;

$R^{11}$ and $R^{12}$ are independently selected from H, $C_1$-$C_6$alkyl, $C_1$-$C_6$heteroalkyl, $C_1$-$C_6$haloalkyl, aryl, heteroaryl, $C_3$-$C_8$cycloalkyl, and $C_3$-$C_8$heterocycloalkyl, wherein the $C_1$-$C_6$alkyl, $C_1$-$C_6$heteroalkyl, $C_1$-$C_6$haloalkyl, aryl, heteroaryl, $C_3$-$C_8$cycloalkyl, and $C_3$-$C_8$heterocycloalkyl groups of $R^{11}$ and $R^{12}$ are each optionally substituted with 1 to 3 substituents independently selected from halogen, —CN, $R^8$, —$OR^8$, —$C(O)R^8$, ⁻$OC(O)R^8$, —$C(O)OR^8$, —$N(R^9)_2$, —$NR^8C(O)R^8$, —$NR^8C(O)OR^8$, —$C(O)N(R^9)_2$, $C_3$-$C_8$heterocycloalkyl, —$S(O)_2R^8$, —$S(O)_2N(R^9)_2$, —$NR^9S(O)_2R^8$, $C_1$-$C_6$haloalkyl and $C_1$-$C_6$haloalkoxy;

or $R^{11}$ and $R^{12}$ are each independently $C_1$-$C_6$alkyl and taken together with the N atom to which they are attached form an optionally substituted $C_3$-$C_8$heterocycloalkyl ring optionally containing an additional heteroatom selected from N, O and S;

Ring A is phenyl or pyridyl, wherein the phenyl and pyridyl groups of Ring A are optionally substituted with 1 to 3 $R^A$ groups, wherein each $R^A$ is independently selected from —$R^8$, —$R^7$, —$OR^7$, —$OR^8$, —$R^{10}$, —$SR^8$, —$NO_2$, —CN, —$N(R^9)_2$, —$NR^9C(O)R^8$, —$NR^9C(S)R^8$, —$NR^9C(S)R^8$, —$NR^9C(O)N(R^9)_2$, —$NR^9C(S)N(R^9)_2$, —$NR^9CO_2R^8$, —$NR^9NR^9C(O)R^8$, —$NR^9NR^9C(O)N(R^9)_2$, —$NR^9NR^9CO_2R^8$, —$C(O)C(O)R^8$, —$C(O)CH_2C(O)R^8$, —$CO_2R^8$, —$(CH_2)_nCO_2R^8$, —$C(O)R^8$, —$C(S)R^8$, —$C(O)N(R^9)_2$, —$C(S)N(R^9)_2$, —$OC(O)N(R^9)_2$, —$OC(O)R^8$, —$C(O)N(OR^8)R^8$, —$C(NOR^8)R^8$, —$S(O)_2R^8$, —$S(O)_3R^8$, —$SO_2N(R^9)_2$, —$S(O)R^8$, —$NR^9SO_2N(R^9)_2$, —$NR^9SO_2R^8$, —$P(O)(OR^8)_2$, —$OP(O)(OR^8)_2$, —$P(O)(OR^{10})_2$, —$OP(O)(OR^{10})_2$, —$N(OR^8)R^8$, —CH=$CHCO_2R^8$, —C(=NH)—N($R^9$)$_2$, and —$(CH_2)_nNHC(O)R^8$; or two adjacent $R^A$ substituents on Ring A form a 5-6 membered ring that contains up to two heteroatoms as ring members;

n is, independently at each occurrence, 0, 1, 2, 3, 4, 5, 6, 7 or 8;

each m is independently selected from 1, 2, 3, 4, 5 and 6, and t is 1, 2, 3, 4, 5, 6, 7 or 8.

2. The compound of claim 1, wherein:

$R^5$ is selected from halogen, —$C(O)OR^7$, —$C(O)R^7$, —$C(O)N(R^{11}R^{12})$, $N(R^{11}R^{12})$, $N(R^9)_2$, —$NHN(R^9)_2$, -$LR^{10}$, —$OLR^8$, —$OLR^{10}$, —$SR^7$, —$(CH_2)_nOR^7$, —$(CH_2)_nR^7$, $C_1$-$C_6$alkyl, $C_1$-$C_6$haloalkyl, $C_2$-$C_8$alkenyl, $C_2$-$C_8$alkynyl, and $C_1$-$C_6$alkoxy, wherein the $C_1$-$C_6$alkyl, $C_2$-$C_8$alkenyl and $C_2$-$C_8$alkynyl groups $R^5$ are each optionally substituted with 1 to 3 substituents independently selected from halogen, —CN, —$R^7$, —$OR^8$, —$C(O)R^8$, —$OC(O)R^8$, —$C(O)OR^8$, —N($R^9$)$_2$, —$P(O)(OR^8)_2$, —$OP(O)(OR^8)_2$, —$P(O)(OR^{10})_2$, —$OP(O)(OR^{10})_2$, —$C(O)N(R^9)_2$, —$S(O)_2R^8$, —$S(O)_2N(R^9)_2$, and —$NR^9S(O)_2R^8$;

each L is independently selected from a bond, —$O(CH_2)_m)_t$—, and $C_1$-$C_6$alkylene, wherein the $C_1$-$C_6$alkylene of L is substituted with 1 substituent independently selected from —$R^8$;

$R^7$ is selected from $C_1$-$C_6$alkyl, phenyl, naphthyl, heteroaryl, $C_3$-$C_8$cycloalkyl and $C_3$-$C_8$heterocycloalkyl, wherein the $C_1$-$C_6$alkyl, phenyl, naphthyl, heteroaryl, $C_3$-$C_8$cycloalkyl and heterocycloalkyl groups of $R^7$ are each optionally substituted with 1 to 3 $R^{13}$ groups, and each $R^{13}$ is independently selected from halogen, —CN, -$LR^9$, -$LOR^9$, —$OLR^9$, -$LR^{10}$, -$LOR^{10}$, —$OLR^{10}$, $LR^8$, -$LOR^8$, —$OLR^8$, -$LSR^8$, -$LSR^{10}$, -$LC(O)R^8$, —OLC(O)$R^8$, -$LC(O)OR^8$, -$LC(O)OR^{10}$, -$LOC(O)OR^8$, -$LC(O)NR^9R^{11}$, -$LC(O)NR^9R^8$, -$LN(R^9)_2$, -$LNR^9R^8$, -$LNR^9R^{10}$, -$LC(O)N(R^9)_2$, -$LS(O)_2R^8$, -$LS(O)R^8$, -$LC(O)NR^8OH$, -$LNR^9C(O)R^8$, -$LNR^9C(O)OR^8$, -$LS(O)_2N(R^9)_2$, —$OLS(O)_2N(R^9)_2$, -$LNR^9S(O)_2R^8$, -$LC(O)NR^9LN(R^9)_2$, -$LP(O)(OR^8)_2$, -$LOP(O)(OR^8)_2$, -$LP(O)(OR^{10})_2$ and —$OLP(O)(OR^{10})_2$;

each $R^8$ is independently selected from H, —$CH(R^{10})_2$, $C_1$-$C_8$alkyl, $C_2$-$C_8$alkenyl, $C_1$-$C_6$haloalkyl, $C_3$-$C_8$cycloalkyl, $C_2$-$C_8$heterocycloalkyl,- and $C_1$-$C_6$hydroxyalkyl, wherein the $C_1$-$C_8$alkyl and $C_2$-$C_8$alkenyl, $C_3$-$C_8$cycloalkyl, and $C_2$-$C_8$heterocycloalkyl groups of $R^8$ are each optionally substituted with 1 to 3 substituents independently selected from —CN, $R^{11}$, —$OR^{11}$, —$SR^{11}$, —$C(O)R^{11}$, —$OC(O)R^{11}$, —$C(O)N(R^9)_2$, —$C(O)OR^{11}$, —$NR^9C(O)R^{11}$, —$NR^9R^{10}$, $NR^{11}R^{12}$, —$N(R^9)_2$, —$OR^9$, —$OR^{10}$, —$C(O)NR^{11}R^{12}$, —$C(O)NR^{11}OH$, —$S(O)_2R^{11}$, —$S(O)R^{11}$, —$S(O)_2NR^{11}R^{12}$, —$NR^{11}S(O)^2R^{11}$, —$P(O)(OR^{11})_2$, and —$OP(O)(OR^{11})_2$;

each $R^9$ is independently selected from H, —$C(O)R^8$, —$C(O)OR^8$, —$S(O)_2R^{10}$, and —$C_1$-$C_6$ alkyl, or each $R^9$ is independently a $C_1$-$C_6$alkyl that together with the N to which they are attached form a $C_3$-$C_8$heterocycloalkyl, wherein the $C_1$-$C_6$ alkyl or heterocycloalkyl groups of $R^9$ are each optionally substituted with 1 to 2 substituents independently selected from —CN, $R^{11}$, —$OR^{11}$, —$SR^{11}$, —$C(O)R^{11}$, —$OC(O)R^{11}$, —$C(O)OR^{11}$, —$NR^{11}R^{12}$, —$C(O)NR^{11}R^{12}$, —$C(O)NR^{11}OH$, —$S(O)_2R^{11}$—$S(O)_2NR^{11}R^{12}$, —$NR^{11}S(O)_2R^{11}$, —$P(O)(OR^{11})_2$, and —$OP(O)(OR^{11})_2$;

each $R^{10}$ is independently selected from aryl, $C_3$-$C_8$cycloalkyl, $C_3$-$C_8$heterocycloalkyl and heteroaryl, wherein the aryl, $C_3$-$C_8$cycloalkyl, $C_3$-$C_8$heterocycloalkyl and heteroaryl groups are optionally substituted with 1 to 3 substituents selected from halogen, —$R^8$, —$OR^8$, -$LR^9$, -$LOR^9$, —$N(R^9)_2$, —$NR^9C(O)R^8$, —$NR^9CO_2R^8$, —$CO_2R^8$, —$C(O)R^8$ and —$C(O)N(R^9)_2$;

$R^{11}$ is selected from H, $C_1$-$C_6$alkyl, aryl, heteroaryl, $C_3$-$C_8$cycloalkyl, and $C_3$-$C_8$heterocycloalkyl;

$R^{12}$ is H or $C_1$-$C_6$alkyl;

Ring A is phenyl optionally substituted with 1 to 3 $R^A$ groups, wherein each $R^A$ is independently selected from —$R^8$, —$R^7$, —$OR^7$, —$OR^8$, —$R^{10}$, —$OR^{10}$, —$SR^8$, —$NO_2$, —CN, —$N(R^9)_2$, —$NR^9C(O)R^8$, —$NR^9C(S)R^8$, —$NR^9C(O)N(R^9)_2$, —$NR^9C(S)N(R^9)_2$, —NR$^9$CO$_2$R$^8$, —NR$^9$NR$^9$C(O)R$^8$, —NR$^9$NR$^9$C(O)N(R$^9$)$_2$, —NR$^9$NR$^9$CO$_2$R$^8$, —C(O)C(O)R$^8$, —C(O)CH$_2$C(O)R$^8$, —CO$_2$R$^8$, —(CH$_2$)$_n$CO$_2$R$^8$, —C(O)R$^8$, —C(S)R$^8$, —C(O)N(R$^9$)$_2$, —C(S)N(R$^9$)$_2$, —OC(O)N(R$^9$)$_2$, —OC(O)R$^8$, —C(O)N(OR$^8$)R$^8$, —C(NOR$^8$)R$^8$, —S(O)$_2$R$^8$, —S(O)$_3$R$^8$, —SO$_2$N(R$^9$)$_2$, —S(O)R$^8$, —NR$^9$SO$_2$N(R$^9$)$_2$, —NR$^9$SO$_2$R$^8$, —P(O)(OR$^8$)$_2$, —OP(O)(OR$^8$)$_2$, —P(O)(OR$^{10}$)$_2$, —OP(O)(OR$^{10}$)$_2$, —N(OR$^8$)R$^8$, —CH=CHCO$_2$R$^8$, —C(=NH)—N(R$^9$)$_2$, and —(CH$_2$)$_n$NHC(O)R$^8$;

n is, independently at each occurrence, 1, 2, 3, 4, or 5;

each m is independently selected from 1, 2, 3, 4, 5 and 6, and t is 1, 2, 3, or 4.

3. The compound of claim 2, wherein the compound of Formula (I-A) is a compound of Formula (X-A):

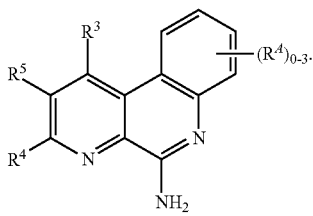

Formula (X-A)

4. The compound of claim 3, wherein the compound of Formula (X-A) is a compound of Formula (XI):

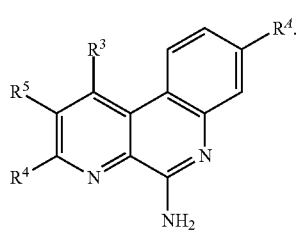

Formula (XI)

5. The compound of claim 4, wherein the compound of Formula (XI) is a compound of Formula (XIII):

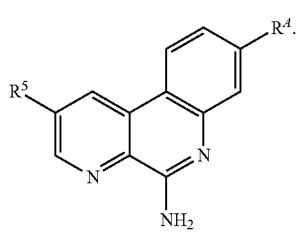

Formula (XIII)

6. The compound of claim 4, wherein,

R$^5$ is selected from —C(O)OR$^7$, —N(R$^9$)$_2$, —NHN(R$^9$)$_2$, -LR$^{10}$, —(CH$_2$)$_n$R$^7$, —C$_1$-C$_6$alkyl, C$_1$-C$_6$haloalkyl, C$_2$-C$_8$alkenyl, C$_2$-C$_8$alkynyl and C$_1$-C$_6$alkoxy, wherein the C$_1$-C$_6$alkyl, C$_2$-C$_8$alkenyl, and C$_2$-C$_8$alkynyl groups of R$^5$ are each optionally substituted with 1 to 3 substituents independently selected from halogen, —CN, —R$^7$, —OR$^8$, —C(O)R$^8$, —OC(O)R$^8$, —C(O)OR$^8$, —N(R$^9$)$_2$, —P(O)(OR$^8$)$_2$, —OP(O)(OR$^8$)$_2$, —P(O)(OR$^{10}$)$_2$, —OP(O)(OR$^{10}$)$_2$, —C(O)N(R$^9$)$_2$, —S(O)$_2$R$^8$, —S(O)$_2$N(R$^9$)$_2$, and —NHS(O)$_2$R$^8$.

7. The compound of claim 6, wherein,

R$^5$ is —(CH$_2$)$_n$R$^7$.

8. The compound of claim 7, wherein,

R$^7$ is selected from phenyl, naphthyl, and heteroaryl, wherein the C$_1$-C$_6$alkyl, phenyl, naphthyl, and heteroaryl groups of R$^7$ are each optionally substituted with 1 to 3 R$^{13}$ groups and each R$^{13}$ is independently selected from halogen, —CN, -LR$^9$, -LOR$^9$, —OLR$^9$, -LR$^{10}$, -LOR$^{10}$, —OLR$^{10}$, -LR$^8$, -LOR$^8$, —OLR$^8$, -LSR$^8$, -LSR$^{10}$, -LC(O)R$^8$, —OLC(O)R$^8$, -LC(O)R$^8$, -LC(O)R$^{10}$, -LOC(O)OR$^8$, -LC(O)NR$^9$R$^{11}$, -LC(O)NR$^9$R$^8$, -LN(R$^9$)$_2$, -LNR$^9$R$^8$, -LNR$^9$R$^{10}$, -LC(O)N(R$^9$)$_2$, -LS(O)$_2$R$^8$, -LS(O)R$^8$, -LC(O)NR$^8$OH, -LNR$^9$C(O)R$^8$, -LNR$^9$C(O)OR$^8$, -LS(O)$_2$N(R$^9$)$_2$, —OLS(O)$_2$N(R$^9$)$_2$, -LNR$^9$S(O)$_2$R$^8$, -LC(O)NR$^9$LN(R$^9$)$_2$, -LP(O)(OR$^8$)$_2$, -LOP(O)(OR$^8$)$_2$, -LP(O)(OR$^{10}$)$_2$ and —OLP(O)(OR$^{10}$)$_2$.

9. The compound of claim 8, wherein the compound is a compound of Formula (XVI):

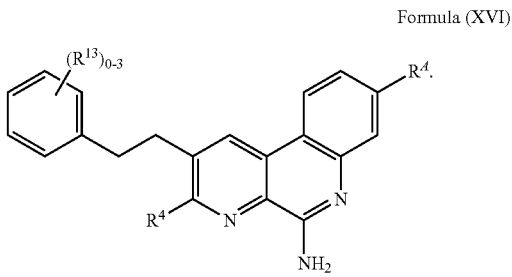

Formula (XVI)

10. The compound of claim 9, wherein the compound is substituted with one to three R$^{13}$ groups selected from -LR$^9$, -LOR$^9$, —OLR$^9$, -LR$^{10}$, -LOR$^{10}$, —OLR$^{10}$, -LR$^8$, -LOR$^8$, —OLR$^8$, -LSR$^8$, -LSR$^{10}$, -LC(O)R$^8$, —OLC(O)R$^8$, -LC(O)OR$^8$, -LC(O)R$^{10}$, -LOC(O)OR$^8$, -LC(O)NR$^9$R$^{11}$, -LC(O)NR$^9$R$^8$, -LN(R$^9$)$_2$, -LNR$^9$R$^8$, -LNR$^9$R$^{10}$, -LC(O)N(R$^9$)$_2$, -LS(O)$_2$R$^8$LS(O)R$^8$, -LC(O)NR$^8$OH, -LNR$^9$C(O)R$^8$, -LNR$^9$C(O)OR$^8$, -LS(O)$_2$N(R$^9$)$_2$, —OLS(O)$_2$N(R$^9$)$_2$, -LNR$^9$S(O)$_2$R$^8$, -LC(O)NR$^9$LN(R$^9$)$_2$, -LP(O)(OR$^8$)$_2$, -LOP(O)(OR$^8$)$_2$, -LP(O)(OR$^{10}$)$_2$ and —OLP(O)(OR$^{10}$)$_2$.

11. The compound of claim 10, wherein, each R$^{13}$ is independently selected from halogen, C$_1$-C$_6$haloalkyl, -LR$^8$, LR$^9$, -LOR$^8$ and —OLR$^8$ and -LP(O)(OR$^8$)$_2$.

12. The compound of claim 11, wherein, each R$^4$ is independently selected from —R$^7$, —OR$^7$, —R$^8$, —OR$^8$, —R$^{10}$, —OR$^{10}$, —SR$^8$, —N(R$^9$)$_2$, —S(O)$_2$R$^8$, —S(O)$_3$R$^8$, —SO$_2$N(R$^9$)$_2$, —S(O)R$^8$, —NR$^9$SO$_2$N(R$^9$)$_2$, —CH=CHCO$_2$R$^8$, (CH$_2$)$_n$CO$_2$R$^8$, —NR$^9$SO$_2$R$^8$, —P(O)(OR$^8$)$_2$, —OP(O)(OR$^8$)$_2$, —P(O)(OR$^{10}$)$_2$, and —OP(O)(OR$^{10}$)$_2$.

13. The compound of claim 12, wherein,

R$^8$ is selected from H, C$_1$-C$_6$alkyl and C$_1$-C$_6$haloalkyl.

14. The compound of claim 9, wherein the compound is substituted with two R$^{13}$ groups independently selected from —CH$_3$, —CH$_2$CH$_3$, —CF$_3$, —CH$_2$OH, —OCH$_3$, —COOCH$_3$, —COOCH$_2$CH$_3$, F, Cl, Br, —CH$_2$OCH$_3$, CH$_2$OCH$_2$CH$_3$, —N(CH$_3$)$_2$, —((O(CH$_2$)$_2$)$_{2-4}$—OH, —O(CH$_2$)$_{2-4}$—OH, —O(CH$_2$)$_{2-4}$—PO$_3$H$_2$), —O(CH$_2$)$_{2-4}$—COOH, —O(CH$_2$)$_{2-4}$—CH(CH$_3$)$_2$, C$_2$-C$_6$ alkyl substituted with 1-3 substituents selected from —OH, —CH$_3$, cyclopropyl, —O(CH$_2$)$_{2-4}$—COOH, —O(CH$_2$)$_{2-4}$(PO$_3$H$_2$), —COOH, COOCH$_3$, and —COOCH$_2$CH$_3$,
and R$^A$ is —CH$_3$.

15. The compound of claim 1 selected from 2-methylbenzo[f][1,7]naphthyridin-5-amine,
2-propylbenzo[f][1,7]naphthyridin-5-amine,
2-ethylbenzo[f][1,7]naphthyridin-5-amine,
2-(3-methoxyphenethyl)benzo[f][1,7]naphthyridin-5-amine,
8-methyl-2-phenethylbenzo[f][1,7]naphthyridin-5-amine,
2-(2-methylphenethyl)benzo[f][1,7]naphthyridin-5-amine,
2-(3-methylphenethyl)benzo[f][1,7]naphthyridin-5-amine,
2-(4-methylphenethyl)benzo[f][1,7]naphthyridin-5-amine,
8-methyl-2-(2-(naphthalen-1-yl)ethyl)benzo[f][1,7]naphthyridin-5-amine,
8-methyl-2-(2-(naphthalen-2-yl)ethyl)benzo[f][1,7]naphthyridin-5-amine,
4-(2-(5-amino-8-methylbenzo[f][1,7]naphthyridin-2-yl)ethyl)benzoic acid,
3-(2-(5-amino-8-methylbenzo[f][1,7]naphthyridin-2-yl)ethyl)benzoic acid,
2-(3-chlorophenethyl)-8-methylbenzo[f][1,7]naphthyridin-5-amine,
2-(2-chlorophenethyl)-8-methylbenzo[f][1,7]naphthyridin-5-amine,
(3-(2-(5-amino-8-methylbenzo[f][1,7]naphthyridin-2-yl)ethyl)phenyl)methanol,
2-(4-chlorophenethyl)-8-methylbenzo[f][1,7]naphthyridin-5-amine,
2-(4-butylphenethyl)benzo[f][1,7]naphthyridin-5-amine,
2-(4-butylphenethyl)-8-methylbenzo[f][1,7]naphthyridin-5-amine,
2-(4-propylphenethyl)benzo[f][1,7]naphthyridin-5-amine,
2-(4-(trifluoromethyl)phenethyl)benzo[f][1,7]naphthyridin-5-amine,
2-(2,5-dimethylphenethyl)-8-methylbenzo[f][1,7]naphthyridin-5-amine,
8-methyl-2-(4-propylphenethyl)benzo[f][1,7]naphthyridin-5-amine,
8-methyl-2-(2,4,5-trimethylphenethyl)benzo[f][1,7]naphthyridin-5-amine,
2-(2,5-dimethylphenethyl)benzo[f][1,7]naphthyridin-5-amine,
2-(4-isopropylphenethyl)-8-methylbenzo[f][1,7]naphthyridin-5-amine,
2-(4-heptylphenethyl)-8-methylbenzo[f][1,7]naphthyridin-5-amine,
2-(4-isobutoxyphenethyl)-8-methylbenzo[f][1,7]naphthyridin-5-amine,
2-(4-((2-methoxyethoxy)methoxy)phenethyl)-8-methylbenzo[f][1,7]naphthyridin-5-amine,
8-methyl-2-(4-(2-phenoxyethoxy)phenethyl)benzo[f][1,7]naphthyridin-5-amine,
8-methyl-2-(4-(4-phenylbutoxy)phenethyl)benzo[f][1,7]naphthyridin-5-amine,
2-(4-(allyloxy)phenethyl)-8-methylbenzo[f][1,7]naphthyridin-5-amine,
8-methyl-2-(4-(3-phenylpropoxy)phenethyl)benzo[f][1,7]naphthyridin-5-amine,
2-(4-(heptan-4-yloxy)phenethyl)-8-methylbenzo[f][1,7]naphthyridin-5-amine,
8-methyl-2-(4-(4-methylpent-3-enyloxy)phenethyl)benzo[f][1,7]naphthyridin-5-amine,
2-(4-(2-cyclohexylethoxy)phenethyl)-8-methylbenzo[f][1,7]naphthyridin-5-amine,
2-(4-isopropoxyphenethyl)-8-methylbenzo[f][1,7]naphthyridin-5-amine,
2-(4-(3,3-dimethylbutoxy)phenethyl)-8-methylbenzo[f][1,7]naphthyridin-5-amine,
8-(2-cyclopropylethyl)-2-(4-(dimethylamino)phenethyl)benzo[f][1,7]naphthyridin-5-amine,
8-(2-cyclopropylethyl)-2-(2,4-dimethylphenethyl)benzo[f][1,7]naphthyridin-5-amine,
N-(4-(2-(5-amino-8-methylbenzo[f][1,7]naphthyridin-2-yl)ethyl)phenyl)acetamide,
N-(4-(2-(5-aminobenzo[f][1,7]naphthyridin-2-yl)ethyl)phenyl)acetamide,
N-(4-(2-(5-amino-8-methylbenzo[f][1,7]naphthyridin-2-yl)ethyl)phenyl)-4-methylbenzenesulfonamide,
4-(2-(5-amino-8-methylbenzo[f][1,7]naphthyridin-2-yl)ethyl)-3-methylbenzonitrile,
4-(2-(5-amino-8-methylbenzo[f][1,7]naphthyridin-2-yl)ethyl)-N-(2-aminoethyl)-3-methylbenzamide,
8-methyl-2-(2-methyl-4-(1H-tetrazol-5-yl)phenethyl)benzo[f][1,7]naphthyridin-5-amine,
methyl 2-(4-(2-(5-amino-8-methylbenzo[f][1,7]naphthyridin-2-yl)ethyl)-3-methylbenzamido)-4-methylpentanoate,
methyl 2-(4-(2-(5-amino-8-methylbenzo[f][1,7]naphthyridin-2-yl)ethyl)-3-methylbenzamido)acetate,
2-(4-(2-(5-amino-8-methylbenzo[f][1,7]naphthyridin-2-yl)ethyl)-3-methylbenzamido)-4-methylpentanoic acid,
2-(4-(2-(5-amino-8-methylbenzo[f][1,7]naphthyridin-2-yl)ethyl)-3-methylbenzamido)acetic acid,
6-(5-amino-8-methylbenzo[f][1,7]naphthyridin-2-yl)hexan-1-ol,
7-(5-amino-8-methylbenzo[f][1,7]naphthyridin-2-yl)heptanoic acid,
11-(5-amino-8-methylbenzo[f][1,7]naphthyridin-2-yl)undecan-1-ol,
ethyl 2-(4-(2-(5-amino-8-methylbenzo[f][1,7]naphthyridin-2-yl)ethyl)-3-methylphenoxy)acetate,
2-(4-(2-(5-amino-8-methylbenzo[f][1,7]naphthyridin-2-yl)ethyl)-3-methylphenoxy)acetic acid,
3-(4-(2-(5-amino-8-methylbenzo[f][1,7]naphthyridin-2-yl)ethyl)-3-methylphenoxy)propanoic acid,
6-(4-(2-(5-amino-8-methylbenzo[f][1,7]naphthyridin-2-yl)ethyl)-3-methylphenoxy)hexanoic acid,
8-methyl-2-(2-methyl-4-(methylthio)phenethyl)benzo[f][1,7]naphthyridin-5-amine,
8-methyl-2-(4-(methylsulfonyl)phenethyl)benzo[f][1,7]naphthyridin-5-amine,
2-(4-(hexyloxy)phenethyl)-8-methylbenzo[f][1,7]naphthyridin-5-amine,
8-methyl-2-(4-phenethoxyphenethyl)benzo[f][1,7]naphthyridin-5-amine,
8-methyl-2-(4-(pentyloxy)phenethyl)benzo[f][1,7]naphthyridin-5-amine,
8-methyl-2-(4-(4-methylpentyloxy)phenethyl)benzo[f][1,7]naphthyridin-5-amine,
2-(2-fluorophenethyl)benzo[f][1,7]naphthyridin-5-amine,
2-(3-fluorophenethyl)benzo[f][1,7]naphthyridin-5-amine,
2-(4-fluorophenethyl)benzo[f][1,7]naphthyridin-5-amine,
2-(2-(thiophen-3-yl)ethyl)benzo[f][1,7]naphthyridin-5-amine,
(5-aminobenzo[f][1,7]naphthyridin-2-yl)methanol,
2-(3,4-dimethylphenethyl)benzo[f][1,7]naphthyridin-5-amine,
2-(3,4-dimethylphenethyl)-8-methylbenzo[f][1,7]naphthyridin-5-amine, 2-(3,5-dimethylphenethyl)-8-methylbenzo[f][1,7]naphthyridin-5-amine,
2-(2-(benzofuran-5-yl)ethyl)-8-methylbenzo[f][1,7]naphthyridin-5-amine,
8-methyl-2-(2-nitroethyl)benzo[f][1,7]naphthyridin-5-amine,
2-(aminomethyl)-8-methylbenzo[f][1,7]naphthyridin-5-amine,
N$^2$,8-dimethylbenzo[f][1,7]naphthyridine-2,5-diamine,
2-(5-amino-8-methylbenzo[f][1,7]naphthyridin-2-yl)-1-phenylethanol,
2-(5-amino-8-methylbenzo[f][1,7]naphthyridin-2-yl)-1-(4-methoxyphenyl)ethanol,
2-(biphenyl-2-yl)-8-methylbenzo[f][1,7]naphthyridin-5-amine,
2-(2-(2,6-dimethylpyridin-3-yl)ethyl)-8-methylbenzo[f][1,7]naphthyridin-5-amine,
2-(2-(5-methoxypyridin-2-yl)ethyl)-8-methylbenzo[f][1,7]naphthyridin-5-amine,
3-(4-(2-(5-amino-8-methylbenzo[f][1,7]naphthyridin-2-yl)ethyl)phenyl)propanoic acid,
6-(2-(5-amino-8-methylbenzo[f][1,7]naphthyridin-2-yl)ethyl)pyridin-3-ol
8-methyl-2-(4-(trifluoromethoxy)phenethyl)benzo[f][1,7]naphthyridin-5-amine,
(E)-3-(4-(2-(5-amino-8-methylbenzo[f][1,7]naphthyridin-2-yl)ethyl)-3-methylphenyl)acrylic acid,
(E)-ethyl 3-(5-amino-2-(4-methoxy-2-methylphenethyl)benzo[f][1,7]naphthyridin-8-yl)acrylate,
(E)-8-(2-cyclopropylvinyl)-2-phenethylbenzo[f][1,7]naphthyridin-5-amine,
8-(2-cyclopropylethyl)-2-phenethylbenzo[f][1,7]naphthyridin-5-amine,
(5-amino-2-phenethylbenzo[f][1,7]naphthyridin-8-yl)methanol,
(5-amino-2-(4-methoxy-2-methylphenethyl)benzo[f][1,7]naphthyridin-8-yl)methanol,
3-(2-(5-aminobenzo[f][1,7]naphthyridin-2-yl)ethyl)phenol,
2-(2-methoxyphenethyl)benzo[f][1,7]naphthyridin-5-amine,
2-(4-ethylphenethyl)benzo[f][1,7]naphthyridin-5-amine,
2-(4-ethylphenethyl)-8-methylbenzo[f][1,7]naphthyridin-5-amine,
2-(4-(dimethylamino)phenethyl)benzo[f][1,7]naphthyridin-5-amine,
2-(4-(piperidin-1-yl)phenethyl)benzo[f][1,7]naphthyridin-5-amine,
2-(4-tert-butylphenethyl)-8-methylbenzo[f][1,7]naphthyridin-5-amine,
8-methyl-2-(4-(piperidin-1-yl)phenethyl)benzo[f][1,7]naphthyridin-5-amine,
2-(4-methoxyphenethyl)-8-methylbenzo[f][1,7]naphthyridin-5-amine,
2-(3,5-dimethoxyphenethyl)-8-methylbenzo[f][1,7]naphthyridin-5-amine,
8-methyl-2-(2-(trifluoromethyl)phenethyl)benzo[f][1,7]naphthyridin-5-amine,
4-(2-(5-amino-8-methylbenzo[f][1,7]naphthyridin-2-yl)ethyl)benzonitrile,
8-methyl-2-(4-(1-morpholinoethyl)phenethyl)benzo[f][1,7]naphthyridin-5-amine,
2-(4-aminophenethyl)-8-methylbenzo[f][1,7]naphthyridin-5-amine,
8-methyl-2-(4-(1-(phenethylamino)ethyl)phenethyl)benzo[f][1,7]naphthyridin-5-amine,
2-(4-(2-(5-amino-8-methylbenzo[f][1,7]naphthyridin-2-yl)ethyl)phenyl)acetonitrile,
2-(4-(piperidin-1-ylmethyl)phenethyl)benzo[f][1,7]naphthyridin-5-amine,
1-(4-(2-(5-aminobenzo[f][1,7]naphthyridin-2-yl)ethyl)benzyl)piperidin-4-ol,
2-(4-(aminomethyl)phenethyl)benzo[f][1,7]naphthyridin-5-amine,
2-(4-((ethylamino)methyl)phenethyl)benzo[f][1,7]naphthyridin-5-amine,
2-(4-(2-aminopropan-2-yl)phenethyl)benzo[f][1,7]naphthyridin-5-amine,
1-(1-(4-(2-(5-aminobenzo[f][1,7]naphthyridin-2-yl)ethyl)phenyl)ethyl)pyrrolidine-3-carboxylic acid,
8-methyl-2-(4-(1-(phenylamino)ethyl)phenethyl)benzo[f][1,7]naphthyridin-5-amine,
2-ethyl-8-methylbenzo[f][1,7]naphthyridin-5-amine,
(5-amino-8-methylbenzo[f][1,7]naphthyridin-2-yl)methanol,
8-methyl-2-propylbenzo[f][1,7]naphthyridin-5-amine,
2-(2-(1H-indol-5-yl)ethyl)-8-methylbenzo[f][1,7]naphthyridin-5-amine,
2-(4-ethoxyphenethyl)-8-methylbenzo[f][1,7]naphthyridin-5-amine,
8-methyl-2-(4-phenoxyphenethyl)benzo[f][1,7]naphthyridin-5-amine,
2-(2,4-dimethylphenethyl)benzo[f][1,7]naphthyridin-5-amine,
2-(2,4-dimethylphenethyl)-8-methylbenzo[f][1,7]naphthyridin-5-amine,
2-(4-methoxy-2-methylphenethyl)-8-methylbenzo[f][1,7]naphthyridin-5-amine,
4-(2-(5-amino-8-methylbenzo[f][1,7]naphthyridin-2-yl)ethyl)-3-methylphenol,
2-(2-(2,3-dihydrobenzofuran-5-yl)ethyl)-8-methylbenzo[f][1,7]naphthyridin-5-amine,
2-(5-amino-8-methylbenzo[f][1,7]naphthyridin-2-yl)ethanol,
8-methylbenzo[f][1,7]naphthyridine-2,5-diamine,
1-(5-amino-8-methylbenzo[f][1,7]naphthyridin-2-yl)propan-2-ol,
2-(5-amino-8-methylbenzo[f][1,7]naphthyridin-2-yl)acetonitrile,
N-(5-amino-8-methylbenzo[f][1,7]naphthyridin-2-yl)acetamide,
2-(5-amino-8-methylbenzo[f][1,7]naphthyridin-2-yl)-1-(2,4-dimethylphenyl)ethanol,
2-(2-(6-methoxy-4-methylpyridin-3-yl)ethyl)-8-methylbenzo[f][1,7]naphthyridin-5-amine,
4-(4-(2-(5-amino-8-methylbenzo[f][1,7]naphthyridin-2-yl)ethyl)phenyl)butan-1-ol,
methyl 3-(4-(2-(5-amino-8-methylbenzo[f][1,7]naphthyridin-2-yl)ethyl)phenyl)propanoate,
3-(4-(2-(5-amino-8-methylbenzo[f][1,7]naphthyridin-2-yl)ethyl)phenyl)propan-1-ol,
4-(4-(2-(5-amino-8-methylbenzo[f][1,7]naphthyridin-2-yl)ethyl)phenyl)-2-methylbutan-2-ol,
2-(4-(aminomethyl)phenethyl)-8-methylbenzo[f][1,7]naphthyridin-5-amine,
(E)-ethyl 3-(4-(2-(5-amino-8-methylbenzo[f][1,7]naphthyridin-2-yl)ethyl)-3-methylphenyl)acrylate,
ethyl 3-(4-(2-(5-amino-8-methylbenzo[f][1,7]naphthyridin-2-yl)ethyl)-3-methylphenyl)propanoate,
2-(4-(2-(5-amino-8-methylbenzo[f][1,7]naphthyridin-2-yl)ethyl)-3-methylbenzyl)propane-1,3-diol,
3-(4-(2-(5-amino-8-methylbenzo[f][1,7]naphthyridin-2-yl)ethyl)-3-methylphenyl)propanoic acid, 5-amino-2-(4-methoxy-2-methylphenethyl)benzo[f][1,7]
naphthyridine-8-carbaldehyde,
ethyl 4-(2-(5-amino-8-methylbenzo[f][1,7]naphthyridin-
2-yl)ethyl)benzoate,
8-methyl-2-(4-methylphenethyl)benzo[f][1,7]naphthyridin-5-amine,
2-(4-(2-(5-amino-8-methylbenzo[f][1,7]naphthyridin-2-yl)ethyl)phenyl)propan-2-ol,
(4-(2-(5-amino-8-methylbenzo[f][1,7]naphthyridin-2-yl)ethyl)phenyl)methanol,
ethyl 4-(2-(5-amino-8-methylbenzo[f][1,7]naphthyridin-2-yl)ethyl)-3-methylbenzoate,
4-(2-(5-amino-8-methylbenzo[f][1,7]naphthyridin-2-yl)ethyl)-3-methylbenzoic acid,
(4-(2-(5-amino-8-methylbenzo[f][1,7]naphthyridin-2-yl)ethyl)-3-methylphenyl)methanol,
8-methyl-2-(2,4,6-trimethylphenethyl)benzo[f][1,7]naphthyridin-5-amine,
2-(4-(2-(5-amino-8-methylbenzo[f][1,7]naphthyridin-2-yl)ethyl)-3-methylphenyl)propan-2-ol,
8-methyl-2-(4-propoxyphenethyl)benzo[f][1,7]naphthyridin-5-amine,
(E)-3-(5-amino-2-(4-methoxy-2-methylphenethyl)benzo[f][1,7]naphthyridin-8-yl)acrylic acid,
ethyl 3-(5-amino-2-(4-methoxy-2-methylphenethyl)benzo[f][1,7]naphthyridin-8-yl)propanoate,
3-(5-amino-2-(4-methoxy-2-methylphenethyl)benzo[f][1,7]naphthyridin-8-yl)propanoic acid,
3-(5-amino-2-(4-methoxy-2-methylphenethyl)benzo[f][1,7]naphthyridin-8-yl)propan-1-ol,
8-(methoxymethyl)benzo[f][1,7]naphthyridin-5-amine,
(5-amino-2-(4-methoxyphenethyl)benzo[f][1,7]naphthyridin-8-yl)methanol,
8-phenethylbenzo[f][1,7]naphthyridin-5-amine,
(5-amino-2-(4-bromophenethyl)benzo[f][1,7]naphthyridin-8-yl)methanol,
2-(4-methoxy-2-methylphenethyl)-8-pentylbenzo[f][1,7]naphthyridin-5-amine,
8-(2-cyclopropylethyl)-2-(4-methoxy-2-methylphenethyl)benzo[f][1,7]naphthyridin-5-amine,
(5-amino-2-(2,4,6-trimethylphenethyl)benzo[f][1,7]naphthyridin-8-yl)methanol,
(5-amino-2-(4-propoxyphenethyl)benzo[f][1,7]naphthyridin-8-yl)methanol,
(2-(2-(1H-indol-5-yl)ethyl)-5-aminobenzo[f][1,7]naphthyridin-8-yl)methanol,
methyl 4-(2-(5-amino-8-methylbenzo[f][1,7]naphthyridin-2-yl)ethyl)-3-methylbenzoate,
4-(2-(5-amino-8-methylbenzo[f][1,7]naphthyridin-2-yl)ethyl)-N,3-dimethylbenzamide,
N-(2-acetamidoethyl)-4-(2-(5-amino-8-methylbenzo[f][1,7]naphthyridin-2-yl)ethyl)-3-methylbenzamide,
4-(2-(5-amino-8-methylbenzo[f][1,7]naphthyridin-2-yl)ethyl)-N-(2-(dimethylamino)ethyl)-N,3-dimethylbenzamide,
2-(4-methoxyphenethyl)benzo[f][1,7]naphthyridin-5-amine,
2-(4-methoxy-2-methylphenethyl)benzo[f][1,7]naphthyridin-5-amine,
4-(2-(5-amino-8-methylbenzo[f][1,7]naphthyridin-2-yl)ethyl)-3-methylbenzamide,
4-(2-(5-amino-8-methylbenzo[f][1,7]naphthyridin-2-yl)ethyl)-N,N,3-trimethylbenzamide,
4-(2-(5-amino-8-methylbenzo[f][1,7]naphthyridin-2-yl)ethyl)-N-(2-hydroxyethyl)-3-methylbenzamide,
4-(2-(5-amino-8-methylbenzo[f][1,7]naphthyridin-2-yl)ethyl)-N-(2-(dimethylamino)ethyl)-3-methylbenzamide,
(4-(2-(5-amino-8-methylbenzo[f][1,7]naphthyridin-2-yl)ethyl)-3-methylphenyl)(pyrrolidin-1-yl)methanone,
4-(2-(5-amino-8-methylbenzo[f][1,7]naphthyridin-2-yl)ethyl)-N-(2-(diethylamino)ethyl)-3-methylbenzamide,
(4-(2-(5-amino-8-methylbenzo[f][1,7]naphthyridin-2-yl)ethyl)-3-methylphenyl)(4-ethylpiperazin-1-yl)methanone,
(4-(2-(5-amino-8-methylbenzo[f][1,7]naphthyridin-2-yl)ethyl)-3-methylphenyl)(piperazin-1-yl)methanone,
4-(2-(5-amino-8-methylbenzo[f][1,7]naphthyridin-2-yl)ethyl)-3-methyl-N-(2-(pyrrolidin-1-yl)ethyl)benzamide,
4-(2-(5-aminobenzo[f][1,7]naphthyridin-2-yl)ethyl)-N-(2-(dimethylamino)ethyl)-N,3-dimethylbenzamide,
4-(2-(5-amino-8-methylbenzo[f][1,7]naphthyridin-2-yl)ethyl)-N-(2-(dimethylamino)ethyl)-N-methylbenzamide,
2-(4-(2-(5-aminobenzo[f][1,7]naphthyridin-2-yl)ethyl)-3-methylphenyl)propan-2-ol,
2-(4-butoxyphenethyl)-8-methylbenzo[f][1,7]naphthyridin-5-amine,
2-(2-(biphenyl-4-yl)ethyl)-8-methylbenzo[f][1,7]naphthyridin-5-amine,
2-((1,3-dihydroisobenzofuran-1-yl)methyl)-8-methylbenzo[f][1,7]naphthyridin-5-amine,
8-methyl-2-(4-(2-methylallyloxy)phenethyl)benzo[f][1,7]naphthyridin-5-amine,
2-(4-(isopentyloxy)phenethyl)-8-methylbenzo[f][1,7]naphthyridin-5-amine,
4-(2-(5-amino-8-methylbenzo[f][1,7]naphthyridin-2-yl)ethyl)phenyl propyl carbonate,
ethyl 5-(4-(2-(5-amino-8-methylbenzo[f][1,7]naphthyridin-2-yl)ethyl)phenoxy)pentanoate,
2-(4-(cyclopentyloxy)phenethyl)-8-methylbenzo[f][1,7]naphthyridin-5-amine,
2-(4-(cyclobutylmethoxy)phenethyl)-8-methylbenzo[f][1,7]naphthyridin-5-amine,
8-methyl-2-(4-(2-morpholinoethoxy)phenethyl)benzo[f][1,7]naphthyridin-5-amine,
2-(4-(2-(5-amino-8-methylbenzo[f][1,7]naphthyridin-2-yl)ethyl)phenoxy)-1-phenylethanone,
5-(4-(2-(5-amino-8-methylbenzo[f][1,7]naphthyridin-2-yl)ethyl)phenoxy)pentanoic acid,
2-(4-(2-(5-amino-8-methylbenzo[f][1,7]naphthyridin-2-yl)ethyl)phenoxy)ethanol,
2-(4-(2-(5-amino-8-methylbenzo[f][1,7]naphthyridin-2-yl)ethyl)phenoxy)-N,N-dimethylacetamide,
8-methyl-2-(2-methyl-4-(2-morpholinoethoxy)phenethyl)benzo[f][1,7]naphthyridin-5-amine,
2-(2-(4-(2-(5-amino-8-methylbenzo[f][1,7]naphthyridin-2-yl)ethyl)-3-methylphenoxy)ethoxy)ethanol,
diethyl 3-(4-(2-(5-amino-8-methylbenzo[f][1,7]naphthyridin-2-yl)ethyl)-3-methylphenoxy)propylphosphonate,
3-(4-(2-(5-amino-8-methylbenzo[f][1,7]naphthyridin-2-yl)ethyl)-3-methylphenoxy)propylphosphonic acid,
2-(4-butoxy-2-methylphenethyl)-8-methylbenzo[f][1,7]naphthyridin-5-amine,
2-(4-(2-(5-aminobenzo[f][1,7]naphthyridin-2-yl)ethyl)-3-methylphenoxy)ethanol,
2-(2-(4-(2-(5-aminobenzo[f][1,7]naphthyridin-2-yl)ethyl)-3-methylphenoxy)ethoxy)ethanol,
ethyl 5-(4-(2-(5-amino-8-methylbenzo[f][1,7]naphthyridin-2-yl)ethyl)-3-methylphenoxy)pentanoate, 5-(4-(2-(5-amino-8-methylbenzo[f][1,7]naphthyridin-2-yl)ethyl)-3-methylphenoxy)pentanoic acid,
2-(4-(2-(5-amino-8-methylbenzo[f][1,7]naphthyridin-2-yl)ethyl)-3-methylphenoxy)ethanol,
4-(2-(5-amino-8-methylbenzo[f][1,7]naphthyridin-2-yl)ethyl)phenyl ethyl carbonate,
methyl 4-(4-(2-(5-amino-8-methylbenzo[f][1,7]naphthyridin-2-yl)ethyl)phenoxy)butanoate,
4-(4-(2-(5-amino-8-methylbenzo[f][1,7]naphthyridin-2-yl)ethyl)phenoxy)butanoic acid,
4-(4-(2-(5-amino-8-methylbenzo[f][1,7]naphthyridin-2-yl)ethyl)-3-methylphenoxy)butanoic acid,
2-(4-(isopentyloxy)-2-methylphenethyl)-8-methylbenzo[f][1,7]naphthyridin-5-amine,
4-(2-(5-amino-8-methylbenzo[f][1,7]naphthyridin-2-yl)ethyl)phenyl hexyl carbonate,
2-(2,4,6-trimethylphenethyl)benzo[f][1,7]naphthyridin-5-amine,
(5-amino-2-(2,4-dimethylphenethyl)benzo[f][1,7]naphthyridin-8-yl)methanol,
diethyl 3-(2-(4-(2-(5-amino-8-methylbenzo[f][1,7]naphthyridin-2-yl)ethyl)-3-methylphenoxy)ethoxy)propylphosphonate,
diethyl 3-(2-(2-(4-(2-(5-amino-8-methylbenzo[f][1,7]naphthyridin-2-yl)ethyl)-3-methylphenoxy)ethoxy)ethoxy)propylphosphonate,
4-(2-(5-amino-8-methylbenzo[f][1,7]naphthyridin-2-yl)ethyl)-3-methylphenyl dimethylsulfamate,
(5-amino-2-(4-(dimethylamino)phenethyl)benzo[f][1,7]naphthyridin-8-yl)methanol,
2-(4-(dimethylamino)phenethyl)-8-methylbenzo[f][1,7]naphthyridin-5-amine,
4-(2-(5-amino-8-methylbenzo[f][1,7]naphthyridin-2-yl)ethyl)phenol,
1-(4-(2-(5-amino-8-methylbenzo[f][1,7]naphthyridin-2-yl)ethyl)phenyl)ethanone,
2-(4-((dimethylamino)methyl)phenethyl)-8-methylbenzo[f][1,7]naphthyridin-5-amine,
2-(4-(1-(dimethylamino)ethyl)phenethyl)-8-methylbenzo[f][1,7]naphthyridin-5-amine,
1-(4-(2-(5-amino-8-methylbenzo[f][1,7]naphthyridin-2-yl)ethyl)phenyl)ethanone oxime,
8-methyl-2-(4-((methylamino)methyl)phenethyl)benzo[f][1,7]naphthyridin-5-amine,
(4-(2-(5-amino-8-methylbenzo[f][1,7]naphthyridin-2-yl)ethyl)benzylamino)ethanol,
8-methyl-2-(4-(pyrrolidin-1-ylmethyl)phenethyl)benzo[f][1,7]naphthyridin-5-amine,
2-(3,4-dimethoxyphenethyl)-8-methylbenzo[f][1,7]naphthyridin-5-amine,
2-(1-(4-(2-(5-amino-8-methylbenzo[f][1,7]naphthyridin-2-yl)ethyl)phenyl)ethylamino)ethanol,
1-(4-(2-(5-amino-8-methylbenzo[f][1,7]naphthyridin-2-yl)ethyl)phenyl)ethanol,
8-methyl-2-(4-(oxazol-5-yl)phenethyl)benzo[f][1,7]naphthyridin-5-amine,
3-(1-(4-(2-(5-amino-8-methylbenzo[f][1,7]naphthyridin-2-yl)ethyl)phenyl)ethylamino)propanenitrile,
(2R)-2-(1-(4-(2-(5-amino-8-methylbenzo[f][1,7]naphthyridin-2-yl)ethyl)phenyl)ethylamino)propan-1-ol,
8-methyl-2-(4-(1-(piperazin-1-yl)ethyl)phenethyl)benzo[f][1,7]naphthyridin-5-amine,
((2S)-1-(1-(4-(2-(5-amino-8-methylbenzo[f][1,7]naphthyridin-2-yl)ethyl)phenyl)ethyl)pyrrolidin-2-yl)methanol,
$N^1$-(1-(4-(2-(5-amino-8-methylbenzo[f][1,7]naphthyridin-2-yl)ethyl)phenyl)ethyl)-$N^2$,$N^2$-dimethylethane-1,2-diamine,
3-(1-(4-(2-(5-amino-8-methylbenzo[f][1,7]naphthyridin-2-yl)ethyl)phenyl)ethylamino)propanoic acid,
8-methyl-2-(4-(1-(4-methylpiperazin-1-yl)ethyl)phenethyl)benzo[f][1,7]naphthyridin-5-amine,
$N^2$-(1-(4-(2-(5-amino-8-methylbenzo[f][1,7]naphthyridin-2-yl)ethyl)phenyl)ethyl)-$N^1$,$N^1$-dimethylpropane-1,2-diamine,
8-methyl-2-(4-(1-(2-(pyridin-4-yl)ethylamino)ethyl)phenethyl)benzo[f][1,7]naphthyridin-5-amine,
$N^1$-(1-(4-(2-(5-amino-8-methylbenzo[f][1,7]naphthyridin-2-yl)ethyl)phenyl)ethyl)-$N^2$,$N^2$-diethylethane-1,2-diamine,
2-(4-(dimethylamino)-2-methylphenethyl)-8-methylbenzo[f][1,7]naphthyridin-5-amine,
1-(1-(4-(2-(5-amino-8-methylbenzo[f][1,7]naphthyridin-2-yl)ethyl)phenyl)ethyl)pyrrolidine-3-carboxylic acid,
4-(1-(4-(2-(5-amino-8-methylbenzo[f][1,7]naphthyridin-2-yl)ethyl)phenyl)ethylamino)phenol,
1-(1-(4-(2-(5-amino-8-methylbenzo[f][1,7]naphthyridin-2yl)ethyl)phenyl)ethyl) pyrrolidin-3-ol, and
2-(4-(2-aminopropan-2-yl)phenethyl)-8-methylbenzo[f][1,7]naphthyridin-5-amine.

16. A pharmaceutical composition comprising a therapeutically effective amount of a compound of Formula (I-A) of claim 1 and a pharmaceutically acceptable carrier.

17. A method for activating a TLR7 receptor, comprising administering to a system or a subject in need thereof, a therapeutically effective amount of a compound of Formula (I-A) of claim 1, or pharmaceutically acceptable salts or pharmaceutical compositions thereof, thereby activating the TLR7 receptor.

18. A pharmaceutical composition comprising a compound of Formula (I-A) of claim 1, an antigen and a pharmaceutically acceptable carrier, wherein the pharmaceutical composition is an immunogenic composition and the a compound of Formula (I-A) is an immune potentiator.

19. A method for enhancing the effectiveness of an immunogenic composition, comprising adding an effective amount of a compound of Formula (I-A) of claim 1 to the immunogenic composition.

20. An immunogenic composition comprising a compound of Formula (I-A) of claim 1, and an antigen, wherein the amount of the compound is an amount effective to enhance an immune response to the antigen in a subject to whom the composition is administered.

21. The compound of claim 10, wherein the compound is substituted with one to three $R^{13}$ groups independently selected from -$LR^{10}$, -$LOR^{10}$, -$LR^8$, -$LOR^8$, -$LSR^8$, -$LC(O)R^8$, -$LC(O)OR^8$, -$LC(O)R^{10}$, -$LOC(O)OR^8$, -$LN(R^9)_2$, -$LNR^9R^{10}$, -$LC(O)N(R^9)_2$, -$LS(O)_2R^8$, —$OLS(O)_2N(R^9)_2$, -$LC(O)NR^9LN(R^9)_2$ and -$LP(O)(OR^8)_2$.

22. The compound of claim 21, wherein,
$R^{10}$ is a phenyl or a heteroaryl, wherein the phenyl is optionally substituted with halogen, —$R^8$, —$OR^8$ or —$N(R^9)_2$.

23. The compound of claim 11, wherein,
each $R^A$ is independently selected from —$R^8$, $CO_2R^8$, —$(CH_2)_nCO_2R^8$ and —$C(O)R^8$.

24. The compound of claim 9, wherein,
$R^A$ is —$R^8$ or $(CH_2)_nCO_2R^8$;
each $R^{13}$ is independently selected from -$LR^8$, -$LOR^8$, and -$LP(O)(OR^8)_2$,
L is a bond or —$(O(CH_2)_m)_t$;
each m is independently selected from 1, 2 or 3;

n is 1, 2 or 3, and
t is 1, 2, 3, or 4.

25. The compound of claim 24, wherein,
$R^8$ is H or $C_1$-$C_6$alkyl.

26. The compound of claim 14 selected from:
2-(4-(2-(5-amino-8-methylbenzo[f][1,7]naphthyridin-2-yl)ethyl)-3-methylphenyl)propan-2-ol;
2-(4-methoxy-2-methylphenethyl)-8-methylbenzo[f][1,7]naphthyridin-5-amine;
2-(2,4-dimethylphenethyl)benzo[f][1,7]naphthyridin-5-amine;
ethyl 4-(2-(5-amino-8-methylbenzo[f][1,7]naphthyridin-2-yl)ethyl)-3-methylbenzoate;
2-(4-(dimethylamino)phenethyl)-8-methylbenzo[f][1,7]naphthyridin-5-amine,
2-(4-(isopentyloxy)-2-methylphenethyl)-8-methylbenzo[f][1,7]naphthyridin-5-amine;
2-(2-(4-(2-(5-amino-8-methylbenzo[f][1,7]naphthyridin-2-yl)ethyl)-3-methylphenoxy)ethoxy)ethanol and
2-(4-methoxyphenethyl)-8-methylbenzo[f][1,7]naphthyridin-5-amine.

\* \* \* \* \*

SEQUENCE LISTING

<160> NUMBER OF SEQ ID NOS: 6

<210> SEQ ID NO 1
<211> LENGTH: 248
<212> TYPE: PRT
<213> ORGANISM: Neisseria meningitidis

<400> SEQUENCE: 1

Val Ala Ala Asp Ile Gly Ala Gly Leu Ala Asp Ala Leu Thr Ala Pro
1               5                   10                  15

Leu Asp His Lys Asp Lys Gly Leu Gln Ser Leu Thr Leu Asp Gln Ser
            20                  25                  30

Val Arg Lys Asn Glu Lys Leu Lys Leu Ala Ala Gln Gly Ala Glu Lys
        35                  40                  45

Thr Tyr Gly Asn Gly Asp Ser Leu Asn Thr Gly Lys Leu Lys Asn Asp
    50                  55                  60

Lys Val Ser Arg Phe Asp Phe Ile Arg Gln Ile Glu Val Asp Gly Gln
65                  70                  75                  80

Leu Ile Thr Leu Glu Ser Gly Glu Phe Gln Val Tyr Lys Gln Ser His
                85                  90                  95

Ser Ala Leu Thr Ala Phe Gln Thr Glu Gln Ile Gln Asp Ser Glu His
            100                 105                 110

Ser Gly Lys Met Val Ala Lys Arg Gln Phe Arg Ile Gly Asp Ile Ala
        115                 120                 125

Gly Glu His Thr Ser Phe Asp Lys Leu Pro Glu Gly Gly Arg Ala Thr
    130                 135                 140

Tyr Arg Gly Thr Ala Phe Gly Ser Asp Asp Ala Gly Gly Lys Leu Thr
145                 150                 155                 160

```
Tyr Thr Ile Asp Phe Ala Ala Lys Gln Gly Asn Gly Lys Ile Glu His
            165                 170                 175

Leu Lys Ser Pro Glu Leu Asn Val Asp Leu Ala Ala Asp Ile Lys
        180                 185                 190

Pro Asp Gly Lys Arg His Ala Val Ile Ser Gly Ser Val Leu Tyr Asn
            195                 200                 205

Gln Ala Glu Lys Gly Ser Tyr Ser Leu Gly Ile Phe Gly Gly Lys Ala
        210                 215                 220

Gln Glu Val Ala Gly Ser Ala Glu Val Lys Thr Val Asn Gly Ile Arg
225                 230                 235                 240

His Ile Gly Leu Ala Ala Lys Gln
                245

<210> SEQ ID NO 2
<211> LENGTH: 247
<212> TYPE: PRT
<213> ORGANISM: Neisseria meningitidis

<400> SEQUENCE: 2

Val Ala Ala Asp Ile Gly Ala Gly Leu Ala Asp Ala Leu Thr Ala Pro
1               5                   10                  15

Leu Asp His Lys Asp Lys Ser Leu Gln Ser Leu Thr Leu Asp Gln Ser
            20                  25                  30

Val Arg Lys Asn Glu Lys Leu Lys Leu Ala Ala Gln Gly Ala Glu Lys
        35                  40                  45

Thr Tyr Gly Asn Gly Asp Ser Leu Asn Thr Gly Lys Leu Lys Asn Asp
    50                  55                  60

Lys Val Ser Arg Phe Asp Phe Ile Arg Gln Ile Glu Val Asp Gly Gln
65                  70                  75                  80

Leu Ile Thr Leu Glu Ser Gly Glu Phe Gln Ile Tyr Lys Gln Asp His
                85                  90                  95

Ser Ala Val Val Ala Leu Gln Ile Glu Lys Ile Asn Asn Pro Asp Lys
            100                 105                 110

Ile Asp Ser Leu Ile Asn Gln Arg Ser Phe Leu Val Ser Gly Leu Gly
        115                 120                 125

Gly Glu His Thr Ala Phe Asn Gln Leu Pro Asp Gly Lys Ala Glu Tyr
    130                 135                 140

His Gly Lys Ala Phe Ser Ser Asp Asp Ala Gly Gly Lys Leu Thr Tyr
145                 150                 155                 160

Thr Ile Asp Phe Ala Ala Lys Gln Gly His Gly Lys Ile Glu His Leu
                165                 170                 175

Lys Thr Pro Glu Gln Asn Val Glu Leu Ala Ala Ala Glu Leu Lys Ala
            180                 185                 190

Asp Glu Lys Ser His Ala Val Ile Leu Gly Asp Thr Arg Tyr Gly Ser
        195                 200                 205

Glu Glu Lys Gly Thr Tyr His Leu Ala Leu Phe Gly Asp Arg Ala Gln
    210                 215                 220

Glu Ile Ala Gly Ser Ala Thr Val Lys Ile Gly Glu Lys Val His Glu
225                 230                 235                 240

Ile Gly Ile Ala Gly Lys Gln
                245

<210> SEQ ID NO 3
<211> LENGTH: 250
<212> TYPE: PRT
<213> ORGANISM: Neisseria meningitidis
```

-continued

<400> SEQUENCE: 3

```
Val Ala Ala Asp Ile Gly Thr Gly Leu Ala Asp Ala Leu Thr Ala Pro
1               5                   10                  15
Leu Asp His Lys Asp Lys Gly Leu Lys Ser Leu Thr Leu Glu Asp Ser
            20                  25                  30
Ile Pro Gln Asn Gly Thr Leu Thr Leu Ser Ala Gln Gly Ala Glu Lys
        35                  40                  45
Thr Phe Lys Ala Gly Asp Lys Asp Asn Ser Leu Asn Thr Gly Lys Leu
    50                  55                  60
Lys Asn Asp Lys Ile Ser Arg Phe Asp Phe Val Gln Lys Ile Glu Val
65                  70                  75                  80
Asp Gly Gln Thr Ile Thr Leu Ala Ser Gly Glu Phe Gln Ile Tyr Lys
                85                  90                  95
Gln Asn His Ser Ala Val Val Ala Leu Gln Ile Glu Lys Ile Asn Asn
            100                 105                 110
Pro Asp Lys Thr Asp Ser Leu Ile Asn Gln Arg Ser Phe Leu Val Ser
        115                 120                 125
Gly Leu Gly Gly Glu His Thr Ala Phe Asn Gln Leu Pro Gly Gly Lys
    130                 135                 140
Ala Glu Tyr His Gly Lys Ala Phe Ser Ser Asp Asp Pro Asn Gly Arg
145                 150                 155                 160
Leu His Tyr Ser Ile Asp Phe Thr Lys Lys Gln Gly Tyr Gly Arg Ile
                165                 170                 175
Glu His Leu Lys Thr Leu Glu Gln Asn Val Glu Leu Ala Ala Ala Glu
            180                 185                 190
Leu Lys Ala Asp Glu Lys Ser His Ala Val Ile Leu Gly Asp Thr Arg
        195                 200                 205
Tyr Gly Ser Glu Glu Lys Gly Thr Tyr His Leu Ala Leu Phe Gly Asp
    210                 215                 220
Arg Ala Gln Glu Ile Ala Gly Ser Ala Thr Val Lys Ile Gly Glu Lys
225                 230                 235                 240
Val His Glu Ile Gly Ile Ala Gly Lys Gln
                245                 250
```

<210> SEQ ID NO 4
<211> LENGTH: 644
<212> TYPE: PRT
<213> ORGANISM: Neisseria meningitidis

<400> SEQUENCE: 4

```
Met Ala Ser Pro Asp Val Lys Ser Ala Asp Thr Leu Ser Lys Pro Ala
1               5                   10                  15
Ala Pro Val Val Ser Glu Lys Glu Thr Glu Ala Lys Glu Asp Ala Pro
            20                  25                  30
Gln Ala Gly Ser Gln Gly Gln Gly Ala Pro Ser Ala Gln Gly Gly Gln
        35                  40                  45
Asp Met Ala Ala Val Ser Glu Glu Asn Thr Gly Asn Gly Gly Ala Ala
    50                  55                  60
Ala Thr Asp Lys Pro Lys Asn Glu Asp Glu Gly Ala Gln Asn Asp Met
65                  70                  75                  80
Pro Gln Asn Ala Ala Asp Thr Asp Ser Leu Thr Pro Asn His Thr Pro
                85                  90                  95
Ala Ser Asn Met Pro Ala Gly Asn Met Glu Asn Gln Ala Pro Asp Ala
            100                 105                 110
```

```
Gly Glu Ser Glu Gln Pro Ala Asn Gln Pro Asp Met Ala Asn Thr Ala
            115                 120                 125
Asp Gly Met Gln Gly Asp Pro Ser Ala Gly Glu Asn Ala Gly
130                 135                 140
Asn Thr Ala Ala Gln Gly Thr Asn Gln Ala Glu Asn Asn Gln Thr Ala
145                 150                 155                 160
Gly Ser Gln Asn Pro Ala Ser Ser Thr Asn Pro Ser Ala Thr Asn Ser
                165                 170                 175
Gly Gly Asp Phe Gly Arg Thr Asn Val Gly Asn Ser Val Val Ile Asp
            180                 185                 190
Gly Pro Ser Gln Asn Ile Thr Leu Thr His Cys Lys Gly Asp Ser Cys
            195                 200                 205
Ser Gly Asn Asn Phe Leu Asp Glu Glu Val Gln Leu Lys Ser Glu Phe
    210                 215                 220
Glu Lys Leu Ser Asp Ala Asp Lys Ile Ser Asn Tyr Lys Lys Asp Gly
225                 230                 235                 240
Lys Asn Asp Gly Lys Asn Asp Lys Phe Val Gly Leu Val Ala Asp Ser
                245                 250                 255
Val Gln Met Lys Gly Ile Asn Gln Tyr Ile Ile Phe Tyr Lys Pro Lys
            260                 265                 270
Pro Thr Ser Phe Ala Arg Phe Arg Arg Ser Ala Arg Ser Arg Arg Ser
            275                 280                 285
Leu Pro Ala Glu Met Pro Leu Ile Pro Val Asn Gln Ala Asp Thr Leu
    290                 295                 300
Ile Val Asp Gly Glu Ala Val Ser Leu Thr Gly His Ser Gly Asn Ile
305                 310                 315                 320
Phe Ala Pro Glu Gly Asn Tyr Arg Tyr Leu Thr Tyr Gly Ala Glu Lys
                325                 330                 335
Leu Pro Gly Gly Ser Tyr Ala Leu Arg Val Gln Gly Glu Pro Ser Lys
            340                 345                 350
Gly Glu Met Leu Ala Gly Thr Ala Val Tyr Asn Gly Glu Val Leu His
            355                 360                 365
Phe His Thr Glu Asn Gly Arg Pro Ser Pro Ser Arg Gly Arg Phe Ala
    370                 375                 380
Ala Lys Val Asp Phe Gly Ser Lys Ser Val Asp Gly Ile Ile Asp Ser
385                 390                 395                 400
Gly Asp Gly Leu His Met Gly Thr Gln Lys Phe Lys Ala Ala Ile Asp
                405                 410                 415
Gly Asn Gly Phe Lys Gly Thr Trp Thr Glu Asn Gly Gly Asp Val
            420                 425                 430
Ser Gly Lys Phe Tyr Gly Pro Ala Gly Glu Glu Val Ala Gly Lys Tyr
            435                 440                 445
Ser Tyr Arg Pro Thr Asp Ala Glu Lys Gly Gly Phe Gly Val Phe Ala
    450                 455                 460
Gly Lys Lys Glu Gln Asp Gly Ser Gly Gly Gly Ala Thr Tyr Lys
465                 470                 475                 480
Val Asp Glu Tyr His Ala Asn Ala Arg Phe Ala Ile Asp His Phe Asn
                485                 490                 495
Thr Ser Thr Asn Val Gly Gly Phe Tyr Gly Leu Thr Gly Ser Val Glu
            500                 505                 510
Phe Asp Gln Ala Lys Arg Asp Gly Lys Ile Asp Ile Thr Ile Pro Val
            515                 520                 525
Ala Asn Leu Gln Ser Gly Ser Gln His Phe Thr Asp His Leu Lys Ser
    530                 535                 540
```

-continued

```
Ala Asp Ile Phe Asp Ala Ala Gln Tyr Pro Asp Ile Arg Phe Val Ser
545                 550                 555                 560

Thr Lys Phe Asn Phe Asn Gly Lys Lys Leu Val Ser Val Asp Gly Asn
            565                 570                 575

Leu Thr Met His Gly Lys Thr Ala Pro Val Lys Leu Lys Ala Glu Lys
                580                 585                 590

Phe Asn Cys Tyr Gln Ser Pro Met Ala Lys Thr Glu Val Cys Gly Gly
            595                 600                 605

Asp Phe Ser Thr Thr Ile Asp Arg Thr Lys Trp Gly Val Asp Tyr Leu
        610                 615                 620

Val Asn Val Gly Met Thr Lys Ser Val Arg Ile Asp Ile Gln Ile Glu
625                 630                 635                 640

Ala Ala Lys Gln

<210> SEQ ID NO 5
<211> LENGTH: 434
<212> TYPE: PRT
<213> ORGANISM: Neisseria meningitidis

<400> SEQUENCE: 5

Met Val Ser Ala Val Ile Gly Ser Ala Val Gly Ala Lys Ser Ala
1               5                   10                  15

Val Asp Arg Arg Thr Thr Gly Ala Gln Thr Asp Asn Val Met Ala
                20                  25                  30

Leu Arg Ile Glu Thr Thr Ala Arg Ser Tyr Leu Arg Gln Asn Asn Gln
            35                  40                  45

Thr Lys Gly Tyr Thr Pro Gln Ile Ser Val Val Gly Tyr Asn Arg His
        50                  55                  60

Leu Leu Leu Leu Gly Gln Val Ala Thr Glu Gly Lys Gln Phe Val
65              70                  75                  80

Gly Gln Ile Ala Arg Ser Glu Gln Ala Ala Glu Gly Val Tyr Asn Tyr
                85                  90                  95

Ile Thr Val Ala Ser Leu Pro Arg Thr Ala Gly Asp Ile Ala Gly Asp
            100                 105                 110

Thr Trp Asn Thr Ser Lys Val Arg Ala Thr Leu Leu Gly Ile Ser Pro
        115                 120                 125

Ala Thr Gln Ala Arg Val Lys Ile Val Thr Tyr Gly Asn Val Thr Tyr
    130                 135                 140

Val Met Gly Ile Leu Thr Pro Glu Glu Gln Ala Gln Ile Thr Gln Lys
145                 150                 155                 160

Val Ser Thr Thr Val Gly Val Gln Lys Val Ile Thr Leu Tyr Gln Asn
                165                 170                 175

Tyr Val Gln Arg Gly Ser Gly Gly Gly Val Ala Ala Asp Ile Gly
            180                 185                 190

Ala Gly Leu Ala Asp Ala Leu Thr Ala Pro Leu Asp His Lys Asp Lys
        195                 200                 205

Gly Leu Gln Ser Leu Thr Leu Asp Gln Ser Val Arg Lys Asn Glu Lys
    210                 215                 220

Leu Lys Leu Ala Ala Gln Gly Ala Glu Lys Thr Tyr Gly Asn Gly Asp
225                 230                 235                 240

Ser Leu Asn Thr Gly Lys Leu Lys Asn Asp Lys Val Ser Arg Phe Asp
                245                 250                 255

Phe Ile Arg Gln Ile Glu Val Asp Gly Gln Leu Ile Thr Leu Glu Ser
            260                 265                 270
```

```
Gly Glu Phe Gln Val Tyr Lys Gln Ser His Ser Ala Leu Thr Ala Phe
            275                 280                 285

Gln Thr Glu Gln Ile Gln Asp Ser Glu His Ser Gly Lys Met Val Ala
290                 295                 300

Lys Arg Gln Phe Arg Ile Gly Asp Ile Ala Gly Glu His Thr Ser Phe
305                 310                 315                 320

Asp Lys Leu Pro Glu Gly Gly Arg Ala Thr Tyr Arg Gly Thr Ala Phe
                325                 330                 335

Gly Ser Asp Asp Ala Gly Gly Lys Leu Thr Tyr Thr Ile Asp Phe Ala
                340                 345                 350

Ala Lys Gln Gly Asn Gly Lys Ile Glu His Leu Lys Ser Pro Glu Leu
                355                 360                 365

Asn Val Asp Leu Ala Ala Ala Asp Ile Lys Pro Asp Gly Lys Arg His
            370                 375                 380

Ala Val Ile Ser Gly Ser Val Leu Tyr Asn Gln Ala Glu Lys Gly Ser
385                 390                 395                 400

Tyr Ser Leu Gly Ile Phe Gly Gly Lys Ala Gln Glu Val Ala Gly Ser
                405                 410                 415

Ala Glu Val Lys Thr Val Asn Gly Ile Arg His Ile Gly Leu Ala Ala
                420                 425                 430

Lys Gln

<210> SEQ ID NO 6
<211> LENGTH: 327
<212> TYPE: PRT
<213> ORGANISM: Neisseria meningitidis

<400> SEQUENCE: 6

Ala Thr Asn Asp Asp Val Lys Lys Ala Ala Thr Val Ala Ile Ala
1               5                   10                  15

Ala Ala Tyr Asn Asn Gly Gln Glu Ile Asn Gly Phe Lys Ala Gly Glu
                20                  25                  30

Thr Ile Tyr Asp Ile Asp Glu Asp Gly Thr Ile Thr Lys Lys Asp Ala
            35                  40                  45

Thr Ala Ala Asp Val Glu Ala Asp Phe Lys Gly Leu Gly Leu Lys
50                  55                  60

Lys Val Val Thr Asn Leu Thr Lys Thr Val Asn Glu Asn Lys Gln Asn
65                  70                  75                  80

Val Asp Ala Lys Val Lys Ala Ala Glu Ser Glu Ile Glu Lys Leu Thr
                85                  90                  95

Thr Lys Leu Ala Asp Thr Asp Ala Ala Leu Ala Asp Thr Asp Ala Ala
            100                 105                 110

Leu Asp Ala Thr Thr Asn Ala Leu Asn Lys Leu Gly Glu Asn Ile Thr
        115                 120                 125

Thr Phe Ala Glu Glu Thr Lys Thr Asn Ile Val Lys Ile Asp Glu Lys
130                 135                 140

Leu Glu Ala Val Ala Asp Thr Val Asp Lys His Ala Glu Ala Phe Asn
145                 150                 155                 160

Asp Ile Ala Asp Ser Leu Asp Glu Thr Asn Thr Lys Ala Asp Glu Ala
                165                 170                 175

Val Lys Thr Ala Asn Glu Ala Lys Gln Thr Ala Glu Glu Thr Lys Gln
            180                 185                 190

Asn Val Asp Ala Lys Val Lys Ala Ala Glu Thr Ala Ala Gly Lys Ala
        195                 200                 205
```

-continued

```
Glu Ala Ala Ala Gly Thr Ala Asn Thr Ala Ala Asp Lys Ala Glu Ala
    210             215             220

Val Ala Ala Lys Val Thr Asp Ile Lys Ala Asp Ile Ala Thr Asn Lys
225             230             235             240

Asp Asn Ile Ala Lys Lys Ala Asn Ser Ala Asp Val Tyr Thr Arg Glu
                245             250             255

Glu Ser Asp Ser Lys Phe Val Arg Ile Asp Gly Leu Asn Ala Thr Thr
                260             265             270

Glu Lys Leu Asp Thr Arg Leu Ala Ser Ala Glu Lys Ser Ile Ala Asp
    275             280             285

His Asp Thr Arg Leu Asn Gly Leu Asp Lys Thr Val Ser Asp Leu Arg
    290             295             300

Lys Glu Thr Arg Gln Gly Leu Ala Glu Gln Ala Ala Leu Ser Gly Leu
305             310             315             320

Phe Gln Pro Tyr Asn Val Gly
                325
```